United States Patent
Zimmermann et al.

(10) Patent No.: US 12,146,195 B2
(45) Date of Patent: Nov. 19, 2024

(54) METHODS FOR LUNG CANCER DETECTION

(71) Applicants: Natera, Inc., San Carlos, CA (US); UCL BUSINESS LTD., London (GB)

(72) Inventors: Bernhard Zimmermann, Manteca, CA (US); Tudor Pompiliu Constantin, Berkley, CA (US); Raheleh Salari, San Carlos, CA (US); Huseyin Eser Kirkizlar, Los Angeles, CA (US); Robert Charles Swanton, London (GB); Mariam Jamal-Hanjani, London (GB); Christopher Abbosh, Herts (GB); Gareth Wilson, Bromley (GB)

(73) Assignee: Natera, Inc., San Carlos, CA (US)

( * ) Notice: Subject to any disclaimer, the term of this patent is extended or adjusted under 35 U.S.C. 154(b) by 0 days.

(21) Appl. No.: 16/092,436

(22) PCT Filed: Apr. 17, 2017

(86) PCT No.: PCT/US2017/028013
§ 371 (c)(1),
(2) Date: Oct. 9, 2018

(87) PCT Pub. No.: WO2017/181202
PCT Pub. Date: Oct. 19, 2017

(65) Prior Publication Data
US 2019/0106751 A1 Apr. 11, 2019

Related U.S. Application Data

(60) Provisional application No. 62/323,589, filed on Apr. 15, 2016.

(51) Int. Cl.
C12Q 1/68 (2018.01)
C12Q 1/6858 (2018.01)
C12Q 1/6886 (2018.01)

(52) U.S. Cl.
CPC ......... *C12Q 1/6886* (2013.01); *C12Q 1/6858* (2013.01); *C12Q 2600/156* (2013.01)

(58) Field of Classification Search
None
See application file for complete search history.

(56) References Cited

U.S. PATENT DOCUMENTS 3,957,654 A 5/1976 Ayres
4,040,785 A 8/1977 Kim et al.
(Continued)

FOREIGN PATENT DOCUMENTS

BR 112017023232 A2 8/2018
CA 2875281 A1 12/2013
(Continued)

OTHER PUBLICATIONS

US 8,501,409 B2, 08/2013, Simen et al. (withdrawn)
(Continued)

*Primary Examiner* — Jeanine A Goldberg

(57) ABSTRACT

The invention provides methods for detecting single nucleotide variants in lung cancer, especially stage 3a lung adenocarcinoma and lung squamous cell carcinoma. Additional methods and compositions, such as reaction mixtures and solid supports comprising clonal populations of nucleic acids, are provided.

12 Claims, 171 Drawing Sheets

(56) References Cited

U.S. PATENT DOCUMENTS

| | | | |
|---|---|---|---|
| 4,683,195 | A | 7/1987 | Mullis et al. |
| 4,942,124 | A | 7/1990 | Church et al. |
| 5,180,812 | A | 1/1993 | Dower et al. |
| 5,314,809 | A | 5/1994 | Erlich et al. |
| 5,319,071 | A | 6/1994 | Dower et al. |
| 5,464,937 | A | 11/1995 | Sims et al. |
| 5,486,477 | A | 1/1996 | Carver |
| 5,488,032 | A | 1/1996 | Dower et al. |
| 5,492,888 | A | 2/1996 | Dower et al. |
| 5,569,582 | A | 10/1996 | Tavernarakis et al. |
| 5,595,890 | A | 1/1997 | Newton et al. |
| 5,635,366 | A | 6/1997 | Cooke et al. |
| 5,645,988 | A | 7/1997 | Vande Woude et al. |
| 5,648,220 | A | 7/1997 | Bianchi et al. |
| 5,714,320 | A | 2/1998 | Kool |
| 5,716,776 | A | 2/1998 | Bogart |
| 5,736,033 | A | 4/1998 | Coleman et al. |
| 5,753,467 | A | 5/1998 | Jensen et al. |
| 5,824,467 | A | 10/1998 | Mascarenhas |
| 5,854,033 | A | 12/1998 | Lizardi |
| 5,860,917 | A | 1/1999 | Comanor et al. |
| 5,891,734 | A | 4/1999 | Gill et al. |
| 5,952,170 | A | 9/1999 | Stroun et al. |
| 5,962,223 | A | 10/1999 | Whiteley et al. |
| 5,972,602 | A | 11/1999 | Hyland et al. |
| 5,976,790 | A | 11/1999 | Pinkel et al. |
| 5,994,148 | A | 11/1999 | Stewart et al. |
| 6,001,611 | A | 12/1999 | Will |
| 6,025,128 | A | 2/2000 | Veltri et al. |
| 6,066,454 | A | 5/2000 | Lipshutz et al. |
| 6,100,029 | A | 8/2000 | Lapidus et al. |
| 6,108,635 | A | 8/2000 | Herren et al. |
| 6,124,120 | A | 9/2000 | Lizardi |
| 6,143,496 | A | 11/2000 | Brown et al. |
| 6,156,504 | A | 12/2000 | Gocke et al. |
| 6,180,349 | B1 | 1/2001 | Ginzinger |
| 6,235,472 | B1 | 2/2001 | Landegren et al. |
| 6,214,558 | B1 | 4/2001 | Shuber et al. |
| 6,221,603 | B1 | 4/2001 | Mahtani |
| 6,258,540 | B1 | 7/2001 | Lo et al. |
| 6,300,077 | B1 | 10/2001 | Shuber et al. |
| 6,329,179 | B1 | 12/2001 | Kopreski |
| 6,335,167 | B1 | 1/2002 | Pinkel et al. |
| 6,479,235 | B1 | 11/2002 | Schumm et al. |
| 6,440,706 | B1 | 12/2002 | Vogelstein et al. |
| 6,489,135 | B1 | 12/2002 | Parrott et al. |
| 6,605,451 | B1 | 8/2003 | Marmaro et al. |
| 6,617,137 | B2 | 9/2003 | Dean et al. |
| 6,720,140 | B1 | 4/2004 | Hartley et al. |
| 6,794,140 | B1 | 9/2004 | Goldsborough |
| 6,807,491 | B2 | 10/2004 | Pavlovic et al. |
| 6,858,412 | B2 | 2/2005 | Willis et al. |
| 6,927,028 | B2 | 8/2005 | Lo et al. |
| 6,852,487 | B1 | 10/2005 | Barany et al. |
| 6,958,211 | B2 | 10/2005 | Vingerhoets et al. |
| 6,964,847 | B1 | 11/2005 | Englert |
| 7,035,739 | B2 | 4/2006 | Schadt et al. |
| 7,058,517 | B1 | 6/2006 | Denton et al. |
| 7,058,616 | B1 | 6/2006 | Larder et al. |
| 7,101,663 | B2 | 9/2006 | Godfrey et al. |
| 7,153,656 | B2 | 12/2006 | Nolan et al. |
| 7,218,764 | B2 | 5/2007 | Vaisberg et al. |
| 7,297,485 | B2 | 11/2007 | Bornarth et al. |
| 7,332,277 | B2 | 2/2008 | Dhallan |
| 7,410,764 | B2 | 8/2008 | Gocke et al. |
| 7,414,118 | B1 | 8/2008 | Mullah et al. |
| 7,442,506 | B2 | 12/2008 | Dhallan |
| 7,459,273 | B2 | 12/2008 | Jones et al. |
| 7,645,576 | B2 | 1/2010 | Lo et al. |
| 7,655,399 | B2 | 2/2010 | Cantor et al. |
| 7,700,325 | B2 | 5/2010 | Cantor et al. |
| 7,718,367 | B2 | 5/2010 | Lo et al. |
| 7,718,370 | B2 | 6/2010 | Dhallan |
| 7,741,463 | B2 | 6/2010 | Gormley et al. |
| 7,785,798 | B2 | 8/2010 | Cantor et al. |
| 7,727,720 | B2 | 9/2010 | Dhallan |
| 7,790,393 | B2 | 9/2010 | Lyamichev et al. |
| 7,790,418 | B2 | 9/2010 | Mayer |
| 7,805,282 | B2 | 11/2010 | Casey |
| 7,838,647 | B2 | 11/2010 | Hahn et al. |
| 7,981,609 | B2 | 7/2011 | Rubin et al. |
| 7,888,017 | B2 | 8/2011 | Quake |
| 8,008,018 | B2 | 9/2011 | Quake et al. |
| 8,024,128 | B2 | 9/2011 | Rabinowitz |
| 8,133,719 | B2 | 3/2012 | Drmanac et al. |
| 8,137,912 | B2 | 5/2012 | Kapur et al. |
| 8,173,370 | B2 | 5/2012 | Oeth et al. |
| 8,168,389 | B2 | 6/2012 | Shoemaker et al. |
| 8,236,503 | B2 | 8/2012 | Faham et al. |
| 8,195,415 | B2 | 10/2012 | Fan et al. |
| 8,296,076 | B2 | 11/2012 | Fan et al. |
| 8,304,187 | B2 | 11/2012 | Fernando |
| 8,318,430 | B2 | 11/2012 | Chuu et al. |
| 8,318,434 | B2 | 11/2012 | Cuppens et al. |
| 8,323,897 | B2 | 12/2012 | Andersen et al. |
| 8,372,584 | B2 | 2/2013 | Shoemaker et al. |
| 8,389,557 | B2 | 3/2013 | Singh et al. |
| 8,389,578 | B2 | 3/2013 | Went et al. |
| 8,450,063 | B2 | 5/2013 | Dube et al. |
| 8,467,976 | B2 | 8/2013 | Lo et al. |
| 8,515,679 | B2 | 9/2013 | Rabinowitz et al. |
| 8,532,930 | B2 | 9/2013 | Rabinowitz et al. |
| 8,609,338 | B2 | 12/2013 | Mitchell et al. |
| 8,679,741 | B2 | 3/2014 | Hoyal-Wrightson et al. |
| 8,682,592 | B2 | 3/2014 | Rabinowitz et al. |
| 8,703,652 | B2 | 4/2014 | Quake et al. |
| 8,706,422 | B2 | 4/2014 | Lo et al. |
| 8,748,103 | B2 | 6/2014 | Faham et al. |
| 8,822,153 | B2 * | 9/2014 | Hayes ............... C12Q 1/686 435/6.12 |
| 8,825,412 | B2 | 9/2014 | Rabinowitz et al. |
| 9,005,894 | B2 | 4/2015 | Ladner et al. |
| 9,051,602 | B2 | 6/2015 | Oliphant et al. |
| 9,085,798 | B2 | 7/2015 | Chee |
| 9,206,475 | B2 | 12/2015 | gerdes et al. |
| 9,228,234 | B2 | 1/2016 | Rabinowitz et al. |
| 9,290,815 | B2 | 3/2016 | Di Pasquale et al. |
| 9,323,888 | B2 | 4/2016 | Rava et al. |
| 9,364,829 | B2 | 6/2016 | Heid et al. |
| 9,404,150 | B2 | 8/2016 | Lee et al. |
| 9,424,392 | B2 | 8/2016 | Rabinowitz et al. |
| 9,453,257 | B2 | 9/2016 | Hoyal-Wrightson et al. |
| 9,476,095 | B2 | 10/2016 | Vogelstein et al. |
| 9,487,829 | B2 | 11/2016 | Vogelstein et al. |
| 9,493,828 | B2 | 11/2016 | Rava et al. |
| 9,506,119 | B2 | 11/2016 | Faham et al. |
| 9,598,731 | B2 | 3/2017 | Talasaz |
| 9,677,118 | B2 | 6/2017 | Zimmermann et al. |
| 9,926,593 | B2 | 3/2018 | Ehrich et al. |
| 9,957,558 | B2 | 5/2018 | Leamon et al. |
| 10,011,870 | B2 | 7/2018 | Zimmermann et al. |
| 10,017,810 | B2 | 7/2018 | Iafrate et al. |
| 10,041,127 | B2 | 8/2018 | Talasaz |
| 10,061,890 | B2 | 8/2018 | Rabinowitz et al. |
| 10,081,839 | B2 | 9/2018 | Rabinowitz et al. |
| 10,083,273 | B2 | 9/2018 | Rabinowitz et al. |
| 10,174,369 | B2 | 1/2019 | Rabinowitz et al. |
| 10,179,937 | B2 | 1/2019 | Babiarz et al. |
| 10,227,652 | B2 | 3/2019 | Rabinowitz et al. |
| 10,229,244 | B2 | 3/2019 | Ghosh |
| 10,240,202 | B2 | 3/2019 | Rabinowitz et al. |
| 10,260,096 | B2 | 4/2019 | Rabinowitz et al. |
| 10,266,893 | B2 | 4/2019 | Rabinowitz et al. |
| 10,308,981 | B2 | 6/2019 | Sparks et al. |
| 10,316,362 | B2 | 6/2019 | Babiarz et al. |
| 10,351,906 | B2 | 7/2019 | Zimmermann et al. |
| 10,385,396 | B2 | 8/2019 | Mitchell et al. |
| 10,392,664 | B2 | 8/2019 | Rabinowitz et al. |
| 10,450,597 | B2 | 10/2019 | Iafrate et al. |
| 10,472,680 | B2 | 11/2019 | Mitchell et al. |
| 10,522,242 | B2 | 12/2019 | Rabinowitz et al. |
| 10,526,658 | B2 | 1/2020 | Babiarz et al. |
| 10,538,814 | B2 | 1/2020 | Babiarz et al. |
| 10,557,172 | B2 | 2/2020 | Babiarz et al. |

(56) References Cited

U.S. PATENT DOCUMENTS

| | | |
|---|---|---|
| 10,597,708 B2 | 3/2020 | Zimmermann et al. |
| 10,597,709 B2 | 3/2020 | Zimmermann et al. |
| 10,597,723 B2 | 3/2020 | Babiarz et al. |
| 10,655,180 B2 | 5/2020 | Babiarz et al. |
| 10,683,552 B2 | 6/2020 | Giulio et al. |
| 10,711,309 B2 | 7/2020 | Rabinowitz et al. |
| 10,731,220 B2 | 8/2020 | Babiarz et al. |
| 10,774,380 B2 | 9/2020 | Ryan et al. |
| 10,793,912 B2 | 10/2020 | Babiarz et al. |
| 10,894,976 B2 | 1/2021 | Stray et al. |
| 11,111,543 B2 | 9/2021 | Rabinowitz et al. |
| 11,111,544 B2 | 9/2021 | Rabinowitz et al. |
| 11,111,545 B2 | 9/2021 | Babiarz et al. |
| 11,130,995 B2 | 9/2021 | Quake et al. |
| 11,319,596 B2 | 5/2022 | Babiarz et al. |
| 11,371,100 B2 | 6/2022 | Babiarz et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2002/0119478 A1 | 8/2002 | Umansky et al. |
| 2002/0182622 A1 | 12/2002 | Nakamura et al. |
| 2003/0009295 A1 | 1/2003 | Markowitz et al. |
| 2003/0040620 A1 | 2/2003 | Langmore et al. |
| 2003/0044388 A1 | 3/2003 | Lo et al. |
| 2003/0065535 A1 | 4/2003 | Karlov et al. |
| 2003/0077586 A1 | 4/2003 | Pavlovic et al. |
| 2003/0087276 A1 | 5/2003 | Kopreski et al. |
| 2003/0101000 A1 | 5/2003 | Bader et al. |
| 2003/0108900 A1 | 6/2003 | Oliphant et al. |
| 2003/0119004 A1 | 6/2003 | Wenz et al. |
| 2003/0138780 A1 | 7/2003 | Gill et al. |
| 2003/0148301 A1 | 8/2003 | Aono et al. |
| 2003/0191005 A1 | 10/2003 | Coelho et al. |
| 2003/0211489 A1 | 11/2003 | Shen et al. |
| 2003/0228613 A1 | 12/2003 | Bornarth et al. |
| 2003/0232348 A1 | 12/2003 | Jones et al. |
| 2003/0232353 A1 | 12/2003 | Kennedy et al. |
| 2003/0235848 A1 | 12/2003 | Neville et al. |
| 2004/0009518 A1 | 1/2004 | Lo et al. |
| 2004/0033596 A1 | 2/2004 | Threadgill et al. |
| 2004/0067493 A1 | 4/2004 | Matsuzaki et al. |
| 2004/0096874 A1 | 5/2004 | Neville et al. |
| 2004/0115629 A1 | 6/2004 | Panzer et al. |
| 2004/0126760 A1 | 7/2004 | Broude |
| 2004/0136967 A1 | 7/2004 | Weiss et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0185495 A1 | 9/2004 | Schueler et al. |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0043894 A1 | 2/2005 | Fernandez |
| 2005/0049793 A1 | 3/2005 | Paterlini-brechot |
| 2005/0053950 A1 | 3/2005 | Ubani et al. |
| 2005/0064476 A1 | 3/2005 | Huang et al. |
| 2005/0079521 A1 | 4/2005 | Beaulieu et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0164252 A1 | 7/2005 | Yeung |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2005/0282185 A1 | 12/2005 | Lo et al. |
| 2006/0014179 A1 | 1/2006 | Roberts |
| 2006/0019278 A1 | 1/2006 | Lo et al. |
| 2006/0040300 A1 | 2/2006 | Dapprich et al. |
| 2006/0046258 A1 | 3/2006 | Lapidus et al. |
| 2006/0051799 A1 | 3/2006 | Iwaki et al. |
| 2006/0052945 A1 | 3/2006 | Rabinowitz et al. |
| 2006/0057618 A1 | 3/2006 | Piper et al. |
| 2006/0068369 A1 | 3/2006 | Coelho et al. |
| 2006/0068394 A1 | 3/2006 | Langmore et al. |
| 2006/0088574 A1 | 4/2006 | Manning et al. |
| 2006/0088871 A1 | 4/2006 | Finkelstein et al. |
| 2006/0088912 A1 | 4/2006 | Yan et al. |
| 2006/0094010 A1 | 5/2006 | Giles et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216153 A1 | 9/2006 | Wobben et al. |
| 2006/0216738 A1 | 9/2006 | Wada et al. |
| 2006/0228721 A1 | 10/2006 | Leamon et al. |
| 2006/0234264 A1 | 10/2006 | Hardenbol |
| 2006/0248031 A1 | 11/2006 | Kates et al. |
| 2006/0281105 A1 | 12/2006 | Li et al. |
| 2006/0292599 A1 | 12/2006 | Ritz et al. |
| 2007/0020640 A1 | 1/2007 | McCloskey et al. |
| 2007/0027636 A1 | 2/2007 | Rabinowitz |
| 2007/0031857 A1 | 2/2007 | Makarov et al. |
| 2007/0037166 A1 | 2/2007 | Wohlgemuth et al. |
| 2007/0042384 A1 | 2/2007 | Li et al. |
| 2007/0059700 A1 | 3/2007 | Tao et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0134658 A1 | 6/2007 | Bohmer |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0231823 A1 | 10/2007 | McKernan et al. |
| 2007/0243549 A1 | 10/2007 | Bischoff |
| 2007/0259351 A1 | 11/2007 | Chinitz |
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0161420 A1 | 7/2008 | Shuber et al. |
| 2008/0164204 A1 | 7/2008 | Hatamian et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0280292 A1 | 11/2008 | Wangh et al. |
| 2008/0286783 A1 | 11/2008 | Hosono et al. |
| 2008/0293589 A1 | 11/2008 | Shapero |
| 2008/0299562 A1 | 12/2008 | Oeth et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176234 A1 | 7/2009 | Drmanac et al. |
| 2009/0176662 A1 | 7/2009 | Rigatti et al. |
| 2009/0221620 A1 | 9/2009 | Luke et al. |

(56) References Cited

U.S. PATENT DOCUMENTS

| | | |
|---|---|---|
| 2009/0233802 A1 | 9/2009 | Bignell et al. |
| 2009/0253183 A1 | 10/2009 | Han |
| 2009/0263800 A1 | 10/2009 | Wohlgemuth et al. |
| 2009/0280479 A1 | 11/2009 | Hoon et al. |
| 2009/0317817 A1 | 12/2009 | Oeth et al. |
| 2010/0012598 A1 | 1/2010 | Dicesare et al. |
| 2010/0035232 A1 | 2/2010 | Ecker et al. |
| 2010/0041048 A1 | 2/2010 | Diehl et al. |
| 2010/0086914 A1 | 4/2010 | bentley et al. |
| 2010/0105049 A1 | 4/2010 | Ehrich et al. |
| 2010/0112575 A1 | 5/2010 | Fan et al. |
| 2010/0112586 A1 | 5/2010 | Stoughton et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129792 A1 | 5/2010 | Makrigiorgos et al. |
| 2010/0129874 A1 | 5/2010 | Mitra et al. |
| 2010/0138165 A1 | 6/2010 | Fan et al. |
| 2010/0155343 A1 | 6/2010 | Battles et al. |
| 2010/0171954 A1 | 7/2010 | Quake et al. |
| 2010/0173394 A1 | 7/2010 | Colston et al. |
| 2010/0184043 A1 | 7/2010 | Mitchell et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216145 A1 | 8/2010 | Duvdevani |
| 2010/0216151 A1 | 8/2010 | Lapdus et al. |
| 2010/0216153 A1 | 8/2010 | Lapidus et al. |
| 2010/0227329 A1 | 9/2010 | Cuppens |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273159 A1 | 10/2010 | Melo |
| 2010/0273219 A1 | 10/2010 | May et al. |
| 2010/0273678 A1 | 10/2010 | Alexandre et al. |
| 2010/0285478 A1 | 11/2010 | Chen et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2010/0326218 A1 | 12/2010 | Boeckh et al. |
| 2011/0015096 A1 | 1/2011 | Chiu |
| 2011/0033862 A1 | 2/2011 | Rabinowitz et al. |
| 2011/0039724 A1 | 2/2011 | Lo et al. |
| 2011/0045462 A1 | 2/2011 | Fu et al. |
| 2011/0064824 A1 | 3/2011 | Lascoste et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0110931 A1 | 5/2011 | Matsui |
| 2011/0111410 A1 | 5/2011 | Ryan et al. |
| 2011/0130558 A1 | 6/2011 | Ritt et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0189677 A1 | 8/2011 | Adli et al. |
| 2011/0201507 A1 | 8/2011 | Rava et al. |
| 2011/0212446 A1 | 9/2011 | Wang et al. |
| 2011/0212846 A1 | 9/2011 | Spier |
| 2011/0224087 A1 | 9/2011 | Quake et al. |
| 2011/0230358 A1 | 9/2011 | Rava |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0294699 A1 | 12/2011 | Lee et al. |
| 2011/0300608 A1 | 12/2011 | Ryan et al. |
| 2011/0301854 A1 | 12/2011 | Curry et al. |
| 2011/0312503 A1 | 12/2011 | Chuu et al. |
| 2011/0318734 A1 | 12/2011 | Lo et al. |
| 2012/0003635 A1 | 1/2012 | Lo et al. |
| 2012/0003637 A1 | 1/2012 | Lo et al. |
| 2012/0010085 A1 | 1/2012 | Rava et al. |
| 2012/0021442 A1 | 1/2012 | Buhimschi et al. |
| 2012/0028814 A1 | 2/2012 | Toloue et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0115140 A1 | 5/2012 | Rivkees et al. |
| 2012/0122701 A1 | 5/2012 | Ryan et al. |
| 2012/0122702 A1 | 5/2012 | Leproust et al. |
| 2012/0135872 A1 | 5/2012 | Chuu et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0190557 A1 | 7/2012 | Oliphant et al. |
| 2012/0191358 A1 | 7/2012 | Oliphant et al. |
| 2012/0196754 A1 | 8/2012 | Quake et al. |
| 2012/0208706 A1 | 8/2012 | Downing et al. |
| 2012/0214678 A1 | 8/2012 | Rava et al. |
| 2012/0251411 A1 | 10/2012 | Jeon |
| 2012/0264121 A1 | 10/2012 | Rava et al. |
| 2012/0264618 A1 | 10/2012 | Nygren |
| 2012/0270212 A1 | 10/2012 | Rabinowitz et al. |
| 2012/0270739 A1 | 10/2012 | Rava et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0022973 A1 | 1/2013 | Hansen et al. |
| 2013/0024127 A1 | 1/2013 | Stuelpnagel |
| 2013/0034546 A1 | 2/2013 | Rava et al. |
| 2013/0040375 A1 | 2/2013 | Sparks et al. |
| 2013/0060483 A1 | 3/2013 | Struble et al. |
| 2013/0069869 A1 | 3/2013 | Akao et al. |
| 2013/0071844 A1 | 3/2013 | Makino et al. |
| 2013/0085681 A1 | 4/2013 | Deciu et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0143219 A1 | 6/2013 | Mitchell et al. |
| 2013/0157870 A1 | 6/2013 | Pushkarev et al. |
| 2013/0172211 A1 | 7/2013 | Oliphant et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0231252 A1 | 9/2013 | Mitchell et al. |
| 2013/0237431 A1 | 9/2013 | Lo et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0274135 A1 | 10/2013 | Zhang et al. |
| 2013/0288252 A1 | 10/2013 | Sparks et al. |
| 2013/0303461 A1 | 11/2013 | Iafrate et al. |
| 2013/0310260 A1 | 11/2013 | Kim et al. |
| 2013/0323727 A1 | 12/2013 | Huang et al. |
| 2013/0323731 A1 | 12/2013 | Lo et al. |
| 2013/0325360 A1 | 12/2013 | Deciu et al. |
| 2013/0344066 A1 | 12/2013 | Faham et al. |
| 2014/0032128 A1 | 1/2014 | Rabinowitz et al. |
| 2014/0038830 A1 | 2/2014 | Srinivasan et al. |
| 2014/0045181 A1 | 2/2014 | Lo et al. |
| 2014/0051585 A1 | 2/2014 | Prosen et al. |
| 2014/0065621 A1 | 3/2014 | Mhatre et al. |
| 2014/0066317 A1 | 3/2014 | Talasaz |
| 2014/0087385 A1 | 3/2014 | Rabinowitz et al. |
| 2014/0094373 A1 | 4/2014 | Zimmermann et al. |
| 2014/0100121 A1 | 4/2014 | Lo et al. |
| 2014/0100126 A1 | 4/2014 | Rabinowitz |
| 2014/0100134 A1 | 4/2014 | Rabinowitz et al. |
| 2014/0106975 A1 | 4/2014 | Stoughton et al. |
| 2014/0113795 A1 | 4/2014 | Emerson et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz et al. |
| 2014/0186827 A1 | 7/2014 | Pieprzyk et al. |
| 2014/0193816 A1 | 7/2014 | Rabinowitz et al. |

(56) References Cited

U.S. PATENT DOCUMENTS

| | | |
|---|---|---|
| 2014/0206552 A1 | 7/2014 | Rabinowitz et al. |
| 2014/0227691 A1 | 8/2014 | May et al. |
| 2014/0227705 A1 | 8/2014 | Vogelstein et al. |
| 2014/0242588 A1 | 8/2014 | Van Den Boom et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1 | 9/2014 | Srinivasan et al. |
| 2014/0287934 A1 | 9/2014 | Szelinger et al. |
| 2014/0296081 A1* | 10/2014 | Diehn .................. G16B 30/10 506/8 |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0056617 A1 | 2/2015 | Whitt et al. |
| 2015/0064695 A1 | 3/2015 | Katz et al. |
| 2015/0086477 A1 | 3/2015 | Mitchell et al. |
| 2015/0087535 A1 | 3/2015 | Patel |
| 2015/0099673 A1 | 4/2015 | Fodor |
| 2015/0147815 A1 | 5/2015 | Babiarz et al. |
| 2015/0167069 A1 | 6/2015 | Schutz et al. |
| 2015/0167077 A1 | 6/2015 | Fehr et al. |
| 2015/0197786 A1 | 7/2015 | Osborne et al. |
| 2015/0211050 A1 | 7/2015 | Iafrate et al. |
| 2015/0218631 A1 | 8/2015 | Chuu et al. |
| 2015/0232938 A1 | 8/2015 | Mhatre |
| 2015/0246103 A1 | 9/2015 | Hazout |
| 2015/0265995 A1 | 9/2015 | Head et al. |
| 2015/0299812 A1 | 10/2015 | Talasaz |
| 2015/0315657 A1 | 11/2015 | Rhodes et al. |
| 2015/0322507 A1 | 11/2015 | Zimmermann et al. |
| 2015/0329891 A1 | 11/2015 | Tan et al. |
| 2016/0024581 A1 | 1/2016 | Sarwal et al. |
| 2016/0032396 A1 | 2/2016 | Diehn et al. |
| 2016/0046986 A1 | 2/2016 | Eltoukhy et al. |
| 2016/0053320 A1 | 2/2016 | Schuh et al. |
| 2016/0115541 A1 | 4/2016 | Schutz et al. |
| 2016/0145682 A1 | 5/2016 | Woodward et al. |
| 2016/0186239 A1 | 6/2016 | Sinha |
| 2016/0186253 A1 | 6/2016 | Talasaz et al. |
| 2016/0201124 A1 | 7/2016 | Donahue et al. |
| 2016/0239602 A1 | 8/2016 | Shendure et al. |
| 2016/0244838 A1 | 8/2016 | Babiarz et al. |
| 2016/0257993 A1 | 9/2016 | Fu et al. |
| 2016/0265042 A1 | 9/2016 | Schroeder et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1* | 12/2016 | Babiarz .................. C12Q 1/6883 |
| 2017/0011166 A1 | 1/2017 | Rabinowitz et al. |
| 2017/0107576 A1* | 4/2017 | Babiarz .................. G16B 20/20 |
| 2017/0114411 A1 | 4/2017 | Mitchell |
| 2017/0121716 A1 | 5/2017 | Rodi et al. |
| 2017/0137882 A1 | 5/2017 | Goossens et al. |
| 2017/0145475 A1 | 5/2017 | Hunsley et al. |
| 2017/0152561 A1 | 6/2017 | Hamamah et al. |
| 2017/0218458 A1 | 8/2017 | Fan et al. |
| 2017/0275689 A1 | 9/2017 | Maguire et al. |
| 2017/0283788 A1 | 10/2017 | Khoja et al. |
| 2017/0298427 A1 | 10/2017 | Buis et al. |
| 2017/0314014 A1 | 11/2017 | Green et al. |
| 2017/0342477 A1 | 11/2017 | Jensen et al. |
| 2017/0362649 A1 | 12/2017 | Lieberman-Aiden et al. |
| 2018/0023128 A1 | 1/2018 | Yanai et al. |
| 2018/0025109 A1 | 2/2018 | Rabinowitz et al. |
| 2018/0105807 A1 | 4/2018 | Lo et al. |
| 2018/0127744 A1 | 5/2018 | Hu et al. |
| 2018/0142296 A1 | 5/2018 | Mitchell et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsso et al. |
| 2018/0173846 A1 | 6/2018 | Sigurjonsso et al. |
| 2018/0187241 A1 | 7/2018 | Selvaraj et al. |
| 2018/0201995 A1 | 7/2018 | Rabinowitz et al. |
| 2018/0237841 A1 | 8/2018 | Stray et al. |
| 2018/0251553 A1 | 9/2018 | McGranahan et al. |
| 2018/0265917 A1 | 9/2018 | Barany et al. |
| 2018/0288982 A1 | 10/2018 | Sinha |
| 2018/0298439 A1 | 10/2018 | Ryan et al. |
| 2018/0300448 A1 | 10/2018 | Rabinowitz et al. |
| 2018/0303870 A1 | 10/2018 | Golobish et al. |
| 2018/0320171 A1 | 11/2018 | Withey |
| 2018/0320239 A1 | 11/2018 | Babiarz et al. |
| 2018/0371531 A1 | 12/2018 | Quake et al. |
| 2019/0010543 A1 | 1/2019 | Babiarz et al. |
| 2019/0106737 A1 | 4/2019 | Underhill |
| 2019/0112661 A1 | 4/2019 | Khan et al. |
| 2019/0153521 A1 | 5/2019 | Mitchell et al. |
| 2019/0153525 A1 | 5/2019 | Mitchell et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211376 A1 | 7/2019 | Quake et al. |
| 2019/0211385 A1 | 7/2019 | Sarwar et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |
| 2019/0249241 A1 | 8/2019 | Rabinowitz et al. |
| 2019/0256894 A1 | 8/2019 | Zimmermann et al. |
| 2019/0256906 A1 | 8/2019 | Rabinowitz et al. |
| 2019/0256907 A1 | 8/2019 | Ryan et al. |
| 2019/0256908 A1 | 8/2019 | Rabinowitz et al. |
| 2019/0256909 A1 | 8/2019 | Rabinowitz et al. |
| 2019/0256912 A1 | 8/2019 | Rabinowitz et al. |
| 2019/0256916 A1 | 8/2019 | Babiarz et al. |
| 2019/0256917 A1 | 8/2019 | Babiarz et al. |
| 2019/0256919 A1 | 8/2019 | Babiarz et al. |
| 2019/0256924 A1 | 8/2019 | Vogelstein et al. |
| 2019/0256931 A1 | 8/2019 | Babiarz et al. |
| 2019/0264277 A1 | 8/2019 | Rabinowitz et al. |
| 2019/0264280 A1 | 8/2019 | Rabinowitz et al. |
| 2019/0264288 A1 | 8/2019 | Rabinowitz et al. |
| 2019/0271043 A1 | 9/2019 | Babiarz et al. |
| 2019/0276888 A1 | 9/2019 | Rabinowitz et al. |
| 2019/0284623 A1 | 9/2019 | Rabinowitz et al. |
| 2019/0300950 A1 | 10/2019 | Rabinowitz et al. |
| 2019/0309358 A1 | 10/2019 | Rabinowitz et al. |
| 2019/0309359 A1 | 10/2019 | Zimmermann et al. |
| 2019/0309365 A1 | 10/2019 | Babiarz et al. |
| 2019/0316177 A1 | 10/2019 | Zimmermann et al. |
| 2019/0316184 A1 | 10/2019 | Zimmermann et al. |
| 2019/0316200 A1 | 10/2019 | Rabinowitz et al. |
| 2019/0323076 A1 | 10/2019 | Rabinowitz et al. |
| 2019/0360033 A1 | 11/2019 | Stamm et al. |
| 2019/0360036 A1 | 11/2019 | Rabinowitz et al. |
| 2019/0367972 A1 | 12/2019 | Mitchell et al. |
| 2020/0024653 A1 | 1/2020 | Bethke |
| 2020/0032323 A1 | 1/2020 | Talasaz et al. |
| 2020/0032340 A1 | 1/2020 | Mitchell |
| 2020/0109449 A1 | 4/2020 | Stamm et al. |
| 2020/0121718 A1 | 4/2020 | Novik et al. |
| 2020/0123612 A1 | 4/2020 | Babiarz et al. |
| 2020/0126634 A1 | 4/2020 | Sigurjonsson et al. |
| 2020/0140950 A1 | 5/2020 | Babiarz et al. |
| 2020/0141925 A1 | 5/2020 | Liaw et al. |
| 2020/0149111 A1 | 5/2020 | Babiarz et al. |
| 2020/0157629 A1 | 5/2020 | Babiarz et al. |
| 2020/0165678 A1 | 5/2020 | Mitchell et al. |
| 2020/0172977 A1 | 6/2020 | Rabinowitz et al. |

(56) References Cited

U.S. PATENT DOCUMENTS

| | | |
|---|---|---|
| 2020/0181681 A1 | 6/2020 | Mitchell et al. |
| 2020/0181697 A1 | 6/2020 | Rabinowitz et al. |
| 2020/0190570 A1 | 6/2020 | Ryan et al. |
| 2020/0190573 A1 | 6/2020 | Rabinowitz et al. |
| 2020/0190591 A1 | 6/2020 | Rabinowitz et al. |
| 2020/0208196 A1 | 7/2020 | Zimmermann et al. |
| 2020/0208221 A1 | 7/2020 | Babiarz et al. |
| 2020/0224273 A1 | 7/2020 | Rabinowitz et al. |
| 2020/0232036 A1 | 7/2020 | Rabinowitz et al. |
| 2020/0232037 A1 | 7/2020 | Babiarz et al. |
| 2020/0248264 A1 | 8/2020 | Rabinowitz et al. |
| 2020/0248266 A1 | 8/2020 | Swanton et al. |
| 2020/0316498 A1 | 10/2020 | Mitchell |
| 2020/0318191 A1 | 10/2020 | Babiarz et al. |
| 2020/0347454 A1 | 11/2020 | Babiarz et al. |
| 2020/0350034 A1 | 11/2020 | Rabinowitz et al. |
| 2020/0362415 A1 | 11/2020 | Rabinowitz et al. |
| 2020/0370129 A1 | 11/2020 | Quinn et al. |
| 2020/0385809 A1 | 12/2020 | Ramani et al. |
| 2020/0407788 A1 | 12/2020 | Ryan et al. |
| 2020/0407798 A1 | 12/2020 | Babiarz et al. |
| 2021/0009990 A1 | 1/2021 | Stray et al. |
| 2021/0025005 A1 | 1/2021 | Babiarz et al. |
| 2021/0032692 A1 | 2/2021 | Mitchell et al. |
| 2021/0054459 A1 | 2/2021 | Rabinowitz et al. |
| 2021/0071246 A1 | 3/2021 | Zimmermann et al. |
| 2021/0139969 A1 | 5/2021 | Mitchell et al. |
| 2021/0139983 A1 | 5/2021 | Mitchell et al. |
| 2021/0139988 A1 | 5/2021 | Mitchell et al. |
| 2021/0155988 A1 | 5/2021 | Rabinowitz et al. |
| 2021/0189498 A1 | 6/2021 | Babiarz et al. |
| 2021/0198733 A1 | 7/2021 | Moshkevich et al. |
| 2021/0198742 A1 | 7/2021 | Rabinowitz et al. |
| 2021/0198743 A1 | 7/2021 | Rabinowitz et al. |
| 2021/0222230 A1 | 7/2021 | Zimmermann et al. |
| 2021/0222240 A1 | 7/2021 | Moshkevich et al. |
| 2021/0257048 A1 | 8/2021 | Zimmermann et al. |
| 2021/0269879 A1 | 9/2021 | Mitchell et al. |
| 2021/0301320 A1 | 9/2021 | Mitchell et al. |
| 2021/0324463 A1 | 10/2021 | Rabinowitz et al. |
| 2021/0327538 A1 | 10/2021 | Egilsson et al. |
| 2021/0327542 A1 | 10/2021 | Ryan et al. |
| 2021/0355536 A1 | 11/2021 | Rabinowitz et al. |
| 2022/0025455 A1 | 1/2022 | Zimmermann et al. |
| 2022/0025456 A1 | 1/2022 | Rabinowitz et al. |
| 2022/0033908 A1 | 2/2022 | Rabinowitz et al. |
| 2022/0033909 A1 | 2/2022 | Babiarz et al. |
| 2022/0042103 A1 | 2/2022 | Rabinowitz et al. |
| 2022/0056509 A1 | 2/2022 | Zimmermann |
| 2022/0056534 A1 | 2/2022 | Rivers |
| 2022/0073978 A1 | 3/2022 | Rabinowitz et al. |
| 2022/0073979 A1 | 3/2022 | Rabinowitz et al. |
| 2022/0098667 A1 | 3/2022 | Rabinowitz et al. |
| 2022/0139495 A1 | 5/2022 | Rabinowitz et al. |
| 2022/0145391 A1 | 5/2022 | Mitchell et al. |
| 2022/0154249 A1 | 5/2022 | Zimmermann et al. |
| 2022/0154290 A1 | 5/2022 | Babiarz et al. |
| 2022/0195526 A1 | 6/2022 | Rabinowitz et al. |
| 2022/0213561 A1 | 7/2022 | Babiarz et al. |
| 2022/0251654 A1 | 8/2022 | Hafez et al. |
| 2022/0267849 A1 | 8/2022 | Mitchell et al. |
| 2022/0282335 A1 | 9/2022 | Babiarz et al. |
| 2022/0307086 A1 | 9/2022 | Babiarz et al. |
| 2022/0340963 A1 | 10/2022 | North et al. |
| 2022/0356522 A1 | 11/2022 | Mitchell et al. |
| 2022/0356526 A1 | 11/2022 | Babiarz et al. |
| 2022/0356530 A1 | 11/2022 | Sharma |
| 2022/0403461 A1 | 12/2022 | Kirkizlar et al. |
| 2022/0411875 A1 | 12/2022 | Rabinowitz et al. |
| 2023/0054494 A1 | 2/2023 | Rabinowitz et al. |
| 2023/0053752 A1 | 3/2023 | Rabinowitz et al. |
| 2023/0060579 A1 | 3/2023 | Bethke et al. |
| 2023/0193387 A1 | 6/2023 | Rabinowitz |
| 2023/0203573 A1 | 6/2023 | Swenerton et al. |
| 2023/0212693 A1 | 7/2023 | Rabinowitz et al. |
| 2023/0242998 A1 | 8/2023 | Babiarz et al. |
| 2023/0332221 A1 | 10/2023 | Zimmermann et al. |
| 2023/0343411 A1 | 10/2023 | Rabinowitz et al. |

FOREIGN PATENT DOCUMENTS

| | | |
|---|---|---|
| CN | 1650032 A | 8/2005 |
| CN | 1674028 A | 9/2005 |
| CN | 101675169 A | 3/2010 |
| CN | 102892901 A | 1/2013 |
| CN | 104736722 A | 6/2015 |
| CN | 105229175 A | 1/2016 |
| CN | 107365769 A | 11/2017 |
| CN | 107849604 A | 3/2018 |
| CN | 109661476 A | 4/2019 |
| EA | 201792389 A1 | 5/2018 |
| EP | 0270017 A2 | 6/1988 |
| EP | 1325963 A1 | 7/2003 |
| EP | 1524321 A1 | 4/2005 |
| EP | 1325963 B1 | 9/2006 |
| EP | 1524321 B1 | 7/2009 |
| EP | 2163622 A1 | 3/2010 |
| EP | 2128169 A1 | 12/2010 |
| EP | 2551356 A1 | 1/2013 |
| EP | 2653562 A1 | 10/2013 |
| EP | 2902500 A1 | 8/2015 |
| EP | 3026124 A1 | 6/2016 |
| EP | 2315849 B1 | 11/2017 |
| EP | 3285193 A1 | 2/2018 |
| EP | 2877594 B1 | 12/2019 |
| EP | 3187597 B1 | 6/2020 |
| EP | 3134541 B1 | 8/2020 |
| EP | 3760730 A1 | 1/2021 |
| EP | 3760731 A1 | 1/2021 |
| EP | 3760732 A1 | 1/2021 |
| EP | 3824470 | 5/2021 |
| EP | 3443119 B1 | 2/2022 |
| GB | 2488358 | 8/2012 |
| JP | 2965699 | 8/1999 |
| JP | 2002-530121 A | 9/2002 |
| JP | 2002-300894 A | 10/2002 |
| JP | 2003/521252 A | 7/2003 |
| JP | 2004502466 A | 1/2004 |
| JP | 2004121087 A | 4/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2008-263974 A | 11/2008 |
| JP | 2008/271980 A | 11/2008 |
| JP | 2010-509922 A | 4/2010 |
| JP | 2011/508662 A | 3/2011 |
| JP | 2011/516069 A | 5/2011 |
| JP | 2012085556 A | 5/2012 |
| JP | 2013509883 A | 3/2013 |
| JP | 2014118334 A1 | 8/2014 |
| JP | 2015-535681 | 12/2015 |
| JP | 2016502849 A | 2/2016 |
| RU | 2290078 C1 | 12/2006 |
| WO | 95/01796 | 1/1995 |
| WO | WO9623067 A1 | 8/1996 |
| WO | 1996036736 A2 | 11/1996 |
| WO | 98/39474 | 9/1998 |
| WO | 98/44151 | 10/1998 |
| WO | WO9937773 A1 | 7/1999 |
| WO | 00/18957 | 4/2000 |
| WO | 2001007640 A2 | 2/2001 |
| WO | 0134844 A1 | 5/2001 |
| WO | 01/57269 A2 | 8/2001 |
| WO | 179851 A1 | 10/2001 |
| WO | 200190419 A2 | 11/2001 |
| WO | 2002004672 A2 | 1/2002 |
| WO | 02/44411 A1 | 6/2002 |
| WO | 2002055985 A2 | 7/2002 |
| WO | 02/070751 A1 | 9/2002 |
| WO | 2002076377 | 10/2002 |
| WO | 02/090505 A2 | 11/2002 |
| WO | 03/000919 A2 | 1/2003 |
| WO | 03/018757 A3 | 3/2003 |

(56) References Cited

FOREIGN PATENT DOCUMENTS

| | | |
|---|---|---|
| WO | 03/020974 A3 | 3/2003 |
| WO | 2003031646 A1 | 4/2003 |
| WO | 3050532 A1 | 6/2003 |
| WO | 2003062441 A1 | 7/2003 |
| WO | 0190419 A9 | 11/2003 |
| WO | 3102595 A1 | 12/2003 |
| WO | 3106623 A2 | 12/2003 |
| WO | 2004/051218 A2 | 6/2004 |
| WO | 2004069849 A2 | 8/2004 |
| WO | 2004070005 A2 | 8/2004 |
| WO | 2004070007 A2 | 8/2004 |
| WO | 2004081183 | 9/2004 |
| WO | WO2004078999 A1 | 9/2004 |
| WO | 2004087863 A2 | 10/2004 |
| WO | 2005003375 A2 | 1/2005 |
| WO | 2005021793 A1 | 3/2005 |
| WO | 2005023091 A2 | 3/2005 |
| WO | 2005030999 A1 | 4/2005 |
| WO | 2005035725 A2 | 4/2005 |
| WO | 2005/039389 A3 | 5/2005 |
| WO | 2005100401 A2 | 10/2005 |
| WO | 2005123779 A2 | 12/2005 |
| WO | 2007145612 A1 | 6/2006 |
| WO | 2006110855 A2 | 10/2006 |
| WO | 2006/128192 A2 | 11/2006 |
| WO | 2007/011903 A3 | 1/2007 |
| WO | 2007/052006 A1 | 5/2007 |
| WO | 2007057647 A1 | 5/2007 |
| WO | 2007062164 A3 | 5/2007 |
| WO | 2007/073171 A2 | 6/2007 |
| WO | 2007070280 A2 | 6/2007 |
| WO | 2007070482 A2 | 6/2007 |
| WO | 2007075836 A2 | 7/2007 |
| WO | 2007/092473 A2 | 8/2007 |
| WO | 2007086935 A2 | 8/2007 |
| WO | 2007/117256 A1 | 10/2007 |
| WO | 2007117039 A1 | 10/2007 |
| WO | 2007132167 A2 | 11/2007 |
| WO | 2007/147073 A2 | 12/2007 |
| WO | 2007/147076 A2 | 12/2007 |
| WO | 2007140417 A2 | 12/2007 |
| WO | 2007147074 A2 | 12/2007 |
| WO | 2007147079 A2 | 12/2007 |
| WO | 2008024473 A2 | 2/2008 |
| WO | 2008048931 A1 | 4/2008 |
| WO | 2008/061213 A2 | 5/2008 |
| WO | 2008051928 A2 | 5/2008 |
| WO | 2008056937 A1 | 5/2008 |
| WO | 2008059578 A1 | 5/2008 |
| WO | 2008079374 A2 | 7/2008 |
| WO | 2008081451 A2 | 7/2008 |
| WO | 2008084405 A2 | 7/2008 |
| WO | 2008115427 A2 | 9/2008 |
| WO | 2008115497 A2 | 9/2008 |
| WO | 2008118988 A1 | 10/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/032779 A2 | 3/2009 |
| WO | 2009/036525 A2 | 3/2009 |
| WO | 2009030100 A1 | 3/2009 |
| WO | 2009032781 A2 | 3/2009 |
| WO | 2009033178 A1 | 3/2009 |
| WO | 2009049889 A1 | 4/2009 |
| WO | 2009017784 A2 | 5/2009 |
| WO | 2009064897 A2 | 5/2009 |
| WO | 2009091934 A1 | 7/2009 |
| WO | 2009092035 A2 | 7/2009 |
| WO | 2009/105531 A1 | 8/2009 |
| WO | 2009099602 A1 | 8/2009 |
| WO | 2009100029 A1 | 8/2009 |
| WO | 2009117122 A2 | 9/2009 |
| WO | 2009120808 A2 | 10/2009 |
| WO | 2009145828 A2 | 12/2009 |
| WO | 2009146335 A1 | 12/2009 |
| WO | 2010014920 A1 | 2/2010 |
| WO | 2010017214 A1 | 2/2010 |
| WO | 2010/033639 A2 | 3/2010 |
| WO | 2010/033652 A1 | 3/2010 |
| WO | 2010033578 A2 | 3/2010 |
| WO | 2010042831 A2 | 4/2010 |
| WO | 2010045617 A2 | 4/2010 |
| WO | 2010075459 | 7/2010 |
| WO | 2010/088288 A2 | 8/2010 |
| WO | 2010115016 A2 | 10/2010 |
| WO | 2010115154 A1 | 10/2010 |
| WO | 2010118016 A2 | 10/2010 |
| WO | 2010/127186 A1 | 11/2010 |
| WO | WO2011015944 A2 | 2/2011 |
| WO | 2011/023078 A1 | 3/2011 |
| WO | 2011/032078 A1 | 3/2011 |
| WO | 2011041485 A1 | 4/2011 |
| WO | 2011/051283 A1 | 5/2011 |
| WO | 2011057094 | 5/2011 |
| WO | WO2011057061 A1 | 5/2011 |
| WO | 2011/090556 A1 | 7/2011 |
| WO | 2011087760 | 7/2011 |
| WO | 2011102998 A2 | 8/2011 |
| WO | WO2011094646 A1 | 8/2011 |
| WO | 2011/118603 | 9/2011 |
| WO | 2011109440 A1 | 9/2011 |
| WO | WO2011118603 A1 | 9/2011 |
| WO | 2011/142836 A2 | 11/2011 |
| WO | 2011140433 A2 | 11/2011 |
| WO | 2011146632 A1 | 11/2011 |
| WO | 2012/019200 A2 | 2/2012 |
| WO | 2012/028746 A1 | 3/2012 |
| WO | 2012042374 A2 | 4/2012 |
| WO | 2012/058488 A1 | 5/2012 |
| WO | 2012-083189 A2 | 6/2012 |
| WO | 201283250 | 6/2012 |
| WO | 2012088456 A2 | 6/2012 |
| WO | 20120071621 | 6/2012 |
| WO | 2012092426 | 7/2012 |
| WO | 2012108920 A1 | 8/2012 |
| WO | WO2012122374 A2 | 9/2012 |
| WO | 2012/142531 A2 | 10/2012 |
| WO | 2007/149791 A2 | 12/2012 |
| WO | 2013030577 | 3/2013 |
| WO | 2013/045432 A1 | 4/2013 |
| WO | 2013/049892 A1 | 4/2013 |
| WO | 2013052557 A2 | 4/2013 |
| WO | 2013/078470 A2 | 5/2013 |
| WO | 2013/086464 A1 | 6/2013 |
| WO | 2013/123220 A1 | 8/2013 |
| WO | 2013/138510 A1 | 9/2013 |
| WO | 2013/138510 A9 | 9/2013 |
| WO | 20130130848 | 9/2013 |
| WO | 2013/159035 A2 | 10/2013 |
| WO | 2013/169339 A1 | 11/2013 |
| WO | 2013/177220 A1 | 11/2013 |
| WO | 2013/181651 A1 | 12/2013 |
| WO | 2013190441 A2 | 12/2013 |
| WO | 2014/004726 A1 | 1/2014 |
| WO | 2014/014497 A1 | 1/2014 |
| WO | 20140018080 | 1/2014 |
| WO | 2014026277 A1 | 2/2014 |
| WO | 2014/035986 A1 | 3/2014 |
| WO | 2014039556 A1 | 3/2014 |
| WO | WO2014099919 A2 | 6/2014 |
| WO | 2014/122288 A1 | 8/2014 |
| WO | 2014/1424290 A1 | 8/2014 |
| WO | 2014/145078 A1 | 9/2014 |
| WO | 2014/145232 A2 | 9/2014 |
| WO | 2014/149134 A2 | 9/2014 |
| WO | 2014/150300 A2 | 9/2014 |
| WO | 2014/151117 A1 | 9/2014 |
| WO | WO2014143989 A1 | 9/2014 |
| WO | WO2014194113 A2 | 12/2014 |
| WO | WO-2015006668 A1 * | 1/2015 ............. G06F 19/18 |

(56) References Cited

FOREIGN PATENT DOCUMENTS

| | | | |
|---|---|---|---|
| WO | WO2015035177 A1 | 3/2015 | |
| WO | 2015/048535 A1 | 4/2015 | |
| WO | 2015/070086 A1 | 5/2015 | |
| WO | WO2015069933 A1 | 5/2015 | |
| WO | 2015/100427 A1 | 7/2015 | |
| WO | WO-2015134552 A1 * | 9/2015 | ........... C12N 9/1252 |
| WO | WO2015138997 A1 | 9/2015 | |
| WO | 2015/148494 A1 | 10/2015 | |
| WO | 2015/164432 A1 | 10/2015 | |
| WO | WO2015169947 A1 | 11/2015 | |
| WO | WO2015178978 A2 | 11/2015 | |
| WO | 2016/009059 A1 | 1/2016 | |
| WO | 2016009224 A1 | 1/2016 | |
| WO | WO2016001411 A1 | 1/2016 | |
| WO | WO2016028316 A1 | 2/2016 | |
| WO | 2016/065295 A1 | 4/2016 | |
| WO | WO2016063122 A1 | 4/2016 | |
| WO | 2016/077313 A1 | 5/2016 | |
| WO | WO2016123698 A1 | 8/2016 | |
| WO | 2016/138080 A1 | 9/2016 | |
| WO | 2016/183106 A1 | 11/2016 | |
| WO | WO2016176662 A1 | 11/2016 | |
| WO | 2016/193490 A1 | 12/2016 | |
| WO | 2016192956 A1 | 12/2016 | |
| WO | WO2017011329 A1 | 1/2017 | |
| WO | 2017-045654 A1 | 3/2017 | |
| WO | 2017/058784 A1 | 4/2017 | |
| WO | WO2017091865 A1 | 6/2017 | |
| WO | 2017/176852 A1 | 10/2017 | |
| WO | 2017/181146 A1 | 10/2017 | |
| WO | 2017/181202 A2 | 10/2017 | |
| WO | 2017205540 A1 | 11/2017 | |
| WO | WO2017190106 A1 | 11/2017 | |
| WO | 2018/009723 A1 | 1/2018 | |
| WO | 2018/083467 A1 | 5/2018 | |
| WO | WO2018085597 A1 | 5/2018 | |
| WO | WO2018085603 A1 | 5/2018 | |
| WO | 2018/106798 A1 | 6/2018 | |
| WO | WO2018119422 A1 | 6/2018 | |
| WO | 2018/136562 A2 | 7/2018 | |
| WO | 2018/156418 A1 | 8/2018 | |
| WO | WO2018237078 A1 | 12/2018 | |
| WO | WO2018237081 A1 | 12/2018 | |
| WO | WO2019006561 A1 | 1/2019 | |
| WO | WO2019008408 A1 | 1/2019 | |
| WO | 2019/046817 A1 | 3/2019 | |
| WO | WO2019053243 A1 | 3/2019 | |
| WO | WO2019109053 A1 | 6/2019 | |
| WO | WO2019118926 A1 | 6/2019 | |
| WO | 2019/140298 A1 | 7/2019 | |
| WO | 2019/161244 A1 | 8/2019 | |
| WO | 2019/200228 A1 | 10/2019 | |
| WO | 2019/241349 A1 | 12/2019 | |
| WO | 2020/010255 A1 | 1/2020 | |
| WO | 2020/018522 A1 | 1/2020 | |
| WO | 2020/041449 A1 | 2/2020 | |
| WO | 2020/076957 A1 | 4/2020 | |
| WO | 2020/106987 A1 | 5/2020 | |
| WO | 2020104670 A1 | 5/2020 | |
| WO | 2020/131699 A2 | 6/2020 | |
| WO | WO2020131955 A1 | 6/2020 | |
| WO | 2020/214547 A1 | 10/2020 | |
| WO | WO2020206290 A1 | 10/2020 | |
| WO | 2020/247263 A1 | 12/2020 | |
| WO | 2021/055968 A1 | 3/2021 | |
| WO | 2007100911 A2 | 9/2021 | |
| WO | 2021/243045 A1 | 12/2021 | |
| WO | 2022/015676 A1 | 1/2022 | |
| WO | 2022182878 | 9/2022 | |
| WO | 2022197864 | 9/2022 | |
| WO | 2023014597 A1 | 2/2023 | |
| WO | 2023034090 A1 | 3/2023 | |
| WO | 2023133131 A1 | 7/2023 | |
| WO | 2011/130751 | 10/2023 | |
| WO | 2023/192224 A1 | 10/2023 | |
| WO | 2011/146942 A | 11/2023 | |
| WO | 2011/153254 A | 12/2023 | |

OTHER PUBLICATIONS

Gundry et al. Base-pair neutral homozygotes can be discriminated by calibrated high-resolution melting of small amplicons. Nucleic Acids Research, 2008; vol. 36, No. 10: 3401-3408. (Year: 2008).*
Forshew et al. Noninvasive Identification and Monitoring of Cancer Mutations by Targeted Deep Sequencing of Plasma DNA. Cancer Genomics, 2012; vol. 4; Issue 136; 136ra68: 1-12. (Year: 2012).*
Forshew et al. Noninvasive Identification and Monitoring of Cancer Mutations by Targeted Deep Sequencing of Plasma DNA. Cancer Genomics, 2012; vol. 4; Issue 136; 136ra68: 1-12. Supplemental materials. (Year: 2012).*
Hodgkinson et al. Tumorigenicity and genetic profiling of circulating tumor cells in small-cell lung cancer. Nature Medicine; 2014; 20 (8): 897-905. (Year: 2014).*
Scarpa et al. Molecular Typing of Lung Adenocarcinoma on Cytological Samples Using a Multigene Next Generation Sequencing Panel PLOS One; 2013; 8 (11): e80478, p. 1-6. (Year: 2013).*
Tseng et al. Thorac Oncol., 2015;10: 603-610. (Year: 2015).*
Tseng et al. Thorac Oncol., 2015;10: 603-610. Supplemental Tables. (Year: 2015).*
Tseng et al. Thorac Oncol., 2015;10: 603-610. Supplemental Figure. (Year: 2015).*
Lanman et al. PLOS ONE; 2015; DOI:10.1371/journal.pone. 0140712: p. 1-27. (Year: 2015).*
Park et al. JAMA Oncol. 2016;2(3):305-312 (Published online on Dec. 30, 2015). (Year: 2015).*
Kirkizlar et al, Translational Oncology; 2015; 8; 5: 407-416. (Year: 2015).*
Lee et al. Cancer Letters; 2006; 237: 89-94. (Year: 2006).*
Scarpa et al. PLOS ONE; 2013; 8; 11: e80478: p. 1-6. (Year: 2013).*
Zheng et al. International Journal of Oncology; 2013; 43: 755-764. (Year: 2015).*
Jamal-Hanjani et al. Annals of Oncology; Jan. 2016; 27: 862-867. (Year: 2016).*
Kim et al. Lung Cancer; 2013; 80; 249-255. (Year: 2013).*
Wood et al. Cancer Treatment Reviews; 2015; 41; 361-375. (Year: 2015).*
Wang, W.-P. et al., "Multiplex single nucleotide polymorphism genotyping by adapter ligation-mediated allele-specific amplification", Analytical Biochemistry, vol. 355, May 5, 2006, 240-248.
"Blast of AAAAAAAAATTTAAAAAAAAATTT(http://blast.ncbi.nlm.nih.gov/Blast.cgi, downloaded May 4, 2015)".
"CompetitivePCR Guide,", TaKaRa Biomedicals, Lit. # L0126 Rev. Aug. 1999, 9 pgs.
"Db SNP rs2056688 (http://www.ncbi.nlm.nih.gov/projects/SNP/snp_ref.cgi?rs=2056688, downloaded May 4, 2015".
"Declaration by Dr. Zimmerman of Oct. 30, 2014 filed in U.S. Appl. No. 14/044,434".
"European Application No. 014198110, European Search Report Mailed Apr. 28, 2015, 3 pages."
"Finishing the Euchromatic Sequence of the Human Genome", Nature vol. 431,(Oct. 21, 2004), 931-945.
"FixedMedium, dictionary definition, Academic Press Dictionary of Science andTechnology", Retrieved from the Internet: <URL:www.credoreference.com/entry/apdst/fixed_medium>, 1996, 1 pg.
"GeneticsHome Reference", http://ghr.nlm.nih.gov/handbook/genomicresearch/snp, Feb. 28, 2014, 1-2.
"Ion Ampli Seq Comprehensive Cancer Panel, product brochure, Life TechnologiesCorporation. Retrieved from the Internet", <URL:https://tools.lifetechnologies.com/content/sfs/brochures/Ion_Comp CancerPanel_Flyer.pdf>, 2012, 2 pgs.
"IonAmpliSeq Designer Provides Full Flexibility to Sequence Genes of Your Choice,product brochure, Life Technologies Corporation", Retrieved from the Internet<URL: http://tools.lifetechnologies.com/content/sfs/brochures/IonAmpliSeq_CustomPanels_AppNote_CO1.

(56) References Cited

OTHER PUBLICATIONS

"Merriam-Webster.com (http://www.merriam-webster.com/dictionary/universal, downloaded Jul. 23, 2014)".
"Multiplexing with RainDrop Digital PCR", RainDance Technologies, Application Note, 2013, 1-2.
"NucleicAcids, Linkers and Primers: Random Primers", New England BioLabs 1998/99Catalog, 1998, 121 and 284.
"PRIMER3, information sheet, Sourceforge.net. [retrieved on Nov. 12, 2012]. Retrieved from the Internet: <URL: http://primer3.sourceforge.net/>", 2009, 1 pg.
"www.fatsecret.com" (printed from internet Nov. 1, 2014).
PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).
The Bump (Panorama Test, attached, Jul. 1, 2013).
What to Expect (Weird Harmony results, attached, May 1, 2015).
Wikipedia (attached, available at https://en.wikipedia.org/wiki/Stimulant, accessed Mar. 14, 2016).
"Guideline related to genetic examination", Societies Related to Genetic Medicine, Japanese Society for Genetic Counseling, Japanese Society for Gene Diagnosis and Therapy, Japan Society of Obstetrics and Gynecology, 2003, 2-15.
"How Many Carbs in a Potato?, [Online]", Retrieved from the Internet: <http://www.newhealthguide.org/How-Many-Carbs-In-A-Potato.html>, Nov. 1, 2014, 3 pages.
"Random variable", In the Penguin Dictionary of Mathematics. Retrieved from http://www.credoreference.com/entry/penguinmath/random _ variable, 2008, 1 page.
Abbosh, C. et al., "Phylogenetic ctDNA analysis depicts early-stage lung cancer evolution", Nature, vol. 545, May 25, 2017, 446-451.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Agarwal, Ashwin. et al., "Commercial Landscape of Noninvasive Prenatal Testing in the United States", Prenatal Diagnosis, 33, 2013, 521-531.
Alaeddini, R. et al., "Forensic implications of genetic analyses from degraded DNA—A review", Forensic Science International: Genetics, vol. 4, 2010, 148-157.
Alberts, B. et al., "Chapter 20: Germ Cells and Fertilization", Molecular Biology of the Cell, Fourth Edition, 2002, 1127-1156.
Alberts, B. et al., "Chapter 4: DNA and Chromosomes", Molecular Biology of the Cell, Fourth Edition, 2002, 191-234.
Alkan, Can et al., "Personalized Copy Number and Segmental Duplication Maps Using Next-Generation Sequencing", Nature Genetics, 41, 10, 2009, 1061-1068.
Allaire, F R. , "Mate selection by selection index theory", Theoretical Applied Genetics, 57(6), 1980, 267-272.
Allawi, Hatim T. et al., "Thermodynamics of internal C•T Mismatches in DNA", Nucleic Acids Research, 26 (11), 1998, 2694-2701.
Anker, P. et al., "Detection of circulating tumour DNA in the blood (plasma/serum) of cancer patients", Cancer and Metastasis Reviews, vol. 18, 1999, 65-73.
Antonarakis, S. E. et al., "Chromosome 21 and Down Syndrome: From Genomics to Pathophysiology", Nature Reviews Genetics, vol. 5, Oct. 2004, 725-738.
Aoki, Yasuhiro , "Statistical and Probabilistic Bases of Forensic DNA Testing", The Journal of the Iwate Medical Association, 2002, vol. 54, p. 81-94.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Bada, Michael A. et al., "Computational Modeling of Structural Experimental Data", Methods in Enzymology, 317, 2000, 470-491.
Ballif, B. C. et al., "Detection of Low-Level Mosaicism by Array CGH in Routine Diagnostic Specimens", American Journal of Medical Genetics Part A, vol. 140A, 2006, 2757-2767.
Beaumont, Mark A et al., "The Bayesian Revolution in Genetics", Nature Reviews Genetics, 5, 2004, 251-261.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bentley, David R et al., "Accurate Whole Human Genome Sequencing Using Reversible Terminator Chemistry", Nature, 456, 6, 2008, 53-59.
Bermudez, M. et al., "Single-cell sequencing and mini-sequencing for preimplantation genetic diagnosis", Prenatal Diagnosis, 23, 2003, 669-677.
Beroud, C. et al., "Prenatal diagnosis of spinal muscular atrophy by genetic analysis of circulating fetal cells", The Lancet, vol. 361, Mar. 22, 2003, 1013-1014.
Bevinetto, Gina , Bevinetto (5 Foods All Pregnant Women Need, American Baby, available at http://www.parents.com/pregnancy/mybody/nutrition/5greatpregnancyfoods/, Apr. 15, 2008).
Bianchi, D W. et al., "Fetal gender and aneuploidy detection using fetal cells maternal blood: analysis of NIFTY I data", Prenat Diagn 2002; 22, 2002, 609-615.
Bianchi, D. W. , "Circulating Fetal DNA: Its Origin and Diagnostic Potential—A Review", Placenta, vol. 25, Supplemental A, May 2004, S93-S101.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Bianchi, D. W. , "Review: Fetal Cells in the Maternal Circulation: Feasibility for Prenatal Diagnosis", British Journal of Haematology, vol. 105, 1999, 574-583.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.
Bisignano, et al., "PGD and Aneuploidy Screening for 24 Chromosomes: Advantages and Disadvantages of Competing Platforms", Reproductive BioMedicine Online, 23, 2011, 677-685.
Bodenreider, O. , "The Unified Medical Language System (UMLS): Integrating Biomedical Terminology", Nucleic Acids Research, 32, (Database issue), 2004, D267-D270.
Breithaupt, Holger , "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.
Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.
Butler, J. et al., "The Development of Reduced Size STR Amplicons as Tools for Analysis of Degraded DNA", Journal of Forensic Sciences, vol. 48, No. 5, 2003, 1054-1064.

(56) References Cited

OTHER PUBLICATIONS

Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.

Cairns, Paul et al., "Homozygous Deletions of 9p21 in Primary Human Bladder Tumors Detected by Comparative Multiplex Polymerase Chain Reaction", Cancer Research, 54, 1994, 1422-1424.

Caliendo, Angela , "Multiplex PCR and Emerging Technologies for the Detection of Respiratory Pathogens", Clinical Infectious Diseases, 52(4), 2011, S326-S330.

Cansar, , "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.

Carnevale, Alessandra et al., "Attitudes of Mexican Geneticists Towards Prenatal Diagnosis and Selective Abortion", American Journal of Medical Genetics, 75, 1998, 426-431.

Carvalho, B. et al., "Exploration, normalization, and genotype calls of high-density oligonucleotide SNP array data", Biostatistics, vol. 8, No. 2, 2007, 485-499.

Casbon, J. A. et al., "A method for counting PCR template molecules with application to next-generation sequencing", Nucleic Acids Research, vol. 39, No. 12, Apr. 13, 2011, 1-8.

Chakraborty, R. et al., "Paternity Exclusion by DNA Markers: Effects of Paternal Mutations", Journal of Forensic Sciences, vol. 41, No. 4, Jul. 1996, 671-677.

Chan, K.C. et al., "Size Distributions of Maternal and Fetal DNA in Maternal Plasma", Clinical Chemistry, vol. 50, No. 1, 2004, 88-92.

Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.

Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.

Chen, X. Q. et al., "Microsatellite alterations in plasma DNA of small cell lung cancer patients", Nature Medicine, vol. 2, No. 9, Sep. 1996, 1033-1035.

Chetty, Shilpa et al., "Uptake of Noninvasive Prenatal Testing (NIPT) in Women Following Positive Aneuploidy Screening", Prenatal Diagnosis,33, 2013, 542-546.

Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.

Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.

Chiu, Rossa W. et al., "Effects of Blood-Processing Protocols on Fetal and Total DNA Quantification in Maternal Plasma", Clinical Chemistry, 47(9), 2001, 1607-1613.

Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.

Chiu, Rossa W.K. et al., "Non-Invasive Prenatal Diagnosis by Single Molecule Counting Technologies", Trends in Genetics, 25 (7), 2009, 324-331.

Chiu, Rossa W.K. et al., "Noninvasive Prenatal Diagnosis of Fetal Chromosomal Aneuploidy by Massively Parallel Genomic Sequencing of DNA in Maternal Plasma (with Supporting Information)", PNAS, vol. 105, No. 51, 2008, 20458-20463.

Choi, M. et al., "Genetic diagnosis by whole exome capture and massively parallel DNA sequencing", PNAS, vol. 106, No. 45, Nov. 10, 2009, 19096-19101.

Chu, T. et al., "Statistical Considerations for Digital Approaches to Non-Invasive Fetal Genotyping", Bioinformatics (Advance Access publication), 26 (22), 2010, 2863-2866.

Chu, Tianjiao et al., "Statistical Model for Whole Genome Sequencing and its Application to Minimally Invasive Diagnosis of Fetal Genetic Disease", Bioinformatics, 25(10), 2009, 1244-1250.

Chu, Tianjiao et al., "A Novel Approach Toward the Challenge of Accurately Quantifying Fetal DNA in Maternal Plasma", Prenatal Diagnosis,30, 2010, 1226-1229.

Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.

Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.

Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.

Coombes, R. C. , "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.

Cossu, Gianfranco et al., "Rh D/d Genotyping by Quantitative Polymerase Chain Reaction and Capillary Zone Electrophoresis", Electrophoresis, 17, 1996, 1911-1915.

Coyle, J. F. et al., "Standards for detailed clinical models as the basis for medical data exchange and decision support", International Journal of Medical Informatics, 69(2-3), 2003, 157-174.

Craig, D. W. et al., "Identification of genetic variants using barcoded multiplexed sequencing", Nature Methods, vol. 5, Oct. 2008, 887-893.

Cross, Jillian et al., "Resolution of trisomic mosaicism in prenatal diagnosis: estimated performance of a 50K SNP microarray", Prenat Diagn 2007; 27, 2007, 1197-1204.

D'Aquila, Richard et al., "Maximizing sensitivity and specificity of PCR by pre-amplification heating", Nucleic Acids Research, 19(13), 1991, p. 3749.

Daruwala, Raoul-Sam et al., "A Versatile Statistical Analysis Algorithm to Detect Genome Copy Number Variation", PNAS, 101(46), 2004, 16292-16297.

De Bruin, E. et al., "Spatial and temporal diversity in genomic instability processes defines lung cancer evolution", Science, vol. 346, No. 6206, Oct. 10, 2014, 251-256.

De Vries, et al., "Diagnostic genome profiling in mental retardation", Am J Hum Genet, 77, published online Aug. 30, 2005, 2005, 606-616.

Deangelis, M. et al., "Solid-phase Reversible Immobilization for the Isolation of PCR Products", Nucleic Acids Research, 23 (22), 1995, 4742-4743.

Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.

Deutsch, S. et al., "Detection of aneuploidies by paralogous sequence quantification", J Med Genet, vol. 41, 2004, 908-915.

Devaney, S. et al., "Noninvasive Fetal Sex Determination Using Cell-Free Fetal DNA: A Systematic Review and Meta-analysis", JAMA, 306 (6), 2011, 627-636.

Dhallan, et al., "Methods to Increase the Percentage of Free Fetal DNA Recovered from the Maternal Circulation", JAMA, 291(9), 2004, 1114-1119.

Dhallan, Ravinder et al., "A non-invasive test for prenatal diagnosis based on fetal DNA present in maternal blood: a preliminary study", The Lancet, 369, 2007, 474-481.

Dieffenbach, C W. et al., "General concepts for PCR primer design", Genome Research. PCR methods and Applications vol. 3, 1993, S30-S37.

Dietmaier, W. et al., "Multiple Mutation Analyses in Single Tumor Cells with Improved Whole Genome Amplification", American Journal of Pathology, vol. 154, No. 1, Jan. 1999, 83-95.

Ding, C et al., "Direct molecular haplotyping of long-range genomic DNA with M1-PCR", PNAS 100(13), 2003, 7449-7453.

Dodge, Y. , "Bayes' Theorem", The Concise Encyclopedia of Statistics, 2008, 30-31.

(56) References Cited

OTHER PUBLICATIONS

Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na—K+—Cl-Cotransporter (NKCC1) in Asthmatic Subjects", Genome Res., 11, 2001, 1473-1483.
Donaghue, C. et al., "Detection of mosaicism for primary trisomies in prenatal samples by QF-PCR and karyotype analysis", Prenatal Diagnosis, vol. 25, 2005, 65-72.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H , "Mild Course of Fetal Rh D Haemolytic Disease due to Maternal Alloimmunisation to Paternal HLA Class I and II Antigens", Vox Sang, 68, 1995, 243-247.
Ellison, Aaron M. , "Bayesian Inference in Ecology", Ecology Letters, vol. 7, 2004, 509-520.
Ellonen, P. et al., "Development of SNP Microarray for Supplementary Paternity Testing", International Congress Series, 1261, 2004, 12-14.
EP06838311.6, , "European Communication and Extended European Search Report", mailed Dec. 30, 2008, 8 pgs.
EP08742125.1, , "European Communication pursuant to Article 94(3) EPC and Examination Report", mailed Feb. 12, 2010, 5 pgs.
Everitt, B. S. , "Medical Statistics From A to Z", 2003, 3 pages.
Fan, et al., "Whole-genome molecular haplotyping of single cells", Nature Biotechnology, vol. 29, No. 1, Jan. 1, 2011, 51-57.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Fan, Jian-Bing et al., "Highly Parallel Genomic Assay", Nature Reviews, 7, 2006, 632-644.
Fazio, Gennaro et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Ford, E. et al., "A method for generating highly multiplexed ChIP-seq libraries", BMC Research Notes, vol. 7, No. 312, May 22, 2014, 1-5.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, Mackenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Garcia-Murillas, I. et al., "Mutation tracking in circulating tumor DNA predicts relapse in early breast cancer", Science Translational Medicine, vol. 7, No. 302, Aug. 26, 2015, 1-2.
Gardina, P. et al., "Ploidy Status and Copy Number Aberrations in Primary Glioblastomas Defined by Integrated Analysis of Allelic Ratios, Signal Ratios and Loss of Heterozygosity Using 500K Snp Mapping Arrays", BMC Genomics, 9 (489), (doi:10.1186/1471-2164-9-489), 2008, 16 pgs.
Geiss, G. K. et al., "Direct multiplexed measurement of gene expression with color-coded probe pairs", Nature Biotechnology, vol. 26, No. 3, Feb. 17, 2008, 317-325.
Ghanta, Sujana et al., "Non-Invasive Prenatal Detection of Trisomy 21 Using Tandem Single Nucleotide Polymorphisms", PLoS ONE, 5 (10), 2010, 10 pgs.
Gjertson, David W. et al., "Assessing Probability of Paternity and the Product Rule in DNA Systems", Genetica, 96, 1995, 89-98.
Greenwalt, T. et al., "The Quantification of Fetomaternal Hemorrhage by an Enzyme-Linked Antibody Test with Glutaraldehyde Fixation", Vox Sang, 63, 1992, 268-271.
Guerra, J. , "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Gunderson, K. L. et al., "A genome-wide scalable SNP genotyping assay using microarray technology", Nature Genetics, vol. 37, No. 5, May 2005, 549-554.
Hall, M. , "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Han, S-W et al., "Predictive and Prognostic Impact of Epidermal Growth Factor Receptor Mutation in Non-Small-Cell Lung Cancer

(56) References Cited

OTHER PUBLICATIONS

Patients Treated With Gefitinib", Journal of Clinical Oncology, vol. 23, No. 11, Apr. 10, 2005, 2493-2501.

Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.

Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.

Hardenbol, P. , "Multiplexed Genotyping With Sequence-Tagged Molecular Inversion Probes", Nature Biotechnology, 21 (6), 2003, 673-678.

Hardenbol, Paul et al., "Highly multiplexed molecular inversion probe genotyping: Over 10,000 targeted SNPs genotyped in a singled tube assay", Genome Research, 15, 2005, 269-275.

Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.

Harper, J. C. et al., "Recent Advances and Future Developments in PGD", Prenatal Diagnosis, 19, 1999, 1193-1199.

Harton, G.L. et al., "Preimplantation Genetic Testing for Marfan Syndrome", Molecular Human Reproduction, 2 (9), 1996, 713-715.

Hartwell, L. H. et al., "Chapter 11: The Direct Detection of Genotype Distinguishes Individual Genomes", Genetics: From Genes to Genomes, Second Edition, 2004, 371-414.

Hartwell, L. H. et al., "Chapter 13: Chromosomal Rearrangements and Changes in Chromosome Number Reshape Eukaryotic Genomes", Genetics: From Genes to Genomes, Second Edition, 2004, 441-486.

Hattori, M. et al., "The DNA sequence of human chromosome 21", Nature, vol. 405, May 18, 2000, 311-319.

Hawkins, T. et al., "Whole genome amplification—applications and advances", Current Opinion in Biotechnology, 13, 2002, 65-67.

Hayden, et al., "Multiplex-Ready PCR: A new method for multiplexed SSR and SNP genotyping", BMC Genomics 2008, 9(80), 1-12.

Hellani, A. et al., "Clinical Application of Multiple Displacement Amplification in Preimplantation Genetic Diagnosis", Reproductive BioMedicine Online, 10 (3), 2005, 376-380.

Hellani, Ali et al., "Multiple displacement amplification on single cell and possible PGD applications", Molecular Human Reproduction, 10(11), 2004, 847-852.

Hojsgaard, S. et al., "BIFROST—Block recursive models induced from relevant knowledge, observations, and statistical techniques", Computational Statistics & Data Analysis, 19(2), 1995, 155-175.

Hollas, B. et al., "A stochastic approach to count RN A molecules using DNA sequencing methods", Lecture Notes in Computer Science, vol. 2812, 2003, 55-62.

Holleley, et al., "Multiplex Manager 1.0: a Cross-Platform Computer Program that Plans and Optimizes Multiplex PCR", BioTechniques46:511-517 (Jun. 2009), 511-517.

Hollox, E. et al., "Extensive Normal Copy Number Variation of a β-Defensin Antimicrobial-Gene Cluster", Am. J. Hum. Genet., 73, 2003, 591-600.

Homer, et al., "Resolving Individuals Contributing Trace Amounts of DNA to Highly Complex Mixtures Using High-Density SNP Genotyping Microarrays", PLOS Genetics, 4(8), 2008, 9 pgs.

Hoogendoorn, Bastiaan et al., "Genotyping Single Nucleotide Polymorphisms by Primer Extension and High Performance Liquid Chromatography", Hum Genet, 104, 1999, 89-93.

Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.

Hospital, F. et al., "A General Algorithm to Compute Multilocus Genotype Frequencies Under Various Mating Systems" vol. 12, No. 6, Jan. 1, 1996 (Jan. 1, 1996), pp. 455-462.

Howie, et al., "Fast and accurate genotype imputation in genome-wide association studies through pre-phasing", Nature Genetics, vol. 44, No. 8, Jul. 22, 2012, 955-959.

Hu, Dong Gui et al., "Aneuploidy Detection in Single Cells Using DNA Array-Based Comparative Genomic Hybridization", Molecular Human Reproduction, 10(4), 2004, 283-289.

Hug, H. et al., "Measurement of the number of molecules of a single mRNA species in a complex mRNA preparation", J. Theor. Biol., vol. 221, 2003, 615-624.

Hultin, E. et al., "Competitive enzymatic reaction to control allele-specific extensions", Nucleic Acids Research, vol. 33, No. 5, Mar. 14, 2005, 1-10.

Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.

Illumina, , "Patent Owner Illumina's Preliminary Response to Petition", Oct. 17, 2018, 75 pgs.

Illumina, , "Petition for Inter Partes Review of U.S. Pat. No. 8,682,592", Jun. 13, 2019, 91 pages.

Illumina, , "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.

Illumina, , "Plaintiff/Counterclaim-Defendant Illumina, Inc.'S Patent L.R. 3-3 Contentions for U.S. Patent Preliminary Invalidity Contentions for U.S. Pat. No. 8,682,592", Oct. 9, 2018, 81 pages.

Illumina Catalog, , "Paired-End Sample Preparation Guide, Illumina Catalog# PE-930-1 001, Part# 1005063 Rev. E", 2011, 1-40.

Illumina, Inc., , "Declaration of David Peters, Ph.D. in Support of Petition for Inter Partes Review of U.S. Pat. No. 8,682,592", Jun. 13, 2019, 136 pages.

*Illumina, Inc. V. Natera, Inc.*, , "Order Re: Claim Construction", Jan. 30, 2019, 16 pgs.

Ishii, et al., "Optimization of Annealing Temperature to Reduce Bias Caused by a Primer Mismatch in Multitemplate PCR", Applied and Environmental Microbiology, Aug. 2001, p. 3753-3755.

Jabara, C. B. et al., "Accurate sampling and deep sequencing of the HIV-1 protease gene using a Primer ID", PNAS, vol. 108, No. 50, Dec. 13, 2011, 20166-20171.

Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.

Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.

Jamal-Hanjani, M. et al., "Tracking Genomic Cancer Evolution for Precision Medicine: The Lung TRACERx Study", PLOS Biology, vol. 12, No. 7, Jul. 2014, 1-7.

Jamal-Hanjani, M. et al., "Tracking the Evolution of Non-Small-Cell Lung Cancer", The New England Journal of Medicine, vol. 376, No. 22, Jun. 1, 2017, 2109-2121.

Jarvie, T. , "Next generation sequencing technologies", Drug Discovery Today: Technologies, vol. 2, No. 3, 2005, 255-260.

Jenkins, S. et al., "High-throughput SNP genotyping", Comparative and Functional Genomics, vol. 3, Dec. 5, 2001, 57-66.

Johnson, D.S. et al., "Comprehensive Analysis of Karyotypic Mosaicism Between Trophectoderm and Inner Cell Mass", Molecular Human Reproduction, 16(12), 2010, 944-949.

Johnson D.S, et al., "Preclinical Validation of a Microarray Method for Full Molecular Karyotyping of Blastomeres in a 24-h Protocol", Human Reproduction, 25 (4), 2010, 1066-1075.

Kamat, A. A. et al., "Quantification of total plasma cell-free DNA in ovarian cancer using real-time PCR", Ann N Y Acad Sci., vol. 1075, Sep. 2006, 230-234.

Kaplinski, Lauris et al., "MultiPLX: Automatic Grouping and Evaluation of PCR Primers", Bioinformatics, 21(8), 2005, 1701-1702.

Kazakov, V.I. et al., "Extracellular DNA in the Blood of Pregnant Women", Tsitologia, vol. 37, No. 3, 1995, 1-8.

Kijak, G. et al., "Discrepant Results in the Interpretation of HIV-1 Drug-Resistance Genotypic Data Among Widely Used Algorithms", HIV Medicine, 4, 2003, 72-78.

(56) References Cited

OTHER PUBLICATIONS

Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Kinde, I. et al., "Detection and quantification of rare mutations with massively parallel sequencing", PNAS, vol. 108, No. 23, Jun. 7, 2011, 9530-9535.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Kivioja, T. et al., "Counting absolute numbers of molecules using unique molecular identifiers", Nature Methods, Advance Online Publication, Nov. 20, 2011, 1-5.
Konfortov, Bernard A. et al., "An Efficient Method for Multi-Locus Molecular Haplotyping", Nucleic Acids Research, 35(1), e6, 2007, 8 pgs.
Krjutskov, K. et al., "Development of a single tube 640-plex genotyping method for detection of nucleic acid variations on microarrays", Nucleic Acids Research, vol. 36, No. 12, May 23, 2008, 7 pages.
Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Kunishima, S. et al., "First description of somatic mosaicism in MYH9 disorders", British Journal of Haematology, vol. 128, 2005, 360-365.
Kwok, P. Y. , "High-throughput genotyping assay approaches", Pharmacogenomics, vol. 1, No. 1, 2000, 1-5.
Lambert-Messerlian, G. et al., "Adjustment of Serum Markers in First Trimester Screening", Journal of Medical Screening, 16 (2), 2009, 102-103.
Lander, E. S. et al., "Initial sequencing and analysis of the human genome", Nature, vol. 409, Feb. 15, 2001, 860-921.
Lathi, Ruth B. et al., "Informatics Enhanced SNP Microarray Analysis of 30 Miscarriage Samples Compared to Routine Cytogenetics", PLoS ONE, 7(3), 2012, 5 pgs.
Leary, R. J. et al., "Development of Personalized Tumor Biomarkers Using Massively Parallel Sequencing", Science Translational Medicine, vol. 2, No. 20, Feb. 24, 2010, 1-8.
Leary, Rebecca J et al., "Detection of Chromosomal Alterations in the Circulation of Cancer Patients with Whole-Genome Sequencing", Science Translational Medicine, 4, 162, 2012, 12.
Levsky, J. M. et al., "Fluorescence in situ hybridization: past, present and future", Journal of Cell Science, vol. 116, No. 14, 2003, 2833-2838.
Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.
Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphisms", Clinical Chemistry, 50, 6, 2004, 1002-1011.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.

Liao, J. et al., "An Alternative Linker-Mediated Polymerase Chain Reaction Method Using a Dideoxynucleotide to Reduce Amplification Background", Analytical Biochemistry 253, 137-139 (1997).
Liew, Michael et al., "Genotyping of Single-Nucleotide Polymorphisms", Clinical Chemistry, 50(7), 2004, 1156-1164.
Lindroos, Katatina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Aug. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, , "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet,2, 8676, 1989, 1363-1365.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences, 731, 1994, 204-213.
Lo, et al., "Two-way cell traffic between mother and fetus: biologic and clinical implications", Blood, 88(11), Dec. 1, 1996, 4390-4395.
Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.
Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Y.M. Dennis et al., "Maternal Plasma DNA Sequencing Reveals the Genome-Wide Genetic and Mutational Profile of the Fetus", Science Translational Medicine,, 2 (61), 2010, 13.
Lo, Y.M. Dennis et al., "Plasma placental RNA allelic ratio permits noninvasive prenatal chromosomal aneuploidy detection", Nature Medicine, 13 (2), 2007, 218-223.
Lo, Y.M. Dennis et al., "Presence of Fetal DNA in Maternal Plasma and Serum", The Lancet, 350, 1997, 485-487.
Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.
Lo, Y-M D. , "Non-invasive prenatal diagnosis using fetal cells in maternal blood", J. Clin. Pathol., vol. 47, 1994, 1060-1065.
Lo, Y-M.D et al., "Detection of Single-Copy Fetal DNA Sequence from Maternal Blood", The Lancet, 335, 1990, 1463-1464.
Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M.D. et al., "Detection of Fetal RhD Sequence from Peripheral Blood of Sensitized RhD-Negative Pregnant Women", British Journal of Haematology, 87, 1994, 658-660.
Lo, Y-M.D. et al., "Prenatal Determination of Fetal RhD Status by Analysis of Peripheral Blood of Rhesus Negative Mothers", The Lancet, 341, 1993, 1147-1148.
Lu, I. et al., "Establishment of a system based on universal multiplex-PCR for screening genetically modified crops", Anal. Bioanal. Chem, vol. 396, Oct. 24, 2009, 2055-2064.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.

(56) References Cited

OTHER PUBLICATIONS

Ma, Xiaotu et al., "Rise and fall of subclones from diagnosis to relapse in pediatric B-acute lymphoblastic leukaemia", Nature Communications, vol. 6, Mar. 19, 2015, 1-12.

Magbanua, M. J et al., "Abstract PD2-01: Personalized serial circulating tumor DNA (ctDNA) analysis in high-risk early stage breast cancer patients to monitor and predict response to neoadjuvant therapy and outcome in the I-SPY 2 TRIAL", Cancer Research, vol. 79, No. 4 Supplement, Feb. 15, 2019.

Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.

Maniatis, T. et al., "In: Molecular Cloning: A Laboratory Manual", Cold Spring Harbor Laboratory, New York, Thirteenth Printing, 1986, 458-459.

Mansfield, Elaine S, "Diagnosis of Down Syndrome and Other Aneuploidies Using Quantitative Polymerase Chain Reaction and Small Tandem Repeat Polymorphisms", Human Molecular Genetics, 2, 1, 1993, 43-50.

Mardis, E. R., "The impact of next-generation sequencing technology on genetics", Trends in Genetics, vol. 24, No. 3, Feb. 11, 2008, 133-141.

Margulies, M. et al., "Genome sequencing in microfabricated high-density picolitre reactors", Nature, vol. 437, Sep. 15, 2005, 376-380.

Margulies, M. et al., "Genome sequencing in microfabricated high-density picolitre reactors plus Supplemental Methods", Nature, vol. 437, Sep. 15, 2005, 40 pgs.

Markoulatos, P. et al., "Multiplex Polymerase Chain Reaction: A Practical Approach", Journal of Clinical Laboratory Analysis, vol. 16, 2002, 47-51.

May, Robert M., "How Many Species Are There on Earth?", Science, 241, 16 Sep. 1988, 1441-1449.

Mcbride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.

Mccloskey, M. L. et al., "Encoding PCR Products with Batch-stamps and Barcodes", Biochem Genet., vol. 45, Oct. 23, 2007, 761-767.

Mccray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.

Mcdonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.

Mennuti, M. et al., "Is It Time to Sound an Alarm About False-Positive Cell-Free DNA Testing for Fetal Aneuploidy?", American Journal of Obstetrics, 2013, 5 pgs.

Merriam-Webster, , "Medical Definition of Stimulant", http://www.merriam-webster.com/medical/stimulant, Mar. 14, 2016, 7 pages.

Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.

Mertes, F. et al., "Targeted enrichment of genomic DNA regions for next-generation sequencing", Briefings in Functional Genomics, vol. 10, No. 6, Nov. 26, 2011, 374-386.

Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.

Miller, Robert R., "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.

Miner, B. E. et al., "Molecular barcodes detect redundancy and contamination in hairpin-bisulfite PCR", Nucleic Acids Research, vol. 32, No. 17, Sep. 30, 2004, 1-4.

Minkoff, E. et al., "Stem Cells, Cell Division, and Cancer", Biology Today Third Edition, Chapter 12, 2004, 10 pages.

Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.

Munne, S. et al., "Chromosome abnormalities in human embryos", Human Reproduction update, 4 (6), 842-855.

Munne, S. et al., "Chromosome Abnormalities in Human Embryos", Textbook of Assisted Reproductive Techniques, 2004, pp. 355-377.

Munne, S. et al., "Improved implantation after preimplantation genetic diagnosis of aneuploidy", Reproductive BioMedicine Online, vol. 7., No. 1., May 15, 2003, 91-97.

Murtaza, M. et al., "Non-Invasive Analysis of Acquired Resistance to Cancer Therapy by Sequencing of Plasma DNA", Nature (doi:10.1038/nature12065), 2013, 6 pgs.

Muse, Spencer V., "Examining rates and patterns of nucleotide substitution in plants", Plant Molecular Biology 42: 25-43, 2000.

Myers, Chad L. et al., "Accurate Detection of Aneuploidies in Array CGH and Gene Expression Microarray Data", Bioinformatics, 20(18), 2004, 3533-3543.

Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.

Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.

Natera, Inc., , "Declaration of Sandra L. Haberny", May 16, 2019, 3 pages.

Natera, Inc., , "Defendant Natera, Inc.'s Invalidity Contentions Under Patent L.R. 3-3; Document Production Accompanying Invalidity Contentions Under Patent L.R. 3-4", Aug. 20, 2018, 17 pages.

Natera, Inc., , "Exhibit 8 Ehrich Invalidity Chart", Aug. 20, 2018, 16 pages.

Natera, Inc., , "Exhibits A-H to Haberny Declaration", May 16, 2019, 192 pages.

Natera, Inc., , "Motion to Dismiss", May 16, 2019, 2 pages.

Natera, Inc., , "Natera Inc.'s First Amended Answer, Affirmative Defenses and Counterclaims", Aug. 16, 2018, 28 pages.

Natera, Inc., , "Natera, Inc.'s Supplemental Objections and Response to Plaintiff Illumina, Inc.'s Interrogatory No. 8", Mar. 20, 2019, 29 pages.

Natera, Inc., , "Opening Brief in Support of Motion to Dismiss", May 16, 2019, 26 pages.

Natera, Inc., , "Petitioner Reply Per Board Order of Nov. 2, 2018 (Paper No. 10)", Nov. 9, 2018, 8 pgs.

Newman, A. M. et al., "Integrated digital error suppression for improved detection of circulating tumor DNA", Nature Biotechnology, vol. 34, No. 5, May 2016, 547-555.

Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.

Nguyen-Dumont, T., "A high-plex PCR approach for massively parallel sequencing", BioTechniques, vol. 55, No. 2, Aug. 2013, 69-74.

Nicolaides, K. et al., "Noninvasive Prenatal Testing for Fetal Trisomies in a Routinely Screened First-Trimester Population", American Journal of Obstetrics (article in press), 207, 2012, 1.e1-1.e6.

Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.

Nicolaides, Kypros H. et al., "Prenatal Detection of Fetal Triploidy from Cell-Free DNA Testing in Maternal Blood", Fetal Diagnosis and Therapy, 2013, 1-6.

(56) References Cited

OTHER PUBLICATIONS

Nygren, et al., "Quantification of Fetal DNA by Use of Methylation-Based DNA Discrimination", Clinical Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
O'Malley, R et al., "An adapter ligation-mediated PCR method for high-throughput mapping of T-DNA inserts in the *Arabidopsis* genome", Nat. Protoc., 2, 2007, 2910-2917.
Orozco A.F., et al., "Placental Release of Distinct DNA-Associated Micro-Particles into Maternal Circulation: Reflective of Gestation Time and Preeclampsia", Placenta,30, 2009, 891-897.
Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J et al., "Genome coverage and sequence fidelity of Φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Palomaki, G. E. et al., "DNA sequencing of maternal plasma to detect Down syndrome: An international clinical validation study", Genetics In Medicine, vol. 13, No. 1, Nov. 2011, 913-920.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Papadopoulou, E. et al., "Cell-Free DNA and RNA in Plasma as a New Molecular Marker for Prostate Cancer", Oncology Research, vol. 14, 2004, 439-445.
Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.
Pastinen, T. et al., "Minisequencing: A Specific Tool for DNA Analysis and Diagnostics on Oligonucleotide Arrays", Genome Research, vol. 7, 1997, 606-614.
Pathak, A. et al., "Circulating Cell-Free DNA in Plasma/Serum of Lung Cancer Patients as a Potential Screening and Prognostic Tool", Clinical Chemistry, 52, 2006, 1833-1842.
PCT/US2006/045281, , "International Preliminary Report on Patentability", mailed May 27, 2008, 1 pg.
PCT/US2006/045281, , "International Search Report and Written Opinion", mailed Sep. 28, 2007, 7 pgs.
PCT/US2008/003547, , "International Search Report", mailed Apr. 15, 2009, 5 pgs.
PCT/US2009/034506, , "International Search Report", mailed Jul. 8, 2009, 2 pgs.
PCT/US2009/045335, , "International Search Report", mailed Jul. 27, 2009, 1 pg.
PCT/US2009/052730, , "International Search Report", mailed Sep. 28, 2009, 1 pg.
PCT/US2010/050824, , "International Search Report", mailed Nov. 15, 2010, 2 pgs.
PCT/US2011/037018, , "International Search Report", mailed Sep. 27, 2011, 2 pgs.
PCT/US2011/061506, , "International Search Report", mailed Mar. 16, 2012, 1 pgs.
PCT/US2011/066938, , "International Search Report", mailed Jun. 20, 2012, 1 pg.
PCT/US2012066339, , "International Search Report", mailed Mar. 5, 2013, 1 pg.
PCT/US2013/028378, , "International Search Report and Written Opinion", mailed May 28, 2013, 11 pgs.
PCT/US2013/57924, , "International Search Report and Written Opinion", mailed Feb. 18, 2014, 8 pgs.
PCT/US2014/051926, , "International Search Report and Written Opinion", Dec. 9, 2014, 3 pgs.
Pearson, K. , "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pena, Sergio D.J et al., "Paternity Testing in the DNA Era", Trends In Genetics, 10, 6, 1994, 204-209.
Pergament, E. et al., "Single-Nucleotide Polymorphism-Based Noninvasive Prenatal Screening in a High-Risk and Low-Risk Cohort", Obstetrics & Gynecology, vol. 124, No. 2, Part 1, Aug. 2014, 210-218 + Appendices.
Perkel, Jeffrey M. , "Overcoming the Challenges of Multiplex PCR", Biocompare Editorial Article, Null, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, D. , "List of Materials Considered By David Peters, Ph.D.", Jun. 13, 2019, 2 pages.
Peters, David P. et al., "Noninvasive Prenatal Diagnosis of a Fetal Microdeletion Syndrome", New England Journal of Medicine, 365(19), 2011, 1847-1848.
Pfaffl, Michael W. , "Relative Expression Software Tool (REST ©) for Group-Wise Comparison and Statistical Analysis of Relative Expression Results in real-Time PCR", Nucleic Acids Research, 30(9), 2002, 10 pgs.
Phillips, C. et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics, 1(5), 2008, 1-15.
Poirier, K. et al., "Maternal mosaicism for mutations in the ARX gene in a family with X linked mental retardation", Human Genetics, vol. 118, Aug. 3, 2005, 45-48.
Poon, L. L. et al., "Differential DNA Methylation between Fetus and Mother as a Strategy for Detecting Fetal DNA in Maternal Plasma", Clinical Chemistry, vol. 48, No. 1, 2002, 35-41.
Popova, T. et al., "Genome Alteration Print (GAP): a tool to visualize and mine complex cancer genomic profiles obtained by SNP arrays", Genome Biology, vol. 10, R128, Nov. 11, 2009, 1-14.
Porreca, Gregory J et al., "Multiplex Amplification of Large Sets of Human Exons", Nature Methods, 4, (advance online publication), 2007, 6.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Quinn, G. P. et al., "Experimental Design and Data Analysis for Biologists", Graphical Exploration of Data, 2002, 64-67.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterility, vol. 97, No. 2, Feb. 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.

(56) References Cited

OTHER PUBLICATIONS

Rachlin, J. et al., "Computational tradeoffs in multiplex PCR assay design for SNP genotyping", BMC Genomics, vol. 6, No. 102, Jul. 25, 2005, 11 pages.
Ragoussis, J., "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Reinert, T. et al., "Analysis of circulating tumour DNA to monitor disease burden following colorectal cancer surgery", Gut, vol. 65, 2016, 625-634.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online]. Retrieved from Internet :<http://www.youandyourfamily.com/article.php?story=Eating+by+Trimester>, 2014, 3.
Riley, D. E., "DNA Testing: An Introduction for Non-Scientists An Illustrated Explanation", Scientific Testimony: An Online Journal, http://www.scientific.org/tutorials/articles/riley/riley.html, Apr. 6, 2005, 22 pages.
Riva, F., "Patient-Specific Circulating Tumor DNA Detection during Neoadjuvant Chemotherapy in Triple-Negative Breast Cancer", Clinical Chemistry, vol. 63, No. 3, 2017, 691-699.
Rogaeva, E. et al., "The Solved and Unsolved Mysteries of the Genetics of Early-Onset Alzheimer's Disease", NeuroMolecular Medicine, vol. 2, 2002, 1-10.
Roper, Stephen M. et al., "Forensic Aspects of DNA-Based Human Identity Testing", Journal of Forensic Nursing, 4, 2008, 150-156.
Roux, K., "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russell, L. M., "X Chromosome Loss and Ageing", Cytogenetic and Genome Res., 116, 2007, 181-185.
Ryan, A. et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nucleic Acids Research, 18(21), 1990, 6409-6412.
Sahota, A., "Evaluation of Seven PCR-Based Assays for the Analysis of Microchimerism", Clinical Biochemistry, vol. 31, No. 8., 1998, 641-645.
Saker, A. et al., "Genetic characterisation of circulating fetal cells allows non-invasive prenatal diagnosis of cystic fibrosis", Prenatal Diagnosis, vol. 26, Jul. 11, 2006, 906-916.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris, "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Sasabe, Yutaka, "Genetic Diagnosis of Gametes and Embryos Resulting from ART", Japanese Journal of Fertility and Sterility, vol. 46, No. 1, 2001, 43-46.
Schmitt, M. W. et al., "Detection of ultra-rare mutations by next-generation sequencing", PNAS, vol. 109, No. 36, Sep. 4, 2012, 14508-14513.
Schoumans, J et al., "Detection of chromosomal imbalances in children with idiopathic mental retardation by array based comparative genomic hybridisation (array-CGH)", JMed Genet, 42, 2005, 699-705.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Sham, P. et al., "DNA Pooling: A Tool for Large-Scale Association Studies", Nature Reviews Genetics, vol. 3, Nov. 2002, 862-871.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, R. et al., "High-throughput SNP genotyping on universal bead arrays", Mutation Research, vol. 573, Feb. 11, 2005, 70-82.
Shen, Zhiyong, "MPprimer: a program for reliable multiplex PCR primer design", BMC Bioinformatics 2010, 11:143, 1-7.
Sherlock, J et al., "Assessment of Diagnostic Quantitative Fluorescent Multiplex Polymerase Chain Reaction Assays Performed on Single Cells", Annals of Human Genetics, 62, 1, 1998, 9-23.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.
Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balancing Primer Efficiencies and Improving Detection Success", Methods in Ecology and Evolution, 3, 2012, 898-905.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Snijders, Antoine et al., "Assembly of Microarrays for Genome-Wide Measurement of DNA Copy Number", Nature Genetic, 29, 2001, 263-264.
Snyder, T. M. et al., "Universal noninvasive detection of solid organ transplant rejection", PNAS, vol. 108, No. 15, Apr. 12, 2011, 6229-6234.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.

(56) References Cited

OTHER PUBLICATIONS

Spiro, Alexander et al., "A Bead-Based Method for Multiplexed Identification and Quantitation of DNA Sequences Using Flow Cytometry", Applied and Environmental Microbiology, 66, 10, 2000, 4258- 4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, Mathews. et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Steyerberg, E.W et al., "Application of Shrinkage Techniques in Logistic Regression Analysis: A Case Study", Statistica Neerlandica, 55(1), 2001, 76-88.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y et al., ""Inferring combined CNV/SNP haplotypes from genotype data"", Bioinformatics, vol. 26, No. 11,1, Jun. 1, 2010, 1437-1445.
Sun, Guihua et al., "SNPs in human miRNA genes affect biogenesis and function", RNA, 15(9), 2009, 1640-1651.
Sweet-Kind Singer, J. A. et al., "Log-penalized linear regression", IEEE International Symposium on Information Theory, 2003. Proceedings, 2003, 286.
Taliun, D. et al., "Efficient haplotype block recognition of very long and dense genetic sequences", BMC Bioinformatics, vol. 15 (10), 2014, 1-18.
Tamura, et al., "Sibling Incest and formulation of paternity probability: case report", Legal Medicine, 2000, vol. 2, p. 189-196.
Tang, et al., , Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Tebbutt, S. J. et al., "Microarray genotyping resource to determine population stratification in genetic association studies of complex disease", BioTechniques, vol. 37, Dec. 2004, 977-985.
Ten Bosch, J. , "Keeping Up With the Next Generation Massively Parallel Sequencing in Clinical Diagnostics", Journal of Molecular Diagnostics, vol. 10, No. 6, 2008, 484-492.
Tewhey, R. et al., "The importance of phase information for human genomics", Nature Reviews Genetics, vol. 12, No. 3, Mar. 1, 2011, 215-223.
The International Hapmap Consort, , "The International HapMap Project", Nature, vol. 426, Dec. 18, 2003, 789-796.
Thermofisher Scientific, , "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Thomas, M.R et al., "The Time of Appearance and Disappearance of Fetal DNA from the Maternal Circulation", Prenatal Diagnosis, 15, 1995, 641-646.
Tiersch, T. R. et al., "Reference Standards for Flow Cytometry and Application in Comparative Studies of Nuclear DNA Content", Cytometry, vol. 10, Mar. 21, 1989, 706-710.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Tu, J. et al., "Pair-barcode high-throughput sequencing for large-scale multiplexed sample analysis", BMC Genomics, vol. 13, No. 43, Jan. 25, 2012, 1-9.
Turner, E. et al., "Massively Parallel Exon Capture and Library-Free Resequencing Across 16 Genomes", Nature Methods, 6 (5), 2009, 315-316.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Vallone, Peter , "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18(11), 2008, 1844-1850.
Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, D. G. et al., "Large-Scale Identification, Mapping, and Genotyping of Single-Nucleotide Polymorphisms in the Human Genome", Science, vol. 280, May 15, 1998, 1077-1082.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, T.L. et al., "Digital karyotyping", PNAS, vol. 99, No. 25, Dec. 10, 2002, 16156-16161.
Wang, Yuker et al., "Allele quantification using molecular inversion probes (MIP)", Nucleic Acids Research, vol. 33, No. 21, Nov. 28, 2005, 14 pgs.
Wapner, R. et al., "Chromosomal Microarray Versus Karyotyping for Prenatal Diagnosis", The New England Journal of Medicine, 367 (23), 2012, 2175-2184.
Wapner, R. et al., "First-Trimester Screening for Trisomies 21 and 18", The New England Journal of Medicine, vol. 349, No. 15, Oct. 9, 2003, 1405-1413.
Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.
Weiss, C. A. , "Chapter 8: Confidence Intervals for One Population Mean", Introductory Statistics, Sixth Edition, 2002, 340-381.
Wells, D , "Microarray for Analysis and Diagnosis of Human Embryos", 12th International Congress on Prenatal Diagnosis and Therapy, Budapest, Hungary, 2004, 9-17.
Wells, Dagan , "Advances in Preimplantation Genetic Diagnosis", European Journal of Obstetrics and Gynecology and Reproductive Biology, 115S, 2004, S97-S101.
Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.

(56) References Cited

OTHER PUBLICATIONS

Wen, Daxing et al., "Universal Multiples PCR: A Novel Method of Simultaneous Amplification of Multiple DNA Fragments", Plant Methods, 8(32), Null, 2012, 1-9.
Wikipedia, , "Buffy coat", Retrieved from "https://en.wikipedia.orgJw/index.php?title=Buffy_coat&oldid=900992886", Jun. 9, 2019, 2 pgs.
Wikipedia, , "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.
Wilton, et al., "Birth of a Healthy Infant After Preimplantation Confirmation of Euploidy by Comparative Genomic Hybridization", N. Engl. J. Med., 345(21), 2001, 1537-1541.
Wilton, L. , "Preimplantation Genetic Diagnosis and Chromosome Analysis of Blastomeres Using Comparative Genomic Hybridization", Human Reproduction Update, 11 (1), 2005, 33-41.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Wright, C. et al., "The use of cell-free fetal nucleic acids in maternal blood for non-invasive prenatal diagnosis", Human Reproduction Update, vol. 15, No. 1, 2009, 139-151.
Wright, C. F. et al., "Cell-free fetal DNA and RNA in maternal blood: implications for safer antenatal testing", BMJ, vol. 39, Jul. 18, 2009, 161-165.
Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Xu, S. et al., "Circulating tumor DNA identified by targeted sequencing in advanced-stage non-small cell lung cancer patients", Cancer Letters, vol. 370, 2016, 324-331.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Zhang, L. et al., "Whole genome amplification from a single cell: Implications for genetic analysis", Proc. Nat'l. Acad. Sci. USA, vol. 89, Jul. 1992, 5847-5851.
Zhang, Rui et al., "Quantifying RNA allelic ratios by microfluidic multiplex PCR and sequencing", Nature Methods, 11(1), 2014, 51-56.
Zhao, Xiaojun. et al., "An Integrated View of Copy Number and Allelic Alterations in the Cancer Genome Using Single Nucleotide Polymorphism Arrays", Cancer Research, 64, 2004, 3060-3071.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.

Zimmermann, B. , "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.
Allan, J. et al., "Micrococcal Nuclease Does Not Substantially Bias Nucleosome Mapping", Journal of Molecular Biology, vol. 417, Jan. 30, 2012, 152-164.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
Cheung, V. G. et al., "Whole genome amplification using a degenerate oligonucleotide primer allows hundreds of genotypes to be performed on less than one nanogram of genomic DNA", Proceedings of the National Academy of Sciences, USA, vol. 93, Dec. 1996, 14676-14679.
Dawson, S.J. et al., "Analysis of Circulating Tumor DNA to Monitor Metastatic Breast Cancer", The New England Journal of Medicine, vol. 368, No. 13, Mar. 28, 280136, 1199-1209.
Diehl, F. et al., "Circulating mutant DNA to assess tumor dynamics", Nature Medicine, vol. 14, No. 9, Jul. 31, 2008, 985-990.
Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.
Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix S1, Nov. 2016, 890-902.
Imielinski, M. et al., "Mapping the Hallmarks of Lung Adenocarcinoma with Massively Parallel Sequencing", Cell, vol. 150, Sep. 14, 2012, 1107-1120.
Lindberg, J. et al., "Exome Sequencing of Prostate Cancer Supports the Hypothesis of Independent Tumour Origins", European Urology, vol. 63, 2013, 347-353.
NCBI, , "dbSNP record for rs1294331", Retrieved from the Internet: <URL: www.ncbi.nlm.nih.gov/snp/?term=rs 1294331 >, 2019, 2 pgs.
NCBI, , "dbSNP record for rs1872575", Retrieved from the Internet: <URL: www.ncbi.nlm.nih.gov/snp/?term=rs1872575, 2019, 2 pgs.
NCBI, , "dbSNP record for rs2362450", Retrieved from the Internet: <URL: www.ncbi.nlm.nih.gov/snp/?term=rs2362450>, 2019, 1 pg.
NCBI, , "dbSNP record for rs2384571", Retrieved from the Internet: <URL: www.ncbi.nlm.nih.gov/snp/?term=rs2384571>, 2019, 2 pgs.
NCBI, , "dbSNP record for rs2498982", Retrieved from the Internet: <URL: www.ncbi.nlm.nih.gov/snp/?term=rs2498982>, 2019, 3 pgs.
NCBI, , "dbSNP record for rs3731877", Retrieved from the Internet: <URL: www.ncbi.nlm.nih.gov/snp/?term=rs3731877>, 2019, 2 pgs.
Schwarzenbach, H. et al., "Cell~free nucleic acids as biomarkers in cancer patients", Nature Reviews: Cancer, vol. 11, Jun. 2011, 426-437.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.
Tounta, G. et al., "A Multiplex PCR for Non-invasive Fetal RHD Genotyping Using Cell-free Fetal DNA", in vivo, vol. 25, 2011, 411-418.
Tzimagiorgis, G. et al., "Recovering circulating extracellular or cell-free RNA from bodily fluids", Cancer Epidemiology, vol. 35, 2011, 580-589.
Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.
Widlak, P. et al., "Cleavage Preferences of the Apoptotic Endonuclease DFF 40 (Caspase~activated DNase or Nuclease) on Naked DNA and Chromatin Substrates", The Journal of Biological Chemistry, vol. 275, No. 11, Mar. 17, 2000, 8228-8232.

(56) References Cited

OTHER PUBLICATIONS

Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.
Zachariah, R. et al., "Circulating cell-free DNA as a potential biomarker for minimal and mild endometriosis", Reproductive BioMedicine Online, vol. 18, No. 3, Jan. 27, 2009, 4007-411.
Gholami, M. et al., "A tailed PCR procedure for cost-effective, two-order multiplex sequencing of candidate genes in polyploid plants", Plant Biotechnology Journal, vol. 10, 2012, 635-645.
He, QZ et al., "A method for improving the accuracy of non-invasive prenatal screening by cell-free foetal DNA size selection", British Journal of Biomedical science, vol. 75, No. 3, Jul. 2018, 133-138.
Sanchez, C. et al., "New insights into structural features and optimal detection of circulating tumor DNA determined by single-strand DNA analysis", Nature Partner Journals, vol. 3, No. 31, Nov. 23, 2018, 12 pgs.
Vallone, P. M. et al., "A multiplex allele-specific primer extension assay for forensically informative SNPs distributed throughout the mitochondrial genome", Int J Legal Medicine, vol. 118, Feb. 4, 2004, 147-157.
Van Den Oever, J. M. et al., "Single Molecule Sequencing of Free DNA from Maternal Plasma for Noninvasive Trisomy 21 Detection", Clinical Chemistry, vol. 58, No. 4, 2012, 699-706.
Wittwer, C. T. et al., "Real-Time Multiplex PCR Assays", Methods, vol. 25, 2001, 430-448.
Zhang, J. et al., "Presence of Donor- and Recipient-derived DNA in Cell-free Urine Samples of Renal Transplantation Recipients: Urinary DNA Chimerism", Clinical Chemistry, vol. 45, No. 10, 1999, 1741-1746.
Andras, S. C. et al., "Strategies for Signal Amplification in Nucleic Acid Detection", Molecular Biotechnology, vol. 19, 2001, 29-44.
Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.
Diehl, F. et al., "Detection and quantification of mutations in the plasma of patients with colorectal tumors", PNAS, vol. 102, No. 45, Nov. 8, 2005, 16368-16373.
Fouquet, C. et al., "Rapid and Sensitive p53 Alteration Analysis in Biopsies from Lung Cancer Patients Using a Functional Assay and a Universal Oligonudeotide Array: A Prospective Study", Clinical Cancer Research, vol. 10, May 15, 2004, 3479-3489.
Spertini, D. et al., "Screening of Transgenic Plants by Amplification of Unknown Genomic DNA Flanking T-DNA", BioTechniques, vol. 27, Aug. 1999, 308-314.
Ambardar, S. et al., "High Throughput Sequencing: An Overview of Sequencing Chemistry", Indian J. Microbiol., vol. 56, No. 4, 2016, 394-404.
Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.
Avgidou, K. et al., "Prospective first-trimester screening for trisomy 21 in 30,564 pregnancies", American Journal of Obstetrics and Gynecology, vol. 192, 2005, 1761-1767.
Barski, A. et al., "High-Resolution Profiling of Histone Methylations in the Human Genome", Cell, vol. 129, May 18, 2007, 823-837.
Bashashati, A. et al., "Distinct evolutionary trajectories of primary high-grade serous ovarian cancers revealed through spatial mutational profiling", Journal of Pathology, vol. 231, 2013, 21-34.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter, L. L. et al., "Discovery and genetic localization of Down syndrome cerebellar phenotypes using the Ts65Dn mouse", Human Molecular Genetics, vol. 9, No. 2, Jan. 2000, 195-202.

Bennett, S. T. et al., "Toward the $1000 human genome", Pharmacogenomics, vol. 6, No. 4, 2005, 373-382.
Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.
Blow, N. , "The personal side of genomics", Nature, vol. 449, Oct. 4, 2007, 627-630.
Canick, J. A. et al., "The impact of maternal plasma DNA fetal fraction on next generation sequencing tests for common fetal aneuploidies", Prenatal Diagnosis, vol. 33, 2013, 667-674.
Chitty, L. S. et al., "Noninvasive Prenatal Screening for Genetic Diseases Using Massively Parallel Sequencing of Maternal Plasma DNA", Cold Spring Harbor Perspectives in Medicine, vol. 5, No. 9, 2015, 20 pages.
Chiu, R.W.K. et al., "Hypermethylation of RASSF1A in Human and Rhesus Placentas", The American Journal of Pathology, vol. 170, No. 3, Mar. 2007, 941-950.
Clausen, F. B. et al., "Improvement in fetal DNA extraction from maternal plasma. Evaluation of the NucliSens Magnetic Extraction system and the QIAamp DSP Virus Kit in comparison with the QIAamp DNA Blood Mini Kit", Prenatal Diagnosis, vol. 27, 2007, 6-10.
Cronn, R. et al., "Multiplex sequencing of plant chloroplast genomes using Solexa sequencing-by-synthesis technology", Nucleic Acids Research, vol. 36, No. 19, Aug. 27, 2008, 11 pgs.
De Jong, M. M. et al., "Genes other than BRCA 1 and BRCA2 involved in breast cancer susceptibility", J. Med. Genet., vol. 39, 2009, 225-242.
Di, X. et al., "Dynamic model based algorithms for screening and genotyping", Bioinformatics, vol. 21, No. 9, 2005, 1958-1963.
Ding, C. et al., "MS analysis of single-nucleotide differences in circulating nucleic acids: Application to noninvasive prenatal diagnosis", PNAS, vol. 101, No. 29, Jul. 20, 2004, 10762-10767.
Eltoukhy, H. et al., "Modeling and Base-Calling for DNA Sequencing-By-Synthesis", IEEE, 2006, II-1032-II-1035.
Faham, M. et al., "Deep-sequencing approach for minimal residual disease detection in acute lymphoblastic leukemia", Blood Journal, vol. 120, No. 26, Dec. 20, 2012, 5173-5180.
Falcon, O. , "Screening for trisomy 21 by fetal tricuspid regurgitation, nuchal translucency and maternal serum free b-hCG and PAPP-A at 11 + 0 to 13 + 6 weeks", Ultrasound Obstet Gynecol, vol. 27, 2006, 151-155.
Fan, J.-B. et al., "Highly Parallel SNP Genotyping", Cold Spring Harbor Symposia on Quantitative Biology, vol. LXVIII, Feb. 2003, 69-78.
Gao, F. et al., "Characterizing Immunoglobulin Repertoire from Whole Blood by a Personal Genome Sequencer", PLOS One, vol. 8, No. 9, Sep. 13, 2013, 8 pgs.
Gautier, E. et al., "Fetal RhD genotyping by maternal serum analysis: A two-year experience", American Journal of Obstetrics and Gynecology, vol. 192, 2005, 666-669.
Gnirke, A. et al., "Solution hybrid selection with ultra-long oligonucleotides for massively parallel targeted sequencing", Nature Biotechnology, vol. 27, No. 2, Feb. 2009, 182-189.
Hosono, S. et al., "Unbiased Whole-Genome Amplification Directly From Clinical Samples", Genome Research, vol. 13, 2003, 954-964.
Hou, X. et al., "Analysis of the Repertoire Features of TCR Beta Chain CDR3 in Human by High-Throughput Sequencing", Cellular Physiology and Biochemistry, vol. 39, Jul. 21, 2019, 651-667.
Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.
Illumina, , "Automated GoldenGate™ Genotyping on the BeadStation 500", Pub. No. 970-2004-002, 2004, 2 pages.
Illumina, , "GoldenGate Assay Workflow: Illumina's GoldenGate assay protocol provides high-quality, high-multiplex genotyping results with a streamlined workflow", Pub. No. 370-2004-006, 2004, 2 pages.
Illumina, , "Illumina Extends BeadArray Technology to Address Wider Range of SNP Genotyping Projects; New Microarray Offerings Enable Genotyping at 384 and 786 Multiplex", https://www.businesswire.com/news/home/20040504006011/en/Illumina-Extends-

(56) References Cited

OTHER PUBLICATIONS

BeadArray-Technology-to-Address-Wider-Range-of-SNP-Genotyping-Projects-New-Microarray-Offerings-Enable-Genotyping-at-384-and-786-Multiplex, May 4, 2004, 2 pages.
Illumina, , "Illumina® Beadstation 500: A Scalable System That Grows With Your Research Requirements", Pub. No. 970-2005-003, Jul. 1, 2005, 4 pages.
Illumina, , "Illumina Announces Benchtop SNP Genotyping System", Press Release, Nov. 5, 2003, 3 pages.
Illumina, , "Illumina Begins Shipment of BeadStation 500G Benchtop Genotyping System", Press Release, Apr. 15, 2004, 3 pages.
Illumina, , "MiSeq System Information Sheet", 2018, 3 pgs.
Illumina, , "Preparing Samples for Sequencing Genomic DNA", Part # 11251892 Rev. A, 2007, 18 pages.
Illumina, , "Products & Services", support contact sitemap legal privacy +1 858.202.4566 © 2007 Illumina, Inc. All rights reserved. https://we b. archive .o rg/web/20070321 001 025/http ://www. ii lu m ina.co m/pagesn rn. ii mn?ID= 70, Mar. 21, 2007, 3 pages.
Illumina, , "Technology: Solexa Sequencing Technology", https://web.archive.org/web/20070521 081517/http://www.illumina.com/pages. ilmn?I D=203, May 21, 2007, 1 page.
Innan, H. et al., "The Pattern of Polymorphism on Human Chromosome 21", Genome Research, vol. 13, 2003, 1158-1168.
Jett, K. et al., "Clinical and genetic aspects of neurofibromatosis 1", Genetics in Medicine, vol. 12, No. 1, Jan. 2010, 11 pages.
Jiang, P. et al., "The Long and Short of Circulating Cell-Free DNA and the Ins and Outs of Molecular Diagnostics", Trends in Genetics, vol. 32, No. 6, Jun. 2016, 360-371.
Johnson, D. S. et al., "Genome-Wide Mapping of in Vivo Protein-DNA Interactions", Science, vol. 316, Jun. 8, 2007, 1497-1502.
Kamel, A. M. et al., "A simple strategy for breakpoint fragment determination in chronic myeloid leukemia", Cancer Genetics and Cytogenetics, vol. 122, 2000, 110-115.
Keller, M. C. et al., "Non-Pathological Paternal Isodisomy of Chromosome 2 Detected From a Genome-Wide SNP Scan", American Journal of Medical Genetics, Part A, 2009, 1823-1826.
Kukita, Y. et al., "High-fidelity target sequencing of individual molecules identified using barcode sequences: de nova detection and absolute quantitation of mutations in plasma cell-free DNA from cancer patients", DNA Research, vol. 22, No. 4, Jun. 29, 2015, 269-277.
Landegren, U. et al., "Padlock and proximity probes for in situ and array-based analyses: tools for the post-genomic era", Comparative and Functional Genomics, vol. 4, 2003, 525-530.
Lapaire, O. et al., "Array-CGH analysis of cell-free fetal DNA in 10 mL of amniotic fluid supernatant", Prenatal Diagnosis, vol. 27, May 17, 2007, 616-621.
Lapierre, J.M. et al., "Analysis of uncultured amniocytes by comparative genomic hybridization: a prospective prenatal study", Prenatal Diagnosis, vol. 20, 2000, 123-131.
Lasken, R. S. et al., "Whole genome amplification: abundant supplies of DNA from precious samples or clinical specimens", TRENDS in Biotechnology, vol. 21, No. 12, Dec. 2003, 531-535.
Li, R. et al., "SNP detection for massively parallel whole-genome resequencing", Genome Research, vol. 19, 2009, 1124-1132.
Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.
Lo, Y.M.D. , "Fetal DNA in Maternal Plasma: Biology and Diagnostic Applications", Clinical Chemistry, vol. 46, No. 12, 2000, 1903-1906.
Masuzaki, H. et al., "Detection of cell free placental DNA in maternal plasma: direct evidence from three cases of confined placental mosaicism", J Med Genet, vol. 41, 2004, 289-292.
Matsuzaki, H. et al., "Genotyping over 100,000 SNPs on a pair of oligonucleotide arrays", Nature Methods, vol. 1, No. 2, Nov. 2004, 109-111.
Morris, J. K. et al., "Trends in Down's syndrome live births and antenatal diagnoses in England and Wales from 1989 to 2008: analysis of data from the National Down Syndrome Cytogenetic Register", BMJ Online, vol. 339, Oct. 2009, 5 pages.
Nagalla, S. R. et al., "Proteomic Analysis of Maternal Serum in Down Syndrome: Identification of Novel Protein Biomarkers", Journal of Proteome Research, vol. 6, Mar. 21, 2007, 1245-1257.
Nilsson, M. et al., "Padlock Probes: Circularizing Oligonucleotides for Localized DNA Detection", Science, vol. 265, Sep. 10, 1994, 2085-2088.
Oliphant, A. et al., "Bead.Array™ Technology: Enabling an Accurate, Cost-Effective Approach to High-Throughput Genotyping", Bio Techniques, vol. 32, Jun. 2002, S56-S6.
Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.
Pask, R. et al., "Investigating the utility of combining 29 whole genome amplification and highly multiplexed single nucleotide polymorphism BeadArray TM genotyping", BMC Biotechnology, vol. 4, No. 15, Jul. 27, 2004, 8 pages.
Patil, N. et al., "Blocks of Limited Haplotype Diversity Revealed by High-Resolution Scanning of Human Chromosome 21", Science, vol. 294, Nov. 23, 2001, 1719-1723.
Paunio, T. et al., "Preimplantation diagnosis by whole-genome amplification, PCR amplification, and solid-phase minisequencing of blastomere DNA", Clinical Chemistry, vol. 42, No. 9, 1996, 1382-1390.
Philip, J. et al., "Late First-Trimester Invasive Prenatal Diagnosis: Results of an International Randomized Trial", American College of Obstetricians and Gynecologists, vol. 103, No. 6, Jun. 2004, 1164-1173.
Pirker, C. et al., "Whole Genome Amplification for CGH Analysis: Linker-Adapter PCR as the Method of Choice for Difficult and Limited Samples", Cytometry Part A, vol. 61A, 2004, 26-34.
Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.
Reeves, R. H. et al., "Too much of a good thing: mechanisms of gene action in Down syndrome", Trends in Genetics, vol. 17, No. 2, Feb. 2, 2001, 83-88.
Robertson, G. et al., "Genome-wide profiles of STAT1 DNA association using chromatin immunoprecipitation and massively parallel sequencing", Nature Methods, vol. 4, No. 8, Aug. 2007, 651-657.
Roman, B. L. et al., "Non-Radioisotopic AFLP Method Using PCR Primers Fluorescently Labeled with CyA 5", BioTechniques, vol. 26, Feb. 1999, 236-238.
Ruano, G. et al., "Haplotype of multiple polymorphisms resolved by enzymatic amplification of single DNA molecules", Proc. Nati. Acad. Sci. USA, vol. 87, Aug. 1990, 6296-6300.
Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.
Schubert, , "Picking out prenatal DNA", Nature Medicine, vol. 10, No. 785, Aug. 2004, 1 page.
Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.
Short, N. J. et al., "Targeted next-generation sequencing of circulating cell-free DNA vs bone marrow in patients with acute myeloid leukemia", Blood Advances, vol. 4, No. 8, Apr. 23, 2020, 1670-1677.
Siebert, P. D. et al., "An improved PCR method for walking in uncloned genomic DNA", Nucleic Acids Research, vol. 23, No. 6, 1995, 1087-1088.
Sivertsson, A. et al., "Pyrosequencing as an Alternative to Single-Strand Conformation Polymorphism Analysis for Detection of N-ras Mutations in Human Melanoma Metastases", Clinical Chemistry, vol. 48, No. 12, 2002, 2164-2170.
Spencer, K. et al., "Maternal serum levels of dimeric inhibin A in pregnancies affected by trisomy 21 in the first trimester", Prenatal Diagnosis, vol. 21, 2001, 441-444.

(56) References Cited

OTHER PUBLICATIONS

Spencer, K. et al., "Maternal serum levels of total activin-A in first-trimester trisomy 21 pregnancies", Prenatal Diagnosis, vol. 21, 2001, 270-273.
Stewart, C. M. et al., "Circulating cell-free DNA for non-invasive cancer management", Cancer Genetics, vol. 228-229, 2018, 169-179.
Swinkels, D. W. et al., "Effects of Blood-Processing Protocols on Cell-free DNA Quantification in Plasma", Clinical Chemistry, vol. 49, No. 3, 2003, 525-526.
Syvanen, A.C., "Toward genome-wide SNP genotyping", Nature Genetics Supplement, vol. 37, Jun. 2005, S5-S10.
Tewhey, R. et al., "Microdroplet-based PCR enrichment for large-scale targeted sequencing", Nature Biotechnology, vol. 27, No. 11, Nov. 2009, 1025-1031.
Tsangaris, G. T. et al., "Proteomic analysis of amniotic fluid in pregnancies with Down syndrome", Proteomics, vol. 6, 2006, 4410-4419.
Vogelstein, B. et al., "Digital PCR", Proc. Natl. Acad. Sci. USA, vol. 96, Aug. 1999, 9236-9241.
Von Eggeling, F. et al., "Applications of Random PCR", Cellular and Molecular Biology, vol. 41, No. 5, 1995, 653-670.
Wu, T.L. et al., "Cell-free DNA: measurement in various carcinomas and establishment of normal reference range", Clinica Chimica Acta, vol. 321, 2002, 77-87.
Yamada, T. et al., "PrimerStation: a highly specific multiplex genomic PCR primer design server for the human genome", Nucleic Acids Research, vol. 34, 2006, W665-W669.
Yaron, Y., "The implications of non-invasive prenatal testing failures: a review of an under-discussed phenomenon", Prenatal Diagnosis, vol. 36, 2016, 391-396.
Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.
Zhou, W. et al., "Counting alleles to predict recurrence of early-stage colorectal cancers", The Lancet, vol. 359, Jan. 19, 2002, 219-225.
Zimmermann, B. et al., "Digital PCR: a powerful new tool for noninvasive prenatal diagnosis?", Prenatal Diagnosis, vol. 28, Nov. 10, 2008, 1087-1093.
Zimmermann, B. et al., "Novel Real-Time Quantitative PCR Test for Trisomy 21", Clinical Chemistry, vol. 48, No. 2, 2002, 362-363.
Zimmermann, B. et al., "Optimized Real-Time Quantitative PCR Measurement of Male Fetal DNA in Maternal Plasma", Clinical Chemistry, vol. 51, No. 9, 2005, 1598-1604.
Zimmermann, B. et al., "Real-Time Quantitative Polymerase Chain Reaction Measurement of Male Fetal DNA in Maternal Plasma", Methods in Molecular Medicine, vol. 132, 2007, 43-49.
Zimmermann, B. et al., "Use of Real-Time Polymerase Chain Reaction for the Detection of Fetal Aneuploidies", Methods in Molecular Biology, vol. 336, Feb. 2006, 83-100.
Zlotogora, J., "Penetrance and expressivity in the molecular age", Genetics in Medicine, vol. 5, No. 5, 2003, 347-352.
"Abstracts for CNAPS III Circulating Nucleic Acids in Plasma and Serum and Serum Proteomics", Clinical Chemistry, vol. 49, No. 11, 2003, 33 pages.
"Abstracts for CNAPS IV Circulating Nucleic Acids in Plasma/Serum", Fourth International Conference on Circulating Nucleic Acids in Plasma/Serum (CNAPS-IV), 2005, 40 pages.
Abaan, O. D. et al., "The Exomes of the NCI-60 Panel: A Genomic Resource for Cancer Biology and Systems Pharmacology", Cancer Res., vol. 73, No. 14, Jul. 15, 2013, 4372-4382.
Agbor-Enoh, S. et al., "Donor-derived cell-free DNA predicts allograft failure and mortality after lung transplantation", EBioMedicine, vol. 40, 2019, 541-553.
Amicucci, P. et al., "Prenatal Diagnosis of Myotonic Dystrophy Using Fetal DNA Obtained from Maternal Plasma", Clinical Chemistry, vol. 46, No. 2, 2000, 301-302.

Anker, P. et al., "Circulating DNA in Plasma or Serum", Medicina, vol. 60, 2000, 699-702.
Auld, D. S., "Use of Chelating Agents to Inhibit Enzymes", Methods in Enzymology, vol. 158, 1988, 110-114.
Bale, J. R. et al., "Reducing Birth Defects: Meeting the Challenge in the Developing World", Institute of Medicine of the National Academies, 2003, 270 pgs.
Banfi, G. et al., "The role of ethylenediamine tetraacetic acid (EDTA) as in vitro anticoagulant for diagnostic purposes", Clin. Chem., vol. 45, No. 5, 2007, 565-576.
Barra, G. B. et al., "EDTA-mediated inhibition of DNases protects circulating cell-free DNA from ex vivo degradation in blood samples", Clinical Biochemistry, vol. 48, 2015, 976-981.
Bergen, A. W. et al., "Effects of DNA mass on multiple displacement whole genome amplification and genotyping performance", BMC Biotechnology, vol. 5, No. 24, Sep. 16, 2005, 11 pgs.
Bischoff, F. Z. et al., "Cell-free fetal DNA in maternal blood: kinetics, source and structure", Human Reproduction Update, vol. 11, No. 1, 2005, 59-67.
Bischoff, F. Z. et al., "Intact fetal cells in maternal plasma: are they really there?", Lancet, vol. 361, 2003, 139-140.
Board, R.E. et al., "Detection of BRAF mutations in the tumour and serum of patients enrolled in the AZD6244 (ARRY-142886) advanced melanoma phase II study", British Journal of Cancer, vol. 101, 2009, 1724-1730.
Boudsocq, F. et al., "Sulfolobus solfataricus P2 DNA polymerase IV (Dpo4): an archael DinB-like DNA polymerase with lesion-bypass properties akin to eukaryotic polη", Nucleic Acids Research, vol. 29, No. 22, 2001, 4607-4616.
Bouma, B. N. et al., "Human Blood Coagulation Factor", The Journal of Biological Chemistry, vol. 252, No. 18, 1977, 6432-6437.
Brinza, D. et al., "2SNP: scalable phasing based on 2-SNP haplotypes", Bioinformatics, vol. 22, No. 3, 2006, 371-373.
Browning, S. R. et al., "Rapid and Accurate Haplotype Phasing and Missing-Data Inference for Whole-Genome Association Studies by Use of Localized Haplotype Clustering", The American Journal of Human Genetics, vol. 81, Nov. 2007, 1084-1097.
Bryant, A. P., "Terminology of Sugars", Ind. Eng. Chem., vol. 26, No. 2, 1933, 231.
Burkey, B. F. et al., "Hepatic apolipoprotein J is secreted as a lipoprotein", Journal of Lipid Research, vol. 33, 1992, 1517-1526.
Calin, G. A. et al., "A MicroRNA Signature Associated with Prognosis and Progression in Chronic Lymphocytic Leukemia", N Engl J Med, vol. 353, 2005, 1793-1801.
Cao, Y. et al., "Clinical Evaluation of Branched DNA Signal Amplification for Quantifying HIV Type 1 in Human Plasma", AIDS Research and Human Retroviruses, vol. 11, No. 3, 1995, 353-361.
Chen, C. P. et al., "Fetal DNA in maternal plasma: the prenatal detection of a paternally inherited fetal aneuploidy", Prenatal Diagnosis, vol. 20, 2000, 353-357.
Chim, S. S. et al., "Detection and Characterization of Placental MicroRNAs in Maternal Plasma", Clinical Chemistry, vol. 54, No. 3, 2008, 482-490.
Chinnapapagari, S. K. et al., "Treatment of Maternal Blood Samples with Formaldehyde Does Not Alter the Proportion of Circulatory Fetal Nucleic Acids (DNA and mRNA) in Maternal Plasma", Clinical Chemistry, vol. 51, No. 3, 2005, 653-655.
Choi, Y. et al., "Comparison of phasing strategies for whole human genomes", PLOS Genetics, Apr. 5, 2018, 26 pages.
Chung, G. T. et al., "Lack of Dramatic Enrichment of Fetal DNA in Maternal Plasma by Formaldehyde Treatment", Clinical Chemistry, vol. 51, No. 3, 2005, 655-658.
Ciriello, G. et al., "Emerging landscape of oncogenic signatures across human cancers", Nature Genetics, vol. 45, No. 10, Oct. 2013, 1127-1135.
Couraud, S. et al., "Noninvasive Diagnosis of Actionable Mutations by Deep Sequencing of Circulating Free DNA in lung Cancer from Never-Smokers: A Proof-of-Concept Study from BioCAST / IFCT-1002", Clinical Cancer Research, vol. 20, No. 17, Jul. 10, 2014, 4613-4624.
Couraud, S. et al., "Supplementary Data for Noninvasive Diagnosis of Actionable Mutations by Deep Sequencing of Circulating Free

(56) References Cited

OTHER PUBLICATIONS

DNA in lung Cancer from Never-Smokers: A Proof-of-Concept Study from BioCAST / IFCT-1002", 2014, 13 pages.
Delaneau, O. et al., "Shape-IT: new rapid and accurate algorithm for haplotype inference", BMC Bioinformatics, vol. 9, No. 540, Dec. 16, 2008, 14 pages.
Dias-Santagata, D. et al., "Braf V600E Mutations Are Common in Pleomorphic Xanthoastrocytoma: Diagnostic and Therapeutic Implications", PLoS One, vol. 6, No. 3, Mar. 2011, 9 pages.
Dickover, R. E. et al., "Optimization of Specimen-Handling Procedures for Accurate Quantitation of Levels of Human Immunodeficiency Virus RNA in Plasma by Reverse Transcriptase PCR", Journal of Clinical Microbiology, vol. 36, No. 4, 1998, 1070-1073.
Dowd, P. et al., "On the mechanism of the anticlotting action of vitamin R quinone", Proc. Natl. Acad. Sci. USA, vol. 92, 1995, 8171-8175.
Downward, J., "Targeting Ras Signalling Pathways in Cancer Therapy", Nature Reviews, vol. 3, Jan. 2003, 11-22.
Dressman, D. et al., "Transforming single DNA molecules into fluorescent magnetic particles for detection and enumeration of genetic variations", PNAS, vol. 100, No. 15, Jul. 22, 2003, 8817-8822.
Erlich, R. L. et al., "Next-generation sequencing for HLA typing of class loci", BMC Genomics, vol. 12, No. 42, 2011, 13 pages.
Eronen, L. et al., "HaploRec: efficient and accurate large-scale reconstruction of haplotypes", BMC Bioinformatics, vol. 7, No. 542, Dec. 22, 2006, 18 pages.
Fackenthal, J. D. et al., "Aberrant RNA splicing and its functional consequences in cancer cells", Disease Models & Mechanisms, vol. 1, 2008, 37-42.
Fortina, P. et al., "Detection of the most common mutations causing beta-thalassemia in Mediterraneans using a multiplex amplification refractory mutation system (MARMS)", Genome Res., vol. 2, 1992, 163-166.
Fortina, P. et al., "DOP-PCR Amplification of Whole Genomic DNA and Microchip-Based Capillary Electrophoresis", Methods in Molecular Biology: Capillary Electrophoresis of Nucleic Acids, vol. II Practical Applications of Capillary Electrophoresis, 2001, 211-219.
Griffiths, A. J. et al., "An Introduction to Genetic Analysis", Sixth Edition, 1996, 5 pages.
Grunenwald, H., "Optimization of Polymerase Chain Reactions", Methods in Biology, vol. 226, 2003, 89-99.
Gu, H. et al., "Diagnostic role of microRNA expression profile in the serum of pregnant women with fetuses with neural tube defects", Journal of Neurochemistry, vol. 122, 2012, 641-649.
Hahn, S. et al., "Current applications of single-cell PCR", CMLS Cellular and Molecular. Life Sciences, vol. 57, 2000, 96-105.
Howie, B. N. et al., "A Flexible and Accurate Genotype Imputation Method for the Next Generation of Genome-Wide Association Studies", PLoS Genetics, vol. 5, No. 6, Jun. 2009, 15 pages.
Hu, Y. et al., "Detection of Extrahepatic Hepatitis C Virus Replication by a Novel, Highly Sensitive, Single-Tube Nested Polymerase Chain Reaction", Am. J. Clin Pathol., vol. 119, 2003, 95-100.
Huang, J. et al., "Whole genome DNA copy number changes identified by high density oligonucleotide arrays", Human Genomics, vol. 1, No. 4, May 2004, 287-299.
Hung, E.C.W. et al., "Detection of circulating fetal nucleic acids: a review of methods and applications", J. Clin. Pathol., vol. 62, 2009, 308-313.
Illumina, , "History of Sequencing by Synthesis", https://www.illumina.com/science/technology/next-generation-sequencing/illumina-sequencing-history.html, 2020, 3 pages.
Illumina, , "Preparing Samples for Sequencing Genomic DNA", (available at http://zazil.ibt.unam.mx/usmb/wpcontent/uploads/2016/05/1003806_Genomic_DNA_Sample_Prep.pdf), Part # 1003806 Rev. A, 2007, 20 pages.
Ivanov, M. et al., "Non-random fragmentation patterns in circulating cell-free DNA reflect epigenetic regulation", BMC Genomics, vol. 16 (Suppl 13):S1, Jun. 2015, 12 pgs.
Jennings, C. et al., "Investigation of Effects of Acid Citrate Dextrose and EDTA on Ability to Quantitatively Culture Human Immunodeficiency Virus", Journal of Clinical Microbiology, vol. 38, No. 9, 2000, 3522.
Jewesburty, E.C.O., "Reactions after Transfusion of Stored Blood", The British Medical Journal, vol. 1, No. 4191, 1941, 664-665.
Johnson, J. B. et al., "Differential mechanisms of complementmediated neutralization of the closely related paramyxoviruses simian virus 5 and mumps virus", Virology, vol. 376, No. 1, 2008, 112-123.
Johnson, K. L. et al., "Interlaboratory Comparison of Fetal Male DNA Detection from Common Maternal Plasma Samples by Real-Time PC", Clinical Chemistry, vol. 50, No. 3, 2004, 516-521.
Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.
Keith, L. et al., "Clinical Experience With the Prevention of Rh-Isoimmunization: A Historical Comparative Analysis", American Journal of Reproductive Immunology, vol. 5, 1984, 84-89.
Kiernan, J. A., "Formaldehyde, formalin, paraformaldehyde and glutaraldehyde: What they are and what they do.", Microscopy Today, vol. 1, 2000, 8-12.
Kimmel, G. et al., "GERBIL: Genotype resolution and block identification using likelihood", PNAS, vol. 102, No. 1, Jan. 4, 2005, 158-162.
Kirkness, E. F. et al., "Sequencing of isolated sperm cells for direct haplotyping of a human genome", Genome Research, vol. 23, 2013, 826-832.
Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.
Kumar, P. et al., "Ethylenegycol-Bis-(B-Aminoethylether)Tetraacetate as a Blood Anticoagulant: Preservation of Antigen-Presenting Cell Function and Antigen-Specific Proliferative Response of Peripheral Blood Mononuclear Cells from Stored Blood", Clinical and Diagnostic Laboratory Immunology, vol. 7, No. 4, 2000, 578-583.
Langmore, J., "Quality Control and Pre-Qualifications of NGS Libraries Made from Clinical Samples", ABRF 2013 Satellite Workshop, Mar. 2, 2013, 35 pages.
Lecomte, T. et al., "Detection of Free-Circulating Tumor- Associated DNA in Plasma of Colorectal Cancer Patients and Its Association With Prognosis", Int. J. Cancer, vol. 100, 2002, 542-548.
Lee, T. et al., "Down syndrome and cell-free fetal DNA in archived maternal serum", AmJ Obstet Gynecol, vol. 187, No. 5, 1217-1221, Nov. 2002.
Lee, T.H. et al., "Quantitation of genomic DNA in plasma and serum samples: higher concentrations of genomic DNA found in serum than in plasma", Transfusion, vol. 41, Feb. 2001, 276-282.
Lichtenstein, A. V. et al., "Circulating Nucleic Acids and Apoptosis", Annals New York Academy of Sciences, vol. 945, 1993, 239-249.
Lo, Y.M.D. et al., "Prenatal diagnosis: progress through plasma nucleic acids", Nature Reviews, vol. 8, 2007, 71-77.
Lovmar, L. et al., "Quantitative evaluation by minisequencing and microarrays reveals accurate multiplexed SNP genotyping of whole genome amplified DN", Nucleic Acids Research, vol. 31, No. 21, 2003,, 9 pgs.
Lu, S. et al., "Probing Meiotic Recombination and Aneuploidy of Single Sperm Cells by Whole-Genome Sequencing", Science, vol. 338, Dec. 21, 2012, 1627-1630.
Mackiewicz, D. et al., "Distribution of Recombination Hotspots in the Human Genome - A Comparison of Computer Simulations with Real Data", PLOS One, vol. 8, No. 6, Jun. 2013, 11 pages.
Marshutina, N. V. et al., "Comparative Clinical and Diagnostic Significance of Some Serological Tumor Associated Markers for Different Histological Types of Lung Cancer", Russian Oncological Journal, vol. 3, 2010, 13-16.
Mcdonald, J. P. et al., "Novel thermostable Y-family polymerases: applications for the PCR amplification of damaged or ancient DNAs", Nucleic Acids Research, vol. 34, No. 4, 2006, 1102-1111.

(56) References Cited

OTHER PUBLICATIONS

Meyerson, M. et al., "Advances in understanding cancer genomes through second-generation sequencing", Nature Reviews: Genetics, vol. 11, Oct. 2010, 685-696.

Mikkelsen, T. S. et al., "Genome-wide maps of chromatin state in pluripotent and lineage-committed cells", Nature, vol. 448, No. 2, Aug. 2007, 553-562.

Murali, R. et al., "Crystal structure of Taq DNA polymerase in complex with an inhibitory Fab: The Fab is directed against an intermediate in the helix-coil dynamics of the enzyme", Proc. Natl. Acad. Sci. USA, vol. 95, Oct. 1998, 12562-12567.

Nishigaki, K. et al., "Random PCR-Based Genome Sequencing: A Non-Divide-and-Conquer Strategy", DNA Research, vol. 7, 2000, 19-26.

Olive, M. et al., "Characterization of the DiFi Rectal Carcinoma Cell Line Derived from a Familial Adenomatous Polyposis Patient", In Vitro Cellular & Developmental Biology, vol. 29A, No. 3, Part 1, Mar. 1993, 239-248.

Olney, R. S et al., "Chorionic Villus Sampling and Amniocentesis: Recommendations for Prenatal Counseling", MMWR: Recommendations and Reports, 44(RR-9), Jul. 21, 1995, 1-12.

Parker, A. V. et al., "The Effect of Sodium Citrate on the Stimulation of Polymorphonuclear Leukocytes", Investigative Ophthalmology & Visual Science, vol. 26, 1985, 1257-1261.

Pelizzari, C. A. et al., "Quantitative analysis of DNA array autoradiographs", Nucleic Acids Research, vol. 28, No. 22, 2000, 4577-4581.

Qin, Z. S. et al., "Partition-Ligation-Expectation-Maximization Algorithm for Haplotype Inference with Single-Nucleotide Polymorphisms", Am. J. Hum Genet., vol. 71, 2002, 1242-1247.

Quan, P. C. et al., "Studies on the mechanism of NK cell lysis", The Journal of Immunology, vol. 128, 1982, 1786-1791.

Quinlan, M. P. , "Amniocentesis: Indications and Risks", American Medical Association Journal of Ethics: Virtual Mentor, vol. 10, No. 5, May 2008, 304-306.

Rabinowitz, M. , "A System and Method for Integrating, Validating and Applying Genetic and Clinical Data to Enhance Medical Decisions", Nov. 29, 2005, 155 pgs.

Rhoads, A. et al., "PacBio Sequencing and Its Applications", Genomics Proteomics Bioinformatics, vol. 13, Nov. 2, 2015, 278-289.

Rosado, J. A. et al., "Tyrosine kinases activate store-mediated Ca2+ entry in human platelets through the reorganization of the actin cytoskeleton", Biochem. J., vol. 351, 2000, 429-437.

Rosen, D. R. et al., "Mutations in Cu/Zn superoxide dismutase gene are associated with familial amyotrophic lateral sclerosis", Nature, vol. 362, Mar. 4, 1993, 59-62.

Ryan, B. M. et al., "A prospective study of circulating mutant KRAS2 in the serum of patients with colorectal neoplasia: strong prognostic indicator in postoperative follow up", Gut, vol. 52, 2003, 101-108.

Sahukhal, G. S. et al., "msaABCR operon positively regulates biofilm development by repressing proteases and autolysis in *Staphlococcus aureus*", FEMS Microbiology Letters, vol. 362, No. 4, 2015, 1-10.

Saito, H. et al., "Prenatal DNA diagnosis of a single-gene disorder from maternal plasma", The Lancet, vol. 356, Sep. 30, 2000, 1170.

Scheet, P. et al., "A Fast and Flexible Statistical Model for Large-Scale Population Genotype Data: Applications to Inferring Missing Genotypes and Haplotypic Phase", The American Journal of Human Genetics, vol. 78, Apr. 2006, 629-644.

Schwarzenbach, H. et al., "Evaluation of cell-free tumour DNA and RNA in patients with breast cancer and benign breast disease", Molecular BioSystems, vol. 7, 2011, 2848-2854.

Shendure, J. et al., "Accurate Multiplex Polony Sequencing of an Evolved Bacterial Genome", Science, Nov. 30, 2007, 18-24.

Shendure, J. et al., "Next-generation DNA sequencing", Nature Biotechnology, vol. 26, No. 10, Oct. 2008, 1135-1145.

Shinozaki, M. et al., "Utility of Circulating B-RAF DNA Mutation in Serum for Monitoring Melanoma Patients Receiving Biochemotherapy", Clin Cancer Res, vol. 13, No. 7, Apr. 1, 2007, 2068-2074.

Shokralla, S. et al., "Next-generation DNA barcoding: using next-generation sequencing to enhance and accelerate DNA barcode capture from single specimens", Molecular Ecology Resources, vol. 14, 2014, 892-901.

Solomon, M. J. et al., "Formaldehyde-mediated DNA-protein crosslinking: A probe for in vivo chromatin structures", Proc. Natl. Acad. Sci. USA, vol. 82, 1985, 6470-6474.

Stephens, M. et al., "Accounting for Decay of Linkage Disequilibrium in Haplotype Inference and Missing-Data Imputation", Am. J. Hum. Genet., vol. 76, 2005, 449-462.

Su, Z. et al., "A Platform for Rapid Detection of Multiple Oncogenic Mutations With Relevance to Targeted Therapy in Non-Small-Cell Lung Cancer", The Journal of Molecular Diagnostics,, vol. 13, No. 1, Jan. 2011, 74-84.

Taback, B. et al., "Quantification of Circulating DNA in the Plasma and Serum of Cancer Patients", Ann. N.Y. Acad. Sci, vol. 1022, 2004, 17-24.

Takashima, Y. et al., "Expansion-contraction of photoresponsive artificial muscle regulated by host-guest interactions", Nature Communications, vol. 3, No. 1270, Dec. 11, 2012, 8 pages.

Thavarajah, R. et al., "Chemical and physical basics of routine formaldehyde fixation", Journal of Oral and Maxillofacial Pathology, vol. 16, No. 3, 2012, 400-405.

Tsui, N. B. et al., "Systematic micro-array based identification of placental mRNA in maternal plasma: towards non-invasive prenatal gene expression profiling", J. Med. Genet, vol. 41, 2004, 461-467.

Urbaniak, S. J. et al., "RhD haemolytic disease of the fetus and the newborn", Blood Reviews, vol. 14, 2000, 44-61.

Van Uitert, I. et al., "The influence of different membrane components on the electrical stability of bilayer lipid membranes", Biochimica et Biophysica Acta, vol. 1798, 2010, 21-31.

Wang, J. et al., "Genome-wide Single-Cell Analysis of Recombination Activity and De Novo Mutation Rates in Human Sperm", Cell, vol. 150, Jul. 20, 2012, 402-412.

Wang, S. et al., "Potential Clinical Significance of a Plasma-Based KRAS Mutation Analysis in Patients with Advanced Non-Small Cell Lung Cancer", Clin Cancer Res, vol. 16, No. 4, Feb. 15, 2010, 1324-1330.

Wei, C. et al., "Detection and Quantification by Homogeneous PCR of Cell-free Fetal DNA in Maternal Plasma", Clinical Chemistry, vol. 47, No. 2, 2001, 336-338.

Winsor, E. J. et al., "Maternal Cell Contamination in Uncultured Amniotic Fluid", Prenatal Diagnosis, vol. 16, 1996, 49-54.

Xu, W. et al., "A Novel Universal Primer-Multiplex-PCR Method with Sequencing Gel Electrophoresis Analysis", PLOS One, vol. 7, No. 1, Jan. 17, 2012, 10 pgs.

Yamada, T. et al., "Detection of K-ras Gene Mutations in Plasma DNA of Patients with Pancreatic Adenocarcinoma: Correlation with Clinicopathological Features", Clinical Cancer Research, vol. 4, Jun. 1998, 1527-1532.

Abd-Elsalam, Kamel A. , "Bioinformatic Tools and Guideline for PCR Primer Design", African Journal of Biotechnology, vol. 2, 2003, pp. 91-95.

Adalsteinsson, V. A. et al., "Scalable whole-exome sequencing of cell-free DNA reveals high concordance with metastatic tumors", Nature Communications, vol. 18, No. 1324, 2017, 13 pages.

Adinolfi, M. et al., "Rapid Detection of Aneuploidies by Microsatellite and the Quantitative Fluorescent Polymerase Chain Reaction", Prenatal Diagnosis, vol. 17, No. 13, 1997, 1299-1311.

Alizadeh, Mehdi et al., "Quantitative Assessment of Hematopoietic Chimerism after Bone Marrow Transplantation by Real-time Quantitative Polymerase Chain Reaction", Blood, vol. 99, No. 12, Jun. 15, 2002, 4618-4625.

Ansorge, Wilhelm J. , "Next-generation DNA Sequencing Techniques", New Biotechnology, vol. 25, No. 4, Feb. 2, 2009, 195-203.

Arandjelovic, M. et al., "Two-Step Multiplex Polymerase Chain Reaction improves the Speed and Accuracy of Genotyping Using DNA from Noninvasive and Museum Samples", Molecular Ecology Resources, vol. 9, 2009, pp. 28-36.

(56) References Cited

OTHER PUBLICATIONS

Avent, Neil D. et al., "Cell-free Fetal DNA in the Maternal Serum and Plasma: Current and Evolving Applications", Current Opinion in Obstretrics and Gynecology, vol. 21, No. 2, Apr. 1, 2009, 175-179.
Ayala, et al., "Long-Term Follow-Up of Donor Chimerism Tolerance After Human Liver Transplantation", Liver Transplantation, vol. 15, No. 6,, May 28, 2009, 581-591.
Balavoine, Guillaume , "Identification of Members of Several Homeobox Genes in a Planarian Using a Ligation-Mediated Polymerase Chain Reaction Technique", Nucleic Acids Research, vol. 24, 1996, pp. 1547-1553.
Balduini, et al., "Utility of Biochemical Markers in the Follow-up Heart Transplant Recipients", Transplantation Proceedings, vol. 35, No. 8, Dec. 1, 2003, 3075-3078.
Barbazuk, et al., "SNP Discovery via 454 Transcriptome Sequencing", The Plant Journal, vol. 51, Jul. 27, 2007, 910-918.
Bartlett, John M. et al., "PCR Protocols", PCR Protocols, vol. 226, 2003, 519 pages.
Baxter-Lowe, et al., "Tracking Microchimeric DNA in Plasma to Diagnose and Manage Organ Transplant Rejection", Clinical Chemistry, vol. 52, No. 4, Apr. 1, 2006, 559-561.
Beck, et al., "Next Generation Sequencing of Serum Circulating Nucleic Acids from Patients with Invasive Ductal Breast Cancer Reveals Differences to Healthy and Nonmalignant Controls", Molecular Cancer Research, vol. 8, No. 3, Mar. 1, 2010, 335-342.
Beck, J. et al., "Profile of the Circulating DNA in Apparently Healthy Individuals", Clinical Chemistry, vol. 55, No. 4, 2009, 730-738.
Belostotsky, Dmitry A. et al., "Plant Systems Biology", Methods in Molecular Biology, vol. 553, Aug. 25, 2009, 3-408.
Bender, et al., "A Multiplex SNP Typing Approach for the DNA Pyrosequencing Technology", International Congress Series, vol. 1288, Apr. 20, 2006, 73-75.
Benjamini, Y. et al., "Controlling the False Discovery Rate: A Practical and Powerful Approach to Multiple Testing", Journal of the Royal Statistical Society, Series B (Methodological), vol. 57, No. 1, 1995, 289-300.
Bentley, et al., "High-resolution, High-throughput HLA Genotyping by Next-generation Sequencing", Tissue Antigens, vol. 74, No. 5, Nov. 1, 2009, 393-403.
Bianchi, D W. et al., "Insights Into Fetal and Neonatal Development Through Analysis of Cell-Free RNA in Body Fluids", Early Human Development, vol. 86, No. 11, Nov. 2010, 747-752.
Blomquist, T M. et al., "Targeted RNA-Sequencing with Competitive Multiplex-PCR Amplicon Libraries", Plos One, vol. 8, Issue 11, Nov. 2013, 14 pages.
Bordoni, et al., "Evaluation of Human Gene Variant Detection in Amplicon Pools by the GS-FLX Parallel Pyrosequencer", BMC Genomics, vol. 9, Oct. 8, 2008, 1-8.
Brastianos, P. K. et al., "Genomic Characterization of Brain Metastases Reveals Branched Evolution and Potential Therapeutic Targets", Cancer Discovery, vol. 5, Sep. 26, 2015, 1164-1177.
Brockman, et al., "Quality Scores and SNP Detection in Sequencing-by-synthesis Systems", Genome Research, vol. 18, No. 5, May 1, 2008, 763-770.
Broude, N E. et al., "High-Level Multiplex DNA Amplification", Antisense & Nucleic Acid Drug Development, vol. 11, 2001, 327-332.
Broude, N. E. et al., "High Multiplexity PCR Based on PCR Suppression", DNA Amplification Current Technologies and Applications, 2004, 61-76.
Broude, N. E. et al., "Multiplex Allele-specific Target Amplification based on PCR Suppression", PNAS, vol. 98, No. 1, Jan. 2, 2001, 206-211.
Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.

Bustamante-Aragones, Ana et al., "New Strategy for the Prenatal Detection/Exclusion of Paternal Cystic Fibrosis Mutations in Maternal Plasma", Journal of Cystic Fibrosis, vol. 7, Issue 6, Nov. 1, 2008, 505-510.
Butler, et al., "Cardiovascular Magnetic Resonance in the Diagnosis of Acute Heart Transplant Rejection: A Review", Journal of Cardiovascular Magnetic Resonance, vol. 11, No. 1, Mar. 12, 2009, 1-11.
Campbell, P. J. et al., "Subclonal phylogenetic structures in cancer revealed by ultra-deep sequencing", PNAS, vol. 105, No. 35, Sep. 2, 2008, 13081-13086.
Castleberry, C. D. et al., "Quantification of Circulating Cell-Free DNA in Pediatric Heart Transplant Recipients", Journal of Heart and Lung Transplantation, vol. 30, No. 4, Apr. 1, 2011, S139.
Chan, Allen K. et al., "Cell-free Nucleic Acids in Plasma, Serum and Urine: A New Tool in Molecular Diagnosis", Annals of Clinical Biochemistry, vol. 40, Issue 2, Mar. 1, 2003, 122-130.
Chavali, Sreenivas et al., "Oligonucleotide Properties Determination and Primer Designing: A Critical Examination of Predictions", Bioinformatics, vol. 21, 2005, pp. 3918-3925.
Chen, Bing-Yuan et al., "PCR Cloning Protocols", PCR Cloning Protocols, vol. 192, 2002, 434 pages.
Church, et al., "Multiplex DNA Sequencing", Science, vol. 240, No. 4849, Apr. 8, 1988, 185-188.
Crespo-Leiro, et al., "Gene Expression Profiling for Monitoring Graft Rejection in Heart Transplant Recipients", Transplantation Proceedings, vol. 41, No. 6, Jul. 1, 2009, 2240-2243.
Cunningham, K. S. et al., "An approach to endomyocardial biopsy interpretation", Journal of Clinical Pathology, vol. 59, No. 2, Mar. 2006, 121-129.
Dahl, et al., "Multigene Amplification and Massively Parallel Sequencing for Cancer Mutation Discovery", Proceedings of the National Academy of Sciences, vol. 104, No. 22, May 29, 2007, 9387-9392.
Dambrin, et al., "A New Rejection Criteria in the Heterotopically Placed Rat Heart by Non-invasive Measurement of Dp/Dtmax", The Journal of Heart and Lung Transplantation, vol. 18, No. 6, Jun. 18, 1999, 524-531.
Deb, Mahua et al., "Development of a Multiplexed PCR Detection Method for Barley and Cereal Yellow Dwarf Viruses, Wheat Spindle Streak Virus, Wheat Streak Mosaic Virus and Soil-Borne Wheat Mosaic Virus", Journal of Virological Methods, vol. 148, 2008, pp. 17-24.
Delgado, P. O. et al., "Characterization of cell-free circulating DNA in plasma in patients with prostate cancer", Tumor Biol., vol. 34, 983-986, 2013.
Doostzadeh, et al., "High Throughput Automated Allele Frequency Estimation by Pyrosequencing", PLoS ONE, vol. 3, No. 7, Jul. 16, 2008, 1-4.
Dorit, D. L. , "cDNA Amplification Using One-sided (Anchored) Pcr", Current Protocols in Molecular Biology, vol. 17, 1992, pp. 15.6.1-15.6.10.
Dorit, Robert L. et al., "One-sided Anchored Polymerase Chain Reaction for Amplification and Sequencing of Complementary DNA", Methods in Enzymology, vol. 218 1993, pp. 36-47.
Edwards, M. C. et al., "Multiplex PCR: Advantages, Development, and Applications", Genome Research, vol. 3, 1994, S65-S75.
Efron, B. et al., "Bootstrap Methods for Standard Errors, Confidence Intervals, and Other Measures of Statistical Accuracy", Statistical Science, vol. 1, No. 1, 1986, 54-77.
Elnifro, Elfath M. , "Multiplex PCR: Optimization and Application in Diagnostic Virology", Clinical Microbiology Reviews, vol. 13, 2000, pp. 559-570.
Erijman, Ariel et al., "Transfer-PCR (TPCR): A Highway For DNA Cloning and Protein Engineering", Journal of Structural Biology, vol. 175, 2011, pp. 171-177.
European Commission, , "The 7th International Conference on Circulating Nucleic Acids in Plasma and Serum (CNAPS VII) in Madrid—Spain", The International Conference on Circulating Nucleic Acids in Plasma and Serum, Oct. 24, 2011, 2 pgs.
Fan, C H. et al., "Detection of Aneuploidy with Digital Polymerase Chain Reaction", Analytical Chemistry, vol. 79, No. 19, Oct. 1, 2007, 7576-7579.

(56) References Cited

OTHER PUBLICATIONS

Fan, H. C. et al., "In Principle Method for Noninvasive Determination of the Fetal Genome", Nat. Prec., 2010, 16 pgs.
Fitzgerald, , "Intravascular Ultrasound Imaging of Coronary Arteries: Is Three Layers the Norm?", Circulation, vol. 86, No. 1, Jul. 1, 1992, 154-158.
Fournie, et al., "Plasma DNA as a Marker of Cancerous Cell Death. Investigations in Patients Suffering From Lung Cancer and in Nude Mice Bearing Human Tumours", Cancer Letters, vol. 91, No. 2, May 8, 1995, 221-227.
Fredriksson, M et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.
Frohman, M A. et al., "On Beyond Classic RACE (Rapid Amplification of cDNA Ends)", Genome Research, vol. 4, 1994, S40-S58.
Fu, Yao-Wen et al., "Presence of Donor-and-recipientderived Dna Microchimerism in the Cell-free Blood Samples of Renal Transplantation Recipients Associates With the Acceptance of Transplanted Kidneys", Asian Journal of Andrology, vol. 8, No. 4, Jul. 1, 2006, 477-482.
Gadi, V. K. et al., "Soluble Donor DNA Concentrations in Recipient Serum Correlate with Pancreas-Kidney Rejection", Clinical Chemistry, vol. 52, No. 3, 2006, 379-382.
Gao, et al., "Relation of Donor Age and Preexisting Coronary Artery Disease on Angiography and Intracoronary Ultrasound to Later Development of Accelerated Allograft Coronary Artery Disease", The American Journal of Cardiology, vol. 29, No. 3, Mar. 1, 1997, 623-629.
Gao, Ming et al., "Characterization of dull1, a Maize Gene Coding for a Novel Starch Synthase", The Plant Cell, vol. 10, 1998, pp. 399-412.
Garcia Moreira, V. et al., "Cell-Free DNA as a Noninvasive Acute Rejection Marker in Renal Transplantation", Clinical Chemistry, vol. 55, No. 11, 2009, 1958-1966.
Geifman- Holtzman, et al., "Prenatal Diagnosis: Update on Invasive Versus Noninvasive Fetal Diagnostic Testing From Maternal Blood", Expert Review of Molecular Diagnostics, vol. 8, No. 6, Nov. 1, 2008, 727-751.
Gielis, E. M. et al., "Cell-Free DNA: An Upcoming Biomarker in Transplantation", American Journal of Transplantation, vol. 15, 2015, 2541-2551.
Gineikiene, Egle et al., "Single Nucleotide Polymorphism-based System Improves the Applicability of Quantitative PCR for Chimerism Monitoring", Journal of Molecular Diagnostics, vol. 11, No. 1, Jan. 1, 2009, 66-74.
Gingeras, et al., "Fifty Years of Molecular (DNA/RNA) Diagnostics", Clinical Chemistry, vol. 51, No. 3, Jan. 13, 2005, 661-671.
Girnita, Diana M. et al., "Disparate Distribution of 16 Candidate Single Nucleotide Polymorphisms Among Racial and Ethnic Groups of Pediatric Heart Transplant Patients", Transplantation, vol. 82, No. 12, Dec. 27, 2006, 1774-1780.
Go, A. T. et al., "Non-invasive aneuploidy detection using free fetal DNA and RNA in maternal plasma: recent progress and future possibilities", Human Reproduction Update, vol. 17, No. 3, 2011, 372-382.
Goncalves-Primo, A. et al., "Investigation of Apoptosis-Related Gene Expression Levels in Preimplantation Biopsies as Predictors of Delayed Kidney Graft Function", Transplantation, vol. 97, No. 12, Jun. 27, 2014.
Gordon, et al., "Disease-Specific Motifs Can Be Identified in Circulating Nucleic Acids From Live Elk and Cattle Infected With Transmissible Spongiform Encephalopathies", Nucleic Acids Research, vol. 37. No. 2, Feb. 1, 2009, 550-556.
Gorringe, et al., "Large-scale Genomic Analysis of Ovarian Carcinomas", Molecular oncology, vol. 3, No. 2, Apr. 1, 2009, 157-164.
Gouya, et al., "Coronary Artery Stenosis In High-risk Patients: 64-section Ct and Coronary Angiography-Prospective Study and Analysis of Discordance", Radiology, vol. 252, No. 2, Aug. 1, 2009, 377-385.
Gregory, et al., "Comparison of Sixty-Four-Slice Multidetector Computed Tomographic Coronary Sngiography to Coronary Angiography With Intravascular Ultrasound for the Detection of Transplant Vasculopathy", The American Journal of Cardiology, vol. 98, No. 7, Aug. 4, 2006, 877-884.
Guo, H et al., "A Specific and Versatile Genome Walking Technique", Gene, vol. 381, 2006, 18-23.
Gwee, Pai-Chung et al., "Simultaneous Genotyping of Seven Single-nucleotide Polymorphisms in the Mdr1 Gene by Single-tube Multiplex Minisequencing", Pai-Chung Gwee et al., "Simultaneous Genotyping of Seven Single-nucleotide Polymorphisms in the Mdr1 Gene by Single-tube Multiplex Minisequencing", Clinical chemistry, Apr. 2003, vol. 49, Issue. 3, pp. 672-676., Apr. 1, 2003, 672-676.
Hahn, et al., "Non-invasive Prenatal Diagnostics Using Next Generation Sequencing: Technical, Legal and Social Challenges", Expert Opinion on Medical Diagnostics, vol. 6, No. 6, Nov. 1, 2012, 517-528.
Hahn, S. et al., "Quantification of Circulating DNA: In the Preparation Lies the Rub", Clinical Chemistry, vol. 47, No. 9, 2001, 1577-1578.
Halford, William P. , "The Essential Prerequisites for Quantitative RT-PCR", Nature Biotechnology, vol. 17, 1999, 1 page.
Handley, D. et al., "Noninvasive prenatal chromosomal aneuploidy detection using plasma cell-free nucleic acid", Expert Rev Obstet. Gynecol, vol. 5, No. 5, 2010, 581-590.
Hao, T. B. et al., "Circulating cell-free DNA in serum as a biomarker for diagnosis and prognostic prediction of colorectal cancer", British Journal of Cancer, vol. 111, Aug. 26, 2014, 1482-1489.
Heaton, Paul R. et al., "Heminested PCR Assay for Detection of Six Genotypes of Rabies and Rabies-related Viruses", Journal of Clinical Microbiology, vol. 35, 1997, pp. 2762-2766.
Heidary, M. et al., "The dynamic range of circulating tumor DNA in metastatic breast cancer", Breast Cancer Research, vol. 16, No. 421, 2014, 10 pages.
Henegariu, O. et al., "Multiplex PCR: Critical Parameters and Step-by-Step Protocol", Biotechniques, vol. 23, 1997, pp. 504-511.
Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.
Hoberman, Rose et al., "A Probabilistic Approach for SNP Discovery in High-throughput Human Resequencing Data", Genome Research, vol. 19, Jul. 15, 2009, 1542-1552.
Hochberg, et al., "A Novel Rapid Single Nucleotide Polymorphism (SNP)-Based Method for Assessment of Hematopoietic Chimerism After Allogeneic Stem Cell Transplantation", Blood, vol. 101, No. 1, Jan. 1, 2003, 363-369.
Hodges, et al., "Genome-wide In Situ Exon Capture For Selective Resequencing", Nature Genetics, vol. 39, No. 12, Nov. 4, 2007, 1522-1527.
Hoffmann, Steven et al., "Donor Genomics Influence Graft Events: The Effect of Donor Polymorphisms on Acute Rejection and Chronic Allograft Nephropathy", Kidney International, vol. 66, No. 4, Oct. 1, 2004, 1686-1693.
Holt, et al., "Detecting SNPS and Estimating Allele Frequencies in Clonal Bacterial Populations by Sequencing Pooled DNA", Bioinformatics, vol. 25, No. 16, Aug. 15, 2009, 2074-2075.
Horai, et al., "Novel Implantable Device to Detect Cardiac Allograft Rejection", Circulation, vol. 120, No. Suppl 1, Sep. 15, 2009, 185-190.
Hosmillo, Myra D. et al., "Development of Universal SYBR Green Real-time RT-PCR for the Rapid Detection and Quantitation of Bovine and Porcine Toroviruses", Journal of Virological Methods, vol. 168, 2010, pp. 212-217.
Hu, Hao et al., "Mutation Screening in 86 Known X-linked Mental Retardation Genes by Droplet-based Multiplex Pcr and Massive Parallel Sequencing", Hao Hu et al., "Mutation Screening in 86 Known X-linked Mental Retardation Genes by Droplet-based Multiplex Pcr and Massive Parallel Sequencing", Hugo J, Dec. 2009, vol. 3, pp. 41-49., Dec. 1, 2009, 41-49.
Huang, D. J. et al., "Reliable detection of Trisomy 21 using MALDI-TOF mass spectrometry", Genetics in Medicine, vol. 8, Nov. 2006, 728-734.

(56) References Cited

OTHER PUBLICATIONS

Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593-1595.
Hyndman, D L. et al., "PCR Primer Design", Methods in Molecular Biology, vol. 226, Second Edition, 2003, 81-88.
Illumina, "Genomic Sequencing", Data Sheet: Sequencing, 2010, 38939-38944.
Illumina, "HiSeq 2500 Sequencing System", System Specification Sheet: Sequencing, available via URL https://www.illumina.com/documents/products/datasheets/datasheet_hiseq2500.pdf, 2015, 4 pgs.
Illumina, "TruSeq™ RNA and DNA Library Preparation Kits v2", Data Sheet: Illumina® Sequencing, 2014, 4.
Ingman, et al., "SNP Frequency Estimation Using Massively Parallel Sequencing of Pooled DNA", European Journal of Human Genetics, vol. 17, No. 3, Oct. 15, 2008, 383-386.
Interewicz, B. et al., "DNA Released from Ischemic and Rejecting Organs as an Indicator of Graft Cellular Damage", Annals of Transplantation, vol. 9, No. 2, May 1, 2004, 42-45.
Iskow, R. C. et al., "Natural Mutagenesis of Human Genomes by Endogenous Retrotransposons", Cell, vol. 141, Jun. 25, 2010, 1253-1261.
Jen, J. et al., "An Overview on the Isolation and Analysis of Circulating Tumor DNA in Plasma and Serum", Annals New York Academy of Sciences, 2000, 8-12.
Jung, K. et al., "Cell-free DNA in the blood as a solid tulnor biomarker—A critical appraisal of the literature", Clinica Chimica Acta, vol. 411, 2010, 1611-1624.
Juppner, H. et al., "Functional Properties of the PTH/PTHrP Receptor", Bone, vol. 17, No. 2 Supplement, Aug. 1995, 39S-42S.
Kalendar, Ruslan et al., "Java Web Tools for PCR, in Silico PCR, and Oligonucleotide Assembly and Analysis", Genomics, vol. 98, 2011, pp. 137-144.
Kane, M. et al., "Application of Less Primer Method to Commercial Kits", Forensic Science International: Genetics Supplement Series, vol. 1, Issue 1, 2008, 41-43.
Kane, M. , "Application of Less Primer Method to Multiplex PCR", International Congress Series, vol. 1288, 2006, pp. 694-696.
Kapadia, Samir R. et al., "Impact of Intravascular Ultrasound in Understanding Transplant Coronary Artery Disease", Current Opinion in Cardiology, vol. 14, No. 2, Mar. 1, 1999, 1-19.
Karger, et al., "DNA Sequencing by Capillary Electrophoresis", Electrophoresis, vol. 30, Supplement 1, Jun. 1, 2009, 1-11.
Karoui, Noureddine E. et al., "Getting More from Digital SNP Data", Statistics in Medicine, vol. 25, Issue 18, Jan. 5, 2006, 3124-3133.
Kass, et al., "Diagnosis of Graft Coronary Artery Disease", Current Opinion in Cardiology, vol. 22, No. 2, Mar. 1, 2007, 139-145.
Kathiresan, Sekar et al., "Genome-wide Association of Early-onset Myocardial Infarction With Common Single Nucleotide Polymorphisms, Common Copy Number Variants, and Rare Copy Number Variants", Nature Genetics, vol. 41, No. 3, Mar. 1, 2009, 1-23.
Kennedy, S. R. et al., "Detecting ultralow-frequency mutations by Duplex Sequencing", Nature Protocols, vol. 9, No. 11, 2014, 2586-2606.
Kibbe, Warren A. , "Oligocalc: An Online Oligonucleotide Properties Calculator", Nucleic Acids Research, vol. 35, 2007, pp. W43-W46.
Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.
Kivioja, T. et al., "Counting absolute number of molecules using unique molecular identifiers", Nature Proceedings, Apr. 14, 2011, 18 pgs.
Kivioja, T. et al., "Counting absolute numbers of molecules using unique molecular identifiers", Nature Methods, vol. 9, No. 1, Jan. 2012, 72-76.
Kobashigawa, et al., "Multicenter Intravascular Ultrasound Validation Study Among Heart Transplant Recipients", Journal of the American College of Cardiology, vol. 45, No. 9, May 3, 2005, 1532-1537.
Koboldt, et al., "VarScan: Variant Detection in Massively Parallel Sequencing of Individual and Pooled Samples", Bioinformatics, vol. 25, No. 17, Jun. 19, 2009, 2283-2285.
Koelman, et al., "Donor-derived Soluble HLA Plasma Levels Can Not Be Used to Monitor Graft Rejection in Heart Transplant Recipients", Transplant Immunology, vol. 8, No. 1, Mar. 1, 2000, 57-64.
Koide, K. et al., "Fragmentation of cell-free fetal DNA in plasma and urine of pregnant women", Prenatal Diagnosis, vol. 25, 2005, 604-607.
Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.
Konfortov, B A. et al., "A High-Resolution HAPPY Map of Dictyostelium discoideum Chromosome 6", Genome Research, vol. 10, No. 11, Nov. 2000, 1737-1742.
Kopreski, Ms et al., "Detection of mutant K-ras DNA in plasma or serum of patients with colorectal cancer", British Journal of Cancer, vol. 76, No. 10, 1997, 1293-1299.
Koressaar, Triinu et al., "Enhancements and Modifications of Primer Design Program Primer3", Bioinformatics, vol. 23, 2007, pp. 1289-1291.
Korn, et al., "Integrated Genotype Calling and Association Analysis of SNPS, Common Copy Number Polymorphisms and Rare CNVS", Nature Genetics, vol. 40, No. 10, Oct. 1, 2008, 1253-1260.
Kuhn, H. et al., "Rolling-circle amplification under topological constraints", Nucleic Acids Research, vol. 30, No. 2, 2002, 574-580.
Lambert, et al., "Quantification of Maternal Microchimerism by HLA-Specific Real-time Polymerase Chain Reaction", Arthritis and Rheumatism, vol. 50, No. 3, Mar. 1, 2004, 906-914.
Lardeux, Frederic et al., "Optimization of a Semi-nested Multiplex PCR to Identify Plasmodium Parasites in Wild-Caught Anopheles in Bolivia, and Its Application to Field Epidemiological Studies", Transactions of the Royal Society of Tropical Medicine and Hygiene, vol. 102, 2008, pp. 485-492.
Larsen, J. B. et al., "Single-step Nested Multiplex PCR to Differentiate Between Various Bivalve Larvae", Marine Biology, vol. 146, 2005, pp. 1119-1129.
Lavebrat, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.
Lavebratt, Catharina et al., "Pyrosequencing-based SNP Allele Frequency Estimation In DNA Pools", Human Mutation, vol. 23, Issue 1, Dec. 19, 2003, 92-97.
Lavrentieva, I et al., "High Polymorphism Level of Genomic Sequences Flanking Insertion Sites of Human Endogenous Retroviral Long Terminal Repeats", FEBS Letters, vol. 443, No. 3, Jan. 29, 1999, 341-347.
Leamon, John H. et al., "A massively parallel PicoTiterPlate based platform for discrete picoliter-scale polymerase chain reactions", Electrophoresis, vol. 24, No. 21, Nov. 1, 2003, 3769-3777.
Lee, J et al., "Anchored Multiplex PCR Enables Sensitive and Specific Detection of Variants in Circulating Tumor DNA by Next-Generation Sequencing", DOI:https://doi.org/10.1016/j.cancergen.2017.04.049, Cancer Genetics 214-215, 2017, 47.
Levsky, Jeffrey M. et al., "Efficacy of Coronary Ct Angiography: Where We Are, Where We Are Going and Where We Want to Be", Journal of Cardiovascular Computed Tomography, vol. 3, Supplement 2, Nov. 2, 2009, s99-s108.
Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.
Li, et al., "Mapping Short DNA Sequencing Reads and Calling Variants Using Mapping Quality Scores", Genome Research, vol. 18, No. 11,, Aug. 19, 2008, 1851-1858.

(56) References Cited

OTHER PUBLICATIONS

Li, et al., "Multiplex Padlock Targeted Sequencing Reveals Human Hypermutable CpG Variations", Genome Research, vol. 19, No. 9, Jun. 12, 2009, 1606-1615.
Li, et al., "SOAP2: An Improved Ultrafast Tool for Short Read Alignment", Bioinformatics, vol. 25, No. 15, Aug. 1, 2009, 1966-1967.
Li, Ying et al., "Detection of Donor-specific DNA Polymorphisms in the Urine of Renal Transplant Recipients", Clinical Chemistry, vol. 49, No. 4, Apr. 1, 2003, 655-658.
Li, Ying et al., "Ready detection of donor-specific single-nucleotide polymorphisms in the urine of renal transplant recipients by matrix-assisted laser desorption/ionization time-of-flight mass spectrometry", Ying Li et al., "Ready detection of donor-specific single-nucleotide polymorphisms in the urine of renal transplant recipients by matrix-assisted laser desorption/ionization time-of-flight mass spectrometry", Clin Chem, Oct. 2005, vol. 51,Issue. 10,pp. 1903-1904, Oct. 1, 2005, 1903-1904.
Liljedahl, Ulrika et al., "Detecting Imbalanced Expression of SNP Alleles by Minisequencing on Microarrays", BMC Biotechnology, vol. 4, Article No. 24, Oct. 22, 2004, 1-10.
Lo, et al., "Next-generation Sequencing of Plasma/Serum DNA: An Emerging Research and Molecular Diagnostic Tool", Clinical Chemistry, vol. 55, No. 4, Apr. 1, 2009, 607-608.
Lo, et al., "Presence of Donor-specific Dna in Plasma of Kidney and Liver-transplant Recipients", Lancet, vol. 351, No. 9112, May 2, 1998, 1329-1330.
Lo, Y M. et al., "Circulating Nucleic Acids in Plasma and Serum: An Overview", Annals of the New York Academy of Sciences, vol. 945, Sep. 1, 2001, 1-7.
Loh, Elwyn, "Anchored PCR: Amplification with Single-sided Specificity", Methods, vol. 2, 1991, pp. 11-19.
Lui, Yanni Y. et al., "Circulating DNA in Plasma and Serum: Biology, Preanalytical Issues and Diagnostic Applications", Clinical Chemistry and Laboratory Medicine, vol. 40, No. 10, Oct. 29, 2002, 962-968.
Lui, Yanni Y. et al., "Origin of Plasma Cell-Free DNA after Solid Organ Transplantation", Clinical Chemistry, vol. 49, No. 3, Mar. 1, 2003, 495-496.
Lun, Fiona M. et al., "Microfluidics Digital PCR Reveals a Higher Than Expected Fraction of Fetal DNA in Maternal Plasma", Clinical Chemistry, vol. 54, No. 10, Aug. 14, 2008, 1664-1672.
Marguiles, M. et al., "Genome Sequencing in Open Microfabricated High Density Picoliter Reactors", Nature, vol. 437, No. 7057, Sep. 15, 2005, 376-380.
Marianes, Alexis E. et al., "Targets of Somatic Hypermutation within Immunoglobulin Light Chain Genes in Zebrafish", Immunology, vol. 132, 2010, pp. 240-255.
Maron, Jill L. et al., "Cell-free Fetal DNA Plasma Extraction and Real- time Polymerase Chain Reaction Quantification", Methods in Molecular Medicine, vol. 132, Aug. 1, 2007, 51-63.
Martinez-Lopez, J. et al., "Real-time PCR Quantification of Haematopoietic Chimerism after Transplantation: A Comparison Between TaqMan and Hybridization Probes Technologies", International Journal of Laboratory Hematology, vol. 32, Issue 1, Part 1, May 12, 2009, e17-e25.
Martins, et al., "Quantification of Donor-derived DNA in Serum: A New Approach of Acute Rejection Diagnosis in a Rat Kidney Transplantation Model", Transplantation Proceedings, vol. 37, No. 1,, Jan. 1, 2005, 87-88.
Matsubara, T. et al., "Pantropic Retroviral Vectors Integrate and Express in Cells of the Malaria Mosquito, *Anopheles gambiae*", PNAS, vol. 93, 1996, pp. 6181-6185.
Messmer, Trudy O. et al., "Application of a Nested, Multiplex PCR to Psittacosis Outbreaks", Journal of Clinical Microbiology, vol. 35, No. 8, 1997, pp. 2043-2046.
Metzker, M. L. et al., "Polymerase Chain Reaction", Encyclopedia of Medical Devices and Instrumentation, vol. 5, Second Edition, 2006, 380-387.
Metzker, M. L. et al., "Quantitation of Mixed-Base Populations of HIV-1 Variants by Automated DNA Sequencing with BODIPY Dye-Labeled Primers", BioTechniques, vol. 25, Sep. 1998, 446-462.
Meuzelaar, Linda S. et al., "Megaplex PCR: A Strategy for Multiplex Amplification", Nature Methods, vol. 4, 2007, pp. 835-837.
Meyer, M et al., "Illumina Sequencing Library Preparation for Highly Multiplexed Target Capture and Sequencing", Cold Spring Harbor Protocols, vol. 2010, Issue 6, Jun. 2010, 1-10.
Milani, et al., "Genotyping Single Nucleotide Polymorphisms by Multiplex Minisequencing Using Tag-arrays", DNA Microarrays for Biomedical Research, vol. 529, Jan. 16, 2009, 215-229.
Miramontes, Pedro et al., "DNA Dimer Correlations Reflect in Vivo Conditions and Discriminate Among Nearest-neighbor Base Pair Free Energy Parameter Measures", Physica A, vol. 321, 2003, pp. 577-586.
Mitra, S. et al., "Chapter 4 Classification Techniques", Introduction to Machine Learning and Bioinformatics, First Edition, 2008, 101-127.
Moreau, Valerie et al., "Zip Nucleic Acids: New High Affinity Oligonucleotides as Potent Primers for PCR and Reverse Transcription", Nucleic Acids Research, vol. 37, No. 19, e130, 2009, 14 pages.
Moreira, et al., "Increase in and Clearance of Cell-free Plasma DNA in Hemodialysis Quantified by Real-time PCR", Clinical Chemistry and Laboratory Medicine, vol. 44, No. 12, Dec. 13, 2006, 1410-1415.
Nakamura, N. et al., "Ex Vivo Liver Perfusion with Arterial Blood from a Pig with Ischemic Liver Failure", Artificial Organs, vol. 23, No. 2, 1999, 153-160.
Namlos, H. M. et al., "Noninvasive Detection of ctDNA Reveals Intratumor Heterogeneity and Is Associated with Tumor Burden in Gastrointestinal Stromal Tumor", Molecular Cancer Therapeutics, vol. 17, No. 11, 2018, 2473-2480.
Nawroz, H et al., "Microsatellite Alterations in Serum DNA of Head and Neck Cancer Patients", Nature Medicine, vol. 2, No. 9, Sep. 1996, 1035-1037.
Neve, B. et al., "Rapid SNP Allele Frequency Determination in Genomic DNA Pools by Pyrosequencing", BioTechniques, vol. 32, No. 5, May 1, 2002, 1138-1142.
Ng, et al., "Multiplex Sequencing of Paired-end Ditags (MS-PET): A Strategy for the Ultra-high-throughput Analysis of Transcriptomes and Genomes", Nucleic Acids Research, vol. 34, No. 12, Jul. 13, 2006, 1-10.
Nishiwaki, Morie et al., "Genotyping of Human Papillomaviruses by a Novel One-step Typing Method With Multiplex PCR and Clinical Applications", Journal of Clinical Microbiology, vol. 46, 2008, pp. 1161-1168.
Norton, S. E. et al., "A stabilizing reagent prevents cell-free DNA contamination by cellular DNA in plasma during blood sample storage and shipping as determined by digital PCR", Clin Biochem., vol. 46, No. 15, Oct. 2013, 1561-1565.
Nui, A. et al., "The Functional Integrity of a Normothermic Perfusion System Using Artificial Blood in Pig Liver", Journal of Surgical Research, Vo. 131, 2006, 189-198.
O'Connell, G. C. et al., "High Interspecimen Variability in Nucleic Acid Extraction Efficiency Necessitates the Use of Spike-In Control for Accurate qPCR-based Measurement of Plasma Cell-Free DNA Levels", Lab Medicine, vol. 48, 2017, 332-338.
Oeth, et al., "iPLEX™ Assay: Increased Plexing Efficiency and Flexibility for MassARRAY System Through Single Base Primer Extension with Mass-Modified Terminators", Sequenom Application Note Doc. No. 8876-006, Apr. 28, 2005, 1-12.
Ohara, O et al., "One-sided Polymerase Chain Reaction: The Amplification of cDNA", Proceedings of the National Academy of Sciences, vol. 86, 1989, 5673-5677.
Ohira, T. et al., "Tumor volume determines the feasibility of cell-free DNA sequencing for mutation detection in non-small cell lung cancer", Cancer Science, vol. 107, 2016, 1660-1666.
Okou, et al., "Microarray-based Genomic Selection for High-throughput Resequencing", Nature Methods, vol. 4, No. 11, Oct. 14, 2007, 907-909.

(56) References Cited

OTHER PUBLICATIONS

Okou, David T. et al., "Combining Microarray-based Genomic Selection (MGS) with the Illumina Genome Analyzer Platform to Sequence Diploid Target Regions", Annals of Human Genetics, vol. 73, No. 5, Aug. 6, 2009, 502-513.
Olerup, O. et al., "HLA-DR typing by PCR amplification with sequence-specific primers (PCR-SSP) in 2 hours: an alternative to serological DR typing in clinical practice including donor-recipient matching in cadaveric transplantation", Tissue Antigens, vol. 39, No. 5, May 1992, 225-235.
Olivarius, S et al., "High-throughput Verification of Transcriptional starting Sites by Deep-RACE", Bio Techniques, vol. 46, No. 2, Feb. 2009, 130-132.
Oliver, Dwight H. et al., "Use of Single Nucleotide Polymorphisms (SNP) and Real-time Polymerase Chain Reaction for Bone Marrow Engraftment Analysis", The Journal of Molecular Diagnostics, vol. 2, No. 4, Nov. 1, 2000, 202-208.
Olivier, et al., "The Invader Assay for SNP Genotyping", Mutation Research, vol. 573, No. 1-2, Jun. 3, 2005, 103-110.
Orsouw, et al., "Complexity Reduction of Polymorphic Sequences (Crops): A Novel Approach for Large-scale Polymorphism Discovery in Complex Genomes", PLoS ONE, vol. 11:e1172, Nov. 14, 2017, 1-10.
Owczarzy, Richard et al., "Melting Temperatures of Nucleic Acids: Discrepancies in Analysis", Biophysical Chemistry, vol. 117, 2005, pp. 207-215.
Paik, P. K. et al., "Next-Generation Sequencing of Stage IV Squamous Cell Lung Cancers Reveals an Association of P13K Aberrations and Evidence of Clonal Heterogeneity in Patients with Brain Metastases", Cancer Discovery, vol. 5, Apr. 30, 2015, 610-621.
Pakstis, et al., "Candidate SNPs for a Universal Individual Identification Panel", Human Genetics, vol. 121, No. 3-4,, Feb. 27, 2007, 305-317.
Pakstis, et al., "SNPS for Individual Identification", Forensic Science International, vol. 1, May 22, 2008, 479-481.
Palka-Santini, Maria et al., "Large Scale Multiplex PCR Improves Pathogen Detection by DNA Microarrays", BMC Microbiology, vol. 9, No. 1, 2009, 14 pages.
Panjkovich, Alejandro et al., "Comparison of Different Melting Temperature Calculation Methods for Short DNA Sequences", Bioinformatics, vol. 21, 2005, pp. 711-722.
Paruzynski, A. et al., "Genome-wide high-throughput integrome analyses by nrLAM-PCR and next-generation sequencing", Nature Protocols, vol. 5, No. 8, Jul. 8, 2010, 1379-1395.
Perakis, S. et al., "Advances in Circulating Tumor DNA Analysis", Advances in Clinical Chemistry, vol. 80, 2017, 73-153.
Pfaffl, Michael W. , "Quantification Strategies in Real-time PCR", A-Z of quantitative PCR, 2004, pp. 87-112.
Pinard, et al., "Assessment of Whole Genome Amplification-induced Bias Through High-throughput, Massively Parallel Whole Genome Sequencing", BMC Genomics, vol. 7:216, Aug. 23, 2006, 1-21.
Pourmand, et al., "Multiplex Pyrosequencing", Nucleic Acid Research, vol. 30, No. 7, Apr. 1, 2002, 1-5.
Prabhu, et al., "Overlapping Pools for High-throughput Targeted Resequencing", Genome Research, vol. 19, May 15, 2009, 1254-1261.
Profitt, J et al., "Isolation and Characterisation of Recombination Events Involving Immunoglobulin Heavy Chain Switch Regions in Multiple Myeloma Using Long Distance Vectorette PCR (Ldv-pcr)", Leukemia, vol. 13, No. 7, Jul. 1999, 1100-1107.
Puszyk, William M. et al., "Noninvasive Prenatal Diagnosis of Aneuploidy Using Cell-free Nucleic Acids in Maternal Blood: Promises and Unanswered Questions", Prenatal Diagnosis, vol. 28, No. 1, Nov. 16, 2007, 1-6.
Qiagen, , "QIAamp DNA Mini Kit and QIAamp DNA Blood Mini Kit Handbook", QIAamp DNA Mini Kit and QIAamp DNA Blood Mini Kit Handbook, Feb. 2003 ("Qiagen (2003)"), 2003, 68 pages.
Raindance Technologies, et al., "RainDance Technologies Introduces the RDT 1000", RainDance Technologies, Nov. 12, 2008.
Ravipati, Goutham et al., "Comparison of Sensitivity, Specificity, Positive Predictive Value, and Negative Predictive Value of Stress Testing Versus 64-Multislice Coronary Computed Tomography Angiography in Predicting Obstructive Coronary Artery Disease Diagnosed by Coronary Angiogr", The American Journal of Cardiology, Coronary Artery Disease. vol. 101, Issue 6, Mar. 15, 2008, 774-775.
Roche Diagnostics, et al., "Versatile Nucleic Acid Purification", MagnaPure Manual, Feb. 3, 2012.
Ross, P. et al., "Quantitative Approach to Single-Nucleotide Polymorphism Analysis Using MALDI-TOF Mass Spectrometry", BioTechniques, vol. 29, Sep. 2000, 620-629.
Rothberg, et al., "The Development and Impact of 454 Sequencing", Nature Biotechnology, vol. 26, No. 10, Oct. 9, 2008, 1117-1124.
Rubio, J. M. et al., "Semi-nested, Multiplex Polymerase Chain Reaction for Detection of Human Malaria Parasites and Evidence of Plasmodium Vivax Infection in Equatorial Guinea", The American Journal of Tropical Medicine and Hygiene, vol. 60, 1999, pp. 183-187.
Ruschendorf, et al., "Alohomora: A Tool for Linkage Analysis Using 10K SNP Array Data", Bioinformatics Applications Notes, vol. 21, No. 9, Jan. 12, 2005, 2123-2125.
Sanger, et al., "Nucleotide Sequence of Bacteriophage Lambda DNA", Journal of Molecular Biology, vol. 162, No. 4, Dec. 25, 1982, 729-773.
Santalucia, Jr., J. , "Physical Principles and Visual-OMP Software for Optimal PCR Design", Methods in Molecular Biology, vol. 402, 2007, 3-33.
Schaaf, C. P. et al., "Copy Number and SNP Arrays in Clinical Diagnostics", Annu. Rev. Genomics Hum. Genet., vol. 12, 2011, 25-51.
Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.
Schwarzenbach, H. et al., "Detection and Characterization of Circulating Microsatellite-DNA in Blood of Patients with Breast Cancer", Ann. N.Y. Acad. Sci., vol. 1022, 2004, 25-32.
Shapero, M. H. et al., "MARA: A Novel Approach for Highly Multiplexed Locus-specific SNP Genotyping Using High-density DNA Oligonucleotide Arrays", Nucleic Acids Research, vol. 32, No. 22, 2004, 1-9.
Sharples, et al., "Diagnostic Accuracy of Coronary Angiography and Risk Factors for Post-heart-transplant Cardiac Allograft Vasculopathy", Transplantation, vol. 76, No. 4, Aug. 27, 2003, 679-682.
Shyamala, Venkatakrishna et al., "Genome Walking by Single-Specific-Primer Polymerase Chain Reaction: SSP-PCR", Gene, vol. 84, 1989, pp. 1-8.
Singh, Vinayak K. et al., "PCR Primer Design", Molecular Biology Today, vol. 2, 2001, pp. 27-32.
Smith, et al., "Rapid Whole-genome Mutational Profiling using Next-generation Sequencing Technologies", Genome Research, vol. 18, Sep. 4, 2008, 1638-1642.
Smith, James F. et al., "Cell-free Fetal DNA in Maternal Plasma", Neo Reviews, vol. 9, No. 8, Aug. 1, 2008, e332-e337.
Solexa, "Application Note: DNA Sequencing", 2006, 1-2.
Sorenson, G. D. et al., "Soluble Normal and Mutated DNA Sequences from Single-Copy Genes in Human Blood", Cancer Epdemiology, Biomarkers & Prevention, vol. 3, Jan./Feb. 1994, 67-71.
Spes, et al., "Diagnostic and Prognostic Value of Serial Dobutamine Stress Echocardiography for Noninvasive Assessment of Cardiac Allograft Vasculopathy: A Comparison With Coronary Angiography and Intravascular Ultrasound", Circulation, vol. 100, No. 5, Aug. 3, 1999, 509-515.
Spindler, K.L. G. et al., "Cell-free DNA in healthy individuals, noncancerous disease and strong prognostic value in colorectal cancer", International Journal of Cancer, vol. 135, 2014, 2984-2991.
Spindler, K.-L. G. et al., "Cell-Free DNA in Metastatic Colorectal Cancer: A Systematic Review and Meta-Analysis", The Oncologist, vol. 22, 2017, 1049-1055.

(56) References Cited

OTHER PUBLICATIONS

Stewart, S. et al., "Revision of the 1990 Working Formulation for the Standardization of Nomenclature in the Diagnosis of Heart Rejection", The Journal of Heart and Lung Transplantation, vol. 24, No. 11, Nov. 2005, 1710-1720.

Stiller, et al., "Direct Multiplex Sequencing (DMPS)—A Novel Method for Targeted High-thoroughput Sequencing of Ancient and Highly Degraded DNA", Genome Research, vol. 19, No. 10, Jul. 27, 2009, 1843-1848.

Stolerman, Elliot S. et al., "Haplotype structure of the ENPP1 Gene and Nominal Association of the K121Q missense single nucleotide polymorphism with glycemic traits in the Framingham Heart Study", Diabetes, vol. 57, Issue 7, Jul. 1, 2008, 1971-1977.

Stone, J. P. et al., "Ex Vivo Normothermic Perfusion Induces Donor-Derived Leukocyte Mobilization and Removal Prior to Renal Transplantation", Kidney Int Rep., vol. 1, No. 4, Aug. 6, 2016, 230-239.

Swarup, V. et al., "Circulating (cell-free) nucleic acids—A promising, non-invasive tool for early detection of several human diseases", FEBS Letters, vol. 581, 2007, 795-799.

Takala, et al., "A High-throughput Method for Quantifying Alleles and Haplotypes of the Malaria Vaccine Candidate Plasmodium Falciparum Merozoite Surface Protein-1 19 kDa", Malaria Journal, vol. 5:31, Apr. 20, 2006, 1-10.

Thompson, J. C. et al., "Detection of Therapeutically Targetable Driver and Resistance Mutations in Lung Cancer Patients by Next-Generation Sequencing of Cell-Free Circulating Tumor DNA", Clin Cancer Res, vol. 22, No. 23, Dec. 1, 2016, 5772-5782.

Thornton, Brenda et al., "Real-time Pcr (qPCR) Primer Design Using Free Online Software", Biochemistry and Molecular Biology Education, vol. 39, 2011, pp. 145-154.

Tong, et al., "Diagnostic Developments Involving Cell-free (Circulating) Nucleic Acids", Clinica Chimica Acta, vol. 363, No. 1-2, Aug. 26, 2005, 187-196.

Toshikazu, et al., "Estimation of Haplotype Frequencies, Linkage-disequilibrium Measures, and Combination of Haplotype Copies in Each Pool by Use of Pooled DNA Data", American Journal of Human Genetics, vol. 72, Jan. 17, 2003, 384-398.

Tounta, G et al., "Non-invasive prenatal diagnosis using cell-free fetal nucleic acids in maternal plasma: Progress overview beyond predictive and personalized diagnosis", EPMA Journal, vol. 2, Issue 2, 2011, 163-171.

Treff, N. R. et al., "Single Cell Whole Genome Amplification Technique Significantly Impacts the Accuracy and Precision of Microarray Based 23 Chromosome Aneuploidy Screening", Poster Presentations Preimplantation Genetic Diagnosis, vol. 88, Supplement 1, Sep. 1, 2007, S231.

Troeger, C. et al., "Approximately Half of the Erythroblasts in Maternal Blood are of Fetal Origin", Molecular Human Reproduction, vol. 5, No. 12, Dec. 1, 1999, 1162-1165.

Troutt, et al., "Ligation-anchored PCR: A Simple Amplification Technique with Single-sided Specificity", Proceedings of the National Academy of Sciences, vol. 89, Oct. 1992, 9823-9825.

Tsang, Jason C. et al., "Circulating Nucleic Acids in Plasma/Serum", Pathology, vol. 39, No. 2, Apr. 1, 2007, 197-207.

Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.

Tuzcu, et al., "Intravascular Ultrasound Evidence of Angiographically Silent Progression in Coronary Atherosclerosis Predicts Long-term Morbidity and Mortality After Cardiac Transplantation", The American Journal of Cardiology, vol. 45, No. 9, May 3, 2005, 1538-1542.

Umetani, N. et al., "Increased Integrity of Free Circulating DNA in Sera of Patients with Colorectal or Periampullary Cancer: Direct Quantitative PCR for ALU Repeats", Clinical Chemistry, vol. 52, No. 6, 2006, 1062-1069.

Urbanova, M. et al., "Circulating Nucleic Acids as a New Diagnostic Tool", Cellular & Molecular Biology Letters, vol. 15, 2010, 242-259.

Vallone, Peter M. et al., "Demonstration of Rapid Multiplex PCR Amplification Involving 16 Genetic Loci", Forensic Science International: Genetics, vol. 3, 2008, pp. 42-45.

Vanneste, Marion et al., "Functional Genomic Screening Independently Identifies CUL3 as a Mediator of Vemurafenib Resistance via Src-RAC1 Signaling Axis", Frontiers in Oncology, vol. 10, 2020, 16 pages.

Verlaan, et al., "Allele-specific Chromatin Remodeling in the ZPBP22/GSDMB/ORMDL3 Locus Associated with the Risk of Asthma and Autoimmune Disease", The American Journal of Human Genetics, vol. 85, No. 3, Sep. 11, 2009, 377-393.

Verlaan, et al., "Targeted Screening of Cis-Regulatory Variation in Human Haplotypes", Genome Research, vol. 19, No. 1, Jan. 1, 2009, 118-127.

Vlaminck, I. D. et al., "Circulating Cell-Free DNA Enables Non-invasive Diagnosis of Heart Transplant Rejection", Sci Transl Med., vol. 6, No. 241, Jun. 18, 2018, 26 pages.

Voelkerding, et al., "Next-generation Sequencing: From Basic Research to Diagnostics", Clinical Chemistry, vol. 55, No. 4, Apr. 1, 2009, 641-658.

Von Ahsen, Nicolas et al., "Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas", Clinical Chemistry, vol. 47, 2001, pp. 1956-1961.

Wartell, Roger M. et al., "Thermal Denaturation of DNA Molecules: A Comparison of Theory with Experiment", Physics Reports, vol. 126, 1985, pp. 67-107.

Wasson, Jon et al., "Assessing Allele Frequencies of Single Nucleotide Polymorphisms in DNA Pools by Pyrosequencing Technology", BioTechniques, vol. 32, No. 5, May 1, 2002, 1144-1152.

Watt, Heather L. , "Sex Diagnosis of Preimplantation Porcine Embryos through PCR Amplification of the Sry Gene", Sex Diagnosis of Preimplantation Porcine Embryos Through PCR Amplification of the SRY Gene (1998) ("Watt (1998)"), 1998, 151 pages.

Wei, Ting et al., "Novel Approaches to Mitigate Primer Interaction and Eliminate Inhibitors in Multiplex PCR, Demonstrated Using an Assay for Detection of three Strawberry Viruses", Journal of Virological Methods, vol. 151, 2008, pp. 132-139.

Wellnhofer, et al., "Angiographic Assessment of Cardiac Allograft Vasculopathy: Results of a Consensus Conference of the Task Force for Thoracic Organ Transplantation of the German Cardiac Society", Transplant International, vol. 23, No. 11, Aug. 19, 2010, 1094-1104.

Wiedmann, Ralph T. et al., "SNP Discovery in Swine by Reduced Representation and High Throughput Pyrosequencing", BMC Genetics, vol. 9, Article No. 81, Dec. 4, 2008, 1-7.

Wilkening, Stefan et al., "Determination of Allele Frequency in Pooled DNA: Comparison of Three PCR-based Methods", Bio Techniques, vol. 39, No. 6, May 30, 2005, 853-857.

Wilkinson, Sarah T. et al., "Decreased MHC Class II Expression in Diffuse Large B-Cell Lymphoma does not Correlate with CPG Methylation of Ciita Promoters III and IV", Leuk Lymphoma, vol. 50, 2009, pp. 1875-1878.

Witherspoon, David J. et al., "Mobile Element Scanning (Me-scan) by Targeted High-throughput Sequencing", BMC Genomics, vol. 410, 2010, 15 pages.

Wong, K. H. et al., "Multiplex Illumina Sequencing Using DNA Barcoding", Current Protocols in Molecular Biology, vol. 101, Jan. 2013, 7.11.1-7.11.11.

Wright, Caroline et al., "Cell-free Fetal Nucleic Acids for Noninvasive Prenatal Diagnosis", PHG Foundation, Jan. 1, 2009, 1-64.

Xia, et al., "Simultaneous Quantitative Assessment of Circulating Cell-free Mitochondrial and Nuclear DNA by Multiplex Real-time PCR", Genetics and Molecular Biology, vol. 32, No. 1, Mar. 1, 2009, 20-24.

Xian, et al., "Advances on Circulating Fetal DNA in Maternal Plasma", Chinese Medical Journal, vol. 120, No. 14, Jul. 2, 2007, 1256-1259.

(56) References Cited

OTHER PUBLICATIONS

Xie, et al., "CNV-SEQ, A New Method to Detect Copy Number Variation Using Highthroughput Sequencing", BMC Bioinformatics, vol. 10:80, Mar. 6, 2009, 1-9.
Xue, et al., "Optimizing the Yield and Utility of Circulating Cell-free DNA From Plasma and Serum", Clinica Chimica Acta, vol. 404, No. 2, Jun. 27, 2009, 100-104.
Yang, Lin et al., "64-MDCT Coronary Angiography of Patients With Atrial Fibrillation: Influence of Heart Rate on Image Quality and Efficacy in Evalution of Coronary Artery Disease", AJR, vol. 193, No. 3, Sep. 1, 2009, 795-801.
Yijen, et al., "Noninvasive Evaluation of Cardiac Allograft Rejection by Cellular and Functional Cardiac Magnetic Resonance", JACC: Cardiovacular Imaging, vol. 2, No. 6, Jun. 1, 2009, 731-741.
Yilmaz, A. et al., "Comparative Evaluation of Left and Right Ventricular Endomyocardial Biopsy", Circulation, vol. 122, No. 9, Aug. 31, 2010, 900-909.
Yuanxin, Yan et al., "T-linker-specific Ligation PCR (T-linker Pcr): An Advanced PCR Technique for Chromosome Walking or for Isolation of Tagged DNA Ends", Nucleic Acids Research, vol. 31, No. 12, e68, 2003, 7 pages.
Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.
Zhang, et al., "Use of PCR and PCR-SSP for Detection of Urinary Donor-Origin Dna in Renal Transplant Recipients With Acute Rejection", Chinese Medical Journal, vol. 116, No. 2, Feb. 2003, 191-194.
Zhang, Kun et al., "Digital RNA Alleotyping Reveals Tissue-specific and Allele-specific Gene Expression in Human", Nature Methods, vol. 6, No. 8, Jul. 20, 2009, 613-618.
Zhao, et al., "Urinary Thromboxane B2 in Cardiac Transplant Patients as a Screening Method of Rejection", Prostaglandins, vol. 54, No. 6, Dec. 1, 1997, 881-889.
Zheng, Z et al., "Anchored Multiplex PCR for Targeted Next-generation Sequencing", Nature Medicine, vol. 20, No. 12, Dec. 2014, 1479-1486.
Zhong, X Y. et al., "Detection of Fetal Rhesus D and Sex Using Fetal DNA from Maternal Plasma by Multiplex Polymerase Chain Reaction", British Journal of Obstetrics and Gynaecology, vol. 107, Jun. 2000, 766-769.
Zhong, Xiao Y. et al., "Cell-free DNA in Urine: A Marker for Kidney Graft Rejection, but Not for Prenatal Diagnosis ?", Annals of the New York Academy of Sciences, vol. 945, Sep. 1, 2001, 250-257.
Zhou, et al., "Pyrosequencing, A High-throughput Method for Detecting Single Nucleotide Polymorphisms in the Dihydrofolate Reductase and Dihydropteroate Synthetase Genes of Plasmodiym Falciparum", Journal of Clinical Microbiology, vol. 44, No. 11, Nov. 1, 2006, 3900-3910.
Zimmer, et al., "Transplant Coronary Artery Disease", JACC: Cardiovascular Interventions, vol. 3, No. 4, Apr. 1, 2010, 367-377.
Ahmadian, A. et al., "Analysis of the p53 Tumor Suppressor Gene by Pyrosequencing", BioTechniques, vol. 28, Jan. 2000, 140-147.
Bau, Stephan et al., "Targeted next-generation sequencing by specific capture of multiple genomic loci using low-volume microfluidic DNA arrays", Anal Bioanal Chem, vol. 393, 2009, 171-175.
Benesova, et al., "Mutation-based detection and monitoring of cell-free tumor DNA in peripheral blood of cancer patients", Analytical Biochemistry, vol. 433, 2013, 227-234.
Birkenkamp-Demtroder, et al., "Longitudinal assessment of multiplex patient-specific ctDNA biomarkers in bladder cancer for diagnosis, surveillance and recurrence", Annals of Oncology, Oxford University Press NLD, vol. 29, No. Supplement 8, 2018, viii26.
Bolotin, D. A. et al., "MIXCR: software for comprehensive adaptive immunity profiling", Nature, vol. 12, No. 5, May 2015, 380-381.
Brochet, X. et al., "IMGT/V-QUEST: the highly customized and integrated system for IG and TR standardized V-J and V-D-J sequence analysis", Nucleic Acids Research, vol. 36, May 23, 2008, W503-W508.

Bunnapradist, S. et al., "Using both the fraction and Quantity of Donor-Derived Cell-free DNA to Detect Kidney Allograft Rejection", JASN, vol. 32, 2021, 2439-2441.
Burnham, P. et al., "Single-stranded DNA library preparation uncovers the origin and diversity of ultrashort cell-free DNA in plasma", Scientific Reports, vol. 6, No. 27859, Jun. 14, 2016, 9 pages.
Cawkwell, L. et al., "Rapid detection of allele loss in colorectal tumours using microsatellites and fluorescent DNA technology", Br. J. Cancer, vol. 67, 1993, 1262-1267.
Chen, et al., "Non-invasive prenatal diagnosis using fetal DNA in maternal plasma: a preliminary study for identification of paternally-inherited alleles using single nucleotide polymorphisms", BMJ Open, 5(7), 2015, 1-8.
Chothia, C. et al., "Canonical structures for the hypervariable regions of immunoglobulins", Journal of Molecular Biology, vol. 196, No. 4, Aug. 20, 1987, 901-917.
Chun, et al., "Dual priming oligonucleotide system for the multiplex detection of respiratory viruses and SNP genotyping of CYP2C19 gene", Nucleic Acids Research, vol. 35, No. 6, 2007, 1-6.
Costa, J.-M. et al., "Fetal RHD genotyping in maternal serum during the first trimester of pregnancy", British Journal of Haematology, vol. 119, 2002, 255-260.
Croft, Jr., Daniel et al., "Performance of Whole-Genome Amplified DNA Isolated from Serum and Plasma on High-Density Single Nucleotide Polymorphism Arrays", Journal of Molecular Diagnostics, 10(3), 2008, 249-257.
Daniels, G. et al., "Fetal blood group genotyping from DNA from maternal plasma: an important advance in the management and prevention of haemolytic disease of the fetus and newborn", Vox Sanguinis, vol. 87, 2004, 223-232.
Deusen, et al., "Comprehensive Detection of Driver Mutations in Acute Myeloid Leukemia Including Internal Tandem Duplications with Anchored Multiplex PCR and Next-Generation Sequencing", Blood, vol. 128, No. 22, 2016, 5251.
Diaz, et al., "Liquid Biopsies: Genotyping Circulating Tumor DNA", Journal of Clinical Oncology, vol. 32, No. 6, 2014, 579-586.
Diehl, et al., "Detection and quantification of mutations in the plasma of patients with colorectal tumors", Proceedings of the National Academy of Sciences, vol. 102, 2005, 16368-16373.
Ehlayel, A. et al., "Emerging monitoring technologies in kidney transplantation", Pediatric Nephrology, vol. 36, 2021, 3077-3087.
Findlay, I. et al., "Allelic drop-out and preferential amplification in single cells and human blastomeres: implications for preimplantation diagnosis of sex and cystic fibrosis", Molecular Human Reproduction, vol. 1, 1995, 1609-1618.
Glaab, W. E. et al., "A novel assay for allelic discrimination that combines the fluorogenic 5' nuclease polymerase chain reaction (TaqMan) and mismatch amplification mutation assay", Mutation Research, vol. 430, 1999, 12 pgs.
Grenda, R. , "Torque teno (TTV) viral load as a biomarker of immunosuppressive strength after kidney transplantation in children", Pediatric Nephrology, vol. 36, May 27, 2020, 3 pages.
Gusella, J. et al., "Precise localization of human B-globin gene complex on chromosome 11", Proc. Natl. Acad. Sci USA, vol. 76, No. 10, Oct. 1979, 5239-5243.
Hainer & Fazzio, "High-Resolution Chromatin Profiling Using Cut&Run", Current Protocols in Molecular Biology, 2019, 1-22.
Hiendleder, et al., "Functional genomics: tools for improving farm animal health and welfare", Rev. Sci. Tech. Off. Int. Epiz., 24 (1), 2005, 354-377.
Illumina, "HumanOmni1-Quad BeadChip", Illumina DNA Analysis, Pub. No. 370-21009-007, 2009, 1 page.
Illumina, "HumanOmni2.5-8 BeadChips: Next-Generation GWAS Content for Genotyping and CNV Analysis", Data Sheet: DNA Analysis, Pub. No. 370-2011-008, 2011, 1 page.
Illumina, "Illumina Adapter Sequences", Published by Illumina, 2018, 1-45.
Jordens, et al., "Amplification with molecular beacon primers and reverse line blotting for the detection and typing of human papillomaviruses", Journal of Virological Methods, vol. 89, 2000, 29-37.
Kaboev, et al., "PCR hot start using primers with the structure of molecular beacons (hairpin-like structure)", Nucleic Acids Research, vol. 28, 2000, 1-2.

(56) References Cited

OTHER PUBLICATIONS

Keshavjee, S. H. et al., "The role of dextran 40 and potassium in extended hypothermic lung preservation for transplantation", The Journal of Thoracic and Cardiovascular Surgery, vol. 103, No. 2, 1992.

Kittler, R. et al., "A Whole Genome Amplification Method to Generate Long Fragments from Low Quantities of Genomic DNA", Analytical Biochemistry, vol. 300, 2002, 237-244.

Ku, et al., "Exome versus transcriptome sequencing in identifying coding region variants", Expert Review of Molecular Diagnostics, vol. 12, 2012, 241-251.

Kulifaj, D. et al., "Development of a standardized real time PCR for Torque teno viruses (TTV) viral load detection and quantification: A new tool for immune monitoring", Journal of Clinical Virology, vol. 105, 2018, 118-127.

Lajoie, B. R. et al., "The Hitchhiker's Guide to Hi-C Analysis: Practical guidelines", Methods: Author manuscript, vol. 72, Jan. 2015, 65-75.

Landegren, U. et al., "Reading Bits of Genetic Information: Methods for Single-Nucleotide Polymorphism Analysis", Genome Research, vol. 8, No. 8, 769-776, 1997.

Lo, Y.M. D et al., "Prenatal Diagnosis of Fetal RhD Status by Molecular Analysis of Maternal Plasma", The New England Journal of Medicine, vol. 339, No. 24, 1998, 1734-1738.

Marusyk, et al., "Causes and consequences", Biochimica et Biophysica Acta, vol. 1805, 2010, 105-117.

Namlos, H.M. et al., "Use of liquid biopsies to monitor disease progression in a sarcoma patient: a case report", BMC Cancer, vol. 17, No. 1, 2017, 2-3.

Nelson, C. M. et al., "Whole genome transcription profiling of Anaplasma phagocytohilum in human and tick host cells by tiling array analysis", BMC Genomics, vol. 9, No. 364, Jul. 31, 2008, 16 pgs.

Nilsson, et al., "Analyzing genes using closing and replicating circles", Trends in Biotechnology, 24, 2006, 83-88.

Ohya, K. et al., "Detection of the CTG Repeat Expansion in Congenital Myotonic Dystrophy", Jpn J. Human Genet, vol. 42, 1997, 169-180.

Raemdonck, Dirk Van et al., "Ex-vivo lung perfusion", Transplant International, vol. 28, Issue 6, Special Issue: Focus Issue: Machine Perfusion, 2014, 643-656.

Rechitsky, S. et al., "Allele Dropout in Polar Bodies and Blastomeres", Journal of Assisted Reproduction and Genetics, vol. 15, No. 5, 1998, 253-257.

Schutz, E. et al., "Graft-derived cell-free DNA, a noninvasive early rejection and graft damage marker in liver transplantation: A prospective, observational, multicenter cohort study", PLOS Medicine, vol. 14, No. 4, Apr. 25, 2017, 19 pgs.

Selzner, Markus et al., "Normothermic Ex Vivo Liver Perfusion Using Steen Solution as Perfusate for Human Liver Transplantation: First North American Results", Liver Transplantation, vol. 22, Issue 11, 2016.

Sethi, Himanshu et al., "Analytical validation of the Signatera (TM) RUO assay, a highly sensitive patient-specific multiplex PCR NGS-based noninvasive cancer recurrence detection and therapy monitoring assay", Cancer Research, vol. 78, No. 13, 2018, 4542.

Tie, et al., "Circulating tumor DNA as an early marker of therapeutic response in patients with metastatic colorectal cancer", Annals of Oncology, vol. 26, No. 8, 2015, 1715-1722.

Toth, T. et al., "Prenatal Detection of Trisomy 13 From Amniotic Fluid by Quantitative Fluorescent Polymerase Chain Reaction", Prenatal Diagnosis, vol. 18, 1998, 669-674.

Tungwiwat, et al., "Non-invasive fetal sex determination using a conventional nested PCR analysis of fetal DNA in maternal plasma", Clinica Chimica Acta, vol. 334, No. 1-2, 2003, 173-177.

Ventura-Aguiar, P. et al., "Donor-derived Cell-free DNA Shows High Sensitivity for the Diagnosis of Pancreas Graft Rejection in Simultaneous Pancreas-Kidney Transplantation", Transplantation, vol. 00, No. 00, 2022, 8 pages.

Volckmar, et al., "A field guide for cancer diagnostics using cell-free DNA: From principles to practice and clinical applications", Genes Chromosomes Cancer, 2018, 123-139.

Wagner, F. F. et al., "RHD gene deletion occurred in the Rhesus box", Blood, vol. 95, No. 12, 2000, 3662-3668.

Wang, et al., "Molecular inversion probes: a novel microarray technology and its application in cancer research", Cancer Genetics, 205, 2012, 341-355.

Wangkumhang, P. et al., "WASP: a Web-based Allele-Specific PCR assay designing tool for detecting SNPs and mutations", BMC Genomics, vol. 8, No. 275, Aug. 14, 2007, 9 pgs.

Whitlam, J. B. et al., "Diagnostic application of kidney allograft-derived absolute cell-free DNA levels during transplant dysfunction", Am J Transplant, vol. 19, 2019, 1037-1049.

Ye, et al., "Primer-BLAST: a tool to design target-specific primers for polymerase chain reaction", BMC Bioinformatics, 13:134, 2012, 11 pages.

Benn, Peter et al., "Current Controversies in Prenatal Diagnosis 2: NIPT results suggesting maternal cancer should always be disclosed", Prenetal Diagnosis, vol. 39, No. 5, 2018, 339-343.

Bianchi, Diana W. et al., "Noninvasive Prenatal Testing and Incidental Detection of Occult Maternal Malignancies", JAMA The Journal of the American Medical Association, vol. 314, No. 2, 2015, 162.

Chen, Ke et al., "Multiplex PCR with the Blunt Hairpin Primers for Next Generation Sequencing", Biotechnology and Bioprocess Engineering, vol. 22, 2017, 347-351.

Chung, et al., "Cell-free DNA fetal fraction and pregnancy outcome", American Journal of Obstetrics & Gynecology, vol. 222, No. 1, 2019, S157.

Dharajiya, Nilesh et al., "Incidental Detection of Maternal Neoplasia in Noninvasive Prenatal Testing", Clinical Chemistry, vol. 64, No. 2, 2018, 329-335.

Ji, Xing et al., "Copy number variation profile in noninvasive prenatal testing (NIPT) can identify co-existing maternal malignancies: Case reports and a literature review", Taiwanese Journal of Obstetrics and Gynecology, vol. 57, No. 6, 2018, 871-877.

Lenaerts, Liesbeth et al., "Noninvasive Prenatal Testing and Detection of Occult Maternal Malignancies", Clinical Chemistry, vol. 65, No. 12, 2019, 1484-1486.

Lin, et al., "A new diagnostic system for ultra-sensitive and specific detection and quantification of Candidatus Liberibacter asiaticus, the bacterium associated with citrus Huanglongbing", J Microbial Methods, 2010, 17-25.

Livergood, "Adverse perinatal outcomes and cell free DNA no calls: Beyond low fetal fraction", American Journal of Obstetrics & Gynecology, vol. 218, No. 1, 2018, S169.

Llop, et al., "Development of a highly sensitive nested-PCR procedure using a single closed tube for detection of Erwinia amylovora in asymptomatic plant material", Appl Environ Microbial., 2000, 2071-8.

Margulies, et al., "Genome Sequencing in Open Microfabricated High Density Picoliter Reactors", Nature, 437(7057), 2005, 376-380.

Norton, et al., "Perinatal and genetic outcomes associated with no call cfDNA results in 18,496 pregnancies", American Journal of Obstetrics & Gynecology, vol. 224, No. 2, 2021, S3.

Scheffer, et al., "Association between low fetal fraction in cell-free DNA testing and adverse pregnancy outcome: A systematic review", Prenatal Diagnosis, vol. 41, No. 10, 2021, 1287-1295.

Sigdel, Tara et al., "Optimizing Detection of Kidney Transplant Injury by Assessment of Donor-Derived Cell-Free DNA via Massively Multiplex PCR", Journal of Clinical Medicine, vol. 8, No. 1, 2018, 19.

Sigdel, Tara et al., "Plasma Donor-Derived Cell-Free DNA Quantification by massively multiplex PCR Distinguishes Kidney Transplant Acute Rejection", Transplantation, vol. 102, No. 7s, 2018, s178-s179.

Thermofisher Scientific, "How Ion AmpliSeq Targeted Sequencing Technology Works", https://www.thermofisher.com/us/en/home/life-science/ sequencing/next-generation-sequencing/ion-torrent-next-

(56) References Cited

OTHER PUBLICATIONS generation-sequencing-workflow/ion-torrent-next-generation-sequencing-select-targets/ampliseq-target-selection/how-ampliseq-technology-work.
Wang, et al., "DNA Degradation Test Predicts Success in Whole-Genome Amplification from Diverse Clinical Samples", Journal of Molecular Diagnostics, vol. 9, 2007, 441-451.
Xie, et al., "Designing highly multiplex PCR primer sets with Simulated Annealing Design using Dimer Likelihood Estimation (SADDLE )", Nat Commun., 2022, 1881.
Bewersdorf, Jan Philipp et al., "From clonal hematopoiesis to myeloid leukemia and what happens in between: Will improved understanding lead to new therapeutic and preventive opportunities?", Blood Reviews, vol. 37, 2019, 6.
Coombs, Catherine et al., "Therapy-Related Clonal Hematopoiesis in Patients with Non-hematologic Cancers Is Common and Associated with Adverse Clinical Outcomes", Cell Stem Cell, vol. 21, No. 3, 2017, 374.
Giulio, Genovese et al., "Hematopoiesis and Blood-Cancer Risk Inferred from Blood DNA Sequence", The New England Journal of Medicine, vol. 371, No. 26, 2014, 2477-2487.
Jaiswal, Siddhartha et al., "Clonal hematopoiesis in human aging and disease", Science, vol. 366, No. 6465, 2019, 4.
Kiyomi, Morita et al., "Clearance of Somatic Mutations at Remission and the Risk of Relapse in Acute Myeloid Leukemia", J Clin Oncol, vol. 36, No. 18, 2018, 1788-1797.
Maheswaran, S. et al., "Detection of Mutations in EGFR in Circulating Lung-Cancer Cells", N Engl J Med, vol. 359, No. 4, Jul. 24, 2008, 366-377.
Steensma, D. P. et al., "Clonal hematopoiesis of indeterminate potential and its distinction from myelodysplastic syndromes", Blood, vol. 126, No. 1, 2015, 9-16.
Vandekerkhove, G et al., "Circulating Tumor DNA Reveals Clinically Actionable Somatic Genome of Metastatic Bladder Cancer", Clinical Cancer Research, 2017, 6487-6497.
Yamauchi Medical Clinic, "Chromosome abnormality", http://www.yamauchi-iin.com/kaisetu/1241.htm, (Dec. 10, 2015 updated), Dec. 10, 2015, 3 pages.
Abbosh, et al., "Phylogenetic ctDNA analysis depicts early-stage lung cancer evolution", Nature, 2017, 446-453.
Blomquist, et al., "Targeted RNA-Sequencing with Competitive Multiplex-PCR Amplicon Libraries", PLOS ONE, 2013, vol. 8, Issue 11.
Chang, et al., "Identification of individual DNA molecule of *Mycobacterium tuberculosis* by nested PCR-RLFP and capillary electrophoresis", National Library of Medicine, 2008, 182-8.
Fire, et al., "Rolling replication of short DNA circles", PNAS, 1995, 4641-4645.
Kane, et al., "Application of less primer method to PCR", DNA Polymorphism, 2004, vol. 13, pp. 34-37.
Khater & Khauli, "Pseudorejection and true rejection after kidney transplantation: classification and clinical significance", Urol Int., 90(4), 2012, 373-80.
Koeppe, et al., "HIV-1-Specific CD4+ T-Cell Responses Are Not Associated With Significant Viral Epitope Variation in Persons With Persistent Plasma Viremia", J Acquir Immune Defic Syndr, 2006, 41:140-148.
Krishnakumar, S. et al., "A comprehensive assay for targeted multiplex amplification of human DNA sequences", PNAS, vol. 105, No. 27, Jul. 8, 2008, 9296-9301.
Lizardi, et al., "Mutation detection and single-molecule counting using isothermal rolling-circle amplification", Nature Genetics, 1998, 225-232.
Mamanova, L. et al., "Target-enrichment strategies for next-generation sequencing", Nat Methods, vol. 7, 2010, 111-118.
Mamun, et al., "The *Escherichia coli* UVM response is accompanied by an SOS-independent error-prone DNA replication activity demonstrable in vitro", Molecular Microbiology, 2000, 368-380.
Metzker, Michael, Declaration of Michael L. Metzker, Ph.D. from IPR2018-01317, 2004.
Mueller, P. R. et al., "In Vivo Footprinting of a Muscle Specific Enhancer by Ligation Mediated PCR", Science, vol. 249, Nov. 10, 1989, 780-786.
No Author Listed, "Jury Rules in Favor of Natera, Finding All Asserted Patents Valid and Infrindged by ArcherDX/Invitae; Awards $19.35 Million in Past Damages for Royalties and Lost Profits", Natera Press Release, 2023, 4 pgs.
No Author Listed, "*Natera Inc.* vs. *ArcherDx* Verdict Form, Case 1:20-cv-00125-GBW", 2023, 1-12.
Peng, Q et al., "Reducing amplification artifacts in high multiplex amplicon sequencing by using molecular barcodes", BMC Genomics, vol. 16. No. 586, 2015, 12 pages.
Reinert, et al., "Analysis of Plasma Cell-Free DNA by Ultradeep Sequencing in Patients With Stages I to UI Colorectal Cancer", JAMA Oncology, 2019, 1-74.
Stone, J. P. et al., "Altered Immunogenicity of Donor Lungs via Removal of Passenger Leukocytes Using Ex Vivo Lung Perfusion", American Journal of Transplantation, vol. 16, 2016, 33-43.
Valenza, F. et al., "The Consumption of Glucose During Ex Vivo Lung Perfusion Correlates with Lung Edema", Transplantation Proceedings, vol. 43, 2011, 993-996.
18820195.8, "Extended European Search Report", (M1290.70015EP00), mailed Jan. 27, 2021, 9 pages.
18821381.3, "Extended European Search Report", (M1290.70021EP00), mailed Feb. 15, 2021, 9 pages.
Adamek, Martina et al., "A fast and simple method for detecting and quantifying donor-derived cell-free DNA in sera of solid organ transplant recipients as a biomarker for graft function", Clinical Chemistry and Laboratory Medicine : Journal of the Forum of the European Societies of Clinical Chemistry, vol. 54, No. 7, doi:10.1515/CCLM-2015-0622, ISSN 1437-4331, (Jul. 1, 2016), pp. 1147-1155.
Agbor-Enoh, et al., "Applying rigor and reproducibility standards to assay donor-derived cell-free DNA as a non-invasive method for detection of acute rejection and graft injury after heart transplantation", J Heart Lung Transplant, 36(9):1004-1012. doi: 10.1016/j.healun.2017.05.026. Epub May 20, 2017., 17 pages.
Agbor-Enoh, et al., "Cell-Free DNA to Detect Heart Allograft Acute Rejection", Circulation, Mar. 23, 2021;143(12): doi: 10.1161/CIRCULATIONAHA.120.049098. Epub Jan. 13, 2021, 1184-1197.
Ahmed, et al., "Cell Free DNA and Procalcitonin as Early Markers of Complications in ICU Patients with Multiple Trauma and Major Surgery", Clin Lab, Dec. 1, 2016;62(12) ; doi: 10.7754/Clin.Lab.2016.160615., 2395-2404.
Alachkar, "Serum and urinary biomarkers in acute kidney transplant rejection", Nephrol Ther., Feb. 2012;8(1): doi: 10.1016/j.nephro.2011.07.409. Epub Oct. 21, 2011, 13-19.
Almeida, et al., "Evaluation of 16 SNPs allele-specific to quantify post hSCT chimerism by SYBR green-based qRT-PCR", J Clin Pathol., Mar. 2013;66(3):. doi: 10.1136/jclinpath-2012-201224. Epub Jan. 2, 2013., 238-242.
Andargie, et al., "Cell-free DNA maps COVID-19 tissue injury and risk of death and can cause tissue injury", JCI Insight, Apr. 8, 2021;6(7):e147610. doi: 10.1172/jci.insight.147610, 20 pages.
Arshad, et al., "Elevated Cell-Free Mitochondrial DNA in Filtered Plasma Is Associated With HIV Infection and Inflammation", J Acquir Immune Defic Syndr., May 1, 2018;78(1): doi: 10.1097/QAI.0000000000001650., 111-118.
Avanzini, Stefano et al., "A mathematical model of ctDNA shedding predicts tumor detection size", Science Advances, vol. 6, Issue eabc4308, Dec. 11, 2020, 9 pages.
Avriel, et al., "Admission Cell Free DNA Levels Predict 28-Day Mortality in Patients with Severe Sepsis in Intensive Care", PLoS One., Jun. 23, 2014;9(6):e100514. doi: 10.1371/journal.pone.0100514. eCollection 2014., 7 pages.
Ayyadevara, et al., "Discrimination of primer 3'-nucleotide mismatch by taq DNA polymerase during polymerase chain reaction", Anal Biochem. Aug. 15, 2000, 284(1), 11-18.
Bai, et al., "Detection and quantification of heteroplasmic mutant mitochondrial DNA by real-time amplification refractory mutation system quantitative PCR analysis: a single-step approach", Clin Chem., Jun. 2004; 50(6); Epub Apr. 8, 2004., 996-1001.

(56) References Cited

OTHER PUBLICATIONS

Bergallo, et al., "A novel TaqMAMA assay for allelic discrimination of TLR9 rs352140 polymorphism", J Virol Methods, May 2017;243. doi: 10.1016/j.jviromet.2017.01.015. Epub Jan. 28, 2017., 25-30.

Bergallo, et al., "Evaluation of IFN-y polymorphism+874 T/A in patients with recurrent tonsillitis by PCR real time mismatch amplification mutation assay (MAMA real time PCR)", Cytokine., Feb. 2015; 71(2): Epub Dec. 2014., 278-282.

Bezieau, et al., "High incidence of N and K-Ras activating mutations in multiple myeloma and primary plasma cell leukemia at diagnosis", Hum Mutat., Sep. 2001;18(3):. doi: 10.1002/humu.1177, 212-224.

Bienkowski, et al., "Liquid biopsy for minimally invasive heart transplant monitoring: a pilot study", J Clin Pathol., Aug. 2020;73(8): doi: 10.1136/jclinpath-2019-205926. Epub Dec. 5, 2019., 507-510.

Board, et al., "Detection of PIK3CA mutations in circulating free DNA in patients with breast cancer", Breast Cancer Res Treat, Apr. 2010;120(2): doi: 10.1007/s10549-010-0747-9. Epub Jan. 28, 2010, 461-467.

Board, et al., "Multiplexed assays for detection of mutations in PIK3CA", Clin Chem., Apr. 2008; 54(4), 757-760.

Braun, et al., "Limitation of Circulating cfDNA Under the Use of a Cytokine Elimination Adsorber (CytoSorb) in Cardiac Surgery", The Thoracic and Cardiovascular Surgeon, Jan. 2018; 66(S01): S1-S110, 1 page.

Bronkhorst, et al., "The emerging role of cell-free DNA as a molecular marker for cancer management", Biomol Detect Quantif, Mar. 18, 2019;17:100087. doi: 10.1016/j.bdq.2019.100087., 23 pages.

Burgstaller, et al., "Mitochondrial DNA heteroplasmy in ovine fetuses and sheep cloned by somatic cell nuclear transfer", BMC Dev Biol., Dec. 21, 2007;7:141, 10 pages.

Cabel, et al., "Circulating tumor DNA changes for early monitoring of anti-PD1 immunotherapy: a proof-of-concept study", Ann Oncol., Aug. 1, 2017;28(8); doi: 10.1093/annonc/mdx212., 1996-2001.

Cagliani, et al., "Deoxyribonuclease Reduces Tissue Injury and Improves Survival After Hemorrhagic Shock", J Surg Res., May 2020;249: doi: 10.1016/j.jss.2019.11.036. Epub Jan. 8, 2020., 104-113.

Castells, et al., "K-ras mutations in DNA extracted from the plasma of patients with pancreatic carcinoma: diagnostic utility and prognostic significance", J Clin Oncol., Feb. 1999;17(2): doi: 10.1200/JCO.1999.17.2.578., 578-584.

Castleberry, et al., "Quantification of Circulating Cell-Free DNA in Pediatric Heart Transplant Recipients", Journal of Heart and Lung Transplantation, Apr. 1, 2011; 30(4): ISSN: 1053-2498, DOI: 10.1016/j.healun.2011.01.415, S139.

Chan, et al., "Bioinformatics analysis of circulating cell-free DNA sequencing data", Clin Biochem., Oct. 2015;48(15); doi: 10.1016/j.clinbiochem.2015.04.022. Epub May 9, 2015., 962-975.

Chan, Allen et al., "Cancer Genome Scanning in Plasma: Detection of Tumor-Associated Copy Number Aberrations, Single-Nucleotide Variants, and Tumoral Heterogeneity by Massively Parallel Sequencing", Clinical Chemistry, 2013, 211-224.

Chan, Allen, "Scanning for Cancer Genomic Changes in Plasma: Toward an Era of Personalized Blood-Based Tumor Markers", Clinical Chemistry, 2013, 1553-1555.

Chen, et al., "Non-invasive prenatal diagnosis using fetal DNA in maternal plasma: a preliminary study for identification of paternally-inherited alleles using single nucleotide polymorphisms", BMJ Open, Jul. 22, 2015;5(7):e007648. doi: 10.1136/bmjopen-2015-007648., 8 pages.

Chen, Kevin et al., "Commercial ctDNA Assays for Minimal Residual Disease Detection of Solid Tumors", Molecular Diagnosis & Therapy, vol. 25, Issue 6, Nov. 1, 2021, 757-774.

Cheng, et al., "Cell-Free DNA in Blood Reveals Significant Cell, Tissue and Organ Specific injury and Predicts COVID-19 Severity", medRxiv., Jul. 29, 2020;2020.07.27.20163188. doi: 10.1101/2020.07.27.20163188., 16 pages.

Chiu, et al., "Effects of blood-processing protocols on fetal and total DNA quantification in maternal plasma", Clin Chem., Sep. 2001;47(9): PubMed PMID: 11514393., 1607-1613.

Chiu, et al., "Noninvasive prenatal exclusion of congenital adrenal hyperplasia by maternal plasma analysis: a feasibility study", Clin Chem., May 2002;48(5), 778-780.

Chu, et al., "A novel approach toward the challenge of accurately quantifying fetal DNA in maternal plasma", Prenat Diagn., Dec. 2010;30(12-13): doi: 10.1002/pd.2656, 1226-1229.

Clementi, et al., "The Role of Cell-Free Plasma DNA in Critically Ill Patients with Sepsis", Blood Purif., 2016;41(1-3): doi: 10.1159/000440975. Epub Oct. 20, 2015, 34-40.

Daly, "Circulating donor-derived cell-free DNA: a true biomarker for cardiac allograft rejection?", Ann Transl Med., Mar. 2015;3(4):47. doi:10.3978/j.issn.2305-5839.2015.01.35, 6 pages.

Dandel, et al., "Non-invasive cardiac allograft rejection surveillance: reliability and clinical value for prevention of heart failure", Heart Fail Rev., Mar. 2021;26(2): doi: 10.1007/s10741-020-10023-3. Epub Sep. 5, 2020., 319-336.

Dastsooz, et al., "Multiplex Arms Pcr to Detect 8 Common Mutations of ATP7B Gene in Patients With Wilson Disease", Hepat Mon., May 1, 20136;13(5):e8375. doi: 10.5812/hepatmon.8375. eCollection 2013., 7 pages.

De Vlaminck, et al., "Circulating cell-free DNA enables noninvasive diagnosis of heart transplant rejection", Sci Transl Med., Jun. 1, 20148;6(241):241ra77. doi: 10.1126/scitranslmed.3007803, 20 pages.

De Vlaminck, et al., "Circulating cell-free DNA enables noninvasive diagnosis of heart transplant rejection", Sci Transl Med., Jun. 1, 20148;6(241):241ra77. Supplemental Materials., 6 pages.

De Vlaminck, et al., "Noninvasive monitoring of infection and rejection after lung transplantation", Proc Natl Acad Sci U S A, Oct. 2, 20157;112(43): doi: 10.1073/pnas.1517494112. Epub Oct. 1, 20152., 13336- 13341.

Delgado, et al., "Characterization of cell-free circulating DNA in plasma in patients with prostate cancer", Tumour Biol., Apr. 2013;34(2): doi: 10.1007/s13277-012-0634-6. Epub Dec. 2, 20127, 983-986.

Deshpande, et al., "Relationship Between Donor Fraction Cell-Free DNA and Treatment for Rejection in Heart Transplantation", Pediatric Transplantation, Jun. 2022; 26(4):e14264. https://doi.org/10.1111/petr.14264, 11 pages.

Dey, et al., "A plasma telomeric cell-free DNA level in unaffected women with BRCA1 or/and BRCA2 mutations: a pilot study. Oncotarget", Oncotarget, Dec. 2, 20179;9(3): doi: 10.18632/oncotarget.23767. eCollection Jan. 9, 2018., 4214-4222.

Ding, et al., "New Progress in Plasma Cell-free DNA in Clinical Applications", Progress in Modern Biomedicine, 2016; 18: 3476, 3593-3596.

Dwivedi, et al., "Prognostic utility and characterization of cell-free DNA in patients with severe sepsis", Crit Care, Aug. 13, 2012;16(4):R151. doi: 10.1186/cc11466., 11 pages.

Fleischhacker, et al., "Circulating nucleic acids (CNAs) and cancer—a survey", Biochim Biophys Acta, Jan. 2007;1775(1): doi: 10.1016/j.bbcan.2006.10.001. Epub Oct. 7, 2006., 181-232.

García Moreira, et al., "Cell-free DNA as a noninvasive acute rejection marker in renal transplantation", Clin Chem., Nov. 2009;55(11): doi:10.1373/clinchem.2009.129072. Epub Sep. 3, 2009, 1958-1966.

Garnacho-Montero, et al., "Prognostic and diagnostic value of eosinopenia, C-reactive protein, procalcitonin, and circulating cell-free DNA in critically ill patients admitted with suspicion of sepsis", Crit Care, Jun. 5, 2014;18(3):R116. doi: 10.1186/cc13908, 9 pages.

Ge, et al., "Haplotype block: a new type of forensic DNA markers", Int J Legal Med, 2010, 353-361.

Ghanta, et al., "Non-invasive prenatal detection of trisomy 21using tandem single nucleotide polymorphisms", PLoS One, Oct. 8, 2010;5(10):e13184. doi: 10.1371/journal.pone.0013184, 10 pages.

Gielis, et al., "Cell-Free DNA: An Upcoming Biomarker in Transplantation", Am J Transplant, Oct. 2015;15(10): doi: 10.1111/ajt.13387. Epub Jul. 16, 2015, 2541-2551.

Gielis, et al., "Plasma donor-derived cell-free DNA kinetics after kidney transplantation using a single tube multiplex PCR assay", PLoS One, 2018; 13(12): e0208207, 16 pages.

(56) References Cited

OTHER PUBLICATIONS

Glaab, et al., "A novel assay for allelic discrimination that combines the fluorogenic 5' nuclease polymerase chain reaction (TaqMan) and mismatch amplification mutation assay", Mutat Res., Nov. 29, 1999;430(1), 1-12.
Goessl, C. et al., "DNA Alterations in Body Fluids as Molecular Tumor Markers for Urological Malignancies", European Urology, vol. 41, 2002, 668-676.
Gordon, et al., "An Algorithm Measuring Donor Cell-Free DNA in Plasma of Cellular and Solid Organ Transplant Recipients That Does Not Require Donor or Recipient Genotyping", Front Cardiovasc Med., Sep. 22, 2016;3:33. eCollection 2016., 10 pages.
Gordon, Paul et al., "An Algorithm Measuring Donor Cell-Free DNA in Plasma of Cellular and Solid Organ Transplant Recipients That Does Not Require Donor or Recipient Genotyping", Frontiers in Cardiovascular Medicine, 2016, vol. 3.
Gormally, et al., "Amount of DNA in plasma and cancer risk: a prospective study", Int J Cancer, Sep. 20, 2004;111(5): doi: 10.1002/ijc.20327, 746-749.
Gotoh, et al., "Prediction of MYCN amplification in neuroblastoma using serum DNA and real-time quantitative polymerase chain reaction", J Clin Oncol., Aug. 1, 2005;23(22): PubMed PMID: 16051962., 5205-5210.
Gripp, et al., "*Homo sapiens* KRAS proto-oncogene, GTPase (KRAS), RefSeqGene (LRG_344) on chromosome 12", GenBank Submission; Accession No. NG_007524, version NG_007524.2, Aug. 16, 2020., 16 Pages.
Grskovic, et al., "Validation of a Clinical-Grade Assay to Measure Donor-Derived Cell-Free DNA in Solid Organ Transplant Recipients", J Mol Diagn., Nov. 2016;18(6): doi: 10.1016/j.jmoldx.2016.07.003. Epub 2016, 890-902.
Guedj, et al., "A refined molecular taxonomy of breast cancer", Oncogene, Mar. 1, 2012;31(9):1196-206. doi: 10.1038/onc.2011.301. Epub Jul. 25, 2011., 34 pages.
Hasi, et al., "Acetaldehyde dehydrogenase 2 SNP rs671 and susceptibility to essential hypertension in Mongolians: a case control study", Genet Mol Res., Mar. 29, 2011;10(1). doi: 10.4238/vol10-1gmr1056., 537-543.
Hidestrand, et al., "Highly sensitive noninvasive cardiac transplant rejection monitoring using targeted quantification of donor-specific cell-free deoxyribonucleic acid", J Am Coll Cardiol., Apr. 1, 2014;63(12). doi:10.1016/j.jacc.2013.09.029. Epub Oct. 16, 2013., 1224-1226.
Hidestrand, et al., "Highly Sensitive Transplant Rejection Surveillance Using Targeted Detection of Donor Specific Cell Free Dna", J Heart Lung Transplant, Apr. 2012; 31(4), S91-S92.
Hidestrand, et al., "Influence of temperature during transportation on cellfree DNA analysis", Fetal Diagn Ther., 2012; 31, 122-128.
Hidestrand, et al., "Quantification of Circulating Donor Specific Cell Free DNA Is an Exquisitely Sensitive Non-Invasive Indicator of Injury to the Donor Heart", J Heart Lung Transplant, 2013; 32, S101-S102.
Hoerning, et al., "Quantitative real-time ARMS-qPCR for mitochondrial DNA enables accurate detection of microchimerism in renal transplant recipients", Pediatr Transplant, Dec. 2011;15(8). doi: 10.1111/j.1399-3046.2011.01581.x. Epub Oct. 4, 2011, 809-818.
Hou, et al., "Application of tetra primer ARMS-PCR approach for detection of Fusarium graminearum genotypes with resistance to carbendazim", Australian Plant Pathology, Jan. 1, 2013; 42(1), 73-78.
Huang, et al., "Circulating cell-free DNA levels correlate with postresuscitation survival rates in out-of-hospital cardiac arrest patients", Resuscitation, Feb. 2012;83(2): doi: 10.1016/j.resuscitation.2011.07.039. Epub Aug. 22, 2011., 213-218.
Huang, et al., "*Homo sapiens* TSC complex subunit 1 (TSC1), RefSeqGene (LRG_486) on chromosome 9", GenBank Submission; Accession No. NG_012386, version NG_012386.1, Sep. 21, 2020, 20 Pages.
Hudecova, Irena, "Digital PCR analysis of circulating nucleic acids", Clin Biochem., Oct. 2015;48(15): doi: 10.1016/j.clinbiochem.2015.03.015. Epub Mar. 28, 2015, 948-956.
Hugon, et al., "Influence of intention to adhere, beliefs and satisfaction about medicines on adherence in solid organ transplant recipients", Transplantation., Jul. 27, 2014;98(2): doi: 10.1097/TP.0000000000000221, 222-228.
Jing, et al., "Cell-free DNA: characteristics, detection and its applications in myocardial infarction", Curr Pharm Des., 2013;19(28): doi: 10.2174/13816128113199280012., 5135-5145.
Jordan, et al., "Donor-derived Cell-free DNA Identifies Antibody-mediated Rejection in Donor Specific Antibody Positive Kidney Transplant Recipients", Transplant Direct, 2018;4(9): e379, 5 pages.
Jung, et al., "Cell-free DNA in the blood as a solid tumor biomarker—a critical appraisal of the literature", Clin Chim Acta., Nov. 11, 2010;411(21-22): doi: 10.1016/j.cca.2010.07.032. Epub Aug. 2, 2010., 1611-1624.
Jung, Klaus et al., "Increased cell-free DNA in plasma of patients with metastatic spread in prostate cancer", Cancer Letters, 2004, 173-180.
Kaper, Fiona et al., "Abstract 1164: Parallel preparation of targeted resequencing libraries from 480 genomic regions using multiplex PCR on the Access Array system", American Association for Cancer Research, 2010, 1-2.
Kaper, Fiona et al., "Parallel Preparation of Targeted Resequencing Libraries from 480 Genomic Regions Using Multiplex PCR on the Access Array System", Fluidigm Poster, 2011, 1 pg.
Karapetis, et al., "K-ras mutations and benefit from cetuximab in advanced colorectal cancer", N Engl J Med., Oct. 23, 2008;359(17). doi: 10.1056/NEJMoa0804385., 1757-1765.
Khush, et al., "Circulating cell-free DNA as a non-invasive marker of pediatric heart transplant rejection and immunosuppressive treatment", J Heart Lung Transplantation, Apr. 2016. 35(4): Abstract 181, S75.
Khush, et al., "Noninvasive detection of graft injury after heart transplant using donorderived cellfree DNA: A prospective multicenter study", Am J Transplant, Oct. 2019;19(10): doi: 10.1111/ajt.15339. Epub Apr. 8, 2019., 2889-2899.
Kindel, et al., "Early Changes in Donor Fraction Cell-free DNA in Newly Transplanted Heart Transplant Patients", ISHLT DF cfDNA declanation poster, 2018, 1 Page.
Kirkizlar, et al., "Detection of Clonal and Subclonal Copy-Number Variants in Cell-Free DNA from Patients with Breast Cancer Using a Massively Multiplexed PCR Methodology", Transl Oncol., Oct. 2015;8(5): doi: 10.1016/j.tranon.2015.08.004., 407-416.
Kirsch-Gerweck, et al., "HaploBlocks: Efficient Detection of Positive Selection in Large Population Genomic Datasets", Mol. Biol. Evol., 2023, 12 pages.
Kuo, et al., "Preimplantation and prenatal genetic diagnosis of aromatic L-amino acid decarboxylase deficiency with an amplification refractory mutation system-quantitative polymerase chain reaction", Taiwan J Obstet Gynecol, Dec. 2011;50(4): doi: 10.1016/j.tjog.2011.10.012., 468-473.
Kustanovich, et al., "Life and death of circulating cell-free DNA", Cancer Biol Ther., 2019;20(8): doi: 10.1080/15384047.2019.1598759. Epub Apr. 16, 2019, 1057-1067.
Lajin, et al., "A quadruplex tetra-primer ARMS-PCR method for the simultaneous detection of TP53 Arg72Pro, IVS3 16bp Del/Ins and IVS6+62A>G, and NQO1 C609T polymorphisms", Gene., Aug. 10, 2012;504(2): Epub May 23, 2012., 268-273.
Lang, et al., "Optimized allele-specific real-time PCR assays for the detection of common mutations in KRAS and BRAF", J Mol Diagn., Jan. 2011;13(1): doi: 10.1016/j.jmoldx.2010.11.007. Epub Dec. 23, 2010., 23-28.
Laurent-Puig, et al., "Clinical relevance of KRAS-mutated subclones detected with picodroplet digital PCR in advanced colorectal cancer treated with anti-EGFR therapy", Clin Cancer Res., Mar. 1, 2015;21(5): doi: 10.1158/1078-0432.CCR-14-0983. Epub Sep. 23, 2014., 1087-1097.
Lecomte, et al., "Detection of free-circulating tumor-associated DNA in plasma of colorectal cancer patients and its association with prognosis", Int J Cancer, Aug. 10, 2002;100(5): doi: 10.1002/ijc.10526., 542-548.
Lee, et al., "Allele-Specific Quantitative PCR for Accurate, Rapid, and Cost-Effective Genotyping", Hum Gene Ther., Jun. 2016;27(6): doi: 10.1089/hum.2016.011. Epub Mar. 17, 2016., 425-435.

(56) References Cited

OTHER PUBLICATIONS

Lefebure, et al., "Prognostic value of circulating mutant DNA in unresectable metastatic colorectal cancer", Ann Surg., Feb. 2010;251(2): doi: 10.1097/SLA.0b013e3181c35c87, 275-280.

Levy, et al., "Analysis of Cell-Free DNA to Assess Risk of Tumoremia Following Endoscopic Ultrasound Fine-Needle Aspiration of Pancreatic Adenocarcinomas", Clin Gastroenterol Hepatol., Oct. 2018;16(10): e1. doi: 10.1016/j.cgh.2018.02.048. Epub Mar. 8, 2018., 1632-1640.

Li, et al., "Multiplex co-amplification of 24 retinoblastoma gene exons after pre-amplification by long-distance PCR", Nucleic Acids Res., Feb. 1, 1996;24(3), 538-539.

Liang, et al., "Cationic nanoparticle as an inhibitor of cell-free DNA-induced inflammation", Nat Commun., Oct. 16, 2018;9(1):4291. doi: 10.1038/s41467-018-06603-5, 14 pages.

Lievre, et al., "KRAS mutations as an independent prognostic factor in patients with advanced colorectal cancer treated with cetuximab", J Clin Oncol., Jan. 20, 2008;26(3): doi: 10.1200/JCO.2007.12.5906., 374-379.

Liu, et al., "ABO chimerism determined by real-time polymerase chain reaction analysis after ABO-incompatible haematopoietic stem cell transplantation", Blood Tranfus, Jan. 2013;11(1): doi: 10.2450/2012.0013-12. Epub Jul. 4, 2012., 43-52.

Liu, et al., "Comparison of next-generation sequencing systems", J Biomed Biotechnol., 2012;2012: doi: 10.1155/2012/251364. Epub Jul. 5, 2012., 1-11.

Lo, et al., "Plasma placental RNA allelic ratio permits noninvasive prenatal chromosomal aneuploidy detection", Nat Med., Feb. 2007;13(2): doi: 10.1038/nm1530. Epub Jan. 7, 2007., 218-223.

Lo, et al., "Transplantation monitoring by plasma DNA sequencing", Clin Chem., Jul. 2011;57(7): doi: 10.1373/clinchem.2011.166686. PubMed PMID: 21566070., 941-942.

Luo, et al., "Detection of usual and atypical aldehyde dehydrogenase alleles by mismatch amplification mutation assay", Clin Chem Lab Med., Dec. 2001;39(12): doi: 10.1515/CCLM.2001.189., 1195-1197.

Mak, et al., "Rapid diagnosis of Wilson disease by a 28-mutation panel: real-time amplification refractory mutation system in diagnosing acute Wilsonian liver failure", Clin Chim Acta., Dec. 2008; 398(1-2): doi: 10.1016/j.cca.2008.08.002. Epub Aug. 8, 2008., 39-42.

Manage, et al., "Genotyping single nucleotide polymorphisms in human genomic DNA with an automated and self-contained PCR cassette", J Mol Diagn., Sep. 2014;16(5): doi:10.1016/j.jmoldx.2014.04.004. Epub Jul. 2, 2014., 550-557.

Martinez-Herrero, et al., "Cancer protection elicited by a single nucleotide polymorphism close to the adrenomedullin gene", J Clin Endocrinol Metab., Apr. 2013;98(4): doi: 10.1210/jc.2012-4193. Epub Feb. 28, 2013., E807-E810.

Mehra, et al., "Gene expression profiles and B-type natriuretic peptide elevation in heart transplantation: more than a hemodynamic marker", Circulation, Jul. 4, 2006;114(1 Suppl), I21-I26.

Mehra, et al., "International Society for Heart and Lung Transplantation working formulation of a standardized nomenclature for cardiac allograft vasculopathy—2010", J Heart Lung Transplant, Jul. 2010;29(7) .doi: 10.1016/j.healun.2010.05.017., 717-727.

Mengel, et al., "The molecular phenotype of heart transplant biopsies: relationship to histopathological and clinical variables", Am J Transplant, Sep. 2010;10(9): doi: 10.1111/j.1600-6143.2010.03182.x., 2105-2115.

Misale, et al., "Emergence of KRAS mutations and acquired resistance to anti-EGFR therapy in colorectal cancer", Nature, Jun. 28, 2012;486(7404): doi: 10.1038/nature11156., 532-536.

Mouliere, et al., "Circulating Cell-Free DNA from Colorectal Cancer Patients May Reveal High KRAS or BRAF Mutation Load", Transl Oncol., Jun. 1, 2013;6(3): doi: 10.1593/tlo.12445. Print Jun. 2013., 319-328.

Myers, et al., "ACB-PCR quantification of somatic oncomutation", Methods Mol Biol., 2014;1105: doi:10.1007/978-1-62703-739-6_27, 345-363.

Newton, et al., "Analysis of any point mutation in DNA. The amplification refractory mutation system (ARMS)", Nucleic Acids Res., Apr. 11, 1989;17(7): doi: 10.1093/nar/17.7.2503, 2503-2516.

No Author Listed, "The Journal of Heart and Lung Transplantation", Apr. 2012., vol. 31, Issue 4, Supplement, pp. A1-A4, S1-S310. https://www.google.de/searchq=The+Journal+of+Heart+and+Lung+Transplantation+Volume+31,+Issue+4,+Supplement&sourceid=ie7&rls=com.microsoft:en-US:IE-Address&ie=&oe=#spf=1604593918239, Last Accessed: Oct. 13, 2015., A1-A4.

No Author Listed, NIH, "Quantitative Detection of Circulating Donor-Specific DNA in Organ Transplant Recipients (DTRT—Multi-Center Study) (DTRT)", ClinicalTrials.gov Identifier: NCT02109575., Apr. 10, 2014, Last updated Mar. 26, 2021, 9 pages.

North, et al., "Cell-free DNA donor fraction analysis in pediatric and adult heart transplant patients by multiplexed allele-specific quantitative PCR: Validation of a rapid and highly sensitive clinical test for stratification of rejection probability", PLoS One, Jan. 13, 2020;15(1):e0227385. doi: 10.1371/journal.pone.0227385. eCollection 2020., 48 pages.

Oeth, et al., "Qualitative and quantitative genotyping using single base primer extension coupled with matrix-assisted laser desorption/ionization time-of-flight mass spectrometry (MassARRAY®).", Methods Mol. Biol., 2009; 578, 307-343.

Orou, et al., "Allele-specific competitive blocker PCR: a one-step method with applicability to pool screening", Hum Mutat., 1995;6(2): doi: 10.1002/humu.1380060209., 163-169.

Parsons, et al., "Allele-specific competitive blocker-PCR detection of rare base substitution", Methods Mol Biol., 2005;291, 235-245.

PCT/US2017/059808, "International Preliminary Report on Patentability", (M1290.70010WO00), mailed May 16, 2019, 8 pages.

PCT/US2017/059808, "International Search Report and Written Opinion for Application", (M1290.70010WO00), mailed Jan. 25, 2018, 12 pages.

PCT/US2018/038598, "International Preliminary Report on Patentability", (M1290.70015WO00), mailed Jan. 2, 2020, 6 pages.

PCT/US2018/038598, "International Search Report and Written Opinion", (M1290.70015WO00), mailed Sep. 7, 2018, 8 pages.

PCT/US2018/038609, "International Preliminary Report on Patentability", (M1290.70021WO00), mailed Jan. 2, 2020, 7 pages.

PCT/US2018/038609, "International Search Report and Written Opinion", (M1290.70021WO00), mailed Sep. 10, 2018, 9 pages.

Peng, et al., "Comparison of K-ras mutations in lung, colorectal and gastric cancer", Oncol Lett., Aug. 2014;8(2): doi: 10.3892/ol.2014.2205. Epub May 30, 2014., 561-565.

Peyster, et al., "Advanced Morphologic Analysis for Diagnosing Allograft Rejection: The Case of Cardiac Transplant Rejection", Transplantation, Aug. 2018;102(8): doi: 10.1097/TP.0000000000002189., 1230-1239.

Price, et al., "Cost-effective interrogation of single nucleotide polymorphisms using the mismatch amplification mutation assay and capillary electrophoresis", Electrophoresis, Dec. 2010;31(23-24): doi: 10.1002/elps.201000379., 3881-3888.

Purhonen, et al., "Human plasma cell-free DNA as a predictor of infectious complications of neutropenic fever in hematological patients", Infect Dis (Lond)., Apr. 2015;47(4): doi: 10.3109/00365548.2014.985711. Epub Feb. 9, 2015., 255-259.

Qin, et al., "Quantitative assessment of hematopoietic chimerism by quantitative real-time polymerase chain reaction of sequence polymorphism systems after hematopoietic stem cell transplantation", Chin Med J (Engl), Aug. 2011;124(15), 2301-2308.

Quail, et al., "A tale of three next generation sequencing platforms: comparison of Ion torrent, pacific biosciences and illumina MiSeq sequencers", BMC Genomics, Jul. 24, 2012;13:341. doi: 10.1186/1471-2164-13-341, 13 pages.

Ragalie, et al., "Description of Longitudinal Measurement of Donor Fraction of Cell-Free DNA and Correlation to Clinical Outcomes", ISHLT poster, 2018, 1 page.

Ragalie, et al., "Noninvasive Assay for Donor Fraction of Cell-Free DNA in Pediatric Heart Transplant Recipients", J Am Coll Cardiol., Jun. 26, 2018;71(25): doi: 10.1016/j.jacc.2018.04.026, 2982-2983.

(56) References Cited

OTHER PUBLICATIONS

Richmond, et al., "Donor fraction cell-free DNA and rejection in adult and pediatric heart transplantation", J Heart Lung Transplant, May 2020;39(5): doi: 10.1016/j.healun.2019.11.015. Epub Nov. 29, 2019., 454-463.

Roedder, et al., "Biomarkers in solid organ transplantation: establishing personalized transplantation medicine", Genome Med., Jun. 8, 2011;3(6):37, 12 pages.

Sanmamed, et al., "Quantitative cell-free circulating BRAFV600E mutation analysis by use of droplet digital PCR in the follow-up of patients with melanoma being treated with BRAF inhibitors", Clin Chem., Jan. 2015;61(1): doi: 10.1373/clinchem.2014.230235. Epub Nov. 19, 2014., 297-304.

Sapio, et al., "Detection of BRAF mutation in thyroid papillary carcinomas by mutant allele-specific PCR amplification (MASA)", Eur J Endocrinol., Feb. 2006;154(2): doi: 10.1530/eje.1.02072, 341-348.

Saukkonen, et al., "Cell-free plasma DNA as a predictor of outcome in severe sepsis and septic shock.", Clin Chem., Jun. 2008;54(6): doi: 10.1373/clinchem.2007.101030. Epub Apr. 17, 2008. PubMed PMID: 18420731., 1000-1007.

Schnittger, et al., "Development and validation of a real-time quantification assay to detect and monitor BRAFV600E mutations in hairy cell leukemia", Blood., Mar. 29, 2012;119(13): doi: 10.1182/blood-2011-10-383323. Epub Feb. 13, 2012., 3151-3154.

Schutz, et al., "Graft-derived cell-free DNA, a noninvasive early rejection and graft damage marker in liver transplantation: A prospective, observational, multicenter cohort study", PLOS Med., Apr. 25, 2017;14(4):e1002286. doi: 10.1371/journal.pmed.1002286. eCollection Apr. 2017., 19 pages.

Schwarzenbach, et al., "Cell-free nucleic acids as biomarkers in cancer patients", Nat Rev Cancer, Jun. 2011;11(6): doi: 10.1038/nrc3066. Epub May 12, 2011, 426-437.

Scott, et al., "Elevated nuclear and mitochondrial cell-free deoxyribonucleic acid measurements are associated with death after infant cardiac surgery", J Thorac Cardiovasc Surg., Aug. 2022;164(2): doi: 10.1016/j.jtcvs.2021.10.066. Epub Dec. 24, 2021., 367-375.

Scott, et al., "Total Cell-Free DNA Predicts Death and Infection Following Pediatric and Adult Heart Transplantation", Ann Thorac Surg., Oct. 2021;112(4): doi: 10.1016/j.athoracsur.2020.08.006. Epub Oct. 8, 2020., 1282-1289.

Sefrioui, et al., "Clinical value of chip-based digital-PCR platform for the detection of circulating DNA in metastatic colorectal cancer", Dig Liver Dis., Oct. 2015;47(10): doi: 10.1016/j.dld.2015.05.023. Epub Jun. 5, 2015, 884-890.

Sheffield, et al., "Attachment of a 40-base-pair G + C-rich sequence (GC-clamp) to genomic DNA fragments by the polymerase chain reaction results in improved detection of single-base changes", Proc Natl Acad Sci U S A, Jan. 1989;86(1), 232-236.

Shi, et al., "Development of a single multiplex amplification refractory mutation system PCR for the detection of rifampin-resistant *Mycobacterium tuberculosis*", Gene., Nov. 1, 2013; 530(1): Epub Aug. 19, 2013, 95-99.

Shimabukuro-Vornhagen, et al., "Cytokine release syndrome", J Immunother Cancer, Jun. 15, 2018;6(1):56. doi: 10.1186/s40425-018-0343-9, 14 pages.

Sigdel, et al., "A rapid noninvasive assay for the detection of renal transplant injury", Transplantation, Jul. 15, 2013;96(1): doi: 10.1097/TP.0b013e318295ee5a., 97-101.

Singh, et al., "Aspergillus infections in transplant recipients", Clin Microbiol Rev., Jan. 2005;18(1), 44-69.

Snyder, et al., "Universal noninvasive detection of solid organ transplant rejection", Proc Natl Acad Sci U S A, Apr. 12, 2011;108(15): doi: 10.1073/pnas.1013924108. Epub Mar. 28, 2011. PubMed PMID: 21444804; PubMed Central PMCID: PMC3076856., 6229-6234.

Sparks, et al., "Noninvasive prenatal detection and selective analysis of cell-free DNA obtained from maternal blood: evaluation for trisomy 21 and trisomy 18", Am J Obstet Gynecol., Apr. 2012;206(4): doi: 10.1016/j.ajog.2012.01.030. Epub Jan. 26, 2012, 319.e1-319.e9.

Sparks, et al., "Selective analysis of cell-free DNA in maternal blood for evaluation of fetal trisomy", Prenat Diagn., Jan. 2012;32(1). Epub Jan. 6, 2012., 3-9.

Spindler, et al., "Cell-free DNA in healthy individuals, noncancerous disease and strong prognostic value in colorectal cancer", Int J Cancer, Dec. 15, 2014;135(12): doi: 10.1002/ijc.28946. Epub Jun. 17, 2014, 2984-2991.

Spindler, et al., "KRAS-mutated plasma DNA as predictor of outcome from irinotecan monotherapy in metastatic colorectal cancer", Br J Cancer, Dec. 10, 2013;109(12). doi: 10.1038/bjc.2013.633. Epub Nov. 21, 2013., 3067-3072.

Spindler, et al., "Quantitative cell-free DNA, KRAS, and BRAF mutations in plasma from patients with metastatic colorectal cancer during treatment with cetuximab and irinotecan", Clin Cancer Res., Feb. 15, 2012;18(4). doi: 10.1158/1078-0432.CCR-11-0564. Epub Jan. 6, 2012., 1177-1185.

Stein, "Next-Generation Sequencing Update", Genetic Engineering & Biotechnology News, Sep. 1, 2008; 28(15). https://www.genengnews.com/magazine/97/next-generation-sequencing-update/, 10 pages.

Steinborn, et al., "Coexistence of Bos taurus and B. indicus mitochondrial DNAs in nuclear transfer-derived somatic cattle clones", Genetics, Oct. 2002;162(2), 823-829.

Stemmer, et al., "Use of magnetic beads for plasma cell-free DNA extraction: toward automation of plasma DNA analysis for molecular diagnostics", Clin Chem., Nov. 2003;49(11): PubMed PMID: 14578335., 1953-1955.

Strausberg, et al., "*Homo sapiens* placenta-specific 4, mRNA (cDNA clone MGC:120720 Image:7939530), complete cds", GenBank Submission; Accession No. BC093685, version BC093685.1., Jan. 18, 2007, 2 Pages.

Strohmeier, et al., "Multiplex genotyping of KRAS point mutations in tumor cell DNA by allele-specific real-time PCR on a centrifugal microfluidic disk segment", Microchimica Acta., 2014;181 (13-14), 1681-1688.

Suzuki, et al., "Characterization of circulating DNA in healthy human plasma", Clin Chim Acta., Jan. 2008;387(1-2): doi: 10.1016/j.cca.2007.09.001. Epub Sep. 8, 2007., 55-58.

Swinkels, et al., "Effects of blood-processing protocols on cell-free DNA quantification in plasma", Clin Chem., Mar. 2003;49(3): PubMed PMID: 12600978, 525-526.

Tabernero, et al., "Analysis of circulating DNA and protein biomarkers to predict the clinical activity of regorafenib and assess prognosis in patients with metastatic colorectal cancer: a retrospective, exploratory analysis of the CORRECT trial", Lancet Oncol., Aug. 2015;16(8): doi: 10.1016/S1470-2045(15)00138-2. Epub Jul. 13, 2015., 937-948.

Taira, et al., "Novel high-speed droplet-allele specific-polymerase chain reaction: application in the rapid genotyping of single nucleotide polymorphisms", Clin Chim Acta., Sep. 23, 2013;424: doi: 10.1016/j.cca.2013.04.024. Epub May 17, 2013., 39-46.

Taira, et al., "Quantitative monitoring of single nucleotide mutations by allele-specific quantitative PCR can be used for the assessment of minimal residual disease in patients with hematological malignancies throughout their clinical course", Clin Chim Acta., Jan. 14, 2011;412(1-2): doi: 10.1016/j.cca.2010.09.011. Epub Sep. 16, 2010., 53-58.

Takai, et al., "Clinical utility of circulating tumor DNA for molecular assessment in pancreatic cancer", Sci Rep., Dec. 16, 2015;5:18425. doi: 10.1038/srep18425., 10 pages.

Taly, et al., "Multiplex picodroplet digital PCR to detect KRAS mutations in circulating DNA from the plasma of colorectal cancer patients", Clin Chem., Dec. 2013;59(12): doi: 10.1373/clinchem.2013.206359. Epub Aug. 12, 2013., 1722-1731.

Tamkovich, et al., "Circulating nucleic acids in blood of healthy male and female donors", Clin Chem., Jul. 2005; 51(7): PubMed PMID: 15976134., 1317-1319.

Tanem, et al., "Abstract 16873: Association of Preoperative Cell-Free DNA Levels and Outcome Following Pediatric Cardiopulmonary Bypass", Circulation, Nov. 17, 2020; 142(S3): https://doi.org/10.1161/circ.142.suppl_3.16873., 1-6.

(56) References Cited

OTHER PUBLICATIONS

Thierry, et al., "A Targeted Q-PCR-Based Method for Point Mutation Testing by Analyzing Circulating DNA for Cancer Management Care", Methods Mol Biol., 2016;1392: doi: 10.1007/978-1-4939-3360-0_1, 1-16.
Thierry, et al., "Clinical validation of the detection of KRAS and BRAF mutations from circulating tumor DNA", Nat Med., Apr. 2014;20(4): doi: 10.1038/nm.3511. Epub Mar. 23, 2014., 430-435.
Tomita-Mitchell, et al., "Human gene copy No. spectra analysis in congenital heart malformations", Physiol Genomics, May 1, 2012;44(9): doi: 10.1152/physiolgenomics.00013.2012. Epub Feb. 7, 2012., 518-541.
Tong, et al., "Diagnostic developments involving cell-free (circulating) nucleic acids", Clin Chim Acta., Jan. 2006;363(1-2): Epub Aug. 26, 2005. Review. PubMed PMID: 16126188, 187-196.
Van Orsouw, et al., "Rapid design of denaturing gradient-based two-dimensional electrophoretic gene mutational scanning tests", Nucleic Acids Res., May 15, 1998;26(10), 2398-2406.
Vannucchi, et al., "A quantitative assay for JAK2(V617F) mutation in myeloproliferative disorders by ARMS-PCR and capillary electrophoresis", Leukemia, Jun. 2006;20(6), 1055-1060.
Vargas, D. Y. et al., "Multiplex Real-Time PCR Assays that Measure the Abundance of Extremely Rare Mutations Associated with Cancer", PLOS One, vol. 11, No. 5, May 31, 2016, 26 pgs.
Veseloskva, "The use of cell-free nucleic acids in maternal plasma for non-invasive prenatal diagnosis of monogenic diseases, placental insufficiency-related complications and Down syndrome", Thesis from Charles University in Prague, 2011, 104 pages.
Wangkumhang, et al., "WASP: a Web-based Allele-Specific PCR assay designing tool for detecting SNPs and mutations", BMC Genomics, Aug. 14, 2007;8:275, 9 Pages.
Wapner, et al., "Expanding the scope of noninvasive prenatal testing: detection of fetal microdeletion syndromes", Am J Obstet Gynecol., Mar. 2015;212(3): doi: 10.1016/j.ajog.2014.11.041. Epub Dec. 2, 2014., 332.e1-332.e9.
Wilkins, et al., "IMP PCR primers detect single nucleotide polymorphisms for Anopheles gambiae species identification, Mopti and Savanna rDNA types, and resistance to dieldrin in Anopheles arabiensis", Malar J., Dec. 19, 2006;5:125., 7 pages.
Wong, I. H. et al., "Quantitative Analysis of Tumor-derived Methylated p16INK4a Sequences in Plasma, Serum, and Blood Cells of Hepatocellular Carcinoma Patients", Clinical Cancer Research, vol. 9, Mar. 2003, 1047-1052.
Woude, et al., "Methods of identifying drugs with selective effects against cancer cells", Oct. 7, 1997, Nucleic acid sequence search reports AC: 151794, Accession 151796., 2 Pages.
Yamada, et al., "Detection of K-ras gene mutations in plasma DNA of patients with pancreatic adenocarcinoma: correlation with clinicopathological features", Clin Cancer Res., Jun. 1998;4(6), 1527-1532.
Yi, et al., "PCR/LDR/capillary electrophoresis for detection of single-nucleotide differences between fetal and maternal DNA in maternal plasma", Prenat Diagn., Mar. 2009;29(3): doi: 10.1002/pd.2072., 217-222.
Zangwill, et al., "Effect of endomyocardial biopsy on levels of donor-specific cell-free DNA", J Heart Lung Transplant, Oct. 2019;38(10): doi: 10.1016/j.healun.2019.06.005. Epub Jun. 28, 2019., 1118-1120.
Zhang, et al., "A novel multiplex tetra-primer ARMS-PCR for the simultaneous genotyping of six single nucleotide polymorphisms associated with female cancers", PLoS One, Apr. 17, 2013;8(4):e62126. doi: 10.1371/journal.pone.0062126. Print 2013., 8 pages.

\* cited by examiner

FIG. 16

| Sample ID | cfDNA concentration (ng/ul) | Genome copy equivalents into Library Prep | cfDNA size profile | Hemolysis |
|---|---|---|---|---|
| U_LTX144 | 0.09 | 1,017 | 3 | 2 |
| B_LTX135 | 0.21 | 2,578 | 2 | 0 |
| B_LTX160 | 0.25 | 3,021 | 2 | 1 |
| M_LTX085 | 0.27 | 3,300 | 2 | 0 |
| B_LTX065 | 0.30 | 3,564 | 2 | 0 |
| U_LTX092 | 0.31 | 3,689 | 3 | 2 |
| M_LTX013 | 0.32 | 3,853 | 2 | 0 |
| B_LTX163 | 0.32 | 3,919 | 1 | 0 |
| B_LTX075 | 0.39 | 4,733 | 1 | 0 |
| M_LTX175 | 0.41 | 4,929 | 1 | 0 |
| A_LTX055 | 0.42 | 5,042 | 2 | 0 |
| A_LTX210 | 0.43 | 5,167 | 2 | 0 |
| A_LTX049 | 0.45 | 5,465 | 2 | 0 |
| M_LTX073 | 0.45 | 5,480 | 1 | 0 |
| U_LTX103 | 0.46 | 5,611 | 2 | 0 |
| A_LTX102 | 0.48 | 5,817 | 1 | 0 |
| B_LTX165 | 0.50 | 6,049 | 2 | 0 |
| U_LTX111 | 0.50 | 6,068 | 2 | 0 |
| U_LTX180 | 0.52 | 6,245 | 2 | 0 |
| U_LTX058 | 0.65 | 7,898 | 2 | 1 |
| U_LTX091 | 0.66 | 8,030 | 2 | 0 |
| U_LTX206 | 0.68 | 8,271 | 2 | 1 |
| U_LTX036 | 0.69 | 8,293 | 1 | 0 |
| B_LTX048 | 0.73 | 8,800 | 2 | 0 |
| U_LTX107 | 0.73 | 8,878 | 2 | 0 |

FIG. 16 (CONT.)

| | | | | |
|---|---|---|---|---|
| L_LTX062 | 0.74 | 8,934 | 2 | 0 |
| B_LTX046 | 0.74 | 9,015 | 2 | 0 |
| L_LTX041 | 0.82 | 9,940 | 1 | 0 |
| U_LTX076 | 0.83 | 10,009 | 2 | 0 |
| B_LTX059 | 0.84 | 10,201 | 2 | 0 |
| M_LTX093 | 0.87 | 10,556 | 2 | 0 |
| U_LTX097 | 0.91 | 10,995 | 2 | 0 |
| U_LTX185 | 1.00 | 12,055 | 2 | 0 |
| U_LTX022 | 1.04 | 12,536 | 3 | 1 |
| L_LTX115 | 1.21 | 14,602 | 2 | 0 |
| B_LTX033 | 1.25 | 15,187 | 1 | 0 |
| M_LTX025 | 1.43 | 17,334 | 3 | 1 |
| R_LTX120 | 1.63 | 19,693 | 1 | 0 |
| B_LTX034 | 1.85 | 22,361 | 2 | 1 |
| A_LTX021 | 1.85 | 22,400 | 1 | 0 |
| B_LTX084 | 1.89 | 22,889 | 1 | 0 |
| M_LTX015 | 1.91 | 23,193 | 1 | 0 |
| M_LTX032 | 1.95 | 23,637 | 1 | 2 |
| M_LTX063 | 2.06 | 25,007 | 1 | 0 |
| M_LTX028 | 2.35 | 28,476 | 1 | 0 |
| M_LTX074 | 2.54 | 30,752 | 1 | 0 |
| B_LTX038 | 3.12 | 37,767 | 1 | 0 |
| M_LTX149 | 3.89 | 47,165 | 2 | 1 |
| U_LTX126 | 6.75 | 50,000 | 2 | 1 |
| U_LTX001 | 7.24 | 50,000 | 1 | 0 |

FIG. 17

| Sample | Total assays | Detected in plasma | Negative |
|---|---|---|---|
| LTX001 | 17 | 2 | 15 |
| LTX013 | 15 | 2 | 13 |
| LTX015 | 19 | 17 | 2 |
| LTX021 | 19 | 0 | 19 |
| LTX022 | 20 | 17 | 3 |
| LTX025 | 19 | 15 | 4 |
| LTX028 | 19 | 13 | 6 |
| LTX032 | 17 | 12 | 5 |
| LTX033 | 18 | 13 | 5 |
| LTX034 | 18 | 0 | 18 |
| LTX036 | 19 | 1 | 18 |
| LTX038 | 19 | 16 | 3 |
| LTX041 | 19 | 1 | 18 |
| LTX046 | 18 | 0 | 18 |
| LTX048 | 17 | 1 | 16 |
| LTX049 | 18 | 1 | 17 |
| LTX055 | 21 | 0 | 21 |
| LTX058 | 18 | 8 | 10 |
| LTX059 | 18 | 9 | 9 |
| LTX062 | 18 | 0 | 18 |
| LTX063 | 20 | 15 | 5 |
| LTX065 | 15 | 0 | 15 |
| LTX073 | 22 | 0 | 22 |
| LTX074 | 19 | 7 | 12 |
| LTX075 | 19 | 1 | 18 |
| LTX076 | 20 | 19 | 1 |
| LTX084 | 14 | 0 | 14 |

FIG. 17 (CONT.)

| | | | |
|---|---|---|---|
| LTX085 | 15 | 3 | 12 |
| LTX091 | 18 | 0 | 18 |
| LTX092 | 21 | 18 | 3 |
| LTX093 | 16 | 14 | 2 |
| LTX097 | 18 | 14 | 4 |
| LTX102 | 20 | 0 | 20 |
| LTX103 | 13 | 1 | 12 |
| LTX107 | 19 | 13 | 6 |
| LTX111 | 17 | 5 | 12 |
| LTX115 | 19 | 0 | 19 |
| LTX120 | 18 | 17 | 1 |
| LTX126 | 19 | 6 | 13 |
| LTX135 | 17 | 4 | 13 |
| LTX144 | 19 | 0 | 19 |
| LTX149 | 17 | 12 | 5 |
| LTX160 | 17 | 3 | 14 |
| LTX163 | 19 | 0 | 19 |
| LTX165 | 19 | 11 | 8 |
| LTX175 | 21 | 9 | 12 |
| LTX180 | 17 | 0 | 17 |
| LTX185 | 18 | 0 | 18 |
| LTX210 | 18 | 10 | 8 |

FIG. 18

| Sample | Chr. | Position | Ref | Mut | Ref VAF Plasma | Mut VAF Plasma | Total DOR | Mut DOR |
|---|---|---|---|---|---|---|---|---|
| LTX032 | 6 | 161530837 | T | G | 99.691% | 0.286% | 63656 | 182 |
| LTX063 | 1 | 27102067 | T | G | 99.802% | 0.156% | 52495 | 82 |
| LTX063 | 10 | 108378017 | T | A | 99.839% | 0.143% | 56002 | 80 |
| LTX092 | 2 | 216252943 | G | T | 99.484% | 0.478% | 42289 | 202 |
| LTX107 | 3 | 156272874 | A | G | 94.884% | 5.116% | 3968 | 203 |
| LTX149 | 14 | 70633967 | G | T | 99.754% | 0.211% | 50808 | 107 |
| LTX149 | 1 | 160136470 | T | G | 99.418% | 0.538% | 31966 | 172 |

FIG. 19
Assay Count Based on Genes

| | | | | | |
|---|---|---|---|---|---|
| 28 | TP53 | 2 | PIK3CA | 1 | ZSCAN4 |
| 14 | KRAS | 2 | PIEZO2 | 1 | ZSCAN23 |
| 7 | NF1 | 2 | ODAM | 1 | ZP4 |
| 6 | KEAP1 | 2 | NTRK1 | 1 | ZNF841 |
| 5 | ARHGAP35 | 2 | NPAP1 | 1 | ZNF831 |
| 4 | ZNF521 | 2 | NOTCH1 | 1 | ZNF804B |
| 4 | TRRAP | 2 | NIN | 1 | ZNF582 |
| 4 | NTRK3 | 2 | MLLT10 | 1 | ZNF552 |
| 4 | MYH9 | 2 | MED13L | 1 | ZNF536 |
| 4 | MYH11 | 2 | LAMB4 | 1 | ZNF513 |
| 4 | MGA | 2 | KIAA1549 | 1 | ZNF469 |
| 3 | WRN | 2 | KDM5C | 1 | ZNF318 |
| 3 | STK11 | 2 | JAK2 | 1 | ZIM2 |
| 3 | NFE2L2 | 2 | IL21R | 1 | ZIC4 |
| 3 | MBD1 | 2 | IKZF1 | 1 | ZG16 |
| 3 | KMT2D | 2 | GRM8 | 1 | ZFYVE28 |
| 3 | FBXW7 | 2 | FBXL7 | 1 | ZFHX4 |
| 3 | FAT1 | 2 | FANCC | 1 | ZCCHC5 |
| 3 | DNAH12 | 2 | EZH2 | 1 | YARS |
| 3 | DMD | 2 | ERCC4 | 1 | XRN1 |
| 3 | COL4A1 | 2 | EGFR | 1 | XPC |
| 3 | CHD8 | 2 | DOCK2 | 1 | XDH |
| 3 | ATRX | 2 | DNM2 | 1 | WT1 |
| 3 | ATP2B3 | 2 | DMXL1 | 1 | WNT10B |
| 2 | ZNF423 | 2 | DLL1 | 1 | WHSC1L1 |
| 2 | VWC2 | 2 | CTSF | 1 | WDFY4 |
| 2 | TPR | 2 | CREBBP | 1 | WBP1 |
| 2 | TENM2 | 2 | COL6A6 | 1 | WAS |
| 2 | SPHKAP | 2 | CNTLN | 1 | VWA5B2 |
| 2 | SMARCA4 | 2 | CIART | 1 | VPS16 |
| 2 | SEPT12 | 2 | CDKN2C | 1 | VEPH1 |
| 2 | RYR3 | 2 | CDH7 | 1 | VCP |
| 2 | RYR2 | 2 | CCND1 | 1 | VAT1L |
| 2 | ROS1 | 2 | CCDC168 | 1 | UTP20 |
| 2 | RBM10 | 2 | BIVM-ERCC5 | 1 | USP43 |
| 2 | RB1 | 2 | ATP13A4 | 1 | USP12 |
| 2 | RALGDS | 2 | ATM | 1 | UGGT2 |
| 2 | PXDNL | 2 | ARID2 | 1 | UBR4 |
| 2 | PTPRZ1 | 2 | ARID1A | 1 | UBQLN3 |
| 2 | PROX1 | 2 | ANKLE2 | 1 | U2SURP |
| 2 | POLE | 2 | AFF2 | 1 | U2AF1 |
| 2 | PML | 2 | ADD2 | 1 | TXNRD2 |

FIG. 19 (CONT.)

Assay Count Based on Genes

| | | | | | |
|---|---|---|---|---|---|
| 1 | TUFT1 | 1 | SYK | 1 | SIDT1 |
| 1 | TUBGCP6 | 1 | SUSD3 | 1 | SH3TC1 |
| 1 | TUBGCP4 | 1 | SULT1C3 | 1 | SH3RF1 |
| 1 | TUBG1 | 1 | STXBP5 | 1 | SH3GL1 |
| 1 | TTN | 1 | STOX1 | 1 | SFMBT2 |
| 1 | TTF2 | 1 | STARD9 | 1 | SETDB1 |
| 1 | TSHZ2 | 1 | SSR3 | 1 | SETD2 |
| 1 | TSHR | 1 | SRSF2 | 1 | SETD1B |
| 1 | TSC2 | 1 | SRBD1 | 1 | SETBP1 |
| 1 | TP63 | 1 | SPTA1 | 1 | SERPINB9 |
| 1 | TOMM70A | 1 | SPNS2 | 1 | SERPINB13 |
| 1 | TOMM7 | 1 | SPIDR | 1 | SERPINB10 |
| 1 | TNKS | 1 | SPDL1 | 1 | SERPINA3 |
| 1 | TNFRSF14 | 1 | SORT1 | 1 | SEPT9 |
| 1 | TNFAIP3 | 1 | SORCS1 | 1 | SEMA5A |
| 1 | TMEM5 | 1 | SNTG2 | 1 | SEMA3D |
| 1 | TMEM132D | 1 | SNF8 | 1 | SELP |
| 1 | TMCC1 | 1 | SMCR8 | 1 | SDK2 |
| 1 | TMC8 | 1 | SMAD4 | 1 | SCN10A |
| 1 | TLN1 | 1 | SLX4 | 1 | SCARF1 |
| 1 | TIMELESS | 1 | SLITRK6 | 1 | SCARB1 |
| 1 | TIAM1 | 1 | SLITRK2 | 1 | SCAF8 |
| 1 | THSD4 | 1 | SLIT1 | 1 | SATL1 |
| 1 | TGM6 | 1 | SLCO5A1 | 1 | SARS |
| 1 | TG | 1 | SLCO4C1 | 1 | SAP130 |
| 1 | TFAP2B | 1 | SLC8A3 | 1 | RYR1 |
| 1 | TEX11 | 1 | SLC7A1 | 1 | RTL1 |
| 1 | TET2 | 1 | SLC6A2 | 1 | RTEL1 |
| 1 | TET1 | 1 | SLC4A10 | 1 | RPS2 |
| 1 | TES | 1 | SLC38A7 | 1 | RPN2 |
| 1 | TENM4 | 1 | SLC35A2 | 1 | RPE65 |
| 1 | TCTEX1D1 | 1 | SLC27A4 | 1 | ROBO3 |
| 1 | TCF3 | 1 | SLC26A8 | 1 | RNFT2 |
| 1 | TBC1D7 | 1 | SLC23A2 | 1 | RNF185 |
| 1 | TAOK3 | 1 | SLC22A12 | 1 | RNASET2 |
| 1 | TAF5 | 1 | SLC10A1 | 1 | RIT1 |
| 1 | TAF3 | 1 | SLAMF1 | 1 | RHO |
| 1 | TAC1 | 1 | SKIDA1 | 1 | RGL1 |
| 1 | SZT2 | 1 | SIX5 | 1 | RFT1 |
| 1 | SYTL5 | 1 | SIRT4 | 1 | REST |
| 1 | SYTL2 | 1 | SIN3A | 1 | REG1B |
| 1 | SYNE1 | 1 | SIL1 | 1 | REG1A |

FIG. 19 (CONT.)
Assay Count Based on Genes

| | | | | | |
|---|---|---|---|---|---|
| 1 | RBM19 | 1 | PNPLA3 | 1 | OR56A3 |
| 1 | RBM15 | 1 | PMFBP1 | 1 | OR51F2 |
| 1 | RASA3 | 1 | PLXNA4 | 1 | OR4K1 |
| 1 | RASA1 | 1 | PLOD1 | 1 | OR2W5 |
| 1 | RAI1 | 1 | PLG | 1 | OR2G2 |
| 1 | RAD9B | 1 | PLEKHG4B | 1 | OR2B2 |
| 1 | RAB11FIP5 | 1 | PLCG2 | 1 | OR2AT4 |
| 1 | QPRT | 1 | PLCE1 | 1 | OR2AG2 |
| 1 | PVRL2 | 1 | PKHD1 | 1 | OR13G1 |
| 1 | PTPRM | 1 | PIK3AP1 | 1 | OR11H6 |
| 1 | PTPRD | 1 | PICALM | 1 | OR10Z1 |
| 1 | PTPRC | 1 | PI4KA | 1 | OR10J1 |
| 1 | PTPN1 | 1 | PHOX2B | 1 | OMD |
| 1 | PTK6 | 1 | PHLDB2 | 1 | OC90 |
| 1 | PTGFRN | 1 | PGLYRP2 | 1 | NXPE3 |
| 1 | PTEN | 1 | PFKFB3 | 1 | NUP214 |
| 1 | PSME4 | 1 | PEG3 | 1 | NUP210L |
| 1 | PRUNE2 | 1 | PEAR1 | 1 | NT5C2 |
| 1 | PRRG1 | 1 | PEAK1 | 1 | NSD1 |
| 1 | PRKCB | 1 | PDZD3 | 1 | NRXN1 |
| 1 | PRICKLE3 | 1 | PDP1 | 1 | NRAS |
| 1 | PRICKLE2 | 1 | PDGFRB | 1 | NR2C2 |
| 1 | PRG4 | 1 | PDGFD | 1 | NPY5R |
| 1 | PRF1 | 1 | PDE4DIP | 1 | NPRL2 |
| 1 | PREPL | 1 | PCLO | 1 | NPR1 |
| 1 | PRDM5 | 1 | PCDHGA5 | 1 | NPNT |
| 1 | PRDM16 | 1 | PCDHB14 | 1 | NPAS4 |
| 1 | PRDM1 | 1 | PCDHA4 | 1 | NOTCH3 |
| 1 | PQBP1 | 1 | PAX7 | 1 | NOL4 |
| 1 | PPP1R3A | 1 | PAX5 | 1 | NOA1 |
| 1 | PPM1B | 1 | PACSIN3 | 1 | NLRP7 |
| 1 | PPL | 1 | PABPC5 | 1 | NLRP5 |
| 1 | PPAN | 1 | P2RY13 | 1 | NLN |
| 1 | POU2AF1 | 1 | OTOG | 1 | NKTR |
| 1 | POSTN | 1 | OTOF | 1 | NINL |
| 1 | POPDC3 | 1 | OSBPL1A | 1 | NFKB2 |
| 1 | PON1 | 1 | OSBPL10 | 1 | NELFA |
| 1 | POMT2 | 1 | OR8K3 | 1 | NEB |
| 1 | POLR2B | 1 | OR8A1 | 1 | NDUFV3 |
| 1 | POLR2A | 1 | OR6V1 | 1 | NDUFS1 |
| 1 | POLQ | 1 | OR5W2 | 1 | NDUFB1 |
| 1 | PNPT1 | 1 | OR5AS1 | 1 | NCS1 |

FIG. 19 (CONT.)
Assay Count Based on Genes

| | | | | | |
|---|---|---|---|---|---|
| 1 | NAP1L3 | 1 | MAP3K1 | 1 | KDR |
| 1 | NACAD | 1 | MAGI2 | 1 | KDM5A |
| 1 | NACA | 1 | MAGEC1 | 1 | KCNMB2 |
| 1 | NAA25 | 1 | MAGEB5 | 1 | KCNH3 |
| 1 | N4BP2L2 | 1 | MAD1L1 | 1 | JAM3 |
| 1 | Mar-01 | 1 | LTBP2 | 1 | JAM2 |
| 1 | MYT1 | 1 | LSMEM2 | 1 | JAK1 |
| 1 | MYO1H | 1 | LRTM2 | 1 | ITPR1 |
| 1 | MYO1E | 1 | LRRTM3 | 1 | ITGA2 |
| 1 | MYH4 | 1 | LRRIQ1 | 1 | IRS1 |
| 1 | MYH1 | 1 | LRRC49 | 1 | IRF3 |
| 1 | MYCN | 1 | LRRC27 | 1 | IL4R |
| 1 | MUC16 | 1 | LRP2 | 1 | IL2RB |
| 1 | MTUS2 | 1 | LRP1B | 1 | IL17A |
| 1 | MTNR1B | 1 | LRIT3 | 1 | IFNG |
| 1 | MTHFD1 | 1 | LPAR4 | 1 | HTT |
| 1 | MTA1 | 1 | LPAR3 | 1 | HTR5A |
| 1 | MSL2 | 1 | LIMCH1 | 1 | HTR2C |
| 1 | MRPL37 | 1 | LGR5 | 1 | HSF5 |
| 1 | MPPED2 | 1 | LFNG | 1 | HSD3B7 |
| 1 | MOGAT3 | 1 | LDLR | 1 | HOXB5 |
| 1 | MN1 | 1 | LDHC | 1 | HMHA1 |
| 1 | MMD2 | 1 | LAMC1 | 1 | HLCS |
| 1 | MLLT6 | 1 | KSR2 | 1 | HIST1H4H |
| 1 | MLLT4 | 1 | KRTAP27-1 | 1 | HIST1H3J |
| 1 | MLIP | 1 | KRT78 | 1 | HIST1H3E |
| 1 | MLH1 | 1 | KRT1 | 1 | HIBADH |
| 1 | MITF | 1 | KPRP | 1 | HERPUD1 |
| 1 | METTL13 | 1 | KMT2A | 1 | HERC2 |
| 1 | MET | 1 | KLK2 | 1 | HECTD4 |
| 1 | MED1 | 1 | KLHL13 | 1 | HECTD1 |
| 1 | MDN1 | 1 | KIT | 1 | HDGFRP2 |
| 1 | MCM6 | 1 | KIF26B | 1 | HDAC10 |
| 1 | MCAT | 1 | KIF26A | 1 | HACE1 |
| 1 | MBNL2 | 1 | KIF13A | 1 | GTF3C1 |
| 1 | MBD2 | 1 | KIAA1598 | 1 | GRWD1 |
| 1 | MATK | 1 | KIAA1551 | 1 | GRM3 |
| 1 | MAST4 | 1 | KIAA1109 | 1 | GRIN3A |
| 1 | MAPK8IP3 | 1 | KIAA1009 | 1 | GRIA2 |
| 1 | MAP4K3 | 1 | KIAA0408 | 1 | GREB1 |
| 1 | MAP4K1 | 1 | KHDRBS2 | 1 | GPRC5C |
| 1 | MAP3K4 | 1 | KERA | 1 | GPRASP1 |

FIG. 19 (CONT.)

Assay Count Based on Genes

| | | | | | |
|---|---|---|---|---|---|
| 1 | GPR50 | 1 | FAM92B | 1 | DISC1 |
| 1 | GPR132 | 1 | FAM83H | 1 | DIP2A |
| 1 | GPR125 | 1 | FAM198A | 1 | DICER1 |
| 1 | GPR108 | 1 | F2RL1 | 1 | DIAPH3 |
| 1 | GPI | 1 | EYA1 | 1 | DIAPH2 |
| 1 | GORAB | 1 | EXT2 | 1 | DHTKD1 |
| 1 | GNPTAB | 1 | EXT1 | 1 | DES |
| 1 | GNB1 | 1 | ETV6 | 1 | DCTN4 |
| 1 | GNAS | 1 | ETV1 | 1 | DCAF12L2 |
| 1 | GNA14 | 1 | ETNPPL | 1 | DAGLA |
| 1 | GNA11 | 1 | ERMP1 | 1 | CYP2C8 |
| 1 | GLYR1 | 1 | ERG | 1 | CXorf56 |
| 1 | GC | 1 | ERCC6 | 1 | CTTNBP2 |
| 1 | GBP5 | 1 | EPHA5 | 1 | CTNND2 |
| 1 | GBF1 | 1 | EP300 | 1 | CTHRC1 |
| 1 | GATA2 | 1 | ENOX1 | 1 | CSMD3 |
| 1 | GAS7 | 1 | EMILIN1 | 1 | CREB3L2 |
| 1 | GAP43 | 1 | EIF4A2 | 1 | CPXCR1 |
| 1 | GABRR2 | 1 | EIF3E | 1 | CPS1 |
| 1 | GAB4 | 1 | EIF2A | 1 | CP |
| 1 | G2E3 | 1 | EHD1 | 1 | COQ5 |
| 1 | FUBP1 | 1 | EGFLAM | 1 | COLEC12 |
| 1 | FTSJ1 | 1 | EFHC2 | 1 | COL4A6 |
| 1 | FSIP2 | 1 | EEF2 | 1 | COL1A1 |
| 1 | FSHR | 1 | ECE2 | 1 | CNTNAP4 |
| 1 | FOXS1 | 1 | EBF1 | 1 | CNTN5 |
| 1 | FOXN2 | 1 | DUSP7 | 1 | CNR1 |
| 1 | FNDC3B | 1 | DUSP22 | 1 | CNBD1 |
| 1 | FN1 | 1 | DSG1 | 1 | CLYBL |
| 1 | FMO3 | 1 | DSCAML1 | 1 | CLPB |
| 1 | FMN2 | 1 | DPP10 | 1 | CLEC10A |
| 1 | FLT3 | 1 | DPEP2 | 1 | CIITA |
| 1 | FLII | 1 | DOPEY1 | 1 | CIAO1 |
| 1 | FLI1 | 1 | DOK2 | 1 | CHST14 |
| 1 | FHAD1 | 1 | DOCK4 | 1 | CHRNB1 |
| 1 | FGFR3 | 1 | DNMT3A | 1 | CHRDL2 |
| 1 | FGFR1 | 1 | DNAH6 | 1 | CHEK2 |
| 1 | FGF18 | 1 | DNAH5 | 1 | CHD7 |
| 1 | FDXR | 1 | DNAH2 | 1 | CHD5 |
| 1 | FBXO7 | 1 | DNAH17 | 1 | CEACAM3 |
| 1 | FBP2 | 1 | DNAH14 | 1 | CEACAM16 |
| 1 | FAR2 | 1 | DLG5 | 1 | CDYL2 |

FIG. 19 (CONT.)
Assay Count Based on Genes

| | | | | | |
|---|---|---|---|---|---|
| 1 | CDX2 | 1 | BMS1 | 1 | ADAD1 |
| 1 | CDS1 | 1 | BHMT2 | 1 | ACTRT2 |
| 1 | CDK5RAP2 | 1 | BCOR | 1 | ACTN2 |
| 1 | CDK2 | 1 | BCL3 | 1 | ACTA2 |
| 1 | CDK14 | 1 | BCL11B | 1 | ACSL3 |
| 1 | CDH24 | 1 | BAP1 | 1 | ACSBG1 |
| 1 | CDH18 | 1 | B9D1 | 1 | ACBD7 |
| 1 | CDH11 | 1 | B3GALT2 | 1 | ABL2 |
| 1 | CDH1 | 1 | B2M | 1 | ABL1 |
| 1 | CD4 | 1 | AWAT2 | 1 | ABHD12 |
| 1 | CD300LB | 1 | ATXN2 | 1 | ABCC12 |
| 1 | CD300E | 1 | ATXN1 | 1 | ABCC11 |
| 1 | CD163 | 1 | ATP6V1C2 | 1 | ABCB5 |
| 1 | CCSER1 | 1 | ATP1A4 | 1 | ABCA9 |
| 1 | CCNB1IP1 | 1 | ATG4A | 1 | ABCA6 |
| 1 | CCL7 | 1 | ATG2B | 1 | AARD |
| 1 | CCDC67 | 1 | ATF7IP | 1 | AADACL4 |
| 1 | CCDC36 | 1 | ASXL3 | | |
| 1 | CCDC150 | 1 | ASXL1 | | |
| 1 | CCDC116 | 1 | ASB2 | | |
| 1 | CBLB | 1 | ASAP3 | | |
| 1 | CASS4 | 1 | ARNT | | |
| 1 | CASP8 | 1 | ARMCX4 | | |
| 1 | CASP2 | 1 | ARL14 | | |
| 1 | CARD10 | 1 | ARHGAP36 | | |
| 1 | CALD1 | 1 | AQP8 | | |
| 1 | CADPS2 | 1 | AQP1 | | |
| 1 | CACTIN | 1 | AOX1 | | |
| 1 | CACNA1B | 1 | AMER1 | | |
| 1 | C8B | 1 | ALMS1 | | |
| 1 | C6orf106 | 1 | AKAP9 | | |
| 1 | C4orf51 | 1 | AKAP8L | | |
| 1 | C2orf48 | 1 | AFF3 | | |
| 1 | C20orf26 | 1 | ADH4 | | |
| 1 | C1orf64 | 1 | ADCYAP1R1 | | |
| 1 | C1orf116 | 1 | ADCY9 | | |
| 1 | C1QTNF7 | 1 | ADCY2 | | |
| 1 | C17orf85 | 1 | ADAMTS8 | | |
| 1 | BTN1A1 | 1 | ADAMTS18 | | |
| 1 | BRIP1 | 1 | ADAMTS16 | | |
| 1 | BRCA2 | 1 | ADAM8 | | |
| 1 | BPIFB4 | 1 | ADAM12 | | |

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 1 | SQ1326_Sample010 | LTX180 | Cancer | 1 | 683 | 2279107 | TracerX | 10 | 17 | 7578457 | 1 | 0.491 | C | A |
| 2 | SQ1326_Sample010 | LTX180 | Cancer | 1 | 683 | 2279107 | TracerX | 10 | 18 | 42530965 | 2 | 0.416 | C | A |
| 3 | SQ1326_Sample010 | LTX180 | Cancer | 1 | 683 | 2279107 | TracerX | 10 | 9 | 5055705 | 3 | 0.853 | G | T |
| 4 | SQ1326_Sample010 | LTX180 | Cancer | 1 | 683 | 2279107 | TracerX | 10 | 23 | 39923016 | 4 | 0.355 | C | T |
| 5 | SQ1326_Sample010 | LTX180 | Cancer | 1 | 683 | 2279107 | TracerX | 10 | 2 | 273303728 | 5 | 0.465 | C | G |
| 6 | SQ1326_Sample010 | LTX180 | Cancer | 1 | 683 | 2279107 | TracerX | 10 | 11 | 117307924 | 6 | 0.484 | G | C |
| 7 | SQ1326_Sample010 | LTX180 | Cancer | 1 | 683 | 2279107 | TracerX | 10 | 18 | 28934317 | 7 | 0.906 | A | C |
| 8 | SQ1326_Sample010 | LTX180 | Cancer | 1 | 683 | 2279107 | TracerX | 10 | 6 | 83847081 | 8 | 0.755 | A | T |
| 9 | SQ1326_Sample010 | LTX180 | Cancer | 1 | 683 | 2279107 | TracerX | 10 | 3 | 14199848 | 9 | 0.307 | T | C |
| 10 | SQ1326_Sample010 | LTX180 | Cancer | 1 | 683 | 2279107 | TracerX | 10 | 11 | 4843295 | 10 | 0.397 | G | T |
| 11 | SQ1326_Sample010 | LTX180 | Cancer | 1 | 683 | 2279107 | TracerX | 10 | 23 | 107423820 | 11 | 0.816 | G | T |
| 12 | SQ1326_Sample010 | LTX180 | Cancer | 1 | 683 | 2279107 | TracerX | 10 | 3 | 31725537 | 12 | 0.419 | G | C |
| 13 | SQ1326_Sample010 | LTX180 | Cancer | 1 | 683 | 2279107 | TracerX | 10 | 12 | 14578167 | 13 | 0.407 | G | T |
| 14 | SQ1326_Sample010 | LTX180 | Cancer | 1 | 683 | 2279107 | TracerX | 10 | 4 | 170077668 | 14 | 0.393 | T | A |
| 15 | SQ1326_Sample010 | LTX180 | Cancer | 1 | 683 | 2279107 | TracerX | 10 | 21 | 39763593 | 15 | 0.283 | G | T |
| 16 | SQ1326_Sample010 | LTX180 | Cancer | 1 | 683 | 2279107 | TracerX | 10 | 1 | 1737935 | 16 | 0.319 | C | A |
| 17 | SQ1326_Sample010 | LTX180 | Cancer | 1 | 683 | 2279107 | TracerX | 10 | 21 | 38302632 | 17 | 0.933 | C | A |
| 18 | SQ1325_Sample003 | LTX073 | Cancer | 1 | 675 | 2279100 | TracerX | 3 | 17 | 7578450 | 18 | 0.468 | C | A |
| 19 | SQ1325_Sample003 | LTX073 | Cancer | 1 | 675 | 2279100 | TracerX | 3 | 17 | 7578449 | 19 | 0.483 | C | T |
| 20 | SQ1325_Sample003 | LTX073 | Cancer | 1 | 675 | 2279100 | TracerX | 3 | 12 | 46244139 | 20 | 0.059 | C | T |
| 21 | SQ1325_Sample003 | LTX073 | Cancer | 1 | 675 | 2279100 | TracerX | 3 | 15 | 74327689 | 21 | 0.484 | G | A |
| 22 | SQ1325_Sample003 | LTX073 | Cancer | 1 | 675 | 2279100 | TracerX | 3 | 19 | 10597402 | 22 | 0.776 | G | A |
| 23 | SQ1325_Sample003 | LTX073 | Cancer | 1 | 675 | 2279100 | TracerX | 3 | 5 | 78378719 | 23 | 0.435 | C | A |
| 24 | SQ1325_Sample003 | LTX073 | Cancer | 1 | 675 | 2279100 | TracerX | 3 | 19 | 1623974 | 24 | 0.489 | C | G |
| 25 | SQ1325_Sample003 | LTX073 | Cancer | 1 | 675 | 2279100 | TracerX | 3 | 11 | 44228441 | 25 | 0.689 | G | A |
| 26 | SQ1325_Sample003 | LTX073 | Cancer | 1 | 675 | 2279100 | TracerX | 3 | 4 | 1061157924 | 26 | 0.300 | C | T |
| 27 | SQ1325_Sample003 | LTX073 | Cancer | 1 | 675 | 2279100 | TracerX | 3 | 4 | 71062448 | 27 | 0.399 | G | T |

FIG. 20

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 28 | SQ1326_Sample003 | LTX073 | Cancer | 1 | 675 | 2279100 | TracerX | 3 | 12 | 25398284 | 28 | 0.855 | C | A |
| 29 | SQ1326_Sample003 | LTX073 | Cancer | 1 | 675 | 2279100 | TracerX | 3 | 7 | 138554488 | 29 | 0.376 | T | C |
| 30 | SQ1326_Sample003 | LTX073 | Cancer | 1 | 675 | 2279100 | TracerX | 3 | 16 | 274600800 | 30 | 0.478 | G | T |
| 31 | SQ1326_Sample003 | LTX073 | Cancer | 1 | 675 | 2279100 | TracerX | 3 | 11 | 100061886 | 31 | 0.453 | C | G |
| 32 | SQ1326_Sample003 | LTX073 | Cancer | 1 | 675 | 2279100 | TracerX | 3 | 1 | 214171377 | 32 | 0.921 | C | A |
| 33 | SQ1326_Sample003 | LTX073 | Cancer | 1 | 675 | 2279100 | TracerX | 3 | 1 | 186269250 | 33 | 0.395 | G | T |
| 34 | SQ1326_Sample003 | LTX073 | Cancer | 1 | 675 | 2279100 | TracerX | 3 | 7 | 100839588 | 34 | 0.947 | A | C |
| 35 | SQ1326_Sample003 | LTX073 | Cancer | 1 | 675 | 2279100 | TracerX | 3 | 12 | 120954411 | 35 | 0.406 | T | G |
| 36 | SQ1326_Sample003 | LTX073 | Cancer | 1 | 675 | 2279100 | TracerX | 3 | 23 | 148037179 | 36 | 0.471 | A | C |
| 37 | SQ1326_Sample003 | LTX073 | Cancer | 1 | 675 | 2279100 | TracerX | 3 | 12 | 116452963 | 37 | 0.616 | T | A |
| 38 | SQ1326_Sample003 | LTX073 | Cancer | 1 | 675 | 2279100 | TracerX | 3 | 5 | 65105902 | 38 | 0.461 | G | T |
| 39 | SQ1326_Sample003 | LTX073 | Cancer | 1 | 675 | 2279100 | TracerX | 3 | 2 | 170044574 | 39 | 0.912 | G | A |
| 40 | SQ1326_Sample002 | LTX058 | Cancer | 1 | 674 | 2279099 | TracerX | 2 | 16 | 15932098 | 40 | 0.998 | C | G |
| 41 | SQ1326_Sample002 | LTX058 | Cancer | 1 | 674 | 2279099 | TracerX | 2 | 17 | 7577574 | 41 | 1.000 | T | A |
| 42 | SQ1326_Sample002 | LTX058 | Cancer | 1 | 674 | 2279099 | TracerX | 2 | 4 | 187549863 | 42 | 0.794 | T | A |
| 43 | SQ1326_Sample002 | LTX058 | Cancer | 1 | 674 | 2279099 | TracerX | 2 | 9 | 37002702 | 43 | 0.973 | C | A |
| 44 | SQ1326_Sample002 | LTX058 | Cancer | 1 | 674 | 2279099 | TracerX | 2 | 15 | 88420326 | 44 | 1.000 | C | A |
| 45 | SQ1326_Sample002 | LTX058 | Cancer | 1 | 674 | 2279099 | TracerX | 2 | 12 | 25398285 | 45 | 1.000 | C | T |
| 46 | SQ1326_Sample002 | LTX058 | Cancer | 1 | 674 | 2279099 | TracerX | 2 | 23 | 63410352 | 46 | 0.091 | C | T |
| 47 | SQ1326_Sample002 | LTX058 | Cancer | 1 | 674 | 2279099 | TracerX | 2 | 1 | 160607244 | 47 | 1.000 | C | A |
| 48 | SQ1326_Sample002 | LTX058 | Cancer | 1 | 674 | 2279099 | TracerX | 2 | 6 | 34614534 | 48 | 1.000 | C | T |
| 49 | SQ1326_Sample002 | LTX058 | Cancer | 1 | 674 | 2279099 | TracerX | 2 | 5 | 118456714 | 49 | 1.000 | C | A |
| 50 | SQ1326_Sample002 | LTX058 | Cancer | 1 | 674 | 2279099 | TracerX | 2 | 22 | 50678733 | 50 | 0.901 | G | T |
| 51 | SQ1326_Sample002 | LTX058 | Cancer | 1 | 674 | 2279099 | TracerX | 2 | 2 | 227660463 | 51 | 0.777 | C | T |
| 52 | SQ1326_Sample002 | LTX058 | Cancer | 1 | 674 | 2279099 | TracerX | 2 | 10 | 104156229 | 52 | 0.999 | G | C |
| 53 | SQ1326_Sample002 | LTX058 | Cancer | 1 | 674 | 2279099 | TracerX | 2 | 17 | 6980252 | 53 | 0.892 | G | C |
| 54 | SQ1326_Sample002 | LTX058 | Cancer | 1 | 674 | 2279099 | TracerX | 2 | 3 | 189604317 | 54 | 0.303 | T | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 55 | SQ1326_Sample002 | LTX058 | Cancer | 1 | 674 | 2279099 | TracerX | 2 | 7 | 2564347 | 55 | 0.482 | G | T |
| 56 | SQ1326_Sample002 | LTX058 | Cancer | 1 | 674 | 2279099 | TracerX | 2 | 20 | 25434139 | 56 | 0.445 | C | A |
| 57 | SQ1326_Sample002 | LTX058 | Cancer | 1 | 674 | 2279099 | TracerX | 2 | 17 | 46669614 | 57 | 0.486 | T | G |
| 58 | SQ1326_Sample009 | LTX175 | Cancer | 1 | 682 | 2279106 | TracerX | 9 | 17 | 7577570 | 58 | 1.000 | C | T |
| 59 | SQ1326_Sample009 | LTX175 | Cancer | 1 | 682 | 2279106 | TracerX | 9 | 13 | 28588650 | 59 | 1.000 | C | A |
| 60 | SQ1326_Sample009 | LTX175 | Cancer | 1 | 682 | 2279106 | TracerX | 9 | 19 | 47424497 | 60 | 1.000 | C | G |
| 61 | SQ1326_Sample009 | LTX175 | Cancer | 1 | 682 | 2279106 | TracerX | 9 | 19 | 47424731 | 61 | 1.000 | C | G |
| 62 | SQ1326_Sample009 | LTX175 | Cancer | 1 | 682 | 2279106 | TracerX | 9 | 14 | 20779849 | 62 | 0.874 | C | T |
| 63 | SQ1326_Sample009 | LTX175 | Cancer | 1 | 682 | 2279106 | TracerX | 9 | 15 | 88727481 | 63 | 0.331 | C | T |
| 64 | SQ1326_Sample009 | LTX175 | Cancer | 1 | 682 | 2279106 | TracerX | 9 | 9 | 93636537 | 64 | 0.361 | T | C |
| 65 | SQ1326_Sample009 | LTX175 | Cancer | 1 | 682 | 2279106 | TracerX | 9 | 7 | 154862800 | 65 | 1.000 | C | G |
| 66 | SQ1326_Sample009 | LTX175 | Cancer | 1 | 682 | 2279106 | TracerX | 9 | 2 | 108881772 | 66 | 1.000 | G | T |
| 67 | SQ1326_Sample009 | LTX175 | Cancer | 1 | 682 | 2279106 | TracerX | 9 | 7 | 121652018 | 67 | 1.000 | A | C |
| 68 | SQ1326_Sample009 | LTX175 | Cancer | 1 | 682 | 2279106 | TracerX | 9 | 16 | 77918598 | 68 | 1.000 | G | T |
| 69 | SQ1326_Sample009 | LTX175 | Cancer | 1 | 682 | 2279106 | TracerX | 9 | 17 | 32597315 | 69 | 0.458 | A | C |
| 70 | SQ1326_Sample009 | LTX175 | Cancer | 1 | 682 | 2279106 | TracerX | 9 | 4 | 92520188 | 70 | 0.974 | C | A |
| 71 | SQ1326_Sample009 | LTX175 | Cancer | 1 | 682 | 2279106 | TracerX | 9 | 17 | 67029876 | 71 | 0.959 | T | G |
| 72 | SQ1326_Sample009 | LTX175 | Cancer | 1 | 682 | 2279106 | TracerX | 9 | 8 | 77776619 | 72 | 0.947 | A | C |
| 73 | SQ1326_Sample009 | LTX175 | Cancer | 1 | 682 | 2279106 | TracerX | 9 | 2 | 54147457 | 73 | 0.870 | G | T |
| 74 | SQ1326_Sample009 | LTX175 | Cancer | 1 | 682 | 2279106 | TracerX | 9 | 12 | 53070879 | 74 | 0.475 | C | G |
| 75 | SQ1326_Sample009 | LTX175 | Cancer | 1 | 682 | 2279106 | TracerX | 9 | 12 | 109865278 | 75 | 0.498 | A | C |
| 76 | SQ1326_Sample009 | LTX175 | Cancer | 1 | 682 | 2279106 | TracerX | 9 | 17 | 72610163 | 76 | 1.000 | G | T |
| 77 | SQ1326_Sample009 | LTX175 | Cancer | 1 | 682 | 2279106 | TracerX | 9 | 5 | 9190458 | 77 | 0.491 | G | T |
| 78 | SQ1326_Sample009 | LTX175 | Cancer | 1 | 682 | 2279106 | TracerX | 9 | 2 | 44556189 | 78 | 0.390 | T | G |
| 79 | SQ1326_Sample011 | LTX185 | Cancer | 1 | 684 | 2279108 | TracerX | 11 | 17 | 36259261 | 79 | NaN | C | G |
| 80 | SQ1326_Sample011 | LTX185 | Cancer | 1 | 684 | 2279108 | TracerX | 11 | 17 | 7579377 | 80 | 0.211 | G | A |
| 81 | SQ1326_Sample011 | LTX185 | Cancer | 1 | 684 | 2279108 | TracerX | 11 | 19 | 10610481 | 81 | 0.488 | A | C |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 82 | SQ1326_Sample011 | LTX185 | Cancer | 1 | 684 | 2279108 | TracerX | 11 | 1 | 110882959 | 82 | 0.442 | C | T |
| 83 | SQ1326_Sample011 | LTX185 | Cancer | 1 | 684 | 2279108 | TracerX | 11 | 1 | 2494684 | 83 | 0.776 | C | T |
| 84 | SQ1326_Sample011 | LTX185 | Cancer | 1 | 684 | 2279108 | TracerX | 11 | 5 | 56178457 | 84 | 0.071 | G | A |
| 85 | SQ1326_Sample011 | LTX185 | Cancer | 1 | 684 | 2279108 | TracerX | 11 | 23 | 53239695 | 85 | 0.340 | C | T |
| 86 | SQ1326_Sample011 | LTX185 | Cancer | 1 | 684 | 2279108 | TracerX | 11 | 16 | 81968086 | 86 | 0.738 | C | T |
| 87 | SQ1326_Sample011 | LTX185 | Cancer | 1 | 684 | 2279108 | TracerX | 11 | 9 | 97873900 | 87 | 0.873 | C | G |
| 88 | SQ1326_Sample011 | LTX185 | Cancer | 1 | 684 | 2279108 | TracerX | 11 | 16 | 27556751 | 88 | 0.431 | C | A |
| 89 | SQ1326_Sample011 | LTX185 | Cancer | 1 | 684 | 2279108 | TracerX | 11 | 6 | 88853702 | 89 | 0.975 | C | A |
| 90 | SQ1326_Sample011 | LTX185 | Cancer | 1 | 684 | 2279108 | TracerX | 11 | 17 | 67082851 | 90 | 0.314 | A | T |
| 91 | SQ1326_Sample011 | LTX185 | Cancer | 1 | 684 | 2279108 | TracerX | 11 | 11 | 119057379 | 91 | 0.430 | G | C |
| 92 | SQ1326_Sample011 | LTX185 | Cancer | 1 | 684 | 2279108 | TracerX | 11 | 11 | 118343868 | 92 | 0.969 | C | G |
| 93 | SQ1326_Sample011 | LTX185 | Cancer | 1 | 684 | 2279108 | TracerX | 11 | 2 | 48602421 | 93 | 0.434 | G | C |
| 94 | SQ1326_Sample011 | LTX185 | Cancer | 1 | 684 | 2279108 | TracerX | 11 | 16 | 85141463 | 94 | 0.773 | G | T |
| 95 | SQ1326_Sample011 | LTX185 | Cancer | 1 | 684 | 2279108 | TracerX | 11 | 1 | 245849542 | 95 | 0.423 | C | A |
| 96 | SQ1326_Sample011 | LTX185 | Cancer | 1 | 684 | 2279108 | TracerX | 11 | 4 | 2339145 | 96 | 0.457 | C | G |
| 97 | SQ1326_Sample011 | LTX185 | Cancer | 1 | 684 | 2279108 | TracerX | 11 | 23 | 118678418 | 97 | 0.757 | C | G |
| 98 | SQ1326_Sample008 | LTX163 | Cancer | 1 | 681 | 2279105 | TracerX | 8 | 17 | 7577099 | 98 | 0.224 | C | T |
| 99 | SQ1326_Sample008 | LTX163 | Cancer | 1 | 681 | 2279105 | TracerX | 8 | 15 | 42019435 | 99 | 0.612 | T | C |
| 100 | SQ1326_Sample008 | LTX163 | Cancer | 1 | 681 | 2279105 | TracerX | 8 | 8 | 31014903 | 100 | 0.465 | G | A |
| 101 | SQ1326_Sample008 | LTX163 | Cancer | 1 | 681 | 2279105 | TracerX | 8 | 16 | 4829736 | 101 | 0.444 | C | G |
| 102 | SQ1326_Sample008 | LTX163 | Cancer | 1 | 681 | 2279105 | TracerX | 8 | 22 | 28196336 | 102 | 0.493 | C | A |
| 103 | SQ1326_Sample008 | LTX163 | Cancer | 1 | 681 | 2279105 | TracerX | 8 | 15 | 41961225 | 103 | 0.374 | C | T |
| 104 | SQ1326_Sample008 | LTX163 | Cancer | 1 | 681 | 2279105 | TracerX | 8 | 16 | 68772312 | 104 | NaN | C | C |
| 105 | SQ1326_Sample008 | LTX163 | Cancer | 1 | 681 | 2279105 | TracerX | 8 | 1 | 150802432 | 105 | 0.255 | G | A |
| 106 | SQ1326_Sample008 | LTX163 | Cancer | 1 | 681 | 2279105 | TracerX | 8 | 1 | 51439886 | 106 | 0.749 | G | A |
| 107 | SQ1326_Sample008 | LTX163 | Cancer | 1 | 681 | 2279105 | TracerX | 8 | 17 | 9850237 | 107 | 0.338 | C | T |
| 108 | SQ1326_Sample008 | LTX163 | Cancer | 1 | 681 | 2279105 | TracerX | 8 | 19 | 47440656 | 108 | 0.577 | G | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 109 | SQ1326_Sample008 | LTX163 | Cancer | 1 | 681 | 2279105 | TracerX | 8 | 17 | 74732533 | 109 | NaN | G | A |
| 110 | SQ1326_Sample008 | LTX163 | Cancer | 1 | 681 | 2279105 | TracerX | 8 | 17 | 29483072 | 110 | 0.924 | C | G |
| 111 | SQ1326_Sample008 | LTX163 | Cancer | 1 | 681 | 2279105 | TracerX | 8 | 3 | 15084467 | 111 | 0.418 | G | T |
| 112 | SQ1326_Sample008 | LTX163 | Cancer | 1 | 681 | 2279105 | TracerX | 8 | 19 | 50162959 | 112 | 0.486 | G | C |
| 113 | SQ1326_Sample008 | LTX163 | Cancer | 1 | 681 | 2279105 | TracerX | 8 | 7 | 22862311 | 113 | 0.473 | G | C |
| 114 | SQ1326_Sample008 | LTX163 | Cancer | 1 | 681 | 2279105 | TracerX | 8 | 6 | 53989658 | 114 | 0.871 | G | C |
| 115 | SQ1326_Sample008 | LTX163 | Cancer | 1 | 681 | 2279105 | TracerX | 8 | 9 | 97325660 | 115 | 0.461 | G | C |
| 116 | SQ1326_Sample008 | LTX163 | Cancer | 1 | 681 | 2279105 | TracerX | 8 | 5 | 169144389 | 116 | 0.881 | T | G |
| 117 | SQ1326_Sample004 | LTX111 | Cancer | 1 | 676 | 2279101 | TracerX | 4 | 12 | 25380254 | 117 | 0.416 | C | G |
| 118 | SQ1326_Sample004 | LTX111 | Cancer | 1 | 676 | 2279101 | TracerX | 4 | 17 | 7577100 | 118 | 0.976 | T | C |
| 119 | SQ1326_Sample004 | LTX111 | Cancer | 1 | 676 | 2279101 | TracerX | 4 | 2 | 178098810 | 119 | 1.000 | C | G |
| 120 | SQ1326_Sample004 | LTX111 | Cancer | 1 | 676 | 2279101 | TracerX | 4 | 11 | 5529966 | 120 | 0.940 | C | A |
| 121 | SQ1326_Sample004 | LTX111 | Cancer | 1 | 676 | 2279101 | TracerX | 4 | 1 | 169566365 | 121 | 1.000 | A | C |
| 122 | SQ1326_Sample004 | LTX111 | Cancer | 1 | 676 | 2279101 | TracerX | 4 | 11 | 130289177 | 122 | 0.995 | A | C |
| 123 | SQ1326_Sample004 | LTX111 | Cancer | 1 | 676 | 2279101 | TracerX | 4 | 2 | 179650690 | 123 | 1.000 | C | A |
| 124 | SQ1326_Sample004 | LTX111 | Cancer | 1 | 676 | 2279101 | TracerX | 4 | 23 | 107393382 | 124 | 0.499 | G | T |
| 125 | SQ1326_Sample004 | LTX111 | Cancer | 1 | 676 | 2279101 | TracerX | 4 | 12 | 53241845 | 125 | 0.466 | G | C |
| 126 | SQ1326_Sample004 | LTX111 | Cancer | 1 | 676 | 2279101 | TracerX | 4 | 9 | 130550571 | 126 | NaN | G | C |
| 127 | SQ1326_Sample004 | LTX111 | Cancer | 1 | 676 | 2279101 | TracerX | 4 | 6 | 52052591 | 127 | 0.299 | C | A |
| 128 | SQ1326_Sample004 | LTX111 | Cancer | 1 | 676 | 2279101 | TracerX | 4 | 19 | 9088996 | 128 | 0.439 | G | C |
| 129 | SQ1326_Sample004 | LTX111 | Cancer | 1 | 676 | 2279101 | TracerX | 4 | 5 | 150029516 | 129 | NaN | C | G |
| 130 | SQ1326_Sample004 | LTX111 | Cancer | 1 | 676 | 2279101 | TracerX | 4 | 6 | 105233172 | 130 | 0.603 | G | A |
| 131 | SQ1326_Sample004 | LTX111 | Cancer | 1 | 676 | 2279101 | TracerX | 4 | 14 | 20404706 | 131 | 0.409 | T | A |
| 132 | SQ1326_Sample004 | LTX111 | Cancer | 1 | 676 | 2279101 | TracerX | 4 | 3 | 150281319 | 132 | 0.856 | G | C |
| 133 | SQ1326_Sample004 | LTX111 | Cancer | 1 | 676 | 2279101 | TracerX | 4 | 19 | 48949644 | 133 | 0.390 | G | A |
| 134 | SQ1326_Sample004 | LTX111 | Cancer | 1 | 676 | 2279101 | TracerX | 4 | 11 | 55681303 | 134 | 0.483 | C | A |
| 135 | SQ1326_Sample004 | LTX111 | Cancer | 1 | 676 | 2279101 | TracerX | 4 | 8 | 21766938 | 135 | 0.480 | C | G |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 136 | SQ1326_Sample001 | LTX032 | Cancer | 1 | 673 | 2279098 | TracerX | 1 | 17 | 59876567 | 136 | 1.000 | C | A |
| 137 | SQ1326_Sample001 | LTX032 | Cancer | 1 | 673 | 2279098 | TracerX | 1 | 17 | 7578528 | 137 | 1.000 | A | C |
| 138 | SQ1326_Sample001 | LTX032 | Cancer | 1 | 673 | 2279098 | TracerX | 1 | 8 | 30989960 | 138 | 1.000 | G | C |
| 139 | SQ1326_Sample001 | LTX032 | Cancer | 1 | 673 | 2279098 | TracerX | 1 | 1 | 51439769 | 139 | 0.944 | A | G |
| 140 | SQ1326_Sample001 | LTX032 | Cancer | 1 | 673 | 2279098 | TracerX | 1 | 6 | 161530838 | 140 | 1.000 | G | T |
| 141 | SQ1326_Sample001 | LTX032 | Cancer | 1 | 673 | 2279098 | TracerX | 1 | 9 | 140865874 | 141 | 1.000 | C | G |
| 142 | SQ1326_Sample001 | LTX032 | Cancer | 1 | 673 | 2279098 | TracerX | 1 | 20 | 20269532 | 142 | 1.000 | G | T |
| 143 | SQ1326_Sample001 | LTX032 | Cancer | 1 | 673 | 2279098 | TracerX | 1 | 11 | 61490377 | 143 | 1.000 | G | T |
| 144 | SQ1326_Sample001 | LTX032 | Cancer | 1 | 673 | 2279098 | TracerX | 1 | 3 | 50387387 | 144 | 0.969 | C | A |
| 145 | SQ1326_Sample001 | LTX032 | Cancer | 1 | 673 | 2279098 | TracerX | 1 | 1 | 170513981 | 145 | 0.903 | C | G |
| 146 | SQ1326_Sample001 | LTX032 | Cancer | 1 | 673 | 2279098 | TracerX | 1 | 9 | 8331595 | 146 | 1.000 | A | T |
| 147 | SQ1326_Sample001 | LTX032 | Cancer | 1 | 673 | 2279098 | TracerX | 1 | 5 | 5303830 | 147 | 0.992 | G | T |
| 148 | SQ1326_Sample001 | LTX032 | Cancer | 1 | 673 | 2279098 | TracerX | 1 | 7 | 155530332 | 148 | NaN | G | T |
| 149 | SQ1326_Sample001 | LTX032 | Cancer | 1 | 673 | 2279098 | TracerX | 1 | 7 | 86415632 | 149 | 0.989 | G | C |
| 150 | SQ1326_Sample001 | LTX032 | Cancer | 1 | 673 | 2279098 | TracerX | 1 | 12 | 117188100 | 150 | 0.860 | C | A |
| 151 | SQ1326_Sample001 | LTX032 | Cancer | 1 | 673 | 2279098 | TracerX | 1 | 20 | 574429470 | 151 | 0.988 | G | T |
| 152 | SQ1326_Sample001 | LTX032 | Cancer | 1 | 673 | 2279098 | TracerX | 1 | 4 | 57865825 | 152 | 1.000 | C | G |
| 153 | SQ1326_Sample005 | LTX126 | Cancer | 1 | 677 | 2279102 | TracerX | 5 | 6 | 26285720 | 153 | 0.964 | G | G |
| 154 | SQ1326_Sample005 | LTX126 | Cancer | 1 | 677 | 2279102 | TracerX | 5 | 3 | 178952085 | 154 | 1.000 | A | G |
| 155 | SQ1326_Sample005 | LTX126 | Cancer | 1 | 677 | 2279102 | TracerX | 5 | 8 | 38274849 | 155 | 0.833 | G | T |
| 156 | SQ1326_Sample005 | LTX126 | Cancer | 1 | 677 | 2279102 | TracerX | 5 | 12 | 68549195 | 156 | 0.972 | C | A |
| 157 | SQ1326_Sample005 | LTX126 | Cancer | 1 | 677 | 2279102 | TracerX | 5 | 15 | 59528785 | 157 | 1.000 | T | A |
| 158 | SQ1326_Sample005 | LTX126 | Cancer | 1 | 677 | 2279102 | TracerX | 5 | 22 | 17488851 | 158 | 0.995 | C | A |
| 159 | SQ1326_Sample005 | LTX126 | Cancer | 1 | 677 | 2279102 | TracerX | 5 | 23 | 69898677 | 159 | 0.997 | T | A |
| 160 | SQ1326_Sample005 | LTX126 | Cancer | 1 | 677 | 2279102 | TracerX | 5 | 12 | 133303956 | 160 | 0.999 | G | T |
| 161 | SQ1326_Sample005 | LTX126 | Cancer | 1 | 677 | 2279102 | TracerX | 5 | 22 | 37531447 | 161 | 0.903 | G | A |
| 162 | SQ1326_Sample005 | LTX126 | Cancer | 1 | 677 | 2279102 | TracerX | 5 | 23 | 31222095 | 162 | 0.882 | G | A |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 163 | SQ1326_Sample005 | LTX126 | Cancer | 1 | 677 | 2279102 | TracerX | 5 | 23 | 101910673 | 163 | 0.724 | C | T |
| 164 | SQ1326_Sample005 | LTX126 | Cancer | 1 | 677 | 2279102 | TracerX | 5 | 16 | 49671888 | 164 | 0.721 | C | T |
| 165 | SQ1326_Sample005 | LTX126 | Cancer | 1 | 677 | 2279102 | TracerX | 5 | 12 | 85450615 | 165 | 0.360 | G | A |
| 166 | SQ1326_Sample005 | LTX126 | Cancer | 1 | 677 | 2279102 | TracerX | 5 | 10 | 21804258 | 166 | 0.683 | C | T |
| 167 | SQ1326_Sample005 | LTX126 | Cancer | 1 | 677 | 2279102 | TracerX | 5 | 1 | 16332578 | 167 | 0.708 | G | A |
| 168 | SQ1326_Sample005 | LTX126 | Cancer | 1 | 677 | 2279102 | TracerX | 5 | 10 | 98764454 | 168 | 0.300 | A | G |
| 169 | SQ1326_Sample005 | LTX126 | Cancer | 1 | 677 | 2279102 | TracerX | 5 | 21 | 44324122 | 169 | NaN | C | G |
| 170 | SQ1326_Sample005 | LTX126 | Cancer | 1 | 677 | 2279102 | TracerX | 5 | 5 | 169138975 | 170 | 0.464 | C | G |
| 171 | SQ1326_Sample005 | LTX126 | Cancer | 1 | 677 | 2279102 | TracerX | 5 | 16 | 24135236 | 171 | 0.348 | C | A |
| 172 | SQ1326_Sample005 | LTX126 | Cancer | 1 | 677 | 2279102 | TracerX | 5 | 7 | 121965604 | 172 | 0.885 | C | T |
| 173 | SQ1326_Sample012 | LTX210 | Cancer | 1 | 685 | 2279109 | TracerX | 12 | 19 | 1207033 | 173 | 1.000 | A | T |
| 174 | SQ1326_Sample012 | LTX210 | Cancer | 1 | 685 | 2279109 | TracerX | 12 | 9 | 139409757 | 174 | 0.396 | C | T |
| 175 | SQ1326_Sample012 | LTX210 | Cancer | 1 | 685 | 2279109 | TracerX | 12 | 13 | 98043699 | 175 | 1.000 | G | T |
| 176 | SQ1326_Sample012 | LTX210 | Cancer | 1 | 685 | 2279109 | TracerX | 12 | 4 | 164449923 | 176 | 1.000 | G | A |
| 177 | SQ1326_Sample012 | LTX210 | Cancer | 1 | 685 | 2279109 | TracerX | 12 | 10 | 135084385 | 177 | 1.000 | C | G |
| 178 | SQ1326_Sample012 | LTX210 | Cancer | 1 | 685 | 2279109 | TracerX | 12 | 23 | 92927241 | 178 | 0.491 | T | T |
| 179 | SQ1326_Sample012 | LTX210 | Cancer | 1 | 685 | 2279109 | TracerX | 12 | 13 | 86369947 | 179 | 1.000 | A | G |
| 180 | SQ1326_Sample012 | LTX210 | Cancer | 1 | 685 | 2279109 | TracerX | 12 | 7 | 45124878 | 180 | 0.999 | C | T |
| 181 | SQ1326_Sample012 | LTX210 | Cancer | 1 | 685 | 2279109 | TracerX | 12 | 23 | 147733580 | 181 | 0.476 | A | C |
| 182 | SQ1326_Sample012 | LTX210 | Cancer | 1 | 685 | 2279109 | TracerX | 12 | 19 | 57325219 | 182 | 0.275 | T | A |
| 183 | SQ1326_Sample012 | LTX210 | Cancer | 1 | 685 | 2279109 | TracerX | 12 | 1 | 158617494 | 183 | 0.481 | T | G |
| 184 | SQ1326_Sample012 | LTX210 | Cancer | 1 | 685 | 2279109 | TracerX | 12 | 1 | 89732158 | 184 | 0.834 | G | T |
| 185 | SQ1326_Sample012 | LTX210 | Cancer | 1 | 685 | 2279109 | TracerX | 12 | 23 | 26236064 | 185 | 0.318 | A | A |
| 186 | SQ1326_Sample012 | LTX210 | Cancer | 1 | 685 | 2279109 | TracerX | 12 | 4 | 15444043 | 186 | 0.940 | C | T |
| 187 | SQ1326_Sample012 | LTX210 | Cancer | 1 | 685 | 2279109 | TracerX | 12 | 14 | 64924932 | 187 | 1.000 | A | T |
| 188 | SQ1326_Sample012 | LTX210 | Cancer | 1 | 685 | 2279109 | TracerX | 12 | 2 | 186656211 | 188 | 1.000 | A | T |
| 189 | SQ1326_Sample012 | LTX210 | Cancer | 1 | 685 | 2279109 | TracerX | 12 | 6 | 28403341 | 189 | 1.000 | T | G |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 190 | SQ1326_Sample012 | LTX210 | Cancer | 1 | 685 | 2279109 | TracerX | 12 | 7 | 84694809 | 190 | 1.000 | G | C |
| 191 | SQ1326_Sample012 | LTX210 | Cancer | 1 | 685 | 2279109 | TracerX | 12 | 6 | 10796281 | 191 | NaN | C | G |
| 192 | SQ1310_Sample007 | LTX093 | Cancer | 2 | 394 | 2321999 | TracerX | 7 | 17 | 7578419 | 192 | NaN | C | A |
| 193 | SQ1310_Sample007 | LTX093 | Cancer | 2 | 394 | 2321999 | TracerX | 7 | 19 | 30936574 | 193 | 1.000 | G | C |
| 194 | SQ1310_Sample007 | LTX093 | Cancer | 2 | 394 | 2321999 | TracerX | 7 | 1 | 240256602 | 194 | 1.000 | C | G |
| 195 | SQ1310_Sample007 | LTX093 | Cancer | 2 | 394 | 2321999 | TracerX | 7 | 19 | 42301524 | 195 | 1.000 | C | A |
| 196 | SQ1310_Sample007 | LTX093 | Cancer | 2 | 394 | 2321999 | TracerX | 7 | 9 | 80144088 | 196 | 1.000 | T | G |
| 197 | SQ1310_Sample007 | LTX093 | Cancer | 2 | 394 | 2321999 | TracerX | 7 | 23 | 77913358 | 197 | 1.000 | G | T |
| 198 | SQ1310_Sample007 | LTX093 | Cancer | 2 | 394 | 2321999 | TracerX | 7 | 2 | 207003321 | 198 | 1.000 | A | C |
| 199 | SQ1310_Sample007 | LTX093 | Cancer | 2 | 394 | 2321999 | TracerX | 7 | 11 | 64111487 | 199 | NaN | C | A |
| 200 | SQ1310_Sample007 | LTX093 | Cancer | 2 | 394 | 2321999 | TracerX | 7 | 1 | 117527379 | 200 | 0.991 | C | A |
| 201 | SQ1310_Sample007 | LTX093 | Cancer | 2 | 394 | 2321999 | TracerX | 7 | 7 | 142750239 | 201 | 0.995 | G | A |
| 202 | SQ1310_Sample007 | LTX093 | Cancer | 2 | 394 | 2321999 | TracerX | 7 | 19 | 15281250 | 202 | 0.869 | C | A |
| 203 | SQ1310_Sample007 | LTX093 | Cancer | 2 | 394 | 2321999 | TracerX | 7 | 11 | 124748000 | 203 | 0.995 | C | A |
| 204 | SQ1310_Sample007 | LTX093 | Cancer | 2 | 394 | 2321999 | TracerX | 7 | 17 | 40765025 | 204 | 1.000 | T | A |
| 205 | SQ1310_Sample007 | LTX093 | Cancer | 2 | 394 | 2321999 | TracerX | 7 | 4 | 100057700 | 205 | 0.410 | C | G |
| 206 | SQ1310_Sample007 | LTX093 | Cancer | 2 | 394 | 2321999 | TracerX | 7 | 3 | 113321899 | 206 | 1.000 | G | T |
| 207 | SQ1310_Sample007 | LTX093 | Cancer | 2 | 394 | 2321999 | TracerX | 7 | 16 | 773877648 | 207 | 1.000 | G | C |
| 208 | SQ1310_Sample007 | LTX093 | Cancer | 2 | 394 | 2321999 | TracerX | 7 | 6 | 35911801 | 208 | 1.000 | G | C |
| 209 | SQ1310_Sample001 | LTX001 | Cancer | 2 | 385 | 2321991 | TracerX | 1 | 5 | 13781004 | 209 | 1.000 | T | G |
| 210 | SQ1310_Sample001 | LTX001 | Cancer | 2 | 385 | 2321991 | TracerX | 1 | 11 | 108122671 | 210 | 0.921 | T | C |
| 211 | SQ1310_Sample001 | LTX001 | Cancer | 2 | 385 | 2321991 | TracerX | 1 | 18 | 47806296 | 211 | 0.467 | T | A |
| 212 | SQ1310_Sample001 | LTX001 | Cancer | 2 | 385 | 2321991 | TracerX | 1 | 12 | 25398284 | 212 | 0.975 | C | A |
| 213 | SQ1310_Sample001 | LTX001 | Cancer | 2 | 385 | 2321991 | TracerX | 1 | 16 | 569765054 | 213 | 0.737 | G | T |
| 214 | SQ1310_Sample001 | LTX001 | Cancer | 2 | 385 | 2321991 | TracerX | 1 | 15 | 42052629 | 214 | 0.387 | C | T |
| 215 | SQ1310_Sample001 | LTX001 | Cancer | 2 | 385 | 2321991 | TracerX | 1 | 3 | 43095052 | 215 | 0.983 | C | G |
| 216 | SQ1310_Sample001 | LTX001 | Cancer | 2 | 385 | 2321991 | TracerX | 1 | 6 | 43322883 | 216 | 0.988 | C | G |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 217 | SQ1310_Sample001 | LTX001 | Cancer | 2 | 385 | 2321991 | TracerX | 1 | 17 | 72436822 | 217 | 0.943 | G | T |
| 218 | SQ1310_Sample001 | LTX001 | Cancer | 2 | 385 | 2321991 | TracerX | 1 | 12 | 118293344 | 218 | 0.428 | C | A |
| 219 | SQ1310_Sample001 | LTX001 | Cancer | 2 | 385 | 2321991 | TracerX | 1 | 3 | 42672772 | 219 | 0.410 | G | C |
| 220 | SQ1310_Sample001 | LTX001 | Cancer | 2 | 385 | 2321991 | TracerX | 1 | 19 | 46269066 | 220 | NaN | G | C |
| 221 | SQ1310_Sample001 | LTX001 | Cancer | 2 | 385 | 2321991 | TracerX | 1 | 1 | 144922008 | 221 | 0.387 | G | C |
| 222 | SQ1310_Sample001 | LTX001 | Cancer | 2 | 385 | 2321991 | TracerX | 1 | 3 | 151046539 | 222 | 0.916 | G | C |
| 223 | SQ1310_Sample001 | LTX001 | Cancer | 2 | 385 | 2321991 | TracerX | 1 | 2 | 96933576 | 223 | 0.460 | G | C |
| 224 | SQ1310_Sample001 | LTX001 | Cancer | 2 | 385 | 2321991 | TracerX | 1 | 2 | 559208555 | 224 | 0.373 | A | T |
| 225 | SQ1310_Sample001 | LTX001 | Cancer | 2 | 385 | 2321991 | TracerX | 1 | 12 | 133306622 | 225 | 0.497 | C | G |
| 226 | SQ1310_Sample001 | LTX001 | Cancer | 2 | 385 | 2321991 | TracerX | 1 | 1 | 23763111 | 226 | 0.475 | C | A |
| 227 | SQ1310_Sample009 | LTX115 | Cancer | 2 | 396 | 2322001 | TracerX | 9 | 12 | 25398284 | 227 | 0.479 | C | G |
| 228 | SQ1310_Sample009 | LTX115 | Cancer | 2 | 396 | 2322001 | TracerX | 9 | 16 | 2131629 | 228 | 0.290 | C | A |
| 229 | SQ1310_Sample009 | LTX115 | Cancer | 2 | 396 | 2322001 | TracerX | 9 | 21 | 44524456 | 229 | 0.682 | G | A |
| 230 | SQ1310_Sample009 | LTX115 | Cancer | 2 | 396 | 2322001 | TracerX | 9 | 7 | 98553923 | 230 | 0.783 | A | T |
| 231 | SQ1310_Sample009 | LTX115 | Cancer | 2 | 396 | 2322001 | TracerX | 9 | 4 | 153245506 | 231 | 0.798 | G | C |
| 232 | SQ1310_Sample009 | LTX115 | Cancer | 2 | 396 | 2322001 | TracerX | 9 | 17 | 29654855 | 232 | 0.316 | A | T |
| 233 | SQ1310_Sample009 | LTX115 | Cancer | 2 | 396 | 2322001 | TracerX | 9 | 3 | 130300717 | 233 | 0.361 | C | A |
| 234 | SQ1310_Sample009 | LTX115 | Cancer | 2 | 396 | 2322001 | TracerX | 9 | 12 | 64178784 | 234 | 0.743 | A | T |
| 235 | SQ1310_Sample009 | LTX115 | Cancer | 2 | 396 | 2322001 | TracerX | 9 | 19 | 58326109 | 235 | 0.497 | C | A |
| 236 | SQ1310_Sample009 | LTX115 | Cancer | 2 | 396 | 2322001 | TracerX | 9 | 1 | 127726481 | 236 | 0.315 | A | T |
| 237 | SQ1310_Sample009 | LTX115 | Cancer | 2 | 396 | 2322001 | TracerX | 9 | 23 | 48337045 | 237 | 0.459 | G | A |
| 238 | SQ1310_Sample009 | LTX115 | Cancer | 2 | 396 | 2322001 | TracerX | 9 | 2 | 74687176 | 238 | 0.473 | C | T |
| 239 | SQ1310_Sample009 | LTX115 | Cancer | 2 | 396 | 2322001 | TracerX | 9 | 11 | 66333530 | 239 | 0.683 | C | T |
| 240 | SQ1310_Sample009 | LTX115 | Cancer | 2 | 396 | 2322001 | TracerX | 9 | 11 | 66333529 | 240 | 0.368 | C | T |
| 241 | SQ1310_Sample009 | LTX115 | Cancer | 2 | 396 | 2322001 | TracerX | 9 | 4 | 158262528 | 241 | 0.681 | C | T |
| 242 | SQ1310_Sample009 | LTX115 | Cancer | 2 | 396 | 2322001 | TracerX | 9 | 10 | 90703560 | 242 | 0.786 | C | A |
| 243 | SQ1310_Sample009 | LTX115 | Cancer | 2 | 396 | 2322001 | TracerX | 9 | 10 | 98408473 | 243 | 0.492 | G | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 244 | SQ1310_Sample009 | LTX115 | Cancer | 2 | 396 | 2322001 | TracerX | 9 | 16 | 76389396 | 244 | 0.363 | G | T |
| 245 | SQ1310_Sample009 | LTX115 | Cancer | 2 | 396 | 2322001 | TracerX | 9 | 1 | 57415347 | 245 | 0.827 | C | G |
| 246 | SQ1310_Sample004 | LTX062 | Cancer | 2 | 388 | 2321994 | TracerX | 4 | 12 | 25398285 | 246 | 0.291 | C | A |
| 247 | SQ1310_Sample004 | LTX062 | Cancer | 2 | 388 | 2321994 | TracerX | 4 | 2 | 25467082 | 247 | 0.426 | C | T |
| 248 | SQ1310_Sample004 | LTX062 | Cancer | 2 | 388 | 2321994 | TracerX | 4 | 4 | 41748254 | 248 | NaN | G | A |
| 249 | SQ1310_Sample004 | LTX062 | Cancer | 2 | 388 | 2321994 | TracerX | 4 | 14 | 93264047 | 249 | NaN | C | T |
| 250 | SQ1310_Sample004 | LTX062 | Cancer | 2 | 388 | 2321994 | TracerX | 4 | 1 | 151534599 | 250 | 0.342 | G | T |
| 251 | SQ1310_Sample004 | LTX062 | Cancer | 2 | 388 | 2321994 | TracerX | 4 | 13 | 27649347 | 251 | 0.762 | C | T |
| 252 | SQ1310_Sample004 | LTX062 | Cancer | 2 | 388 | 2321994 | TracerX | 4 | 7 | 30962189 | 252 | NaN | C | G |
| 253 | SQ1310_Sample004 | LTX062 | Cancer | 2 | 388 | 2321994 | TracerX | 4 | 12 | 57114850 | 253 | 0.879 | G | G |
| 254 | SQ1310_Sample004 | LTX062 | Cancer | 2 | 388 | 2321994 | TracerX | 4 | 3 | 157081234 | 254 | 0.486 | T | A |
| 255 | SQ1310_Sample004 | LTX062 | Cancer | 2 | 388 | 2321994 | TracerX | 4 | 15 | 33872331 | 255 | 0.446 | C | G |
| 256 | SQ1310_Sample004 | LTX062 | Cancer | 2 | 388 | 2321994 | TracerX | 4 | 14 | 95080872 | 256 | 0.412 | G | T |
| 257 | SQ1310_Sample004 | LTX062 | Cancer | 2 | 388 | 2321994 | TracerX | 4 | 4 | 123336585 | 257 | 0.399 | G | T |
| 258 | SQ1310_Sample004 | LTX062 | Cancer | 2 | 388 | 2321994 | TracerX | 4 | 2 | 1006623339 | 258 | 0.438 | C | G |
| 259 | SQ1310_Sample004 | LTX062 | Cancer | 2 | 388 | 2321994 | TracerX | 4 | 7 | 90613523 | 259 | 0.380 | A | T |
| 260 | SQ1310_Sample004 | LTX062 | Cancer | 2 | 388 | 2321994 | TracerX | 4 | 5 | 15937153 | 260 | 0.465 | G | A |
| 261 | SQ1310_Sample004 | LTX062 | Cancer | 2 | 388 | 2321994 | TracerX | 4 | 5 | 11082937 | 261 | 0.358 | C | A |
| 262 | SQ1310_Sample004 | LTX062 | Cancer | 2 | 388 | 2321994 | TracerX | 4 | 5 | 167645554 | 262 | 0.358 | C | A |
| 263 | SQ1310_Sample004 | LTX062 | Cancer | 2 | 388 | 2321994 | TracerX | 4 | 5 | 118469290 | 263 | 0.725 | G | T |
| 264 | SQ1310_Sample004 | LTX062 | Cancer | 2 | 388 | 2321994 | TracerX | 4 | 22 | 44322935 | 264 | 0.383 | C | A |
| 265 | SQ1310_Sample004 | LTX062 | Cancer | 2 | 388 | 2321994 | TracerX | 4 | 21 | 32638512 | 265 | 0.499 | A | C |
| 266 | SQ1310_Sample006 | LTX092 | Cancer | 2 | 393 | 2321998 | TracerX | 6 | 19 | 10597426 | 266 | 1.000 | C | A |
| 267 | SQ1310_Sample006 | LTX092 | Cancer | 2 | 393 | 2321998 | TracerX | 6 | 17 | 7577547 | 267 | 1.000 | G | A |
| 268 | SQ1310_Sample006 | LTX092 | Cancer | 2 | 393 | 2321998 | TracerX | 6 | 1 | 156838370 | 268 | 1.000 | C | T |
| 269 | SQ1310_Sample006 | LTX092 | Cancer | 2 | 393 | 2321998 | TracerX | 6 | 1 | 156838371 | 269 | 1.000 | G | T |
| 270 | SQ1310_Sample006 | LTX092 | Cancer | 2 | 393 | 2321998 | TracerX | 6 | 7 | 116397709 | 270 | 1.000 | T | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 271 | SQ1310_Sample006 | LTX092 | Cancer | 2 | 393 | 2321998 | TracerX | 6 | 16 | 15841950 | 271 | 1.000 | G | A |
| 272 | SQ1310_Sample006 | LTX092 | Cancer | 2 | 393 | 2321998 | TracerX | 6 | 10 | 72358092 | 272 | 1.000 | G | T |
| 273 | SQ1310_Sample006 | LTX092 | Cancer | 2 | 393 | 2321998 | TracerX | 6 | 17 | 29701147 | 273 | 0.926 | C | T |
| 274 | SQ1310_Sample006 | LTX092 | Cancer | 2 | 393 | 2321998 | TracerX | 6 | 2 | 202151263 | 274 | 0.328 | G | T |
| 275 | SQ1310_Sample006 | LTX092 | Cancer | 2 | 393 | 2321998 | TracerX | 6 | 17 | 48266784 | 275 | 0.993 | G | C |
| 276 | SQ1310_Sample006 | LTX092 | Cancer | 2 | 393 | 2321998 | TracerX | 6 | 18 | 22806392 | 276 | 0.960 | C | A |
| 277 | SQ1310_Sample006 | LTX092 | Cancer | 2 | 393 | 2321998 | TracerX | 6 | 17 | 36873205 | 277 | 1.000 | T | G |
| 278 | SQ1310_Sample006 | LTX092 | Cancer | 2 | 393 | 2321998 | TracerX | 6 | 19 | 58190005 | 278 | 1.000 | G | T |
| 279 | SQ1310_Sample006 | LTX092 | Cancer | 2 | 393 | 2321998 | TracerX | 6 | 14 | 77745131 | 279 | 1.000 | C | A |
| 280 | SQ1310_Sample006 | LTX092 | Cancer | 2 | 393 | 2321998 | TracerX | 6 | 1 | 247752158 | 280 | 1.000 | C | A |
| 281 | SQ1310_Sample006 | LTX092 | Cancer | 2 | 393 | 2321998 | TracerX | 6 | 8 | 114186036 | 281 | 1.000 | G | T |
| 282 | SQ1310_Sample006 | LTX092 | Cancer | 2 | 393 | 2321998 | TracerX | 6 | 1 | 852979719 | 282 | 1.000 | A | T |
| 283 | SQ1310_Sample006 | LTX092 | Cancer | 2 | 393 | 2321998 | TracerX | 6 | 2 | 216252944 | 283 | 1.000 | G | T |
| 284 | SQ1310_Sample006 | LTX092 | Cancer | 2 | 393 | 2321998 | TracerX | 6 | 3 | 111632181 | 284 | 0.991 | G | A |
| 285 | SQ1310_Sample008 | LTX107 | Cancer | 2 | 393 | 2321998 | TracerX | 6 | 14 | 99641378 | 285 | 1.000 | T | C |
| 286 | SQ1310_Sample008 | LTX107 | Cancer | 2 | 393 | 2321998 | TracerX | 6 | 2 | 197583282 | 286 | 1.000 | G | A |
| 287 | SQ1310_Sample008 | LTX107 | Cancer | 2 | 395 | 2322000 | TracerX | 8 | 6 | 168363207 | 287 | 0.949 | G | A |
| 288 | SQ1310_Sample008 | LTX107 | Cancer | 2 | 395 | 2322000 | TracerX | 8 | 19 | 109067762 | 288 | 1.000 | G | A |
| 289 | SQ1310_Sample008 | LTX107 | Cancer | 2 | 395 | 2322000 | TracerX | 8 | 3 | 105389088 | 289 | 0.993 | G | C |
| 290 | SQ1310_Sample008 | LTX107 | Cancer | 2 | 395 | 2322000 | TracerX | 8 | 7 | 889655145 | 290 | 1.000 | C | A |
| 291 | SQ1310_Sample008 | LTX107 | Cancer | 2 | 395 | 2322000 | TracerX | 8 | 18 | 31324126 | 291 | 1.000 | G | T |
| 292 | SQ1310_Sample008 | LTX107 | Cancer | 2 | 395 | 2322000 | TracerX | 8 | 19 | 554441944 | 292 | 1.000 | G | A |
| 293 | SQ1310_Sample008 | LTX107 | Cancer | 2 | 395 | 2322000 | TracerX | 8 | 3 | 1562772875 | 293 | 1.000 | A | A |
| 294 | SQ1310_Sample008 | LTX107 | Cancer | 2 | 395 | 2322000 | TracerX | 8 | 7 | 82595317 | 294 | 1.000 | C | A |
| 295 | SQ1310_Sample008 | LTX107 | Cancer | 2 | 395 | 2322000 | TracerX | 8 | 5 | 76128834 | 295 | 0.999 | T | G |
| 296 | SQ1310_Sample008 | LTX107 | Cancer | 2 | 395 | 2322000 | TracerX | 8 | 7 | 1114422930 | 296 | 1.000 | A | C |
| 297 | SQ1310_Sample008 | LTX107 | Cancer | 2 | 395 | 2322000 | TracerX | 8 | 2 | 49210252 | 297 | 1.000 | G | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 298 | SQ1310_Sample008 | LTX107 | Cancer | 2 | 395 | 2322000 | TracerX | 8 | 15 | 78463865 | 298 | 1.000 | G | C |
| 299 | SQ1310_Sample008 | LTX107 | Cancer | 2 | 395 | 2322000 | TracerX | 8 | 8 | 133045358 | 299 | 0.999 | G | C |
| 300 | SQ1310_Sample008 | LTX107 | Cancer | 2 | 395 | 2322000 | TracerX | 8 | 11 | 124440051 | 300 | 0.999 | C | T |
| 301 | SQ1310_Sample008 | LTX107 | Cancer | 2 | 395 | 2322000 | TracerX | 8 | 8 | 61750713 | 301 | 0.223 | G | A |
| 302 | SQ1310_Sample008 | LTX107 | Cancer | 2 | 395 | 2322000 | TracerX | 8 | 23 | 140996113 | 302 | 0.459 | G | T |
| 303 | SQ1310_Sample008 | LTX107 | Cancer | 2 | 395 | 2322000 | TracerX | 8 | 19 | 15586421 | 303 | 0.428 | G | T |
| 304 | SQ1310_Sample008 | LTX107 | Cancer | 2 | 395 | 2322000 | TracerX | 8 | 7 | 20689746 | 304 | 0.817 | G | C |
| 305 | SQ1310_Sample008 | LTX107 | Cancer | 2 | 395 | 2322000 | TracerX | 8 | 23 | 32381072 | 305 | 0.946 | A | C |
| 306 | SQ1310_Sample005 | LTX085 | Cancer | 2 | 389 | 2321995 | TracerX | 5 | 4 | 55561909 | 306 | 0.999 | A | G |
| 307 | SQ1310_Sample005 | LTX085 | Cancer | 2 | 389 | 2321995 | TracerX | 5 | 12 | 102155369 | 307 | 0.430 | C | G |
| 308 | SQ1310_Sample005 | LTX085 | Cancer | 2 | 389 | 2321995 | TracerX | 5 | 1 | 186294922 | 308 | 0.854 | T | C |
| 309 | SQ1310_Sample005 | LTX085 | Cancer | 2 | 389 | 2321995 | TracerX | 5 | 7 | 148544318 | 309 | 0.761 | G | A |
| 310 | SQ1310_Sample005 | LTX085 | Cancer | 2 | 389 | 2321995 | TracerX | 5 | 2 | 70919577 | 310 | 0.477 | G | C |
| 311 | SQ1310_Sample005 | LTX085 | Cancer | 2 | 389 | 2321995 | TracerX | 5 | 12 | 6923449 | 311 | 0.806 | A | G |
| 312 | SQ1310_Sample005 | LTX085 | Cancer | 2 | 389 | 2321995 | TracerX | 5 | 7 | 107704397 | 312 | 0.756 | T | C |
| 313 | SQ1310_Sample005 | LTX085 | Cancer | 2 | 389 | 2321995 | TracerX | 5 | 2 | 315982323 | 313 | 0.720 | A | G |
| 314 | SQ1310_Sample005 | LTX085 | Cancer | 2 | 389 | 2321995 | TracerX | 5 | 3 | 193132437 | 314 | 0.401 | C | A |
| 315 | SQ1310_Sample005 | LTX085 | Cancer | 2 | 389 | 2321995 | TracerX | 5 | 23 | 48762531 | 315 | 0.404 | A | G |
| 316 | SQ1310_Sample005 | LTX085 | Cancer | 2 | 389 | 2321995 | TracerX | 5 | 1 | 159409831 | 316 | 1.000 | A | C |
| 317 | SQ1310_Sample005 | LTX085 | Cancer | 2 | 389 | 2321995 | TracerX | 5 | 16 | 25232800 | 317 | 0.392 | G | A |
| 318 | SQ1310_Sample005 | LTX085 | Cancer | 2 | 389 | 2321995 | TracerX | 5 | 18 | 63526274 | 318 | 0.991 | C | T |
| 319 | SQ1310_Sample005 | LTX085 | Cancer | 2 | 389 | 2321995 | TracerX | 5 | 1 | 67243012 | 319 | 0.730 | A | G |
| 320 | SQ1310_Sample005 | LTX085 | Cancer | 2 | 389 | 2321995 | TracerX | 5 | 20 | 49195748 | 320 | 0.835 | T | C |
| 321 | SQ1310_Sample003 | LTX028 | Cancer | 2 | 387 | 2321993 | TracerX | 3 | 16 | 11000781 | 321 | 1.000 | G | A |
| 322 | SQ1310_Sample003 | LTX028 | Cancer | 2 | 387 | 2321993 | TracerX | 3 | 18 | 22804610 | 322 | 1.000 | C | G |
| 323 | SQ1310_Sample003 | LTX028 | Cancer | 2 | 387 | 2321993 | TracerX | 3 | 16 | 27454289 | 323 | 1.000 | C | A |
| 324 | SQ1310_Sample003 | LTX028 | Cancer | 2 | 387 | 2321993 | TracerX | 3 | 6 | 117638319 | 324 | 1.000 | G | A |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 325 | SQ1310_Sample003 | LTX028 | Cancer | 2 | 387 | 2321993 | TracerX | 3 | 10 | 22016857 | 325 | 0.999 | G | T |
| 326 | SQ1310_Sample003 | LTX028 | Cancer | 2 | 387 | 2321993 | TracerX | 3 | 10 | 21823709 | 326 | 0.983 | G | T |
| 327 | SQ1310_Sample003 | LTX028 | Cancer | 2 | 387 | 2321993 | TracerX | 3 | 19 | 38942485 | 327 | 1.000 | A | C |
| 328 | SQ1310_Sample003 | LTX028 | Cancer | 2 | 387 | 2321993 | TracerX | 3 | 16 | 55705930 | 328 | 0.999 | C | G |
| 329 | SQ1310_Sample003 | LTX028 | Cancer | 2 | 387 | 2321993 | TracerX | 3 | 19 | 56896362 | 329 | 1.000 | T | A |
| 330 | SQ1310_Sample003 | LTX028 | Cancer | 2 | 387 | 2321993 | TracerX | 3 | 1 | 238053905 | 330 | 1.000 | C | G |
| 331 | SQ1310_Sample003 | LTX028 | Cancer | 2 | 387 | 2321993 | TracerX | 3 | 18 | 21957404 | 331 | 0.392 | C | A |
| 332 | SQ1310_Sample003 | LTX028 | Cancer | 2 | 387 | 2321993 | TracerX | 3 | 1 | 153658292 | 332 | 0.798 | A | T |
| 333 | SQ1310_Sample003 | LTX028 | Cancer | 2 | 387 | 2321993 | TracerX | 3 | 10 | 12139797 | 333 | 0.430 | C | G |
| 334 | SQ1310_Sample003 | LTX028 | Cancer | 2 | 387 | 2321993 | TracerX | 3 | 11 | 5969433 | 334 | 1.000 | T | G |
| 335 | SQ1310_Sample003 | LTX028 | Cancer | 2 | 387 | 2321993 | TracerX | 3 | 18 | 10696430 | 335 | 1.000 | A | T |
| 336 | SQ1310_Sample003 | LTX028 | Cancer | 2 | 387 | 2321993 | TracerX | 3 | 6 | 170592441 | 336 | 0.997 | G | T |
| 337 | SQ1310_Sample003 | LTX028 | Cancer | 2 | 387 | 2321993 | TracerX | 3 | 1 | 237817673 | 337 | 0.805 | A | C |
| 338 | SQ1310_Sample003 | LTX028 | Cancer | 2 | 387 | 2321993 | TracerX | 3 | 1 | 43904447 | 338 | NaN | A | C |
| 339 | SQ1310_Sample002 | LTX025 | Cancer | 2 | 386 | 2321992 | TracerX | 2 | 6 | 27879686 | 339 | 0.860 | G | A |
| 340 | SQ1310_Sample002 | LTX025 | Cancer | 2 | 386 | 2321992 | TracerX | 2 | 22 | 29095912 | 340 | 1.000 | C | A |
| 341 | SQ1310_Sample002 | LTX025 | Cancer | 2 | 386 | 2321992 | TracerX | 2 | 23 | 152807895 | 341 | 1.000 | T | G |
| 342 | SQ1310_Sample002 | LTX025 | Cancer | 2 | 386 | 2321992 | TracerX | 2 | 19 | 3113467 | 342 | 1.000 | C | A |
| 343 | SQ1310_Sample002 | LTX025 | Cancer | 2 | 386 | 2321992 | TracerX | 2 | 16 | 3786795 | 343 | 1.000 | C | T |
| 344 | SQ1310_Sample002 | LTX025 | Cancer | 2 | 386 | 2321992 | TracerX | 2 | 3 | 57448502 | 344 | 1.000 | C | T |
| 345 | SQ1310_Sample002 | LTX025 | Cancer | 2 | 386 | 2321992 | TracerX | 2 | 7 | 91691662 | 345 | 1.000 | G | A |
| 346 | SQ1310_Sample002 | LTX025 | Cancer | 2 | 386 | 2321992 | TracerX | 2 | 19 | 4362364 | 346 | 0.972 | G | C |
| 347 | SQ1310_Sample002 | LTX025 | Cancer | 2 | 386 | 2321992 | TracerX | 2 | 13 | 29600029 | 347 | 1.000 | G | T |
| 348 | SQ1310_Sample002 | LTX025 | Cancer | 2 | 386 | 2321992 | TracerX | 2 | 12 | 122261145 | 348 | 1.000 | G | A |
| 349 | SQ1310_Sample002 | LTX025 | Cancer | 2 | 386 | 2321992 | TracerX | 2 | 15 | 24922479 | 349 | 0.995 | G | A |
| 350 | SQ1310_Sample002 | LTX025 | Cancer | 2 | 386 | 2321992 | TracerX | 2 | 9 | 79322437 | 350 | 1.000 | C | A |
| 351 | SQ1310_Sample002 | LTX025 | Cancer | 2 | 386 | 2321992 | TracerX | 2 | 2 | 10894174 | 351 | 1.000 | C | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 352 | SQ1310_Sample002 | LTX025 | Cancer | 2 | 386 | 2321992 | TracerX | 2 | 11 | 56085828 | 352 | 1.000 | G | T |
| 353 | SQ1310_Sample002 | LTX025 | Cancer | 2 | 386 | 2321992 | TracerX | 2 | 12 | 1940586 | 353 | 0.466 | G | C |
| 354 | SQ1310_Sample002 | LTX025 | Cancer | 2 | 386 | 2321992 | TracerX | 2 | 6 | 170592096 | 354 | 0.841 | C | G |
| 355 | SQ1310_Sample002 | LTX025 | Cancer | 2 | 386 | 2321992 | TracerX | 2 | 5 | 140603250 | 355 | 0.475 | A | C |
| 356 | SQ1310_Sample002 | LTX025 | Cancer | 2 | 386 | 2321992 | TracerX | 2 | 4 | 1991518 | 356 | 0.996 | C | A |
| 357 | SQ1310_Sample002 | LTX025 | Cancer | 2 | 386 | 2321992 | TracerX | 2 | 2 | 70905982 | 357 | 0.998 | C | G |
| 358 | SQ1310_Sample002 | LTX025 | Cancer | 2 | 386 | 2321992 | TracerX | 2 | 11 | 93088652 | 358 | 0.887 | C | T |
| 359 | SQ1310_Sample010 | LTX120 | Cancer | 2 | 397 | 2322002 | TracerX | 10 | 17 | 7578527 | 359 | 1.000 | A | G |
| 360 | SQ1310_Sample010 | LTX120 | Cancer | 2 | 397 | 2322002 | TracerX | 10 | 7 | 137597807 | 360 | 1.000 | C | G |
| 361 | SQ1310_Sample010 | LTX120 | Cancer | 2 | 397 | 2322002 | TracerX | 10 | 10 | 8006756 | 361 | 0.999 | G | T |
| 362 | SQ1310_Sample010 | LTX120 | Cancer | 2 | 397 | 2322002 | TracerX | 10 | 7 | 27582682 | 362 | 1.000 | C | A |
| 363 | SQ1310_Sample010 | LTX120 | Cancer | 2 | 397 | 2322002 | TracerX | 10 | 10 | 96798759 | 363 | 1.000 | G | T |
| 364 | SQ1310_Sample010 | LTX120 | Cancer | 2 | 397 | 2322002 | TracerX | 10 | 13 | 43986184 | 364 | 0.998 | C | T |
| 365 | SQ1310_Sample010 | LTX120 | Cancer | 2 | 397 | 2322002 | TracerX | 10 | 18 | 346453 | 365 | 1.000 | G | T |
| 366 | SQ1310_Sample010 | LTX120 | Cancer | 2 | 397 | 2322002 | TracerX | 10 | 20 | 30432471 | 366 | 0.999 | G | T |
| 367 | SQ1310_Sample010 | LTX120 | Cancer | 2 | 397 | 2322002 | TracerX | 10 | 1 | 182993071 | 367 | 0.977 | G | A |
| 368 | SQ1310_Sample010 | LTX120 | Cancer | 2 | 397 | 2322002 | TracerX | 10 | 3 | 49294386 | 368 | 1.000 | C | G |
| 369 | SQ1310_Sample010 | LTX120 | Cancer | 2 | 397 | 2322002 | TracerX | 10 | 3 | 50324123 | 369 | 1.000 | A | T |
| 370 | SQ1310_Sample010 | LTX120 | Cancer | 2 | 397 | 2322002 | TracerX | 10 | 1 | 6206306 | 370 | 1.000 | C | T |
| 371 | SQ1310_Sample010 | LTX120 | Cancer | 2 | 397 | 2322002 | TracerX | 10 | 9 | 5798962 | 371 | 1.000 | C | G |
| 372 | SQ1310_Sample010 | LTX120 | Cancer | 2 | 397 | 2322002 | TracerX | 10 | 20 | 62323174 | 372 | 0.965 | G | A |
| 373 | SQ1310_Sample010 | LTX120 | Cancer | 2 | 397 | 2322002 | TracerX | 10 | 3 | 38768524 | 373 | 0.984 | G | T |
| 374 | SQ1310_Sample010 | LTX120 | Cancer | 2 | 397 | 2322002 | TracerX | 10 | 2 | 141359067 | 374 | 0.921 | A | G |
| 375 | SQ1310_Sample010 | LTX120 | Cancer | 2 | 397 | 2322002 | TracerX | 10 | 2 | 211521351 | 375 | 1.000 | G | T |
| 376 | SQ1310_Sample010 | LTX120 | Cancer | 2 | 397 | 2322002 | TracerX | 10 | 9 | 131107700 | 376 | 1.000 | C | A |
| 377 | SQ1328_Sample002 | LTX041 | Cancer | 3 | 706 | 2279159 | TracerX | 2 | 23 | 152830557 | 377 | 0.490 | C | G |
| 378 | SQ1328_Sample002 | LTX041 | Cancer | 3 | 706 | 2279159 | TracerX | 2 | 12 | 25398285 | 378 | 0.337 | C | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 379 | SQ1328_Sample002 | LTX041 | Cancer | 3 | 706 | 2279159 | TracerX | 2 | 4 | 153245455 | 379 | 0.382 | C | A |
| 380 | SQ1328_Sample002 | LTX041 | Cancer | 3 | 706 | 2279159 | TracerX | 2 | 17 | 7579378 | 380 | 0.888 | G | T |
| 381 | SQ1328_Sample002 | LTX041 | Cancer | 3 | 706 | 2279159 | TracerX | 2 | 13 | 103520588 | 381 | 0.775 | G | T |
| 382 | SQ1328_Sample002 | LTX041 | Cancer | 3 | 706 | 2279159 | TracerX | 2 | 16 | 158440020 | 382 | 0.720 | C | T |
| 383 | SQ1328_Sample002 | LTX041 | Cancer | 3 | 706 | 2279159 | TracerX | 2 | 10 | 104857113 | 383 | 0.926 | G | C |
| 384 | SQ1328_Sample002 | LTX041 | Cancer | 3 | 706 | 2279159 | TracerX | 2 | 11 | 85733463 | 384 | 0.450 | C | G |
| 385 | SQ1328_Sample002 | LTX041 | Cancer | 3 | 706 | 2279159 | TracerX | 2 | 23 | 90691588 | 385 | 0.789 | G | T |
| 386 | SQ1328_Sample002 | LTX041 | Cancer | 3 | 706 | 2279159 | TracerX | 2 | 12 | 7636270 | 386 | 0.426 | G | T |
| 387 | SQ1328_Sample002 | LTX041 | Cancer | 3 | 706 | 2279159 | TracerX | 2 | 2 | 79348040 | 387 | 0.416 | C | A |
| 388 | SQ1328_Sample002 | LTX041 | Cancer | 3 | 706 | 2279159 | TracerX | 2 | 16 | 68023965 | 388 | 1.000 | C | A |
| 389 | SQ1328_Sample002 | LTX041 | Cancer | 3 | 706 | 2279159 | TracerX | 2 | 13 | 110804825 | 389 | 0.416 | C | A |
| 390 | SQ1328_Sample002 | LTX041 | Cancer | 3 | 706 | 2279159 | TracerX | 2 | 14 | 105920600 | 390 | 0.825 | G | T |
| 391 | SQ1328_Sample002 | LTX041 | Cancer | 3 | 706 | 2279159 | TracerX | 2 | 1 | 171761246 | 391 | 0.909 | G | T |
| 392 | SQ1328_Sample002 | LTX041 | Cancer | 3 | 706 | 2279159 | TracerX | 2 | 1 | 150259318 | 392 | 0.458 | G | C |
| 393 | SQ1328_Sample002 | LTX041 | Cancer | 3 | 706 | 2279159 | TracerX | 2 | 6 | 62390879 | 393 | 0.290 | C | A |
| 394 | SQ1328_Sample002 | LTX041 | Cancer | 3 | 706 | 2279159 | TracerX | 2 | 16 | 4896197 | 394 | 0.852 | C | A |
| 395 | SQ1328_Sample002 | LTX041 | Cancer | 3 | 706 | 2279159 | TracerX | 2 | 13 | 110804826 | 395 | 0.421 | C | C |
| 396 | SQ1328_Sample008 | LTX097 | Cancer | 3 | 715 | 2279165 | TracerX | 8 | 17 | 7577580 | 396 | 1.000 | T | C |
| 397 | SQ1328_Sample008 | LTX097 | Cancer | 3 | 715 | 2279165 | TracerX | 8 | 1 | 115256529 | 397 | 1.000 | T | C |
| 398 | SQ1328_Sample008 | LTX097 | Cancer | 3 | 715 | 2279165 | TracerX | 8 | 2 | 178098966 | 398 | 1.000 | C | T |
| 399 | SQ1328_Sample008 | LTX097 | Cancer | 3 | 715 | 2279165 | TracerX | 8 | 7 | 98609727 | 399 | 1.000 | G | A |
| 400 | SQ1328_Sample008 | LTX097 | Cancer | 3 | 715 | 2279165 | TracerX | 8 | 15 | 42059002 | 400 | 1.000 | G | C |
| 401 | SQ1328_Sample008 | LTX097 | Cancer | 3 | 715 | 2279165 | TracerX | 8 | 5 | 66460021 | 401 | 1.000 | G | A |
| 402 | SQ1328_Sample008 | LTX097 | Cancer | 3 | 715 | 2279165 | TracerX | 8 | 1 | 2939112 | 402 | 1.000 | G | C |
| 403 | SQ1328_Sample008 | LTX097 | Cancer | 3 | 715 | 2279165 | TracerX | 8 | 2 | 136615556 | 403 | 1.000 | C | T |
| 404 | SQ1328_Sample008 | LTX097 | Cancer | 3 | 715 | 2279165 | TracerX | 8 | 19 | 1083272 | 404 | 1.000 | C | T |
| 405 | SQ1328_Sample008 | LTX097 | Cancer | 3 | 715 | 2279165 | TracerX | 8 | 7 | 75932205 | 405 | NaN | C | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 406 | SQ1328_Sample008 | LTX097 | Cancer | 3 | 715 | 2279165 | TracerX | 8 | 19 | 3978139 | 406 | 0.376 | G | A |
| 407 | SQ1328_Sample008 | LTX097 | Cancer | 3 | 715 | 2279165 | TracerX | 8 | 19 | 39087699 | 407 | 0.751 | G | A |
| 408 | SQ1328_Sample008 | LTX097 | Cancer | 3 | 715 | 2279165 | TracerX | 8 | 16 | 72184618 | 408 | NaN | C | G |
| 409 | SQ1328_Sample008 | LTX097 | Cancer | 3 | 715 | 2279165 | TracerX | 8 | 22 | 37903864 | 409 | 1.000 | A | C |
| 410 | SQ1328_Sample008 | LTX097 | Cancer | 3 | 715 | 2279165 | TracerX | 8 | 7 | 121612669 | 410 | 1.000 | A | C |
| 411 | SQ1328_Sample008 | LTX097 | Cancer | 3 | 715 | 2279165 | TracerX | 8 | 22 | 36722683 | 411 | 0.982 | G | A |
| 412 | SQ1328_Sample008 | LTX097 | Cancer | 3 | 715 | 2279165 | TracerX | 8 | 17 | 10398519 | 412 | 1.000 | G | A |
| 413 | SQ1328_Sample008 | LTX097 | Cancer | 3 | 715 | 2279165 | TracerX | 8 | 11 | 134018480 | 413 | 1.000 | G | A |
| 414 | SQ1328_Sample008 | LTX097 | Cancer | 3 | 715 | 2279165 | TracerX | 8 | 5 | 52386370 | 414 | 0.749 | T | C |
| 415 | SQ1328_Sample005 | LTX055 | Cancer | 3 | 709 | 2279162 | TracerX | 5 | 12 | 25398285 | 415 | 0.393 | C | A |
| 416 | SQ1328_Sample005 | LTX055 | Cancer | 3 | 709 | 2279162 | TracerX | 5 | 17 | 29483017 | 416 | 0.484 | G | T |
| 417 | SQ1328_Sample005 | LTX055 | Cancer | 3 | 709 | 2279162 | TracerX | 5 | 4 | 41749461 | 417 | 0.498 | C | G |
| 418 | SQ1328_Sample005 | LTX055 | Cancer | 3 | 709 | 2279162 | TracerX | 5 | 19 | 51380137 | 418 | 0.300 | C | A |
| 419 | SQ1328_Sample005 | LTX055 | Cancer | 3 | 709 | 2279162 | TracerX | 5 | 1 | 78430779 | 419 | 0.407 | C | A |
| 420 | SQ1328_Sample005 | LTX055 | Cancer | 3 | 709 | 2279162 | TracerX | 5 | 12 | 25398284 | 420 | 0.483 | C | A |
| 421 | SQ1328_Sample005 | LTX055 | Cancer | 3 | 709 | 2279162 | TracerX | 5 | 1 | 236882203 | 421 | 0.310 | T | A |
| 422 | SQ1328_Sample005 | LTX055 | Cancer | 3 | 709 | 2279162 | TracerX | 5 | 15 | 28513699 | 422 | 0.407 | C | A |
| 423 | SQ1328_Sample005 | LTX055 | Cancer | 3 | 709 | 2279162 | TracerX | 5 | 1 | 183775513 | 423 | 0.868 | C | G |
| 424 | SQ1328_Sample005 | LTX055 | Cancer | 3 | 709 | 2279162 | TracerX | 5 | 12 | 101739472 | 424 | 0.754 | G | T |
| 425 | SQ1328_Sample005 | LTX055 | Cancer | 3 | 709 | 2279162 | TracerX | 5 | 18 | 315523112 | 425 | 0.421 | C | A |
| 426 | SQ1328_Sample005 | LTX055 | Cancer | 3 | 709 | 2279162 | TracerX | 5 | 23 | 100745059 | 426 | 0.496 | A | C |
| 427 | SQ1328_Sample005 | LTX055 | Cancer | 3 | 709 | 2279162 | TracerX | 5 | 5 | 384250079 | 427 | 0.374 | C | G |
| 428 | SQ1328_Sample005 | LTX055 | Cancer | 3 | 709 | 2279162 | TracerX | 5 | 3 | 178543485 | 428 | 0.862 | G | C |
| 429 | SQ1328_Sample005 | LTX055 | Cancer | 3 | 709 | 2279162 | TracerX | 5 | 4 | 57796165 | 429 | 0.793 | G | C |
| 430 | SQ1328_Sample005 | LTX055 | Cancer | 3 | 709 | 2279162 | TracerX | 5 | 4 | 123184698 | 430 | 0.411 | G | T |
| 431 | SQ1328_Sample005 | LTX055 | Cancer | 3 | 709 | 2279162 | TracerX | 5 | 4 | 85530655 | 431 | 0.837 | G | T |
| 432 | SQ1328_Sample005 | LTX055 | Cancer | 3 | 709 | 2279162 | TracerX | 5 | 5 | 174099 | 432 | 0.789 | A | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 433 | SQ1328_Sample005 | LTX055 | Cancer | 3 | 709 | 2279162 | TracerX | 5 | 16 | 80718770 | 433 | 0.387 | G | C |
| 434 | SQ1328_Sample005 | LTX055 | Cancer | 3 | 709 | 2279162 | TracerX | 5 | 12 | 32145428 | 434 | 0.898 | G | C |
| 435 | SQ1328_Sample005 | LTX055 | Cancer | 3 | 709 | 2279162 | TracerX | 5 | 23 | 37985925 | 435 | 0.389 | G | C |
| 436 | SQ1328_Sample010 | LTX165 | Cancer | 3 | 717 | 2279167 | TracerX | 10 | 17 | 7578457 | 436 | 1.000 | C | T |
| 437 | SQ1328_Sample010 | LTX165 | Cancer | 3 | 717 | 2279167 | TracerX | 10 | 4 | 153245381 | 437 | 1.000 | T | A |
| 438 | SQ1328_Sample010 | LTX165 | Cancer | 3 | 717 | 2279167 | TracerX | 10 | 13 | 28542956 | 438 | NaN | G | C |
| 439 | SQ1328_Sample010 | LTX165 | Cancer | 3 | 717 | 2279167 | TracerX | 10 | 13 | 32929041 | 439 | 1.000 | G | T |
| 440 | SQ1328_Sample010 | LTX165 | Cancer | 3 | 717 | 2279167 | TracerX | 10 | 11 | 111228171 | 440 | 0.996 | G | T |
| 441 | SQ1328_Sample010 | LTX165 | Cancer | 3 | 717 | 2279167 | TracerX | 10 | 17 | 71361424 | 441 | 1.000 | C | A |
| 442 | SQ1328_Sample010 | LTX165 | Cancer | 3 | 717 | 2279167 | TracerX | 10 | 14 | 31061546 | 442 | 1.000 | G | A |
| 443 | SQ1328_Sample010 | LTX165 | Cancer | 3 | 717 | 2279167 | TracerX | 10 | 16 | 48174630 | 443 | 1.000 | A | C |
| 444 | SQ1328_Sample010 | LTX165 | Cancer | 3 | 717 | 2279167 | TracerX | 10 | 10 | 28224075 | 444 | NaN | G | T |
| 445 | SQ1328_Sample010 | LTX165 | Cancer | 3 | 717 | 2279167 | TracerX | 10 | 4 | 22394224 | 445 | 1.000 | T | A |
| 446 | SQ1328_Sample010 | LTX165 | Cancer | 3 | 717 | 2279167 | TracerX | 10 | 6 | 27858176 | 446 | 0.996 | C | G |
| 447 | SQ1328_Sample010 | LTX165 | Cancer | 3 | 717 | 2279167 | TracerX | 10 | 19 | 11226802 | 447 | 0.867 | C | T |
| 448 | SQ1328_Sample010 | LTX165 | Cancer | 3 | 717 | 2279167 | TracerX | 10 | 4 | 106880244 | 448 | 1.000 | G | A |
| 449 | SQ1328_Sample010 | LTX165 | Cancer | 3 | 717 | 2279167 | TracerX | 10 | 1 | 117644093 | 449 | 0.978 | G | A |
| 450 | SQ1328_Sample010 | LTX165 | Cancer | 3 | 717 | 2279167 | TracerX | 10 | 18 | 10784905 | 450 | 0.300 | C | T |
| 451 | SQ1328_Sample010 | LTX165 | Cancer | 3 | 717 | 2279167 | TracerX | 10 | 10 | 6264869 | 451 | 0.398 | C | T |
| 452 | SQ1328_Sample010 | LTX165 | Cancer | 3 | 717 | 2279167 | TracerX | 10 | 11 | 72141386 | 452 | 0.351 | G | A |
| 453 | SQ1328_Sample010 | LTX165 | Cancer | 3 | 717 | 2279167 | TracerX | 10 | 14 | 105518356 | 453 | 0.875 | C | T |
| 454 | SQ1328_Sample010 | LTX165 | Cancer | 3 | 717 | 2279167 | TracerX | 10 | 3 | 121228960 | 454 | 0.370 | G | A |
| 455 | SQ1328_Sample010 | LTX165 | Cancer | 3 | 717 | 2279167 | TracerX | 10 | 11 | 30433103 | 455 | 0.443 | G | T |
| 456 | SQ1328_Sample001 | LTX021 | Cancer | 3 | 705 | 2279158 | TracerX | 1 | 9 | 95179143 | 456 | 0.704 | G | A |
| 457 | SQ1328_Sample001 | LTX021 | Cancer | 3 | 705 | 2279158 | TracerX | 1 | 5 | 149514547 | 457 | 0.271 | C | A |
| 458 | SQ1328_Sample001 | LTX021 | Cancer | 3 | 705 | 2279158 | TracerX | 1 | 5 | 158140143 | 458 | 0.468 | T | G |
| 459 | SQ1328_Sample001 | LTX021 | Cancer | 3 | 705 | 2279158 | TracerX | 1 | 23 | 76938197 | 459 | 0.453 | C | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 460 | SQ1328_Sample001 | LTX021 | Cancer | 3 | 705 | 2279158 | TracerX | 1 | 1 | 232172482 | 460 | 0.439 | G | T |
| 461 | SQ1328_Sample001 | LTX021 | Cancer | 3 | 705 | 2279158 | TracerX | 1 | 6 | 161143509 | 461 | 0.379 | C | A |
| 462 | SQ1328_Sample001 | LTX021 | Cancer | 3 | 705 | 2279158 | TracerX | 1 | 8 | 48626203 | 462 | 0.392 | G | T |
| 463 | SQ1328_Sample001 | LTX021 | Cancer | 3 | 705 | 2279158 | TracerX | 1 | 1 | 150256855 | 463 | 0.405 | G | C |
| 464 | SQ1328_Sample001 | LTX021 | Cancer | 3 | 705 | 2279158 | TracerX | 1 | 23 | 144906375 | 464 | 0.849 | T | A |
| 465 | SQ1328_Sample001 | LTX021 | Cancer | 3 | 705 | 2279158 | TracerX | 1 | 7 | 126173825 | 465 | 0.913 | G | C |
| 466 | SQ1328_Sample001 | LTX021 | Cancer | 3 | 705 | 2279158 | TracerX | 1 | 17 | 17700179 | 466 | 0.498 | C | G |
| 467 | SQ1328_Sample001 | LTX021 | Cancer | 3 | 705 | 2279158 | TracerX | 1 | 13 | 114748827 | 467 | 0.870 | G | T |
| 468 | SQ1328_Sample001 | LTX021 | Cancer | 3 | 705 | 2279158 | TracerX | 1 | 23 | 37312417 | 468 | 0.399 | C | A |
| 469 | SQ1328_Sample001 | LTX021 | Cancer | 3 | 705 | 2279158 | TracerX | 1 | 12 | 112528627 | 469 | 0.397 | C | G |
| 470 | SQ1328_Sample001 | LTX021 | Cancer | 3 | 705 | 2279158 | TracerX | 1 | 3 | 148924116 | 470 | 0.421 | T | G |
| 471 | SQ1328_Sample001 | LTX021 | Cancer | 3 | 705 | 2279158 | TracerX | 1 | 17 | 72859324 | 471 | 0.310 | T | A |
| 472 | SQ1328_Sample001 | LTX021 | Cancer | 3 | 705 | 2279158 | TracerX | 1 | 2 | 45826689 | 472 | 0.481 | T | G |
| 473 | SQ1328_Sample001 | LTX021 | Cancer | 3 | 705 | 2279158 | TracerX | 1 | 12 | 12006363 | 473 | 0.803 | G | C |
| 474 | SQ1328_Sample001 | LTX021 | Cancer | 3 | 705 | 2279158 | TracerX | 1 | 14 | 94420800 | 474 | 0.345 | T | A |
| 475 | SQ1328_Sample006 | LTX059 | Cancer | 3 | 713 | 2279163 | TracerX | 6 | 22 | 36715609 | 475 | 0.996 | G | C |
| 476 | SQ1328_Sample006 | LTX059 | Cancer | 3 | 713 | 2279163 | TracerX | 6 | 13 | 103519140 | 476 | 0.335 | T | A |
| 477 | SQ1328_Sample006 | LTX059 | Cancer | 3 | 713 | 2279163 | TracerX | 6 | 15 | 72039278 | 477 | 0.997 | C | A |
| 478 | SQ1328_Sample006 | LTX059 | Cancer | 3 | 713 | 2279163 | TracerX | 6 | 4 | 72618298 | 478 | 0.987 | C | G |
| 479 | SQ1328_Sample006 | LTX059 | Cancer | 3 | 713 | 2279163 | TracerX | 6 | 7 | 113558795 | 479 | 1.000 | G | T |
| 480 | SQ1328_Sample006 | LTX059 | Cancer | 3 | 713 | 2279163 | TracerX | 6 | 6 | 167369586 | 480 | 0.972 | G | C |
| 481 | SQ1328_Sample006 | LTX059 | Cancer | 3 | 713 | 2279163 | TracerX | 6 | 7 | 126173256 | 481 | 0.813 | T | C |
| 482 | SQ1328_Sample006 | LTX059 | Cancer | 3 | 713 | 2279163 | TracerX | 6 | 9 | 1044499652 | 482 | 0.998 | C | A |
| 483 | SQ1328_Sample006 | LTX059 | Cancer | 3 | 713 | 2279163 | TracerX | 6 | 1 | 15635212 | 483 | 0.999 | G | A |
| 484 | SQ1328_Sample006 | LTX059 | Cancer | 3 | 713 | 2279163 | TracerX | 6 | 6 | 152599226 | 484 | 0.409 | G | T |
| 485 | SQ1328_Sample006 | LTX059 | Cancer | 3 | 713 | 2279163 | TracerX | 6 | 4 | 121737614 | 485 | 1.000 | G | T |
| 486 | SQ1328_Sample006 | LTX059 | Cancer | 3 | 713 | 2279163 | TracerX | 6 | 6 | 89981387 | 486 | 0.934 | G | A |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 487 | SQ1328_Sample006 | LTX059 | Cancer | 3 | 713 | 2279163 | TracerX | 6 | 1 | 109778027 | 487 | 0.996 | A | G |
| 488 | SQ1328_Sample006 | LTX059 | Cancer | 3 | 713 | 2279163 | TracerX | 6 | 11 | 74424521 | 488 | 0.294 | C | T |
| 489 | SQ1328_Sample006 | LTX059 | Cancer | 3 | 713 | 2279163 | TracerX | 6 | 23 | 48759725 | 489 | 0.231 | C | T |
| 490 | SQ1328_Sample006 | LTX059 | Cancer | 3 | 713 | 2279163 | TracerX | 6 | 20 | 55033411 | 490 | 0.997 | A | T |
| 491 | SQ1328_Sample006 | LTX059 | Cancer | 3 | 713 | 2279163 | TracerX | 6 | 3 | 142089350 | 491 | 0.295 | C | T |
| 492 | SQ1328_Sample006 | LTX059 | Cancer | 3 | 713 | 2279163 | TracerX | 6 | 17 | 1538596 | 492 | 0.493 | G | T |
| 493 | SQ1328_Sample007 | LTX084 | Cancer | 3 | 714 | 2279164 | TracerX | 7 | 12 | 25398284 | 493 | 0.856 | C | G |
| 494 | SQ1328_Sample007 | LTX084 | Cancer | 3 | 714 | 2279164 | TracerX | 7 | 16 | 14029154 | 494 | 0.840 | G | T |
| 495 | SQ1328_Sample007 | LTX084 | Cancer | 3 | 714 | 2279164 | TracerX | 7 | 2 | 51255338 | 495 | 0.918 | G | T |
| 496 | SQ1328_Sample007 | LTX084 | Cancer | 3 | 714 | 2279164 | TracerX | 7 | 1 | 12024323 | 496 | 0.476 | G | T |
| 497 | SQ1328_Sample007 | LTX084 | Cancer | 3 | 714 | 2279164 | TracerX | 7 | 17 | 56540520 | 497 | 0.353 | C | A |
| 498 | SQ1328_Sample007 | LTX084 | Cancer | 3 | 714 | 2279164 | TracerX | 7 | 5 | 101595952 | 498 | 0.426 | C | T |
| 499 | SQ1328_Sample007 | LTX084 | Cancer | 3 | 714 | 2279164 | TracerX | 7 | 13 | 60413543 | 499 | 0.311 | C | A |
| 500 | SQ1328_Sample007 | LTX084 | Cancer | 3 | 714 | 2279164 | TracerX | 7 | 1 | 207196454 | 500 | 0.346 | C | T |
| 501 | SQ1328_Sample007 | LTX084 | Cancer | 3 | 714 | 2279164 | TracerX | 7 | 7 | 78256448 | 501 | 0.276 | C | T |
| 502 | SQ1328_Sample007 | LTX084 | Cancer | 3 | 714 | 2279164 | TracerX | 7 | 4 | 41663444 | 502 | 0.463 | C | A |
| 503 | SQ1328_Sample007 | LTX084 | Cancer | 3 | 714 | 2279164 | TracerX | 7 | 1 | 689103211 | 503 | 0.372 | C | A |
| 504 | SQ1328_Sample007 | LTX084 | Cancer | 3 | 714 | 2279164 | TracerX | 7 | 1 | 19449434 | 504 | 0.921 | C | A |
| 505 | SQ1328_Sample007 | LTX084 | Cancer | 3 | 714 | 2279164 | TracerX | 7 | 10 | 68687168 | 505 | 0.888 | G | T |
| 506 | SQ1328_Sample007 | LTX084 | Cancer | 3 | 714 | 2279164 | TracerX | 7 | 18 | 63477161 | 506 | 0.774 | G | T |
| 507 | SQ1328_Sample009 | LTX135 | Cancer | 3 | 716 | 2279166 | TracerX | 9 | 12 | 49434516 | 507 | 0.977 | C | A |
| 508 | SQ1328_Sample009 | LTX135 | Cancer | 3 | 716 | 2279166 | TracerX | 9 | 14 | 21869106 | 508 | 0.860 | C | T |
| 509 | SQ1328_Sample009 | LTX135 | Cancer | 3 | 716 | 2279166 | TracerX | 9 | 12 | 25398284 | 509 | 1.000 | C | A |
| 510 | SQ1328_Sample009 | LTX135 | Cancer | 3 | 716 | 2279166 | TracerX | 9 | 15 | 45007672 | 510 | 0.990 | C | G |
| 511 | SQ1328_Sample009 | LTX135 | Cancer | 3 | 716 | 2279166 | TracerX | 9 | 1 | 27023307 | 511 | NaN | C | G |
| 512 | SQ1328_Sample009 | LTX135 | Cancer | 3 | 716 | 2279166 | TracerX | 9 | 19 | 10600420 | 512 | 0.970 | C | G |
| 513 | SQ1328_Sample009 | LTX135 | Cancer | 3 | 716 | 2279166 | TracerX | 9 | 14 | 81610301 | 513 | 0.986 | C | A |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 514 | SQ1328_Sample009 | LTX135 | Cancer | 3 | 716 | 2279156 | TracerX | 9 | 15 | 88727459 | 514 | 0.451 | T | A |
| 515 | SQ1328_Sample009 | LTX135 | Cancer | 3 | 716 | 2279156 | TracerX | 9 | 17 | 7578190 | 515 | 0.231 | T | C |
| 516 | SQ1328_Sample009 | LTX135 | Cancer | 3 | 716 | 2279156 | TracerX | 9 | 17 | 29663397 | 516 | 0.933 | G | T |
| 517 | SQ1328_Sample009 | LTX135 | Cancer | 3 | 716 | 2279156 | TracerX | 9 | 1 | 3329196 | 517 | NaN | G | A |
| 518 | SQ1328_Sample009 | LTX135 | Cancer | 3 | 716 | 2279156 | TracerX | 9 | 19 | 45262781 | 518 | 0.881 | C | T |
| 519 | SQ1328_Sample009 | LTX135 | Cancer | 3 | 716 | 2279156 | TracerX | 9 | 11 | 128680482 | 519 | 0.202 | C | T |
| 520 | SQ1328_Sample009 | LTX135 | Cancer | 3 | 716 | 2279156 | TracerX | 9 | 3 | 69928297 | 520 | 1.000 | G | T |
| 521 | SQ1328_Sample009 | LTX135 | Cancer | 3 | 716 | 2279156 | TracerX | 9 | 21 | 31709951 | 521 | 0.857 | G | C |
| 522 | SQ1328_Sample009 | LTX135 | Cancer | 3 | 716 | 2279156 | TracerX | 9 | 8 | 109260902 | 522 | 0.475 | G | C |
| 523 | SQ1328_Sample009 | LTX135 | Cancer | 3 | 716 | 2279156 | TracerX | 9 | 23 | 69262973 | 523 | 0.474 | G | C |
| 524 | SQ1328_Sample009 | LTX135 | Cancer | 3 | 716 | 2279156 | TracerX | 9 | 17 | 7674212 | 524 | 0.781 | C | G |
| 525 | SQ1328_Sample009 | LTX135 | Cancer | 3 | 716 | 2279156 | TracerX | 9 | 7 | 1976519 | 525 | 0.877 | T | A |
| 526 | SQ1328_Sample009 | LTX135 | Cancer | 3 | 708 | 2279161 | TracerX | 4 | 1 | 179087864 | 526 | 0.781 | T | A |
| 527 | SQ1328_Sample004 | LTX048 | Cancer | 3 | 708 | 2279161 | TracerX | 4 | 7 | 13975490 | 527 | 0.905 | C | G |
| 528 | SQ1328_Sample004 | LTX048 | Cancer | 3 | 708 | 2279161 | TracerX | 4 | 22 | 36688117 | 528 | 0.489 | T | A |
| 529 | SQ1328_Sample004 | LTX048 | Cancer | 3 | 708 | 2279161 | TracerX | 4 | 19 | 1009549 | 529 | NaN | C | T |
| 530 | SQ1328_Sample004 | LTX048 | Cancer | 3 | 708 | 2279161 | TracerX | 4 | 5 | 170883636 | 530 | 0.813 | G | T |
| 531 | SQ1328_Sample004 | LTX048 | Cancer | 3 | 708 | 2279161 | TracerX | 4 | 2 | 79312626 | 531 | 0.348 | G | A |
| 532 | SQ1328_Sample004 | LTX048 | Cancer | 3 | 708 | 2279161 | TracerX | 4 | 6 | 1475271134 | 532 | 0.314 | C | A |
| 533 | SQ1328_Sample004 | LTX048 | Cancer | 3 | 708 | 2279161 | TracerX | 4 | 6 | 26225746 | 533 | 0.439 | C | A |
| 534 | SQ1328_Sample004 | LTX048 | Cancer | 3 | 708 | 2279161 | TracerX | 4 | 23 | 44108149 | 534 | 1.000 | C | A |
| 535 | SQ1328_Sample004 | LTX048 | Cancer | 3 | 708 | 2279161 | TracerX | 4 | 14 | 235233992 | 535 | 0.440 | C | G |
| 536 | SQ1328_Sample004 | LTX048 | Cancer | 3 | 708 | 2279161 | TracerX | 4 | 23 | 49040341 | 536 | 0.583 | C | T |
| 537 | SQ1328_Sample004 | LTX048 | Cancer | 3 | 708 | 2279161 | TracerX | 4 | 6 | 16326778 | 537 | 0.824 | C | A |
| 538 | SQ1328_Sample004 | LTX048 | Cancer | 3 | 708 | 2279161 | TracerX | 4 | 1 | 255565074 | 538 | 0.039 | G | A |
| 539 | SQ1328_Sample004 | LTX048 | Cancer | 3 | 708 | 2279161 | TracerX | 4 | 14 | 20692485 | 539 | 0.601 | C | T |
| 540 | SQ1328_Sample004 | LTX048 | Cancer | 3 | 708 | 2279161 | TracerX | 4 | 7 | 115890528 | 540 | 0.264 | C | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 541 | SQ1328_Sample004 | LTX048 | Cancer | 3 | 708 | 2279161 | TracerX | 4 | 13 | 100425110 | 541 | 0.481 | T | G |
| 542 | SQ1328_Sample004 | LTX048 | Cancer | 3 | 708 | 2279161 | TracerX | 4 | 22 | 19883040 | 542 | 0.263 | G | A |
| 543 | SQ1328_Sample004 | LTX048 | Cancer | 3 | 708 | 2279161 | TracerX | 4 | 17 | 18219954 | 543 | 0.706 | C | T |
| 544 | SQ1328_Sample003 | LTX046 | Cancer | 3 | 707 | 2279160 | TracerX | 3 | 17 | 7579485 | 544 | 0.459 | C | A |
| 545 | SQ1328_Sample003 | LTX046 | Cancer | 3 | 707 | 2279160 | TracerX | 3 | 7 | 55241708 | 545 | 0.445 | G | C |
| 546 | SQ1328_Sample003 | LTX046 | Cancer | 3 | 707 | 2279160 | TracerX | 3 | 18 | 48604750 | 546 | 0.362 | G | A |
| 547 | SQ1328_Sample003 | LTX046 | Cancer | 3 | 707 | 2279160 | TracerX | 3 | 23 | 152830448 | 547 | 0.432 | G | A |
| 548 | SQ1328_Sample003 | LTX046 | Cancer | 3 | 707 | 2279160 | TracerX | 3 | 19 | 45375306 | 548 | 0.449 | C | C |
| 549 | SQ1328_Sample003 | LTX046 | Cancer | 3 | 707 | 2279160 | TracerX | 3 | 2 | 228882599 | 549 | 0.679 | C | T |
| 550 | SQ1328_Sample003 | LTX046 | Cancer | 3 | 707 | 2279160 | TracerX | 3 | 10 | 118689468 | 550 | 0.801 | C | G |
| 551 | SQ1328_Sample003 | LTX046 | Cancer | 3 | 707 | 2279160 | TracerX | 3 | 3 | 4847939 | 551 | 0.418 | C | A |
| 552 | SQ1328_Sample003 | LTX046 | Cancer | 3 | 707 | 2279160 | TracerX | 3 | 16 | 58713976 | 552 | 0.461 | C | G |
| 553 | SQ1328_Sample003 | LTX046 | Cancer | 3 | 707 | 2279160 | TracerX | 3 | 4 | 57839436 | 553 | 0.406 | G | A |
| 554 | SQ1328_Sample003 | LTX046 | Cancer | 3 | 707 | 2279160 | TracerX | 3 | 22 | 43539119 | 554 | 0.500 | C | C |
| 555 | SQ1328_Sample003 | LTX046 | Cancer | 3 | 707 | 2279160 | TracerX | 3 | 4 | 164272221 | 555 | 0.413 | C | A |
| 556 | SQ1328_Sample003 | LTX046 | Cancer | 3 | 707 | 2279160 | TracerX | 3 | 13 | 30107108 | 556 | 0.942 | G | A |
| 557 | SQ1328_Sample003 | LTX046 | Cancer | 3 | 707 | 2279160 | TracerX | 3 | 21 | 27071135 | 557 | 0.431 | C | A |
| 558 | SQ1328_Sample003 | LTX046 | Cancer | 3 | 707 | 2279160 | TracerX | 3 | 1 | 237754064 | 558 | 0.360 | C | T |
| 559 | SQ1328_Sample003 | LTX046 | Cancer | 3 | 707 | 2279160 | TracerX | 3 | 17 | 19261251 | 559 | 0.876 | C | T |
| 560 | SQ1328_Sample003 | LTX046 | Cancer | 3 | 707 | 2279160 | TracerX | 3 | 10 | 15121020 | 560 | 0.296 | G | A |
| 561 | SQ1328_Sample003 | LTX046 | Cancer | 3 | 707 | 2279160 | TracerX | 3 | 11 | 78574162 | 561 | 0.346 | C | A |
| 562 | SQ1328_Sample004 | LTX036 | Cancer | 4 | 724 | 2279191 | TracerX | 4 | 17 | 7579398 | 562 | 0.889 | C | A |
| 563 | SQ1329_Sample004 | LTX036 | Cancer | 4 | 724 | 2279191 | TracerX | 4 | 19 | 1220502 | 563 | NaN | G | T |
| 564 | SQ1329_Sample004 | LTX036 | Cancer | 4 | 724 | 2279191 | TracerX | 4 | 12 | 133256551 | 564 | 0.380 | C | A |
| 565 | SQ1329_Sample004 | LTX036 | Cancer | 4 | 724 | 2279191 | TracerX | 4 | 18 | 22805714 | 565 | 0.583 | C | T |
| 566 | SQ1329_Sample004 | LTX036 | Cancer | 4 | 724 | 2279191 | TracerX | 4 | 1 | 19018437 | 566 | 0.827 | C | A |
| 567 | SQ1329_Sample004 | LTX036 | Cancer | 4 | 724 | 2279191 | TracerX | 4 | 11 | 108186565 | 567 | 0.319 | A | T |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 568 | SQ1329_Sample004 | LTX036 | Cancer | 4 | 724 | 2279191 | TracerX | 4 | 11 | 55798386 | 568 | 0.774 | C | A |
| 569 | SQ1329_Sample004 | LTX036 | Cancer | 4 | 724 | 2279191 | TracerX | 4 | 16 | 4933402 | 569 | 1.000 | C | A |
| 570 | SQ1329_Sample004 | LTX036 | Cancer | 4 | 724 | 2279191 | TracerX | 4 | 19 | 56539619 | 570 | 0.829 | C | G |
| 571 | SQ1329_Sample004 | LTX036 | Cancer | 4 | 724 | 2279191 | TracerX | 4 | 2 | 39559089 | 571 | 0.388 | T | G |
| 572 | SQ1329_Sample004 | LTX036 | Cancer | 4 | 724 | 2279191 | TracerX | 4 | 17 | 48252792 | 572 | NaN | G | T |
| 573 | SQ1329_Sample004 | LTX036 | Cancer | 4 | 724 | 2279191 | TracerX | 4 | 10 | 7262401 | 573 | 0.384 | C | A |
| 574 | SQ1329_Sample004 | LTX036 | Cancer | 4 | 724 | 2279191 | TracerX | 4 | 2 | 128774019 | 574 | 0.888 | C | A |
| 575 | SQ1329_Sample004 | LTX036 | Cancer | 4 | 724 | 2279191 | TracerX | 4 | 7 | 49815508 | 575 | 0.489 | A | C |
| 576 | SQ1329_Sample004 | LTX036 | Cancer | 4 | 724 | 2279191 | TracerX | 4 | 9 | 135983408 | 576 | 0.498 | T | A |
| 577 | SQ1329_Sample004 | LTX036 | Cancer | 4 | 724 | 2279191 | TracerX | 4 | 6 | 2895637 | 577 | 0.456 | G | T |
| 578 | SQ1329_Sample004 | LTX036 | Cancer | 4 | 724 | 2279191 | TracerX | 4 | 1 | 193150241 | 578 | 0.823 | A | T |
| 579 | SQ1329_Sample004 | LTX036 | Cancer | 4 | 724 | 2279191 | TracerX | 4 | 5 | 140187899 | 579 | 0.396 | A | C |
| 580 | SQ1329_Sample004 | LTX036 | Cancer | 4 | 724 | 2279191 | TracerX | 4 | 15 | 43694034 | 580 | 0.496 | A | C |
| 581 | SQ1329_Sample002 | LTX022 | Cancer | 4 | 722 | 2279189 | TracerX | 2 | 3 | 115439665 | 581 | 0.417 | A | A |
| 582 | SQ1329_Sample002 | LTX022 | Cancer | 4 | 722 | 2279189 | TracerX | 2 | 17 | 7578190 | 582 | 1.000 | T | T |
| 583 | SQ1329_Sample002 | LTX022 | Cancer | 4 | 722 | 2279189 | TracerX | 2 | 18 | 22807056 | 583 | 1.000 | C | A |
| 584 | SQ1329_Sample002 | LTX022 | Cancer | 4 | 722 | 2279189 | TracerX | 2 | 4 | 187532858 | 584 | 0.999 | C | A |
| 585 | SQ1329_Sample002 | LTX022 | Cancer | 4 | 722 | 2279189 | TracerX | 2 | 5 | 176710869 | 585 | 1.000 | A | T |
| 586 | SQ1329_Sample002 | LTX022 | Cancer | 4 | 722 | 2279189 | TracerX | 2 | 8 | 88365909 | 586 | 1.000 | G | T |
| 587 | SQ1329_Sample002 | LTX022 | Cancer | 4 | 722 | 2279189 | TracerX | 2 | 9 | 97887448 | 587 | 1.000 | C | A |
| 588 | SQ1329_Sample002 | LTX022 | Cancer | 4 | 722 | 2279189 | TracerX | 2 | 18 | 47802230 | 588 | 1.000 | C | A |
| 589 | SQ1329_Sample002 | LTX022 | Cancer | 4 | 722 | 2279189 | TracerX | 2 | 18 | 47800615 | 589 | 1.000 | C | A |
| 590 | SQ1329_Sample002 | LTX022 | Cancer | 4 | 722 | 2279189 | TracerX | 2 | 16 | 14024630 | 590 | 1.000 | A | A |
| 591 | SQ1329_Sample002 | LTX022 | Cancer | 4 | 722 | 2279189 | TracerX | 2 | 12 | 129559276 | 591 | 1.000 | C | T |
| 592 | SQ1329_Sample002 | LTX022 | Cancer | 4 | 722 | 2279189 | TracerX | 2 | 1 | 247836132 | 592 | 1.000 | C | T |
| 593 | SQ1329_Sample002 | LTX022 | Cancer | 4 | 722 | 2279189 | TracerX | 2 | 7 | 117432761 | 593 | 1.000 | G | A |
| 594 | SQ1329_Sample002 | LTX022 | Cancer | 4 | 722 | 2279189 | TracerX | 2 | 6 | 151153840 | 594 | 1.000 | A | G |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 595 | SQ1329_Sample002 | LTX022 | Cancer | 4 | 722 | 2279189 | TracerX | 2 | 5 | 167645878 | 595 | 1.000 | T | G |
| 596 | SQ1329_Sample002 | LTX022 | Cancer | 4 | 722 | 2279189 | TracerX | 2 | 9 | 35714237 | 596 | 1.000 | T | G |
| 597 | SQ1329_Sample002 | LTX022 | Cancer | 4 | 722 | 2279189 | TracerX | 2 | 9 | 123220803 | 597 | 0.322 | C | C |
| 598 | SQ1329_Sample002 | LTX022 | Cancer | 4 | 722 | 2279189 | TracerX | 2 | 19 | 6732134 | 598 | 0.499 | C | G |
| 599 | SQ1329_Sample002 | LTX022 | Cancer | 4 | 722 | 2279189 | TracerX | 2 | 8 | 70674006 | 599 | 0.999 | G | T |
| 600 | SQ1329_Sample002 | LTX022 | Cancer | 4 | 722 | 2279189 | TracerX | 2 | 2 | 1168816 | 600 | 0.902 | T | C |
| 601 | SQ1329_Sample002 | LTX022 | Cancer | 4 | 722 | 2279189 | TracerX | 2 | 9 | 95841793 | 601 | 1.000 | G | C |
| 602 | SQ1329_Sample006 | LTX049 | Cancer | 4 | 729 | 2279193 | TracerX | 6 | 12 | 25398284 | 602 | 0.782 | C | A |
| 603 | SQ1329_Sample006 | LTX049 | Cancer | 4 | 729 | 2279193 | TracerX | 6 | 1 | 3313149 | 603 | 0.909 | G | T |
| 604 | SQ1329_Sample006 | LTX049 | Cancer | 4 | 729 | 2279193 | TracerX | 6 | 19 | 11152100 | 604 | 0.491 | A | T |
| 605 | SQ1329_Sample006 | LTX049 | Cancer | 4 | 729 | 2279193 | TracerX | 6 | 15 | 88680726 | 605 | 0.412 | C | A |
| 606 | SQ1329_Sample006 | LTX049 | Cancer | 4 | 729 | 2279193 | TracerX | 6 | 12 | 46244010 | 606 | 0.416 | G | C |
| 607 | SQ1329_Sample006 | LTX049 | Cancer | 4 | 729 | 2279193 | TracerX | 6 | 23 | 76939413 | 607 | 0.405 | T | A |
| 608 | SQ1329_Sample006 | LTX049 | Cancer | 4 | 729 | 2279193 | TracerX | 6 | 16 | 2121841 | 608 | NaN | G | T |
| 609 | SQ1329_Sample006 | LTX049 | Cancer | 4 | 729 | 2279193 | TracerX | 6 | 23 | 48547447 | 609 | 1.000 | C | A |
| 610 | SQ1329_Sample006 | LTX049 | Cancer | 4 | 729 | 2279193 | TracerX | 6 | 3 | 57457248 | 610 | 0.885 | C | A |
| 611 | SQ1329_Sample006 | LTX049 | Cancer | 4 | 729 | 2279193 | TracerX | 6 | 19 | 10897345 | 611 | 0.471 | C | A |
| 612 | SQ1329_Sample006 | LTX049 | Cancer | 4 | 729 | 2279193 | TracerX | 6 | 3 | 128200113 | 612 | 0.780 | G | A |
| 613 | SQ1329_Sample006 | LTX049 | Cancer | 4 | 729 | 2279193 | TracerX | 6 | 20 | 51870588 | 613 | 0.467 | G | T |
| 614 | SQ1329_Sample006 | LTX049 | Cancer | 4 | 729 | 2279193 | TracerX | 6 | 2 | 116520170 | 614 | 0.434 | C | G |
| 615 | SQ1329_Sample006 | LTX049 | Cancer | 4 | 729 | 2279193 | TracerX | 6 | 21 | 47987434 | 615 | 0.835 | G | T |
| 616 | SQ1329_Sample006 | LTX049 | Cancer | 4 | 729 | 2279193 | TracerX | 6 | 17 | 72519788 | 616 | 0.375 | C | A |
| 617 | SQ1329_Sample006 | LTX049 | Cancer | 4 | 729 | 2279193 | TracerX | 6 | 8 | 9437749 | 617 | 0.422 | C | G |
| 618 | SQ1329_Sample006 | LTX049 | Cancer | 4 | 729 | 2279193 | TracerX | 6 | 12 | 111953997 | 618 | 0.478 | C | A |
| 619 | SQ1329_Sample006 | LTX049 | Cancer | 4 | 729 | 2279193 | TracerX | 6 | 8 | 523233848 | 619 | 0.780 | C | G |
| 620 | SQ1329_Sample006 | LTX049 | Cancer | 4 | 729 | 2279193 | TracerX | 6 | 3 | 129370350 | 620 | 0.336 | C | G |
| 621 | SQ1329_Sample007 | LTX063 | Cancer | 4 | 730 | 2279194 | TracerX | 7 | 9 | 135982591 | 621 | 1.000 | C | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 622 | SQ1329_Sample007 | LTX063 | Cancer | 4 | 730 | 2279194 | TracerX | 7 | 17 | 7578263 | 622 | 1.000 | G | A |
| 623 | SQ1329_Sample007 | LTX063 | Cancer | 4 | 730 | 2279194 | TracerX | 7 | 3 | 57430962 | 623 | 1.000 | G | A |
| 624 | SQ1329_Sample007 | LTX063 | Cancer | 4 | 730 | 2279194 | TracerX | 7 | 1 | 271102068 | 624 | 1.000 | G | T |
| 625 | SQ1329_Sample007 | LTX063 | Cancer | 4 | 730 | 2279194 | TracerX | 7 | 16 | 65016009 | 625 | 1.000 | C | G |
| 626 | SQ1329_Sample007 | LTX063 | Cancer | 4 | 730 | 2279194 | TracerX | 7 | 11 | 32449506 | 626 | 0.997 | T | A |
| 627 | SQ1329_Sample007 | LTX063 | Cancer | 4 | 730 | 2279194 | TracerX | 7 | 15 | 74326870 | 627 | 0.911 | C | T |
| 628 | SQ1329_Sample007 | LTX063 | Cancer | 4 | 730 | 2279194 | TracerX | 7 | 7 | 50450378 | 628 | 0.958 | C | G |
| 629 | SQ1329_Sample007 | LTX063 | Cancer | 4 | 730 | 2279194 | TracerX | 7 | 16 | 15811171 | 629 | 0.715 | C | T |
| 630 | SQ1329_Sample007 | LTX063 | Cancer | 4 | 730 | 2279194 | TracerX | 7 | 10 | 50732500 | 630 | 1.000 | C | A |
| 631 | SQ1329_Sample007 | LTX063 | Cancer | 4 | 730 | 2279194 | TracerX | 7 | 7 | 31144522 | 631 | 1.000 | A | C |
| 632 | SQ1329_Sample007 | LTX063 | Cancer | 4 | 730 | 2279194 | TracerX | 7 | 10 | 108378016 | 632 | 1.000 | C | A |
| 633 | SQ1329_Sample007 | LTX063 | Cancer | 4 | 730 | 2279194 | TracerX | 7 | 2 | 73302776 | 633 | 1.000 | C | A |
| 634 | SQ1329_Sample007 | LTX063 | Cancer | 4 | 730 | 2279194 | TracerX | 7 | 12 | 125298872 | 634 | 1.000 | C | A |
| 635 | SQ1329_Sample007 | LTX063 | Cancer | 4 | 730 | 2279194 | TracerX | 7 | 10 | 70332109 | 635 | 0.757 | G | T |
| 636 | SQ1329_Sample007 | LTX063 | Cancer | 4 | 730 | 2279194 | TracerX | 7 | 8 | 144812392 | 636 | 0.434 | C | A |
| 637 | SQ1329_Sample007 | LTX063 | Cancer | 4 | 730 | 2279194 | TracerX | 7 | 6 | 26508774 | 637 | 0.992 | T | A |
| 638 | SQ1329_Sample007 | LTX063 | Cancer | 4 | 730 | 2279194 | TracerX | 7 | 2 | 11770074 | 638 | 0.994 | C | A |
| 639 | SQ1329_Sample007 | LTX063 | Cancer | 4 | 730 | 2279194 | TracerX | 7 | 19 | 15511627 | 639 | 0.992 | G | T |
| 640 | SQ1329_Sample007 | LTX063 | Cancer | 4 | 730 | 2279194 | TracerX | 7 | 7 | 49815709 | 640 | 1.000 | G | C |
| 641 | SQ1329_Sample009 | LTX144 | Cancer | 4 | 732 | 2279196 | TracerX | 9 | 22 | 41566508 | 641 | 0.757 | G | A |
| 642 | SQ1329_Sample009 | LTX144 | Cancer | 4 | 732 | 2279196 | TracerX | 9 | 11 | 69465952 | 642 | 0.360 | C | T |
| 643 | SQ1329_Sample009 | LTX144 | Cancer | 4 | 732 | 2279196 | TracerX | 9 | 7 | 50459535 | 643 | 0.835 | A | T |
| 644 | SQ1329_Sample009 | LTX144 | Cancer | 4 | 732 | 2279196 | TracerX | 9 | 7 | 98588208 | 644 | 0.218 | C | A |
| 645 | SQ1329_Sample009 | LTX144 | Cancer | 4 | 732 | 2279196 | TracerX | 9 | 17 | 29664428 | 645 | 0.430 | C | T |
| 646 | SQ1329_Sample009 | LTX144 | Cancer | 4 | 732 | 2279196 | TracerX | 9 | 4 | 3201640 | 646 | 0.878 | G | G |
| 647 | SQ1329_Sample009 | LTX144 | Cancer | 4 | 732 | 2279196 | TracerX | 9 | 1 | 186303604 | 647 | 0.887 | T | A |
| 648 | SQ1329_Sample009 | LTX144 | Cancer | 4 | 732 | 2279196 | TracerX | 9 | 13 | 110844627 | 648 | 0.291 | G | T |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 649 | SQ1329_Sample009 | LTX144 | Cancer | 4 | 732 | 2279196 | TracerX | 9 | 3 | 183957527 | 649 | 0.437 | C | A |
| 650 | SQ1329_Sample009 | LTX144 | Cancer | 4 | 732 | 2279196 | TracerX | 9 | 10 | 49944072 | 650 | 0.375 | C | G |
| 651 | SQ1329_Sample009 | LTX144 | Cancer | 4 | 732 | 2279196 | TracerX | 9 | 23 | 130220369 | 651 | 0.811 | T | A |
| 652 | SQ1329_Sample009 | LTX144 | Cancer | 4 | 732 | 2279196 | TracerX | 9 | 2 | 84864406 | 652 | 0.391 | C | A |
| 653 | SQ1329_Sample009 | LTX144 | Cancer | 4 | 732 | 2279196 | TracerX | 9 | 7 | 131864446 | 653 | 0.872 | C | A |
| 654 | SQ1329_Sample009 | LTX144 | Cancer | 4 | 732 | 2279196 | TracerX | 9 | 16 | 1812912 | 654 | NaN | C | G |
| 655 | SQ1329_Sample009 | LTX144 | Cancer | 4 | 732 | 2279196 | TracerX | 9 | 6 | 345914 | 655 | 0.863 | C | A |
| 656 | SQ1329_Sample009 | LTX144 | Cancer | 4 | 732 | 2279196 | TracerX | 9 | 22 | 50688115 | 656 | 0.478 | C | G |
| 657 | SQ1329_Sample009 | LTX144 | Cancer | 4 | 732 | 2279196 | TracerX | 9 | 7 | 134618237 | 657 | 0.407 | A | C |
| 658 | SQ1329_Sample009 | LTX144 | Cancer | 4 | 732 | 2279196 | TracerX | 9 | 2 | 44459475 | 658 | 0.393 | C | A |
| 659 | SQ1329_Sample009 | LTX144 | Cancer | 4 | 732 | 2279196 | TracerX | 9 | 2 | 162762359 | 659 | 0.429 | C | G |
| 660 | SQ1329_Sample005 | LTX038 | Cancer | 4 | 725 | 2279192 | TracerX | 5 | 14 | 51196324 | 660 | 1.000 | G | A |
| 661 | SQ1329_Sample005 | LTX038 | Cancer | 4 | 725 | 2279192 | TracerX | 5 | 1 | 65332716 | 661 | 1.000 | C | A |
| 662 | SQ1329_Sample005 | LTX038 | Cancer | 4 | 725 | 2279192 | TracerX | 5 | 16 | 4836063 | 662 | 1.000 | G | C |
| 663 | SQ1329_Sample005 | LTX038 | Cancer | 4 | 725 | 2279192 | TracerX | 5 | 2 | 178098810 | 663 | 1.000 | C | G |
| 664 | SQ1329_Sample005 | LTX038 | Cancer | 4 | 725 | 2279192 | TracerX | 5 | 9 | 134010388 | 664 | 1.000 | A | T |
| 665 | SQ1329_Sample005 | LTX038 | Cancer | 4 | 725 | 2279192 | TracerX | 5 | 11 | 69456203 | 665 | 1.000 | C | G |
| 666 | SQ1329_Sample005 | LTX038 | Cancer | 4 | 725 | 2279192 | TracerX | 5 | 1 | 27106535 | 666 | 1.000 | G | A |
| 667 | SQ1329_Sample005 | LTX038 | Cancer | 4 | 725 | 2279192 | TracerX | 5 | 12 | 131276458 | 667 | NaN | G | T |
| 668 | SQ1329_Sample005 | LTX038 | Cancer | 4 | 725 | 2279192 | TracerX | 5 | 9 | 139413985 | 668 | 0.670 | C | T |
| 669 | SQ1329_Sample005 | LTX038 | Cancer | 4 | 725 | 2279192 | TracerX | 5 | 23 | 76939312 | 669 | 0.999 | G | A |
| 670 | SQ1329_Sample005 | LTX038 | Cancer | 4 | 725 | 2279192 | TracerX | 5 | 3 | 370061826 | 670 | 1.000 | G | A |
| 671 | SQ1329_Sample005 | LTX038 | Cancer | 4 | 725 | 2279192 | TracerX | 5 | 4 | 55980381 | 671 | 1.000 | G | A |
| 672 | SQ1329_Sample005 | LTX038 | Cancer | 4 | 725 | 2279192 | TracerX | 5 | 1 | 198700816 | 672 | 1.000 | G | C |
| 673 | SQ1329_Sample005 | LTX038 | Cancer | 4 | 725 | 2279192 | TracerX | 5 | 12 | 464400 | 673 | 1.000 | C | T |
| 674 | SQ1329_Sample005 | LTX038 | Cancer | 4 | 725 | 2279192 | TracerX | 5 | 1 | 158576657 | 674 | 1.000 | G | T |
| 675 | SQ1329_Sample005 | LTX038 | Cancer | 4 | 725 | 2279192 | TracerX | 5 | 23 | 88008704 | 675 | 1.000 | C | A |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 676 | SQ1329_Sample005 | LTX038 | Cancer | 4 | 725 | 2279192 | TracerX | 5 | 3 | 64132613 | 676 | 1.000 | C | A |
| 677 | SQ1329_Sample005 | LTX038 | Cancer | 4 | 725 | 2279192 | TracerX | 5 | 6 | 177772153 | 677 | 0.416 | G | C |
| 678 | SQ1329_Sample005 | LTX038 | Cancer | 4 | 725 | 2279192 | TracerX | 5 | 5 | 169020496 | 678 | 0.444 | A | C |
| 679 | SQ1329_Sample005 | LTX038 | Cancer | 4 | 725 | 2279192 | TracerX | 5 | 15 | 71276480 | 679 | 1.000 | G | T |
| 680 | SQ1329_Sample003 | LTX034 | Cancer | 4 | 723 | 2279190 | TracerX | 3 | 3 | 52436393 | 680 | 0.758 | G | A |
| 681 | SQ1329_Sample003 | LTX034 | Cancer | 4 | 723 | 2279190 | TracerX | 3 | 7 | 148508719 | 681 | 0.672 | C | T |
| 682 | SQ1329_Sample003 | LTX034 | Cancer | 4 | 723 | 2279190 | TracerX | 3 | 17 | 7578535 | 682 | 0.260 | T | C |
| 683 | SQ1329_Sample003 | LTX034 | Cancer | 4 | 723 | 2279190 | TracerX | 3 | 13 | 48955550 | 683 | 0.411 | C | T |
| 684 | SQ1329_Sample003 | LTX034 | Cancer | 4 | 723 | 2279190 | TracerX | 3 | 6 | 848958087 | 684 | 0.391 | G | A |
| 685 | SQ1329_Sample003 | LTX034 | Cancer | 4 | 723 | 2279190 | TracerX | 3 | 23 | 125298988 | 685 | 0.449 | C | G |
| 686 | SQ1329_Sample003 | LTX034 | Cancer | 4 | 723 | 2279190 | TracerX | 3 | 14 | 104639409 | 686 | 0.396 | C | T |
| 687 | SQ1329_Sample003 | LTX034 | Cancer | 4 | 723 | 2279190 | TracerX | 3 | 23 | 78010800 | 687 | 0.407 | G | A |
| 688 | SQ1329_Sample003 | LTX034 | Cancer | 4 | 723 | 2279190 | TracerX | 3 | 3 | 142735152 | 688 | 0.488 | A | C |
| 689 | SQ1329_Sample003 | LTX034 | Cancer | 4 | 723 | 2279190 | TracerX | 3 | 16 | 88501136 | 689 | 0.271 | T | C |
| 690 | SQ1329_Sample003 | LTX034 | Cancer | 4 | 723 | 2279190 | TracerX | 3 | 15 | 75692456 | 690 | 0.394 | C | A |
| 691 | SQ1329_Sample003 | LTX034 | Cancer | 4 | 723 | 2279190 | TracerX | 3 | 12 | 56827393 | 691 | 0.410 | T | A |
| 692 | SQ1329_Sample003 | LTX034 | Cancer | 4 | 723 | 2279190 | TracerX | 3 | 10 | 70646154 | 692 | 0.358 | G | A |
| 693 | SQ1329_Sample003 | LTX034 | Cancer | 4 | 723 | 2279190 | TracerX | 3 | 5 | 138456816 | 693 | 0.749 | G | A |
| 694 | SQ1329_Sample003 | LTX034 | Cancer | 4 | 723 | 2279190 | TracerX | 3 | 17 | 75471896 | 694 | 0.435 | G | A |
| 695 | SQ1329_Sample003 | LTX034 | Cancer | 4 | 723 | 2279190 | TracerX | 3 | 12 | 118610456 | 695 | 0.765 | C | A |
| 696 | SQ1329_Sample003 | LTX034 | Cancer | 4 | 723 | 2279190 | TracerX | 3 | 3 | 135870296 | 696 | 0.313 | C | T |
| 697 | SQ1329_Sample001 | LTX013 | Cancer | 4 | 721 | 2279188 | TracerX | 1 | 3 | 160395441 | 697 | 0.870 | C | A |
| 698 | SQ1329_Sample001 | LTX013 | Cancer | 4 | 721 | 2279188 | TracerX | 1 | 9 | 133730371 | 698 | 0.840 | A | G |
| 699 | SQ1329_Sample001 | LTX013 | Cancer | 4 | 721 | 2279188 | TracerX | 1 | 5 | 15937258 | 699 | 0.684 | G | A |
| 700 | SQ1329_Sample001 | LTX013 | Cancer | 4 | 721 | 2279188 | TracerX | 1 | 2 | 152403968 | 700 | 0.774 | C | T |
| 701 | SQ1329_Sample001 | LTX013 | Cancer | 4 | 721 | 2279188 | TracerX | 1 | 23 | 114141751 | 701 | 0.348 | C | T |
| 702 | SQ1329_Sample001 | LTX013 | Cancer | 4 | 721 | 2279188 | TracerX | 1 | 6 | 13316860 | 702 | 1.000 | G | C |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 703 | SQ1329_Sample001 | LTX013 | Cancer | 4 | 721 | 2279188 | TracerX | 1 | 3 | 183994479 | 703 | 0.691 | T | C |
| 704 | SQ1329_Sample001 | LTX013 | Cancer | 4 | 721 | 2279188 | TracerX | 1 | 10 | 105147056 | 704 | 0.688 | C | T |
| 705 | SQ1329_Sample001 | LTX013 | Cancer | 4 | 721 | 2279188 | TracerX | 1 | 17 | 181154751 | 705 | 0.538 | C | T |
| 706 | SQ1329_Sample001 | LTX013 | Cancer | 4 | 721 | 2279188 | TracerX | 1 | 8 | 38205421 | 706 | 0.729 | T | A |
| 707 | SQ1329_Sample001 | LTX013 | Cancer | 4 | 721 | 2279188 | TracerX | 1 | 6 | 127768763 | 707 | 0.815 | T | A |
| 708 | SQ1329_Sample001 | LTX013 | Cancer | 4 | 721 | 2279188 | TracerX | 1 | 16 | 29706404 | 708 | 0.455 | C | T |
| 709 | SQ1329_Sample001 | LTX013 | Cancer | 4 | 721 | 2279188 | TracerX | 1 | 14 | 31592236 | 709 | 0.206 | G | A |
| 710 | SQ1329_Sample001 | LTX013 | Cancer | 4 | 721 | 2279188 | TracerX | 1 | 23 | 150348926 | 710 | 0.995 | G | A |
| 711 | SQ1329_Sample001 | LTX013 | Cancer | 4 | 721 | 2279188 | TracerX | 1 | 23 | 117044028 | 711 | 0.274 | C | T |
| 712 | SQ1329_Sample001 | LTX013 | Cancer | 4 | 721 | 2279188 | TracerX | 1 | 14 | 74988688 | 712 | 0.241 | C | T |
| 713 | SQ1329_Sample008 | LTX065 | Cancer | 4 | 731 | 2279195 | TracerX | 8 | 22 | 36702581 | 713 | 0.451 | C | T |
| 714 | SQ1329_Sample008 | LTX065 | Cancer | 4 | 731 | 2279195 | TracerX | 8 | 17 | 7577127 | 714 | 0.807 | G | A |
| 715 | SQ1329_Sample008 | LTX065 | Cancer | 4 | 731 | 2279195 | TracerX | 8 | 5 | 86629154 | 715 | 0.383 | C | T |
| 716 | SQ1329_Sample008 | LTX065 | Cancer | 4 | 731 | 2279195 | TracerX | 8 | 13 | 103385643 | 716 | 0.976 | A | C |
| 717 | SQ1329_Sample008 | LTX065 | Cancer | 4 | 731 | 2279195 | TracerX | 8 | 2 | 73679889 | 717 | 0.414 | G | T |
| 718 | SQ1329_Sample008 | LTX065 | Cancer | 4 | 731 | 2279195 | TracerX | 8 | 11 | 64360338 | 718 | 0.487 | G | T |
| 719 | SQ1329_Sample008 | LTX065 | Cancer | 4 | 731 | 2279195 | TracerX | 8 | 5 | 150133163 | 719 | 0.338 | G | T |
| 720 | SQ1329_Sample008 | LTX065 | Cancer | 4 | 731 | 2279195 | TracerX | 8 | 13 | 103390487 | 720 | 0.791 | G | T |
| 721 | SQ1329_Sample008 | LTX065 | Cancer | 4 | 731 | 2279195 | TracerX | 8 | 16 | 48209286 | 721 | 0.483 | G | T |
| 722 | SQ1329_Sample008 | LTX065 | Cancer | 4 | 731 | 2279195 | TracerX | 8 | 14 | 101347192 | 722 | 0.793 | C | T |
| 723 | SQ1329_Sample008 | LTX065 | Cancer | 4 | 731 | 2279195 | TracerX | 8 | 4 | 109674077 | 723 | 0.405 | C | A |
| 724 | SQ1329_Sample008 | LTX065 | Cancer | 4 | 731 | 2279195 | TracerX | 8 | 20 | 4837662 | 724 | 0.661 | C | T |
| 725 | SQ1329_Sample008 | LTX065 | Cancer | 4 | 731 | 2279195 | TracerX | 8 | 6 | 51523873 | 725 | 0.297 | T | A |
| 726 | SQ1329_Sample008 | LTX065 | Cancer | 4 | 731 | 2279195 | TracerX | 8 | 13 | 96530052 | 726 | 0.850 | C | A |
| 727 | SQ1329_Sample008 | LTX065 | Cancer | 4 | 731 | 2279195 | TracerX | 8 | 2 | 220283462 | 727 | 0.417 | T | A |
| 728 | SQ1329_Sample010 | LTX149 | Cancer | 4 | 733 | 2279197 | TracerX | 10 | 23 | 53239876 | 728 | 1.000 | G | A |
| 729 | SQ1329_Sample010 | LTX149 | Cancer | 4 | 733 | 2279197 | TracerX | 10 | 16 | 3786719 | 729 | 1.000 | G | A |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 730 | SQ1329_Sample010 | LTX149 | Cancer | 4 | 733 | 2279197 | TracerX | 10 | 6 | 117647416 | 730 | 1.000 | C | T |
| 731 | SQ1329_Sample010 | LTX149 | Cancer | 4 | 733 | 2279197 | TracerX | 10 | 1 | 160136469 | 731 | 1.000 | G | T |
| 732 | SQ1329_Sample010 | LTX149 | Cancer | 4 | 733 | 2279197 | TracerX | 10 | 11 | 176629929 | 732 | 1.000 | C | T |
| 733 | SQ1329_Sample010 | LTX149 | Cancer | 4 | 733 | 2279197 | TracerX | 10 | 2 | 201462193 | 733 | 1.000 | A | G |
| 734 | SQ1329_Sample010 | LTX149 | Cancer | 4 | 733 | 2279197 | TracerX | 10 | 8 | 117950562 | 734 | 0.964 | G | T |
| 735 | SQ1329_Sample010 | LTX149 | Cancer | 4 | 733 | 2279197 | TracerX | 10 | 16 | 49669770 | 735 | 0.991 | C | T |
| 736 | SQ1329_Sample010 | LTX149 | Cancer | 4 | 733 | 2279197 | TracerX | 10 | 19 | 3783189 | 736 | 1.000 | C | T |
| 737 | SQ1329_Sample010 | LTX149 | Cancer | 4 | 733 | 2279197 | TracerX | 10 | 14 | 70633968 | 737 | 1.000 | G | A |
| 738 | SQ1329_Sample010 | LTX149 | Cancer | 4 | 733 | 2279197 | TracerX | 10 | 6 | 50791187 | 738 | 0.994 | C | A |
| 739 | SQ1329_Sample010 | LTX149 | Cancer | 4 | 733 | 2279197 | TracerX | 10 | 20 | 62837060 | 739 | 1.000 | G | G |
| 740 | SQ1329_Sample010 | LTX149 | Cancer | 4 | 733 | 2279197 | TracerX | 10 | 11 | 47200023 | 740 | 1.000 | C | G |
| 741 | SQ1329_Sample010 | LTX149 | Cancer | 4 | 733 | 2279197 | TracerX | 10 | 3 | 52087959 | 741 | 0.496 | T | G |
| 742 | SQ1329_Sample010 | LTX149 | Cancer | 4 | 733 | 2279197 | TracerX | 10 | 3 | 101520185 | 742 | 0.681 | A | G |
| 743 | SQ1329_Sample010 | LTX149 | Cancer | 4 | 733 | 2279197 | TracerX | 10 | 15 | 40763898 | 743 | 0.484 | G | T |
| 744 | SQ1329_Sample010 | LTX149 | Cancer | 4 | 733 | 2279197 | TracerX | 10 | 10 | 134161560 | 744 | 0.400 | C | T |
| 745 | SQ1311_Sample007 | LTX102 | Cancer | 5 | 778 | 2322029 | TracerX | 7 | 8 | 30948434 | 745 | 0.763 | T | A |
| 746 | SQ1311_Sample007 | LTX102 | Cancer | 5 | 778 | 2322029 | TracerX | 7 | 8 | 118847703 | 746 | 0.866 | C | G |
| 747 | SQ1311_Sample007 | LTX102 | Cancer | 5 | 778 | 2322029 | TracerX | 7 | 12 | 25398284 | 747 | NaN | C | A |
| 748 | SQ1311_Sample007 | LTX102 | Cancer | 5 | 778 | 2322029 | TracerX | 7 | 7 | 138603666 | 748 | 0.359 | A | G |
| 749 | SQ1311_Sample007 | LTX102 | Cancer | 5 | 778 | 2322029 | TracerX | 7 | 17 | 7577538 | 749 | 0.649 | C | T |
| 750 | SQ1311_Sample007 | LTX102 | Cancer | 5 | 778 | 2322029 | TracerX | 7 | 12 | 49416133 | 750 | 0.735 | G | A |
| 751 | SQ1311_Sample007 | LTX102 | Cancer | 5 | 778 | 2322029 | TracerX | 7 | 9 | 132963250 | 751 | 0.864 | G | T |
| 752 | SQ1311_Sample007 | LTX102 | Cancer | 5 | 778 | 2322029 | TracerX | 7 | 1 | 156883232 | 752 | 0.474 | G | T |
| 753 | SQ1311_Sample007 | LTX102 | Cancer | 5 | 778 | 2322029 | TracerX | 7 | 8 | 52721778 | 753 | 0.789 | C | A |
| 754 | SQ1311_Sample007 | LTX102 | Cancer | 5 | 778 | 2322029 | TracerX | 7 | 13 | 33109925 | 754 | 0.356 | C | A |
| 755 | SQ1311_Sample007 | LTX102 | Cancer | 5 | 778 | 2322029 | TracerX | 7 | 11 | 92714903 | 755 | 0.465 | T | A |
| 756 | SQ1311_Sample007 | LTX102 | Cancer | 5 | 778 | 2322029 | TracerX | 7 | 12 | 49361733 | 756 | 0.350 | C | G |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 757 | SQ1311_Sample007 | LTX102 | Cancer | 5 | 778 | 2322029 | TracerX | 7 | 15 | 77425561 | 757 | 0.400 | C | A |
| 758 | SQ1311_Sample007 | LTX102 | Cancer | 5 | 778 | 2322029 | TracerX | 7 | 15 | 33855180 | 758 | 0.826 | A | C |
| 759 | SQ1311_Sample007 | LTX102 | Cancer | 5 | 778 | 2322029 | TracerX | 7 | 18 | 51731448 | 759 | 0.485 | A | C |
| 760 | SQ1311_Sample007 | LTX102 | Cancer | 5 | 778 | 2322029 | TracerX | 7 | 6 | 90398306 | 760 | 0.389 | G | C |
| 761 | SQ1311_Sample007 | LTX102 | Cancer | 5 | 778 | 2322029 | TracerX | 7 | 19 | 4488790 | 761 | 0.467 | G | C |
| 762 | SQ1311_Sample007 | LTX102 | Cancer | 5 | 778 | 2322029 | TracerX | 7 | 9 | 17135350 | 762 | 0.444 | A | T |
| 763 | SQ1311_Sample007 | LTX102 | Cancer | 5 | 778 | 2322029 | TracerX | 7 | 9 | 17135349 | 763 | 0.468 | G | T |
| 764 | SQ1311_Sample007 | LTX102 | Cancer | 5 | 778 | 2322029 | TracerX | 7 | 11 | 85459443 | 764 | 0.384 | T | A |
| 765 | SQ1311_Sample001 | LTX015 | Cancer | 5 | 769 | 2322021 | TracerX | 1 | 3 | 186501407 | 765 | 1.000 | G | T |
| 766 | SQ1311_Sample001 | LTX015 | Cancer | 5 | 769 | 2322021 | TracerX | 1 | 18 | 61262379 | 766 | 1.000 | G | T |
| 767 | SQ1311_Sample001 | LTX015 | Cancer | 5 | 769 | 2322021 | TracerX | 1 | 17 | 7578394 | 767 | 1.000 | G | C |
| 768 | SQ1311_Sample001 | LTX015 | Cancer | 5 | 769 | 2322021 | TracerX | 1 | 16 | 2014284 | 768 | 1.000 | G | A |
| 769 | SQ1311_Sample001 | LTX015 | Cancer | 5 | 769 | 2322021 | TracerX | 1 | 3 | 178917564 | 769 | 1.000 | T | C |
| 770 | SQ1311_Sample001 | LTX015 | Cancer | 5 | 769 | 2322021 | TracerX | 1 | 13 | 49027177 | 770 | 0.977 | C | T |
| 771 | SQ1311_Sample001 | LTX015 | Cancer | 5 | 769 | 2322021 | TracerX | 1 | 2 | 10350625 | 771 | 1.000 | G | T |
| 772 | SQ1311_Sample001 | LTX015 | Cancer | 5 | 769 | 2322021 | TracerX | 1 | 3 | 130285569 | 772 | 1.000 | G | T |
| 773 | SQ1311_Sample001 | LTX015 | Cancer | 5 | 769 | 2322021 | TracerX | 1 | 8 | 104388139 | 773 | 1.000 | G | T |
| 774 | SQ1311_Sample001 | LTX015 | Cancer | 5 | 769 | 2322021 | TracerX | 1 | 19 | 52568449 | 774 | 0.929 | G | T |
| 775 | SQ1311_Sample001 | LTX015 | Cancer | 5 | 769 | 2322021 | TracerX | 1 | 22 | 32894496 | 775 | 0.999 | T | A |
| 776 | SQ1311_Sample001 | LTX015 | Cancer | 5 | 769 | 2322021 | TracerX | 1 | 12 | 71898461 | 776 | 0.999 | G | T |
| 777 | SQ1311_Sample001 | LTX015 | Cancer | 5 | 769 | 2322021 | TracerX | 1 | 8 | 94935116 | 777 | 1.000 | G | C |
| 778 | SQ1311_Sample001 | LTX015 | Cancer | 5 | 769 | 2322021 | TracerX | 1 | 3 | 193120500 | 778 | 1.000 | A | C |
| 779 | SQ1311_Sample001 | LTX015 | Cancer | 5 | 769 | 2322021 | TracerX | 1 | 14 | 70246051 | 779 | 1.000 | G | T |
| 780 | SQ1311_Sample001 | LTX015 | Cancer | 5 | 769 | 2322021 | TracerX | 1 | 11 | 6790165 | 780 | 1.000 | C | A |
| 781 | SQ1311_Sample001 | LTX015 | Cancer | 5 | 769 | 2322021 | TracerX | 1 | 4 | 71066286 | 781 | 0.989 | C | G |
| 782 | SQ1311_Sample001 | LTX015 | Cancer | 5 | 769 | 2322021 | TracerX | 1 | 5 | 7626280 | 782 | 1.000 | A | T |
| 783 | SQ1311_Sample001 | LTX015 | Cancer | 5 | 769 | 2322021 | TracerX | 1 | 17 | 10354175 | 783 | 0.745 | C | G |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 784 | SQ1311_Sample003 | LTX074 | Cancer | 5 | 771 | 2322023 | TracerX | 3 | 17 | 7578206 | 784 | 0.959 | T | C |
| 785 | SQ1311_Sample003 | LTX074 | Cancer | 5 | 771 | 2322023 | TracerX | 3 | 10 | 89717615 | 785 | 0.864 | C | T |
| 786 | SQ1311_Sample003 | LTX074 | Cancer | 5 | 771 | 2322023 | TracerX | 3 | 9 | 5069164 | 786 | 0.984 | A | G |
| 787 | SQ1311_Sample003 | LTX074 | Cancer | 5 | 771 | 2322023 | TracerX | 3 | 3 | 47139542 | 787 | 0.693 | G | A |
| 788 | SQ1311_Sample003 | LTX074 | Cancer | 5 | 771 | 2322023 | TracerX | 3 | 20 | 31023115 | 788 | 0.982 | G | T |
| 789 | SQ1311_Sample003 | LTX074 | Cancer | 5 | 771 | 2322023 | TracerX | 3 | 12 | 49420108 | 789 | 0.948 | C | G |
| 790 | SQ1311_Sample003 | LTX074 | Cancer | 5 | 771 | 2322023 | TracerX | 3 | 1 | 150935141 | 790 | 0.940 | G | C |
| 791 | SQ1311_Sample003 | LTX074 | Cancer | 5 | 771 | 2322023 | TracerX | 3 | 19 | 47424096 | 791 | 0.365 | C | G |
| 792 | SQ1311_Sample003 | LTX074 | Cancer | 5 | 771 | 2322023 | TracerX | 3 | 20 | 57829494 | 792 | 1.000 | C | G |
| 793 | SQ1311_Sample003 | LTX074 | Cancer | 5 | 771 | 2322023 | TracerX | 3 | 17 | 76490183 | 793 | 0.982 | C | G |
| 794 | SQ1311_Sample003 | LTX074 | Cancer | 5 | 771 | 2322023 | TracerX | 3 | 1 | 33272142 | 794 | 0.433 | C | A |
| 795 | SQ1311_Sample003 | LTX074 | Cancer | 5 | 771 | 2322023 | TracerX | 3 | 16 | 27374243 | 795 | 0.345 | G | T |
| 796 | SQ1311_Sample003 | LTX074 | Cancer | 5 | 771 | 2322023 | TracerX | 3 | 4 | 1806572 | 796 | NaN | T | G |
| 797 | SQ1311_Sample003 | LTX074 | Cancer | 5 | 771 | 2322023 | TracerX | 3 | 8 | 134145841 | 797 | 0.987 | G | C |
| 798 | SQ1311_Sample003 | LTX074 | Cancer | 5 | 771 | 2322023 | TracerX | 3 | 12 | 110956536 | 798 | 0.440 | C | G |
| 799 | SQ1311_Sample003 | LTX074 | Cancer | 5 | 771 | 2322023 | TracerX | 3 | 12 | 120741431 | 799 | 0.780 | C | A |
| 800 | SQ1311_Sample003 | LTX074 | Cancer | 5 | 771 | 2322023 | TracerX | 3 | 7 | 1077706249 | 800 | 0.930 | A | T |
| 801 | SQ1311_Sample003 | LTX074 | Cancer | 5 | 771 | 2322023 | TracerX | 3 | 19 | 3611966 | 801 | 0.989 | G | C |
| 802 | SQ1311_Sample003 | LTX074 | Cancer | 5 | 771 | 2322023 | TracerX | 3 | 17 | 29653132 | 802 | 0.413 | C | G |
| 803 | SQ1311_Sample004 | LTX075 | Cancer | 5 | 772 | 2322024 | TracerX | 4 | 7 | 55259515 | 803 | 0.158 | T | G |
| 804 | SQ1311_Sample004 | LTX075 | Cancer | 5 | 772 | 2322024 | TracerX | 4 | 17 | 7578403 | 804 | 0.425 | C | A |
| 805 | SQ1311_Sample004 | LTX075 | Cancer | 5 | 772 | 2322024 | TracerX | 4 | 23 | 47040716 | 805 | 0.928 | G | T |
| 806 | SQ1311_Sample004 | LTX075 | Cancer | 5 | 772 | 2322024 | TracerX | 4 | 23 | 47039288 | 806 | NaN | T | G |
| 807 | SQ1311_Sample004 | LTX075 | Cancer | 5 | 772 | 2322024 | TracerX | 4 | 18 | 8376593 | 807 | 0.752 | G | A |
| 808 | SQ1311_Sample004 | LTX075 | Cancer | 5 | 772 | 2322024 | TracerX | 4 | 12 | 49949724 | 808 | 0.481 | C | G |
| 809 | SQ1311_Sample004 | LTX075 | Cancer | 5 | 772 | 2322024 | TracerX | 4 | 20 | 2840714 | 809 | 0.820 | C | T |
| 810 | SQ1311_Sample004 | LTX075 | Cancer | 5 | 772 | 2322024 | TracerX | 4 | 2 | 223787502 | 810 | 0.281 | C | A |

FIG. 20 (CONT.)

| Row number | SampleId | SampleName | SampleType | Pool | Barcode | Seqid | Project | SampleNumber | Chr | Pos | Row number | MutConf | Ref | Mut |
|---|---|---|---|---|---|---|---|---|---|---|---|---|---|---|
| 811 | SQ1311_Sample004 | LTX075 | Cancer | 5 | 772 | 2322024 | TracerX | 4 | 20 | 31676821 | 811 | 0.299 | G | A |
| 812 | SQ1311_Sample004 | LTX075 | Cancer | 5 | 772 | 2322024 | TracerX | 4 | 17 | 47010696 | 812 | 0.428 | G | C |
| 813 | SQ1311_Sample004 | LTX075 | Cancer | 5 | 772 | 2322024 | TracerX | 4 | 17 | 37571363 | 813 | 0.437 | G | C |
| 814 | SQ1311_Sample004 | LTX075 | Cancer | 5 | 772 | 2322024 | TracerX | 4 | 12 | 116457705 | 814 | 0.335 | C | T |
| 815 | SQ1311_Sample004 | LTX075 | Cancer | 5 | 772 | 2322024 | TracerX | 4 | 17 | 3717712 | 815 | 0.402 | C | T |
| 816 | SQ1311_Sample004 | LTX075 | Cancer | 5 | 772 | 2322024 | TracerX | 4 | 4 | 146653666 | 816 | 0.408 | G | C |
| 817 | SQ1311_Sample004 | LTX075 | Cancer | 5 | 772 | 2322024 | TracerX | 4 | 3 | 172065111 | 817 | 0.387 | G | C |
| 818 | SQ1311_Sample004 | LTX075 | Cancer | 5 | 772 | 2322024 | TracerX | 4 | 10 | 127843807 | 818 | 0.627 | G | A |
| 819 | SQ1311_Sample004 | LTX075 | Cancer | 5 | 772 | 2322024 | TracerX | 4 | 6 | 105609358 | 819 | 0.982 | A | G |
| 820 | SQ1311_Sample004 | LTX075 | Cancer | 5 | 772 | 2322024 | TracerX | 4 | 1 | 247654898 | 820 | 0.849 | T | C |
| 821 | SQ1311_Sample004 | LTX075 | Cancer | 5 | 772 | 2322024 | TracerX | 4 | 14 | 92583089 | 821 | 0.496 | G | T |
| 822 | SQ1311_Sample002 | LTX033 | Cancer | 5 | 770 | 2322022 | TracerX | 2 | 17 | 7577082 | 822 | 1.000 | C | T |
| 823 | SQ1311_Sample002 | LTX033 | Cancer | 5 | 770 | 2322022 | TracerX | 2 | 19 | 10600447 | 823 | 1.000 | G | A |
| 824 | SQ1311_Sample002 | LTX033 | Cancer | 5 | 770 | 2322022 | TracerX | 2 | 17 | 4439438 | 824 | 1.000 | G | A |
| 825 | SQ1311_Sample002 | LTX033 | Cancer | 5 | 770 | 2322022 | TracerX | 2 | 20 | 62165606 | 825 | 1.000 | G | T |
| 826 | SQ1311_Sample002 | LTX033 | Cancer | 5 | 770 | 2322022 | TracerX | 2 | 1 | 152732873 | 826 | 1.000 | C | A |
| 827 | SQ1311_Sample002 | LTX033 | Cancer | 5 | 770 | 2322022 | TracerX | 2 | 7 | 4947050 | 827 | 1.000 | G | T |
| 828 | SQ1311_Sample002 | LTX033 | Cancer | 5 | 770 | 2322022 | TracerX | 2 | 17 | 7350222 | 828 | 1.000 | C | A |
| 829 | SQ1311_Sample002 | LTX033 | Cancer | 5 | 770 | 2322022 | TracerX | 2 | 22 | 21167719 | 829 | 1.000 | G | A |
| 830 | SQ1311_Sample002 | LTX033 | Cancer | 5 | 770 | 2322022 | TracerX | 2 | 3 | 100093927 | 830 | 1.000 | G | T |
| 831 | SQ1311_Sample002 | LTX033 | Cancer | 5 | 770 | 2322022 | TracerX | 2 | 20 | 35862487 | 831 | 0.997 | T | C |
| 832 | SQ1311_Sample002 | LTX033 | Cancer | 5 | 770 | 2322022 | TracerX | 2 | 2 | 26700580 | 832 | 0.904 | G | A |
| 833 | SQ1311_Sample002 | LTX033 | Cancer | 5 | 770 | 2322022 | TracerX | 2 | 23 | 96684657 | 833 | 1.000 | G | T |
| 834 | SQ1311_Sample002 | LTX033 | Cancer | 5 | 770 | 2322022 | TracerX | 2 | 13 | 38172799 | 834 | 0.874 | T | C |
| 835 | SQ1311_Sample002 | LTX033 | Cancer | 5 | 770 | 2322022 | TracerX | 2 | 3 | 147121807 | 835 | 1.000 | C | A |
| 836 | SQ1311_Sample002 | LTX033 | Cancer | 5 | 770 | 2322022 | TracerX | 2 | 9 | 35057128 | 836 | 0.836 | C | T |
| 837 | SQ1311_Sample002 | LTX033 | Cancer | 5 | 770 | 2322022 | TracerX | 2 | 16 | 29791531 | 837 | 1.000 | G | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 838 | SQ1311_Sample002 | LTX033 | Cancer | 5 | 770 | 2322022 | TracerX | 2 | 19 | 57286130 | 838 | 0.677 | C | T |
| 839 | SQ1311_Sample002 | LTX033 | Cancer | 5 | 770 | 2322022 | TracerX | 2 | 17 | 76134464 | 839 | 0.416 | G | A |
| 840 | SQ1311_Sample006 | LTX091 | Cancer | 5 | 777 | 2322028 | TracerX | 6 | 19 | 10602907 | 840 | 0.338 | G | A |
| 841 | SQ1311_Sample006 | LTX091 | Cancer | 5 | 777 | 2322028 | TracerX | 6 | 19 | 1220487 | 841 | 0.358 | G | A |
| 842 | SQ1311_Sample006 | LTX091 | Cancer | 5 | 777 | 2322028 | TracerX | 6 | 6 | 106555068 | 842 | 0.889 | G | A |
| 843 | SQ1311_Sample006 | LTX091 | Cancer | 5 | 777 | 2322028 | TracerX | 6 | 1 | 155874286 | 843 | 0.499 | A | C |
| 844 | SQ1311_Sample006 | LTX091 | Cancer | 5 | 777 | 2322028 | TracerX | 6 | 12 | 91449475 | 844 | 0.467 | A | C |
| 845 | SQ1311_Sample006 | LTX091 | Cancer | 5 | 777 | 2322028 | TracerX | 6 | 11 | 74800278 | 845 | 0.438 | G | T |
| 846 | SQ1311_Sample006 | LTX091 | Cancer | 5 | 777 | 2322028 | TracerX | 6 | 1 | 54675768 | 846 | 0.336 | C | A |
| 847 | SQ1311_Sample006 | LTX091 | Cancer | 5 | 777 | 2322028 | TracerX | 6 | 17 | 8045743 | 847 | NaN | A | C |
| 848 | SQ1311_Sample006 | LTX091 | Cancer | 5 | 777 | 2322028 | TracerX | 6 | 1 | 214170777 | 848 | 0.334 | G | T |
| 849 | SQ1311_Sample006 | LTX091 | Cancer | 5 | 777 | 2322028 | TracerX | 6 | 1 | 109859508 | 849 | 0.886 | C | G |
| 850 | SQ1311_Sample006 | LTX091 | Cancer | 5 | 777 | 2322028 | TracerX | 6 | 7 | 142988670 | 850 | 0.388 | G | T |
| 851 | SQ1311_Sample006 | LTX091 | Cancer | 5 | 777 | 2322028 | TracerX | 6 | 17 | 9559744 | 851 | 0.738 | C | T |
| 852 | SQ1311_Sample006 | LTX091 | Cancer | 5 | 777 | 2322028 | TracerX | 6 | 12 | 114380190 | 852 | 0.778 | A | G |
| 853 | SQ1311_Sample006 | LTX091 | Cancer | 5 | 777 | 2322028 | TracerX | 6 | 14 | 95562863 | 853 | 0.704 | T | C |
| 854 | SQ1311_Sample006 | LTX091 | Cancer | 5 | 777 | 2322028 | TracerX | 6 | 12 | 112668613 | 854 | 0.375 | G | A |
| 855 | SQ1311_Sample006 | LTX091 | Cancer | 5 | 777 | 2322028 | TracerX | 6 | 4 | 110791343 | 855 | 0.553 | C | T |
| 856 | SQ1311_Sample006 | LTX091 | Cancer | 5 | 777 | 2322028 | TracerX | 6 | 2 | 16082277 | 856 | 0.775 | G | A |
| 857 | SQ1311_Sample006 | LTX091 | Cancer | 5 | 777 | 2322028 | TracerX | 6 | 15 | 42980590 | 857 | 0.910 | C | G |
| 858 | SQ1311_Sample006 | LTX091 | Cancer | 5 | 777 | 2322028 | TracerX | 6 | 22 | 31592935 | 858 | 0.295 | C | T |
| 859 | SQ1311_Sample005 | LTX076 | Cancer | 5 | 773 | 2322025 | TracerX | 5 | 4 | 187521078 | 859 | 1.000 | C | T |
| 860 | SQ1311_Sample005 | LTX076 | Cancer | 5 | 773 | 2322025 | TracerX | 5 | 17 | 7577090 | 860 | 1.000 | C | G |
| 861 | SQ1311_Sample005 | LTX076 | Cancer | 5 | 773 | 2322025 | TracerX | 5 | 12 | 133225515 | 861 | 1.000 | C | A |
| 862 | SQ1311_Sample005 | LTX076 | Cancer | 5 | 773 | 2322025 | TracerX | 5 | 14 | 21868192 | 862 | 1.000 | G | A |
| 863 | SQ1311_Sample005 | LTX076 | Cancer | 5 | 773 | 2322025 | TracerX | 5 | 14 | 21868191 | 863 | 1.000 | T | A |
| 864 | SQ1311_Sample005 | LTX076 | Cancer | 5 | 773 | 2322025 | TracerX | 5 | 6 | 1381996330 | 864 | 0.925 | C | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 865 | SQ1311_Sample005 | LTX076 | Cancer | 5 | 773 | 2322025 | TracerX | 5 | 16 | 4043420 | 865 | 1.000 | T | A |
| 866 | SQ1311_Sample005 | LTX076 | Cancer | 5 | 773 | 2322025 | TracerX | 5 | 7 | 98574134 | 866 | 1.000 | T | A |
| 867 | SQ1311_Sample005 | LTX076 | Cancer | 5 | 773 | 2322025 | TracerX | 5 | 11 | 18434326 | 867 | 1.000 | G | T |
| 868 | SQ1311_Sample005 | LTX076 | Cancer | 5 | 773 | 2322025 | TracerX | 5 | 17 | 7416153 | 868 | 1.000 | G | T |
| 869 | SQ1311_Sample005 | LTX076 | Cancer | 5 | 773 | 2322025 | TracerX | 5 | 11 | 119045783 | 869 | NaN | G | A |
| 870 | SQ1311_Sample005 | LTX076 | Cancer | 5 | 773 | 2322025 | TracerX | 5 | 5 | 19838947 | 870 | 1.000 | C | T |
| 871 | SQ1311_Sample005 | LTX076 | Cancer | 5 | 773 | 2322025 | TracerX | 5 | 19 | 45209082 | 871 | 1.000 | C | T |
| 872 | SQ1311_Sample005 | LTX076 | Cancer | 5 | 773 | 2322025 | TracerX | 5 | 23 | 32482787 | 872 | 1.000 | C | G |
| 873 | SQ1311_Sample005 | LTX076 | Cancer | 5 | 773 | 2322025 | TracerX | 5 | 2 | 228884112 | 873 | 1.000 | C | A |
| 874 | SQ1311_Sample005 | LTX076 | Cancer | 5 | 773 | 2322025 | TracerX | 5 | 16 | 3656696 | 874 | 1.000 | T | A |
| 875 | SQ1311_Sample005 | LTX076 | Cancer | 5 | 773 | 2322025 | TracerX | 5 | 10 | 104136546 | 875 | 1.000 | G | A |
| 876 | SQ1311_Sample005 | LTX076 | Cancer | 5 | 773 | 2322025 | TracerX | 5 | 10 | 79595553 | 876 | 1.000 | C | A |
| 877 | SQ1311_Sample005 | LTX076 | Cancer | 5 | 773 | 2322025 | TracerX | 5 | 8 | 72182032 | 877 | 1.000 | C | G |
| 878 | SQ1311_Sample005 | LTX076 | Cancer | 5 | 773 | 2322025 | TracerX | 5 | 3 | 53125957 | 878 | 1.000 | G | C |
| 879 | SQ1311_Sample005 | LTX076 | Cancer | 5 | 773 | 2322025 | TracerX | 5 | 3 | 129251434 | 879 | 1.000 | C | A |
| 880 | SQ1311_Sample009 | LTX160 | Cancer | 5 | 780 | 2322031 | TracerX | 9 | 12 | 25398284 | 880 | 1.000 | G | A |
| 881 | SQ1311_Sample009 | LTX160 | Cancer | 5 | 780 | 2322031 | TracerX | 9 | 19 | 47491255 | 881 | 0.753 | C | T |
| 882 | SQ1311_Sample009 | LTX160 | Cancer | 5 | 780 | 2322031 | TracerX | 9 | 19 | 11138504 | 882 | 0.371 | G | C |
| 883 | SQ1311_Sample009 | LTX160 | Cancer | 5 | 780 | 2322031 | TracerX | 9 | 7 | 97361937 | 883 | 0.992 | G | C |
| 884 | SQ1311_Sample009 | LTX160 | Cancer | 5 | 780 | 2322031 | TracerX | 9 | 11 | 64622898 | 884 | 1.000 | T | A |
| 885 | SQ1311_Sample009 | LTX160 | Cancer | 5 | 780 | 2322031 | TracerX | 9 | 10 | 43292571 | 885 | 0.390 | C | A |
| 886 | SQ1311_Sample009 | LTX160 | Cancer | 5 | 780 | 2322031 | TracerX | 9 | 18 | 61602264 | 886 | 0.401 | C | A |
| 887 | SQ1311_Sample009 | LTX160 | Cancer | 5 | 780 | 2322031 | TracerX | 9 | 7 | 150777840 | 887 | NaN | NaN | C |
| 888 | SQ1311_Sample009 | LTX160 | Cancer | 5 | 780 | 2322031 | TracerX | 9 | 2 | 27601137 | 888 | 0.473 | C | A |
| 889 | SQ1311_Sample009 | LTX160 | Cancer | 5 | 780 | 2322031 | TracerX | 9 | 22 | 21990773 | 889 | 0.374 | C | T |
| 890 | SQ1311_Sample009 | LTX160 | Cancer | 5 | 780 | 2322031 | TracerX | 9 | 4 | 8229319 | 890 | 0.817 | G | A |
| 891 | SQ1311_Sample009 | LTX160 | Cancer | 5 | 780 | 2322031 | TracerX | 9 | 5 | 140744399 | 891 | 0.783 | C | T |

FIG. 20 (CONT.)

| Row number | SampleId | SampleName | SampleType | Pool | Barcode | SeqId | Project | SampleNumber | Chr | Pos | Row number | MutConf | Ref | Mut |
|---|---|---|---|---|---|---|---|---|---|---|---|---|---|---|
| 892 | SQ1311_Sample009 | LTX160 | Cancer | 5 | 780 | 2322031 | TracerX | 9 | 12 | 29464049 | 892 | 0.389 | T | C |
| 893 | SQ1311_Sample009 | LTX160 | Cancer | 5 | 780 | 2322031 | TracerX | 9 | 10 | 46999601 | 893 | NaN | G | A |
| 894 | SQ1311_Sample009 | LTX160 | Cancer | 5 | 780 | 2322031 | TracerX | 9 | 15 | 24921526 | 894 | 0.398 | G | T |
| 895 | SQ1311_Sample009 | LTX160 | Cancer | 5 | 780 | 2322031 | TracerX | 9 | 11 | 104034545 | 895 | 0.409 | G | T |
| 896 | SQ1311_Sample009 | LTX160 | Cancer | 5 | 780 | 2322031 | TracerX | 9 | 11 | 66190163 | 896 | 0.161 | G | A |
| 897 | SQ1311_Sample009 | LTX160 | Cancer | 5 | 780 | 2322031 | TracerX | 9 | 4 | 66356134 | 897 | 0.940 | G | A |
| 898 | SQ1311_Sample009 | LTX160 | Cancer | 5 | 780 | 2322031 | TracerX | 9 | 20 | 23755907 | 898 | 0.415 | G | T |
| 899 | SQ1311_Sample008 | LTX103 | Cancer | 5 | 779 | 2322030 | TracerX | 8 | 17 | 7578406 | 899 | 0.343 | C | T |
| 900 | SQ1311_Sample008 | LTX103 | Cancer | 5 | 779 | 2322030 | TracerX | 8 | 14 | 51226346 | 900 | 0.909 | C | T |
| 901 | SQ1311_Sample008 | LTX103 | Cancer | 5 | 779 | 2322030 | TracerX | 8 | 12 | 56360899 | 901 | 0.494 | G | C |
| 902 | SQ1311_Sample008 | LTX103 | Cancer | 5 | 779 | 2322030 | TracerX | 8 | 1 | 154127373 | 902 | 0.490 | G | C |
| 903 | SQ1311_Sample008 | LTX103 | Cancer | 5 | 779 | 2322030 | TracerX | 8 | 14 | 96777916 | 903 | 0.406 | G | C |
| 904 | SQ1311_Sample008 | LTX103 | Cancer | 5 | 779 | 2322030 | TracerX | 8 | 19 | 34857281 | 904 | 0.255 | C | A |
| 905 | SQ1311_Sample008 | LTX103 | Cancer | 5 | 779 | 2322030 | TracerX | 8 | 23 | 84362885 | 905 | 0.579 | A | G |
| 906 | SQ1311_Sample008 | LTX103 | Cancer | 5 | 779 | 2322030 | TracerX | 8 | 10 | 96043655 | 906 | 0.929 | G | T |
| 907 | SQ1311_Sample008 | LTX103 | Cancer | 5 | 779 | 2322030 | TracerX | 8 | 19 | 10220867 | 907 | 0.921 | C | T |
| 908 | SQ1311_Sample008 | LTX103 | Cancer | 5 | 779 | 2322030 | TracerX | 8 | 20 | 25304046 | 908 | 0.937 | C | T |
| 909 | SQ1311_Sample008 | LTX103 | Cancer | 5 | 779 | 2322030 | TracerX | 8 | 16 | 30999142 | 909 | NaN | A | G |
| 910 | SQ1311_Sample008 | LTX103 | Cancer | 5 | 779 | 2322030 | TracerX | 8 | 7 | 94937446 | 910 | NaN | T | C |
| 911 | SQ1311_Sample008 | LTX103 | Cancer | 5 | 779 | 2322030 | TracerX | 8 | 1 | 171076966 | 911 | 0.961 | G | A |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 1 | 99.972% | 0.000% | 14477 | 0 | 0.001% | 0.004% | TRANSVERSION | 0.0000 | 1 | 0 | 1 | 1 |
| 2 | 99.976% | 0.000% | 50554 | 0 | 0.002% | 0.002% | TRANSVERSION | 0.0000 | 2 | 0 | 2 | 1 |
| 3 | 99.966% | 0.003% | 32344 | 1 | 0.002% | 0.004% | TRANSVERSION | 0.0031 | 3 | 0 | 2 | 1 |
| 4 | 99.969% | 0.028% | 42542 | 12 | 0.040% | 0.015% | TRANSITION | 0.0282 | 4 | 0 | 1 | 1 |
| 5 | 100.000% | 0.000% | 9969 | 0 | 0.004% | 0.007% | TRANSVERSION | 0.0000 | 5 | 0 | 4 | 1 |
| 6 | 99.949% | 0.000% | 29318 | 0 | 0.001% | 0.002% | TRANSVERSION | 0.0000 | 6 | 0 | 4 | 1 |
| 7 | 99.960% | 0.002% | 44659 | 1 | 0.001% | 0.001% | TRANSVERSION | 0.0022 | 7 | 0 | 4 | 1 |
| 8 | 99.980% | 0.005% | 64660 | 3 | 0.004% | 0.002% | TRANSVERSION | 0.0046 | 8 | 0 | 4 | 1 |
| 9 | 99.987% | 0.006% | 61846 | 4 | 0.011% | 0.005% | TRANSITION | 0.0065 | 9 | 0 | 3 | 0.5 |
| 10 | 99.943% | 0.000% | 52505 | 0 | 0.003% | 0.004% | TRANSVERSION | 0.0000 | 10 | 0 | 4 | 1 |
| 11 | 99.954% | 0.006% | 49973 | 3 | 0.003% | 0.003% | TRANSVERSION | 0.0060 | 11 | 0 | 4 | 0.5 |
| 12 | 99.965% | 0.000% | 69116 | 0 | 0.001% | 0.001% | TRANSVERSION | 0.0000 | 12 | 0 | 4 | 0.5 |
| 13 | 99.970% | 0.001% | 72565 | 1 | 0.003% | 0.004% | TRANSVERSION | 0.0014 | 13 | 0 | 4 | 1 |
| 14 | 99.989% | 0.002% | 61574 | 1 | 0.003% | 0.002% | TRANSVERSION | 0.0016 | 14 | 0 | 4 | 1 |
| 15 | 99.942% | 0.002% | 53762 | 1 | 0.004% | 0.002% | TRANSVERSION | 0.0019 | 15 | 0 | 3 | 1 |
| 16 | 99.959% | 0.000% | 50965 | 0 | 0.003% | 0.002% | TRANSVERSION | 0.0000 | 16 | 0 | 4 | 1 |
| 17 | 99.962% | 0.008% | 60185 | 5 | 0.002% | 0.002% | TRANSVERSION | 0.0083 | 17 | 0 | 4 | 1 |
| 18 | 99.942% | 0.000% | 8654 | 0 | 0.004% | 0.007% | TRANSVERSION | 0.0000 | 18 | 0 | 1 | 1 |
| 19 | 99.942% | 0.000% | 8638 | 0 | 0.002% | 0.004% | TRANSVERSION | 0.0000 | 19 | 0 | 1 | 1 |
| 20 | 99.983% | 0.010% | 40946 | 4 | 0.032% | 0.008% | TRANSITION | 0.0098 | 20 | 0 | 1 | 1 |
| 21 | 99.970% | 0.000% | 6673 | 0 | 0.003% | 0.009% | TRANSVERSION | 0.0000 | 21 | 0 | 2 | 1 |
| 22 | 99.943% | 0.057% | 15688 | 9 | 0.039% | 0.016% | TRANSVERSION | 0.0574 | 22 | 0 | 2 | 1 |
| 23 | 99.976% | 0.000% | 33277 | 0 | 0.002% | 0.003% | TRANSVERSION | 0.0000 | 23 | 0 | 2 | 1 |
| 24 | 99.979% | 0.000% | 18943 | 0 | 0.001% | 0.002% | TRANSVERSION | 0.0000 | 24 | 0 | 2 | 1 |
| 25 | 99.967% | 0.028% | 39485 | 11 | 0.027% | 0.011% | TRANSITION | 0.0279 | 25 | 0 | 1 | 1 |
| 26 | 99.983% | 0.017% | 29005 | 5 | 0.035% | 0.018% | TRANSITION | 0.0172 | 26 | 0 | 2 | 1 |
| 27 | 99.974% | 0.003% | 30822 | 1 | 0.004% | 0.005% | TRANSVERSION | 0.0032 | 27 | 0 | 2 | 0.5 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 28 | 99.973% | 0.004% | 47600 | 2 | 0.002% | 0.002% | TRANSVERSION | 0.0042 | 28 | 0 | 1 | 0.75 |
| 29 | 99.974% | 0.022% | 23218 | 5 | 0.024% | 0.009% | TRANSITION | 0.0215 | 29 | 0 | 2 | 0.75 |
| 30 | 99.968% | 0.000% | 12593 | 0 | 0.001% | 0.003% | TRANSVERSION | 0.0000 | 30 | 0 | 2 | 0.5 |
| 31 | 99.955% | 0.000% | 61693 | 0 | 0.001% | 0.001% | TRANSVERSION | 0.0000 | 31 | 0 | 4 | 0.75 |
| 32 | 99.939% | 0.015% | 19768 | 3 | 0.004% | 0.004% | TRANSVERSION | 0.0152 | 32 | 0 | 4 | 1 |
| 33 | 99.949% | 0.006% | 47266 | 3 | 0.007% | 0.004% | TRANSVERSION | 0.0063 | 33 | 0 | 4 | 0.5 |
| 34 | 99.975% | 0.006% | 16257 | 1 | 0.001% | 0.002% | TRANSVERSION | 0.0062 | 34 | 0 | 4 | 0.75 |
| 35 | 99.984% | 0.000% | 55749 | 0 | 0.002% | 0.002% | TRANSVERSION | 0.0000 | 35 | 0 | 4 | 0.5 |
| 36 | 99.963% | 0.000% | 61921 | 0 | 0.001% | 0.001% | TRANSVERSION | 0.0000 | 36 | 0 | 4 | 0.25 |
| 37 | 99.964% | 0.005% | 61889 | 3 | 0.005% | 0.002% | TRANSVERSION | 0.0048 | 37 | 0 | 4 | 0.25 |
| 38 | 99.962% | 0.000% | 18559 | 0 | 0.002% | 0.003% | TRANSVERSION | 0.0000 | 38 | 0 | 4 | 0.25 |
| 39 | 99.960% | 0.005% | 37928 | 2 | 0.001% | 0.002% | TRANSVERSION | 0.0053 | 39 | 0 | 4 | 0.25 |
| 40 | 99.941% | 0.047% | 34038 | 16 | 0.003% | 0.003% | TRANSVERSION | 0.0470 | 40 | 1 | 2 | 1 |
| 41 | 99.773% | 0.206% | 28622 | 59 | 0.001% | 0.002% | TRANSVERSION | 0.2061 | 41 | 1 | 1 | 1 |
| 42 | 99.983% | 0.010% | 40090 | 4 | 0.007% | 0.004% | TRANSVERSION | 0.0100 | 42 | 0 | 2 | 1 |
| 43 | 99.894% | 0.059% | 8498 | 5 | 0.005% | 0.010% | TRANSVERSION | 0.0588 | 43 | 0 | 2 | 1 |
| 44 | 99.825% | 0.115% | 53250 | 61 | 0.001% | 0.001% | TRANSVERSION | 0.1146 | 44 | 1 | 2 | 1 |
| 45 | 99.866% | 0.132% | 49129 | 65 | 0.027% | 0.007% | TRANSITION | 0.1323 | 45 | 1 | 1 | 0.8 |
| 46 | 99.991% | 0.006% | 34059 | 2 | 0.029% | 0.009% | TRANSITION | 0.0059 | 46 | 0 | 1 | 0.2 |
| 47 | 99.862% | 0.087% | 27625 | 24 | 0.004% | 0.003% | TRANSVERSION | 0.0869 | 47 | 1 | 4 | 1 |
| 48 | 99.869% | 0.073% | 39700 | 29 | 0.004% | 0.003% | TRANSVERSION | 0.0730 | 48 | 1 | 4 | 1 |
| 49 | 99.921% | 0.039% | 49306 | 19 | 0.002% | 0.002% | TRANSVERSION | 0.0385 | 49 | 1 | 4 | 1 |
| 50 | 99.973% | 0.003% | 29698 | 1 | 0.001% | 0.001% | TRANSVERSION | 0.0034 | 50 | 0 | 4 | 0.2 |
| 51 | 99.943% | 0.005% | 21052 | 1 | 0.004% | 0.004% | TRANSVERSION | 0.0048 | 51 | 0 | 4 | 0.2 |
| 52 | 99.927% | 0.047% | 19164 | 9 | 0.001% | 0.002% | TRANSVERSION | 0.0470 | 52 | 1 | 3 | 0.4 |
| 53 | 99.981% | 0.004% | 47991 | 2 | 0.001% | 0.001% | TRANSVERSION | 0.0042 | 53 | 0 | 4 | 0.4 |
| 54 | 99.971% | 0.002% | 61783 | 1 | 0.004% | 0.002% | TRANSVERSION | 0.0016 | 54 | 0 | 4 | 0.4 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 55 | 100.000% | 0.000% | 5663 | 0 | 0.003% | 0.005% | TRANSVERSION | 0.0000 | 55 | 0 | 4 | 0.2 |
| 56 | 99.935% | 0.000% | 25969 | 0 | 0.003% | 0.005% | TRANSVERSION | 0.0000 | 56 | 0 | 4 | 0.2 |
| 57 | 99.972% | 0.000% | 21116 | 0 | 0.001% | 0.002% | TRANSVERSION | 0.0000 | 57 | 0 | 4 | 0.2 |
| 58 | 98.373% | 1.628% | 32812 | 534 | 0.032% | 0.012% | TRANSITION | 1.6275 | 58 | 1 | 1 | 1 |
| 59 | 98.402% | 1.540% | 73891 | 1138 | 0.004% | 0.003% | TRANSVERSION | 1.5401 | 59 | 1 | 2 | 1 |
| 60 | 98.877% | 1.095% | 60378 | 661 | 0.001% | 0.001% | TRANSVERSION | 1.0948 | 60 | 1 | 2 | 1 |
| 61 | 98.930% | 1.062% | 23644 | 251 | 0.001% | 0.001% | TRANSVERSION | 1.0616 | 61 | 1 | 2 | 1 |
| 62 | 99.960% | 0.034% | 32773 | 11 | 0.016% | 0.008% | TRANSITION | 0.0336 | 62 | 0 | 2 | 0.25 |
| 63 | 99.982% | 0.018% | 44346 | 8 | 0.028% | 0.013% | TRANSITION | 0.0180 | 63 | 0 | 2 | 0.5 |
| 64 | 99.981% | 0.017% | 51495 | 9 | 0.020% | 0.007% | TRANSITION | 0.0175 | 64 | 0 | 2 | 0.25 |
| 65 | 94.742% | 5.155% | 8729 | 450 | 0.000% | 0.003% | TRANSVERSION | 5.1552 | 65 | 1 | 4 | 1 |
| 66 | 98.701% | 1.267% | 71290 | 903 | 0.003% | 0.002% | TRANSVERSION | 1.2667 | 66 | 1 | 4 | 1 |
| 67 | 99.289% | 0.698% | 69158 | 483 | 0.001% | 0.001% | TRANSVERSION | 0.6984 | 67 | 1 | 4 | 1 |
| 68 | 98.704% | 1.274% | 58804 | 749 | 0.002% | 0.002% | TRANSVERSION | 1.2737 | 68 | 1 | 4 | 0.5 |
| 69 | 99.966% | 0.000% | 38169 | 0 | 0.001% | 0.002% | TRANSVERSION | 0.0000 | 69 | 0 | 4 | 0.5 |
| 70 | 99.969% | 0.012% | 64287 | 8 | 0.003% | 0.002% | TRANSVERSION | 0.0124 | 70 | 0 | 4 | 0.5 |
| 71 | 99.991% | 0.005% | 42207 | 2 | 0.001% | 0.001% | TRANSVERSION | 0.0047 | 71 | 0 | 4 | 0.25 |
| 72 | 99.987% | 0.002% | 47087 | 1 | 0.002% | 0.002% | TRANSVERSION | 0.0021 | 72 | 0 | 4 | 0.25 |
| 73 | 99.956% | 0.004% | 50364 | 2 | 0.002% | 0.002% | TRANSVERSION | 0.0040 | 73 | 0 | 4 | 0.25 |
| 74 | 99.974% | 0.000% | 66068 | 0 | 0.000% | 0.001% | TRANSVERSION | 0.0000 | 74 | 0 | 4 | 0.25 |
| 75 | 99.989% | 0.000% | 36577 | 0 | 0.001% | 0.002% | TRANSVERSION | 0.0000 | 75 | 0 | 4 | 0.5 |
| 76 | 98.124% | 1.829% | 31925 | 584 | 0.004% | 0.003% | TRANSVERSION | 1.8293 | 76 | 1 | 4 | 0.25 |
| 77 | 99.981% | 0.000% | 32415 | 0 | 0.002% | 0.001% | TRANSVERSION | 0.0000 | 77 | 0 | 4 | 0.25 |
| 78 | 99.966% | 0.000% | 61764 | 0 | 0.002% | 0.002% | TRANSVERSION | 0.0000 | 78 | 0 | 4 | 0.25 |
| 79 | 100.000% | 0.000% | 71 | 0 | 0.000% | 0.000% | TRANSVERSION | 0.0000 | 79 |  | 2 | 0.5 |
| 80 | 99.988% | 0.006% | 16867 | 1 | 0.032% | 0.018% | TRANSITION | 0.0059 | 80 | 0 | 1 | 1 |
| 81 | 99.990% | 0.000% | 19887 | 0 | 0.001% | 0.003% | TRANSVERSION | 0.0000 | 81 | 0 | 2 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 82 | 99.972% | 0.028% | 14228 | 4 | 0.030% | 0.027% | TRANSITION | 0.0281 | 82 | 0 | 2 | 1 |
| 83 | 99.957% | 0.039% | 23264 | 9 | 0.027% | 0.015% | TRANSITION | 0.0387 | 83 | 0 | 2 | 1 |
| 84 | 99.988% | 0.005% | 56212 | 3 | 0.024% | 0.008% | TRANSITION | 0.0053 | 84 | 0 | 2 | 0.5 |
| 85 | 99.974% | 0.026% | 22944 | 6 | 0.033% | 0.012% | TRANSITION | 0.0262 | 85 | 0 | 1 | 0.5 |
| 86 | 99.964% | 0.030% | 46584 | 14 | 0.025% | 0.006% | TRANSITION | 0.0301 | 86 | 0 | 2 | 1 |
| 87 | 99.975% | 0.002% | 43265 | 1 | 0.001% | 0.001% | TRANSVERSION | 0.0023 | 87 | 0 | 1 | 0.5 |
| 88 | 99.968% | 0.002% | 56062 | 1 | 0.002% | 0.002% | TRANSVERSION | 0.0018 | 88 | 0 | 4 | 1 |
| 89 | 99.953% | 0.027% | 29734 | 8 | 0.005% | 0.004% | TRANSVERSION | 0.0269 | 89 | 0 | 4 | 1 |
| 90 | 99.969% | 0.002% | 45430 | 1 | 0.004% | 0.003% | TRANSVERSION | 0.0022 | 90 | 0 | 4 | 1 |
| 91 | 99.983% | 0.000% | 34744 | 0 | 0.002% | 0.002% | TRANSVERSION | 0.0000 | 91 | 0 | 4 | 0.5 |
| 92 | 99.971% | 0.007% | 54767 | 4 | 0.001% | 0.001% | TRANSVERSION | 0.0073 | 92 | 0 | 4 | 0.5 |
| 93 | 99.971% | 0.000% | 58575 | 0 | 0.001% | 0.002% | TRANSVERSION | 0.0000 | 93 | 0 | 4 | 0.5 |
| 94 | 99.976% | 0.003% | 58973 | 2 | 0.003% | 0.002% | TRANSVERSION | 0.0034 | 94 | 0 | 4 | 0.5 |
| 95 | 99.974% | 0.000% | 26862 | 0 | 0.003% | 0.003% | TRANSVERSION | 0.0000 | 95 | 0 | 4 | 0.5 |
| 96 | 99.995% | 0.000% | 21218 | 0 | 0.002% | 0.003% | TRANSVERSION | 0.0000 | 96 | 0 | 4 | 0.5 |
| 97 | 99.967% | 0.003% | 32926 | 1 | 0.002% | 0.002% | TRANSVERSION | 0.0030 | 97 | 0 | 4 | 0.5 |
| 98 | 99.987% | 0.013% | 30955 | 4 | 0.030% | 0.011% | TRANSITION | 0.0129 | 98 | 0 | 1 | 1 |
| 99 | 99.985% | 0.012% | 59968 | 7 | 0.011% | 0.004% | TRANSITION | 0.0117 | 99 | 0 | 2 | 0.666667 |
| 100 | 100.000% | 0.000% | 2359 | 0 | 0.023% | 0.035% | TRANSITION | 0.0000 | 100 | 0 | 1 | 0.666667 |
| 101 | 99.935% | 0.000% | 39856 | 0 | 0.001% | 0.002% | TRANSVERSION | 0.0000 | 101 | 0 | 2 | 0.333333 |
| 102 | 99.960% | 0.000% | 4979 | 0 | 0.002% | 0.006% | TRANSVERSION | 0.0000 | 102 | 0 | 2 | 0.333333 |
| 103 | 99.964% | 0.026% | 61348 | 16 | 0.029% | 0.010% | TRANSITION | 0.0261 | 103 | 0 | 2 | 0.333333 |
| 104 | 100.000% | 0.000% | 4066 | 0 | 0.000% | 0.000% | TRANSITION | 0.0000 | 104 | 0 | 1 | 0.333333 |
| 105 | 99.982% | 0.016% | 61873 | 10 | 0.028% | 0.009% | TRANSITION | 0.0162 | 105 | 0 | 2 | 0.333333 |
| 106 | 99.955% | 0.041% | 49019 | 20 | 0.032% | 0.008% | TRANSITION | 0.0408 | 106 | 0 | 1 | 0.333333 |
| 107 | 99.976% | 0.024% | 20716 | 5 | 0.038% | 0.017% | TRANSITION | 0.0241 | 107 | 0 | 2 | 0.333333 |
| 108 | 99.962% | 0.002% | 55268 | 1 | 0.002% | 0.002% | TRANSVERSION | 0.0018 | 108 | 0 | 2 | 0.333333 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 109 | 99.905% | 0.000% | 1051 | 0 | 0.066% | 0.135% | TRANSITION | 0.0000 | 109 | 0 | 2 | 0.333333 |
| 110 | 99.965% | 0.002% | 45220 | 1 | 0.001% | 0.001% | TRANSVERSION | 0.0022 | 110 | 0 | 1 | 0.333333 |
| 111 | 99.975% | 0.001% | 75824 | 1 | 0.002% | 0.003% | TRANSVERSION | 0.0013 | 111 | 0 | 4 | 0.333333 |
| 112 | 99.885% | 0.000% | 20870 | 0 | 0.001% | 0.002% | TRANSVERSION | 0.0000 | 112 | 0 | 4 | 0.333333 |
| 113 | 99.971% | 0.000% | 31239 | 0 | 0.001% | 0.002% | TRANSVERSION | 0.0000 | 113 | 0 | 4 | 0.333333 |
| 114 | 99.955% | 0.002% | 64117 | 1 | 0.002% | 0.003% | TRANSVERSION | 0.0016 | 114 | 0 | 4 | 0.333333 |
| 115 | 99.956% | 0.000% | 22915 | 0 | 0.000% | 0.001% | TRANSVERSION | 0.0000 | 115 | 0 | 4 | 0.333333 |
| 116 | 99.984% | 0.001% | 76682 | 1 | 0.001% | 0.001% | TRANSVERSION | 0.0013 | 116 | 0 | 4 | 0.333333 |
| 117 | 99.977% | 0.000% | 60030 | 0 | 0.001% | 0.001% | TRANSVERSION | 0.0000 | 117 | 0 | 2 | 0.666667 |
| 118 | 99.888% | 0.102% | 21494 | 22 | 0.038% | 0.011% | TRANSITION | 0.1024 | 118 | 1 | 1 | 0.666667 |
| 119 | 99.869% | 0.080% | 41218 | 33 | 0.001% | 0.001% | TRANSVERSION | 0.0801 | 119 | 1 | 1 | 0.666667 |
| 120 | 99.952% | 0.016% | 25196 | 4 | 0.003% | 0.004% | TRANSVERSION | 0.0159 | 120 | 0 | 4 | 0.666667 |
| 121 | 99.829% | 0.140% | 35666 | 50 | 0.001% | 0.003% | TRANSVERSION | 0.1402 | 121 | 1 | 4 | 0.666667 |
| 122 | 99.956% | 0.019% | 43161 | 8 | 0.001% | 0.001% | TRANSVERSION | 0.0185 | 122 | 1 | 4 | 0.666667 |
| 123 | 99.917% | 0.034% | 44468 | 15 | 0.002% | 0.002% | TRANSVERSION | 0.0337 | 123 | 1 | 4 | 0.666667 |
| 124 | 100.000% | 0.000% | 1605 | 0 | 0.001% | 0.005% | TRANSVERSION | 0.0000 | 124 | 0 | 4 | 0.666667 |
| 125 | 99.982% | 0.000% | 22756 | 0 | 0.001% | 0.002% | TRANSVERSION | 0.0000 | 125 | 0 | 4 | 0.333333 |
| 126 | 99.884% | 0.000% | 859 | 0 | 0.000% | 0.000% | TRANSVERSION | 0.0000 | 126 |  | 4 | 0.333333 |
| 127 | 99.974% | 0.000% | 62614 | 0 | 0.003% | 0.002% | TRANSVERSION | 0.0000 | 127 | 0 | 4 | 0.333333 |
| 128 | 99.963% | 0.000% | 42874 | 0 | 0.001% | 0.002% | TRANSVERSION | 0.0000 | 128 | 0 | 4 | 0.333333 |
| 129 | 100.000% | 0.000% | 941 | 0 | 0.007% | 0.026% | TRANSVERSION | 0.0000 | 129 |  | 4 | 0.333333 |
| 130 | 99.953% | 0.045% | 44915 | 20 | 0.043% | 0.009% | TRANSITION | 0.0445 | 130 | 0 | 4 | 0.333333 |
| 131 | 99.980% | 0.000% | 4893 | 0 | 0.006% | 0.005% | TRANSVERSION | 0.0000 | 131 | 0 | 4 | 0.333333 |
| 132 | 99.974% | 0.002% | 53432 | 1 | 0.001% | 0.001% | TRANSVERSION | 0.0019 | 132 | 0 | 4 | 0.333333 |
| 133 | 99.959% | 0.031% | 9799 | 3 | 0.033% | 0.015% | TRANSITION | 0.0306 | 133 | 0 | 4 | 0.333333 |
| 134 | 100.000% | 0.000% | 1721 | 0 | 0.002% | 0.003% | TRANSVERSION | 0.0000 | 134 | 0 | 4 | 0.333333 |
| 135 | 99.980% | 0.000% | 5048 | 0 | 0.004% | 0.008% | TRANSVERSION | 0.0000 | 135 | 0 | 4 | 0.333333 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 136 | 99.528% | 0.442% | 70369 | 311 | 0.002% | 0.002% | TRANSVERSION | 0.4420 | 136 | 1 | 1 | 1 |
| 137 | 99.649% | 0.339% | 23921 | 81 | 0.001% | 0.002% | TRANSVERSION | 0.3386 | 137 | 1 | 1 | 1 |
| 138 | 99.813% | 0.150% | 84682 | 127 | 0.002% | 0.002% | TRANSVERSION | 0.1500 | 138 | 1 | 1 | 1 |
| 139 | 99.926% | 0.067% | 54063 | 36 | 0.025% | 0.011% | TRANSITION | 0.0666 | 139 | 0 | 2 | 0.5 |
| 140 | 99.686% | 0.283% | 63649 | 180 | 0.002% | 0.001% | TRANSVERSION | 0.2828 | 140 | 1 | 4 | 1 |
| 141 | 99.726% | 0.231% | 30270 | 70 | 0.001% | 0.002% | TRANSVERSION | 0.2313 | 141 | 1 | 4 | 1 |
| 142 | 99.714% | 0.246% | 74474 | 183 | 0.002% | 0.003% | TRANSVERSION | 0.2457 | 142 | 1 | 4 | 1 |
| 143 | 99.604% | 0.334% | 40375 | 135 | 0.005% | 0.003% | TRANSVERSION | 0.3344 | 143 | 1 | 4 | 1 |
| 144 | 99.965% | 0.010% | 40343 | 4 | 0.001% | 0.003% | TRANSVERSION | 0.0099 | 144 | 0 | 4 | 0.25 |
| 145 | 99.958% | 0.005% | 82361 | 4 | 0.002% | 0.001% | TRANSVERSION | 0.0049 | 145 | 0 | 4 | 0.25 |
| 146 | 99.844% | 0.138% | 33236 | 46 | 0.003% | 0.003% | TRANSVERSION | 0.1384 | 146 | 1 | 4 | 0.5 |
| 147 | 99.915% | 0.064% | 14139 | 9 | 0.005% | 0.006% | TRANSVERSION | 0.0637 | 147 | 1 | 4 | 0.25 |
| 148 | 99.880% | 0.120% | 831 | 1 | 0.008% | 0.030% | TRANSVERSION | 0.1203 | 148 |  | 4 | 0.25 |
| 149 | 99.965% | 0.012% | 51042 | 6 | 0.001% | 0.001% | TRANSVERSION | 0.0118 | 149 | 1 | 4 | 0.5 |
| 150 | 99.963% | 0.007% | 29354 | 2 | 0.003% | 0.004% | TRANSVERSION | 0.0068 | 150 | 0 | 4 | 0.25 |
| 151 | 99.774% | 0.201% | 3975 | 8 | 0.008% | 0.022% | TRANSVERSION | 0.2013 | 151 | 1 | 3 | 0.25 |
| 152 | 99.923% | 0.054% | 64692 | 35 | 0.002% | 0.002% | TRANSVERSION | 0.0541 | 152 | 1 | 4 | 0.25 |
| 153 | 99.948% | 0.014% | 49582 | 7 | 0.002% | 0.002% | TRANSVERSION | 0.0141 | 153 | 0 | 4 | 0.25 |
| 154 | 99.887% | 0.109% | 53989 | 59 | 0.020% | 0.007% | TRANSITION | 0.1093 | 154 | 1 | 1 | 1 |
| 155 | 99.960% | 0.003% | 32779 | 1 | 0.002% | 0.003% | TRANSVERSION | 0.0031 | 155 | 0 | 1 | 0.142857 |
| 156 | 99.926% | 0.069% | 87068 | 60 | 0.028% | 0.009% | TRANSITION | 0.0689 | 156 | 1 | 4 | 1 |
| 157 | 99.908% | 0.063% | 49063 | 31 | 0.006% | 0.003% | TRANSVERSION | 0.0632 | 157 | 1 | 4 | 1 |
| 158 | 99.903% | 0.061% | 8248 | 5 | 0.001% | 0.004% | TRANSVERSION | 0.0606 | 158 | 1 | 4 | 1 |
| 159 | 99.953% | 0.032% | 68302 | 22 | 0.005% | 0.002% | TRANSVERSION | 0.0322 | 159 | 1 | 4 | 1 |
| 160 | 99.906% | 0.066% | 28751 | 19 | 0.003% | 0.004% | TRANSVERSION | 0.0661 | 160 | 1 | 4 | 1 |
| 161 | 99.938% | 0.062% | 25870 | 16 | 0.027% | 0.012% | TRANSITION | 0.0618 | 161 | 0 | 4 | 1 |
| 162 | 99.897% | 0.097% | 55471 | 54 | 0.045% | 0.014% | TRANSITION | 0.0973 | 162 | 0 | 4 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 163 | 99.958% | 0.038% | 47354 | 18 | 0.028% | 0.011% | TRANSITION | 0.0380 | 163 | 0 | 4 | 1 |
| 164 | 99.936% | 0.056% | 37608 | 21 | 0.044% | 0.017% | TRANSITION | 0.0558 | 164 | 0 | 4 | 0.142857 |
| 165 | 99.970% | 0.029% | 66173 | 19 | 0.034% | 0.011% | TRANSITION | 0.0287 | 165 | 0 | 4 | 0.142857 |
| 166 | 99.968% | 0.029% | 78312 | 23 | 0.027% | 0.008% | TRANSITION | 0.0294 | 166 | 0 | 4 | 0.142857 |
| 167 | 99.950% | 0.047% | 32060 | 15 | 0.036% | 0.014% | TRANSITION | 0.0468 | 167 | 0 | 4 | 0.142857 |
| 168 | 99.985% | 0.004% | 46212 | 2 | 0.011% | 0.007% | TRANSITION | 0.0043 | 168 | 0 | 4 | 0.142857 |
| 169 | 99.976% | 0.000% | 8252 | 0 | 0.000% | 0.000% | TRANSVERSION | 0.0000 | 169 | 0 | 4 | 0.142857 |
| 170 | 99.971% | 0.000% | 37813 | 0 | 0.001% | 0.001% | TRANSVERSION | 0.0000 | 170 | 0 | 4 | 0.142857 |
| 171 | 99.974% | 0.003% | 77091 | 2 | 0.004% | 0.002% | TRANSVERSION | 0.0026 | 171 | 0 | 4 | 0.142857 |
| 172 | 99.942% | 0.051% | 46949 | 24 | 0.028% | 0.009% | TRANSITION | 0.0511 | 172 | 0 | 4 | 0.142857 |
| 173 | 98.324% | 1.651% | 8176 | 135 | 0.002% | 0.007% | TRANSVERSION | 1.6512 | 173 | 1 | 1 | 1 |
| 174 | 99.976% | 0.024% | 12381 | 3 | 0.028% | 0.017% | TRANSITION | 0.0242 | 174 | 0 | 2 | 0.2 |
| 175 | 99.673% | 0.295% | 58380 | 172 | 0.003% | 0.002% | TRANSVERSION | 0.2946 | 175 | 1 | 4 | 1 |
| 176 | 99.545% | 0.408% | 48968 | 200 | 0.006% | 0.003% | TRANSVERSION | 0.4084 | 176 | 1 | 4 | 1 |
| 177 | 98.926% | 1.074% | 3073 | 33 | 0.002% | 0.008% | TRANSVERSION | 1.0739 | 177 | 1 | 4 | 1 |
| 178 | 99.979% | 0.000% | 23718 | 0 | 0.000% | 0.001% | TRANSVERSION | 0.0000 | 178 | 0 | 4 | 0.2 |
| 179 | 99.916% | 0.075% | 59837 | 45 | 0.008% | 0.003% | TRANSVERSION | 0.0752 | 179 | 1 | 4 | 0.2 |
| 180 | 99.907% | 0.058% | 22506 | 13 | 0.003% | 0.003% | TRANSVERSION | 0.0578 | 180 | 1 | 4 | 0.2 |
| 181 | 99.979% | 0.000% | 23830 | 0 | 0.001% | 0.001% | TRANSVERSION | 0.0000 | 181 | 0 | 4 | 0.2 |
| 182 | 99.981% | 0.006% | 46406 | 3 | 0.010% | 0.003% | TRANSVERSION | 0.0065 | 182 | 0 | 4 | 0.2 |
| 183 | 99.970% | 0.000% | 36822 | 0 | 0.001% | 0.001% | TRANSVERSION | 0.0000 | 183 | 0 | 4 | 0.2 |
| 184 | 99.969% | 0.009% | 58499 | 5 | 0.005% | 0.003% | TRANSVERSION | 0.0085 | 184 | 0 | 4 | 0.2 |
| 185 | 99.988% | 0.003% | 32083 | 1 | 0.006% | 0.004% | TRANSVERSION | 0.0031 | 185 | 0 | 4 | 0.2 |
| 186 | 99.954% | 0.010% | 50217 | 5 | 0.003% | 0.002% | TRANSVERSION | 0.0100 | 186 | 0 | 4 | 0.2 |
| 187 | 99.555% | 0.426% | 57577 | 245 | 0.004% | 0.003% | TRANSVERSION | 0.4255 | 187 | 1 | 4 | 0.6 |
| 188 | 99.667% | 0.330% | 62131 | 205 | 0.007% | 0.002% | TRANSVERSION | 0.3300 | 188 | 1 | 4 | 0.6 |
| 189 | 99.199% | 0.758% | 61781 | 468 | 0.001% | 0.002% | TRANSVERSION | 0.7575 | 189 | 1 | 4 | 0.6 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 190 | 99.548% | 0.399% | 55943 | 223 | 0.002% | 0.001% | TRANSVERSION | 0.3986 | 190 | 1 | 4 | 0.6 |
| 191 | 100.000% | 0.000% | 149 | 0 | 0.000% | 0.000% | TRANSVERSION | 0.0000 | 191 |  | 4 | 0.4 |
| 192 | 100.000% | 0.000% | 2 | 0 | 0.000% | 0.000% | TRANSVERSION | 0.0000 | 192 | 1 | 1 | 1 |
| 193 | 99.040% | 0.924% | 5627 | 52 | 0.002% | 0.006% | TRANSVERSION | 0.9241 | 193 | 1 | 4 | 0.75 |
| 194 | 99.473% | 0.496% | 3226 | 16 | 0.001% | 0.005% | TRANSVERSION | 0.4960 | 194 | 1 | 4 | 1 |
| 195 | 99.339% | 0.638% | 59757 | 381 | 0.003% | 0.002% | TRANSVERSION | 0.6376 | 195 | 1 | 4 | 0.75 |
| 196 | 99.847% | 0.130% | 43880 | 57 | 0.001% | 0.002% | TRANSVERSION | 0.1299 | 196 | 1 | 4 | 0.75 |
| 197 | 99.311% | 0.663% | 30631 | 203 | 0.002% | 0.002% | TRANSVERSION | 0.6627 | 197 | 1 | 4 | 0.75 |
| 198 | 99.181% | 0.813% | 61660 | 501 | 0.000% | 0.000% | TRANSVERSION | 0.8125 | 198 | 1 | 4 | 0.75 |
| 199 | 100.000% | 0.000% | 550 | 0 | 0.012% | 0.036% | TRANSVERSION | 0.0000 | 199 |  | 4 | 0.25 |
| 200 | 99.950% | 0.029% | 33957 | 10 | 0.002% | 0.003% | TRANSVERSION | 0.0294 | 200 | 1 | 4 | 0.25 |
| 201 | 99.909% | 0.091% | 56197 | 51 | 0.023% | 0.009% | TRANSITION | 0.0908 | 201 | 1 | 4 | 0.25 |
| 202 | 99.959% | 0.006% | 17008 | 1 | 0.003% | 0.005% | TRANSVERSION | 0.0059 | 202 | 0 | 4 | 0.25 |
| 203 | 99.955% | 0.041% | 26680 | 11 | 0.003% | 0.003% | TRANSVERSION | 0.0412 | 203 | 1 | 4 | 0.25 |
| 204 | 81.308% | 0.061% | 53848 | 33 | 0.003% | 0.007% | TRANSVERSION | 0.0613 | 204 | 1 | 4 | 0.25 |
| 205 | 99.973% | 0.001% | 72785 | 1 | 0.002% | 0.001% | TRANSVERSION | 0.0014 | 205 | 0 | 4 | 0.25 |
| 206 | 99.437% | 0.535% | 39229 | 210 | 0.003% | 0.002% | TRANSVERSION | 0.5353 | 206 | 1 | 4 | 0.75 |
| 207 | 99.880% | 0.051% | 52604 | 27 | 0.003% | 0.002% | TRANSVERSION | 0.0513 | 207 | 1 | 4 | 0.25 |
| 208 | 99.873% | 0.095% | 57676 | 55 | 0.001% | 0.001% | TRANSVERSION | 0.0954 | 208 | 1 | 4 | 0.25 |
| 209 | 99.732% | 0.218% | 63348 | 138 | 0.001% | 0.001% | TRANSVERSION | 0.2178 | 209 | 1 | 4 | 1 |
| 210 | 99.978% | 0.016% | 82128 | 13 | 0.007% | 0.003% | TRANSITION | 0.0158 | 210 | 0 | 1 | 1 |
| 211 | 99.991% | 0.000% | 23429 | 0 | 0.002% | 0.004% | TRANSVERSION | 0.0000 | 211 | 0 | 2 | 1 |
| 212 | 99.930% | 0.019% | 73340 | 14 | 0.003% | 0.003% | TRANSVERSION | 0.0191 | 212 | 0 | 1 | 0.666667 |
| 213 | 99.956% | 0.005% | 59282 | 3 | 0.004% | 0.003% | TRANSVERSION | 0.0051 | 213 | 0 | 2 | 0.666667 |
| 214 | 99.962% | 0.034% | 92382 | 31 | 0.037% | 0.009% | TRANSITION | 0.0336 | 214 | 0 | 2 | 0.333333 |
| 215 | 99.927% | 0.011% | 17895 | 2 | 0.001% | 0.001% | TRANSVERSION | 0.0112 | 215 | 1 | 4 | 1 |
| 216 | 99.963% | 0.011% | 45876 | 5 | 0.001% | 0.001% | TRANSVERSION | 0.0109 | 216 | 1 | 4 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 217 | 99.963% | 0.008% | 24021 | 2 | 0.001% | 0.002% | TRANSVERSION | 0.0083 | 217 | 0 | 4 | 1 |
| 218 | 99.972% | 0.003% | 32009 | 1 | 0.004% | 0.004% | TRANSVERSION | 0.0031 | 218 | 0 | 4 | 0.666667 |
| 219 | 99.961% | 0.000% | 59620 | 0 | 0.001% | 0.001% | TRANSVERSION | 0.0000 | 219 | 0 | 4 | 0.333333 |
| 220 | 99.939% | 0.000% | 4882 | 0 | 0.001% | 0.003% | TRANSVERSION | 0.0000 | 220 | 0 | 4 | 0.333333 |
| 221 | 99.978% | 0.001% | 131526 | 1 | 0.001% | 0.001% | TRANSVERSION | 0.0008 | 221 | 0 | 3 | 0.333333 |
| 222 | 99.974% | 0.003% | 37763 | 1 | 0.001% | 0.002% | TRANSVERSION | 0.0026 | 222 | 0 | 4 | 0.666667 |
| 223 | 99.953% | 0.000% | 33961 | 0 | 0.001% | 0.001% | TRANSVERSION | 0.0000 | 223 | 0 | 4 | 0.666667 |
| 224 | 99.985% | 0.000% | 26187 | 0 | 0.005% | 0.004% | TRANSVERSION | 0.0000 | 224 | 0 | 4 | 0.666667 |
| 225 | 99.955% | 0.000% | 22347 | 0 | 0.000% | 0.001% | TRANSVERSION | 0.0000 | 225 | 0 | 4 | 0.333333 |
| 226 | 99.980% | 0.000% | 39791 | 0 | 0.001% | 0.001% | TRANSVERSION | 0.0000 | 226 | 0 | 4 | 0.333333 |
| 227 | 99.969% | 0.000% | 65241 | 0 | 0.002% | 0.005% | TRANSVERSION | 0.0000 | 227 | 0 | 1 | 0.6 |
| 228 | 99.918% | 0.000% | 29121 | 0 | 0.007% | 0.005% | TRANSVERSION | 0.0000 | 228 | 0 | 1 | 0.6 |
| 229 | 99.956% | 0.030% | 50130 | 15 | 0.027% | 0.009% | TRANSITION | 0.0299 | 229 | 0 | 1 | 0.6 |
| 230 | 99.974% | 0.002% | 42283 | 1 | 0.002% | 0.002% | TRANSVERSION | 0.0024 | 230 | 0 | 2 | 0.6 |
| 231 | 99.966% | 0.001% | 75805 | 1 | 0.001% | 0.001% | TRANSVERSION | 0.0013 | 231 | 0 | 1 | 0.6 |
| 232 | 99.993% | 0.002% | 45188 | 1 | 0.006% | 0.004% | TRANSVERSION | 0.0022 | 232 | 0 | 1 | 0.6 |
| 233 | 99.971% | 0.001% | 101704 | 1 | 0.002% | 0.001% | TRANSVERSION | 0.0010 | 233 | 0 | 4 | 0.6 |
| 234 | 99.989% | 0.006% | 79007 | 5 | 0.005% | 0.002% | TRANSVERSION | 0.0063 | 234 | 0 | 4 | 0.6 |
| 235 | 99.945% | 0.000% | 12695 | 0 | 0.001% | 0.003% | TRANSVERSION | 0.0000 | 235 | 0 | 4 | 0.6 |
| 236 | 99.979% | 0.003% | 87332 | 3 | 0.005% | 0.002% | TRANSVERSION | 0.0034 | 236 | 0 | 4 | 0.6 |
| 237 | 99.926% | 0.000% | 10781 | 0 | 0.004% | 0.006% | TRANSVERSION | 0.0000 | 237 | 0 | 4 | 0.6 |
| 238 | 99.954% | 0.002% | 48304 | 1 | 0.002% | 0.005% | TRANSVERSION | 0.0021 | 238 | 0 | 4 | 0.2 |
| 239 | 99.962% | 0.035% | 52014 | 18 | 0.031% | 0.010% | TRANSITION | 0.0346 | 239 | 0 | 4 | 0.2 |
| 240 | 99.975% | 0.023% | 52000 | 12 | 0.028% | 0.010% | TRANSITION | 0.0231 | 240 | 0 | 4 | 0.2 |
| 241 | 99.960% | 0.034% | 84689 | 29 | 0.031% | 0.010% | TRANSITION | 0.0342 | 241 | 0 | 4 | 0.4 |
| 242 | 99.964% | 0.005% | 54973 | 3 | 0.004% | 0.003% | TRANSVERSION | 0.0055 | 242 | 0 | 4 | 0.4 |
| 243 | 99.963% | 0.000% | 13642 | 0 | 0.001% | 0.003% | TRANSVERSION | 0.0000 | 243 | 0 | 4 | 0.4 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 244 | 99.958% | 0.002% | 98269 | 2 | 0.003% | 0.002% | TRANSVERSION | 0.0020 | 244 | 0 | 4 | 0.4 |
| 245 | 99.966% | 0.003% | 93289 | 3 | 0.002% | 0.001% | TRANSVERSION | 0.0032 | 245 | 0 | 4 | 0.4 |
| 246 | 99.975% | 0.000% | 56951 | 0 | 0.004% | 0.003% | TRANSVERSION | 0.0000 | 246 | 0 | 1 | 1 |
| 247 | 99.958% | 0.035% | 28357 | 10 | 0.038% | 0.016% | TRANSITION | 0.0353 | 247 | 0 | 1 | 1 |
| 248 | 100.000% | 0.000% | 787 | 0 | 0.087% | 0.160% | TRANSITION | 0.0000 | 248 | | 2 | 0.25 |
| 249 | NaN | NaN | 0 | NaN | 0.027% | 0.003% | TRANSITION | #VALUE! | 249 | | 2 | 0.25 |
| 250 | 99.963% | 0.004% | 72134 | 3 | 0.006% | 0.003% | TRANSVERSION | 0.0042 | 250 | 0 | 4 | 0.25 |
| 251 | 99.967% | 0.001% | 71880 | 1 | 0.001% | 0.001% | TRANSVERSION | 0.0014 | 251 | 0 | 4 | 1 |
| 252 | 99.979% | 0.000% | 34082 | 0 | 0.000% | 0.001% | TRANSVERSION | 0.0000 | 252 | 0 | 4 | 1 |
| 253 | 99.970% | 0.003% | 30289 | 1 | 0.001% | 0.002% | TRANSVERSION | 0.0033 | 253 | 0 | 3 | 0.25 |
| 254 | 99.982% | 0.000% | 77312 | 0 | 0.001% | 0.001% | TRANSVERSION | 0.0000 | 254 | 0 | 4 | 0.25 |
| 255 | 99.986% | 0.000% | 62479 | 0 | 0.001% | 0.002% | TRANSVERSION | 0.0000 | 255 | 0 | 4 | 0.25 |
| 256 | 99.981% | 0.002% | 64251 | 1 | 0.002% | 0.001% | TRANSVERSION | 0.0016 | 256 | 0 | 4 | 0.25 |
| 257 | 99.949% | 0.000% | 80603 | 0 | 0.001% | 0.002% | TRANSVERSION | 0.0000 | 257 | 0 | 4 | 0.25 |
| 258 | 99.961% | 0.000% | 43541 | 0 | 0.002% | 0.002% | TRANSVERSION | 0.0000 | 258 | 0 | 4 | 0.5 |
| 259 | 99.914% | 0.003% | 76783 | 2 | 0.003% | 0.002% | TRANSVERSION | 0.0026 | 259 | 0 | 4 | 0.5 |
| 260 | 99.962% | 0.000% | 18443 | 0 | 0.003% | 0.004% | TRANSVERSION | 0.0000 | 260 | 0 | 4 | 0.25 |
| 261 | 99.926% | 0.000% | 39036 | 0 | 0.004% | 0.003% | TRANSVERSION | 0.0000 | 261 | 0 | 4 | 0.25 |
| 262 | 99.970% | 0.002% | 101412 | 2 | 0.003% | 0.002% | TRANSVERSION | 0.0020 | 262 | 0 | 4 | 0.25 |
| 263 | 99.970% | 0.005% | 60021 | 3 | 0.005% | 0.003% | TRANSVERSION | 0.0050 | 263 | 0 | 4 | 0.25 |
| 264 | 99.963% | 0.003% | 64825 | 2 | 0.004% | 0.003% | TRANSVERSION | 0.0031 | 264 | 0 | 4 | 0.25 |
| 265 | 99.987% | 0.000% | 46646 | 0 | 0.000% | 0.001% | TRANSVERSION | 0.0000 | 265 | 0 | 4 | 0.25 |
| 266 | 97.253% | 2.723% | 29118 | 793 | 0.003% | 0.004% | TRANSVERSION | 2.7234 | 266 | 1 | 2 | 1 |
| 267 | 98.080% | 1.865% | 28748 | 536 | 0.005% | 0.004% | TRANSVERSION | 1.8645 | 267 | 1 | 1 | 1 |
| 268 | 96.963% | 3.037% | 5564 | 169 | 0.004% | 0.011% | TRANSVERSION | 3.0374 | 268 | 1 | 1 | 1 |
| 269 | 96.885% | 3.043% | 5553 | 169 | 0.002% | 0.008% | TRANSVERSION | 3.0434 | 269 | 1 | 2 | 1 |
| 270 | 99.073% | 0.916% | 80238 | 735 | 0.006% | 0.003% | TRANSVERSION | 0.9160 | 270 | 1 | 2 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 271 | 97.311% | 2.689% | 25919 | 697 | 0.044% | 0.018% | TRANSITION | 2.6891 | 271 | 1 | 2 | 1 |
| 272 | 98.909% | 1.078% | 29963 | 323 | 0.002% | 0.003% | TRANSVERSION | 1.0780 | 272 | 1 | 1 | 1 |
| 273 | 99.937% | 0.061% | 61931 | 38 | 0.030% | 0.009% | TRANSITION | 0.0614 | 273 | 0 | 1 | 0.333333 |
| 274 | 99.986% | 0.000% | 41743 | 0 | 0.004% | 0.003% | TRANSVERSION | 0.0000 | 274 | 0 | 1 | 0.333333 |
| 275 | 99.916% | 0.035% | 14256 | 5 | 0.002% | 0.003% | TRANSVERSION | 0.0351 | 275 | 1 | 2 | 0.666667 |
| 276 | 99.983% | 0.017% | 5783 | 1 | 0.002% | 0.006% | TRANSVERSION | 0.0173 | 276 | 0 | 2 | 0.666667 |
| 277 | 98.700% | 1.285% | 19923 | 256 | 0.001% | 0.002% | TRANSVERSION | 1.2849 | 277 | 1 | 3 | 1 |
| 278 | 98.933% | 1.036% | 44901 | 465 | 0.002% | 0.001% | TRANSVERSION | 1.0356 | 278 | 1 | 4 | 1 |
| 279 | 97.891% | 2.070% | 27640 | 572 | 0.002% | 0.002% | TRANSVERSION | 2.0695 | 279 | 1 | 4 | 1 |
| 280 | 98.262% | 1.713% | 44127 | 756 | 0.002% | 0.002% | TRANSVERSION | 1.7132 | 280 | 1 | 4 | 1 |
| 281 | 98.087% | 1.869% | 66818 | 1249 | 0.003% | 0.002% | TRANSVERSION | 1.8693 | 281 | 1 | 4 | 1 |
| 282 | 99.113% | 0.860% | 40483 | 348 | 0.007% | 0.004% | TRANSVERSION | 0.8596 | 282 | 1 | 4 | 1 |
| 283 | 99.487% | 0.478% | 42297 | 202 | 0.004% | 0.004% | TRANSVERSION | 0.4776 | 283 | 1 | 4 | 0.333333 |
| 284 | 99.949% | 0.028% | 68742 | 19 | 0.004% | 0.003% | TRANSVERSION | 0.0276 | 284 | 1 | 4 | 0.333333 |
| 285 | 98.546% | 1.423% | 3163 | 45 | 0.005% | 0.010% | TRANSVERSION | 1.4227 | 285 | 1 | 3 | 0.333333 |
| 286 | 99.595% | 0.362% | 91620 | 332 | 0.000% | 0.001% | TRANSVERSION | 0.3624 | 286 | 1 | 4 | 0.333333 |
| 287 | 99.759% | 0.241% | 1658 | 4 | 0.040% | 0.045% | TRANSITION | 0.2413 | 287 | 0 | 2 | 0.428571 |
| 288 | 99.168% | 0.823% | 33283 | 274 | 0.035% | 0.013% | TRANSITION | 0.8232 | 288 | 1 | 1 | 0.857143 |
| 289 | 99.915% | 0.081% | 80383 | 65 | 0.027% | 0.008% | TRANSITION | 0.0809 | 289 | 1 | 1 | 0.285714 |
| 290 | 99.284% | 0.693% | 60298 | 418 | 0.000% | 0.000% | TRANSVERSION | 0.6932 | 290 | 1 | 4 | 0.714286 |
| 291 | 99.625% | 0.349% | 67377 | 235 | 0.003% | 0.002% | TRANSVERSION | 0.3488 | 291 | 1 | 4 | 0.714286 |
| 292 | 98.816% | 1.164% | 76375 | 889 | 0.007% | 0.003% | TRANSVERSION | 1.1540 | 292 | 1 | 4 | 0.714286 |
| 293 | 94.860% | 5.064% | 3969 | 201 | 0.002% | 0.008% | TRANSVERSION | 5.0642 | 293 | 1 | 4 | 0.857143 |
| 294 | 99.130% | 0.843% | 71507 | 603 | 0.003% | 0.002% | TRANSVERSION | 0.8433 | 294 | 1 | 4 | 0.714286 |
| 295 | 99.943% | 0.020% | 80608 | 16 | 0.001% | 0.001% | TRANSVERSION | 0.0198 | 295 | 1 | 4 | 0.285714 |
| 296 | 99.925% | 0.044% | 61121 | 27 | 0.001% | 0.001% | TRANSVERSION | 0.0442 | 296 | 1 | 4 | 0.285714 |
| 297 | 99.432% | 0.526% | 93367 | 491 | 0.002% | 0.002% | TRANSVERSION | 0.5259 | 297 | 1 | 4 | 0.428571 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 298 | 99.513% | 0.457% | 83501 | 382 | 0.001% | 0.001% | TRANSVERSION | 0.4575 | 298 | 1 | 4 | 0.428571 |
| 299 | 99.654% | 0.296% | 2025 | 6 | 0.002% | 0.009% | TRANSVERSION | 0.2963 | 299 | 1 | 4 | 0.428571 |
| 300 | 99.919% | 0.041% | 80002 | 33 | 0.004% | 0.003% | TRANSVERSION | 0.0412 | 300 | 1 | 4 | 0.142857 |
| 301 | 99.975% | 0.001% | 67129 | 1 | 0.006% | 0.003% | TRANSVERSION | 0.0015 | 301 | 0 | 4 | 0.142857 |
| 302 | 99.984% | 0.000% | 30715 | 0 | 0.001% | 0.001% | TRANSVERSION | 0.0000 | 302 | 0 | 4 | 0.142857 |
| 303 | 99.973% | 0.000% | 25849 | 0 | 0.002% | 0.002% | TRANSVERSION | 0.0000 | 303 | 0 | 4 | 0.142857 |
| 304 | 99.971% | 0.001% | 83844 | 1 | 0.001% | 0.001% | TRANSVERSION | 0.0012 | 304 | 0 | 4 | 0.142857 |
| 305 | 99.990% | 0.003% | 31447 | 1 | 0.000% | 0.001% | TRANSVERSION | 0.0032 | 305 | 0 | 4 | 0.142857 |
| 306 | 99.947% | 0.052% | 88196 | 46 | 0.012% | 0.004% | TRANSITION | 0.0522 | 306 | 1 | 2 | 0.5 |
| 307 | 99.965% | 0.000% | 48607 | 0 | 0.002% | 0.002% | TRANSITION | 0.0000 | 307 | 0 | 2 | 0.5 |
| 308 | 99.955% | 0.042% | 59816 | 25 | 0.025% | 0.008% | TRANSITION | 0.0418 | 308 | 0 | 2 | 0.5 |
| 309 | 99.930% | 0.065% | 38307 | 25 | 0.048% | 0.012% | TRANSITION | 0.0653 | 309 | 0 | 2 | 0.5 |
| 310 | 99.967% | 0.000% | 33571 | 0 | 0.001% | 0.002% | TRANSITION | 0.0000 | 310 | 0 | 4 | 0.5 |
| 311 | 99.966% | 0.022% | 46446 | 10 | 0.014% | 0.006% | TRANSITION | 0.0215 | 311 | 0 | 4 | 0.5 |
| 312 | 99.980% | 0.013% | 55513 | 7 | 0.010% | 0.005% | TRANSVERSION | 0.0126 | 312 | 0 | 4 | 0.5 |
| 313 | 99.965% | 0.029% | 37441 | 11 | 0.023% | 0.008% | TRANSITION | 0.0294 | 313 | 0 | 4 | 0.5 |
| 314 | 99.979% | 0.000% | 47327 | 0 | 0.002% | 0.002% | TRANSVERSION | 0.0000 | 314 | 0 | 4 | 0.5 |
| 315 | 99.986% | 0.014% | 6960 | 1 | 0.015% | 0.011% | TRANSITION | 0.0144 | 315 | 0 | 4 | 0.5 |
| 316 | 99.922% | 0.047% | 72794 | 34 | 0.001% | 0.001% | TRANSVERSION | 0.0467 | 316 | 1 | 4 | 0.5 |
| 317 | 99.973% | 0.025% | 36619 | 9 | 0.027% | 0.009% | TRANSITION | 0.0246 | 317 | 0 | 4 | 0.5 |
| 318 | 99.909% | 0.088% | 66147 | 58 | 0.033% | 0.008% | TRANSITION | 0.0877 | 318 | 1 | 4 | 0.5 |
| 319 | 99.970% | 0.028% | 90771 | 25 | 0.023% | 0.005% | TRANSITION | 0.0275 | 319 | 0 | 4 | 0.5 |
| 320 | 99.962% | 0.027% | 47558 | 13 | 0.016% | 0.007% | TRANSITION | 0.0273 | 320 | 0 | 4 | 0.5 |
| 321 | 99.491% | 0.509% | 41425 | 211 | 0.041% | 0.018% | TRANSITION | 0.5094 | 321 | 1 | 2 | 0.75 |
| 322 | 99.768% | 0.205% | 74486 | 153 | 0.001% | 0.001% | TRANSVERSION | 0.2054 | 322 | 1 | 2 | 0.75 |
| 323 | 99.833% | 0.139% | 56941 | 79 | 0.001% | 0.002% | TRANSVERSION | 0.1387 | 323 | 1 | 2 | 0.75 |
| 324 | 99.831% | 0.169% | 72635 | 123 | 0.029% | 0.007% | TRANSITION | 0.1693 | 324 | 1 | 2 | 0.75 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 325 | 99.906% | 0.053% | 75808 | 40 | 0.003% | 0.003% | TRANSVERSION | 0.0528 | 325 | 1 | 2 | 0.625 |
| 326 | 99.851% | 0.124% | 40400 | 5 | 0.007% | 0.016% | TRANSVERSION | 0.1238 | 326 | 1 | 2 | 0.625 |
| 327 | 99.872% | 0.114% | 35895 | 41 | 0.000% | 0.001% | TRANSVERSION | 0.1142 | 327 | 1 | 4 | 0.75 |
| 328 | 99.925% | 0.046% | 28160 | 13 | 0.002% | 0.002% | TRANSVERSION | 0.0462 | 328 | 1 | 4 | 0.75 |
| 329 | 99.897% | 0.096% | 78027 | 75 | 0.003% | 0.002% | TRANSVERSION | 0.0961 | 329 | 1 | 4 | 0.75 |
| 330 | 99.733% | 0.241% | 83100 | 200 | 0.001% | 0.001% | TRANSVERSION | 0.2407 | 330 | 1 | 4 | 0.75 |
| 331 | 99.964% | 0.001% | 69110 | 1 | 0.004% | 0.005% | TRANSVERSION | 0.0014 | 331 | 0 | 4 | 0.125 |
| 332 | 99.994% | 0.002% | 81559 | 2 | 0.002% | 0.002% | TRANSVERSION | 0.0025 | 332 | 0 | 4 | 0.125 |
| 333 | 99.964% | 0.000% | 74652 | 0 | 0.001% | 0.001% | TRANSVERSION | 0.0000 | 333 | 0 | 4 | 0.125 |
| 334 | 99.940% | 0.017% | 93616 | 16 | 0.000% | 0.001% | TRANSVERSION | 0.0171 | 334 | 1 | 4 | 0.125 |
| 335 | 99.835% | 0.103% | 45536 | 47 | 0.008% | 0.004% | TRANSVERSION | 0.1032 | 335 | 1 | 4 | 0.625 |
| 336 | 99.925% | 0.040% | 34883 | 14 | 0.002% | 0.003% | TRANSVERSION | 0.0401 | 336 | 1 | 4 | 0.125 |
| 337 | 99.967% | 0.005% | 82249 | 4 | 0.003% | 0.002% | TRANSVERSION | 0.0049 | 337 | 0 | 4 | 0.125 |
| 338 | 99.980% | 0.000% | 64365 | 0 | 0.000% | 0.000% | TRANSVERSION | 0.0000 | 338 | 0 | 4 | 0.125 |
| 339 | 99.963% | 0.003% | 97626 | 3 | 0.001% | 0.001% | TRANSVERSION | 0.0031 | 339 | 0 | 4 | 0.125 |
| 340 | 99.560% | 0.418% | 68473 | 286 | 0.003% | 0.003% | TRANSVERSION | 0.4177 | 340 | 1 | 1 | 1 |
| 341 | 99.475% | 0.494% | 9522 | 47 | 0.006% | 0.007% | TRANSVERSION | 0.4936 | 341 | 1 | 2 | 1 |
| 342 | 99.837% | 0.134% | 14147 | 19 | 0.000% | 0.002% | TRANSVERSION | 0.1343 | 342 | 1 | 2 | 1 |
| 343 | 99.913% | 0.057% | 49157 | 28 | 0.004% | 0.003% | TRANSVERSION | 0.0570 | 343 | 1 | 2 | 0.75 |
| 344 | 99.752% | 0.218% | 83034 | 181 | 0.000% | 0.001% | TRANSVERSION | 0.2180 | 344 | 1 | 2 | 1 |
| 345 | 99.734% | 0.262% | 63459 | 166 | 0.029% | 0.009% | TRANSITION | 0.2616 | 345 | 1 | 2 | 1 |
| 346 | 99.713% | 0.287% | 7653 | 22 | 0.071% | 0.039% | TRANSITION | 0.2875 | 346 | 1 | 2 | 0.25 |
| 347 | 99.600% | 0.381% | 72757 | 277 | 0.002% | 0.002% | TRANSITION | 0.3807 | 347 | 1 | 2 | 1 |
| 348 | 99.686% | 0.272% | 6998 | 19 | 0.002% | 0.007% | TRANSVERSION | 0.2715 | 348 | 1 | 4 | 0.75 |
| 349 | 99.900% | 0.095% | 60776 | 58 | 0.028% | 0.009% | TRANSITION | 0.0954 | 349 | 1 | 4 | 0.75 |
| 350 | 99.685% | 0.286% | 82909 | 237 | 0.003% | 0.002% | TRANSVERSION | 0.2859 | 350 | 1 | 4 | 1 |
| 351 | 99.681% | 0.260% | 68893 | 179 | 0.002% | 0.002% | TRANSVERSION | 0.2598 | 351 | 1 | 4 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 352 | 99.709% | 0.253% | 71913 | 182 | 0.004% | 0.002% | TRANSVERSION | 0.2531 | 352 | 1 | 4 | 1 |
| 353 | 99.964% | 0.000% | 16490 | 0 | 0.003% | 0.004% | TRANSVERSION | 0.0000 | 353 | 0 | 4 | 0.25 |
| 354 | 99.970% | 0.003% | 65904 | 2 | 0.002% | 0.002% | TRANSVERSION | 0.0030 | 354 | 0 | 4 | 0.25 |
| 355 | 99.985% | 0.000% | 61843 | 0 | 0.001% | 0.001% | TRANSVERSION | 0.0000 | 355 | 0 | 4 | 0.25 |
| 356 | 99.953% | 0.028% | 46350 | 13 | 0.002% | 0.002% | TRANSVERSION | 0.0280 | 356 | 1 | 4 | 0.25 |
| 357 | 99.929% | 0.027% | 40789 | 11 | 0.001% | 0.001% | TRANSVERSION | 0.0270 | 357 | 1 | 4 | 0.25 |
| 358 | 99.959% | 0.039% | 114279 | 45 | 0.023% | 0.006% | TRANSITION | 0.0394 | 358 | 0 | 4 | 0.25 |
| 359 | 99.799% | 0.201% | 26914 | 54 | 0.015% | 0.008% | TRANSITION | 0.2006 | 359 | 1 | 1 | 1 |
| 360 | 99.645% | 0.327% | 57140 | 187 | 0.001% | 0.002% | TRANSVERSION | 0.3273 | 360 | 1 | 2 | 1 |
| 361 | 99.772% | 0.200% | 69657 | 139 | 0.004% | 0.010% | TRANSVERSION | 0.1996 | 361 | 1 | 4 | 1 |
| 362 | 99.668% | 0.295% | 80791 | 238 | 0.003% | 0.002% | TRANSVERSION | 0.2946 | 362 | 1 | 4 | 1 |
| 363 | 99.790% | 0.176% | 78486 | 138 | 0.002% | 0.001% | TRANSVERSION | 0.1758 | 363 | 1 | 4 | 1 |
| 364 | 99.720% | 0.272% | 91402 | 249 | 0.045% | 0.024% | TRANSITION | 0.2724 | 364 | 1 | 4 | 1 |
| 365 | 99.705% | 0.260% | 59290 | 154 | 0.004% | 0.002% | TRANSVERSION | 0.2597 | 365 | 1 | 4 | 1 |
| 366 | 99.680% | 0.296% | 4060 | 12 | 0.005% | 0.012% | TRANSVERSION | 0.2956 | 366 | 1 | 4 | 1 |
| 367 | 99.854% | 0.146% | 15736 | 23 | 0.034% | 0.018% | TRANSITION | 0.1462 | 367 | 1 | 4 | 1 |
| 368 | 99.641% | 0.321% | 71286 | 229 | 0.001% | 0.001% | TRANSVERSION | 0.3212 | 368 | 1 | 4 | 1 |
| 369 | 99.822% | 0.164% | 29256 | 48 | 0.004% | 0.004% | TRANSVERSION | 0.1641 | 369 | 1 | 4 | 1 |
| 370 | 99.864% | 0.114% | 61237 | 70 | 0.001% | 0.001% | TRANSVERSION | 0.1143 | 370 | 1 | 4 | 1 |
| 371 | 99.862% | 0.131% | 94027 | 123 | 0.041% | 0.009% | TRANSITION | 0.1308 | 371 | 1 | 4 | 1 |
| 372 | 99.771% | 0.207% | 9157 | 19 | 0.047% | 0.031% | TRANSITION | 0.2075 | 372 | 1 | 4 | 1 |
| 373 | 99.938% | 0.030% | 46460 | 14 | 0.004% | 0.004% | TRANSITION | 0.0301 | 373 | 1 | 4 | 1 |
| 374 | 99.944% | 0.050% | 50145 | 25 | 0.024% | 0.008% | TRANSITION | 0.0499 | 374 | 0 | 4 | 0.5 |
| 375 | 99.909% | 0.052% | 59049 | 31 | 0.003% | 0.003% | TRANSVERSION | 0.0525 | 375 | 1 | 4 | 0.5 |
| 376 | 99.790% | 0.210% | 28119 | 59 | 0.027% | 0.010% | TRANSITION | 0.2098 | 376 | 1 | 4 | 0.5 |
| 377 | 99.951% | 0.000% | 6162 | 0 | 0.001% | 0.003% | TRANSITION | 0.0000 | 377 | 0 | 2 | 0.75 |
| 378 | 99.959% | 0.000% | 53167 | 0 | 0.003% | 0.003% | TRANSVERSION | 0.0000 | 378 | 0 | 1 | 0.75 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 379 | 99.945% | 0.002% | 58130 | 1 | 0.003% | 0.002% | TRANSVERSION | 0.0017 | 379 | 0 | 1 | 0.75 |
| 380 | 99.982% | 0.006% | 16280 | 1 | 0.003% | 0.005% | TRANSVERSION | 0.0061 | 380 | 0 | 1 | 0.75 |
| 381 | 99.985% | 0.003% | 58261 | 2 | 0.003% | 0.003% | TRANSVERSION | 0.0034 | 381 | 0 | 1 | 0.75 |
| 382 | 99.956% | 0.044% | 24768 | 11 | 0.037% | 0.017% | TRANSITION | 0.0444 | 382 | 0 | 2 | 0.75 |
| 383 | 99.956% | 0.005% | 59448 | 3 | 0.001% | 0.002% | TRANSVERSION | 0.0050 | 383 | 0 | 2 | 0.75 |
| 384 | 99.979% | 0.000% | 37507 | 0 | 0.001% | 0.002% | TRANSVERSION | 0.0000 | 384 | 0 | 2 | 0.75 |
| 385 | 99.924% | 0.011% | 27778 | 3 | 0.007% | 0.004% | TRANSVERSION | 0.0108 | 385 | 0 | 2 | 0.75 |
| 386 | 99.979% | 0.002% | 52331 | 1 | 0.002% | 0.003% | TRANSVERSION | 0.0019 | 386 | 0 | 4 | 0.75 |
| 387 | 99.960% | 0.000% | 65149 | 0 | 0.001% | 0.001% | TRANSVERSION | 0.0000 | 387 | 0 | 4 | 0.75 |
| 388 | 99.940% | 0.053% | 43191 | 23 | 0.003% | 0.002% | TRANSVERSION | 0.0533 | 388 | 1 | 4 | 0.75 |
| 389 | 99.964% | 0.000% | 22501 | 0 | 0.004% | 0.004% | TRANSVERSION | 0.0000 | 389 | 0 | 4 | 0.5 |
| 390 | 99.951% | 0.005% | 42840 | 2 | 0.003% | 0.003% | TRANSVERSION | 0.0047 | 390 | 0 | 4 | 0.25 |
| 391 | 99.976% | 0.007% | 41272 | 3 | 0.002% | 0.003% | TRANSVERSION | 0.0073 | 391 | 0 | 4 | 0.25 |
| 392 | 99.969% | 0.000% | 45400 | 0 | 0.001% | 0.002% | TRANSVERSION | 0.0000 | 392 | 0 | 4 | 0.75 |
| 393 | 99.982% | 0.000% | 49402 | 0 | 0.003% | 0.002% | TRANSVERSION | 0.0000 | 393 | 0 | 4 | 0.75 |
| 394 | 99.956% | 0.008% | 36246 | 3 | 0.006% | 0.010% | TRANSVERSION | 0.0083 | 394 | 0 | 4 | 0.75 |
| 395 | 99.978% | 0.000% | 22500 | 0 | 0.003% | 0.004% | TRANSVERSION | 0.0000 | 395 | 0 | 4 | 0.5 |
| 396 | 97.547% | 2.449% | 23933 | 586 | 0.030% | 0.011% | TRANSITION | 2.4485 | 396 | 1 | 1 | 0.875 |
| 397 | 96.750% | 3.246% | 24859 | 807 | 0.018% | 0.010% | TRANSITION | 3.2463 | 397 | 1 | 1 | 0.875 |
| 398 | 97.921% | 2.076% | 39401 | 818 | 0.024% | 0.009% | TRANSITION | 2.0761 | 398 | 1 | 2 | 0.75 |
| 399 | 98.570% | 1.419% | 36794 | 522 | 0.040% | 0.013% | TRANSITION | 1.4187 | 399 | 1 | 2 | 0.75 |
| 400 | 98.892% | 1.049% | 51880 | 544 | 0.002% | 0.002% | TRANSVERSION | 1.0486 | 400 | 1 | 2 | 0.625 |
| 401 | 95.243% | 4.758% | 10804 | 514 | 0.062% | 0.031% | TRANSITION | 4.7575 | 401 | 1 | 4 | 0.75 |
| 402 | 98.289% | 1.694% | 29400 | 498 | 0.002% | 0.003% | TRANSVERSION | 1.6939 | 402 | 1 | 4 | 0.625 |
| 403 | 98.933% | 1.064% | 60623 | 645 | 0.031% | 0.009% | TRANSITION | 1.0640 | 403 | 1 | 4 | 0.625 |
| 404 | 98.855% | 1.145% | 4717 | 54 | 0.041% | 0.026% | TRANSITION | 1.1448 | 404 | 1 | 4 | 0.75 |
| 405 | 100.000% | 0.000% | 288 | 0 | 0.000% | 0.000% | TRANSVERSION | 0.0000 | 405 | | 4 | 0.125 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 406 | 99.972% | 0.028% | 17818 | 5 | 0.034% | 0.017% | TRANSITION | 0.0281 | 406 | 0 | 4 | 0.125 |
| 407 | 99.950% | 0.038% | 26127 | 10 | 0.029% | 0.011% | TRANSITION | 0.0383 | 407 | 0 | 4 | 0.125 |
| 408 | 99.939% | 0.000% | 1652 | 0 | 0.000% | 0.000% | TRANSVERSION | 0.0000 | 408 | 0 | 4 | 0.125 |
| 409 | 99.675% | 0.306% | 20615 | 63 | 0.001% | 0.002% | TRANSVERSION | 0.3056 | 409 | 1 | 4 | 0.5 |
| 410 | 99.950% | 0.037% | 54285 | 20 | 0.001% | 0.001% | TRANSVERSION | 0.0368 | 410 | 1 | 4 | 0.125 |
| 411 | 99.899% | 0.097% | 28805 | 28 | 0.033% | 0.010% | TRANSITION | 0.0972 | 411 | 1 | 3 | 0.375 |
| 412 | 99.838% | 0.159% | 43904 | 70 | 0.032% | 0.009% | TRANSITION | 0.1594 | 412 | 1 | 4 | 0.375 |
| 413 | 99.069% | 0.929% | 51583 | 479 | 0.031% | 0.008% | TRANSITION | 0.9286 | 413 | 1 | 4 | 0.125 |
| 414 | 99.985% | 0.011% | 45487 | 5 | 0.009% | 0.004% | TRANSITION | 0.0110 | 414 | 0 | 4 | 0.25 |
| 415 | 99.971% | 0.002% | 44550 | 1 | 0.003% | 0.003% | TRANSVERSION | 0.0022 | 415 | 0 | 1 | 1 |
| 416 | 99.989% | 0.000% | 9510 | 0 | 0.002% | 0.004% | TRANSVERSION | 0.0000 | 416 | 0 | 1 | 1 |
| 417 | 99.971% | 0.000% | 17025 | 0 | 0.000% | 0.002% | TRANSVERSION | 0.0000 | 417 | 0 | 1 | 1 |
| 418 | 99.975% | 0.001% | 72154 | 1 | 0.003% | 0.002% | TRANSVERSION | 0.0014 | 418 | 0 | 2 | 1 |
| 419 | 99.932% | 0.003% | 61366 | 2 | 0.004% | 0.004% | TRANSVERSION | 0.0033 | 419 | 0 | 1 | 0.333333 |
| 420 | 99.980% | 0.000% | 44549 | 0 | 0.005% | 0.018% | TRANSVERSION | 0.0000 | 420 | 0 | 1 | 0.333333 |
| 421 | 99.986% | 0.003% | 58029 | 2 | 0.006% | 0.003% | TRANSVERSION | 0.0034 | 421 | 0 | 1 | 1 |
| 422 | 99.976% | 0.003% | 37156 | 1 | 0.004% | 0.004% | TRANSVERSION | 0.0027 | 422 | 0 | 4 | 1 |
| 423 | 99.970% | 0.004% | 47036 | 2 | 0.002% | 0.001% | TRANSVERSION | 0.0043 | 423 | 0 | 4 | 1 |
| 424 | 99.970% | 0.004% | 49800 | 2 | 0.003% | 0.002% | TRANSVERSION | 0.0040 | 424 | 0 | 4 | 1 |
| 425 | 99.967% | 0.003% | 60837 | 2 | 0.003% | 0.003% | TRANSVERSION | 0.0033 | 425 | 0 | 4 | 0.333333 |
| 426 | 99.975% | 0.000% | 20341 | 0 | 0.000% | 0.002% | TRANSVERSION | 0.0000 | 426 | 0 | 4 | 0.333333 |
| 427 | 99.965% | 0.002% | 56447 | 1 | 0.002% | 0.002% | TRANSVERSION | 0.0018 | 427 | 0 | 4 | 0.333333 |
| 428 | 99.954% | 0.003% | 60758 | 2 | 0.001% | 0.002% | TRANSVERSION | 0.0033 | 428 | 0 | 4 | 0.333333 |
| 429 | 99.960% | 0.002% | 50130 | 1 | 0.002% | 0.002% | TRANSVERSION | 0.0020 | 429 | 0 | 4 | 0.333333 |
| 430 | 99.968% | 0.003% | 34821 | 1 | 0.003% | 0.003% | TRANSVERSION | 0.0029 | 430 | 0 | 4 | 0.666667 |
| 431 | 99.965% | 0.008% | 62649 | 5 | 0.005% | 0.005% | TRANSVERSION | 0.0080 | 431 | 0 | 4 | 0.333333 |
| 432 | 99.975% | 0.007% | 28421 | 2 | 0.005% | 0.005% | TRANSVERSION | 0.0070 | 432 | 0 | 4 | 0.333333 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 433 | 99.970% | 0.002% | 60124 | 1 | 0.002% | 0.002% | TRANSVERSION | 0.0017 | 433 | 0 | 4 | 0.333333 |
| 434 | 99.969% | 0.005% | 64923 | 3 | 0.001% | 0.002% | TRANSVERSION | 0.0046 | 434 | 0 | 4 | 0.333333 |
| 435 | 99.964% | 0.003% | 36312 | 1 | 0.003% | 0.003% | TRANSVERSION | 0.0028 | 435 | 0 | 4 | 0.333333 |
| 436 | 99.487% | 0.458% | 18112 | 83 | 0.001% | 0.003% | TRANSITION | 0.4583 | 436 | 1 | 1 | 1 |
| 437 | 99.812% | 0.186% | 48994 | 91 | 0.007% | 0.005% | TRANSVERSION | 0.1857 | 437 | 1 | 1 | 1 |
| 438 | 99.941% | 0.000% | 5112 | 0 | 0.000% | 0.000% | TRANSVERSION | 0.0000 | 438 | 0 | 2 | 1 |
| 439 | 99.770% | 0.140% | 38706 | 54 | 0.004% | 0.004% | TRANSVERSION | 0.1395 | 439 | 1 | 2 | 1 |
| 440 | 99.807% | 0.174% | 41373 | 72 | 0.048% | 0.016% | TRANSITION | 0.1740 | 440 | 1 | 2 | 0.25 |
| 441 | 99.745% | 0.236% | 10600 | 25 | 0.004% | 0.006% | TRANSVERSION | 0.2359 | 441 | 1 | 4 | 1 |
| 442 | 99.716% | 0.258% | 54178 | 140 | 0.001% | 0.001% | TRANSVERSION | 0.2584 | 442 | 1 | 4 | 1 |
| 443 | 99.916% | 0.065% | 53601 | 35 | 0.005% | 0.002% | TRANSVERSION | 0.0653 | 443 | 1 | 4 | 1 |
| 444 | NaN | NaN | 0 | NaN | 0.001% | 0.001% | TRANSVERSION | #VALUE! | 444 | 1 | 4 | 1 |
| 445 | 99.887% | 0.060% | 60005 | 36 | 0.002% | 0.002% | TRANSVERSION | 0.0600 | 445 | 1 | 4 | 0.25 |
| 446 | 99.967% | 0.021% | 23994 | 5 | 0.000% | 0.001% | TRANSVERSION | 0.0208 | 446 | 0 | 4 | 0.25 |
| 447 | 99.931% | 0.059% | 40835 | 24 | 0.033% | 0.011% | TRANSITION | 0.0588 | 447 | 1 | 4 | 0.25 |
| 448 | 99.884% | 0.116% | 58558 | 68 | 0.025% | 0.007% | TRANSITION | 0.1161 | 448 | 1 | 4 | 0.25 |
| 449 | 99.920% | 0.075% | 78586 | 59 | 0.026% | 0.009% | TRANSITION | 0.0751 | 449 | 0 | 4 | 0.25 |
| 450 | 99.948% | 0.039% | 59427 | 23 | 0.054% | 0.015% | TRANSITION | 0.0387 | 450 | 0 | 4 | 0.5 |
| 451 | 99.818% | 0.023% | 21986 | 5 | 0.025% | 0.013% | TRANSITION | 0.0227 | 451 | 0 | 4 | 0.5 |
| 452 | 99.969% | 0.028% | 35318 | 10 | 0.034% | 0.012% | TRANSITION | 0.0283 | 452 | 0 | 4 | 0.75 |
| 453 | 99.934% | 0.060% | 16648 | 10 | 0.029% | 0.012% | TRANSITION | 0.0601 | 453 | 0 | 4 | 0.25 |
| 454 | 99.958% | 0.036% | 74654 | 27 | 0.040% | 0.011% | TRANSITION | 0.0362 | 454 | 0 | 4 | 0.25 |
| 455 | 99.971% | 0.000% | 48955 | 0 | 0.001% | 0.001% | TRANSVERSION | 0.0000 | 455 | 0 | 4 | 1 |
| 456 | 99.965% | 0.030% | 56545 | 17 | 0.026% | 0.009% | TRANSITION | 0.0301 | 456 | 0 | 4 | 0.25 |
| 457 | 99.942% | 0.003% | 60010 | 2 | 0.007% | 0.003% | TRANSVERSION | 0.0033 | 457 | 0 | 2 | 1 |
| 458 | 99.971% | 0.000% | 54965 | 0 | 0.001% | 0.001% | TRANSVERSION | 0.0000 | 458 | 0 | 2 | 0.75 |
| 459 | 99.951% | 0.000% | 28542 | 0 | 0.002% | 0.004% | TRANSVERSION | 0.0000 | 459 | 0 | 1 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 460 | 99.946% | 0.002% | 46587 | 1 | 0.002% | 0.003% | TRANSVERSION | 0.0021 | 460 | 0 | 4 | 0.75 |
| 461 | 99.984% | 0.000% | 63619 | 0 | 0.002% | 0.002% | TRANSVERSION | 0.0000 | 461 | 0 | 4 | 0.75 |
| 462 | 99.971% | 0.000% | 64453 | 0 | 0.002% | 0.002% | TRANSVERSION | 0.0000 | 462 | 0 | 4 | 0.5 |
| 463 | 99.974% | 0.000% | 74213 | 0 | 0.001% | 0.002% | TRANSVERSION | 0.0000 | 463 | 0 | 4 | 0.25 |
| 464 | 99.970% | 0.015% | 79666 | 12 | 0.008% | 0.003% | TRANSVERSION | 0.0151 | 464 | 0 | 4 | 0.25 |
| 465 | 99.968% | 0.003% | 58832 | 2 | 0.001% | 0.001% | TRANSVERSION | 0.0034 | 465 | 0 | 4 | 0.25 |
| 466 | 99.993% | 0.000% | 13594 | 0 | 0.000% | 0.002% | TRANSVERSION | 0.0000 | 466 | 0 | 4 | 0.25 |
| 467 | 99.953% | 0.010% | 29658 | 3 | 0.004% | 0.004% | TRANSVERSION | 0.0101 | 467 | 0 | 4 | 0.25 |
| 468 | 99.966% | 0.000% | 84581 | 0 | 0.003% | 0.004% | TRANSVERSION | 0.0000 | 468 | 0 | 4 | 0.25 |
| 469 | 99.966% | 0.000% | 64535 | 0 | 0.002% | 0.002% | TRANSVERSION | 0.0000 | 469 | 0 | 4 | 0.25 |
| 470 | 99.941% | 0.000% | 83191 | 0 | 0.001% | 0.002% | TRANSVERSION | 0.0000 | 470 | 0 | 4 | 0.25 |
| 471 | 99.970% | 0.000% | 30288 | 0 | 0.007% | 0.006% | TRANSVERSION | 0.0000 | 471 | 0 | 4 | 0.25 |
| 472 | 99.978% | 0.000% | 54921 | 0 | 0.000% | 0.001% | TRANSVERSION | 0.0000 | 472 | 0 | 4 | 0.25 |
| 473 | 99.964% | 0.001% | 75082 | 1 | 0.001% | 0.002% | TRANSVERSION | 0.0013 | 473 | 0 | 3 | 0.25 |
| 474 | 99.982% | 0.002% | 45023 | 1 | 0.004% | 0.003% | TRANSVERSION | 0.0022 | 474 | 0 | 4 | 0.25 |
| 475 | 99.943% | 0.036% | 28012 | 10 | 0.002% | 0.003% | TRANSVERSION | 0.0357 | 475 | 1 | 2 | 0.75 |
| 476 | 99.997% | 0.000% | 38900 | 0 | 0.004% | 0.003% | TRANSVERSION | 0.0000 | 476 | 0 | 1 | 0.25 |
| 477 | 99.934% | 0.058% | 12121 | 7 | 0.001% | 0.003% | TRANSVERSION | 0.0578 | 477 | 1 | 4 | 0.75 |
| 478 | 99.960% | 0.012% | 52093 | 6 | 0.001% | 0.001% | TRANSVERSION | 0.0115 | 478 | 1 | 4 | 0.75 |
| 479 | 99.894% | 0.054% | 53542 | 29 | 0.005% | 0.003% | TRANSVERSION | 0.0542 | 479 | 1 | 4 | 0.75 |
| 480 | 99.884% | 0.058% | 1728 | 1 | 0.003% | 0.010% | TRANSVERSION | 0.0579 | 480 | 0 | 4 | 0.75 |
| 481 | 99.931% | 0.053% | 73577 | 46 | 0.045% | 0.010% | TRANSITION | 0.0625 | 481 | 0 | 4 | 0.75 |
| 482 | 99.889% | 0.111% | 6281 | 7 | 0.003% | 0.006% | TRANSVERSION | 0.1115 | 482 | 1 | 4 | 0.75 |
| 483 | 99.897% | 0.100% | 46791 | 47 | 0.027% | 0.007% | TRANSITION | 0.1005 | 483 | 1 | 4 | 0.75 |
| 484 | 99.951% | 0.004% | 28449 | 1 | 0.005% | 0.005% | TRANSVERSION | 0.0035 | 484 | 0 | 4 | 0.5 |
| 485 | 99.894% | 0.075% | 45356 | 34 | 0.003% | 0.003% | TRANSVERSION | 0.0750 | 485 | 1 | 4 | 0.5 |
| 486 | 99.931% | 0.069% | 13021 | 9 | 0.025% | 0.010% | TRANSITION | 0.0691 | 486 | 0 | 4 | 0.75 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 487 | 99.908% | 0.088% | 26093 | 23 | 0.014% | 0.008% | TRANSITION | 0.0881 | 487 | 1 | 4 | 0.5 |
| 488 | 99.974% | 0.023% | 26653 | 6 | 0.034% | 0.011% | TRANSITION | 0.0225 | 488 | 0 | 4 | 0.25 |
| 489 | 100.000% | 0.000% | 6979 | 0 | 0.033% | 0.017% | TRANSITION | 0.0000 | 489 | 0 | 4 | 0.25 |
| 490 | 99.948% | 0.034% | 34821 | 12 | 0.003% | 0.003% | TRANSVERSION | 0.0345 | 490 | 1 | 4 | 0.25 |
| 491 | 99.980% | 0.018% | 55334 | 10 | 0.030% | 0.012% | TRANSITION | 0.0181 | 491 | 0 | 4 | 0.25 |
| 492 | 99.943% | 0.000% | 3507 | 0 | 0.002% | 0.005% | TRANSVERSION | 0.0000 | 492 | 0 | 4 | 0.25 |
| 493 | 99.958% | 0.002% | 61185 | 1 | 0.001% | 0.003% | TRANSVERSION | 0.0016 | 493 | 0 | 1 | 1 |
| 494 | 99.968% | 0.005% | 44316 | 2 | 0.003% | 0.003% | TRANSVERSION | 0.0045 | 494 | 0 | 2 | 1 |
| 495 | 99.887% | 0.019% | 5289 | 1 | 0.005% | 0.012% | TRANSVERSION | 0.0189 | 495 | 0 | 4 | 0.666667 |
| 496 | 99.935% | 0.000% | 10738 | 0 | 0.003% | 0.006% | TRANSVERSION | 0.0000 | 496 | 0 | 4 | 0.666667 |
| 497 | 99.970% | 0.001% | 87734 | 1 | 0.002% | 0.001% | TRANSVERSION | 0.0011 | 497 | 0 | 4 | 1 |
| 498 | 99.956% | 0.030% | 29758 | 9 | 0.031% | 0.018% | TRANSITION | 0.0302 | 498 | 0 | 4 | 1 |
| 499 | 99.974% | 0.000% | 60598 | 0 | 0.003% | 0.002% | TRANSVERSION | 0.0000 | 499 | 0 | 4 | 1 |
| 500 | 99.973% | 0.027% | 26381 | 7 | 0.042% | 0.018% | TRANSITION | 0.0265 | 500 | 0 | 4 | 0.333333 |
| 501 | 99.979% | 0.020% | 65957 | 13 | 0.027% | 0.007% | TRANSITION | 0.0197 | 501 | 0 | 4 | 0.666667 |
| 502 | 99.976% | 0.000% | 46673 | 0 | 0.001% | 0.002% | TRANSVERSION | 0.0000 | 502 | 0 | 4 | 0.666667 |
| 503 | 99.959% | 0.002% | 65398 | 1 | 0.003% | 0.002% | TRANSVERSION | 0.0015 | 503 | 0 | 4 | 0.666667 |
| 504 | 99.957% | 0.004% | 51150 | 2 | 0.001% | 0.002% | TRANSVERSION | 0.0039 | 504 | 0 | 4 | 0.666667 |
| 505 | 99.931% | 0.007% | 67139 | 5 | 0.003% | 0.003% | TRANSVERSION | 0.0074 | 505 | 0 | 4 | 0.666667 |
| 506 | 99.971% | 0.006% | 64823 | 4 | 0.005% | 0.003% | TRANSVERSION | 0.0062 | 506 | 0 | 4 | 0.333333 |
| 507 | 99.897% | 0.057% | 8738 | 5 | 0.005% | 0.008% | TRANSVERSION | 0.0572 | 507 | 0 | 1 | 0.6 |
| 508 | 99.919% | 0.076% | 40702 | 31 | 0.047% | 0.013% | TRANSITION | 0.0762 | 508 | 0 | 2 | 0.8 |
| 509 | 99.865% | 0.102% | 45945 | 47 | 0.002% | 0.002% | TRANSITION | 0.1023 | 509 | 1 | 1 | 0.8 |
| 510 | 99.919% | 0.050% | 22206 | 11 | 0.003% | 0.005% | TRANSVERSION | 0.0495 | 510 | 1 | 2 | 0.8 |
| 511 | 100.000% | 0.000% | 58 | 0 | 0.000% | 0.000% | TRANSVERSION | 0.0000 | 511 |  | 1 | 0.8 |
| 512 | 99.918% | 0.060% | 31888 | 19 | 0.004% | 0.008% | TRANSVERSION | 0.0596 | 512 | 0 | 2 | 0.8 |
| 513 | 99.962% | 0.019% | 42513 | 8 | 0.002% | 0.002% | TRANSVERSION | 0.0188 | 513 | 1 | 1 | 0.8 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 514 | 99.964% | 0.000% | 33678 | 0 | 0.001% | 0.002% | TRANSVERSION | 0.0000 | 514 | 0 | 2 | 0.8 |
| 515 | 99.989% | 0.004% | 28487 | 1 | 0.012% | 0.006% | TRANSITION | 0.0035 | 515 | 0 | 1 | 0.8 |
| 516 | 99.976% | 0.005% | 55316 | 3 | 0.001% | 0.002% | TRANSVERSION | 0.0054 | 516 | 0 | 1 | 0.8 |
| 517 | 98.879% | 1.121% | 446 | 5 | 0.097% | 0.200% | TRANSITION | 1.1211 | 517 | | 2 | 0.8 |
| 518 | 99.920% | 0.080% | 6261 | 5 | 0.030% | 0.023% | TRANSITION | 0.0799 | 518 | 0 | 2 | 0.8 |
| 519 | 99.991% | 0.000% | 11391 | 0 | 0.033% | 0.019% | TRANSITION | 0.0000 | 519 | 0 | 2 | 0.6 |
| 520 | 99.849% | 0.080% | 45153 | 36 | 0.003% | 0.002% | TRANSVERSION | 0.0797 | 520 | 1 | 2 | 0.2 |
| 521 | 99.947% | 0.004% | 53113 | 2 | 0.002% | 0.002% | TRANSVERSION | 0.0038 | 521 | 0 | 4 | 0.2 |
| 522 | 99.951% | 0.000% | 28817 | 0 | 0.001% | 0.011% | TRANSVERSION | 0.0000 | 522 | 0 | 4 | 0.2 |
| 523 | 99.959% | 0.000% | 7406 | 0 | 0.005% | 0.001% | TRANSVERSION | 0.0000 | 523 | 0 | 4 | 0.2 |
| 524 | 99.965% | 0.001% | 71884 | 1 | 0.001% | 0.002% | TRANSVERSION | 0.0014 | 524 | 0 | 4 | 0.2 |
| 525 | 99.979% | 0.004% | 28417 | 1 | 0.001% | 0.002% | TRANSVERSION | 0.0035 | 525 | 0 | 4 | 0.2 |
| 526 | 99.958% | 0.012% | 33149 | 4 | 0.008% | 0.005% | TRANSVERSION | 0.0121 | 526 | 0 | 2 | 0.75 |
| 527 | 99.961% | 0.018% | 28033 | 5 | 0.006% | 0.004% | TRANSVERSION | 0.0178 | 527 | 0 | 2 | 0.75 |
| 528 | 99.973% | 0.000% | 14738 | 0 | 0.001% | 0.002% | TRANSVERSION | 0.0000 | 528 | 0 | 2 | 0.25 |
| 529 | 99.788% | 0.000% | 942 | 0 | 0.000% | 0.000% | TRANSVERSION | 0.0000 | 529 | | 4 | 1 |
| 530 | 99.949% | 0.003% | 29342 | 1 | 0.002% | 0.003% | TRANSVERSION | 0.0034 | 530 | 0 | 4 | 0.75 |
| 531 | 99.973% | 0.003% | 33782 | 1 | 0.004% | 0.002% | TRANSVERSION | 0.0030 | 531 | 0 | 4 | 0.75 |
| 532 | 99.980% | 0.017% | 35315 | 6 | 0.024% | 0.008% | TRANSITION | 0.0170 | 532 | 0 | 4 | 1 |
| 533 | 99.966% | 0.000% | 32791 | 0 | 0.002% | 0.002% | TRANSVERSION | 0.0000 | 533 | 0 | 4 | 0.75 |
| 534 | 99.871% | 0.100% | 34957 | 35 | 0.003% | 0.002% | TRANSVERSION | 0.1001 | 534 | 1 | 4 | 1 |
| 535 | 99.978% | 0.000% | 277651 | 0 | 0.002% | 0.002% | TRANSVERSION | 0.0000 | 535 | 0 | 4 | 0.25 |
| 536 | 99.916% | 0.063% | 4776 | 3 | 0.052% | 0.033% | TRANSITION | 0.0628 | 536 | 0 | 4 | 0.25 |
| 537 | 99.969% | 0.003% | 32668 | 1 | 0.002% | 0.002% | TRANSITION | 0.0031 | 537 | 0 | 4 | 0.25 |
| 538 | 100.000% | 0.000% | 25456 | 0 | 0.029% | 0.010% | TRANSITION | 0.0000 | 538 | 0 | 4 | 0.25 |
| 539 | 99.958% | 0.039% | 31042 | 12 | 0.038% | 0.011% | TRANSITION | 0.0387 | 539 | 0 | 4 | 0.25 |
| 540 | 99.968% | 0.023% | 69644 | 16 | 0.033% | 0.008% | TRANSITION | 0.0230 | 540 | 0 | 4 | 0.25 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 541 | 99.969% | 0.000% | 38711 | 0 | 0.001% | 0.002% | TRANSVERSION | 0.0000 | 541 | 0 | 4 | 0.25 |
| 542 | 99.978% | 0.022% | 18522 | 4 | 0.046% | 0.019% | TRANSITION | 0.0216 | 542 | 0 | 4 | 0.25 |
| 543 | 99.968% | 0.029% | 30893 | 9 | 0.025% | 0.007% | TRANSITION | 0.0291 | 543 | 0 | 4 | 0.25 |
| 544 | 99.981% | 0.000% | 10613 | 0 | 0.003% | 0.004% | TRANSVERSION | 0.0000 | 544 | 0 | 1 | 1 |
| 545 | 99.971% | 0.000% | 44705 | 0 | 0.002% | 0.002% | TRANSVERSION | 0.0000 | 545 | 0 | 1 | 1 |
| 546 | 99.965% | 0.026% | 57494 | 15 | 0.029% | 0.008% | TRANSITION | 0.0261 | 546 | 0 | 2 | 0.25 |
| 547 | 99.953% | 0.047% | 8470 | 4 | 0.047% | 0.032% | TRANSITION | 0.0472 | 547 | 0 | 2 | 0.25 |
| 548 | 99.957% | 0.000% | 21102 | 0 | 0.002% | 0.003% | TRANSVERSION | 0.0000 | 548 | 0 | 4 | 1 |
| 549 | 99.947% | 0.053% | 22644 | 12 | 0.049% | 0.020% | TRANSITION | 0.0530 | 549 | 0 | 4 | 0.75 |
| 550 | 99.957% | 0.001% | 83931 | 1 | 0.001% | 0.001% | TRANSVERSION | 0.0012 | 550 | 0 | 4 | 0.25 |
| 551 | 99.975% | 0.001% | 67130 | 1 | 0.002% | 0.002% | TRANSVERSION | 0.0015 | 551 | 0 | 4 | 0.25 |
| 552 | 99.956% | 0.000% | 15922 | 0 | 0.002% | 0.003% | TRANSVERSION | 0.0000 | 552 | 0 | 4 | 0.25 |
| 553 | 99.973% | 0.000% | 56035 | 0 | 0.002% | 0.002% | TRANSVERSION | 0.0000 | 553 | 0 | 4 | 0.5 |
| 554 | 100.000% | 0.000% | 2337 | 0 | 0.000% | 0.000% | TRANSVERSION | 0.0000 | 554 | 0 | 4 | 0.5 |
| 555 | 99.960% | 0.000% | 60560 | 0 | 0.001% | 0.002% | TRANSVERSION | 0.0000 | 555 | 0 | 4 | 0.25 |
| 556 | 99.977% | 0.006% | 17658 | 1 | 0.001% | 0.002% | TRANSVERSION | 0.0057 | 556 | 0 | 4 | 0.25 |
| 557 | 99.977% | 0.000% | 68504 | 0 | 0.001% | 0.001% | TRANSVERSION | 0.0000 | 557 | 0 | 4 | 0.25 |
| 558 | 99.958% | 0.037% | 62274 | 23 | 0.041% | 0.011% | TRANSITION | 0.0369 | 558 | 0 | 4 | 0.25 |
| 559 | 99.940% | 0.060% | 25194 | 15 | 0.031% | 0.012% | TRANSITION | 0.0595 | 559 | 0 | 4 | 0.25 |
| 560 | 99.971% | 0.003% | 65977 | 2 | 0.005% | 0.002% | TRANSVERSION | 0.0030 | 560 | 0 | 4 | 0.25 |
| 561 | 99.972% | 0.000% | 38908 | 0 | 0.003% | 0.003% | TRANSVERSION | 0.0000 | 561 | 0 | 4 | 0.25 |
| 562 | 99.973% | 0.013% | 14942 | 2 | 0.004% | 0.005% | TRANSVERSION | 0.0134 | 562 | 0 | 1 | 0.625 |
| 563 | 99.944% | 0.000% | 1797 | 0 | 0.000% | 0.000% | TRANSVERSION | 0.0000 | 563 | 0 | 1 | 0.625 |
| 564 | 99.973% | 0.002% | 60259 | 1 | 0.003% | 0.002% | TRANSITION | 0.0017 | 564 | 0 | 2 | 0.625 |
| 565 | 99.958% | 0.040% | 62456 | 25 | 0.040% | 0.011% | TRANSITION | 0.0400 | 565 | 0 | 2 | 0.625 |
| 566 | 99.975% | 0.004% | 28380 | 1 | 0.002% | 0.003% | TRANSVERSION | 0.0035 | 566 | 0 | 2 | 0.125 |
| 567 | 99.991% | 0.002% | 66495 | 1 | 0.003% | 0.002% | TRANSVERSION | 0.0015 | 567 | 0 | 1 | 0.375 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 568 | 99.976% | 0.003% | 67920 | 2 | 0.003% | 0.002% | TRANSVERSION | 0.0029 | 568 | 0 | 4 | 0.5 |
| 569 | 99.914% | 0.063% | 51092 | 32 | 0.003% | 0.002% | TRANSVERSION | 0.0626 | 569 | 1 | 4 | 0.5 |
| 570 | 99.956% | 0.002% | 48243 | 1 | 0.002% | 0.002% | TRANSVERSION | 0.0021 | 570 | 0 | 4 | 0.5 |
| 571 | 99.982% | 0.000% | 77368 | 0 | 0.001% | 0.001% | TRANSVERSION | 0.0000 | 571 | 0 | 4 | 0.125 |
| 572 | 100.000% | 0.000% | 596 | 0 | 0.004% | 0.018% | TRANSVERSION | 0.0000 | 572 |   | 4 | 0.125 |
| 573 | 99.961% | 0.002% | 46677 | 1 | 0.003% | 0.003% | TRANSVERSION | 0.0021 | 573 | 0 | 4 | 0.125 |
| 574 | 99.967% | 0.009% | 42395 | 4 | 0.004% | 0.003% | TRANSVERSION | 0.0094 | 574 | 0 | 4 | 0.125 |
| 575 | 100.000% | 0.000% | 3455 | 0 | 0.002% | 0.005% | TRANSVERSION | 0.0000 | 575 | 0 | 4 | 0.125 |
| 576 | 99.985% | 0.000% | 52008 | 0 | 0.000% | 0.001% | TRANSVERSION | 0.0000 | 576 | 0 | 3 | 0.375 |
| 577 | 99.978% | 0.000% | 18554 | 0 | 0.003% | 0.004% | TRANSVERSION | 0.0000 | 577 | 0 | 4 | 0.375 |
| 578 | 99.978% | 0.002% | 80204 | 2 | 0.001% | 0.001% | TRANSVERSION | 0.0025 | 578 | 0 | 4 | 0.125 |
| 579 | 99.941% | 0.008% | 50489 | 4 | 0.008% | 0.004% | TRANSVERSION | 0.0079 | 579 | 0 | 4 | 0.125 |
| 580 | 99.982% | 0.000% | 62239 | 0 | 0.000% | 0.001% | TRANSVERSION | 0.0000 | 580 | 0 | 4 | 0.125 |
| 581 | 99.971% | 0.000% | 69281 | 0 | 0.001% | 0.001% | TRANSVERSION | 0.0000 | 581 | 0 | 4 | 0.125 |
| 582 | 99.573% | 0.424% | 29984 | 127 | 0.012% | 0.005% | TRANSITION | 0.4236 | 582 | 1 | 1 | 0.5 |
| 583 | 99.844% | 0.125% | 39085 | 49 | 0.003% | 0.003% | TRANSVERSION | 0.1254 | 583 | 1 | 2 | 0.333333 |
| 584 | 99.856% | 0.077% | 38854 | 30 | 0.007% | 0.005% | TRANSVERSION | 0.0772 | 584 | 1 | 2 | 0.333333 |
| 585 | 99.914% | 0.073% | 77901 | 57 | 0.006% | 0.003% | TRANSVERSION | 0.0732 | 585 | 1 | 2 | 0.166667 |
| 586 | 99.772% | 0.212% | 68920 | 146 | 0.003% | 0.002% | TRANSVERSION | 0.2118 | 586 | 1 | 2 | 0.166667 |
| 587 | 99.871% | 0.096% | 87104 | 84 | 0.005% | 0.004% | TRANSVERSION | 0.0964 | 587 | 1 | 1 | 0.166667 |
| 588 | 99.856% | 0.132% | 8353 | 11 | 0.002% | 0.004% | TRANSVERSION | 0.1317 | 588 | 1 | 2 | 0.5 |
| 589 | 99.643% | 0.297% | 5043 | 15 | 0.007% | 0.010% | TRANSVERSION | 0.2974 | 589 | 1 | 2 | 0.166667 |
| 590 | 99.854% | 0.103% | 39777 | 41 | 0.004% | 0.002% | TRANSVERSION | 0.1031 | 590 | 1 | 2 | 0.333333 |
| 591 | 99.799% | 0.194% | 38229 | 74 | 0.031% | 0.013% | TRANSITION | 0.1936 | 591 | 1 | 2 | 0.166667 |
| 592 | 99.541% | 0.434% | 64087 | 278 | 0.002% | 0.004% | TRANSVERSION | 0.4338 | 592 | 1 | 4 | 0.5 |
| 593 | 99.628% | 0.366% | 16117 | 59 | 0.002% | 0.005% | TRANSVERSION | 0.3661 | 593 | 1 | 4 | 0.5 |
| 594 | 99.905% | 0.088% | 70665 | 62 | 0.014% | 0.004% | TRANSITION | 0.0877 | 594 | 1 | 4 | 0.333333 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 595 | 99.755% | 0.215% | 67474 | 145 | 0.001% | 0.002% | TRANSVERSION | 0.2149 | 595 | 1 | 4 | 0.5 |
| 596 | 99.848% | 0.152% | 34824 | 53 | 0.018% | 0.010% | TRANSITION | 0.1522 | 596 | 1 | 4 | 0.166667 |
| 597 | 99.962% | 0.001% | 74173 | 1 | 0.003% | 0.002% | TRANSVERSION | 0.0013 | 597 | 0 | 4 | 0.166667 |
| 598 | 99.962% | 0.000% | 5238 | 0 | 0.001% | 0.002% | TRANSVERSION | 0.0000 | 598 | 0 | 4 | 0.166667 |
| 599 | 99.937% | 0.037% | 83096 | 31 | 0.005% | 0.003% | TRANSVERSION | 0.0373 | 599 | 1 | 4 | 0.166667 |
| 600 | 99.959% | 0.039% | 58594 | 23 | 0.020% | 0.007% | TRANSITION | 0.0393 | 600 | 0 | 4 | 0.166667 |
| 601 | 99.909% | 0.070% | 18621 | 13 | 0.001% | 0.002% | TRANSVERSION | 0.0698 | 601 | 1 | 4 | 0.166667 |
| 602 | 99.961% | 0.002% | 45600 | 1 | 0.002% | 0.001% | TRANSVERSION | 0.0022 | 602 | 0 | 1 | 1 |
| 603 | 99.919% | 0.007% | 13642 | 1 | 0.003% | 0.007% | TRANSVERSION | 0.0073 | 603 | 0 | 2 | 1 |
| 604 | 99.985% | 0.000% | 13616 | 0 | 0.002% | 0.004% | TRANSVERSION | 0.0000 | 604 | 0 | 1 | 1 |
| 605 | 99.958% | 0.003% | 33593 | 1 | 0.004% | 0.004% | TRANSVERSION | 0.0030 | 605 | 0 | 2 | 1 |
| 606 | 99.973% | 0.000% | 56570 | 0 | 0.001% | 0.001% | TRANSVERSION | 0.0000 | 606 | 0 | 2 | 1 |
| 607 | 99.981% | 0.004% | 51503 | 2 | 0.005% | 0.004% | TRANSVERSION | 0.0039 | 607 | 0 | 1 | 1 |
| 608 | 100.000% | 0.000% | 601 | 0 | 0.000% | 0.000% | TRANSVERSION | 0.0000 | 608 |  | 1 | 1 |
| 609 | 99.867% | 0.098% | 14246 | 14 | 0.002% | 0.004% | TRANSVERSION | 0.0983 | 609 | 1 | 2 | 1 |
| 610 | 99.939% | 0.004% | 22910 | 1 | 0.002% | 0.003% | TRANSVERSION | 0.0044 | 610 | 0 | 2 | 1 |
| 611 | 99.945% | 0.000% | 14614 | 0 | 0.003% | 0.006% | TRANSVERSION | 0.0000 | 611 | 0 | 1 | 0.5 |
| 612 | 99.939% | 0.061% | 19600 | 12 | 0.041% | 0.017% | TRANSITION | 0.0612 | 612 | 0 | 2 | 0.5 |
| 613 | 99.955% | 0.000% | 37781 | 0 | 0.001% | 0.002% | TRANSVERSION | 0.0000 | 613 | 0 | 2 | 1 |
| 614 | 99.961% | 0.000% | 48193 | 0 | 0.001% | 0.002% | TRANSVERSION | 0.0000 | 614 | 0 | 4 | 1 |
| 615 | 99.975% | 0.004% | 23882 | 1 | 0.002% | 0.003% | TRANSVERSION | 0.0042 | 615 | 0 | 4 | 1 |
| 616 | 99.982% | 0.003% | 33777 | 1 | 0.004% | 0.003% | TRANSVERSION | 0.0030 | 616 | 0 | 4 | 1 |
| 617 | 99.952% | 0.000% | 47995 | 0 | 0.002% | 0.002% | TRANSVERSION | 0.0000 | 617 | 0 | 4 | 0.5 |
| 618 | 99.971% | 0.000% | 17113 | 0 | 0.001% | 0.003% | TRANSVERSION | 0.0000 | 618 | 0 | 4 | 0.5 |
| 619 | 99.958% | 0.003% | 38334 | 1 | 0.002% | 0.003% | TRANSVERSION | 0.0026 | 619 | 0 | 4 | 0.5 |
| 620 | 99.963% | 0.002% | 64054 | 1 | 0.003% | 0.001% | TRANSVERSION | 0.0016 | 620 | 0 | 4 | 0.5 |
| 621 | 99.204% | 0.741% | 9174 | 68 | 0.003% | 0.007% | TRANSVERSION | 0.7412 | 621 | 1 | 2 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 622 | 99.536% | 0.459% | 41387 | 190 | 0.048% | 0.015% | TRANSITION | 0.4591 | 622 | 1 | 1 | 0.833333 |
| 623 | 99.753% | 0.245% | 72187 | 177 | 0.030% | 0.010% | TRANSITION | 0.2452 | 623 | 1 | 2 | 0.833333 |
| 624 | 99.794% | 0.153% | 52430 | 80 | 0.001% | 0.001% | TRANSVERSION | 0.1526 | 624 | 1 | 1 | 0.666667 |
| 625 | 99.798% | 0.148% | 57294 | 85 | 0.002% | 0.002% | TRANSVERSION | 0.1484 | 625 | 1 | 2 | 0.666667 |
| 626 | 99.785% | 0.179% | 2796 | 5 | 0.002% | 0.009% | TRANSVERSION | 0.1788 | 626 | 1 | 1 | 0.666667 |
| 627 | 99.912% | 0.088% | 25139 | 22 | 0.037% | 0.017% | TRANSITION | 0.0875 | 627 | 0 | 2 | 0.333333 |
| 628 | 99.983% | 0.006% | 17917 | 1 | 0.001% | 0.003% | TRANSVERSION | 0.0056 | 628 | 0 | 2 | 0.333333 |
| 629 | 99.934% | 0.066% | 10618 | 7 | 0.051% | 0.020% | TRANSITION | 0.0659 | 629 | 0 | 2 | 0.333333 |
| 630 | 99.809% | 0.148% | 64258 | 95 | 0.004% | 0.003% | TRANSVERSION | 0.1478 | 630 | 1 | 4 | 0.666667 |
| 631 | 99.813% | 0.157% | 57335 | 90 | 0.001% | 0.002% | TRANSVERSION | 0.1570 | 631 | 1 | 4 | 0.833333 |
| 632 | 99.837% | 0.143% | 55992 | 80 | 0.002% | 0.002% | TRANSVERSION | 0.1429 | 632 | 1 | 4 | 0.666667 |
| 633 | 99.769% | 0.205% | 11237 | 23 | 0.001% | 0.003% | TRANSVERSION | 0.2047 | 633 | 1 | 4 | 0.666667 |
| 634 | 99.752% | 0.200% | 33432 | 67 | 0.002% | 0.002% | TRANSVERSION | 0.2004 | 634 | 1 | 4 | 0.666667 |
| 635 | 99.944% | 0.051% | 62216 | 32 | 0.040% | 0.008% | TRANSITION | 0.0514 | 635 | 0 | 4 | 0.5 |
| 636 | 100.000% | 0.000% | 5633 | 0 | 0.011% | 0.011% | TRANSITION | 0.0000 | 636 | 0 | 4 | 0.333333 |
| 637 | 99.969% | 0.013% | 74807 | 10 | 0.001% | 0.001% | TRANSVERSION | 0.0134 | 637 | 1 | 4 | 0.333333 |
| 638 | 99.955% | 0.026% | 42341 | 11 | 0.004% | 0.002% | TRANSVERSION | 0.0260 | 638 | 1 | 4 | 0.333333 |
| 639 | 99.940% | 0.030% | 26723 | 8 | 0.002% | 0.003% | TRANSITION | 0.0299 | 639 | 1 | 4 | 0.333333 |
| 640 | 99.935% | 0.042% | 35483 | 15 | 0.001% | 0.001% | TRANSVERSION | 0.0423 | 640 | 1 | 4 | 0.333333 |
| 641 | 99.945% | 0.045% | 30822 | 14 | 0.034% | 0.011% | TRANSITION | 0.0454 | 641 | 1 | 1 | 0.333333 |
| 642 | 99.983% | 0.017% | 5775 | 1 | 0.041% | 0.028% | TRANSITION | 0.0173 | 642 | 0 | 2 | 0.333333 |
| 643 | 99.958% | 0.009% | 78893 | 7 | 0.005% | 0.002% | TRANSVERSION | 0.0089 | 643 | 0 | 2 | 0.333333 |
| 644 | 99.975% | 0.023% | 56918 | 13 | 0.039% | 0.010% | TRANSITION | 0.0228 | 644 | 0 | 2 | 0.333333 |
| 645 | 99.965% | 0.000% | 57273 | 0 | 0.001% | 0.001% | TRANSVERSION | 0.0000 | 645 | 0 | 1 | 0.333333 |
| 646 | 99.941% | 0.003% | 32096 | 1 | 0.001% | 0.002% | TRANSVERSION | 0.0031 | 646 | 0 | 4 | 1 |
| 647 | 99.970% | 0.006% | 53469 | 3 | 0.002% | 0.002% | TRANSVERSION | 0.0056 | 647 | 0 | 3 | 0.333333 |
| 648 | 99.983% | 0.000% | 71852 | 0 | 0.003% | 0.002% | TRANSVERSION | 0.0000 | 648 | 0 | 4 | 0.333333 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 649 | 99.995% | 0.000% | 18216 | 0 | 0.003% | 0.003% | TRANSVERSION | 0.0000 | 649 | 0 | 4 | 0.333333 |
| 650 | 99.960% | 0.000% | 70163 | 0 | 0.002% | 0.002% | TRANSVERSION | 0.0000 | 650 | 0 | 4 | 0.333333 |
| 651 | 99.994% | 0.006% | 17203 | 1 | 0.003% | 0.003% | TRANSVERSION | 0.0058 | 651 | 0 | 4 | 0.333333 |
| 652 | 99.970% | 0.000% | 53121 | 0 | 0.002% | 0.002% | TRANSVERSION | 0.0000 | 652 | 0 | 4 | 0.666667 |
| 653 | 99.964% | 0.007% | 30464 | 2 | 0.003% | 0.003% | TRANSVERSION | 0.0066 | 653 | 0 | 4 | 0.666667 |
| 654 | 100.000% | 0.000% | 12939 | 0 | 0.000% | 0.001% | TRANSVERSION | 0.0000 | 654 | 0 | 4 | 0.666667 |
| 655 | 99.969% | 0.005% | 143425 | 7 | 0.003% | 0.001% | TRANSVERSION | 0.0049 | 655 | 0 | 4 | 0.333333 |
| 656 | 99.984% | 0.000% | 12792 | 0 | 0.002% | 0.003% | TRANSVERSION | 0.0000 | 656 | 0 | 4 | 0.333333 |
| 657 | 99.931% | 0.003% | 36474 | 1 | 0.003% | 0.003% | TRANSVERSION | 0.0027 | 657 | 0 | 4 | 0.333333 |
| 658 | 99.980% | 0.000% | 49860 | 0 | 0.002% | 0.002% | TRANSVERSION | 0.0000 | 658 | 0 | 4 | 0.333333 |
| 659 | 99.972% | 0.000% | 72185 | 0 | 0.001% | 0.001% | TRANSVERSION | 0.0000 | 659 | 0 | 4 | 0.333333 |
| 660 | 92.133% | 7.867% | 40245 | 3166 | 0.034% | 0.013% | TRANSITION | 7.8668 | 660 | 1 | 1 | 1 |
| 661 | 97.998% | 1.969% | 63135 | 1243 | 0.003% | 0.000% | TRANSVERSION | 1.9688 | 661 | 1 | 2 | 0.428571 |
| 662 | 97.294% | 2.670% | 33072 | 883 | 0.002% | 0.002% | TRANSVERSION | 2.6699 | 662 | 1 | 2 | 0.285714 |
| 663 | 94.053% | 5.900% | 64203 | 3788 | 0.001% | 0.009% | TRANSVERSION | 5.9000 | 663 | 1 | 1 | 1 |
| 664 | 93.488% | 6.500% | 80373 | 5224 | 0.006% | 0.003% | TRANSVERSION | 6.4997 | 664 | 1 | 2 | 1 |
| 665 | 99.372% | 0.561% | 18007 | 101 | 0.001% | 0.002% | TRANSVERSION | 0.5609 | 665 | 1 | 2 | 0.142857 |
| 666 | 98.386% | 1.602% | 43191 | 692 | 0.034% | 0.009% | TRANSITION | 1.6022 | 666 | 1 | 1 | 0.428571 |
| 667 | 100.000% | 0.000% | 166 | 0 | 0.000% | 0.000% | TRANSVERSION | 0.0000 | 667 |  | 2 | 0.285714 |
| 668 | 99.938% | 0.048% | 21037 | 10 | 0.046% | 0.024% | TRANSITION | 0.0475 | 668 | 0 | 2 | 0.142857 |
| 669 | 99.773% | 0.217% | 17996 | 39 | 0.035% | 0.011% | TRANSITION | 0.2167 | 669 | 1 | 2 | 0.142857 |
| 670 | 99.666% | 0.329% | 58676 | 193 | 0.032% | 0.009% | TRANSITION | 0.3289 | 670 | 1 | 1 | 0.142857 |
| 671 | 99.391% | 0.607% | 66212 | 402 | 0.026% | 0.011% | TRANSITION | 0.6071 | 671 | 1 | 2 | 0.285714 |
| 672 | 99.459% | 0.510% | 54742 | 279 | 0.000% | 0.001% | TRANSVERSION | 0.5097 | 672 | 1 | 2 | 0.142857 |
| 673 | 99.692% | 0.306% | 52596 | 161 | 0.021% | 0.006% | TRANSITION | 0.3061 | 673 | 1 | 2 | 0.142857 |
| 674 | 91.000% | 8.974% | 66390 | 5958 | 0.003% | 0.000% | TRANSVERSION | 8.9742 | 674 | 1 | 4 | 1 |
| 675 | 86.044% | 13.931% | 36473 | 5081 | 0.004% | 0.000% | TRANSVERSION | 13.9310 | 675 | 1 | 4 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 676 | 92.177% | 7.805% | 27791 | 2169 | 0.001% | 0.000% | TRANSVERSION | 7.8047 | 676 | 1 | 4 | 1 |
| 677 | 99.969% | 0.001% | 81844 | 1 | 0.001% | 0.001% | TRANSVERSION | 0.0012 | 677 | 0 | 4 | 0.142857 |
| 678 | 99.975% | 0.000% | 72437 | 0 | 0.001% | 0.001% | TRANSVERSION | 0.0000 | 678 | 0 | 4 | 0.142857 |
| 679 | 99.885% | 0.067% | 96679 | 65 | 0.002% | 0.002% | TRANSVERSION | 0.0672 | 679 | 1 | 4 | 0.142857 |
| 680 | 99.941% | 0.051% | 25271 | 13 | 0.036% | 0.014% | TRANSITION | 0.0514 | 680 | 0 | 1 | 1 |
| 681 | 99.974% | 0.026% | 53764 | 14 | 0.025% | 0.008% | TRANSITION | 0.0260 | 681 | 0 | 2 | 1 |
| 682 | 99.994% | 0.000% | 31176 | 0 | 0.016% | 0.013% | TRANSITION | 0.0000 | 682 | 0 | 1 | 0.5 |
| 683 | 99.954% | 0.041% | 86086 | 35 | 0.043% | 0.012% | TRANSITION | 0.0407 | 683 | 0 | 1 | 0.5 |
| 684 | 99.959% | 0.034% | 70312 | 24 | 0.037% | 0.009% | TRANSITION | 0.0341 | 684 | 0 | 4 | 1 |
| 685 | 99.973% | 0.000% | 33648 | 0 | 0.002% | 0.003% | TRANSVERSION | 0.0000 | 685 | 0 | 4 | 1 |
| 686 | 99.962% | 0.038% | 13078 | 5 | 0.048% | 0.022% | TRANSITION | 0.0382 | 686 | 0 | 4 | 1 |
| 687 | 99.951% | 0.038% | 77292 | 29 | 0.043% | 0.014% | TRANSITION | 0.0375 | 687 | 0 | 4 | 1 |
| 688 | 99.969% | 0.000% | 49154 | 0 | 0.000% | 0.001% | TRANSVERSION | 0.0000 | 688 | 0 | 4 | 1 |
| 689 | 99.983% | 0.015% | 40103 | 6 | 0.028% | 0.010% | TRANSITION | 0.0150 | 689 | 0 | 4 | 0.5 |
| 690 | 99.977% | 0.003% | 89962 | 3 | 0.004% | 0.002% | TRANSVERSION | 0.0033 | 690 | 0 | 4 | 0.5 |
| 691 | 99.977% | 0.004% | 81389 | 3 | 0.004% | 0.003% | TRANSVERSION | 0.0037 | 691 | 0 | 4 | 0.5 |
| 692 | 99.977% | 0.023% | 69281 | 16 | 0.028% | 0.009% | TRANSITION | 0.0231 | 692 | 0 | 4 | 0.5 |
| 693 | 99.961% | 0.039% | 46090 | 18 | 0.031% | 0.007% | TRANSITION | 0.0391 | 693 | 0 | 4 | 0.5 |
| 694 | 99.968% | 0.032% | 9416 | 3 | 0.053% | 0.042% | TRANSITION | 0.0319 | 694 | 0 | 4 | 0.5 |
| 695 | 99.969% | 0.004% | 79850 | 3 | 0.003% | 0.002% | TRANSVERSION | 0.0038 | 695 | 0 | 4 | 0.5 |
| 696 | 99.975% | 0.025% | 60408 | 15 | 0.034% | 0.009% | TRANSITION | 0.0248 | 696 | 0 | 4 | 0.5 |
| 697 | 99.957% | 0.004% | 103482 | 4 | 0.002% | 0.001% | TRANSVERSION | 0.0039 | 697 | 0 | 4 | 0.5 |
| 698 | 99.963% | 0.026% | 50838 | 13 | 0.015% | 0.006% | TRANSITION | 0.0256 | 698 | 0 | 2 | 0.5 |
| 699 | 99.952% | 0.044% | 49653 | 22 | 0.040% | 0.019% | TRANSITION | 0.0443 | 699 | 0 | 4 | 0.5 |
| 700 | 99.929% | 0.069% | 97182 | 67 | 0.051% | 0.012% | TRANSITION | 0.0689 | 700 | 0 | 4 | 0.25 |
| 701 | 99.963% | 0.035% | 37509 | 13 | 0.042% | 0.010% | TRANSITION | 0.0347 | 701 | 0 | 4 | 0.25 |
| 702 | 99.889% | 0.085% | 48512 | 41 | 0.001% | 0.001% | TRANSVERSION | 0.0845 | 702 | 1 | 4 | 0.25 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 703 | 99.976% | 0.020% | 29477 | 6 | 0.020% | 0.010% | TRANSITION | 0.0204 | 703 | 0 | 4 | 0.75 |
| 704 | 99.924% | 0.067% | 77837 | 52 | 0.055% | 0.010% | TRANSITION | 0.0668 | 704 | 0 | 4 | 0.75 |
| 705 | 99.950% | 0.050% | 12050 | 6 | 0.048% | 0.026% | TRANSITION | 0.0498 | 705 | 0 | 4 | 0.5 |
| 706 | 99.976% | 0.006% | 84591 | 5 | 0.005% | 0.002% | TRANSVERSION | 0.0059 | 706 | 0 | 3 | 0.75 |
| 707 | 99.977% | 0.012% | 64964 | 8 | 0.007% | 0.005% | TRANSVERSION | 0.0123 | 707 | 0 | 4 | 0.75 |
| 708 | 99.969% | 0.031% | 3262 | 1 | 0.031% | 0.032% | TRANSITION | 0.0307 | 708 | 0 | 4 | 0.25 |
| 709 | 99.977% | 0.021% | 60894 | 13 | 0.044% | 0.013% | TRANSITION | 0.0213 | 709 | 0 | 4 | 0.25 |
| 710 | 99.813% | 0.184% | 34291 | 63 | 0.041% | 0.013% | TRANSITION | 0.1837 | 710 | 1 | 4 | 0.25 |
| 711 | 99.968% | 0.027% | 40710 | 11 | 0.042% | 0.009% | TRANSITION | 0.0270 | 711 | 0 | 4 | 0.25 |
| 712 | 99.971% | 0.025% | 48639 | 12 | 0.044% | 0.012% | TRANSITION | 0.0247 | 712 | 0 | 4 | 0.25 |
| 713 | 99.925% | 0.062% | 16058 | 10 | 0.063% | 0.035% | TRANSITION | 0.0623 | 713 | 0 | 4 | 0.25 |
| 714 | 99.981% | 0.004% | 25918 | 1 | 0.003% | 0.004% | TRANSVERSION | 0.0039 | 714 | 0 | 1 | 1 |
| 715 | 99.969% | 0.003% | 35877 | 1 | 0.003% | 0.002% | TRANSVERSION | 0.0028 | 715 | 0 | 2 | 1 |
| 716 | 99.963% | 0.005% | 59159 | 3 | 0.000% | 0.001% | TRANSVERSION | 0.0051 | 716 | 0 | 4 | 1 |
| 717 | 99.966% | 0.002% | 53621 | 1 | 0.002% | 0.002% | TRANSVERSION | 0.0019 | 717 | 0 | 4 | 1 |
| 718 | 100.000% | 0.000% | 6231 | 0 | 0.003% | 0.006% | TRANSVERSION | 0.0000 | 718 | 0 | 4 | 1 |
| 719 | 99.945% | 0.000% | 65283 | 0 | 0.002% | 0.002% | TRANSVERSION | 0.0000 | 719 | 0 | 4 | 1 |
| 720 | 99.963% | 0.007% | 29539 | 2 | 0.005% | 0.003% | TRANSVERSION | 0.0068 | 720 | 0 | 4 | 1 |
| 721 | 99.971% | 0.000% | 10349 | 0 | 0.002% | 0.004% | TRANSVERSION | 0.0000 | 721 | 0 | 4 | 1 |
| 722 | 99.901% | 0.099% | 5070 | 5 | 0.057% | 0.039% | TRANSITION | 0.0986 | 722 | 0 | 4 | 1 |
| 723 | 99.964% | 0.000% | 41536 | 0 | 0.002% | 0.003% | TRANSVERSION | 0.0000 | 723 | 0 | 4 | 1 |
| 724 | 99.957% | 0.041% | 51540 | 21 | 0.039% | 0.013% | TRANSITION | 0.0407 | 724 | 0 | 4 | 1 |
| 725 | 99.958% | 0.002% | 52391 | 1 | 0.005% | 0.003% | TRANSVERSION | 0.0019 | 725 | 0 | 4 | 0.666667 |
| 726 | 99.959% | 0.004% | 46624 | 2 | 0.002% | 0.002% | TRANSVERSION | 0.0043 | 726 | 0 | 4 | 0.333333 |
| 727 | 99.977% | 0.008% | 13272 | 1 | 0.008% | 0.006% | TRANSVERSION | 0.0075 | 727 | 0 | 4 | 0.333333 |
| 728 | 99.754% | 0.239% | 41862 | 100 | 0.026% | 0.011% | TRANSITION | 0.2389 | 728 | 1 | 1 | 1 |
| 729 | 99.799% | 0.198% | 38840 | 77 | 0.033% | 0.013% | TRANSITION | 0.1983 | 729 | 1 | 2 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 730 | 99.732% | 0.262% | 33950 | 89 | 0.026% | 0.011% | TRANSITION | 0.2622 | 730 | 1 | 2 | 1 |
| 731 | 99.447% | 0.535% | 31985 | 171 | 0.003% | 0.003% | TRANSVERSION | 0.5346 | 731 | 1 | 4 | 1 |
| 732 | 99.692% | 0.308% | 9088 | 28 | 0.022% | 0.016% | TRANSITION | 0.3081 | 732 | 1 | 4 | 1 |
| 733 | 99.710% | 0.283% | 55830 | 158 | 0.022% | 0.007% | TRANSITION | 0.2830 | 733 | 1 | 4 | 1 |
| 734 | 99.882% | 0.118% | 1701 | 2 | 0.011% | 0.023% | TRANSITION | 0.1176 | 734 | 0 | 4 | 1 |
| 735 | 99.422% | 0.578% | 1903 | 11 | 0.057% | 0.053% | TRANSITION | 0.5780 | 735 | 1 | 4 | 1 |
| 736 | 99.557% | 0.435% | 12648 | 55 | 0.035% | 0.014% | TRANSITION | 0.4349 | 736 | 1 | 4 | 1 |
| 737 | 99.766% | 0.211% | 50771 | 107 | 0.002% | 0.002% | TRANSVERSION | 0.2108 | 737 | 1 | 4 | 1 |
| 738 | 99.859% | 0.141% | 1416 | 2 | 0.002% | 0.010% | TRANSITION | 0.1412 | 738 | 1 | 4 | 1 |
| 739 | 99.636% | 0.347% | 23047 | 80 | 0.058% | 0.023% | TRANSITION | 0.3471 | 739 | 1 | 4 | 1 |
| 740 | 99.231% | 0.752% | 11441 | 86 | 0.001% | 0.002% | TRANSVERSION | 0.7517 | 740 | 1 | 4 | 1 |
| 741 | 99.955% | 0.000% | 17693 | 0 | 0.000% | 0.001% | TRANSVERSION | 0.0000 | 741 | 0 | 4 | 0.25 |
| 742 | 99.961% | 0.031% | 45836 | 14 | 0.029% | 0.012% | TRANSITION | 0.0305 | 742 | 0 | 4 | 0.25 |
| 743 | 99.982% | 0.000% | 5460 | 0 | 0.003% | 0.006% | TRANSVERSION | 0.0000 | 743 | 0 | 4 | 0.25 |
| 744 | 99.950% | 0.045% | 41799 | 19 | 0.051% | 0.021% | TRANSITION | 0.0455 | 744 | 0 | 4 | 0.25 |
| 745 | 99.955% | 0.010% | 73119 | 7 | 0.007% | 0.003% | TRANSVERSION | 0.0096 | 745 | 0 | 4 | 1 |
| 746 | 99.961% | 0.002% | 62233 | 1 | 0.001% | 0.001% | TRANSVERSION | 0.0016 | 746 | 0 | 1 | 1 |
| 747 | 99.965% | 0.002% | 56886 | 1 | 0.018% | 0.083% | TRANSVERSION | 0.0018 | 747 | 0 | 1 | 1 |
| 748 | 99.990% | 0.010% | 85981 | 9 | 0.013% | 0.005% | TRANSITION | 0.0105 | 748 | 0 | 1 | 1 |
| 749 | 99.951% | 0.044% | 40748 | 18 | 0.042% | 0.013% | TRANSITION | 0.0442 | 749 | 0 | 2 | 0.25 |
| 750 | 99.953% | 0.042% | 64465 | 27 | 0.033% | 0.012% | TRANSITION | 0.0419 | 750 | 0 | 1 | 0.25 |
| 751 | 99.960% | 0.005% | 42095 | 2 | 0.002% | 0.002% | TRANSITION | 0.0048 | 751 | 0 | 1 | 0.25 |
| 752 | 99.967% | 0.000% | 9050 | 0 | 0.003% | 0.005% | TRANSVERSION | 0.0000 | 752 | 0 | 4 | 1 |
| 753 | 99.943% | 0.003% | 36934 | 1 | 0.002% | 0.003% | TRANSVERSION | 0.0027 | 753 | 0 | 4 | 1 |
| 754 | 99.964% | 0.005% | 60381 | 3 | 0.006% | 0.003% | TRANSVERSION | 0.0050 | 754 | 0 | 4 | 1 |
| 755 | 99.982% | 0.000% | 27254 | 0 | 0.001% | 0.002% | TRANSVERSION | 0.0000 | 755 | 0 | 4 | 1 |
| 756 | 99.955% | 0.002% | 64942 | 1 | 0.003% | 0.002% | TRANSVERSION | 0.0015 | 756 | 0 | 4 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 757 | 99.967% | 0.003% | 60198 | 2 | 0.004% | 0.003% | TRANSVERSION | 0.0033 | 757 | 0 | 4 | 0.25 |
| 758 | 99.987% | 0.001% | 130760 | 1 | 0.001% | 0.001% | TRANSVERSION | 0.0008 | 758 | 0 | 4 | 0.25 |
| 759 | 99.978% | 0.000% | 76473 | 0 | 0.000% | 0.001% | TRANSVERSION | 0.0000 | 759 | 0 | 4 | 0.25 |
| 760 | 99.955% | 0.000% | 50670 | 0 | 0.002% | 0.001% | TRANSVERSION | 0.0000 | 760 | 0 | 4 | 0.25 |
| 761 | 99.976% | 0.000% | 16811 | 0 | 0.004% | 0.004% | TRANSVERSION | 0.0000 | 761 | 0 | 4 | 0.25 |
| 762 | 99.960% | 0.000% | 12424 | 0 | 0.004% | 0.005% | TRANSVERSION | 0.0000 | 762 | 0 | 4 | 0.25 |
| 763 | 99.944% | 0.000% | 12439 | 0 | 0.003% | 0.004% | TRANSVERSION | 0.0000 | 763 | 0 | 4 | 0.25 |
| 764 | 99.979% | 0.002% | 61410 | 1 | 0.003% | 0.002% | TRANSVERSION | 0.0016 | 764 | 0 | 4 | 0.5 |
| 765 | 95.402% | 4.571% | 7525 | 344 | 0.007% | 0.158% | TRANSVERSION | 4.5714 | 765 | 1 | 2 | 1 |
| 766 | 98.987% | 0.987% | 67498 | 666 | 0.003% | 0.034% | TRANSVERSION | 0.9867 | 766 | 1 | 2 | 1 |
| 767 | 98.928% | 1.072% | 12037 | 129 | 0.012% | 0.037% | TRANSITION | 1.0717 | 767 | 1 | 1 | 1 |
| 768 | 99.542% | 0.455% | 35824 | 163 | 0.032% | 0.018% | TRANSITION | 0.4550 | 768 | 1 | 2 | 1 |
| 769 | 98.901% | 1.098% | 57579 | 632 | 0.016% | 0.038% | TRANSITION | 1.0976 | 769 | 1 | 2 | 1 |
| 770 | 99.912% | 0.081% | 60218 | 49 | 0.030% | 0.010% | TRANSITION | 0.0814 | 770 | 1 | 2 | 0.25 |
| 771 | 99.137% | 0.838% | 43432 | 364 | 0.004% | 0.029% | TRANSVERSION | 0.8381 | 771 | 1 | 4 | 1 |
| 772 | 98.554% | 1.422% | 66601 | 947 | 0.005% | 0.049% | TRANSVERSION | 1.4219 | 772 | 1 | 4 | 1 |
| 773 | 98.607% | 1.365% | 61972 | 846 | 0.004% | 0.047% | TRANSVERSION | 1.3651 | 773 | 1 | 4 | 1 |
| 774 | 99.962% | 0.011% | 61137 | 7 | 0.004% | 0.002% | TRANSVERSION | 0.0115 | 774 | 0 | 4 | 0.5 |
| 775 | 99.950% | 0.039% | 46317 | 18 | 0.005% | 0.003% | TRANSVERSION | 0.0389 | 775 | 1 | 4 | 0.5 |
| 776 | 99.931% | 0.060% | 31766 | 19 | 0.003% | 0.004% | TRANSVERSION | 0.0598 | 776 | 1 | 4 | 0.5 |
| 777 | 99.625% | 0.335% | 40251 | 135 | 0.002% | 0.012% | TRANSVERSION | 0.3354 | 777 | 1 | 4 | 0.25 |
| 778 | 99.944% | 0.041% | 77450 | 32 | 0.001% | 0.002% | TRANSVERSION | 0.0413 | 778 | 1 | 4 | 0.25 |
| 779 | 99.700% | 0.265% | 49036 | 130 | 0.004% | 0.009% | TRANSVERSION | 0.2651 | 779 | 1 | 4 | 0.5 |
| 780 | 99.633% | 0.336% | 54845 | 218 | 0.003% | 0.012% | TRANSVERSION | 0.3362 | 780 | 1 | 4 | 0.5 |
| 781 | 99.966% | 0.012% | 58742 | 7 | 0.001% | 0.001% | TRANSVERSION | 0.0119 | 781 | 1 | 3 | 0.25 |
| 782 | 99.753% | 0.229% | 51517 | 118 | 0.003% | 0.008% | TRANSVERSION | 0.2291 | 782 | 1 | 4 | 0.25 |
| 783 | 99.982% | 0.001% | 72741 | 1 | 0.001% | 0.001% | TRANSVERSION | 0.0014 | 783 | 0 | 4 | 0.25 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 784 | 99.963% | 0.037% | 46235 | 17 | 0.011% | 0.006% | TRANSITION | 0.0368 | 784 | 1 | 1 | 1 |
| 785 | 99.951% | 0.045% | 89461 | 40 | 0.028% | 0.007% | TRANSITION | 0.0447 | 785 | 0 | 1 | 1 |
| 786 | 99.958% | 0.035% | 86328 | 30 | 0.012% | 0.004% | TRANSITION | 0.0348 | 786 | 1 | 2 | 1 |
| 787 | 99.970% | 0.028% | 72443 | 20 | 0.024% | 0.011% | TRANSITION | 0.0276 | 787 | 0 | 1 | 0.75 |
| 788 | 99.957% | 0.017% | 64911 | 11 | 0.002% | 0.002% | TRANSVERSION | 0.0169 | 788 | 1 | 2 | 1 |
| 789 | 99.935% | 0.011% | 27701 | 3 | 0.002% | 0.002% | TRANSVERSION | 0.0108 | 789 | 0 | 1 | 1 |
| 790 | 99.975% | 0.006% | 79790 | 5 | 0.001% | 0.002% | TRANSVERSION | 0.0063 | 790 | 0 | 2 | 0.5 |
| 791 | 99.970% | 0.001% | 76137 | 1 | 0.002% | 0.002% | TRANSVERSION | 0.0013 | 791 | 0 | 2 | 0.25 |
| 792 | 99.919% | 0.045% | 101211 | 46 | 0.001% | 0.003% | TRANSVERSION | 0.0455 | 792 | 1 | 4 | 1 |
| 793 | 99.942% | 0.023% | 17331 | 4 | 0.001% | 0.001% | TRANSVERSION | 0.0231 | 793 | 1 | 4 | 1 |
| 794 | 99.971% | 0.000% | 68959 | 0 | 0.005% | 0.004% | TRANSVERSION | 0.0000 | 794 | 0 | 4 | 0.25 |
| 795 | 99.951% | 0.003% | 36931 | 1 | 0.000% | 0.001% | TRANSVERSION | 0.0027 | 795 | 0 | 4 | 0.25 |
| 796 | 99.976% | 0.000% | 21146 | 0 | 0.001% | 0.002% | TRANSVERSION | 0.0000 | 796 | 0 | 3 | 0.25 |
| 797 | 99.929% | 0.014% | 84985 | 12 | 0.001% | 0.002% | TRANSVERSION | 0.0141 | 797 | 1 | 4 | 0.25 |
| 798 | 99.947% | 0.000% | 62273 | 0 | 0.004% | 0.003% | TRANSVERSION | 0.0000 | 798 | 0 | 4 | 0.25 |
| 799 | 99.963% | 0.006% | 69390 | 4 | 0.008% | 0.003% | TRANSVERSION | 0.0058 | 799 | 0 | 4 | 0.25 |
| 800 | 99.948% | 0.019% | 93840 | 18 | 0.000% | 0.001% | TRANSVERSION | 0.0192 | 800 | 0 | 4 | 0.5 |
| 801 | 99.959% | 0.027% | 7366 | 2 | 0.001% | 0.001% | TRANSVERSION | 0.0272 | 801 | 1 | 4 | 0.5 |
| 802 | 99.970% | 0.000% | 81135 | 0 | 0.030% | 0.009% | TRANSVERSION | 0.0000 | 802 | 0 | 3 | 0.25 |
| 803 | 99.952% | 0.013% | 76660 | 10 | 0.004% | 0.005% | TRANSVERSION | 0.0130 | 803 | 0 | 1 | 1 |
| 804 | 99.952% | 0.000% | 26938 | 0 | 0.003% | 0.009% | TRANSVERSION | 0.0000 | 804 | 0 | 1 | 1 |
| 805 | 99.969% | 0.012% | 16036 | 2 | 0.001% | 0.002% | TRANSVERSION | 0.0125 | 805 | 0 | 2 | 1 |
| 806 | 99.985% | 0.000% | 53610 | 0 | 0.025% | 0.007% | TRANSVERSION | 0.0000 | 806 | 0 | 2 | 1 |
| 807 | 99.963% | 0.032% | 81735 | 26 | 0.001% | 0.002% | TRANSITION | 0.0318 | 807 | 0 | 4 | 0.5 |
| 808 | 99.959% | 0.000% | 29424 | 0 | 0.029% | 0.011% | TRANSITION | 0.0000 | 808 | 0 | 4 | 1 |
| 809 | 99.949% | 0.048% | 73108 | 35 | 0.002% | 0.002% | TRANSVERSION | 0.0479 | 809 | 0 | 4 | 1 |
| 810 | 99.959% | 0.001% | 115923 | 1 | | | TRANSVERSION | 0.0009 | 810 | 0 | 3 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 811 | 99.973% | 0.024% | 67309 | 16 | 0.041% | 0.014% | TRANSITION | 0.0238 | 811 | 0 | 4 | 1 |
| 812 | 99.958% | 0.000% | 71604 | 0 | 0.001% | 0.002% | TRANSVERSION | 0.0000 | 812 | 0 | 4 | 1 |
| 813 | 99.971% | 0.001% | 80208 | 1 | 0.001% | 0.001% | TRANSVERSION | 0.0012 | 813 | 0 | 4 | 0.5 |
| 814 | 99.964% | 0.030% | 126317 | 38 | 0.040% | 0.011% | TRANSITION | 0.0301 | 814 | 0 | 4 | 0.5 |
| 815 | 99.967% | 0.032% | 98576 | 32 | 0.038% | 0.013% | TRANSITION | 0.0325 | 815 | 0 | 4 | 0.5 |
| 816 | 99.970% | 0.001% | 79622 | 1 | 0.002% | 0.002% | TRANSVERSION | 0.0013 | 816 | 0 | 4 | 0.5 |
| 817 | 99.976% | 0.001% | 106264 | 1 | 0.001% | 0.001% | TRANSVERSION | 0.0009 | 817 | 0 | 4 | 0.5 |
| 818 | 99.954% | 0.040% | 109650 | 44 | 0.038% | 0.011% | TRANSITION | 0.0401 | 818 | 0 | 4 | 1 |
| 819 | 99.964% | 0.032% | 99924 | 32 | 0.010% | 0.004% | TRANSITION | 0.0320 | 819 | 1 | 4 | 0.5 |
| 820 | 99.951% | 0.045% | 44558 | 20 | 0.025% | 0.011% | TRANSITION | 0.0449 | 820 | 0 | 4 | 1 |
| 821 | 99.973% | 0.000% | 7295 | 0 | 0.003% | 0.009% | TRANSVERSION | 0.0000 | 821 | 0 | 4 | 0.5 |
| 822 | 94.168% | 5.816% | 31055 | 1806 | 0.040% | 0.200% | TRANSITION | 5.8155 | 822 | 1 | 1 | 1 |
| 823 | 96.913% | 3.084% | 31326 | 966 | 0.037% | 0.106% | TRANSITION | 3.0837 | 823 | 1 | 2 | 1 |
| 824 | 90.657% | 9.343% | 4688 | 438 | 0.047% | 0.323% | TRANSITION | 9.3430 | 824 | 1 | 4 | 1 |
| 825 | 95.646% | 4.327% | 3767 | 163 | 0.008% | 0.149% | TRANSVERSION | 4.3271 | 825 | 1 | 4 | 1 |
| 826 | 96.985% | 2.984% | 16054 | 479 | 0.007% | 0.103% | TRANSVERSION | 2.9837 | 826 | 1 | 4 | 1 |
| 827 | 99.041% | 0.939% | 60374 | 567 | 0.007% | 0.032% | TRANSVERSION | 0.9392 | 827 | 1 | 4 | 1 |
| 828 | 93.279% | 6.680% | 7261 | 485 | 0.011% | 0.230% | TRANSVERSION | 6.6795 | 828 | 1 | 4 | 1 |
| 829 | 99.852% | 0.144% | 82710 | 119 | 0.027% | 0.008% | TRANSITION | 0.1439 | 829 | 1 | 4 | 0.25 |
| 830 | 99.854% | 0.125% | 57696 | 72 | 0.003% | 0.005% | TRANSVERSION | 0.1248 | 830 | 1 | 4 | 0.25 |
| 831 | 99.912% | 0.082% | 67315 | 55 | 0.017% | 0.008% | TRANSITION | 0.0817 | 831 | 1 | 4 | 0.25 |
| 832 | 99.936% | 0.064% | 21844 | 14 | 0.029% | 0.012% | TRANSITION | 0.0641 | 832 | 0 | 4 | 0.25 |
| 833 | 99.777% | 0.199% | 29650 | 59 | 0.004% | 0.007% | TRANSVERSION | 0.1990 | 833 | 1 | 4 | 0.25 |
| 834 | 99.975% | 0.024% | 66806 | 16 | 0.012% | 0.005% | TRANSITION | 0.0240 | 834 | 0 | 4 | 0.25 |
| 835 | 98.602% | 1.371% | 86352 | 1184 | 0.007% | 0.047% | TRANSVERSION | 1.3711 | 835 | 1 | 4 | 0.25 |
| 836 | 99.947% | 0.053% | 15165 | 8 | 0.028% | 0.015% | TRANSITION | 0.0528 | 836 | 0 | 4 | 0.25 |
| 837 | 99.867% | 0.110% | 52496 | 58 | 0.007% | 0.005% | TRANSVERSION | 0.1105 | 837 | 1 | 4 | 0.25 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 838 | 99.954% | 0.044% | 93572 | 41 | 0.039% | 0.009% | TRANSITION | 0.0438 | 838 | 0 | 4 | 0.25 |
| 839 | 99.974% | 0.026% | 15226 | 4 | 0.028% | 0.016% | TRANSITION | 0.0263 | 839 | 0 | 4 | 0.25 |
| 840 | 99.982% | 0.014% | 22020 | 3 | 0.029% | 0.018% | TRANSITION | 0.0136 | 840 | 0 | 2 | 1 |
| 841 | 99.980% | 0.020% | 5071 | 1 | 0.042% | 0.027% | TRANSITION | 0.0197 | 841 | 0 | 1 | 1 |
| 842 | 99.942% | 0.052% | 34529 | 18 | 0.023% | 0.012% | TRANSITION | 0.0521 | 842 | 0 | 1 | 1 |
| 843 | 99.990% | 0.000% | 69072 | 0 | 0.000% | 0.001% | TRANSVERSION | 0.0000 | 843 | 0 | 2 | 1 |
| 844 | 99.979% | 0.000% | 92375 | 0 | 0.000% | 0.001% | TRANSVERSION | 0.0000 | 844 | 0 | 4 | 1 |
| 845 | 99.974% | 0.006% | 15463 | 1 | 0.007% | 0.008% | TRANSVERSION | 0.0065 | 845 | 0 | 4 | 1 |
| 846 | 99.982% | 0.000% | 54778 | 0 | 0.003% | 0.002% | TRANSVERSION | 0.0000 | 846 | 0 | 4 | 1 |
| 847 | 100.000% | 0.000% | 176 | 0 | 0.000% | 0.000% | TRANSVERSION | 0.0000 | 847 |  | 3 | 1 |
| 848 | 99.972% | 0.000% | 53866 | 0 | 0.003% | 0.002% | TRANSVERSION | 0.0000 | 848 | 0 | 4 | 1 |
| 849 | 99.973% | 0.003% | 63569 | 2 | 0.001% | 0.001% | TRANSVERSION | 0.0031 | 849 | 0 | 4 | 0.5 |
| 850 | 99.950% | 0.003% | 61953 | 2 | 0.004% | 0.003% | TRANSVERSION | 0.0032 | 850 | 0 | 4 | 0.5 |
| 851 | 99.961% | 0.036% | 94777 | 34 | 0.028% | 0.010% | TRANSITION | 0.0359 | 851 | 0 | 4 | 0.5 |
| 852 | 99.985% | 0.015% | 20658 | 3 | 0.010% | 0.006% | TRANSITION | 0.0145 | 852 | 0 | 3 | 0.5 |
| 853 | 99.964% | 0.031% | 61106 | 19 | 0.027% | 0.010% | TRANSITION | 0.0311 | 853 | 0 | 4 | 0.5 |
| 854 | 99.936% | 0.055% | 42030 | 23 | 0.063% | 0.013% | TRANSITION | 0.0547 | 854 | 0 | 4 | 0.5 |
| 855 | 99.960% | 0.035% | 96130 | 34 | 0.024% | 0.011% | TRANSITION | 0.0354 | 855 | 0 | 4 | 0.5 |
| 856 | 99.957% | 0.043% | 18555 | 8 | 0.030% | 0.013% | TRANSITION | 0.0431 | 856 | 0 | 3 | 0.5 |
| 857 | 99.976% | 0.004% | 71157 | 3 | 0.001% | 0.001% | TRANSVERSION | 0.0042 | 857 | 0 | 4 | 0.5 |
| 858 | 99.978% | 0.018% | 72628 | 13 | 0.027% | 0.009% | TRANSITION | 0.0179 | 858 | 0 | 4 | 0.5 |
| 859 | 94.143% | 5.849% | 37629 | 2201 | 0.040% | 0.201% | TRANSITION | 5.8492 | 859 | 1 | 2 | 1 |
| 860 | 94.559% | 5.401% | 29975 | 1619 | 0.009% | 0.186% | TRANSVERSION | 5.4012 | 860 | 1 | 1 | 1 |
| 861 | 96.061% | 3.894% | 15561 | 606 | 0.009% | 0.134% | TRANSVERSION | 3.8944 | 861 | 1 | 2 | 1 |
| 862 | 97.696% | 2.299% | 65975 | 1517 | 0.034% | 0.079% | TRANSITION | 2.2994 | 862 | 1 | 2 | 1 |
| 863 | 97.714% | 2.255% | 65998 | 1488 | 0.006% | 0.078% | TRANSITION | 2.2546 | 863 | 1 | 2 | 1 |
| 864 | 99.922% | 0.069% | 43704 | 30 | 0.033% | 0.011% | TRANSITION | 0.0686 | 864 | 0 | 1 | 0.25 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 865 | 92.074% | 7.900% | 52788 | 4170 | 0.011% | 0.272% | TRANSVERSION | 7.8995 | 865 | 1 | 4 | 1 |
| 866 | 90.824% | 9.162% | 20684 | 1895 | 0.002% | 0.001% | TRANSVERSION | 9.1617 | 866 | 1 | 3 | 1 |
| 867 | 95.687% | 4.287% | 62277 | 2670 | 0.009% | 0.148% | TRANSVERSION | 4.2873 | 867 | 1 | 4 | 1 |
| 868 | 96.466% | 3.506% | 28098 | 985 | 0.006% | 0.121% | TRANSVERSION | 3.5056 | 868 | 1 | 4 | 1 |
| 869 | 96.667% | 3.333% | 60 | 2 | 0.044% | 0.235% | TRANSITION | 3.3333 | 869 | | 4 | 0.75 |
| 870 | 97.541% | 2.454% | 84920 | 2084 | 0.041% | 0.084% | TRANSITION | 2.4541 | 870 | 1 | 4 | 0.75 |
| 871 | 98.094% | 1.903% | 70516 | 1342 | 0.054% | 0.065% | TRANSITION | 1.9031 | 871 | 1 | 4 | 0.25 |
| 872 | 99.616% | 0.364% | 55191 | 201 | 0.002% | 0.013% | TRANSVERSION | 0.3642 | 872 | 1 | 4 | 0.25 |
| 873 | 99.447% | 0.528% | 55475 | 293 | 0.002% | 0.018% | TRANSVERSION | 0.5282 | 873 | 1 | 4 | 0.25 |
| 874 | 98.619% | 1.370% | 64097 | 878 | 0.006% | 0.047% | TRANSVERSION | 1.3698 | 874 | 1 | 4 | 0.25 |
| 875 | 99.743% | 0.257% | 26021 | 67 | 0.027% | 0.015% | TRANSITION | 0.2575 | 875 | 1 | 4 | 0.25 |
| 876 | 99.762% | 0.163% | 21426 | 35 | 0.004% | 0.008% | TRANSVERSION | 0.1634 | 876 | 1 | 4 | 0.25 |
| 877 | 99.694% | 0.256% | 75514 | 193 | 0.002% | 0.009% | TRANSVERSION | 0.2556 | 877 | 1 | 4 | 0.25 |
| 878 | 99.635% | 0.330% | 60620 | 200 | 0.002% | 0.011% | TRANSVERSION | 0.3299 | 878 | 1 | 4 | 0.25 |
| 879 | 99.762% | 0.233% | 41216 | 96 | 0.049% | 0.016% | TRANSITION | 0.2329 | 879 | 1 | 4 | 1 |
| 880 | 99.531% | 0.448% | 56451 | 253 | 0.002% | 0.015% | TRANSVERSION | 0.4482 | 880 | 1 | 1 | 1 |
| 881 | 99.934% | 0.060% | 51332 | 31 | 0.044% | 0.018% | TRANSVERSION | 0.0604 | 881 | 0 | 2 | 0.75 |
| 882 | 99.976% | 0.002% | 49566 | 1 | 0.003% | 0.002% | TRANSVERSION | 0.0020 | 882 | 0 | 1 | 0.25 |
| 883 | 99.957% | 0.018% | 32676 | 6 | 0.001% | 0.002% | TRANSVERSION | 0.0184 | 883 | 1 | 4 | 1 |
| 884 | 99.529% | 0.399% | 40096 | 160 | 0.002% | 0.014% | TRANSVERSION | 0.3990 | 884 | 1 | 4 | 1 |
| 885 | 99.972% | 0.005% | 88051 | 4 | 0.005% | 0.003% | TRANSVERSION | 0.0045 | 885 | 0 | 4 | 0.75 |
| 886 | 99.956% | 0.000% | 47765 | 0 | 0.002% | 0.002% | TRANSVERSION | 0.0000 | 886 | 0 | 4 | 0.75 |
| 887 | 99.883% | 0.000% | 853 | 0 | 0.018% | 0.052% | TRANSVERSION | 0.0000 | 887 | | 4 | 1 |
| 888 | 99.914% | 0.000% | 23234 | 0 | 0.001% | 0.003% | TRANSVERSION | 0.0000 | 888 | 0 | 4 | 1 |
| 889 | 99.975% | 0.019% | 31715 | 6 | 0.036% | 0.023% | TRANSITION | 0.0189 | 889 | 0 | 4 | 1 |
| 890 | 99.932% | 0.060% | 13229 | 8 | 0.033% | 0.026% | TRANSITION | 0.0605 | 890 | 0 | 4 | 1 |
| 891 | 99.942% | 0.054% | 53469 | 29 | 0.038% | 0.012% | TRANSITION | 0.0542 | 891 | 0 | 4 | 1 |

FIG. 20 (CONT.)

| Row number | RefVAF | MutVAF | DOR | MutDOR | NormalMean | NormalStdev | ErrorType | MutVAF_PCT | Row number | CALL | driver category | clonal ratio |
|---|---|---|---|---|---|---|---|---|---|---|---|---|
| 892 | 99.981% | 0.014% | 57417 | 8 | 0.015% | 0.007% | TRANSITION | 0.0139 | 892 | 0 | 4 | 0.25 |
| 893 | NaN | NaN | 0 | NaN | 2.751% | 5.365% | TRANSITION | #VALUE! | 893 | | 4 | 0.25 |
| 894 | 99.980% | 0.003% | 39969 | 1 | 0.005% | 0.005% | TRANSVERSION | 0.0025 | 894 | 0 | 4 | 0.25 |
| 895 | 99.953% | 0.002% | 44501 | 1 | 0.003% | 0.002% | TRANSVERSION | 0.0022 | 895 | 0 | 4 | 0.25 |
| 896 | 99.995% | 0.005% | 18708 | 1 | 0.037% | 0.018% | TRANSITION | 0.0053 | 896 | 0 | 4 | 0.25 |
| 897 | 99.891% | 0.103% | 33083 | 34 | 0.046% | 0.015% | TRANSITION | 0.1028 | 897 | 0 | 4 | 0.75 |
| 898 | 99.963% | 0.003% | 34715 | 1 | 0.003% | 0.003% | TRANSVERSION | 0.0029 | 898 | 0 | 4 | 0.75 |
| 899 | 99.967% | 0.020% | 15018 | 3 | 0.038% | 0.020% | TRANSITION | 0.0200 | 899 | 0 | 1 | 1 |
| 900 | 99.933% | 0.067% | 22420 | 15 | 0.032% | 0.011% | TRANSITION | 0.0669 | 900 | 0 | 2 | 0.25 |
| 901 | 99.952% | 0.000% | 8421 | 0 | 0.001% | 0.004% | TRANSVERSION | 0.0000 | 901 | 0 | 4 | 0.5 |
| 902 | 99.980% | 0.000% | 20063 | 0 | 0.001% | 0.002% | TRANSVERSION | 0.0000 | 902 | 0 | 4 | 0.75 |
| 903 | 99.974% | 0.000% | 81736 | 0 | 0.001% | 0.001% | TRANSVERSION | 0.0000 | 903 | 0 | 4 | 0.75 |
| 904 | 99.974% | 0.002% | 58328 | 1 | 0.006% | 0.003% | TRANSVERSION | 0.0017 | 904 | 0 | 4 | 0.25 |
| 905 | 99.983% | 0.017% | 12086 | 2 | 0.016% | 0.014% | TRANSITION | 0.0165 | 905 | 0 | 4 | 1 |
| 906 | 99.960% | 0.008% | 77664 | 6 | 0.002% | 0.002% | TRANSVERSION | 0.0077 | 906 | 0 | 4 | 0.5 |
| 907 | 99.907% | 0.093% | 11862 | 11 | 0.029% | 0.019% | TRANSITION | 0.0927 | 907 | 0 | 4 | 0.25 |
| 908 | 99.931% | 0.065% | 56684 | 37 | 0.028% | 0.010% | TRANSITION | 0.0653 | 908 | 0 | 4 | 0.5 |
| 909 | 99.974% | 0.026% | 19100 | 5 | 0.078% | 0.113% | TRANSITION | 0.0262 | 909 | 0 | 4 | 0.25 |
| 910 | 99.987% | 0.010% | 111296 | 11 | 0.060% | 0.151% | TRANSITION | 0.0099 | 910 | 0 | 4 | 0.25 |
| 911 | 99.923% | 0.073% | 71154 | 52 | 0.035% | 0.012% | TRANSITION | 0.0731 | 911 | 1 | 4 | 0.25 |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 1 | 32.03 | 30.25 | 35.71 | 30.49 | C | 1a | 20 | 16 | 20.6 | 1 | U |
| 2 | 27.86 | 25.605 | 25.22 | 23.9 | C | 1a | 20 | 16 | 20.6 | 2 | U |
| 3 | 27.5 | 26.985 | 28.41 | 25.62 | C | 1a | 20 | 16 | 20.6 | 3 | U |
| 4 | 22.72 | 21.63 | 25.45 | 22.58 |   | 1a | 20 | 16 | 20.6 | 4 | U |
| 5 | 23.65 | 21.51 | 19.09 | 17.98 | C | 1a | 20 | 16 | 20.6 | 5 | U |
| 6 | 24.35 | 21.555 | 25.58 | 25.09 | C | 1a | 20 | 16 | 20.6 | 6 | U |
| 7 | 27 | 23.58 | 25.59 | 23.54 | C | 1a | 20 | 16 | 20.6 | 7 | U |
| 8 | 20.65 | 19.39 | 22.18 | 19.48 | C | 1a | 20 | 16 | 20.6 | 8 | U |
| 9 | 7.65 | 5.53 | 6.24 | 5.04 | S | 1a | 20 | 16 | 20.6 | 9 | U |
| 10 | 7.24 | 6.34 | 8.19 | 6.19 | S | 1a | 20 | 16 | 20.6 | 10 | U |
| 11 | 7.07 | 5.45 | 8.14 | 6.31 |   | 1a | 20 | 16 | 20.6 | 11 | U |
| 12 | 8.16 | 6.06 | 6.73 | 4.73 | S | 1a | 20 | 16 | 20.6 | 12 | U |
| 13 | 25.5 | 23.295 | 33.1 | 29.88 | S | 1a | 20 | 16 | 20.6 | 13 | U |
| 14 | 19.79 | 18.93 | 18.93 | 18.72 | C | 1a | 20 | 16 | 20.6 | 14 | U |
| 15 | 23.12 | 20.885 | 22.42 | 22.09 | S | 1a | 20 | 16 | 20.6 | 15 | U |
| 16 | 16.01 | 13.295 | 20.78 | 19.58 | S | 1a | 20 | 16 | 20.6 | 16 | U |
| 17 | 11.72 | 8.4 | 11.89 | 8.99 | S | 1a | 20 | 16 | 20.6 | 17 | U |
| 18 | 59.9 | 33.9975 | 65.49 | 36.92 | C | 1b | NA | 19 | 18.1 | 18 | M |
| 19 | 59.79 | 33.96 | 65.33 | 36.85 | C | 1b | NA | 19 | 18.1 | 19 | M |
| 20 | 51.02 | 34.4825 | 54.97 | 38.52 | C | 1b | NA | 19 | 18.1 | 20 | M |
| 21 | 45.21 | 30.0225 | 64.86 | 48.84 | C | 1b | NA | 19 | 18.1 | 21 | M |
| 22 | 45.03 | 29.1375 | 50.29 | 35.39 | C | 1b | NA | 19 | 18.1 | 22 | M |
| 23 | 44.4 | 29.23 | 44.56 | 28.89 | C | 1b | NA | 19 | 18.1 | 23 | M |
| 24 | 32.81 | 26.05 | 34.25 | 26.48 | C | 1b | NA | 19 | 18.1 | 24 | M |
| 25 | 25.16 | 14.3125 | 26.8 | 14.05 | C | 1b | NA | 19 | 18.1 | 25 | M |
| 26 | 23.84 | 16.8225 | 30.42 | 19.86 | C | 1b | NA | 19 | 18.1 | 26 | M |
| 27 | 20.37 | 7.64 | 13.48 | 5.98 | S | 1b | NA | 19 | 18.1 | 27 | M |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 28 | 20.08 | 9.8525 | 29.16 | 14.19 | S | 1b | NA | 19 | 18.1 | 28 | M |
| 29 | 18.55 | 9.65 | 9.73 | 6.28 | C | 1b | NA | 19 | 18.1 | 29 | M |
| 30 | 10.53 | 5.4225 | 12.28 | 6.28 | S | 1b | NA | 19 | 18.1 | 30 | M |
| 31 | 48.48 | 22.335 | 50.39 | 24.37 | C | 1b | NA | 19 | 18.1 | 31 | M |
| 32 | 20 | 14.83 | 19.88 | 16.38 | C | 1b | NA | 19 | 18.1 | 32 | M |
| 33 | 7.95 | 4.07 | 7.76 | 4.44 | S | 1b | NA | 19 | 18.1 | 33 | M |
| 34 | 9.75 | 5.785 | 12.8 | 6.37 | S | 1b | NA | 19 | 18.1 | 34 | M |
| 35 | 9.02 | 4.13 | 8.21 | 4.29 | S | 1b | NA | 19 | 18.1 | 35 | M |
| 36 | 6.42 | 1.605 | 7.57 | 1.9 |  | 1b | NA | 19 | 18.1 | 36 | M |
| 37 | 5.76 | 1.44 | 7.35 | 1.84 | S | 1b | NA | 19 | 18.1 | 37 | M |
| 38 | 11.53 | 2.93 | 13.94 | 3.49 | S | 1b | NA | 19 | 18.1 | 38 | M |
| 39 | 5.48 | 1.78 | 6.2 | 2.28 | S | 1b | NA | 19 | 18.1 | 39 | M |
| 40 | 77.53 | 50.772 | 77.37 | 51 | C | 1b | 44 | 40 | 26.1 | 40 | U |
| 41 | 74.69 | 52.464 | 79.86 | 56.55 | C | 1b | 44 | 40 | 26.1 | 41 | U |
| 42 | 51.77 | 25.298 | 49 | 25.81 | C | 1b | 44 | 40 | 26.1 | 42 | U |
| 43 | 48.76 | 26.358 | 40.91 | 17.33 | C | 1b | 44 | 40 | 26.1 | 43 | U |
| 44 | 47.37 | 24.212 | 47.46 | 22.04 | C | 1b | 44 | 40 | 26.1 | 44 | U |
| 45 | 13.98 | 9.532 | 17.64 | 11.37 | S | 1b | 44 | 40 | 26.1 | 45 | U |
| 46 | 9.69 | 1.938 | 10.64 | 2.14 | C | 1b | 44 | 40 | 26.1 | 46 | U |
| 47 | 40.98 | 30.098 | 38.21 | 27.69 | C | 1b | 44 | 40 | 26.1 | 47 | U |
| 48 | 26.82 | 18.344 | 27.37 | 17.01 | C | 1b | 44 | 40 | 26.1 | 48 | U |
| 49 | 23.58 | 14.882 | 21.02 | 13.83 | S | 1b | 44 | 40 | 26.1 | 49 | U |
| 50 | 5.14 | 1.028 | 5.77 | 1.16 | S | 1b | 44 | 40 | 26.1 | 50 | U |
| 51 | 5.99 | 1.262 | 8.35 | 1.67 | S | 1b | 44 | 40 | 26.1 | 51 | U |
| 52 | 25.45 | 6.86 | 27.55 | 7.26 | S | 1b | 44 | 40 | 26.1 | 52 | U |
| 53 | 17.46 | 5.214 | 20.65 | 5.64 | S | 1b | 44 | 40 | 26.1 | 53 | U |
| 54 | 10.08 | 3.466 | 10.18 | 3.14 | S | 1b | 44 | 40 | 26.1 | 54 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 55 | 10.51 | 2.892 | 12.5 | 5.88 | S | 1b | 44 | 40 | 26.1 | 55 | U |
| 56 | 10.01 | 2.73 | 11.46 | 3.17 |  | 1b | 44 | 40 | 26.1 | 56 | U |
| 57 | 13.61 | 2.978 | 5.56 | 1.4 | S | 1b | 44 | 40 | 26.1 | 57 | U |
| 58 | 43.75 | 34.0725 | 46.17 | 36.97 | C | 2b | 65 | 54 | 16.3 | 58 | M |
| 59 | 38.49 | 32.815 | 37.19 | 32.52 | C | 2b | 65 | 54 | 16.3 | 59 | M |
| 60 | 31.78 | 24.745 | 34.01 | 26.6 | C | 2b | 65 | 54 | 16.3 | 60 | M |
| 61 | 30.34 | 22.6625 | 34.43 | 26.53 | C | 2b | 65 | 54 | 16.3 | 61 | M |
| 62 | 17.54 | 4.5025 | 14.49 | 4.11 | S | 2b | 65 | 54 | 16.3 | 62 | M |
| 63 | 17.45 | 7.23 | 14.36 | 6.8 | S | 2b | 65 | 54 | 16.3 | 63 | M |
| 64 | 6.25 | 1.6675 | 7.08 | 1.8 | S | 2b | 65 | 54 | 16.3 | 64 | M |
| 65 | 53.07 | 37.64 | 27.14 | 23.6 | C | 2b | 65 | 54 | 16.3 | 65 | M |
| 66 | 12.22 | 9.1275 | 19.71 | 13.44 | C | 2b | 65 | 54 | 16.3 | 66 | M |
| 67 | 10.69 | 6.8425 | 9.55 | 6.58 | C | 2b | 65 | 54 | 16.3 | 67 | M |
| 68 | 25.96 | 23.9675 | 29.5 | 25.84 | C | 2b | 65 | 54 | 16.3 | 68 | M |
| 69 | 20.09 | 9.465 | 24.07 | 11.01 | S | 2b | 65 | 54 | 16.3 | 69 | M |
| 70 | 14.64 | 6.965 | 13.63 | 6.69 | S | 2b | 65 | 54 | 16.3 | 70 | M |
| 71 | 23.38 | 9.9075 | 18.88 | 8.98 | S | 2b | 65 | 54 | 16.3 | 71 | M |
| 72 | 5.33 | 1.3325 | 4.88 | 1.22 | S | 2b | 65 | 54 | 16.3 | 72 | M |
| 73 | 5.53 | 1.3825 | 5.11 | 1.28 | S | 2b | 65 | 54 | 16.3 | 73 | M |
| 74 | 5.18 | 1.295 | 3.98 | 1 | S | 2b | 65 | 54 | 16.3 | 74 | M |
| 75 | 6.75 | 1.6875 | 6.35 | 1.59 | S | 2b | 65 | 54 | 16.3 | 75 | M |
| 76 | 10.16 | 4.945 | 17.51 | 7.55 | S | 2b | 65 | 54 | 16.3 | 76 | M |
| 77 | 6.01 | 1.5025 | 10.44 | 2.63 | S | 2b | 65 | 54 | 16.3 | 77 | M |
| 78 | 7.92 | 2.1175 | 9.47 | 2.5 | S | 2b | 65 | 54 | 16.3 | 78 | M |
| 79 | 17.33 | 8.805 | 0 | 0 | C | 1a | 18 | 15 | 39.8 | 79 | U |
| 80 | 13.64 | 10.95 | 16.12 | 14.08 | C | 1a | 18 | 15 | 39.8 | 80 | U |
| 81 | 12.57 | 11.485 | 15.49 | 14.15 | C | 1a | 18 | 15 | 39.8 | 81 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 82 | 12.47 | 10.385 | 15.41 | 14.07 | C | 1a | 18 | 15 | 39.8 | 82 | U |
| 83 | 11.21 | 9.385 | 14.4 | 12.1 | C | 1a | 18 | 15 | 39.8 | 83 | U |
| 84 | 8.21 | 4.105 | 7.83 | 3.92 | S | 1a | 18 | 15 | 39.8 | 84 | U |
| 85 | 6.88 | 3.44 | 5.87 | 2.96 |  | 1a | 18 | 15 | 39.8 | 85 | U |
| 86 | 6.45 | 5.755 | 7.35 | 7.1 | C | 1a | 18 | 15 | 39.8 | 86 | U |
| 87 | 5.76 | 3.12 | 4.82 | 2.53 | S | 1a | 18 | 15 | 39.8 | 87 | U |
| 88 | 15.25 | 11.985 | 14.1 | 12.75 | C | 1a | 18 | 15 | 39.8 | 88 | U |
| 89 | 12.04 | 10.385 | 16.42 | 15.31 | C | 1a | 18 | 15 | 39.8 | 89 | U |
| 90 | 11.97 | 11.82 | 13.74 | 12.18 | C | 1a | 18 | 15 | 39.8 | 90 | U |
| 91 | 7.89 | 3.945 | 11.54 | 5.88 | S | 1a | 18 | 15 | 39.8 | 91 | U |
| 92 | 11.49 | 5.85 | 10.98 | 5.56 | S | 1a | 18 | 15 | 39.8 | 92 | U |
| 93 | 9.88 | 5.345 | 8.5 | 4.28 | S | 1a | 18 | 15 | 39.8 | 93 | U |
| 94 | 10.03 | 5.32 | 13.09 | 6.65 | S | 1a | 18 | 15 | 39.8 | 94 | U |
| 95 | 5.03 | 2.515 | 6.25 | 3.13 | S | 1a | 18 | 15 | 39.8 | 95 | U |
| 96 | 5.26 | 2.63 | 3.89 | 1.94 |  | 1a | 18 | 15 | 39.8 | 96 | B |
| 97 | 6.76 | 3.38 | 4.35 | 2.17 | C | 1a | 18 | 15 | 39.8 | 97 | B |
| 98 | 32.3 | 20.5333 | 28.77 | 19.57 | C | 2a | 26 | 25 | 39.8 | 98 | B |
| 99 | 15.27 | 10.8867 | 16.44 | 11.13 | C | 2a | 26 | 25 | 12.9 | 99 | B |
| 100 | 8.12 | 5.67 | 10.81 | 7.18 | S | 2a | 26 | 25 | 12.9 | 100 | B |
| 101 | 7.94 | 2.84 | 6.39 | 2.13 | S | 2a | 26 | 25 | 12.9 | 101 | B |
| 102 | 7.69 | 2.65333 | 10 | 3.33 | S | 2a | 26 | 25 | 12.9 | 102 | B |
| 103 | 7.53 | 2.62 | 5.99 | 2 | S | 2a | 26 | 25 | 12.9 | 103 | B |
| 104 | 6.49 | 2.16333 | 3.57 | 1.19 | S | 2a | 26 | 25 | 12.9 | 104 | B |
| 105 | 6.03 | 2.76333 | 9.85 | 3.83 | S | 2a | 26 | 25 | 12.9 | 105 | B |
| 106 | 5.94 | 1.98 | 5.37 | 1.81 | S | 2a | 26 | 25 | 12.9 | 106 | B |
| 107 | 5.45 | 1.81667 | 6.98 | 2.33 | S | 2a | 26 | 25 | 12.9 | 107 | B |
| 108 | 5.41 | 1.88667 | 5.28 | 1.94 | S | 2a | 26 | 25 | 12.9 | 108 | B |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 109 | 5.36 | 1.78667 | 3.33 | 1.11 | S | 2a | 26 | 25 | 12.9 | 109 | B |
| 110 | 5.31 | 1.77 | 5.62 | 1.88 | S | 2a | 26 | 25 | 12.9 | 110 | B |
| 111 | 7.65 | 2.97667 | 7 | 2.71 | S | 2a | 26 | 25 | 12.9 | 111 | B |
| 112 | 6.67 | 2.76 | 4.81 | 1.78 | S | 2a | 26 | 25 | 12.9 | 112 | B |
| 113 | 7.49 | 3.36 | 8.03 | 3.27 | S | 2a | 26 | 25 | 12.9 | 113 | B |
| 114 | 6.7 | 2.23333 | 4.86 | 1.62 | S | 2a | 26 | 25 | 12.9 | 114 | B |
| 115 | 7.32 | 2.44 | 11.04 | 4.69 | S | 2a | 26 | 25 | 12.9 | 115 | B |
| 116 | 5.03 | 1.73333 | 5.69 | 1.98 | S | 2a | 26 | 25 | 12.9 | 116 | B |
| 117 | 26.5 | 13.49 | 36.23 | 25.46 | S | 1a | 10 | 10 | 20 | 117 | U |
| 118 | 25.61 | 14.96 | 26.94 | 23.94 | C | 1a | 10 | 10 | 20 | 118 | U |
| 119 | 22.31 | 10.91 | 20.78 | 16.07 | S | 1a | 10 | 10 | 20 | 119 | U |
| 120 | 51.34 | 23.4167 | 48.22 | 35.2 | C | 1a | 10 | 10 | 20 | 120 | U |
| 121 | 70.32 | 41.7233 | 70.64 | 60.67 | C | 1a | 10 | 10 | 20 | 121 | U |
| 122 | 66.67 | 30.0567 | 61.38 | 45.12 | C | 1a | 10 | 10 | 20 | 122 | U |
| 123 | 37.25 | 19.6933 | 40.12 | 32.03 |  | 1a | 10 | 10 | 20 | 123 | U |
| 124 | 82.99 | 46.43 | 80.85 | 66.07 | S | 1a | 10 | 10 | 20 | 124 | U |
| 125 | 23.46 | 7.82 | 25.04 | 12.52 | S | 1a | 10 | 10 | 20 | 125 | U |
| 126 | 16.24 | 5.54333 | 79.25 | 39.62 | S | 1a | 10 | 10 | 20 | 126 | U |
| 127 | 10.04 | 3.34667 | 10.17 | 5.08 | S | 1a | 10 | 10 | 20 | 127 | U |
| 128 | 20.7 | 6.9 | 23.99 | 12.01 | S | 1a | 10 | 10 | 20 | 128 | U |
| 129 | 35.66 | 11.96 | 0 | 0 | S | 1a | 10 | 10 | 20 | 129 | U |
| 130 | 23.67 | 8.02333 | 30.53 | 15.26 | S | 1a | 10 | 10 | 20 | 130 | U |
| 131 | 6.06 | 2.02 | 5.08 | 2.54 | S | 1a | 10 | 10 | 20 | 131 | U |
| 132 | 8.83 | 2.94333 | 7.93 | 3.96 | S | 1a | 10 | 10 | 20 | 132 | U |
| 133 | 6.56 | 2.18667 | 5.56 | 2.78 | S | 1a | 10 | 10 | 20 | 133 | U |
| 134 | 6.03 | 2.29333 | 6.13 | 3.07 | S | 1a | 10 | 10 | 20 | 134 | U |
| 135 | 5.24 | 2.23333 | 5.36 | 4.95 | S | 1a | 10 | 10 | 20 | 135 | U |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 136 | 64.17 | 37.595 | 65.73 | 38.43 | C | 1b | NA | 44 | 78 | 136 | M |
| 137 | 50.39 | 28.1425 | 52.11 | 31.25 | C | 1b | NA | 44 | 78 | 137 | M |
| 138 | 36.17 | 18.33 | 33.78 | 20.04 | C | 1b | NA | 44 | 78 | 138 | M |
| 139 | 12.31 | 7.055 | 12.55 | 7.52 | C | 1b | NA | 44 | 78 | 139 | M |
| 140 | 44.76 | 20.7825 | 45.42 | 24.03 |   | 1b | NA | 44 | 78 | 140 | M |
| 141 | 43.96 | 23.4325 | 45.71 | 25.95 | C | 1b | NA | 44 | 78 | 141 | M |
| 142 | 28.92 | 17.8275 | 31.84 | 19.79 | C | 1b | NA | 44 | 78 | 142 | M |
| 143 | 49.51 | 29.2675 | 51.27 | 31.74 | C | 1b | NA | 44 | 78 | 143 | M |
| 144 | 14.57 | 3.7875 | 11.56 | 3.08 | S | 1b | NA | 44 | 78 | 144 | M |
| 145 | 6.16 | 1.6575 | 7.42 | 1.94 | S | 1b | NA | 44 | 78 | 145 | M |
| 146 | 7.42 | 4.8575 | 14.56 | 9.71 | C | 1b | NA | 44 | 78 | 146 | M |
| 147 | 7.16 | 3.8975 | 6.51 | 3.66 | C | 1b | NA | 44 | 78 | 147 | M |
| 148 | 10.07 | 4.615 | 11.89 | 5.72 | S | 1b | NA | 44 | 78 | 148 | M |
| 149 | 10.73 | 4.81 | 10.94 | 4.1 | S | 1b | NA | 44 | 78 | 149 | M |
| 150 | 5.42 | 1.4725 | 2.27 | 0.75 | S | 1b | NA | 44 | 78 | 150 | M |
| 151 | 5.24 | 1.4775 | 1.04 | 0.26 | S | 1b | NA | 44 | 78 | 151 | M |
| 152 | 5.98 | 2.4875 | 6.54 | 3.09 | S | 1b | NA | 44 | 78 | 152 | M |
| 153 | 5.94 | 2.3525 | 9.06 | 3.44 | C | 1b | NA | 44 | 78 | 153 | M |
| 154 | 78.98 | 74.0257 | 81.47 | 75.23 | C | 1b | 50 | 50 | 269.9 | 154 | U |
| 155 | 11.61 | 2.00714 | 11.93 | 1.71 |   | 1b | 50 | 50 | 269.9 | 155 | U |
| 156 | 46.44 | 42.2714 | 46.2 | 43.18 | C | 1b | 50 | 50 | 269.9 | 156 | U |
| 157 | 47.83 | 41.7886 | 43.5 | 40.43 |   | 1b | 50 | 50 | 269.9 | 157 | U |
| 158 | 71.15 | 50.6657 | 50 | 33.69 |   | 1b | 50 | 50 | 269.9 | 158 | U |
| 159 | 34.48 | 26.6871 | 38.66 | 32.2 | C | 1b | 50 | 50 | 269.9 | 159 | U |
| 160 | 39.42 | 37.0743 | 48.42 | 36.16 |   | 1b | 50 | 50 | 269.9 | 160 | U |
| 161 | 81.56 | 74.8286 | 80.98 | 74.95 | C | 1b | 50 | 50 | 269.9 | 161 | U |
| 162 | 55.7 | 50.5129 | 55.72 | 51.58 |   | 1b | 50 | 50 | 269.9 | 162 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 163 | 36.17 | 31.8357 | 40.64 | 32.06 | | 1b | 50 | 50 | 269.9 | 163 | U |
| 164 | 10.76 | 1.53714 | 19.77 | 2.84 | S | 1b | 50 | 50 | 269.9 | 164 | U |
| 165 | 10.58 | 1.51143 | 12.09 | 1.77 | S | 1b | 50 | 50 | 269.9 | 165 | U |
| 166 | 12.32 | 1.76 | 16.03 | 2.29 | S | 1b | 50 | 50 | 269.9 | 166 | U |
| 167 | 7.97 | 1.13857 | 11.06 | 1.6 | S | 1b | 50 | 50 | 269.9 | 167 | U |
| 168 | 7.14 | 1.22429 | 4.91 | 0.83 | S | 1b | 50 | 50 | 269.9 | 168 | U |
| 169 | 5.65 | 0.875714 | 11.87 | 1.71 | S | 1b | 50 | 50 | 269.9 | 169 | U |
| 170 | 5.88 | 0.918571 | 3.34 | 0.51 | S | 1b | 50 | 50 | 269.9 | 170 | U |
| 171 | 5.6 | 1.02429 | 6.08 | 0.98 | S | 1b | 50 | 50 | 269.9 | 171 | U |
| 172 | 5.46 | 0.865714 | 6.46 | 0.99 | S | 1b | 50 | 50 | 269.9 | 172 | U |
| 173 | 66.11 | 56.818 | 65.56 | 54.48 | C | 3a | 35 | 32 | 17 | 173 | A |
| 174 | 7.55 | 1.51 | 5.88 | 1.18 | S | 3a | 35 | 32 | 17 | 174 | A |
| 175 | 34.16 | 22.892 | 40.22 | 26.03 | C | 3a | 35 | 32 | 17 | 175 | A |
| 176 | 40.74 | 32.382 | 32.22 | 27.78 | C | 3a | 35 | 32 | 17 | 176 | A |
| 177 | 52.39 | 40.17 | 81.82 | 53.27 | C | 3a | 35 | 32 | 17 | 177 | A |
| 178 | 19.77 | 4 | 19.27 | 3.85 | | 3a | 35 | 32 | 17 | 178 | A |
| 179 | 16.28 | 3.62 | 19.17 | 4.29 | S | 3a | 35 | 32 | 17 | 179 | A |
| 180 | 9.59 | 1.918 | 10.08 | 2.02 | S | 3a | 35 | 32 | 17 | 180 | A |
| 181 | 21.05 | 4.21 | 24.6 | 4.92 | S | 3a | 35 | 32 | 17 | 181 | A |
| 182 | 5.7 | 1.178 | 5.12 | 1.03 | S | 3a | 35 | 32 | 17 | 182 | A |
| 183 | 7.89 | 1.578 | 3.47 | 0.69 | S | 3a | 35 | 32 | 17 | 183 | A |
| 184 | 5.28 | 1.23 | 6.39 | 1.28 | | 3a | 35 | 32 | 17 | 184 | A |
| 185 | 9.36 | 1.872 | 14.27 | 2.85 | S | 3a | 35 | 32 | 17 | 185 | A |
| 186 | 5.25 | 1.05 | 5.44 | 1.09 | S | 3a | 35 | 32 | 17 | 186 | A |
| 187 | 18.65 | 11.108 | 20.82 | 12.63 | S | 3a | 35 | 32 | 17 | 187 | A |
| 188 | 15.84 | 9.828 | 20.87 | 11.99 | S | 3a | 35 | 32 | 17 | 188 | A |
| 189 | 26.34 | 14.022 | 24.69 | 13.69 | S | 3a | 35 | 32 | 17 | 189 | A |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 190 | 15.62 | 9.344 | 20.77 | 11.8 | S | 3a | 35 | 32 | 17 | 190 | A |
| 191 | 14.13 | 5.554 | 0 | 0 | S | 3a | 35 | 32 | 17 | 191 | A |
| 192 | 53.26 | 37.0875 | 100 | 25 | C | 1b | NA | 32 | 34.8 | 192 | M |
| 193 | 46.74 | 27.8825 | 55.71 | 32.96 | C | 1b | NA | 32 | 34.8 | 193 | M |
| 194 | 39.11 | 25.52 | 13.79 | 6.48 | C | 1b | NA | 32 | 34.8 | 194 | M |
| 195 | 42.95 | 26.1525 | 44.47 | 28.53 | S | 1b | NA | 32 | 34.8 | 195 | M |
| 196 | 30.74 | 14.22 | 27.87 | 13.69 | C | 1b | NA | 32 | 34.8 | 196 | M |
| 197 | 58.57 | 38.155 | 58.1 | 40.61 | C | 1b | NA | 32 | 34.8 | 197 | M |
| 198 | 45.92 | 27.86 | 49.23 | 30.15 | C | 1b | NA | 32 | 34.8 | 198 | M |
| 199 | 33.71 | 8.4275 | 0 | 0 | S | 1b | NA | 32 | 34.8 | 199 | M |
| 200 | 22.31 | 5.5775 | 17.79 | 4.45 | S | 1b | NA | 32 | 34.8 | 200 | M |
| 201 | 19.12 | 4.78 | 18.71 | 4.7 | S | 1b | NA | 32 | 34.8 | 201 | M |
| 202 | 13.9 | 3.475 | 17.13 | 4.28 | S | 1b | NA | 32 | 34.8 | 202 | M |
| 203 | 7.24 | 1.81 | 3.97 | 1.02 | S | 1b | NA | 32 | 34.8 | 203 | M |
| 204 | 7.14 | 1.785 | 7.4 | 1.87 | S | 1b | NA | 32 | 34.8 | 204 | M |
| 205 | 6.81 | 1.7025 | 5.09 | 1.28 | S | 1b | NA | 32 | 34.8 | 205 | M |
| 206 | 31.03 | 16.81 | 39.24 | 21.5 | C | 1b | NA | 32 | 34.8 | 206 | M |
| 207 | 14.22 | 3.565 | 18.17 | 4.77 | S | 1b | NA | 32 | 34.8 | 207 | M |
| 208 | 6.51 | 1.6275 | 10.7 | 2.72 | S | 1b | NA | 32 | 34.8 | 208 | M |
| 209 | 14.35 | 3.84 | 13.3 | 3.51 | S | 1b | NA | 32 | 34.8 | 209 | M |
| 210 | 50.37 | 38.4167 | 50.61 | 38.37 | C | 1b | 40.2 | 26 | 289.5 | 210 | U |
| 211 | 32.87 | 28.5667 | 29.99 | 24.54 | C | 1b | 40.2 | 26 | 289.5 | 211 | U |
| 212 | 32.2 | 28.5333 | 40.84 | 33.73 | C | 1b | 40.2 | 26 | 289.5 | 212 | U |
| 213 | 18.18 | 9.74333 | 19.61 | 10.77 | S | 1b | 40.2 | 26 | 289.5 | 213 | U |
| 214 | 9.54 | 3.18 | 9.21 | 3.08 | S | 1b | 40.2 | 26 | 289.5 | 214 | U |
| 215 | 27.26 | 22.4033 | 36.44 | 30.27 | C | 1b | 40.2 | 26 | 289.5 | 215 | U |
| 216 | 28.25 | 20.8467 | 30.67 | 24.09 | C | 1b | 40.2 | 26 | 289.5 | 216 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 217 | 13.79 | 11.68 | 16.07 | 12.95 | C | 1b | 40.2 | 26 | 289.5 | 217 | U |
| 218 | 15.45 | 7.86 | 16.36 | 8.6 | S | 1b | 40.2 | 26 | 289.5 | 218 | U |
| 219 | 11.47 | 3.82333 | 7.43 | 2.48 | S | 1b | 40.2 | 26 | 289.5 | 219 | U |
| 220 | 5.98 | 1.99333 | 11.37 | 3.79 | S | 1b | 40.2 | 26 | 289.5 | 220 | U |
| 221 | 5.29 | 3.19 | 5.71 | 3.34 | S | 1b | 40.2 | 26 | 289.5 | 221 | U |
| 222 | 16.22 | 8.62333 | 16.6 | 9.01 | S | 1b | 40.2 | 26 | 289.5 | 222 | U |
| 223 | 15.17 | 7.95667 | 17.31 | 9.32 | S | 1b | 40.2 | 26 | 289.5 | 223 | U |
| 224 | 14.87 | 9.09333 | 17.92 | 9.75 | S | 1b | 40.2 | 26 | 289.5 | 224 | U |
| 225 | 6.8 | 2.26667 | 6.02 | 2.01 | S | 1b | 40.2 | 26 | 289.5 | 225 | U |
| 226 | 5.42 | 1.80667 | 6.69 | 2.23 | S | 1b | 40.2 | 26 | 289.5 | 226 | U |
| 227 | 41.61 | 21.454 | 47.07 | 39.73 | C | 1a | 14 | 14 | 48.2 | 227 | L |
| 228 | 37.56 | 19.078 | 52.38 | 30.35 | C | 1a | 14 | 14 | 48.2 | 228 | L |
| 229 | 28.95 | 10.472 | 23.55 | 18.73 | C | 1a | 14 | 14 | 48.2 | 229 | L |
| 230 | 23.6 | 10.528 | 21.53 | 17.22 | C | 1a | 14 | 14 | 48.2 | 230 | L |
| 231 | 23.5 | 11.102 | 23.78 | 18.27 | C | 1a | 14 | 14 | 48.2 | 231 | L |
| 232 | 17 | 8.418 | 15.03 | 12.47 | C | 1a | 14 | 14 | 48.2 | 232 | L |
| 233 | 21.28 | 9.336 | 22.03 | 17.2 | C | 1a | 14 | 14 | 48.2 | 233 | L |
| 234 | 27.02 | 11.704 | 27.39 | 20.58 | C | 1a | 14 | 14 | 48.2 | 234 | L |
| 235 | 13.18 | 6.824 | 10.04 | 8.2 | C | 1a | 14 | 14 | 48.2 | 235 | L |
| 236 | 21.48 | 9.542 | 22.29 | 16.94 |  | 1a | 14 | 14 | 48.2 | 236 | L |
| 237 | 44.08 | 19.888 | 44.15 | 34.44 | S | 1a | 14 | 14 | 48.2 | 237 | L |
| 238 | 7.42 | 1.53 | 5.71 | 1.9 | S | 1a | 14 | 14 | 48.2 | 238 | L |
| 239 | 6.72 | 1.344 | 7.3 | 2.45 | S | 1a | 14 | 14 | 48.2 | 239 | L |
| 240 | 6.64 | 1.426 | 7.29 | 2.43 | S | 1a | 14 | 14 | 48.2 | 240 | L |
| 241 | 6.29 | 1.258 | 7.42 | 2.49 | S | 1a | 14 | 14 | 48.2 | 241 | L |
| 242 | 24.6 | 9.3 | 24.21 | 15.33 | S | 1a | 14 | 14 | 48.2 | 242 | L |
| 243 | 27.95 | 10.504 | 28.2 | 21.92 | C | 1a | 14 | 14 | 48.2 | 243 | L |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 244 | 19.74 | 8.312 | 20.27 | 15.07 | C | 1a | 14 | 14 | 48.2 | 244 | L |
| 245 | 15.42 | 6.884 | 22.48 | 16.33 | S | 1a | 14 | 14 | 48.2 | 245 | L |
| 246 | 37.97 | 23.075 | 39.92 | 26.51 | C | 1a | 24 | 24 | 29.5 | 246 | L |
| 247 | 11.5 | 2.9625 | 12.35 | 3.24 | S | 1a | 24 | 24 | 29.5 | 247 | L |
| 248 | 11.4 | 2.85 | 0 | 0 | S | 1a | 24 | 24 | 29.5 | 248 | L |
| 249 | 8.59 | 2.275 | 7.73 | 2.06 | S | 1a | 24 | 24 | 29.5 | 249 | L |
| 250 | 38.49 | 19.7475 | 43.59 | 23.67 | C | 1a | 24 | 24 | 29.5 | 250 | L |
| 251 | 21.03 | 11.2725 | 25.26 | 14.33 | C | 1a | 24 | 24 | 29.5 | 251 | L |
| 252 | 31.02 | 21.7775 | 29.81 | 22.44 | C | 1a | 24 | 24 | 29.5 | 252 | L |
| 253 | 6.13 | 1.5325 | 7.86 | 1.96 | S | 1a | 24 | 24 | 29.5 | 253 | L |
| 254 | 8.25 | 2.155 | 0 | 0 | S | 1a | 24 | 24 | 29.5 | 254 | L |
| 255 | 22.44 | 5.8025 | 24.56 | 6.16 | S | 1a | 24 | 24 | 29.5 | 255 | L |
| 256 | 18.44 | 4.6475 | 18.7 | 4.68 | S | 1a | 24 | 24 | 29.5 | 256 | L |
| 257 | 14.82 | 3.8275 | 15.74 | 3.95 | S | 1a | 24 | 24 | 29.5 | 257 | L |
| 258 | 8.63 | 4.2575 | 8.83 | 4.42 | S | 1a | 24 | 24 | 29.5 | 258 | L |
| 259 | 7.79 | 3.3925 | 8.65 | 4.16 | S | 1a | 24 | 24 | 29.5 | 259 | L |
| 260 | 7.81 | 2.165 | 8.62 | 2.32 | S | 1a | 24 | 24 | 29.5 | 260 | L |
| 261 | 6.99 | 1.91 | 7.13 | 1.87 | S | 1a | 24 | 24 | 29.5 | 261 | L |
| 262 | 6.64 | 1.855 | 6.36 | 1.74 | S | 1a | 24 | 24 | 29.5 | 262 | L |
| 263 | 5.71 | 1.635 | 6.7 | 1.82 | S | 1a | 24 | 24 | 29.5 | 263 | L |
| 264 | 5.65 | 1.4125 | 6.79 | 1.71 | S | 1a | 24 | 24 | 29.5 | 264 | L |
| 265 | 5.6 | 1.4 | 4.84 | 1.22 | S | 1a | 24 | 24 | 29.5 | 265 | L |
| 266 | 60.1 | 51.8233 | 62.43 | 53.82 | C | 1b | 40 | 40 | 12.2 | 266 | U |
| 267 | 59.93 | 55.45 | 60.29 | 52.94 | | 1b | 40 | 40 | 12.2 | 267 | U |
| 268 | 53.71 | 39.3833 | 67.24 | 52.19 | C | 1b | 40 | 40 | 12.2 | 268 | U |
| 269 | 53.66 | 39.91 | 67.24 | 52.21 | C | 1b | 40 | 40 | 12.2 | 269 | U |
| 270 | 39.01 | 29.5967 | 40.21 | 32.73 | C | 1b | 40 | 40 | 12.2 | 270 | U |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 271 | 34.41 | 28.7267 | 34.6 | 29.26 | C | 1b | 40 | 40 | 12.2 | 271 | U |
| 272 | 32.21 | 29.67 | 43.86 | 37.33 | C | 1b | 40 | 40 | 12.2 | 272 | U |
| 273 | 19.41 | 6.87667 | 16.76 | 6.03 | S | 1b | 40 | 40 | 12.2 | 273 | U |
| 274 | 14.92 | 6.4 | 16.87 | 7.7 | S | 1b | 40 | 40 | 12.2 | 274 | U |
| 275 | 12.09 | 7.46 | 13.97 | 8.11 |  | 1b | 40 | 40 | 12.2 | 275 | U |
| 276 | 6.71 | 4.74 | 5.88 | 4.69 | C | 1b | 40 | 40 | 12.2 | 276 | U |
| 277 | 23.94 | 21.8633 | 23.93 | 20.76 | C | 1b | 40 | 40 | 12.2 | 277 | U |
| 278 | 73.54 | 57.49 | 72.47 | 57.39 | C | 1b | 40 | 40 | 12.2 | 278 | U |
| 279 | 44.65 | 37.11 | 45.53 | 37.13 | C | 1b | 40 | 40 | 12.2 | 279 | U |
| 280 | 35.34 | 27.38 | 35.06 | 26.9 | C | 1b | 40 | 40 | 12.2 | 280 | U |
| 281 | 73.45 | 62.8933 | 71.56 | 61.68 | S | 1b | 40 | 40 | 12.2 | 281 | U |
| 282 | 41.04 | 32.15 | 41.4 | 32.97 | S | 1b | 40 | 40 | 12.2 | 282 | U |
| 283 | 12.05 | 5.03667 | 14.91 | 6.16 | S | 1b | 40 | 40 | 12.2 | 283 | U |
| 284 | 7.06 | 2.64333 | 5.9 | 2.2 |  | 1b | 40 | 40 | 12.2 | 284 | U |
| 285 | 21.32 | 7.89 | 0 | 0 | S | 1b | 40 | 40 | 12.2 | 285 | U |
| 286 | 11.85 | 4.61 | 14.47 | 6.03 | S | 1b | 40 | 40 | 12.2 | 286 | U |
| 287 | 42.64 | 14.2914 | 50.6 | 19.76 | S | 2a | 45 | 45 | 29.3 | 287 | U |
| 288 | 37.04 | 22.2271 | 42.63 | 27.36 | C | 2a | 45 | 45 | 29.3 | 288 | U |
| 289 | 18.98 | 3.86571 | 0.09 | 4.76 | S | 2a | 45 | 45 | 29.3 | 289 | U |
| 290 | 47.11 | 25.7271 | 45.85 | 29.72 | C | 2a | 45 | 45 | 29.3 | 290 | U |
| 291 | 22.22 | 13.1529 | 23.81 | 16.49 | C | 2a | 45 | 45 | 29.3 | 291 | U |
| 292 | 39.74 | 22.85 | 41.47 | 28.17 |  | 2a | 45 | 45 | 29.3 | 292 | U |
| 293 | 81.63 | 46.6329 | 91.67 | 75.56 | C | 2a | 45 | 45 | 29.3 | 293 | U |
| 294 | 46.98 | 25.8586 | 46.74 | 30.7 | S | 2a | 45 | 45 | 29.3 | 294 | U |
| 295 | 21.63 | 4.18571 | 0.11 | 4.44 | S | 2a | 45 | 45 | 29.3 | 295 | U |
| 296 | 18.46 | 3.65714 | 0.13 | 4.3 | S | 2a | 45 | 45 | 29.3 | 296 | U |
| 297 | 16.02 | 6.59286 | 18.22 | 8.62 | S | 2a | 45 | 45 | 29.3 | 297 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 298 | 16.74 | 7.16286 | 19.71 | 9.56 | S | 2a | 45 | 45 | 29.3 | 298 | U |
| 299 | 14.29 | 5.76143 | 14.34 | 6.55 | S | 2a | 45 | 45 | 29.3 | 299 | U |
| 300 | 6.57 | 0.98 | 7.66 | 1.28 | S | 2a | 45 | 45 | 29.3 | 300 | U |
| 301 | 6.49 | 0.927143 | 6.84 | 1.14 | S | 2a | 45 | 45 | 29.3 | 301 | U |
| 302 | 13.19 | 1.88429 | 0 | 2.69 | | 2a | 45 | 45 | 29.3 | 302 | U |
| 303 | 12.39 | 1.77 | 0 | 2.4 | S | 2a | 45 | 45 | 29.3 | 303 | U |
| 304 | 8 | 1.24 | 0 | 1.43 | | 2a | 45 | 45 | 29.3 | 304 | U |
| 305 | 22.98 | 3.47429 | 25.68 | 4.29 | S | 2a | 45 | 45 | 29.3 | 305 | U |
| 306 | 44.11 | 22.055 | 50.35 | 50.35 | | 1b | NA | 42 | 10.9 | 306 | M |
| 307 | 36.34 | 18.17 | 39.78 | 39.78 | | 1b | NA | 42 | 10.9 | 307 | M |
| 308 | 28.24 | 14.12 | 21.41 | 21.41 | | 1b | NA | 42 | 10.9 | 308 | M |
| 309 | 8.09 | 4.045 | 9.23 | 9.23 | | 1b | NA | 42 | 10.9 | 309 | M |
| 310 | 16.33 | 8.165 | 9.62 | 9.62 | | 1b | NA | 42 | 10.9 | 310 | M |
| 311 | 10.92 | 5.46 | 10.47 | 10.47 | | 1b | NA | 42 | 10.9 | 311 | M |
| 312 | 30.66 | 15.33 | 32.79 | 32.79 | | 1b | NA | 42 | 10.9 | 312 | M |
| 313 | 8.94 | 4.47 | 5.95 | 5.95 | | 1b | NA | 42 | 10.9 | 313 | M |
| 314 | 37.04 | 18.52 | 41.92 | 41.92 | | 1b | NA | 42 | 10.9 | 314 | M |
| 315 | 29.08 | 14.54 | 16.04 | 16.04 | | 1b | NA | 42 | 10.9 | 315 | M |
| 316 | 28.34 | 14.17 | 28.03 | 28.03 | | 1b | NA | 42 | 10.9 | 316 | M |
| 317 | 8.57 | 4.285 | 15.23 | 15.23 | | 1b | NA | 42 | 10.9 | 317 | M |
| 318 | 7.21 | 3.605 | 12.06 | 12.06 | | 1b | NA | 42 | 10.9 | 318 | M |
| 319 | 5.72 | 2.86 | 7.26 | 7.26 | | 1b | NA | 42 | 10.9 | 319 | M |
| 320 | 5.56 | 2.78 | 8.27 | 8.27 | | 1b | NA | 42 | 10.9 | 320 | M |
| 321 | 56.35 | 26.1875 | 49.79 | 31.11 | C | 2a | NA | 55 | 94 | 321 | M |
| 322 | 47.27 | 20.33 | 53.25 | 31.47 | C | 2a | NA | 55 | 94 | 322 | M |
| 323 | 35.16 | 18.695 | 33.83 | 25.28 | C | 2a | NA | 55 | 94 | 323 | M |
| 324 | 28.31 | 12.0325 | 27.24 | 17.86 | C | 2a | NA | 55 | 94 | 324 | M |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 325 | 23.88 | 10.1337 | 20.8 | 15.59 | C | 2a | NA | 55 | 94 | 325 | M |
| 326 | 19.46 | 6.95375 | 21.57 | 6.03 | S | 2a | NA | 55 | 94 | 326 | M |
| 327 | 25.87 | 11.6725 | 25.22 | 15.06 | C | 2a | NA | 55 | 94 | 327 | M |
| 328 | 25.43 | 11.8988 | 30.1 | 19.2 | C | 2a | NA | 55 | 94 | 328 | M |
| 329 | 27.32 | 12.4475 | 27.27 | 17.27 | C | 2a | NA | 55 | 94 | 329 | M |
| 330 | 35.81 | 17.7275 | 41.69 | 27.37 | S | 2a | NA | 55 | 94 | 330 | M |
| 331 | 16.93 | 2.11625 | 0.1 | 2.84 | S | 2a | NA | 55 | 94 | 331 | M |
| 332 | 17.2 | 2.15 | 0.02 | 3.62 | S | 2a | NA | 55 | 94 | 332 | M |
| 333 | 12.19 | 2.15375 | 12.81 | 2.96 | S | 2a | NA | 55 | 94 | 333 | M |
| 334 | 9.64 | 1.73875 | 10.19 | 2.42 | S | 2a | NA | 55 | 94 | 334 | M |
| 335 | 26.83 | 9.05375 | 26.47 | 12.61 | S | 2a | NA | 55 | 94 | 335 | M |
| 336 | 6.68 | 0.835 | 3.32 | 0.64 | S | 2a | NA | 55 | 94 | 336 | M |
| 337 | 6.9 | 0.8625 | 7.8 | 1.3 | S | 2a | NA | 55 | 94 | 337 | M |
| 338 | 6.19 | 0.77375 | 6.58 | 1.11 | S | 2a | NA | 55 | 94 | 338 | M |
| 339 | 5.84 | 0.73 | 6.77 | 1.13 | S | 2a | NA | 55 | 94 | 339 | M |
| 340 | 57.36 | 33.8175 | 56.95 | 35.26 | C | 1a | NA | 29 | 57.2 | 340 | M |
| 341 | 48.63 | 32.7975 | 37.14 | 30.25 | C | 1a | NA | 29 | 57.2 | 341 | M |
| 342 | 30.89 | 17.885 | 11.11 | 7.2 | | 1a | NA | 29 | 57.2 | 342 | M |
| 343 | 30.77 | 16.4025 | 7.51 | 4.16 | C | 1a | NA | 29 | 57.2 | 343 | M |
| 344 | 30.22 | 18.6575 | 38.28 | 22.42 | C | 1a | NA | 29 | 57.2 | 344 | M |
| 345 | 19.47 | 14.2375 | 21.77 | 14.83 | C | 1a | NA | 29 | 57.2 | 345 | M |
| 346 | 15.75 | 5.03 | 50 | 18.97 | S | 1a | NA | 29 | 57.2 | 346 | M |
| 347 | 33.52 | 19.915 | 31.13 | 19.76 | C | 1a | NA | 29 | 57.2 | 347 | M |
| 348 | 21.31 | 13.0175 | 17.65 | 10.36 | C | 1a | NA | 29 | 57.2 | 348 | M |
| 349 | 16.99 | 8.6425 | 16.02 | 9.37 | C | 1a | NA | 29 | 57.2 | 349 | M |
| 350 | 31.33 | 20.16 | 38 | 23.21 | C | 1a | NA | 29 | 57.2 | 350 | M |
| 351 | 42.94 | 24.495 | 39.92 | 24.22 | C | 1a | NA | 29 | 57.2 | 351 | M |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 352 | 20.41 | 15.01 | 25.72 | 18.61 | C | 1a | NA | 29 | 57.2 | 352 | M |
| 353 | 7.72 | 1.93 | 10.37 | 2.59 | S | 1a | NA | 29 | 57.2 | 353 | M |
| 354 | 6 | 1.5 | 8.38 | 2.09 | S | 1a | NA | 29 | 57.2 | 354 | M |
| 355 | 6.49 | 1.6225 | 5.14 | 1.3 | S | 1a | NA | 29 | 57.2 | 355 | M |
| 356 | 6.72 | 1.725 | 5.78 | 1.45 | S | 1a | NA | 29 | 57.2 | 356 | M |
| 357 | 5.91 | 1.4775 | 5.18 | 1.3 | S | 1a | NA | 29 | 57.2 | 357 | M |
| 358 | 5.12 | 1.28 | 4.18 | 1.06 | S | 1a | NA | 29 | 57.2 | 358 | M |
| 359 | 36.78 | 29.81 | 53.85 | 38.43 | C | 1a | 10 | 10 | 65 | 359 | R |
| 360 | 28.92 | 20.045 | 26.42 | 20.53 | C | 1a | 10 | 10 | 65 | 360 | R |
| 361 | 19.9 | 15.925 | 15 | 14.22 | C | 1a | 10 | 10 | 65 | 361 | R |
| 362 | 25.37 | 17.445 | 25 | 19.15 | C | 1a | 10 | 10 | 65 | 362 | R |
| 363 | 20.22 | 15.735 | 17.95 | 16.11 | C | 1a | 10 | 10 | 65 | 363 | R |
| 364 | 25.34 | 19.495 | 24.59 | 19.33 | C | 1a | 10 | 10 | 65 | 364 | R |
| 365 | 23.51 | 18.18 | 36.36 | 26.05 | C | 1a | 10 | 10 | 65 | 365 | R |
| 366 | 49.44 | 34.38 | 50 | 36.65 | C | 1a | 10 | 10 | 65 | 366 | R |
| 367 | 19.59 | 16.67 | 27.06 | 13.53 | C | 1a | 10 | 10 | 65 | 367 | R |
| 368 | 25.08 | 19.47 | 19.05 | 16.77 | C | 1a | 10 | 10 | 65 | 368 | R |
| 369 | 12.77 | 9.4 | 7.57 | 6.01 | C | 1a | 10 | 10 | 65 | 369 | R |
| 370 | 13.33 | 10.225 | 7.09 | 6.74 |   | 1a | 10 | 10 | 65 | 370 | R |
| 371 | 9.13 | 7.675 | 18.18 | 12.57 | C | 1a | 10 | 10 | 65 | 371 | R |
| 372 | 10.73 | 8.125 | 11.56 | 5.78 | C | 1a | 10 | 10 | 65 | 372 | R |
| 373 | 12.92 | 9.64 | 12.73 | 10.12 | C | 1a | 10 | 10 | 65 | 373 | R |
| 374 | 6.25 | 4.36 | 12.86 | 8 | C | 1a | 10 | 10 | 65 | 374 | R |
| 375 | 8.33 | 6.53 | 15.12 | 10.6 | C | 1a | 10 | 10 | 65 | 375 | R |
| 376 | 6.5 | 4.31 | 8.16 | 5.4 | C | 1a | 10 | 10 | 65 | 376 | R |
| 377 | 46.67 | 23.3875 | 76.91 | 55.52 |   | 1b | 45 | 43 | 32.8 | 377 | L |
| 378 | 37.39 | 22.1475 | 44.7 | 34.18 | C | 1b | 45 | 43 | 32.8 | 378 | L |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 379 | 36.39 | 20.2675 | 37.56 | 27.15 | C | 1b | 45 | 43 | 32.8 | 379 | L |
| 380 | 33.98 | 19.355 | 37.13 | 26.71 | C | 1b | 45 | 43 | 32.8 | 380 | L |
| 381 | 27.59 | 14.05 | 28.13 | 20.22 | C | 1b | 45 | 43 | 32.8 | 381 | L |
| 382 | 24.29 | 13.7375 | 29.27 | 23.71 | C | 1b | 45 | 43 | 32.8 | 382 | L |
| 383 | 21.71 | 10.4625 | 22.74 | 15.19 | C | 1b | 45 | 43 | 32.8 | 383 | L |
| 384 | 15.81 | 8.59 | 18.28 | 12.54 | C | 1b | 45 | 43 | 32.8 | 384 | L |
| 385 | 37.67 | 19.44 | 24.1 | 16.76 | | 1b | 45 | 43 | 32.8 | 385 | L |
| 386 | 44.74 | 26.995 | 44.9 | 34.41 | C | 1b | 45 | 43 | 32.8 | 386 | L |
| 387 | 26.57 | 16.4825 | 28.41 | 21.98 | C | 1b | 45 | 43 | 32.8 | 387 | L |
| 388 | 13.77 | 6.92 | 14.8 | 9.93 | S | 1b | 45 | 43 | 32.8 | 388 | L |
| 389 | 6.25 | 3.915 | 10.53 | 7.28 | S | 1b | 45 | 43 | 32.8 | 389 | L |
| 390 | 6.83 | 1.8425 | 10.53 | 3.51 | S | 1b | 45 | 43 | 32.8 | 390 | L |
| 391 | 7.75 | 1.9375 | 5.35 | 1.8 | S | 1b | 45 | 43 | 32.8 | 391 | L |
| 392 | 16.23 | 8.3475 | 17.75 | 12.29 | C | 1b | 45 | 43 | 32.8 | 392 | L |
| 393 | 16.15 | 7.7175 | 16.5 | 12.23 | S | 1b | 45 | 43 | 32.8 | 393 | L |
| 394 | 13.16 | 7.5625 | 13.47 | 8.9 | C | 1b | 45 | 43 | 32.8 | 394 | L |
| 395 | 6.1 | 3.8975 | 10.55 | 7.31 | S | 1b | 45 | 43 | 32.8 | 395 | U |
| 396 | 40.44 | 20.7212 | 37.89 | 23.03 | C | 3a | 70 | 70 | 36.3 | 396 | U |
| 397 | 39.28 | 21.1175 | 40.39 | 26 | C | 3a | 70 | 70 | 36.3 | 397 | U |
| 398 | 28.67 | 14.8925 | 27 | 17.83 | C | 3a | 70 | 70 | 36.3 | 398 | U |
| 399 | 14.73 | 8.87625 | 12.46 | 8.78 | C | 3a | 70 | 70 | 36.3 | 399 | U |
| 400 | 13.96 | 8.37 | 16.82 | 10.33 | C | 3a | 70 | 70 | 36.3 | 400 | U |
| 401 | 18.6 | 9.4125 | 31.82 | 19.6 | C | 3a | 70 | 70 | 36.3 | 401 | U |
| 402 | 17.26 | 9.0525 | 30.65 | 18.9 | C | 3a | 70 | 70 | 36.3 | 402 | U |
| 403 | 13.41 | 6.215 | 13.1 | 7.69 | C | 3a | 70 | 70 | 36.3 | 403 | U |
| 404 | 22.27 | 10.5925 | 15.38 | 9.51 | C | 3a | 70 | 70 | 36.3 | 404 | U |
| 405 | 5.65 | 0.78625 | 15.79 | 2.9 | S | 3a | 70 | 70 | 36.3 | 405 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 406 | 10.71 | 1.36125 | 5.82 | 0.92 | S | 3a | 70 | 70 | 36.3 | 406 | U |
| 407 | 7.41 | 0.955 | 8.79 | 1.28 | S | 3a | 70 | 70 | 36.3 | 407 | U |
| 408 | 8.73 | 1.09125 | 14.21 | 2.03 | S | 3a | 70 | 70 | 36.3 | 408 | U |
| 409 | 20.78 | 7.185 | 13.56 | 6.28 | S | 3a | 70 | 70 | 36.3 | 409 | U |
| 410 | 8.56 | 1.32875 | 7.72 | 1.4 | S | 3a | 70 | 70 | 36.3 | 410 | U |
| 411 | 15 | 4.1875 | 15.61 | 5.01 | S | 3a | 70 | 70 | 36.3 | 411 | U |
| 412 | 11.64 | 4.07875 | 18.18 | 6.39 | S | 3a | 70 | 70 | 36.3 | 412 | U |
| 413 | 9.82 | 1.9525 | 9.23 | 2.51 | S | 3a | 70 | 70 | 36.3 | 413 | U |
| 414 | 11.81 | 2.555 | 10.49 | 2.7 | S | 3a | 70 | 70 | 36.3 | 414 | U |
| 415 | 40.95 | 38.5233 | 48.85 | 44.77 | C | 1b | 48 | 40 | 16.6 | 415 | A |
| 416 | 26.57 | 24.2367 | 28.82 | 28.24 | C | 1b | 48 | 40 | 16.6 | 416 | A |
| 417 | 23.46 | 20.8467 | 41.06 | 38.99 | C | 1b | 48 | 40 | 16.6 | 417 | A |
| 418 | 14.73 | 13.0733 | 15.58 | 15.28 | C | 1b | 48 | 40 | 16.6 | 418 | A |
| 419 | 10.47 | 5.07667 | 11.45 | 6.79 | S | 1b | 48 | 40 | 16.6 | 419 | A |
| 420 | 5.14 | 1.71333 | 5.51 | 1.84 | S | 1b | 48 | 40 | 16.6 | 420 | A |
| 421 | 15.21 | 11.5267 | 10.98 | 10.72 | C | 1b | 48 | 40 | 16.6 | 421 | A |
| 422 | 27.87 | 26.0867 | 32.17 | 31.26 | C | 1b | 48 | 40 | 16.6 | 422 | A |
| 423 | 11.59 | 10.4267 | 13.81 | 11.88 | C | 1b | 48 | 40 | 16.6 | 423 | A |
| 424 | 25.58 | 22.5167 | 25.39 | 24.08 | C | 1b | 48 | 40 | 16.6 | 424 | A |
| 425 | 7.6 | 2.53333 | 4.9 | 1.63 | S | 1b | 48 | 40 | 16.6 | 425 | A |
| 426 | 7.55 | 2.51667 | 6.87 | 2.29 |  | 1b | 48 | 40 | 16.6 | 426 | A |
| 427 | 8.02 | 2.67333 | 7.09 | 2.36 | S | 1b | 48 | 40 | 16.6 | 427 | A |
| 428 | 6.02 | 2.00667 | 4.24 | 1.41 | S | 1b | 48 | 40 | 16.6 | 428 | A |
| 429 | 10.97 | 5.04 | 10 | 4.91 | S | 1b | 48 | 40 | 16.6 | 429 | A |
| 430 | 9.84 | 5.10667 | 12.48 | 5.7 | S | 1b | 48 | 40 | 16.6 | 430 | A |
| 431 | 9.21 | 4.43333 | 12.99 | 5.93 | S | 1b | 48 | 40 | 16.6 | 431 | A |
| 432 | 7.53 | 2.68333 | 6.7 | 2.23 | S | 1b | 48 | 40 | 16.6 | 432 | A |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 433 | 8.78 | 2.92667 | 11.9 | 4.11 | S | 1b | 48 | 40 | 16.6 | 433 | A |
| 434 | 7.88 | 2.65667 | 9.3 | 3.17 | S | 1b | 48 | 40 | 16.6 | 434 | A |
| 435 | 24.81 | 8.27 | 19.99 | 6.68 |  | 1b | 48 | 40 | 16.6 | 435 | A |
| 436 | 66.67 | 52.4325 | 65.59 | 53.3 | C | 2b | 39 | 40 | 20 | 436 | B |
| 437 | 53.71 | 44.705 | 53.76 | 42.14 | C | 2b | 39 | 40 | 20 | 437 | B |
| 438 | 42.41 | 36.4025 | 48.94 | 36.64 | C | 2b | 39 | 40 | 20 | 438 | B |
| 439 | 39.77 | 30.0575 | 42.09 | 36.56 | C | 2b | 39 | 40 | 20 | 439 | B |
| 440 | 12.85 | 3.2125 | 14.47 | 3.64 | S | 2b | 39 | 40 | 20 | 440 | B |
| 441 | 53.07 | 36.995 | 45.05 | 35.08 | C | 2b | 39 | 40 | 20 | 441 | B |
| 442 | 52.52 | 34.7975 | 51.05 | 34.23 | C | 2b | 39 | 40 | 20 | 442 | B |
| 443 | 35.06 | 25.29 | 33.22 | 27.53 | C | 2b | 39 | 40 | 20 | 443 | B |
| 444 | 55.54 | 45.1775 | 52.24 | 44.13 | C | 2b | 39 | 40 | 20 | 444 | B |
| 445 | 39.93 | 35.28 | 43.88 | 35.12 | S | 2b | 39 | 40 | 20 | 445 | B |
| 446 | 13.46 | 3.365 | 25.15 | 6.31 | S | 2b | 39 | 40 | 20 | 446 | B |
| 447 | 13.36 | 3.34 | 15.04 | 3.81 | S | 2b | 39 | 40 | 20 | 447 | B |
| 448 | 12.72 | 3.18 | 14.68 | 3.71 | S | 2b | 39 | 40 | 20 | 448 | B |
| 449 | 20.42 | 5.105 | 21.59 | 5.47 | S | 2b | 39 | 40 | 20 | 449 | B |
| 450 | 6.43 | 1.6075 | 11.21 | 2.85 |  | 2b | 39 | 40 | 20 | 450 | B |
| 451 | 27.43 | 12.81 | 41.14 | 19.52 | S | 2b | 39 | 40 | 20 | 451 | B |
| 452 | 17.46 | 7.655 | 19.41 | 8.79 | S | 3a | 43 | 40 | 20 | 452 | A |
| 453 | 34.12 | 18.945 | 40.59 | 20.29 | C | 3a | 43 | 40 | 20 | 453 | A |
| 454 | 8.84 | 2.21 | 9.44 | 2.4 | C | 3a | 43 | 40 | 20 | 454 | A |
| 455 | 8.61 | 2.1525 | 9.71 | 2.43 |  | 2b | 39 | 40 | 20 | 455 | B |
| 456 | 15.57 | 10.385 | 15.3 | 10.11 | S | 3a | 43 | 40 | 73.9 | 456 | A |
| 457 | 10.38 | 8.35 | 11.13 | 7.81 | S | 3a | 43 | 40 | 73.9 | 457 | A |
| 458 | 10.2 | 8.3825 | 10.18 | 8.66 | C | 3a | 43 | 40 | 73.9 | 458 | A |
| 459 | 7.32 | 5.985 | 8.07 | 6.72 | C | 3a | 43 | 40 | 73.9 | 459 | A |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 460 | 10.24 | 7.105 | 15.63 | 11.32 | S | 3a | 43 | 40 | 73.9 | 460 | A |
| 461 | 8.04 | 6.005 | 9.24 | 6.37 | S | 3a | 43 | 40 | 73.9 | 461 | A |
| 462 | 12.56 | 6.9375 | 7.86 | 5.68 | S | 3a | 43 | 40 | 73.9 | 462 | A |
| 463 | 5.01 | 1.2525 | 5.92 | 1.48 | S | 3a | 43 | 40 | 73.9 | 463 | A |
| 464 | 8.53 | 2.16 | 6.22 | 1.56 |   | 3a | 43 | 40 | 73.9 | 464 | A |
| 465 | 5.89 | 3.3475 | 5.15 | 3.04 | S | 3a | 43 | 40 | 73.9 | 465 | A |
| 466 | 8.68 | 3.1375 | 8 | 2.75 | S | 3a | 43 | 40 | 73.9 | 466 | A |
| 467 | 6.91 | 4.3025 | 11.63 | 5.39 |   | 3a | 43 | 40 | 73.9 | 467 | A |
| 458 | 8.12 | 4.2625 | 9.45 | 5.11 | S | 3a | 43 | 40 | 73.9 | 468 | A |
| 469 | 5.73 | 1.4325 | 5.87 | 1.47 | S | 3a | 43 | 40 | 73.9 | 469 | A |
| 470 | 5.11 | 1.2775 | 4.78 | 1.19 | S | 3a | 43 | 40 | 73.9 | 470 | A |
| 471 | 7.32 | 1.83 | 3.86 | 0.97 | S | 3a | 43 | 40 | 73.9 | 471 | A |
| 472 | 5.11 | 1.3025 | 4.97 | 1.24 | S | 3a | 43 | 40 | 73.9 | 472 | A |
| 473 | 10.21 | 3.2775 | 10.74 | 3.97 | S | 3a | 43 | 40 | 73.9 | 473 | A |
| 474 | 8.47 | 3.6575 | 10.69 | 4.51 | S | 3a | 43 | 40 | 73.9 | 474 | A |
| 475 | 26.47 | 13.8175 | 25.46 | 18.31 | C | 1b | NA | 41 | 33.7 | 475 | B |
| 476 | 12.04 | 3.855 | 13.2 | 5.3 | S | 1b | NA | 41 | 33.7 | 476 | B |
| 477 | 13.34 | 8.6125 | 16.36 | 15.37 | C | 1b | NA | 41 | 33.7 | 477 | B |
| 478 | 15.01 | 10.3 | 18.87 | 13.27 | C | 1b | NA | 41 | 33.7 | 478 | B |
| 479 | 17.17 | 9.775 | 19.6 | 14.44 | C | 1b | NA | 41 | 33.7 | 479 | B |
| 480 | 33.16 | 15.17 | 52.58 | 30.3 | C | 1b | NA | 41 | 33.7 | 480 | B |
| 481 | 14.63 | 9.52 | 19.85 | 14.54 | C | 1b | NA | 41 | 33.7 | 481 | B |
| 482 | 29.31 | 14.055 | 33.82 | 19.08 | C | 1b | NA | 41 | 33.7 | 482 | B |
| 483 | 13.24 | 8.565 | 18.54 | 14.08 | C | 1b | NA | 41 | 33.7 | 483 | B |
| 484 | 9.91 | 5.345 | 13.05 | 10.89 | S | 1b | NA | 41 | 33.7 | 484 | B |
| 485 | 14.41 | 6.8075 | 13.76 | 9.61 | S | 1b | NA | 41 | 33.7 | 485 | B |
| 486 | 9.53 | 5.9 | 10.39 | 9.13 |   | 1b | NA | 41 | 33.7 | 486 | B |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 487 | 14.17 | 6.905 | 13.57 | 9.01 | S | 1b | NA | 41 | 33.7 | 487 | B |
| 488 | 7.3 | 1.93 | 4.84 | 1.63 | S | 1b | NA | 41 | 33.7 | 488 | B |
| 489 | 6.35 | 1.5875 | 8.73 | 2.95 |  | 1b | NA | 41 | 33.7 | 489 | B |
| 490 | 12.05 | 3.8 | 11.35 | 4.69 | S | 1b | NA | 41 | 33.7 | 490 | B |
| 491 | 5.81 | 1.5675 | 6.6 | 2.23 | S | 1b | NA | 41 | 33.7 | 491 | B |
| 492 | 5.02 | 1.255 | 0 | 0 | S | 1b | NA | 41 | 33.7 | 492 | B |
| 493 | 17.43 | 12.7767 | 19.69 | 14.02 | C | 2a | 22 | 25 | 75.5 | 493 | B |
| 494 | 10.59 | 7.22667 | 10.06 | 7.44 | C | 2a | 22 | 25 | 75.5 | 494 | B |
| 495 | 13.36 | 9.78667 | 25 | 12.5 | C | 2a | 22 | 25 | 75.5 | 495 | B |
| 496 | 9.47 | 6.42333 | 9.91 | 6.35 | C | 2a | 22 | 25 | 75.5 | 496 | B |
| 497 | 11.3 | 8.55333 | 11.19 | 8.94 | C | 2a | 22 | 25 | 75.5 | 497 | B |
| 498 | 13.33 | 9.77667 | 11.66 | 8.63 | C | 2a | 22 | 25 | 75.5 | 498 | B |
| 499 | 10.01 | 8.97333 | 12.64 | 9.83 | C | 2a | 22 | 25 | 75.5 | 499 | B |
| 500 | 5.97 | 2.90667 | 5.97 | 2.97 | C | 2a | 22 | 25 | 75.5 | 500 | B |
| 501 | 13.93 | 8.69333 | 16.47 | 10.63 | C | 2a | 22 | 25 | 75.5 | 501 | B |
| 502 | 10.44 | 7.73 | 11.11 | 8.62 | C | 2a | 22 | 25 | 75.5 | 502 | B |
| 503 | 9.51 | 6.04333 | 10.37 | 7.05 | C | 2a | 22 | 25 | 75.5 | 503 | B |
| 504 | 9.46 | 5.79667 | 10.54 | 6.45 | C | 2a | 22 | 25 | 75.5 | 504 | B |
| 505 | 8.48 | 6.35667 | 9.65 | 7.66 | C | 2a | 22 | 25 | 75.5 | 505 | B |
| 506 | 5.01 | 2.72333 | 5.74 | 3.2 | C | 2a | 22 | 25 | 75.5 | 506 | B |
| 507 | 38.46 | 17.004 | 36.07 | 19.41 | C | 3a | NA | 37 | 8.5 | 507 | B |
| 508 | 37.76 | 17.76 | 42.59 | 23.43 | C | 3a | NA | 37 | 8.5 | 508 | B |
| 509 | 36.2 | 16.832 | 36.64 | 22.64 | C | 3a | NA | 37 | 8.5 | 509 | B |
| 510 | 35.36 | 16.19 | 36.9 | 20.58 | C | 3a | NA | 37 | 8.5 | 510 | B |
| 511 | 33.18 | 13.816 | 0 | 0 | C | 3a | NA | 37 | 8.5 | 511 | B |
| 512 | 31.91 | 12.108 | 31.16 | 16.11 | C | 3a | NA | 37 | 8.5 | 512 | B |
| 513 | 31.34 | 16.644 | 35.37 | 20.94 | C | 3a | NA | 37 | 8.5 | 513 | B |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 514 | 29.72 | 14.39 | 28.68 | 17.16 | C | 3a | NA | 37 | 8.5 | 514 | B |
| 515 | 28.22 | 13.152 | 32.57 | 16.94 | C | 3a | NA | 37 | 8.5 | 515 | B |
| 516 | 25.85 | 11.136 | 23.96 | 14.16 | C | 3a | NA | 37 | 8.5 | 516 | B |
| 517 | 25.7 | 12.108 | 25 | 6.25 | C | 3a | NA | 37 | 8.5 | 517 | B |
| 518 | 23.87 | 10.928 | 23.04 | 13.56 | C | 3a | NA | 37 | 8.5 | 518 | B |
| 519 | 19.12 | 7.114 | 20.29 | 11.05 | C | 3a | NA | 37 | 8.5 | 519 | B |
| 520 | 13.7 | 4.438 | 13.35 | 5.57 | S | 3a | NA | 37 | 8.5 | 520 | B |
| 521 | 9.09 | 1.818 | 10.69 | 2.67 | S | 3a | NA | 37 | 8.5 | 521 | B |
| 522 | 6.35 | 2.13 | 7.82 | 3.64 | S | 3a | NA | 37 | 8.5 | 522 | B |
| 523 | 7.53 | 1.506 | 18.71 | 4.68 |   | 3a | NA | 37 | 8.5 | 523 | B |
| 524 | 10.24 | 2.048 | 6.23 | 1.57 | S | 3a | NA | 37 | 8.5 | 524 | B |
| 525 | 5.2 | 1.04 | 2.61 | 0.65 | S | 3a | NA | 37 | 8.5 | 525 | B |
| 526 | 24.72 | 16.03 | 23.46 | 20.04 | C | 1b | NA | 42 | 29 | 526 | B |
| 527 | 12.26 | 8.04 | 11.07 | 10.66 | C | 1b | NA | 42 | 29 | 527 | B |
| 528 | 6.96 | 1.74 | 6.64 | 2.21 | S | 1b | NA | 42 | 29 | 528 | B |
| 529 | 29.47 | 16.65 | 50 | 19.44 | C | 1b | NA | 42 | 29 | 529 | B |
| 530 | 22.98 | 16.9325 | 22 | 18.05 | C | 1b | NA | 42 | 29 | 530 | B |
| 531 | 14.89 | 9.145 | 17.61 | 13.65 | C | 1b | NA | 42 | 29 | 531 | B |
| 532 | 19.14 | 13.965 | 25.3 | 20.3 | C | 1b | NA | 42 | 29 | 532 | B |
| 533 | 21.76 | 13.5525 | 22.74 | 17.72 | C | 1b | NA | 42 | 29 | 533 | B |
| 534 | 25 | 17.99 | 26.86 | 23.34 |   | 1b | NA | 42 | 29 | 534 | B |
| 535 | 9.66 | 2.4775 | 9.81 | 3.27 | S | 1b | NA | 42 | 29 | 535 | B |
| 536 | 6.57 | 1.75 | 7.91 | 2.64 | S | 1b | NA | 42 | 29 | 536 | B |
| 537 | 7.68 | 1.92 | 5.79 | 1.93 | S | 1b | NA | 42 | 29 | 537 | B |
| 538 | 11.66 | 2.915 | 11.94 | 4 | S | 1b | NA | 42 | 29 | 538 | B |
| 539 | 14.65 | 3.73 | 17.41 | 5.82 | S | 1b | NA | 42 | 29 | 539 | B |
| 540 | 11.9 | 2.975 | 10.96 | 3.66 | S | 1b | NA | 42 | 29 | 540 | B |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 541 | 6.45 | 1.6125 | 6.29 | 2.1 | S | 1b | NA | 42 | 29 | 541 | B |
| 542 | 13.74 | 3.6775 | 24.18 | 8.07 | S | 1b | NA | 42 | 29 | 542 | B |
| 543 | 6.84 | 2.8425 | 6.5 | 3.9 | S | 1b | NA | 42 | 29 | 543 | B |
| 544 | 37.01 | 25.055 | 36.82 | 25.75 | C | 2b | NA | 47 | 29.7 | 544 | B |
| 545 | 36.05 | 23.4725 | 36.18 | 25.09 | C | 2b | NA | 47 | 29.7 | 545 | B |
| 546 | 15.3 | 3.8825 | 16.16 | 4.17 | S | 2b | NA | 47 | 29.7 | 546 | B |
| 547 | 7.41 | 1.8525 | 17.11 | 4.33 |  | 2b | NA | 47 | 29.7 | 547 | B |
| 548 | 24.22 | 16.2575 | 26.2 | 15.92 | C | 2b | NA | 47 | 29.7 | 548 | B |
| 549 | 9.01 | 7.2025 | 12.43 | 9.53 | C | 2b | NA | 47 | 29.7 | 549 | B |
| 550 | 11.95 | 2.9875 | 11.55 | 2.92 | S | 2b | NA | 47 | 29.7 | 550 | B |
| 551 | 10.47 | 2.6175 | 9.67 | 2.44 | S | 2b | NA | 47 | 29.7 | 551 | B |
| 552 | 9.85 | 2.5175 | 10.45 | 2.62 | S | 2b | NA | 47 | 29.7 | 552 | B |
| 553 | 10.75 | 4.705 | 13.49 | 6.06 | S | 2b | NA | 47 | 29.7 | 553 | B |
| 554 | 9.69 | 5.2325 | 13.89 | 3.47 | S | 2b | NA | 47 | 29.7 | 554 | B |
| 555 | 8.5 | 3.3975 | 6.96 | 3.15 | S | 2b | NA | 47 | 29.7 | 555 | B |
| 556 | 7.67 | 2.4025 | 7.09 | 2.78 | S | 2b | NA | 47 | 29.7 | 556 | B |
| 557 | 6.86 | 2.2825 | 6.05 | 2.26 | S | 2b | NA | 47 | 29.7 | 557 | B |
| 558 | 5.48 | 2.26 | 6.34 | 2.33 | S | 2b | NA | 47 | 29.7 | 558 | B |
| 559 | 11.14 | 2.865 | 13.65 | 3.53 | S | 2b | NA | 47 | 29.7 | 559 | B |
| 560 | 6.75 | 1.6875 | 4.09 | 1.03 | S | 2b | NA | 47 | 29.7 | 560 | B |
| 561 | 5.54 | 1.385 | 3.82 | 0.96 | S | 2b | NA | 47 | 29.7 | 561 | B |
| 562 | 43.95 | 18.8725 | 39.88 | 28.49 | C | 1b | 52 | 25 | 27.4 | 562 | U |
| 563 | 40.91 | 15.5613 | 54.55 | 21.91 | C | 1b | 52 | 25 | 27.4 | 563 | U |
| 564 | 38.74 | 13.3413 | 32.69 | 18.9 | C | 1b | 52 | 25 | 27.4 | 564 | U |
| 565 | 26.63 | 9.495 | 26.47 | 15.87 | C | 1b | 52 | 25 | 27.4 | 565 | U |
| 566 | 15.49 | 2.805 | 13.77 | 4.32 | S | 1b | 52 | 25 | 27.4 | 566 | U |
| 567 | 14.05 | 5.40125 | 15.2 | 8.38 | S | 1b | 52 | 25 | 27.4 | 567 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 568 | 11.38 | 4.6125 | 15.92 | 8.26 | C | 1b | 52 | 25 | 27.4 | 568 | U |
| 569 | 33.77 | 11.4788 | 34.42 | 19.91 | C | 1b | 52 | 25 | 27.4 | 569 | U |
| 570 | 19.7 | 6.965 | 22.22 | 14.4 | C | 1b | 52 | 25 | 27.4 | 570 | U |
| 571 | 5.26 | 0.71875 | 6.56 | 1.39 | S | 1b | 52 | 25 | 27.4 | 571 | U |
| 572 | 7.63 | 1.02125 | 9.33 | 2.15 | S | 1b | 52 | 25 | 27.4 | 572 | U |
| 573 | 9.76 | 1.2975 | 8.29 | 1.88 | S | 1b | 52 | 25 | 27.4 | 573 | U |
| 574 | 5.26 | 0.675 | 5.96 | 1.26 | S | 1b | 52 | 25 | 27.4 | 574 | U |
| 575 | 6.48 | 0.9025 | 6.63 | 1.33 | S | 1b | 52 | 25 | 27.4 | 575 | U |
| 576 | 14.13 | 4.50125 | 13.1 | 6.28 | S | 1b | 52 | 25 | 27.4 | 576 | U |
| 577 | 12.89 | 4.4175 | 11.93 | 6.55 | S | 1b | 52 | 25 | 27.4 | 577 | U |
| 578 | 9.99 | 1.30375 | 9.78 | 1.97 | S | 1b | 52 | 25 | 27.4 | 578 | U |
| 579 | 9.49 | 1.21875 | 11.28 | 2.27 | S | 1b | 52 | 25 | 27.4 | 579 | U |
| 580 | 5.6 | 0.7 | 5.52 | 1.14 | S | 1b | 52 | 25 | 27.4 | 580 | U |
| 581 | 5.4 | 0.68875 | 5.41 | 1.1 | S | 1b | 52 | 25 | 27.4 | 581 | U |
| 582 | 24.62 | 8.12167 | 31.41 | 18.32 | C | 2a | 60 | 24 | 41.4 | 582 | U |
| 583 | 16.96 | 4.81833 | 18.95 | 9.95 | C | 2a | 60 | 24 | 41.4 | 583 | U |
| 584 | 14.76 | 4.42 | 13.71 | 7.57 | C | 2a | 60 | 24 | 41.4 | 584 | U |
| 585 | 13.02 | 2.60667 | 11.45 | 4.35 | S | 2a | 60 | 24 | 41.4 | 585 | U |
| 586 | 12.6 | 3.70167 | 11.16 | 6.4 | C | 2a | 60 | 24 | 41.4 | 586 | U |
| 587 | 10.46 | 3.26333 | 11.11 | 6.71 | C | 2a | 60 | 24 | 41.4 | 587 | U |
| 588 | 10.45 | 4.12333 | 19.93 | 16.34 | C | 2a | 60 | 24 | 41.4 | 588 | U |
| 589 | 9.92 | 3.09167 | 18.14 | 12.77 | C | 2a | 60 | 24 | 41.4 | 589 | U |
| 590 | 9.63 | 3.36833 | 9.66 | 5.95 | C | 2a | 60 | 24 | 41.4 | 590 | U |
| 591 | 10.2 | 3.37 | 10.32 | 6.15 | C | 2a | 60 | 24 | 41.4 | 591 | U |
| 592 | 30.25 | 10.0917 | 28.96 | 18.76 | C | 2a | 60 | 24 | 41.4 | 592 | U |
| 593 | 10.7 | 4.12667 | 16.55 | 11.28 | C | 2a | 60 | 24 | 41.4 | 593 | U |
| 594 | 12.5 | 4.015 | 10.57 | 6.35 | C | 2a | 60 | 24 | 41.4 | 594 | U |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 595 | 18.56 | 6.54167 | 22.29 | 13.2 | C | 2a | 60 | 24 | 41.4 | 595 | U |
| 596 | 6.48 | 1.27667 | 6.68 | 2.3 | C | 2a | 60 | 24 | 41.4 | 596 | U |
| 597 | 13.04 | 2.44 | 11.63 | 4.4 | S | 2a | 60 | 24 | 41.4 | 597 | U |
| 598 | 5.29 | 0.881667 | 3.31 | 1.1 | S | 2a | 60 | 24 | 41.4 | 598 | U |
| 599 | 8.33 | 1.70833 | 11.44 | 4.33 | S | 2a | 60 | 24 | 41.4 | 599 | U |
| 600 | 8.28 | 1.715 | 8.41 | 3.31 | S | 2a | 60 | 24 | 41.4 | 600 | U |
| 601 | 5.85 | 0.975 | 5.74 | 1.93 | C | 2a | 60 | 24 | 41.4 | 601 | U |
| 602 | 36.38 | 30.755 | 41.06 | 35.59 | C | 1b | 22 | 20 | 18 | 602 | A |
| 603 | 31.03 | 18.195 | 31.47 | 23.04 | C | 1b | 22 | 20 | 18 | 603 | A |
| 604 | 30.3 | 24.57 | 35.66 | 30.9 | C | 1b | 22 | 20 | 18 | 604 | A |
| 605 | 27.57 | 25.65 | 30.01 | 24.34 | C | 1b | 22 | 20 | 18 | 605 | A |
| 606 | 25.84 | 22.225 | 24.95 | 21.38 | | 1b | 22 | 20 | 18 | 606 | A |
| 607 | 23.11 | 16.27 | 21.94 | 16.53 | C | 1b | 22 | 20 | 18 | 607 | A |
| 608 | 18.25 | 14.68 | 28.57 | 18.83 | C | 1b | 22 | 20 | 18 | 608 | A |
| 609 | 14.42 | 11.59 | 26.39 | 16.32 | S | 1b | 22 | 20 | 18 | 609 | A |
| 610 | 13.95 | 13.24 | 18.09 | 15.77 | S | 1b | 22 | 20 | 18 | 610 | A |
| 611 | 9.67 | 6.675 | 9.45 | 5.71 | C | 1b | 22 | 20 | 18 | 611 | A |
| 612 | 8.97 | 5.85 | 7.41 | 5.43 | C | 1b | 22 | 20 | 18 | 612 | A |
| 613 | 27.32 | 22.595 | 28.71 | 24.2 | C | 1b | 22 | 20 | 18 | 613 | A |
| 614 | 23.42 | 18.86 | 24.38 | 20.4 | S | 1b | 22 | 20 | 18 | 614 | A |
| 615 | 11.31 | 9.25 | 11.58 | 10.26 | S | 1b | 22 | 20 | 18 | 615 | A |
| 616 | 34.77 | 30.005 | 41.5 | 36.29 | C | 1b | 22 | 20 | 18 | 616 | A |
| 617 | 8.02 | 4.185 | 8.93 | 4.45 | S | 1b | 22 | 20 | 18 | 617 | A |
| 618 | 10.63 | 5.315 | 10.03 | 5.01 | S | 1b | 22 | 20 | 18 | 618 | A |
| 619 | 6.13 | 4.14 | 8.25 | 5.66 | S | 1b | 22 | 20 | 18 | 619 | A |
| 620 | 6.51 | 3.255 | 6.48 | 3.24 | C | 1b | 22 | 20 | 18 | 620 | A |
| 621 | 42.62 | 27.5733 | 46.35 | 33.79 | | 2a | NA | 49 | 82.5 | 621 | M |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 622 | 28.12 | 18.9017 | 31.73 | 25.7 | C | 2a | NA | 49 | 82.5 | 622 | M |
| 623 | 26.5 | 15.755 | 24.98 | 18.28 | C | 2a | NA | 49 | 82.5 | 623 | M |
| 624 | 16.97 | 10.07 | 20.84 | 16.05 |   | 2a | NA | 49 | 82.5 | 624 | M |
| 625 | 16.04 | 7.55833 | 14.42 | 9.08 | C | 2a | NA | 49 | 82.5 | 625 | M |
| 626 | 14.14 | 8.82667 | 33.33 | 16.2 | C | 2a | NA | 49 | 82.5 | 626 | M |
| 627 | 12.98 | 3.545 | 10.84 | 4.74 | S | 2a | NA | 49 | 82.5 | 627 | M |
| 628 | 11.19 | 2.80667 | 8.04 | 3.18 | S | 2a | NA | 49 | 82.5 | 628 | M |
| 629 | 8.96 | 3.445 | 9.3 | 4.02 | S | 2a | NA | 49 | 82.5 | 629 | M |
| 630 | 18.49 | 11.9783 | 20.46 | 15.25 | C | 2a | NA | 49 | 82.5 | 630 | M |
| 631 | 20.06 | 11.93 | 20.44 | 15.43 | C | 2a | NA | 49 | 82.5 | 631 | M |
| 632 | 16.57 | 9.65333 | 20 | 14.51 | C | 2a | NA | 49 | 82.5 | 632 | M |
| 633 | 22.49 | 10.0783 | 15.66 | 10.63 | C | 2a | NA | 49 | 82.5 | 633 | M |
| 634 | 20.45 | 10.255 | 19.75 | 14.66 | C | 2a | NA | 49 | 82.5 | 634 | M |
| 635 | 9.54 | 4.21 | 10.51 | 4.47 | S | 2a | NA | 49 | 82.5 | 635 | M |
| 636 | 7.87 | 2.925 | 2.33 | 0.47 | S | 2a | NA | 49 | 82.5 | 636 | M |
| 637 | 8.78 | 3.23333 | 10.29 | 4.28 | S | 2a | NA | 49 | 82.5 | 637 | M |
| 638 | 7.51 | 2.895 | 9.67 | 4.21 | S | 2a | NA | 49 | 82.5 | 638 | M |
| 639 | 9.11 | 3.35833 | 9.87 | 4.09 | S | 2a | NA | 49 | 82.5 | 639 | M |
| 640 | 7.6 | 2.52833 | 9.2 | 3.41 | C | 2a | NA | 49 | 82.5 | 640 | M |
| 641 | 23.39 | 7.99667 | 22.71 | 7.68 | S | 1b | 35 | 25 | 3.4 | 641 | U |
| 642 | 19.83 | 6.72 | 26.67 | 8.89 | S | 1b | 35 | 25 | 3.4 | 642 | U |
| 643 | 8.97 | 2.99 | 10.17 | 3.39 | S | 1b | 35 | 25 | 3.4 | 643 | U |
| 644 | 7.46 | 2.48667 | 7.3 | 2.45 | S | 1b | 35 | 25 | 3.4 | 644 | U |
| 645 | 6.36 | 2.12 | 5.99 | 2 | S | 1b | 35 | 25 | 3.4 | 645 | U |
| 646 | 32.37 | 26.89 | 29.01 | 27.16 | C | 1b | 35 | 25 | 3.4 | 646 | U |
| 647 | 7.98 | 2.66 | 10.54 | 3.51 | S | 1b | 35 | 25 | 3.4 | 647 | U |
| 648 | 8.99 | 2.99667 | 6.21 | 2.07 | S | 1b | 35 | 25 | 3.4 | 648 | U |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 649 | 5.62 | 1.87333 | 7.61 | 2.58 | S | 1b | 35 | 25 | 3.4 | 649 | U |
| 650 | 26.06 | 8.78333 | 26.77 | 8.93 | S | 1b | 35 | 25 | 3.4 | 650 | U |
| 651 | 34.41 | 11.47 | 37.55 | 12.53 |  | 1b | 35 | 25 | 3.4 | 651 | U |
| 652 | 28.22 | 16.8467 | 27.12 | 16.23 | C | 1b | 35 | 25 | 3.4 | 652 | U |
| 653 | 24.07 | 13.36 | 23.41 | 13.91 | C | 1b | 35 | 25 | 3.4 | 653 | U |
| 654 | 23.01 | 13.4967 | 24.49 | 11.61 | S | 1b | 35 | 25 | 3.4 | 654 | U |
| 655 | 9.58 | 3.23 | 11.19 | 3.82 | S | 1b | 35 | 25 | 3.4 | 655 | U |
| 656 | 21.35 | 7.25 | 9.57 | 3.19 | S | 1b | 35 | 25 | 3.4 | 656 | U |
| 657 | 17.25 | 5.75 | 18.93 | 6.31 | S | 1b | 35 | 25 | 3.4 | 657 | U |
| 658 | 7.1 | 2.36667 | 6.26 | 2.09 | S | 1b | 35 | 25 | 3.4 | 658 | U |
| 659 | 6.48 | 2.16 | 6.19 | 2.06 | S | 1b | 35 | 25 | 3.4 | 659 | U |
| 660 | 61.97 | 41.6643 | 64.73 | 44.76 | C | 2b | NA | 67 | 124.6 | 660 | B |
| 661 | 48.18 | 13.87 | 49.19 | 14.44 | S | 2b | NA | 67 | 124.6 | 661 | B |
| 662 | 37.54 | 10.1971 | 38.31 | 10.38 | S | 2b | NA | 67 | 124.6 | 662 | B |
| 663 | 36.67 | 25.5814 | 38.82 | 26.77 | C | 2b | NA | 67 | 124.6 | 663 | B |
| 664 | 33.84 | 25.0843 | 33.74 | 26.34 | C | 2b | NA | 67 | 124.6 | 664 | B |
| 665 | 31.43 | 5.15 | 16.33 | 2.56 | S | 2b | NA | 67 | 124.6 | 665 | B |
| 666 | 25.96 | 7.77714 | 25 | 7.41 | S | 2b | NA | 67 | 124.6 | 666 | B |
| 667 | 17.48 | 4.42571 | 18.18 | 5.41 | S | 2b | NA | 67 | 124.6 | 667 | B |
| 668 | 15.07 | 2.21 | 5.65 | 0.81 |  | 2b | NA | 67 | 124.6 | 668 | B |
| 669 | 14.52 | 2.08857 | 12.17 | 1.74 |  | 2b | NA | 67 | 124.6 | 669 | B |
| 670 | 11.56 | 1.65143 | 12.11 | 1.75 | S | 2b | NA | 67 | 124.6 | 670 | B |
| 671 | 9.93 | 3.22857 | 9.2 | 3.08 | S | 2b | NA | 67 | 124.6 | 671 | B |
| 672 | 8.62 | 1.23143 | 7.88 | 1.13 | S | 2b | NA | 67 | 124.6 | 672 | B |
| 673 | 5.4 | 0.784286 | 5.05 | 0.75 | C | 2b | NA | 67 | 124.6 | 673 | B |
| 674 | 57.9 | 36.8857 | 56.61 | 37.08 |  | 2b | NA | 67 | 124.6 | 674 | B |
| 675 | 68.22 | 48.89 | 74.72 | 55.5 |  | 2b | NA | 67 | 124.6 | 675 | B |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 676 | 55.49 | 39.15 | 61.63 | 43.95 | C | 2b | NA | 67 | 124.6 | 676 | B |
| 677 | 6.07 | 0.901429 | 5.85 | 0.84 | S | 2b | NA | 67 | 124.6 | 677 | B |
| 678 | 6.45 | 0.921429 | 8.04 | 1.15 | S | 2b | NA | 67 | 124.6 | 678 | B |
| 679 | 5.24 | 0.748571 | 8.52 | 1.22 | S | 2b | NA | 67 | 124.6 | 679 | B |
| 680 | 34.38 | 30.525 | 48.42 | 44.82 | C | 1a | NA | 30 | 73.8 | 680 | B |
| 681 | 30.42 | 25.82 | 27.37 | 24.76 | C | 1a | NA | 30 | 73.8 | 681 | B |
| 682 | 16.33 | 8.165 | 20.7 | 10.4 | S | 1a | NA | 30 | 73.8 | 682 | B |
| 683 | 6.17 | 3.085 | 5.27 | 2.78 | S | 1a | NA | 30 | 73.8 | 683 | B |
| 684 | 27.84 | 23.95 | 26.93 | 24.51 | C | 1a | NA | 30 | 73.8 | 684 | B |
| 685 | 31.81 | 26.47 | 32.21 | 25.17 | | 1a | NA | 30 | 73.8 | 685 | B |
| 686 | 17.44 | 16.095 | 19.23 | 15.17 | C | 1a | NA | 30 | 73.8 | 686 | B |
| 687 | 19.97 | 16.96 | 21.22 | 17.8 | | 1a | NA | 30 | 73.8 | 687 | B |
| 688 | 23.17 | 22.91 | 27.35 | 24.76 | C | 1a | NA | 30 | 73.8 | 688 | B |
| 689 | 21.95 | 10.975 | 22.22 | 11.11 | S | 1a | NA | 30 | 73.8 | 689 | B |
| 690 | 6.77 | 3.385 | 6.18 | 3.1 | S | 1a | NA | 30 | 73.8 | 690 | B |
| 691 | 6.64 | 3.32 | 4.98 | 2.51 | S | 1a | NA | 30 | 73.8 | 691 | B |
| 692 | 5.42 | 2.795 | 7.74 | 3.95 | S | 1a | NA | 30 | 73.8 | 692 | B |
| 693 | 8.16 | 4.08 | 6.72 | 3.4 | S | 1a | NA | 30 | 73.8 | 693 | B |
| 694 | 6.57 | 3.285 | 7.82 | 3.91 | S | 1a | NA | 30 | 73.8 | 694 | B |
| 695 | 5.71 | 2.855 | 6.66 | 3.33 | S | 1a | NA | 30 | 73.8 | 695 | B |
| 696 | 8.5 | 6.23 | 8.5 | 6.53 | S | 1a | NA | 30 | 73.8 | 696 | B |
| 697 | 6.1 | 5.31 | 7.69 | 5.57 | S | 1a | NA | 30 | 73.8 | 697 | B |
| 698 | 7.75 | 3.9925 | 7.9 | 4.85 | C | 1b | NA | 53 | 12.7 | 698 | M |
| 699 | 25.19 | 10.785 | 22.32 | 13.27 | C | 1b | NA | 53 | 12.7 | 699 | M |
| 700 | 6.72 | 3.3925 | 7.44 | 4.52 | | 1b | NA | 53 | 12.7 | 700 | M |
| 701 | 13.18 | 4.27 | 13.32 | 6.33 | | 1b | NA | 53 | 12.7 | 701 | M |
| 702 | 6.45 | 3.17 | 8.97 | 5.73 | C | 1b | NA | 53 | 12.7 | 702 | M |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 703 | 18.71 | 8.835 | 13.23 | 8.86 | C | 1b | NA | 53 | 12.7 | 703 | M |
| 704 | 18.35 | 9.845 | 20.94 | 13.15 | C | 1b | NA | 53 | 12.7 | 704 | M |
| 705 | 9.23 | 4.77 | 11.57 | 7.05 | C | 1b | NA | 53 | 12.7 | 705 | M |
| 706 | 18.69 | 9.5425 | 17.43 | 11.35 | C | 1b | NA | 53 | 12.7 | 706 | M |
| 707 | 16.4 | 7.78 | 17.32 | 10.89 | C | 1b | NA | 53 | 12.7 | 707 | M |
| 708 | 9.78 | 2.9875 | 7.14 | 2.38 | S | 1b | NA | 53 | 12.7 | 708 | M |
| 709 | 7.12 | 2.685 | 7.44 | 3.37 | S | 1b | NA | 53 | 12.7 | 709 | M |
| 710 | 9.4 | 2.35 | 6.52 | 2.21 |  | 1b | NA | 53 | 12.7 | 710 | M |
| 711 | 8.18 | 2.16 | 6.02 | 2.07 | S | 1b | NA | 53 | 12.7 | 711 | M |
| 712 | 5.95 | 1.5725 | 4.46 | 1.5 | C | 1b | NA | 53 | 12.7 | 712 | M |
| 713 | 17.98 | 14.0467 | 15.62 | 15.19 | C | 1a | NA | 20 | 11.8 | 713 | B |
| 714 | 16.36 | 10.7267 | 15.24 | 11.76 | C | 1a | NA | 20 | 11.8 | 714 | B |
| 715 | 10.18 | 9.60333 | 11.88 | 9.74 | C | 1a | NA | 20 | 11.8 | 715 | B |
| 716 | 15.78 | 9.77333 | 15.91 | 11.39 | C | 1a | NA | 20 | 11.8 | 716 | B |
| 717 | 11.29 | 9.80667 | 12.33 | 10.71 | C | 1a | NA | 20 | 11.8 | 717 | B |
| 718 | 10.66 | 8.61333 | 13.49 | 10.73 | C | 1a | NA | 20 | 11.8 | 718 | B |
| 719 | 11.8 | 9.43667 | 13.31 | 10.47 | C | 1a | NA | 20 | 11.8 | 719 | B |
| 720 | 14.95 | 10.4167 | 16.04 | 11.45 | C | 1a | NA | 20 | 11.8 | 720 | B |
| 721 | 10.59 | 9.23667 | 15.47 | 12.63 | C | 1a | NA | 20 | 11.8 | 721 | B |
| 722 | 12.18 | 11.16 | 28.3 | 26.49 | C | 1a | NA | 20 | 11.8 | 722 | B |
| 723 | 10 | 9.47 | 12.31 | 9.7 | C | 1a | NA | 20 | 11.8 | 723 | B |
| 724 | 14.64 | 10.3733 | 10.61 | 9.33 | C | 1a | NA | 20 | 11.8 | 724 | B |
| 725 | 6.4 | 5.48333 | 6.65 | 5.73 | C | 1a | NA | 20 | 11.8 | 725 | B |
| 726 | 5.09 | 4.33333 | 5.51 | 4.93 | S | 1a | NA | 20 | 11.8 | 726 | B |
| 727 | 5.01 | 3.65333 | 2.78 | 1.74 | C | 1a | NA | 20 | 11.8 | 727 | B |
| 728 | 75 | 71 | 77.92 | 75.62 |  | 1b | NA | 32 | 155.6 | 728 | M |
| 729 | 45.55 | 41.7975 | 52.05 | 46.41 | C | 1b | NA | 32 | 155.6 | 729 | M |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 730 | 43.61 | 41.05 | 44.74 | 43.68 | C | 1b | NA | 32 | 155.6 | 730 | M |
| 731 | 57.15 | 55.85 | 61.2 | 60.26 | C | 1b | NA | 32 | 155.6 | 731 | M |
| 732 | 33.96 | 31.2575 | 16.92 | 15.74 | C | 1b | NA | 32 | 155.6 | 732 | M |
| 733 | 45.22 | 39.875 | 42.04 | 40.38 | C | 1b | NA | 32 | 155.6 | 733 | M |
| 734 | 34.98 | 30.2325 | 28.36 | 20.89 | C | 1b | NA | 32 | 155.6 | 734 | M |
| 735 | 43.45 | 42.235 | 66.67 | 53.74 | C | 1b | NA | 32 | 155.6 | 735 | M |
| 736 | 43.12 | 41 | 42.36 | 41.44 | C | 1b | NA | 32 | 155.6 | 736 | M |
| 737 | 39.02 | 36.835 | 43.81 | 42.76 |  | 1b | NA | 32 | 155.6 | 737 | M |
| 738 | 37.55 | 35.16 | 42.86 | 30.49 | C | 1b | NA | 32 | 155.6 | 738 | M |
| 739 | 30.47 | 27.7775 | 30.26 | 29.15 | C | 1b | NA | 32 | 155.6 | 739 | M |
| 740 | 26.72 | 25.865 | 31.03 | 26.83 | C | 1b | NA | 32 | 155.6 | 740 | M |
| 741 | 10.22 | 2.555 | 10.2 | 2.55 | S | 1b | NA | 32 | 155.6 | 741 | M |
| 742 | 8.48 | 2.12 | 9.41 | 2.39 | S | 1b | NA | 32 | 155.6 | 742 | M |
| 743 | 7 | 1.75 | 25 | 6.25 | S | 1b | NA | 32 | 155.6 | 743 | M |
| 744 | 5.48 | 1.49 | 2.76 | 0.75 | S | 1b | NA | 32 | 155.6 | 744 | M |
| 745 | 42.83 | 29.8 | 41.2 | 31.96 | C | 2b | 71 | 56 | 19.2 | 745 | A |
| 746 | 26.32 | 18.3775 | 25.08 | 20.35 | C | 2b | 71 | 56 | 19.2 | 746 | A |
| 747 | 22.77 | 19.8175 | 31.87 | 24.23 | C | 2b | 71 | 56 | 19.2 | 747 | A |
| 748 | 22.59 | 5.6475 | 24.6 | 6.16 | S | 2b | 71 | 56 | 19.2 | 748 | A |
| 749 | 18.82 | 4.705 | 19.11 | 4.84 | S | 2b | 71 | 56 | 19.2 | 749 | A |
| 750 | 18.7 | 4.675 | 24.8 | 6.22 | S | 2b | 71 | 56 | 19.2 | 750 | A |
| 751 | 23.62 | 18.3025 | 29.56 | 24.43 | C | 2b | 71 | 56 | 19.2 | 751 | A |
| 752 | 23.4 | 17.4375 | 27.54 | 21.86 | C | 2b | 71 | 56 | 19.2 | 752 | A |
| 753 | 47.46 | 30.3575 | 47.6 | 34.43 | C | 2b | 71 | 56 | 19.2 | 753 | A |
| 754 | 38.76 | 24.585 | 44.74 | 27.57 | C | 2b | 71 | 56 | 19.2 | 754 | A |
| 755 | 27.2 | 20.6325 | 25.3 | 19.91 | C | 2b | 71 | 56 | 19.2 | 755 | A |
| 756 | 40 | 28.8375 | 36.18 | 24.25 | C | 2b | 71 | 56 | 19.2 | 756 | A |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 757 | 16.12 | 4.03 | 19.12 | 4.78 | S | 2b | 71 | 56 | 19.2 | 757 | A |
| 758 | 15.42 | 3.855 | 20.44 | 5.15 | S | 2b | 71 | 56 | 19.2 | 758 | A |
| 759 | 8.36 | 2.09 | 7.7 | 1.92 | S | 2b | 71 | 56 | 19.2 | 759 | A |
| 760 | 14.29 | 3.5725 | 16.71 | 4.18 | S | 2b | 71 | 56 | 19.2 | 760 | A |
| 761 | 26.49 | 6.6225 | 28.89 | 7.22 | S | 2b | 71 | 56 | 19.2 | 761 | A |
| 762 | 26.86 | 6.8 | 14.29 | 3.96 | S | 2b | 71 | 56 | 19.2 | 762 | A |
| 763 | 26.19 | 6.5475 | 14.29 | 3.57 | S | 2b | 71 | 56 | 19.2 | 763 | A |
| 764 | 24.15 | 8.4975 | 26.14 | 9.56 | S | 2b | 71 | 56 | 19.2 | 764 | A |
| 765 | 72.52 | 66.455 | 75.22 | 70.72 | C | 1b | NA | 32 | 76.5 | 765 | M |
| 766 | 51.19 | 44.72 | 53.6 | 46.33 | C | 1b | NA | 32 | 76.5 | 766 | M |
| 767 | 48.91 | 43.36 | 56.13 | 45.14 | C | 1b | NA | 32 | 76.5 | 767 | M |
| 768 | 40.7 | 22.4825 | 39.35 | 26.26 | C | 1b | NA | 32 | 76.5 | 768 | M |
| 769 | 29.45 | 27.5175 | 29.97 | 27.76 | C | 1b | NA | 32 | 76.5 | 769 | M |
| 770 | 15.19 | 5.0475 | 18.83 | 5.86 | S | 1b | NA | 32 | 76.5 | 770 | M |
| 771 | 33.65 | 26.7175 | 34.97 | 29.85 | C | 1b | NA | 32 | 76.5 | 771 | M |
| 772 | 37.83 | 35.1625 | 39.54 | 36.08 | C | 1b | NA | 32 | 76.5 | 772 | M |
| 773 | 48.23 | 32.475 | 51.03 | 35.3 | C | 1b | NA | 32 | 76.5 | 773 | M |
| 774 | 15.33 | 5.14 | 17.28 | 5.41 | S | 1b | NA | 32 | 76.5 | 774 | M |
| 775 | 18.48 | 8.7875 | 19.66 | 9.5 | S | 1b | NA | 32 | 76.5 | 775 | M |
| 776 | 14.86 | 6.9975 | 16.62 | 7.53 | S | 1b | NA | 32 | 76.5 | 776 | M |
| 777 | 8.29 | 2.1775 | 12.04 | 3.35 | S | 1b | NA | 32 | 76.5 | 777 | M |
| 778 | 6.51 | 2.065 | 7.59 | 2.31 | S | 1b | NA | 32 | 76.5 | 778 | M |
| 779 | 11.64 | 5.725 | 17.07 | 7.85 | S | 1b | NA | 32 | 76.5 | 779 | M |
| 780 | 16.8 | 8.1725 | 19.32 | 9.75 | S | 1b | NA | 32 | 76.5 | 780 | M |
| 781 | 9.11 | 2.3675 | 9.98 | 2.64 | S | 1b | NA | 32 | 76.5 | 781 | M |
| 782 | 7.82 | 2.0425 | 8.6 | 2.38 | S | 1b | NA | 32 | 76.5 | 782 | M |
| 783 | 13.28 | 4.0075 | 15.44 | 5.04 | S | 1b | NA | 32 | 76.5 | 783 | M |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 784 | 24.34 | 16.2475 | 22.14 | 17.31 | C | 1b | NA | 38 | 101.5 | 784 | M |
| 785 | 23.54 | 21.0525 | 24.42 | 22.69 | C | 1b | NA | 38 | 101.5 | 785 | M |
| 786 | 22.54 | 16.8 | 21.33 | 17.98 | C | 1b | NA | 38 | 101.5 | 786 | M |
| 787 | 21.25 | 11.305 | 20.39 | 11.57 | S | 1b | NA | 38 | 101.5 | 787 | M |
| 788 | 16.99 | 14.57 | 16.59 | 13.95 | C | 1b | NA | 38 | 101.5 | 788 | M |
| 789 | 16.38 | 14.065 | 18.3 | 15.33 | C | 1b | NA | 38 | 101.5 | 789 | M |
| 790 | 8.7 | 3.965 | 9.55 | 4.7 | S | 1b | NA | 38 | 101.5 | 790 | M |
| 791 | 5.07 | 2.21 | 4.7 | 2.33 | S | 1b | NA | 38 | 101.5 | 791 | M |
| 792 | 18.41 | 14.0625 | 17.48 | 14.17 | C | 1b | NA | 38 | 101.5 | 792 | M |
| 793 | 17.41 | 13.91 | 0.44 | 0.21 | C | 1b | NA | 38 | 101.5 | 793 | M |
| 794 | 5.53 | 1.7775 | 5.49 | 2.5 | S | 1b | NA | 38 | 101.5 | 794 | M |
| 795 | 5.37 | 2.3075 | 4.1 | 1.98 | S | 1b | NA | 38 | 101.5 | 795 | M |
| 796 | 8.76 | 3.2 | 14.43 | 7.06 | S | 1b | NA | 38 | 101.5 | 796 | M |
| 797 | 6.31 | 2.5175 | 4.67 | 2.24 | S | 1b | NA | 38 | 101.5 | 797 | M |
| 798 | 6.74 | 1.685 | 6.16 | 1.55 | S | 1b | NA | 38 | 101.5 | 798 | M |
| 799 | 10.95 | 2.7375 | 10.97 | 2.75 | S | 1b | NA | 38 | 101.5 | 799 | M |
| 800 | 14.97 | 8.405 | 16.25 | 8.75 | S | 1b | NA | 38 | 101.5 | 800 | M |
| 801 | 18.51 | 9.6875 | 43.9 | 21.55 | S | 1b | NA | 38 | 101.5 | 801 | M |
| 802 | 10.38 | 2.595 | 10.75 | 2.69 | S | 1b | NA | 38 | 101.5 | 802 | M |
| 803 | 81.78 | 80.795 | 83.94 | 81.34 | C | 1a | NA | 16 | 15.6 | 803 | B |
| 804 | 36.12 | 30.82 | 33.53 | 33.2 | C | 1a | NA | 16 | 15.6 | 804 | B |
| 805 | 35.29 | 34.02 | 43.4 | 37.51 |  | 1a | NA | 16 | 15.6 | 805 | B |
| 806 | 31.16 | 29.365 | 28.54 | 27.4 | C | 1a | NA | 16 | 15.6 | 806 | B |
| 807 | 15.83 | 8.74 | 12.12 | 6.95 | C | 1a | NA | 16 | 15.6 | 807 | B |
| 808 | 29.14 | 27.5 | 30.53 | 29.63 | C | 1a | NA | 16 | 15.6 | 808 | B |
| 809 | 22.53 | 21.455 | 24.68 | 23.91 | C | 1a | NA | 16 | 15.6 | 809 | B |
| 810 | 19.94 | 19.59 | 24.74 | 24.28 | C | 1a | NA | 16 | 15.6 | 810 | B |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 811 | 26.24 | 25.915 | 24.88 | 24.69 | C | 1a | NA | 16 | 15.6 | 811 | B |
| 812 | 23.72 | 20.365 | 25.43 | 23.31 | C | 1a | NA | 16 | 15.6 | 812 | B |
| 813 | 9.19 | 4.595 | 10.14 | 5.07 | S | 1a | NA | 16 | 15.6 | 813 | B |
| 814 | 7.89 | 3.945 | 8.8 | 4.42 | S | 1a | NA | 16 | 15.6 | 814 | B |
| 815 | 7.82 | 3.91 | 6.59 | 3.31 | S | 1a | NA | 16 | 15.6 | 815 | B |
| 816 | 7.05 | 3.525 | 16.31 | 8.16 | S | 1a | NA | 16 | 15.6 | 816 | B |
| 817 | 5.34 | 2.67 | 3.9 | 1.95 | S | 1a | NA | 16 | 15.6 | 817 | B |
| 818 | 15.43 | 12.155 | 20.46 | 15.61 | S | 1a | NA | 16 | 15.6 | 818 | B |
| 819 | 12.97 | 8.605 | 13.96 | 8.98 | S | 1a | NA | 16 | 15.6 | 819 | B |
| 820 | 9.88 | 7.64 | 9.47 | 7.19 | C | 1a | NA | 16 | 15.6 | 820 | B |
| 821 | 9.69 | 6.775 | 23.95 | 18.58 | S | 1a | NA | 16 | 15.6 | 821 | B |
| 822 | 78.34 | 59.335 | 78.63 | 61.29 | C | 1b | NA | 35 | 50.1 | 822 | B |
| 823 | 42.34 | 34.15 | 46.56 | 36.29 | C | 1b | NA | 35 | 50.1 | 823 | B |
| 824 | 80.73 | 58.91 | 95.45 | 77.58 | C | 1b | NA | 35 | 50.1 | 824 | B |
| 825 | 39.67 | 31.3625 | 46.6 | 38.46 | C | 1b | NA | 35 | 50.1 | 825 | B |
| 826 | 32.42 | 23.235 | 42.24 | 30.36 | C | 1b | NA | 35 | 50.1 | 826 | B |
| 827 | 11.63 | 9.02 | 10.03 | 7.55 | C | 1b | NA | 35 | 50.1 | 827 | B |
| 828 | 81.45 | 60.375 | 66.57 | 46.85 | C | 1b | NA | 35 | 50.1 | 828 | B |
| 829 | 10.59 | 2.9725 | 12.1 | 3.24 | S | 1b | NA | 35 | 50.1 | 829 | B |
| 830 | 8.55 | 2.235 | 6.22 | 1.75 | S | 1b | NA | 35 | 50.1 | 830 | B |
| 831 | 7.38 | 2.1725 | 6.41 | 1.81 | S | 1b | NA | 35 | 50.1 | 831 | B |
| 832 | 6.32 | 1.925 | 4.13 | 1.36 | | 1b | NA | 35 | 50.1 | 832 | B |
| 833 | 25.35 | 6.71 | 29.48 | 7.77 | S | 1b | NA | 35 | 50.1 | 833 | B |
| 834 | 9.4 | 2.35 | 8.71 | 2.19 | S | 1b | NA | 35 | 50.1 | 834 | B |
| 835 | 5.39 | 1.675 | 5.48 | 2.04 | S | 1b | NA | 35 | 50.1 | 835 | B |
| 836 | 5.3 | 1.5975 | 3.7 | 1.8 | S | 1b | NA | 35 | 50.1 | 836 | B |
| 837 | 15.27 | 4.6675 | 14.84 | 4.53 | S | 1b | NA | 35 | 50.1 | 837 | B |

FIG. 20 (CONT.)

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 838 | 13.71 | 4.5275 | 14.36 | 4.44 | S | 1b | NA | 35 | 50.1 | 838 | B |
| 839 | 10.56 | 2.8025 | 3.17 | 0.94 | S | 1b | NA | 35 | 50.1 | 839 | B |
| 840 | 39.13 | 33.525 | 48.02 | 45.6 | C | 1a | 25 | 15 | 26.5 | 840 | U |
| 841 | 38.75 | 37.945 | 62.5 | 57.57 | C | 1a | 25 | 15 | 26.5 | 841 | U |
| 842 | 36.14 | 34.29 | 37.59 | 35.02 | C | 1a | 25 | 15 | 26.5 | 842 | U |
| 843 | 29.61 | 28.59 | 30.05 | 28.04 | C | 1a | 25 | 15 | 26.5 | 843 | U |
| 844 | 24.69 | 23.185 | 26.89 | 25.23 | C | 1a | 25 | 15 | 26.5 | 844 | U |
| 845 | 23.22 | 22.94 | 27.55 | 25.98 | C | 1a | 25 | 15 | 26.5 | 845 | U |
| 846 | 12.6 | 11.8 | 15.4 | 15.03 | C | 1a | 25 | 15 | 26.5 | 846 | U |
| 847 | 27.78 | 26.155 | 80 | 50 | S | 1a | 25 | 15 | 26.5 | 847 | U |
| 848 | 28.07 | 26.165 | 38.97 | 36.38 | S | 1a | 25 | 15 | 26.5 | 848 | U |
| 849 | 9.12 | 4.56 | 10.93 | 5.46 | S | 1a | 25 | 15 | 26.5 | 849 | U |
| 850 | 10.4 | 5.2 | 9.52 | 4.76 | S | 1a | 25 | 15 | 26.5 | 850 | U |
| 851 | 9.52 | 4.76 | 10.95 | 5.47 | S | 1a | 25 | 15 | 26.5 | 851 | U |
| 852 | 12.77 | 6.385 | 5.91 | 2.96 | S | 1a | 25 | 15 | 26.5 | 852 | U |
| 853 | 11.31 | 5.655 | 10.19 | 5.1 | S | 1a | 25 | 15 | 26.5 | 853 | U |
| 854 | 10.2 | 5.17 | 10.91 | 5.46 | S | 1a | 25 | 15 | 26.5 | 854 | U |
| 855 | 14.1 | 7.05 | 14.48 | 7.24 | S | 1a | 25 | 15 | 26.5 | 855 | U |
| 856 | 10.66 | 5.33 | 10.1 | 5.05 | S | 1a | 25 | 15 | 26.5 | 856 | U |
| 857 | 15.7 | 8.745 | 13.67 | 7.58 | C | 1a | 25 | 15 | 26.5 | 857 | U |
| 858 | 13.37 | 7.405 | 16.98 | 9.11 | C | 1a | 25 | 15 | 26.5 | 858 | U |
| 859 | 53.46 | 43.655 | 41.78 | 35.9 | C | 2a | 60 | 50 | 33 | 859 | U |
| 860 | 44.19 | 37.59 | 41.58 | 34.67 | C | 2a | 60 | 50 | 33 | 860 | U |
| 861 | 27.54 | 17.36 | 33.14 | 19.86 | C | 2a | 60 | 50 | 33 | 861 | U |
| 862 | 17.47 | 14.02 | 16.83 | 15.04 | C | 2a | 60 | 50 | 33 | 862 | U |
| 863 | 16.96 | 14.2225 | 16.89 | 15.07 | C | 2a | 60 | 50 | 33 | 863 | U |
| 864 | 6.73 | 1.6825 | 6.18 | 1.56 | S | 2a | 60 | 50 | 33 | 864 | U |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 865 | 39.88 | 35.6325 | 39.2 | 33.77 | C | 2a | 60 | 50 | 33 | 865 | U |
| 866 | 53.08 | 46.3475 | 47.67 | 41.12 | C | 2a | 60 | 50 | 33 | 866 | U |
| 867 | 38 | 33.5 | 21.52 | 20.38 | C | 2a | 60 | 50 | 33 | 867 | U |
| 868 | 23.08 | 13.39 | 23.22 | 16.57 | S | 2a | 60 | 50 | 33 | 868 | U |
| 869 | 20.18 | 14.6 | 33.33 | 20.24 | S | 2a | 60 | 50 | 33 | 869 | U |
| 870 | 16.14 | 10.2975 | 14.71 | 10.37 | S | 2a | 60 | 50 | 33 | 870 | U |
| 871 | 5.62 | 3.705 | 6.11 | 4.21 | | 2a | 60 | 50 | 33 | 871 | U |
| 872 | 14.64 | 3.66 | 15.33 | 3.84 | S | 2a | 60 | 50 | 33 | 872 | U |
| 873 | 11.2 | 2.8 | 12.92 | 3.23 | S | 2a | 60 | 50 | 33 | 873 | U |
| 874 | 10.67 | 2.6675 | 10.32 | 2.58 | S | 2a | 60 | 50 | 33 | 874 | U |
| 875 | 9.76 | 2.44 | 8.95 | 2.26 | S | 2a | 60 | 50 | 33 | 875 | U |
| 876 | 20.26 | 5.065 | 15.49 | 3.89 | S | 2a | 60 | 50 | 33 | 876 | U |
| 877 | 6.13 | 1.5325 | 5.87 | 1.47 | S | 2a | 60 | 50 | 33 | 877 | U |
| 878 | 7.59 | 1.8975 | 15.7 | 3.92 | S | 2a | 60 | 50 | 33 | 878 | U |
| 879 | 16.58 | 4.145 | 13.99 | 3.54 | C | 2a | 60 | 50 | 33 | 879 | U |
| 880 | 53.99 | 43.445 | 61.73 | 39.77 | C | 1b | 40 | 39 | 10 | 880 | B |
| 881 | 14.39 | 8.9825 | 15.39 | 9.03 | S | 1b | 40 | 39 | 10 | 881 | B |
| 882 | 8.99 | 2.2475 | 9.27 | 1.86 | C | 1b | 40 | 39 | 10 | 882 | B |
| 883 | 19 | 10.855 | 13.39 | 6.16 | C | 1b | 40 | 39 | 10 | 883 | B |
| 884 | 19.29 | 11.9125 | 17.59 | 9.32 | C | 1b | 40 | 39 | 10 | 884 | B |
| 885 | 14 | 9.38 | 18.98 | 9.56 | C | 1b | 40 | 39 | 10 | 885 | B |
| 886 | 14.14 | 9.5525 | 18.3 | 10.1 | C | 1b | 40 | 39 | 10 | 886 | B |
| 887 | 27.45 | 18.0175 | 50 | 19.8 | C | 1b | 40 | 39 | 10 | 887 | B |
| 888 | 25.33 | 12.19 | 21.62 | 9.69 | C | 1b | 40 | 39 | 10 | 888 | B |
| 889 | 21.71 | 13.6 | 17.51 | 9.49 | C | 1b | 40 | 39 | 10 | 889 | B |
| 890 | 13.25 | 10.1825 | 40 | 11.45 | C | 1b | 40 | 39 | 10 | 890 | B |
| 891 | 18.27 | 10.49 | 14.6 | 6.37 | C | 1b | 40 | 39 | 10 | 891 | B |

| Row number | Max VAF in Tumor | Mean VAF in Tumor | Natera Max VAF in tumor | Natera Mean VAF in Tumor | PyCloneCluster | pTNMStage | Lesion1SizePath | Lesion1SizeDe | DNA input | Row number | Hospital |
|---|---|---|---|---|---|---|---|---|---|---|---|
| 892 | 14.29 | 3.5725 | 17.87 | 3.59 | S | 1b | 40 | 39 | 10 | 892 | B |
| 893 | 10.48 | 2.7325 | 100 | 29 |   | 1b | 40 | 39 | 10 | 893 | B |
| 894 | 22.14 | 5.535 | 15.72 | 3.2 | S | 1b | 40 | 39 | 10 | 894 | B |
| 895 | 21.62 | 5.405 | 20.99 | 4.2 | S | 1b | 40 | 39 | 10 | 895 | B |
| 896 | 13.97 | 3.4925 | 16.04 | 3.28 | S | 1b | 40 | 39 | 10 | 896 | B |
| 897 | 19.51 | 8.3525 | 17.06 | 6.33 | S | 1b | 40 | 39 | 10 | 897 | B |
| 898 | 13.58 | 7.3725 | 10.13 | 4.1 | S | 1b | 40 | 39 | 10 | 898 | B |
| 899 | 17.02 | 12.055 | 13.29 | 11.18 | C | 3a | 28 | 20 | 18.5 | 899 | U |
| 900 | 5.17 | 4.2375 | 5.51 | 4.63 | C | 3a | 28 | 20 | 18.5 | 900 | U |
| 901 | 6.71 | 4.875 | 5.85 | 5.11 | C | 3a | 28 | 20 | 18.5 | 901 | U |
| 902 | 7.71 | 6.69 | 13.75 | 11.61 | C | 3a | 28 | 20 | 18.5 | 902 | U |
| 903 | 5.81 | 5.3675 | 5.85 | 4.8 | C | 3a | 28 | 20 | 18.5 | 903 | U |
| 904 | 8.1 | 5.1 | 7.82 | 5.69 | C | 3a | 28 | 20 | 18.5 | 904 | U |
| 905 | 14.18 | 10.19 | 12.85 | 10.94 |   | 3a | 28 | 20 | 18.5 | 905 | U |
| 906 | 12.9 | 6.5675 | 4.15 | 3.24 | C | 3a | 28 | 20 | 18.5 | 906 | U |
| 907 | 10.91 | 5.99 | 16.67 | 10.27 | C | 3a | 28 | 20 | 18.5 | 907 | U |
| 908 | 6 | 4.1425 | 5.9 | 5.11 |   | 3a | 28 | 20 | 18.5 | 908 | U |
| 909 | 6.85 | 1.7125 | 0 | 0 |   | 3a | 28 | 20 | 18.5 | 909 | U |
| 910 | 6.41 | 1.8075 | 0.02 | 0.01 |   | 3a | 28 | 20 | 18.5 | 910 | U |
| 911 | 5.43 | 1.3575 | 0.06 | 0.04 |   | 3a | 28 | 20 | 18.5 | 911 | U |

FIG. 20 (CONT.)

| Row number | Pathological type | LN status | Vasc inv? | Lobe of lung | Madeup name |
|---|---|---|---|---|---|
| 1 | Adenocarcinoma | 0 | No | LUL | 1a LTX180 |
| 2 | Adenocarcinoma | 0 | No | LUL | 1a LTX180 |
| 3 | Adenocarcinoma | 0 | No | LUL | 1a LTX180 |
| 4 | Adenocarcinoma | 0 | No | LUL | 1a LTX180 |
| 5 | Adenocarcinoma | 0 | No | LUL | 1a LTX180 |
| 6 | Adenocarcinoma | 0 | No | LUL | 1a LTX180 |
| 7 | Adenocarcinoma | 0 | No | LUL | 1a LTX180 |
| 8 | Adenocarcinoma | 0 | No | LUL | 1a LTX180 |
| 9 | Adenocarcinoma | 0 | No | LUL | 1a LTX180 |
| 10 | Adenocarcinoma | 0 | No | LUL | 1a LTX180 |
| 11 | Adenocarcinoma | 0 | No | LUL | 1a LTX180 |
| 12 | Adenocarcinoma | 0 | No | LUL | 1a LTX180 |
| 13 | Adenocarcinoma | 0 | No | LUL | 1a LTX180 |
| 14 | Adenocarcinoma | 0 | No | LUL | 1a LTX180 |
| 15 | Adenocarcinoma | 0 | No | LUL | 1a LTX180 |
| 16 | Adenocarcinoma | 0 | No | LUL | 1a LTX180 |
| 17 | Adenocarcinoma | 0 | No | LUL | 1a LTX180 |
| 18 | Adenocarcinoma | 0 | No | LUL | 1b LTX073 |
| 19 | Adenocarcinoma | 0 | No | LUL | 1b LTX073 |
| 20 | Adenocarcinoma | 0 | No | LUL | 1b LTX073 |
| 21 | Adenocarcinoma | 0 | No | LUL | 1b LTX073 |
| 22 | Adenocarcinoma | 0 | No | LUL | 1b LTX073 |
| 23 | Adenocarcinoma | 0 | No | LUL | 1b LTX073 |
| 24 | Adenocarcinoma | 0 | No | LUL | 1b LTX073 |
| 25 | Adenocarcinoma | 0 | No | LUL | 1b LTX073 |
| 26 | Adenocarcinoma | 0 | No | LUL | 1b LTX073 |
| 27 | Adenocarcinoma | 0 | No | LUL | 1b LTX073 |

FIG. 20 (CONT.)

| Row number | Pathological type | LN status | Vasc inv? | Lobe of lung | Madeup name |
|---|---|---|---|---|---|
| 28 | Adenocarcinoma | 0 | No | LUL | 1b LTX073 |
| 29 | Adenocarcinoma | 0 | No | LUL | 1b LTX073 |
| 30 | Adenocarcinoma | 0 | No | LUL | 1b LTX073 |
| 31 | Adenocarcinoma | 0 | No | LUL | 1b LTX073 |
| 32 | Adenocarcinoma | 0 | No | LUL | 1b LTX073 |
| 33 | Adenocarcinoma | 0 | No | LUL | 1b LTX073 |
| 34 | Adenocarcinoma | 0 | No | LUL | 1b LTX073 |
| 35 | Adenocarcinoma | 0 | No | LUL | 1b LTX073 |
| 36 | Adenocarcinoma | 0 | No | LUL | 1b LTX073 |
| 37 | Adenocarcinoma | 0 | No | LUL | 1b LTX073 |
| 38 | Adenocarcinoma | 0 | No | LUL | 1b LTX073 |
| 39 | Adenocarcinoma | 0 | No | LUL | 1b LTX073 |
| 40 | Squamous cell carcinoma | 0 | no | RUL | 1b LTX058 |
| 41 | Squamous cell carcinoma | 0 | no | RUL | 1b LTX058 |
| 42 | Squamous cell carcinoma | 0 | no | RUL | 1b LTX058 |
| 43 | Squamous cell carcinoma | 0 | no | RUL | 1b LTX058 |
| 44 | Squamous cell carcinoma | 0 | no | RUL | 1b LTX058 |
| 45 | Squamous cell carcinoma | 0 | no | RUL | 1b LTX058 |
| 46 | Squamous cell carcinoma | 0 | no | RUL | 1b LTX058 |
| 47 | Squamous cell carcinoma | 0 | no | RUL | 1b LTX058 |
| 48 | Squamous cell carcinoma | 0 | no | RUL | 1b LTX058 |
| 49 | Squamous cell carcinoma | 0 | no | RUL | 1b LTX058 |
| 50 | Squamous cell carcinoma | 0 | no | RUL | 1b LTX058 |
| 51 | Squamous cell carcinoma | 0 | no | RUL | 1b LTX058 |
| 52 | Squamous cell carcinoma | 0 | no | RUL | 1b LTX058 |
| 53 | Squamous cell carcinoma | 0 | no | RUL | 1b LTX058 |
| 54 | Squamous cell carcinoma | 0 | no | RUL | 1b LTX058 |

FIG. 20 (CONT.)

| Row number | Pathological type | LN status | Vasc inv? | Lobe of lung | Madeup name |
|---|---|---|---|---|---|
| 55 | Squamous cell carcinoma | 0 | no | RUL | 1b LTX058 |
| 56 | Squamous cell carcinoma | 0 | no | RUL | 1b LTX058 |
| 57 | Squamous cell carcinoma | 0 | no | RUL | 1b LTX058 |
| 58 | Adenocarcinoma | 1 | No | LLL | 2b LTX175 |
| 59 | Adenocarcinoma | 1 | No | LLL | 2b LTX175 |
| 60 | Adenocarcinoma | 1 | No | LLL | 2b LTX175 |
| 61 | Adenocarcinoma | 1 | No | LLL | 2b LTX175 |
| 62 | Adenocarcinoma | 1 | No | LLL | 2b LTX175 |
| 63 | Adenocarcinoma | 1 | No | LLL | 2b LTX175 |
| 64 | Adenocarcinoma | 1 | No | LLL | 2b LTX175 |
| 65 | Adenocarcinoma | 1 | No | LLL | 2b LTX175 |
| 66 | Adenocarcinoma | 1 | No | LLL | 2b LTX175 |
| 67 | Adenocarcinoma | 1 | No | LLL | 2b LTX175 |
| 68 | Adenocarcinoma | 1 | No | LLL | 2b LTX175 |
| 69 | Adenocarcinoma | 1 | No | LLL | 2b LTX175 |
| 70 | Adenocarcinoma | 1 | No | LLL | 2b LTX175 |
| 71 | Adenocarcinoma | 1 | No | LLL | 2b LTX175 |
| 72 | Adenocarcinoma | 1 | No | LLL | 2b LTX175 |
| 73 | Adenocarcinoma | 1 | No | LLL | 2b LTX175 |
| 74 | Adenocarcinoma | 1 | No | LLL | 2b LTX175 |
| 75 | Adenocarcinoma | 1 | No | LLL | 2b LTX175 |
| 76 | Adenocarcinoma | 1 | No | LLL | 2b LTX175 |
| 77 | Adenocarcinoma | 1 | No | LLL | 2b LTX175 |
| 78 | Adenocarcinoma | 1 | No | LLL | 2b LTX175 |
| 79 | Adenocarcinoma | 0 | Yes | LUL | 1a LTX185 |
| 80 | Adenocarcinoma | 0 | Yes | LUL | 1a LTX185 |
| 81 | Adenocarcinoma | 0 | Yes | LUL | 1a LTX185 |

FIG. 20 (CONT.)

| Row number | Pathological type | LN status | Vasc inv? | Lobe of lung | Madeup name |
|---|---|---|---|---|---|
| 82 | Adenocarcinoma | 0 | Yes | LUL | 1a LTX185 |
| 83 | Adenocarcinoma | 0 | Yes | LUL | 1a LTX185 |
| 84 | Adenocarcinoma | 0 | Yes | LUL | 1a LTX185 |
| 85 | Adenocarcinoma | 0 | Yes | LUL | 1a LTX185 |
| 86 | Adenocarcinoma | 0 | Yes | LUL | 1a LTX185 |
| 87 | Adenocarcinoma | 0 | Yes | LUL | 1a LTX185 |
| 88 | Adenocarcinoma | 0 | Yes | LUL | 1a LTX185 |
| 89 | Adenocarcinoma | 0 | Yes | LUL | 1a LTX185 |
| 90 | Adenocarcinoma | 0 | Yes | LUL | 1a LTX185 |
| 91 | Adenocarcinoma | 0 | Yes | LUL | 1a LTX185 |
| 92 | Adenocarcinoma | 0 | Yes | LUL | 1a LTX185 |
| 93 | Adenocarcinoma | 0 | Yes | LUL | 1a LTX185 |
| 94 | Adenocarcinoma | 0 | Yes | LUL | 1a LTX185 |
| 95 | Adenocarcinoma | 0 | Yes | LUL | 1a LTX185 |
| 96 | Adenocarcinoma | 0 | Yes | LUL | 1a LTX185 |
| 97 | Adenocarcinoma | 0 | Yes | LUL | 1a LTX185 |
| 98 | Adenocarcinoma | 1 | No | RUL | 2a LTX163 |
| 99 | Adenocarcinoma | 1 | No | RUL | 2a LTX163 |
| 100 | Adenocarcinoma | 1 | No | RUL | 2a LTX163 |
| 101 | Adenocarcinoma | 1 | No | RUL | 2a LTX163 |
| 102 | Adenocarcinoma | 1 | No | RUL | 2a LTX163 |
| 103 | Adenocarcinoma | 1 | No | RUL | 2a LTX163 |
| 104 | Adenocarcinoma | 1 | No | RUL | 2a LTX163 |
| 105 | Adenocarcinoma | 1 | No | RUL | 2a LTX163 |
| 106 | Adenocarcinoma | 1 | No | RUL | 2a LTX163 |
| 107 | Adenocarcinoma | 1 | No | RUL | 2a LTX163 |
| 108 | Adenocarcinoma | 1 | No | RUL | 2a LTX163 |

FIG. 20 (CONT.)

| Row number | Pathological type | LN status | Vasc inv? | Lobe of lung | Madeup name |
|---|---|---|---|---|---|
| 109 | Adenocarcinoma | 1 | No | RUL | 2a LTX163 |
| 110 | Adenocarcinoma | 1 | No | RUL | 2a LTX163 |
| 111 | Adenocarcinoma | 1 | No | RUL | 2a LTX163 |
| 112 | Adenocarcinoma | 1 | No | RUL | 2a LTX163 |
| 113 | Adenocarcinoma | 1 | No | RUL | 2a LTX163 |
| 114 | Adenocarcinoma | 1 | No | RUL | 2a LTX163 |
| 115 | Adenocarcinoma | 1 | No | RUL | 2a LTX163 |
| 116 | Adenocarcinoma | 1 | No | RUL | 2a LTX163 |
| 117 | Squamous cell carcinoma | 0 | No | RUL | 1a LTX111 |
| 118 | Squamous cell carcinoma | 0 | No | RUL | 1a LTX111 |
| 119 | Squamous cell carcinoma | 0 | No | RUL | 1a LTX111 |
| 120 | Squamous cell carcinoma | 0 | No | RUL | 1a LTX111 |
| 121 | Squamous cell carcinoma | 0 | No | RUL | 1a LTX111 |
| 122 | Squamous cell carcinoma | 0 | No | RUL | 1a LTX111 |
| 123 | Squamous cell carcinoma | 0 | No | RUL | 1a LTX111 |
| 124 | Squamous cell carcinoma | 0 | No | RUL | 1a LTX111 |
| 125 | Squamous cell carcinoma | 0 | No | RUL | 1a LTX111 |
| 126 | Squamous cell carcinoma | 0 | No | RUL | 1a LTX111 |
| 127 | Squamous cell carcinoma | 0 | No | RUL | 1a LTX111 |
| 128 | Squamous cell carcinoma | 0 | No | RUL | 1a LTX111 |
| 129 | Squamous cell carcinoma | 0 | No | RUL | 1a LTX111 |
| 130 | Squamous cell carcinoma | 0 | No | RUL | 1a LTX111 |
| 131 | Squamous cell carcinoma | 0 | No | RUL | 1a LTX111 |
| 132 | Squamous cell carcinoma | 0 | No | RUL | 1a LTX111 |
| 133 | Squamous cell carcinoma | 0 | No | RUL | 1a LTX111 |
| 134 | Squamous cell carcinoma | 0 | No | RUL | 1a LTX111 |
| 135 | Squamous cell carcinoma | 0 | No | RUL | 1a LTX111 |

FIG. 20 (CONT.)

| Row number | Pathological type | LN status | Vasc inv? | Lobe of lung | Madeup name |
|---|---|---|---|---|---|
| 136 | Squamous cell carcinoma | 0 | No | LUL | 1b LTX032 |
| 137 | Squamous cell carcinoma | 0 | No | LUL | 1b LTX032 |
| 138 | Squamous cell carcinoma | 0 | No | LUL | 1b LTX032 |
| 139 | Squamous cell carcinoma | 0 | No | LUL | 1b LTX032 |
| 140 | Squamous cell carcinoma | 0 | No | LUL | 1b LTX032 |
| 141 | Squamous cell carcinoma | 0 | No | LUL | 1b LTX032 |
| 142 | Squamous cell carcinoma | 0 | No | LUL | 1b LTX032 |
| 143 | Squamous cell carcinoma | 0 | No | LUL | 1b LTX032 |
| 144 | Squamous cell carcinoma | 0 | No | LUL | 1b LTX032 |
| 145 | Squamous cell carcinoma | 0 | No | LUL | 1b LTX032 |
| 146 | Squamous cell carcinoma | 0 | No | LUL | 1b LTX032 |
| 147 | Squamous cell carcinoma | 0 | No | LUL | 1b LTX032 |
| 148 | Squamous cell carcinoma | 0 | No | LUL | 1b LTX032 |
| 149 | Squamous cell carcinoma | 0 | No | LUL | 1b LTX032 |
| 150 | Squamous cell carcinoma | 0 | No | LUL | 1b LTX032 |
| 151 | Squamous cell carcinoma | 0 | No | LUL | 1b LTX032 |
| 152 | Squamous cell carcinoma | 0 | No | LUL | 1b LTX032 |
| 153 | Squamous cell carcinoma | 0 | No | LUL | 1b LTX032 |
| 154 |  | 0 | No | RUL | 1b LTX126 |
| 155 |  | 0 | No | RUL | 1b LTX126 |
| 156 |  | 0 | No | RUL | 1b LTX126 |
| 157 |  | 0 | No | RUL | 1b LTX126 |
| 158 |  | 0 | No | RUL | 1b LTX126 |
| 159 |  | 0 | No | RUL | 1b LTX126 |
| 160 |  | 0 | No | RUL | 1b LTX126 |
| 161 |  | 0 | No | RUL | 1b LTX126 |
| 162 |  | 0 | No | RUL | 1b LTX126 |

| Row number | Pathological type | LN status | Vasc inv? | Lobe of lung | Madeup name |
|---|---|---|---|---|---|
| 163 | | 0 | No | RUL | 1b LTX126 |
| 164 | | 0 | No | RUL | 1b LTX126 |
| 165 | | 0 | No | RUL | 1b LTX126 |
| 166 | | 0 | No | RUL | 1b LTX126 |
| 167 | | 0 | No | RUL | 1b LTX126 |
| 168 | | 0 | No | RUL | 1b LTX126 |
| 169 | | 0 | No | RUL | 1b LTX126 |
| 170 | | 0 | No | RUL | 1b LTX126 |
| 171 | | 0 | No | RUL | 1b LTX126 |
| 172 | | 0 | No | RUL | 1b LTX126 |
| 173 | Adenocarcinoma | 2 | Yes | LUL | 3a LTX210 |
| 174 | Adenocarcinoma | 2 | Yes | LUL | 3a LTX210 |
| 175 | Adenocarcinoma | 2 | Yes | LUL | 3a LTX210 |
| 176 | Adenocarcinoma | 2 | Yes | LUL | 3a LTX210 |
| 177 | Adenocarcinoma | 2 | Yes | LUL | 3a LTX210 |
| 178 | Adenocarcinoma | 2 | Yes | LUL | 3a LTX210 |
| 179 | Adenocarcinoma | 2 | Yes | LUL | 3a LTX210 |
| 180 | Adenocarcinoma | 2 | Yes | LUL | 3a LTX210 |
| 181 | Adenocarcinoma | 2 | Yes | LUL | 3a LTX210 |
| 182 | Adenocarcinoma | 2 | Yes | LUL | 3a LTX210 |
| 183 | Adenocarcinoma | 2 | Yes | LUL | 3a LTX210 |
| 184 | Adenocarcinoma | 2 | Yes | LUL | 3a LTX210 |
| 185 | Adenocarcinoma | 2 | Yes | LUL | 3a LTX210 |
| 186 | Adenocarcinoma | 2 | Yes | LUL | 3a LTX210 |
| 187 | Adenocarcinoma | 2 | Yes | LUL | 3a LTX210 |
| 188 | Adenocarcinoma | 2 | Yes | LUL | 3a LTX210 |
| 189 | Adenocarcinoma | 2 | Yes | LUL | 3a LTX210 |

| Row number | Pathological type | LN status | Vasc inv? | Lobe of lung | Madeup name |
|---|---|---|---|---|---|
| 190 | Adenocarcinoma | 2 | Yes | LUL | 3a LTX210 |
| 191 | Adenocarcinoma | 2 | Yes | LUL | 3a LTX210 |
| 192 | Squamous cell carcinoma | 0 | No | RLL | 1b LTX093 |
| 193 | Squamous cell carcinoma | 0 | No | RLL | 1b LTX093 |
| 194 | Squamous cell carcinoma | 0 | No | RLL | 1b LTX093 |
| 195 | Squamous cell carcinoma | 0 | No | RLL | 1b LTX093 |
| 196 | Squamous cell carcinoma | 0 | No | RLL | 1b LTX093 |
| 197 | Squamous cell carcinoma | 0 | No | RLL | 1b LTX093 |
| 198 | Squamous cell carcinoma | 0 | No | RLL | 1b LTX093 |
| 199 | Squamous cell carcinoma | 0 | No | RLL | 1b LTX093 |
| 200 | Squamous cell carcinoma | 0 | No | RLL | 1b LTX093 |
| 201 | Squamous cell carcinoma | 0 | No | RLL | 1b LTX093 |
| 202 | Squamous cell carcinoma | 0 | No | RLL | 1b LTX093 |
| 203 | Squamous cell carcinoma | 0 | No | RLL | 1b LTX093 |
| 204 | Squamous cell carcinoma | 0 | No | RLL | 1b LTX093 |
| 205 | Squamous cell carcinoma | 0 | No | RLL | 1b LTX093 |
| 206 | Squamous cell carcinoma | 0 | No | RLL | 1b LTX093 |
| 207 | Squamous cell carcinoma | 0 | No | RLL | 1b LTX093 |
| 208 | Squamous cell carcinoma | 0 | No | RLL | 1b LTX093 |
| 209 | Squamous cell carcinoma | 0 | No | RLL | 1b LTX093 |
| 210 | Adenocarcinoma | 0 | No | RUL | 1b LTX001 |
| 211 | Adenocarcinoma | 0 | No | RUL | 1b LTX001 |
| 212 | Adenocarcinoma | 0 | No | RUL | 1b LTX001 |
| 213 | Adenocarcinoma | 0 | No | RUL | 1b LTX001 |
| 214 | Adenocarcinoma | 0 | No | RUL | 1b LTX001 |
| 215 | Adenocarcinoma | 0 | No | RUL | 1b LTX001 |
| 216 | Adenocarcinoma | 0 | No | RUL | 1b LTX001 |

FIG. 20 (CONT.)

| Row number | Pathological type | LN status | Vasc inv? | Lobe of lung | Madeup name |
|---|---|---|---|---|---|
| 217 | Adenocarcinoma | 0 | No | RUL | 1b LTX001 |
| 218 | Adenocarcinoma | 0 | No | RUL | 1b LTX001 |
| 219 | Adenocarcinoma | 0 | No | RUL | 1b LTX001 |
| 220 | Adenocarcinoma | 0 | No | RUL | 1b LTX001 |
| 221 | Adenocarcinoma | 0 | No | RUL | 1b LTX001 |
| 222 | Adenocarcinoma | 0 | No | RUL | 1b LTX001 |
| 223 | Adenocarcinoma | 0 | No | RUL | 1b LTX001 |
| 224 | Adenocarcinoma | 0 | No | RUL | 1b LTX001 |
| 225 | Adenocarcinoma | 0 | No | RUL | 1b LTX001 |
| 226 | Adenocarcinoma | 0 | No | RUL | 1b LTX001 |
| 227 | Adenocarcinoma | ? | No | LUL | 1a LTX115 |
| 228 | Adenocarcinoma | ? | No | LUL | 1a LTX115 |
| 229 | Adenocarcinoma | ? | No | LUL | 1a LTX115 |
| 230 | Adenocarcinoma | ? | No | LUL | 1a LTX115 |
| 231 | Adenocarcinoma | ? | No | LUL | 1a LTX115 |
| 232 | Adenocarcinoma | ? | No | LUL | 1a LTX115 |
| 233 | Adenocarcinoma | ? | No | LUL | 1a LTX115 |
| 234 | Adenocarcinoma | ? | No | LUL | 1a LTX115 |
| 235 | Adenocarcinoma | ? | No | LUL | 1a LTX115 |
| 236 | Adenocarcinoma | ? | No | LUL | 1a LTX115 |
| 237 | Adenocarcinoma | ? | No | LUL | 1a LTX115 |
| 238 | Adenocarcinoma | ? | No | LUL | 1a LTX115 |
| 239 | Adenocarcinoma | ? | No | LUL | 1a LTX115 |
| 240 | Adenocarcinoma | ? | No | LUL | 1a LTX115 |
| 241 | Adenocarcinoma | ? | No | LUL | 1a LTX115 |
| 242 | Adenocarcinoma | ? | No | LUL | 1a LTX115 |
| 243 | Adenocarcinoma | ? | No | LUL | 1a LTX115 |

FIG. 20 (CONT.)

| Row number | Pathological type | LN status | Vasc inv? | Lobe of lung | Madeup name |
|---|---|---|---|---|---|
| 244 | Adenocarcinoma | ? | No | LUL | 1a LTX115 |
| 245 | Adenocarcinoma | ? | No | LUL | 1a LTX115 |
| 246 | Adenocarcinoma | 0 | Yes | RUL | 1a LTX062 |
| 247 | Adenocarcinoma | 0 | Yes | RUL | 1a LTX062 |
| 248 | Adenocarcinoma | 0 | Yes | RUL | 1a LTX062 |
| 249 | Adenocarcinoma | 0 | Yes | RUL | 1a LTX062 |
| 250 | Adenocarcinoma | 0 | Yes | RUL | 1a LTX062 |
| 251 | Adenocarcinoma | 0 | Yes | RUL | 1a LTX062 |
| 252 | Adenocarcinoma | 0 | Yes | RUL | 1a LTX062 |
| 253 | Adenocarcinoma | 0 | Yes | RUL | 1a LTX062 |
| 254 | Adenocarcinoma | 0 | Yes | RUL | 1a LTX062 |
| 255 | Adenocarcinoma | 0 | Yes | RUL | 1a LTX062 |
| 256 | Adenocarcinoma | 0 | Yes | RUL | 1a LTX062 |
| 257 | Adenocarcinoma | 0 | Yes | RUL | 1a LTX062 |
| 258 | Adenocarcinoma | 0 | Yes | RUL | 1a LTX062 |
| 259 | Adenocarcinoma | 0 | Yes | RUL | 1a LTX062 |
| 260 | Adenocarcinoma | 0 | Yes | RUL | 1a LTX062 |
| 261 | Adenocarcinoma | 0 | Yes | RUL | 1a LTX062 |
| 262 | Adenocarcinoma | 0 | Yes | RUL | 1a LTX062 |
| 263 | Adenocarcinoma | 0 | Yes | RUL | 1a LTX062 |
| 264 | Adenocarcinoma | 0 | Yes | RUL | 1a LTX062 |
| 265 | Adenocarcinoma | 0 | Yes | RUL | 1a LTX062 |
| 266 | Adenocarcinoma | 0 | No | RUL | 1b LTX092 |
| 267 | Adenocarcinoma | 0 | No | RUL | 1b LTX092 |
| 268 | Adenocarcinoma | 0 | No | RUL | 1b LTX092 |
| 269 | Adenocarcinoma | 0 | No | RUL | 1b LTX092 |
| 270 | Adenocarcinoma | 0 | No | RUL | 1b LTX092 |

FIG. 20 (CONT.)

| Row number | Pathological type | LN status | Vasc inv? | Lobe of lung | Madeup name |
|---|---|---|---|---|---|
| 271 | Adenocarcinoma | 0 | No | RUL | 1b LTX092 |
| 272 | Adenocarcinoma | 0 | No | RUL | 1b LTX092 |
| 273 | Adenocarcinoma | 0 | No | RUL | 1b LTX092 |
| 274 | Adenocarcinoma | 0 | No | RUL | 1b LTX092 |
| 275 | Adenocarcinoma | 0 | No | RUL | 1b LTX092 |
| 276 | Adenocarcinoma | 0 | No | RUL | 1b LTX092 |
| 277 | Adenocarcinoma | 0 | No | RUL | 1b LTX092 |
| 278 | Adenocarcinoma | 0 | No | RUL | 1b LTX092 |
| 279 | Adenocarcinoma | 0 | No | RUL | 1b LTX092 |
| 280 | Adenocarcinoma | 0 | No | RUL | 1b LTX092 |
| 281 | Adenocarcinoma | 0 | No | RUL | 1b LTX092 |
| 282 | Adenocarcinoma | 0 | No | RUL | 1b LTX092 |
| 283 | Adenocarcinoma | 0 | No | RUL | 1b LTX092 |
| 284 | Adenocarcinoma | 0 | No | RUL | 1b LTX092 |
| 285 | Adenocarcinoma | 0 | No | RUL | 1b LTX092 |
| 286 | Adenocarcinoma | 0 | No | RUL | 1b LTX092 |
| 287 | Squamous cell carcinoma | 1 | Yes | RML | 2a LTX107 |
| 288 | Squamous cell carcinoma | 1 | Yes | RML | 2a LTX107 |
| 289 | Squamous cell carcinoma | 1 | Yes | RML | 2a LTX107 |
| 290 | Squamous cell carcinoma | 1 | Yes | RML | 2a LTX107 |
| 291 | Squamous cell carcinoma | 1 | Yes | RML | 2a LTX107 |
| 292 | Squamous cell carcinoma | 1 | Yes | RML | 2a LTX107 |
| 293 | Squamous cell carcinoma | 1 | Yes | RML | 2a LTX107 |
| 294 | Squamous cell carcinoma | 1 | Yes | RML | 2a LTX107 |
| 295 | Squamous cell carcinoma | 1 | Yes | RML | 2a LTX107 |
| 296 | Squamous cell carcinoma | 1 | Yes | RML | 2a LTX107 |
| 297 | Squamous cell carcinoma | 1 | Yes | RML | 2a LTX107 |

FIG. 20 (CONT.)

| Row number | Pathological type | LN status | Vasc inv? | Lobe of lung | Madeup name |
|---|---|---|---|---|---|
| 298 | Squamous cell carcinoma | 1 | Yes | RML | 2a LTX107 |
| 299 | Squamous cell carcinoma | 1 | Yes | RML | 2a LTX107 |
| 300 | Squamous cell carcinoma | 1 | Yes | RML | 2a LTX107 |
| 301 | Squamous cell carcinoma | 1 | Yes | RML | 2a LTX107 |
| 302 | Squamous cell carcinoma | 1 | Yes | RML | 2a LTX107 |
| 303 | Squamous cell carcinoma | 1 | Yes | RML | 2a LTX107 |
| 304 | Squamous cell carcinoma | 1 | Yes | RML | 2a LTX107 |
| 305 | Squamous cell carcinoma | 1 | Yes | RML | 2a LTX107 |
| 306 | Squamous cell carcinoma | 0 | No | RUL | 1b LTX085 |
| 307 | Squamous cell carcinoma | 0 | No | RUL | 1b LTX085 |
| 308 | Squamous cell carcinoma | 0 | No | RUL | 1b LTX085 |
| 309 | Squamous cell carcinoma | 0 | No | RUL | 1b LTX085 |
| 310 | Squamous cell carcinoma | 0 | No | RUL | 1b LTX085 |
| 311 | Squamous cell carcinoma | 0 | No | RUL | 1b LTX085 |
| 312 | Squamous cell carcinoma | 0 | No | RUL | 1b LTX085 |
| 313 | Squamous cell carcinoma | 0 | No | RUL | 1b LTX085 |
| 314 | Squamous cell carcinoma | 0 | No | RUL | 1b LTX085 |
| 315 | Squamous cell carcinoma | 0 | No | RUL | 1b LTX085 |
| 316 | Squamous cell carcinoma | 0 | No | RUL | 1b LTX085 |
| 317 | Squamous cell carcinoma | 0 | No | RUL | 1b LTX085 |
| 318 | Squamous cell carcinoma | 0 | No | RUL | 1b LTX085 |
| 319 | Squamous cell carcinoma | 0 | No | RUL | 1b LTX085 |
| 320 | Squamous cell carcinoma | 0 | No | RUL | 1b LTX085 |
| 321 | Squamous cell carcinoma | 0 | No | RLL | 2a LTX028 |
| 322 | Squamous cell carcinoma | 0 | No | RLL | 2a LTX028 |
| 323 | Squamous cell carcinoma | 0 | No | RLL | 2a LTX028 |
| 324 | Squamous cell carcinoma | 0 | No | RLL | 2a LTX028 |

FIG. 20 (CONT.)

| Row number | Pathological type | LN status | Vasc inv? | Lobe of lung | Madeup name |
|---|---|---|---|---|---|
| 325 | Squamous cell carcinoma | 0 | No | RLL | 2a LTX028 |
| 326 | Squamous cell carcinoma | 0 | No | RLL | 2a LTX028 |
| 327 | Squamous cell carcinoma | 0 | No | RLL | 2a LTX028 |
| 328 | Squamous cell carcinoma | 0 | No | RLL | 2a LTX028 |
| 329 | Squamous cell carcinoma | 0 | No | RLL | 2a LTX028 |
| 330 | Squamous cell carcinoma | 0 | No | RLL | 2a LTX028 |
| 331 | Squamous cell carcinoma | 0 | No | RLL | 2a LTX028 |
| 332 | Squamous cell carcinoma | 0 | No | RLL | 2a LTX028 |
| 333 | Squamous cell carcinoma | 0 | No | RLL | 2a LTX028 |
| 334 | Squamous cell carcinoma | 0 | No | RLL | 2a LTX028 |
| 335 | Squamous cell carcinoma | 0 | No | RLL | 2a LTX028 |
| 336 | Squamous cell carcinoma | 0 | No | RLL | 2a LTX028 |
| 337 | Squamous cell carcinoma | 0 | No | RLL | 2a LTX028 |
| 338 | Squamous cell carcinoma | 0 | No | RLL | 2a LTX028 |
| 339 | Squamous cell carcinoma | 0 | No | RLL | 2a LTX028 |
| 340 | Squamous cell carcinoma | 0 | yes | RUL | 1a LTX025 |
| 341 | Squamous cell carcinoma | 0 | yes | RUL | 1a LTX025 |
| 342 | Squamous cell carcinoma | 0 | yes | RUL | 1a LTX025 |
| 343 | Squamous cell carcinoma | 0 | yes | RUL | 1a LTX025 |
| 344 | Squamous cell carcinoma | 0 | yes | RUL | 1a LTX025 |
| 345 | Squamous cell carcinoma | 0 | yes | RUL | 1a LTX025 |
| 346 | Squamous cell carcinoma | 0 | yes | RUL | 1a LTX025 |
| 347 | Squamous cell carcinoma | 0 | yes | RUL | 1a LTX025 |
| 348 | Squamous cell carcinoma | 0 | yes | RUL | 1a LTX025 |
| 349 | Squamous cell carcinoma | 0 | yes | RUL | 1a LTX025 |
| 350 | Squamous cell carcinoma | 0 | yes | RUL | 1a LTX025 |
| 351 | Squamous cell carcinoma | 0 | yes | RUL | 1a LTX025 |

FIG. 20 (CONT.)

| Row number | Pathological type | LN status | Vasc inv? | Lobe of lung | Madeup name |
|---|---|---|---|---|---|
| 352 | Squamous cell carcinoma | 0 | yes | RUL | 1a LTX025 |
| 353 | Squamous cell carcinoma | 0 | yes | RUL | 1a LTX025 |
| 354 | Squamous cell carcinoma | 0 | yes | RUL | 1a LTX025 |
| 355 | Squamous cell carcinoma | 0 | yes | RUL | 1a LTX025 |
| 356 | Squamous cell carcinoma | 0 | yes | RUL | 1a LTX025 |
| 357 | Squamous cell carcinoma | 0 | yes | RUL | 1a LTX025 |
| 358 | Squamous cell carcinoma | 0 | yes | RUL | 1a LTX025 |
| 359 | Squamous cell carcinoma | 0 | No | RUL | 1a LTX120 |
| 360 | Squamous cell carcinoma | 0 | No | RUL | 1a LTX120 |
| 361 | Squamous cell carcinoma | 0 | No | RUL | 1a LTX120 |
| 362 | Squamous cell carcinoma | 0 | No | RUL | 1a LTX120 |
| 363 | Squamous cell carcinoma | 0 | No | RUL | 1a LTX120 |
| 364 | Squamous cell carcinoma | 0 | No | RUL | 1a LTX120 |
| 365 | Squamous cell carcinoma | 0 | No | RUL | 1a LTX120 |
| 366 | Squamous cell carcinoma | 0 | No | RUL | 1a LTX120 |
| 367 | Squamous cell carcinoma | 0 | No | RUL | 1a LTX120 |
| 368 | Squamous cell carcinoma | 0 | No | RUL | 1a LTX120 |
| 369 | Squamous cell carcinoma | 0 | No | RUL | 1a LTX120 |
| 370 | Squamous cell carcinoma | 0 | No | RUL | 1a LTX120 |
| 371 | Squamous cell carcinoma | 0 | No | RUL | 1a LTX120 |
| 372 | Squamous cell carcinoma | 0 | No | RUL | 1a LTX120 |
| 373 | Squamous cell carcinoma | 0 | No | RUL | 1a LTX120 |
| 374 | Squamous cell carcinoma | 0 | No | RUL | 1a LTX120 |
| 375 | Squamous cell carcinoma | 0 | No | RUL | 1a LTX120 |
| 376 | Squamous cell carcinoma | 0 | No | RUL | 1a LTX120 |
| 377 | Adenocarcinoma | 0 | No | LUL | 1b LTX041 |
| 378 | Adenocarcinoma | 0 | No | LUL | 1b LTX041 |

FIG. 20 (CONT.)

| Row number | Pathological type | LN status | Vasc inv? | Lobe of lung | Madeup name |
|---|---|---|---|---|---|
| 379 | Adenocarcinoma | 0 | No | LUL | 1b LTX041 |
| 380 | Adenocarcinoma | 0 | No | LUL | 1b LTX041 |
| 381 | Adenocarcinoma | 0 | No | LUL | 1b LTX041 |
| 382 | Adenocarcinoma | 0 | No | LUL | 1b LTX041 |
| 383 | Adenocarcinoma | 0 | No | LUL | 1b LTX041 |
| 384 | Adenocarcinoma | 0 | No | LUL | 1b LTX041 |
| 385 | Adenocarcinoma | 0 | No | LUL | 1b LTX041 |
| 386 | Adenocarcinoma | 0 | No | LUL | 1b LTX041 |
| 387 | Adenocarcinoma | 0 | No | LUL | 1b LTX041 |
| 388 | Adenocarcinoma | 0 | No | LUL | 1b LTX041 |
| 389 | Adenocarcinoma | 0 | No | LUL | 1b LTX041 |
| 390 | Adenocarcinoma | 0 | No | LUL | 1b LTX041 |
| 391 | Adenocarcinoma | 0 | No | LUL | 1b LTX041 |
| 392 | Adenocarcinoma | 0 | No | LUL | 1b LTX041 |
| 393 | Adenocarcinoma | 0 | No | LUL | 1b LTX041 |
| 394 | Adenocarcinoma | 0 | No | LUL | 1b LTX041 |
| 395 | Adenocarcinoma | 0 | No | LUL | 1b LTX041 |
| 396 | Adenocarcinoma | 2 | No | RUL | 3a LTX097 |
| 397 | Adenocarcinoma | 2 | No | RUL | 3a LTX097 |
| 398 | Adenocarcinoma | 2 | No | RUL | 3a LTX097 |
| 399 | Adenocarcinoma | 2 | No | RUL | 3a LTX097 |
| 400 | Adenocarcinoma | 2 | No | RUL | 3a LTX097 |
| 401 | Adenocarcinoma | 2 | No | RUL | 3a LTX097 |
| 402 | Adenocarcinoma | 2 | No | RUL | 3a LTX097 |
| 403 | Adenocarcinoma | 2 | No | RUL | 3a LTX097 |
| 404 | Adenocarcinoma | 2 | No | RUL | 3a LTX097 |
| 405 | Adenocarcinoma | 2 | No | RUL | 3a LTX097 |

| Row number | Pathological type | LN status | Vasc inv? | Lobe of lung | Madeup name |
|---|---|---|---|---|---|
| 406 | Adenocarcinoma | 2 | No | RUL | 3a LTX097 |
| 407 | Adenocarcinoma | 2 | No | RUL | 3a LTX097 |
| 408 | Adenocarcinoma | 2 | No | RUL | 3a LTX097 |
| 409 | Adenocarcinoma | 2 | No | RUL | 3a LTX097 |
| 410 | Adenocarcinoma | 2 | No | RUL | 3a LTX097 |
| 411 | Adenocarcinoma | 2 | No | RUL | 3a LTX097 |
| 412 | Adenocarcinoma | 2 | No | RUL | 3a LTX097 |
| 413 | Adenocarcinoma | 2 | No | RUL | 3a LTX097 |
| 414 | Adenocarcinoma | 2 | No | RUL | 3a LTX097 |
| 415 | Adenocarcinoma | 0 | Yes | LUL | 1b LTX055 |
| 416 | Adenocarcinoma | 0 | Yes | LUL | 1b LTX055 |
| 417 | Adenocarcinoma | 0 | Yes | LUL | 1b LTX055 |
| 418 | Adenocarcinoma | 0 | Yes | LUL | 1b LTX055 |
| 419 | Adenocarcinoma | 0 | Yes | LUL | 1b LTX055 |
| 420 | Adenocarcinoma | 0 | Yes | LUL | 1b LTX055 |
| 421 | Adenocarcinoma | 0 | Yes | LUL | 1b LTX055 |
| 422 | Adenocarcinoma | 0 | Yes | LUL | 1b LTX055 |
| 423 | Adenocarcinoma | 0 | Yes | LUL | 1b LTX055 |
| 424 | Adenocarcinoma | 0 | Yes | LUL | 1b LTX055 |
| 425 | Adenocarcinoma | 0 | Yes | LUL | 1b LTX055 |
| 426 | Adenocarcinoma | 0 | Yes | LUL | 1b LTX055 |
| 427 | Adenocarcinoma | 0 | Yes | LUL | 1b LTX055 |
| 428 | Adenocarcinoma | 0 | Yes | LUL | 1b LTX055 |
| 429 | Adenocarcinoma | 0 | Yes | LUL | 1b LTX055 |
| 430 | Adenocarcinoma | 0 | Yes | LUL | 1b LTX055 |
| 431 | Adenocarcinoma | 0 | Yes | LUL | 1b LTX055 |
| 432 | Adenocarcinoma | 0 | Yes | LUL | 1b LTX055 |

| Row number | Pathological type | LN status | Vasc inv? | Lobe of lung | Madeup name |
|---|---|---|---|---|---|
| 433 | Adenocarcinoma | 0 | Yes | LUL | 1b LTX055 |
| 434 | Adenocarcinoma | 0 | Yes | LUL | 1b LTX055 |
| 435 | Adenocarcinoma | 0 | Yes | LUL | 1b LTX055 |
| 436 | Squamous cell carcinoma | 1 | Yes | LUL | 2b LTX165 |
| 437 | Squamous cell carcinoma | 1 | Yes | LUL | 2b LTX165 |
| 438 | Squamous cell carcinoma | 1 | Yes | LUL | 2b LTX165 |
| 439 | Squamous cell carcinoma | 1 | Yes | LUL | 2b LTX165 |
| 440 | Squamous cell carcinoma | 1 | Yes | LUL | 2b LTX165 |
| 441 | Squamous cell carcinoma | 1 | Yes | LUL | 2b LTX165 |
| 442 | Squamous cell carcinoma | 1 | Yes | LUL | 2b LTX165 |
| 443 | Squamous cell carcinoma | 1 | Yes | LUL | 2b LTX165 |
| 444 | Squamous cell carcinoma | 1 | Yes | LUL | 2b LTX165 |
| 445 | Squamous cell carcinoma | 1 | Yes | LUL | 2b LTX165 |
| 446 | Squamous cell carcinoma | 1 | Yes | LUL | 2b LTX165 |
| 447 | Squamous cell carcinoma | 1 | Yes | LUL | 2b LTX165 |
| 448 | Squamous cell carcinoma | 1 | Yes | LUL | 2b LTX165 |
| 449 | Squamous cell carcinoma | 1 | Yes | LUL | 2b LTX165 |
| 450 | Squamous cell carcinoma | 1 | Yes | LUL | 2b LTX165 |
| 451 | Squamous cell carcinoma | 1 | Yes | LUL | 2b LTX165 |
| 452 | Squamous cell carcinoma | 1 | Yes | LUL | 2b LTX165 |
| 453 | Squamous cell carcinoma | 1 | Yes | LUL | 2b LTX165 |
| 454 | Squamous cell carcinoma | 1 | Yes | LUL | 2b LTX165 |
| 455 | Squamous cell carcinoma | 1 | Yes | LUL | 2b LTX165 |
| 456 | Adenocarcinoma | 2 | Yes | RLL | 3a LTX021 |
| 457 | Adenocarcinoma | 2 | Yes | RLL | 3a LTX021 |
| 458 | Adenocarcinoma | 2 | Yes | RLL | 3a LTX021 |
| 459 | Adenocarcinoma | 2 | Yes | RLL | 3a LTX021 |

| Row number | Pathological type | LN status | Vasc inv? | Lobe of lung | Madeup name |
|---|---|---|---|---|---|
| 460 | Adenocarcinoma | 2 | Yes | RLL | 3a LTX021 |
| 461 | Adenocarcinoma | 2 | Yes | RLL | 3a LTX021 |
| 462 | Adenocarcinoma | 2 | Yes | RLL | 3a LTX021 |
| 463 | Adenocarcinoma | 2 | Yes | RLL | 3a LTX021 |
| 464 | Adenocarcinoma | 2 | Yes | RLL | 3a LTX021 |
| 465 | Adenocarcinoma | 2 | Yes | RLL | 3a LTX021 |
| 466 | Adenocarcinoma | 2 | Yes | RLL | 3a LTX021 |
| 467 | Adenocarcinoma | 2 | Yes | RLL | 3a LTX021 |
| 468 | Adenocarcinoma | 2 | Yes | RLL | 3a LTX021 |
| 469 | Adenocarcinoma | 2 | Yes | RLL | 3a LTX021 |
| 470 | Adenocarcinoma | 2 | Yes | RLL | 3a LTX021 |
| 471 | Adenocarcinoma | 2 | Yes | RLL | 3a LTX021 |
| 472 | Adenocarcinoma | 2 | Yes | RLL | 3a LTX021 |
| 473 | Adenocarcinoma | 2 | Yes | RLL | 3a LTX021 |
| 474 | Adenocarcinoma | 2 | Yes | RLL | 3a LTX021 |
| 475 | Squamous cell carcinoma | 0 | YES | RML | 1b LTX059 |
| 476 | Squamous cell carcinoma | 0 | YES | RML | 1b LTX059 |
| 477 | Squamous cell carcinoma | 0 | YES | RML | 1b LTX059 |
| 478 | Squamous cell carcinoma | 0 | YES | RML | 1b LTX059 |
| 479 | Squamous cell carcinoma | 0 | YES | RML | 1b LTX059 |
| 480 | Squamous cell carcinoma | 0 | YES | RML | 1b LTX059 |
| 481 | Squamous cell carcinoma | 0 | YES | RML | 1b LTX059 |
| 482 | Squamous cell carcinoma | 0 | YES | RML | 1b LTX059 |
| 483 | Squamous cell carcinoma | 0 | YES | RML | 1b LTX059 |
| 484 | Squamous cell carcinoma | 0 | YES | RML | 1b LTX059 |
| 485 | Squamous cell carcinoma | 0 | YES | RML | 1b LTX059 |
| 486 | Squamous cell carcinoma | 0 | YES | RML | 1b LTX059 |

| Row number | Pathological type | LN status | Vasc inv? | Lobe of lung | Madeup name |
|---|---|---|---|---|---|
| 487 | Squamous cell carcinoma | 0 | YES | RML | 1b LTX059 |
| 488 | Squamous cell carcinoma | 0 | YES | RML | 1b LTX059 |
| 489 | Squamous cell carcinoma | 0 | YES | RML | 1b LTX059 |
| 490 | Squamous cell carcinoma | 0 | YES | RML | 1b LTX059 |
| 491 | Squamous cell carcinoma | 0 | YES | RML | 1b LTX059 |
| 492 | Squamous cell carcinoma | 0 | YES | RML | 1b LTX059 |
| 493 | Adenocarcinoma | 1 | No | RLL | 2a LTX084 |
| 494 | Adenocarcinoma | 1 | No | RLL | 2a LTX084 |
| 495 | Adenocarcinoma | 1 | No | RLL | 2a LTX084 |
| 496 | Adenocarcinoma | 1 | No | RLL | 2a LTX084 |
| 497 | Adenocarcinoma | 1 | No | RLL | 2a LTX084 |
| 498 | Adenocarcinoma | 1 | No | RLL | 2a LTX084 |
| 499 | Adenocarcinoma | 1 | No | RLL | 2a LTX084 |
| 500 | Adenocarcinoma | 1 | No | RLL | 2a LTX084 |
| 501 | Adenocarcinoma | 1 | No | RLL | 2a LTX084 |
| 502 | Adenocarcinoma | 1 | No | RLL | 2a LTX084 |
| 503 | Adenocarcinoma | 1 | No | RLL | 2a LTX084 |
| 504 | Adenocarcinoma | 1 | No | RLL | 2a LTX084 |
| 505 | Adenocarcinoma | 1 | No | RLL | 2a LTX084 |
| 506 | Adenocarcinoma | 1 | No | RLL | 2a LTX084 |
| 507 | Adenocarcinoma | 2 | Yes | RUL | 3a LTX135 |
| 508 | Adenocarcinoma | 2 | Yes | RUL | 3a LTX135 |
| 509 | Adenocarcinoma | 2 | Yes | RUL | 3a LTX135 |
| 510 | Adenocarcinoma | 2 | Yes | RUL | 3a LTX135 |
| 511 | Adenocarcinoma | 2 | Yes | RUL | 3a LTX135 |
| 512 | Adenocarcinoma | 2 | Yes | RUL | 3a LTX135 |
| 513 | Adenocarcinoma | 2 | Yes | RUL | 3a LTX135 |

FIG. 20 (CONT.)

| Row number | Pathological type | LN status | Vasc inv? | Lobe of lung | Madeup name |
|---|---|---|---|---|---|
| 514 | Adenocarcinoma | 2 | Yes | RUL | 3a LTX135 |
| 515 | Adenocarcinoma | 2 | Yes | RUL | 3a LTX135 |
| 516 | Adenocarcinoma | 2 | Yes | RUL | 3a LTX135 |
| 517 | Adenocarcinoma | 2 | Yes | RUL | 3a LTX135 |
| 518 | Adenocarcinoma | 2 | Yes | RUL | 3a LTX135 |
| 519 | Adenocarcinoma | 2 | Yes | RUL | 3a LTX135 |
| 520 | Adenocarcinoma | 2 | Yes | RUL | 3a LTX135 |
| 521 | Adenocarcinoma | 2 | Yes | RUL | 3a LTX135 |
| 522 | Adenocarcinoma | 2 | Yes | RUL | 3a LTX135 |
| 523 | Adenocarcinoma | 2 | Yes | RUL | 3a LTX135 |
| 524 | Adenocarcinoma | 2 | Yes | RUL | 3a LTX135 |
| 525 | Adenocarcinoma | 2 | Yes | RUL | 3a LTX135 |
| 526 | Adenocarcinoma | 0 | No | RUL | 1b LTX048 |
| 527 | Adenocarcinoma | 0 | No | RUL | 1b LTX048 |
| 528 | Adenocarcinoma | 0 | No | RUL | 1b LTX048 |
| 529 | Adenocarcinoma | 0 | No | RUL | 1b LTX048 |
| 530 | Adenocarcinoma | 0 | No | RUL | 1b LTX048 |
| 531 | Adenocarcinoma | 0 | No | RUL | 1b LTX048 |
| 532 | Adenocarcinoma | 0 | No | RUL | 1b LTX048 |
| 533 | Adenocarcinoma | 0 | No | RUL | 1b LTX048 |
| 534 | Adenocarcinoma | 0 | No | RUL | 1b LTX048 |
| 535 | Adenocarcinoma | 0 | No | RUL | 1b LTX048 |
| 536 | Adenocarcinoma | 0 | No | RUL | 1b LTX048 |
| 537 | Adenocarcinoma | 0 | No | RUL | 1b LTX048 |
| 538 | Adenocarcinoma | 0 | No | RUL | 1b LTX048 |
| 539 | Adenocarcinoma | 0 | No | RUL | 1b LTX048 |
| 540 | Adenocarcinoma | 0 | No | RUL | 1b LTX048 |

FIG. 20 (CONT.)

| Row number | Pathological type | LN status | Vasc inv? | Lobe of lung | Madeup name |
|---|---|---|---|---|---|
| 541 | Adenocarcinoma | 0 | No | RUL | 1b LTX048 |
| 542 | Adenocarcinoma | 0 | No | RUL | 1b LTX048 |
| 543 | Adenocarcinoma | 0 | No | RUL | 1b LTX048 |
| 544 | Adenocarcinoma | 0 | No | LUL | 2b LTX046 |
| 545 | Adenocarcinoma | 0 | No | LUL | 2b LTX046 |
| 546 | Adenocarcinoma | 0 | No | LUL | 2b LTX046 |
| 547 | Adenocarcinoma | 0 | No | LUL | 2b LTX046 |
| 548 | Adenocarcinoma | 0 | No | LUL | 2b LTX046 |
| 549 | Adenocarcinoma | 0 | No | LUL | 2b LTX046 |
| 550 | Adenocarcinoma | 0 | No | LUL | 2b LTX046 |
| 551 | Adenocarcinoma | 0 | No | LUL | 2b LTX046 |
| 552 | Adenocarcinoma | 0 | No | LUL | 2b LTX046 |
| 553 | Adenocarcinoma | 0 | No | LUL | 2b LTX046 |
| 554 | Adenocarcinoma | 0 | No | LUL | 2b LTX046 |
| 555 | Adenocarcinoma | 0 | No | LUL | 2b LTX046 |
| 556 | Adenocarcinoma | 0 | No | LUL | 2b LTX046 |
| 557 | Adenocarcinoma | 0 | No | LUL | 2b LTX046 |
| 558 | Adenocarcinoma | 0 | No | LUL | 2b LTX046 |
| 559 | Adenocarcinoma | 0 | No | LUL | 2b LTX046 |
| 560 | Adenocarcinoma | 0 | No | LUL | 2b LTX046 |
| 561 | Adenocarcinoma | 0 | No | LUL | 2b LTX046 |
| 562 | Adenocarcinoma | 0 | No | LUL | 2b LTX046 |
| 563 | Adenocarcinoma | 0 | No | RUL | 1b LTX036 |
| 564 | Adenocarcinoma | 0 | No | RUL | 1b LTX036 |
| 565 | Adenocarcinoma | 0 | No | RUL | 1b LTX036 |
| 566 | Adenocarcinoma | 0 | No | RUL | 1b LTX036 |
| 567 | Adenocarcinoma | 0 | No | RUL | 1b LTX036 |

FIG. 20 (CONT.)

| Row number | Pathological type | LN status | Vasc inv? | Lobe of lung | Madeup name |
|---|---|---|---|---|---|
| 568 | Adenocarcinoma | 0 | No | RUL | 1b LTX036 |
| 569 | Adenocarcinoma | 0 | No | RUL | 1b LTX036 |
| 570 | Adenocarcinoma | 0 | No | RUL | 1b LTX036 |
| 571 | Adenocarcinoma | 0 | No | RUL | 1b LTX036 |
| 572 | Adenocarcinoma | 0 | No | RUL | 1b LTX036 |
| 573 | Adenocarcinoma | 0 | No | RUL | 1b LTX036 |
| 574 | Adenocarcinoma | 0 | No | RUL | 1b LTX036 |
| 575 | Adenocarcinoma | 0 | No | RUL | 1b LTX036 |
| 576 | Adenocarcinoma | 0 | No | RUL | 1b LTX036 |
| 577 | Adenocarcinoma | 0 | No | RUL | 1b LTX036 |
| 578 | Adenocarcinoma | 0 | No | RUL | 1b LTX036 |
| 579 | Adenocarcinoma | 0 | No | RUL | 1b LTX036 |
| 580 | Adenocarcinoma | 0 | No | RUL | 1b LTX036 |
| 581 | Adenocarcinoma | 0 | No | RUL | 1b LTX036 |
| 582 | Squamous cell carcinoma | 0 | No | LUL | 2a LTX022 |
| 583 | Squamous cell carcinoma | 0 | No | LUL | 2a LTX022 |
| 584 | Squamous cell carcinoma | 0 | No | LUL | 2a LTX022 |
| 585 | Squamous cell carcinoma | 0 | No | LUL | 2a LTX022 |
| 586 | Squamous cell carcinoma | 0 | No | LUL | 2a LTX022 |
| 587 | Squamous cell carcinoma | 0 | No | LUL | 2a LTX022 |
| 588 | Squamous cell carcinoma | 0 | No | LUL | 2a LTX022 |
| 589 | Squamous cell carcinoma | 0 | No | LUL | 2a LTX022 |
| 590 | Squamous cell carcinoma | 0 | No | LUL | 2a LTX022 |
| 591 | Squamous cell carcinoma | 0 | No | LUL | 2a LTX022 |
| 592 | Squamous cell carcinoma | 0 | No | LUL | 2a LTX022 |
| 593 | Squamous cell carcinoma | 0 | No | LUL | 2a LTX022 |
| 594 | Squamous cell carcinoma | 0 | No | LUL | 2a LTX022 |

FIG. 20 (CONT.)

| Row number | Pathological type | LN status | Vasc inv? | Lobe of lung | Madeup name |
|---|---|---|---|---|---|
| 595 | Squamous cell carcinoma | 0 | No | LUL | 2a LTX022 |
| 596 | Squamous cell carcinoma | 0 | No | LUL | 2a LTX022 |
| 597 | Squamous cell carcinoma | 0 | No | LUL | 2a LTX022 |
| 598 | Squamous cell carcinoma | 0 | No | LUL | 2a LTX022 |
| 599 | Squamous cell carcinoma | 0 | No | LUL | 2a LTX022 |
| 600 | Squamous cell carcinoma | 0 | No | LUL | 2a LTX022 |
| 601 | Squamous cell carcinoma | 0 | No | LUL | 2a LTX022 |
| 602 | Adenocarcinoma | 0 | yes | RML | 1b LTX049 |
| 603 | Adenocarcinoma | 0 | yes | RML | 1b LTX049 |
| 604 | Adenocarcinoma | 0 | yes | RML | 1b LTX049 |
| 605 | Adenocarcinoma | 0 | yes | RML | 1b LTX049 |
| 606 | Adenocarcinoma | 0 | yes | RML | 1b LTX049 |
| 607 | Adenocarcinoma | 0 | yes | RML | 1b LTX049 |
| 608 | Adenocarcinoma | 0 | yes | RML | 1b LTX049 |
| 609 | Adenocarcinoma | 0 | yes | RML | 1b LTX049 |
| 610 | Adenocarcinoma | 0 | yes | RML | 1b LTX049 |
| 611 | Adenocarcinoma | 0 | yes | RML | 1b LTX049 |
| 612 | Adenocarcinoma | 0 | yes | RML | 1b LTX049 |
| 613 | Adenocarcinoma | 0 | yes | RML | 1b LTX049 |
| 614 | Adenocarcinoma | 0 | yes | RML | 1b LTX049 |
| 615 | Adenocarcinoma | 0 | yes | RML | 1b LTX049 |
| 616 | Adenocarcinoma | 0 | yes | RML | 1b LTX049 |
| 617 | Adenocarcinoma | 0 | yes | RML | 1b LTX049 |
| 618 | Adenocarcinoma | 0 | yes | RML | 1b LTX049 |
| 619 | Adenocarcinoma | 0 | yes | RML | 1b LTX049 |
| 620 | Adenocarcinoma | 0 | yes | RML | 1b LTX049 |
| 621 | Squamous cell carcinoma | 1 | YES | RLL | 2a LTX063 |

FIG. 20 (CONT.)

| Row number | Pathological type | LN status | Vasc inv? | Lobe of lung | Madeup name |
|---|---|---|---|---|---|
| 622 | Squamous cell carcinoma | 1 | YES | RLL | 2a LTX063 |
| 623 | Squamous cell carcinoma | 1 | YES | RLL | 2a LTX063 |
| 624 | Squamous cell carcinoma | 1 | YES | RLL | 2a LTX063 |
| 625 | Squamous cell carcinoma | 1 | YES | RLL | 2a LTX063 |
| 626 | Squamous cell carcinoma | 1 | YES | RLL | 2a LTX063 |
| 627 | Squamous cell carcinoma | 1 | YES | RLL | 2a LTX063 |
| 628 | Squamous cell carcinoma | 1 | YES | RLL | 2a LTX063 |
| 629 | Squamous cell carcinoma | 1 | YES | RLL | 2a LTX063 |
| 630 | Squamous cell carcinoma | 1 | YES | RLL | 2a LTX063 |
| 631 | Squamous cell carcinoma | 1 | YES | RLL | 2a LTX063 |
| 632 | Squamous cell carcinoma | 1 | YES | RLL | 2a LTX063 |
| 633 | Squamous cell carcinoma | 1 | YES | RLL | 2a LTX063 |
| 634 | Squamous cell carcinoma | 1 | YES | RLL | 2a LTX063 |
| 635 | Squamous cell carcinoma | 1 | YES | RLL | 2a LTX063 |
| 636 | Squamous cell carcinoma | 1 | YES | RLL | 2a LTX063 |
| 637 | Squamous cell carcinoma | 1 | YES | RLL | 2a LTX063 |
| 638 | Squamous cell carcinoma | 1 | YES | RLL | 2a LTX063 |
| 639 | Squamous cell carcinoma | 1 | YES | RLL | 2a LTX063 |
| 640 | Squamous cell carcinoma | 1 | YES | RLL | 2a LTX063 |
| 641 | Adenocarcinoma | 0 | No | LLL | 1b LTX144 |
| 642 | Adenocarcinoma | 0 | No | LLL | 1b LTX144 |
| 643 | Adenocarcinoma | 0 | No | LLL | 1b LTX144 |
| 644 | Adenocarcinoma | 0 | No | LLL | 1b LTX144 |
| 645 | Adenocarcinoma | 0 | No | LLL | 1b LTX144 |
| 646 | Adenocarcinoma | 0 | No | LLL | 1b LTX144 |
| 647 | Adenocarcinoma | 0 | No | LLL | 1b LTX144 |
| 648 | Adenocarcinoma | 0 | No | LLL | 1b LTX144 |

FIG. 20 (CONT.)

| Row number | Pathological type | LN status | Vasc inv? | Lobe of lung | Madeup name |
|---|---|---|---|---|---|
| 649 | Adenocarcinoma | 0 | No | LLL | 1b LTX144 |
| 650 | Adenocarcinoma | 0 | No | LLL | 1b LTX144 |
| 651 | Adenocarcinoma | 0 | No | LLL | 1b LTX144 |
| 652 | Adenocarcinoma | 0 | No | LLL | 1b LTX144 |
| 653 | Adenocarcinoma | 0 | No | LLL | 1b LTX144 |
| 654 | Adenocarcinoma | 0 | No | LLL | 1b LTX144 |
| 655 | Adenocarcinoma | 0 | No | LLL | 1b LTX144 |
| 656 | Adenocarcinoma | 0 | No | LLL | 1b LTX144 |
| 657 | Adenocarcinoma | 0 | No | LLL | 1b LTX144 |
| 658 | Adenocarcinoma | 0 | No | LLL | 1b LTX144 |
| 659 | Adenocarcinoma | 0 | No | LLL | 1b LTX144 |
| 660 | Squamous cell carcinoma | 0 | Yes | LUL | 2b LTX038 |
| 661 | Squamous cell carcinoma | 0 | Yes | LUL | 2b LTX038 |
| 662 | Squamous cell carcinoma | 0 | Yes | LUL | 2b LTX038 |
| 663 | Squamous cell carcinoma | 0 | Yes | LUL | 2b LTX038 |
| 664 | Squamous cell carcinoma | 0 | Yes | LUL | 2b LTX038 |
| 665 | Squamous cell carcinoma | 0 | Yes | LUL | 2b LTX038 |
| 666 | Squamous cell carcinoma | 0 | Yes | LUL | 2b LTX038 |
| 667 | Squamous cell carcinoma | 0 | Yes | LUL | 2b LTX038 |
| 668 | Squamous cell carcinoma | 0 | Yes | LUL | 2b LTX038 |
| 669 | Squamous cell carcinoma | 0 | Yes | LUL | 2b LTX038 |
| 670 | Squamous cell carcinoma | 0 | Yes | LUL | 2b LTX038 |
| 671 | Squamous cell carcinoma | 0 | Yes | LUL | 2b LTX038 |
| 672 | Squamous cell carcinoma | 0 | Yes | LUL | 2b LTX038 |
| 673 | Squamous cell carcinoma | 0 | Yes | LUL | 2b LTX038 |
| 674 | Squamous cell carcinoma | 0 | Yes | LUL | 2b LTX038 |
| 675 | Squamous cell carcinoma | 0 | Yes | LUL | 2b LTX038 |

FIG. 20 (CONT.)

| Row number | Pathological type | LN status | Vasc inv? | Lobe of lung | Madeup name |
|---|---|---|---|---|---|
| 676 | Squamous cell carcinoma | 0 | Yes | LUL | 2b LTX038 |
| 677 | Squamous cell carcinoma | 0 | Yes | LUL | 2b LTX038 |
| 678 | Squamous cell carcinoma | 0 | Yes | LUL | 2b LTX038 |
| 679 | Squamous cell carcinoma | 0 | Yes | LUL | 2b LTX038 |
| 680 | Adenocarcinoma | 0 | No | RLL | 1a LTX034 |
| 681 | Adenocarcinoma | 0 | No | RLL | 1a LTX034 |
| 682 | Adenocarcinoma | 0 | No | RLL | 1a LTX034 |
| 683 | Adenocarcinoma | 0 | No | RLL | 1a LTX034 |
| 684 | Adenocarcinoma | 0 | No | RLL | 1a LTX034 |
| 685 | Adenocarcinoma | 0 | No | RLL | 1a LTX034 |
| 686 | Adenocarcinoma | 0 | No | RLL | 1a LTX034 |
| 687 | Adenocarcinoma | 0 | No | RLL | 1a LTX034 |
| 688 | Adenocarcinoma | 0 | No | RLL | 1a LTX034 |
| 689 | Adenocarcinoma | 0 | No | RLL | 1a LTX034 |
| 690 | Adenocarcinoma | 0 | No | RLL | 1a LTX034 |
| 691 | Adenocarcinoma | 0 | No | RLL | 1a LTX034 |
| 692 | Adenocarcinoma | 0 | No | RLL | 1a LTX034 |
| 693 | Adenocarcinoma | 0 | No | RLL | 1a LTX034 |
| 694 | Adenocarcinoma | 0 | No | RLL | 1a LTX034 |
| 695 | Adenocarcinoma | 0 | No | RLL | 1a LTX034 |
| 696 | Adenocarcinoma | 0 | No | RLL | 1a LTX034 |
| 697 | Adenocarcinoma | 0 | No | RLL | 1a LTX034 |
| 698 | Adenocarcinoma | 0 | No | LLL | 1b LTX013 |
| 699 | Adenocarcinoma | 0 | No | LLL | 1b LTX013 |
| 700 | Adenocarcinoma | 0 | No | LLL | 1b LTX013 |
| 701 | Adenocarcinoma | 0 | No | LLL | 1b LTX013 |
| 702 | Adenocarcinoma | 0 | No | LLL | 1b LTX013 |

FIG. 20 (CONT.)

| Row number | Pathological type | LN status | Vasc inv? | Lobe of lung | Madeup name |
|---|---|---|---|---|---|
| 703 | Adenocarcinoma | 0 | No | LLL | 1b LTX013 |
| 704 | Adenocarcinoma | 0 | No | LLL | 1b LTX013 |
| 705 | Adenocarcinoma | 0 | No | LLL | 1b LTX013 |
| 706 | Adenocarcinoma | 0 | No | LLL | 1b LTX013 |
| 707 | Adenocarcinoma | 0 | No | LLL | 1b LTX013 |
| 708 | Adenocarcinoma | 0 | No | LLL | 1b LTX013 |
| 709 | Adenocarcinoma | 0 | No | LLL | 1b LTX013 |
| 710 | Adenocarcinoma | 0 | No | LLL | 1b LTX013 |
| 711 | Adenocarcinoma | 0 | No | LLL | 1b LTX013 |
| 712 | Adenocarcinoma | 0 | No | LLL | 1b LTX013 |
| 713 | | 0 | No | LLL | 1a LTX065 |
| 714 | | 0 | No | LLL | 1a LTX065 |
| 715 | | 0 | No | LLL | 1a LTX065 |
| 716 | | 0 | No | LLL | 1a LTX065 |
| 717 | | 0 | No | LLL | 1a LTX065 |
| 718 | | 0 | No | LLL | 1a LTX065 |
| 719 | | 0 | No | LLL | 1a LTX065 |
| 720 | | 0 | No | LLL | 1a LTX065 |
| 721 | | 0 | No | LLL | 1a LTX065 |
| 722 | | 0 | No | LLL | 1a LTX065 |
| 723 | | 0 | No | LLL | 1a LTX065 |
| 724 | | 0 | No | LLL | 1a LTX065 |
| 725 | | 0 | No | LLL | 1a LTX065 |
| 726 | | 0 | No | LLL | 1a LTX065 |
| 727 | | 0 | No | LLL | 1a LTX065 |
| 728 | Squamous cell carcinoma | 0 | No | LUL | 1b LTX149 |
| 729 | Squamous cell carcinoma | 0 | No | LUL | 1b LTX149 |

FIG. 20 (CONT.)

| Row number | Pathological type | LN status | Vasc inv? | Lobe of lung | Madeup name |
|---|---|---|---|---|---|
| 730 | Squamous cell carcinoma | 0 | No | LUL | 1b LTX149 |
| 731 | Squamous cell carcinoma | 0 | No | LUL | 1b LTX149 |
| 732 | Squamous cell carcinoma | 0 | No | LUL | 1b LTX149 |
| 733 | Squamous cell carcinoma | 0 | No | LUL | 1b LTX149 |
| 734 | Squamous cell carcinoma | 0 | No | LUL | 1b LTX149 |
| 735 | Squamous cell carcinoma | 0 | No | LUL | 1b LTX149 |
| 736 | Squamous cell carcinoma | 0 | No | LUL | 1b LTX149 |
| 737 | Squamous cell carcinoma | 0 | No | LUL | 1b LTX149 |
| 738 | Squamous cell carcinoma | 0 | No | LUL | 1b LTX149 |
| 739 | Squamous cell carcinoma | 0 | No | LUL | 1b LTX149 |
| 740 | Squamous cell carcinoma | 0 | No | LUL | 1b LTX149 |
| 741 | Squamous cell carcinoma | 0 | No | LUL | 1b LTX149 |
| 742 | Squamous cell carcinoma | 0 | No | LUL | 1b LTX149 |
| 743 | Squamous cell carcinoma | 0 | No | LUL | 1b LTX149 |
| 744 | Squamous cell carcinoma | 0 | No | LUL | 1b LTX149 |
| 745 | Adenocarcinoma | 0 | No | LLL | 2b LTX102 |
| 746 | Adenocarcinoma | 0 | No | LLL | 2b LTX102 |
| 747 | Adenocarcinoma | 0 | No | LLL | 2b LTX102 |
| 748 | Adenocarcinoma | 0 | No | LLL | 2b LTX102 |
| 749 | Adenocarcinoma | 0 | No | LLL | 2b LTX102 |
| 750 | Adenocarcinoma | 0 | No | LLL | 2b LTX102 |
| 751 | Adenocarcinoma | 0 | No | LLL | 2b LTX102 |
| 752 | Adenocarcinoma | 0 | No | LLL | 2b LTX102 |
| 753 | Adenocarcinoma | 0 | No | LLL | 2b LTX102 |
| 754 | Adenocarcinoma | 0 | No | LLL | 2b LTX102 |
| 755 | Adenocarcinoma | 0 | No | LLL | 2b LTX102 |
| 756 | Adenocarcinoma | 0 | No | LLL | 2b LTX102 |

FIG. 20 (CONT.)

| Row number | Pathological type | LN status | Vasc inv? | Lobe of lung | Madeup name |
|---|---|---|---|---|---|
| 757 | Adenocarcinoma | 0 | No | LLL | 2b LTX102 |
| 758 | Adenocarcinoma | 0 | No | LLL | 2b LTX102 |
| 759 | Adenocarcinoma | 0 | No | LLL | 2b LTX102 |
| 760 | Adenocarcinoma | 0 | No | LLL | 2b LTX102 |
| 761 | Adenocarcinoma | 0 | No | LLL | 2b LTX102 |
| 762 | Adenocarcinoma | 0 | No | LLL | 2b LTX102 |
| 763 | Adenocarcinoma | 0 | No | LLL | 2b LTX102 |
| 764 | Adenocarcinoma | 0 | No | LLL | 2b LTX102 |
| 765 | Squamous cell carcinoma | 0 | No | RLL | 1b LTX015 |
| 766 | Squamous cell carcinoma | 0 | No | RLL | 1b LTX015 |
| 767 | Squamous cell carcinoma | 0 | No | RLL | 1b LTX015 |
| 768 | Squamous cell carcinoma | 0 | No | RLL | 1b LTX015 |
| 769 | Squamous cell carcinoma | 0 | No | RLL | 1b LTX015 |
| 770 | Squamous cell carcinoma | 0 | No | RLL | 1b LTX015 |
| 771 | Squamous cell carcinoma | 0 | No | RLL | 1b LTX015 |
| 772 | Squamous cell carcinoma | 0 | No | RLL | 1b LTX015 |
| 773 | Squamous cell carcinoma | 0 | No | RLL | 1b LTX015 |
| 774 | Squamous cell carcinoma | 0 | No | RLL | 1b LTX015 |
| 775 | Squamous cell carcinoma | 0 | No | RLL | 1b LTX015 |
| 776 | Squamous cell carcinoma | 0 | No | RLL | 1b LTX015 |
| 777 | Squamous cell carcinoma | 0 | No | RLL | 1b LTX015 |
| 778 | Squamous cell carcinoma | 0 | No | RLL | 1b LTX015 |
| 779 | Squamous cell carcinoma | 0 | No | RLL | 1b LTX015 |
| 780 | Squamous cell carcinoma | 0 | No | RLL | 1b LTX015 |
| 781 | Squamous cell carcinoma | 0 | No | RLL | 1b LTX015 |
| 782 | Squamous cell carcinoma | 0 | No | RLL | 1b LTX015 |
| 783 | Squamous cell carcinoma | 0 | No | RLL | 1b LTX015 |

FIG. 20 (CONT.)

| Row number | Pathological type | LN status | Vasc inv? | Lobe of lung | Madeup name |
|---|---|---|---|---|---|
| 784 | Adenocarcinoma | 0 | No | RLL | 1b LTX074 |
| 785 | Adenocarcinoma | 0 | No | RLL | 1b LTX074 |
| 786 | Adenocarcinoma | 0 | No | RLL | 1b LTX074 |
| 787 | Adenocarcinoma | 0 | No | RLL | 1b LTX074 |
| 788 | Adenocarcinoma | 0 | No | RLL | 1b LTX074 |
| 789 | Adenocarcinoma | 0 | No | RLL | 1b LTX074 |
| 790 | Adenocarcinoma | 0 | No | RLL | 1b LTX074 |
| 791 | Adenocarcinoma | 0 | No | RLL | 1b LTX074 |
| 792 | Adenocarcinoma | 0 | No | RLL | 1b LTX074 |
| 793 | Adenocarcinoma | 0 | No | RLL | 1b LTX074 |
| 794 | Adenocarcinoma | 0 | No | RLL | 1b LTX074 |
| 795 | Adenocarcinoma | 0 | No | RLL | 1b LTX074 |
| 796 | Adenocarcinoma | 0 | No | RLL | 1b LTX074 |
| 797 | Adenocarcinoma | 0 | No | RLL | 1b LTX074 |
| 798 | Adenocarcinoma | 0 | No | RLL | 1b LTX074 |
| 799 | Adenocarcinoma | 0 | No | RLL | 1b LTX074 |
| 800 | Adenocarcinoma | 0 | No | RLL | 1b LTX074 |
| 801 | Adenocarcinoma | 0 | No | RLL | 1b LTX074 |
| 802 | Adenocarcinoma | 0 | No | RLL | 1b LTX074 |
| 803 | Adenocarcinoma | ? | No | LUL | 1a LTX075 |
| 804 | Adenocarcinoma | ? | No | LUL | 1a LTX075 |
| 805 | Adenocarcinoma | ? | No | LUL | 1a LTX075 |
| 806 | Adenocarcinoma | ? | No | LUL | 1a LTX075 |
| 807 | Adenocarcinoma | ? | No | LUL | 1a LTX075 |
| 808 | Adenocarcinoma | ? | No | LUL | 1a LTX075 |
| 809 | Adenocarcinoma | ? | No | LUL | 1a LTX075 |
| 810 | Adenocarcinoma | ? | No | LUL | 1a LTX075 |

FIG. 20 (CONT.)

| Row number | Pathological type | LN status | Vasc inv? | Lobe of lung | Madeup name |
|---|---|---|---|---|---|
| 811 | Adenocarcinoma | ? | No | LUL | 1a LTX075 |
| 812 | Adenocarcinoma | ? | No | LUL | 1a LTX075 |
| 813 | Adenocarcinoma | ? | No | LUL | 1a LTX075 |
| 814 | Adenocarcinoma | ? | No | LUL | 1a LTX075 |
| 815 | Adenocarcinoma | ? | No | LUL | 1a LTX075 |
| 816 | Adenocarcinoma | ? | No | LUL | 1a LTX075 |
| 817 | Adenocarcinoma | ? | No | LUL | 1a LTX075 |
| 818 | Adenocarcinoma | ? | No | LUL | 1a LTX075 |
| 819 | Adenocarcinoma | ? | No | LUL | 1a LTX075 |
| 820 | Adenocarcinoma | ? | No | LUL | 1a LTX075 |
| 821 | Adenocarcinoma | ? | No | LUL | 1a LTX075 |
| 822 | Squamous cell carcinoma | 0 | Yes | RLL | 1b LTX033 |
| 823 | Squamous cell carcinoma | 0 | Yes | RLL | 1b LTX033 |
| 824 | Squamous cell carcinoma | 0 | Yes | RLL | 1b LTX033 |
| 825 | Squamous cell carcinoma | 0 | Yes | RLL | 1b LTX033 |
| 826 | Squamous cell carcinoma | 0 | Yes | RLL | 1b LTX033 |
| 827 | Squamous cell carcinoma | 0 | Yes | RLL | 1b LTX033 |
| 828 | Squamous cell carcinoma | 0 | Yes | RLL | 1b LTX033 |
| 829 | Squamous cell carcinoma | 0 | Yes | RLL | 1b LTX033 |
| 830 | Squamous cell carcinoma | 0 | Yes | RLL | 1b LTX033 |
| 831 | Squamous cell carcinoma | 0 | Yes | RLL | 1b LTX033 |
| 832 | Squamous cell carcinoma | 0 | Yes | RLL | 1b LTX033 |
| 833 | Squamous cell carcinoma | 0 | Yes | RLL | 1b LTX033 |
| 834 | Squamous cell carcinoma | 0 | Yes | RLL | 1b LTX033 |
| 835 | Squamous cell carcinoma | 0 | Yes | RLL | 1b LTX033 |
| 836 | Squamous cell carcinoma | 0 | Yes | RLL | 1b LTX033 |
| 837 | Squamous cell carcinoma | 0 | Yes | RLL | 1b LTX033 |

FIG. 20 (CONT.)

| Row number | Pathological type | LN status | Vasc inv? | Lobe of lung | Madeup name |
|---|---|---|---|---|---|
| 838 | Squamous cell carcinoma | 0 | Yes | RLL | 1b LTX033 |
| 839 | Squamous cell carcinoma | 0 | Yes | RLL | 1b LTX033 |
| 840 | Adenocarcinoma | 0 | No | RLL | 1a LTX091 |
| 841 | Adenocarcinoma | 0 | No | RLL | 1a LTX091 |
| 842 | Adenocarcinoma | 0 | No | RLL | 1a LTX091 |
| 843 | Adenocarcinoma | 0 | No | RLL | 1a LTX091 |
| 844 | Adenocarcinoma | 0 | No | RLL | 1a LTX091 |
| 845 | Adenocarcinoma | 0 | No | RLL | 1a LTX091 |
| 846 | Adenocarcinoma | 0 | No | RLL | 1a LTX091 |
| 847 | Adenocarcinoma | 0 | No | RLL | 1a LTX091 |
| 848 | Adenocarcinoma | 0 | No | RLL | 1a LTX091 |
| 849 | Adenocarcinoma | 0 | No | RLL | 1a LTX091 |
| 850 | Adenocarcinoma | 0 | No | RLL | 1a LTX091 |
| 851 | Adenocarcinoma | 0 | No | RLL | 1a LTX091 |
| 852 | Adenocarcinoma | 0 | No | RLL | 1a LTX091 |
| 853 | Adenocarcinoma | 0 | No | RLL | 1a LTX091 |
| 854 | Adenocarcinoma | 0 | No | RLL | 1a LTX091 |
| 855 | Adenocarcinoma | 0 | No | RLL | 1a LTX091 |
| 856 | Adenocarcinoma | 0 | No | RLL | 1a LTX091 |
| 857 | Adenocarcinoma | 0 | No | RLL | 1a LTX091 |
| 858 | Adenocarcinoma | 0 | No | RLL | 1a LTX091 |
| 859 | Squamous cell carcinoma | 0 | Yes | RUL | 2a LTX076 |
| 860 | Squamous cell carcinoma | 0 | Yes | RUL | 2a LTX076 |
| 861 | Squamous cell carcinoma | 0 | Yes | RUL | 2a LTX076 |
| 862 | Squamous cell carcinoma | 0 | Yes | RUL | 2a LTX076 |
| 863 | Squamous cell carcinoma | 0 | Yes | RUL | 2a LTX076 |
| 864 | Squamous cell carcinoma | 0 | Yes | RUL | 2a LTX076 |

FIG. 20 (CONT.)

| Row number | Pathological type | LN status | Vasc inv? | Lobe of lung | Madeup name |
|---|---|---|---|---|---|
| 865 | Squamous cell carcinoma | 0 | Yes | RUL | 2a LTX076 |
| 866 | Squamous cell carcinoma | 0 | Yes | RUL | 2a LTX076 |
| 867 | Squamous cell carcinoma | 0 | Yes | RUL | 2a LTX076 |
| 868 | Squamous cell carcinoma | 0 | Yes | RUL | 2a LTX076 |
| 869 | Squamous cell carcinoma | 0 | Yes | RUL | 2a LTX076 |
| 870 | Squamous cell carcinoma | 0 | Yes | RUL | 2a LTX076 |
| 871 | Squamous cell carcinoma | 0 | Yes | RUL | 2a LTX076 |
| 872 | Squamous cell carcinoma | 0 | Yes | RUL | 2a LTX076 |
| 873 | Squamous cell carcinoma | 0 | Yes | RUL | 2a LTX076 |
| 874 | Squamous cell carcinoma | 0 | Yes | RUL | 2a LTX076 |
| 875 | Squamous cell carcinoma | 0 | Yes | RUL | 2a LTX076 |
| 876 | Squamous cell carcinoma | 0 | Yes | RUL | 2a LTX076 |
| 877 | Squamous cell carcinoma | 0 | Yes | RUL | 2a LTX076 |
| 878 | Squamous cell carcinoma | 0 | Yes | RUL | 2a LTX076 |
| 879 | Squamous cell carcinoma | 0 | Yes | RUL | 2a LTX076 |
| 880 | Adenocarcinoma | ? | No | RLL | 1b LTX160 |
| 881 | Adenocarcinoma | ? | No | RLL | 1b LTX160 |
| 882 | Adenocarcinoma | ? | No | RLL | 1b LTX160 |
| 883 | Adenocarcinoma | ? | No | RLL | 1b LTX160 |
| 884 | Adenocarcinoma | ? | No | RLL | 1b LTX160 |
| 885 | Adenocarcinoma | ? | No | RLL | 1b LTX160 |
| 886 | Adenocarcinoma | ? | No | RLL | 1b LTX160 |
| 887 | Adenocarcinoma | ? | No | RLL | 1b LTX160 |
| 888 | Adenocarcinoma | ? | No | RLL | 1b LTX160 |
| 889 | Adenocarcinoma | ? | No | RLL | 1b LTX160 |
| 890 | Adenocarcinoma | ? | No | RLL | 1b LTX160 |
| 891 | Adenocarcinoma | ? | No | RLL | 1b LTX160 |

FIG. 20 (CONT.)

| Row number | Pathological type | LN status | Vasc inv? | Lobe of lung | Madeup name |
|---|---|---|---|---|---|
| 892 | Adenocarcinoma | ? | No | RLL | 1b LTX160 |
| 893 | Adenocarcinoma | ? | No | RLL | 1b LTX160 |
| 894 | Adenocarcinoma | ? | No | RLL | 1b LTX160 |
| 895 | Adenocarcinoma | ? | No | RLL | 1b LTX160 |
| 896 | Adenocarcinoma | ? | No | RLL | 1b LTX160 |
| 897 | Adenocarcinoma | ? | No | RLL | 1b LTX160 |
| 898 | Adenocarcinoma | ? | No | RLL | 1b LTX160 |
| 899 | Adenocarcinoma | 1 | No | RLL | 3a LTX103 |
| 900 | Adenocarcinoma | 1 | No | RLL | 3a LTX103 |
| 901 | Adenocarcinoma | 1 | No | RLL | 3a LTX103 |
| 902 | Adenocarcinoma | 1 | No | RLL | 3a LTX103 |
| 903 | Adenocarcinoma | 1 | No | RLL | 3a LTX103 |
| 904 | Adenocarcinoma | 1 | No | RLL | 3a LTX103 |
| 905 | Adenocarcinoma | 1 | No | RLL | 3a LTX103 |
| 906 | Adenocarcinoma | 1 | No | RLL | 3a LTX103 |
| 907 | Adenocarcinoma | 1 | No | RLL | 3a LTX103 |
| 908 | Adenocarcinoma | 1 | No | RLL | 3a LTX103 |
| 909 | Adenocarcinoma | 1 | No | RLL | 3a LTX103 |
| 910 | Adenocarcinoma | 1 | No | RLL | 3a LTX103 |
| 911 | Adenocarcinoma | 1 | No | RLL | 3a LTX103 |

FIG. 20 (CONT.)

METHODS FOR LUNG CANCER DETECTION

CROSS-REFERENCE TO RELATED APPLICATIONS

This application claims the benefit of U.S. Provisional Application Ser. No. 62/323,589, filed Apr. 15, 2016, which is hereby incorporated by reference in its entirety.

FIELD OF THE INVENTION

The disclosed inventions relate generally to methods for detecting nucleic acid mutations and fusions using amplification methods such as the polymerase chain reaction (PCR).

BACKGROUND OF THE INVENTION

Detection of mutations associated with cancers whether prior to diagnosis, in making a diagnosis, for disease staging or to monitor treatment efficacy has traditionally relied or solid tumor biopsy samples. Such sampling is highly invasive and not without risk of potentially contributing to metastasis or surgical complications. Better and less invasive methods are needed for detecting mutations associated with cancer.

SUMMARY OF THE INVENTION

Provided herein in one embodiment, is a method for determining the single nucleotide variants present in a lung squamous cell carcinoma. The method in this embodiment, includes generating a set of amplicons by performing a multiplex amplification reaction on nucleic acids isolated from a sample of blood or a fraction thereof from an individual suspected of having a lung squamous cell carcinoma, wherein each amplicon of the set of amplicons spans at least one single nucleotide variant loci of a set of single nucleotide variant loci known to be associated with lung cancer; and
  determining the sequence of at least a segment of each amplicon of the set of amplicons, wherein the segment comprises a single nucleotide variant loci, thereby determining the single nucleotide variants present in the squamous cell carcinoma.

In another embodiment, provided herein is a method for supporting a lung cancer diagnosis for an individual suspected of having lung cancer from a sample of blood or a fraction thereof from the individual. The method includes generating a set of amplicons by performing a multiplex amplification reaction on nucleic acids isolated from the sample, wherein each amplicon of the set of amplicons spans at least one single nucleotide variant loci of a set of single nucleotide variant loci known to be associated with lung cancer; and
  determining the sequence of at least a segment of each amplicon of the set of amplicons, wherein the segment comprises a single nucleotide variant loci, thereby determining whether one or more single nucleotide variants are present in the plurality of single nucleotide variant loci. According to illustrative embodiments,
  the absence of a single nucleotide variant supports a diagnosis of stage 1a, 2a, or 2b adenocarcinoma,
  the presence of a single nucleotide variant supports a diagnosis of squamous cell carcinoma or a stage 2b or 3a adenocarcinoma, and/or
  the presence of 5, 10, 15 or more single nucleotide variants supports a diagnosis of squamous cell carcinoma or a stage 2b or 3 adenocarcinoma.

In certain embodiments, the presence of 5, 10, or 15 or more single nucleotide variants supports a diagnosis of squamous cell carcinoma or a stage 3 adenocarcinoma In illustrative examples of any of the method embodiments provided herein that include an amplification step, the amplification reaction is a PCR reaction, the annealing temperature is between 1 and 15° C. greater than the melting temperature of at least 50, 60, 70, 85, 80, 90, 95, or 100% of the primers of the set of primers, the length of the annealing step in the PCR reaction is between 15 and 60 minutes, the primer concentration in the amplification reaction is between 1 and 10 nM, and the primers in the set of primers, are designed to minimize primer dimer formation.

In any of the method embodiments of the invention, that include determining or detecting the presence of an SNV using an amplification method, an efficiency and an error rate per cycle can be determined for each amplification reaction of the multiplex amplification reaction of the set of single nucleotide variance loci, and the efficiency and the error rate can be used to determine whether a single nucleotide variant at the set of single variant loci is present in the sample. In some of these exemplary embodiments, a confidence is determined and a SNV call is made if a cutoff confidence value is exceeded, such as 90%, 95%, or 98% confidence.

In other embodiments, inventive compositions and solid supports are provided herein.

Other embodiments and features and advantages of the disclosed inventions will be apparent from the following detailed description and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 16 is a table of cfDNA analysis showing DNA concentration, genome copy equivalents into library prep, plasma hemolysis grade, and cDNA profile in all samples.

FIG. 17 is a table of SNVs detected in the plasma for each sample.

FIG. 18 is a table of additional SNVs detected in plasma.

FIG. 19 is a table of assay count based for genes for the experiments in Example 1.

FIG. 20 is a table of information regarding the samples analyzed in the study of Example 1 as well as data generated from the experiment provided in Example 1.

The above-identified figures are provided by way of representation and not limitation.

DETAILED DESCRIPTION OF THE INVENTION

Methods and compositions provided herein improve the detection, diagnosis, staging, screening, treatment, and management of lung cancer. Methods provided herein, in illustrative embodiments analyze single nucleotide variant mutations (SNVs) in circulating fluids, especially circulating tumor DNA. The methods provide the advantage of identifying more of the mutations that are found in a tumor and clonal as well as subclonal mutations, in a single test, rather than multiple tests that would be required, if effective at all, that utilize tumor samples. The methods and compositions can be helpful on their own, or they can be helpful when used along with other methods for detection, diagnosis, staging, screening, treatment, and management of lung cancer, for example to help support the results of these other methods to provide more confidence and/or a definitive result.

Accordingly, provided herein in one embodiment, is a method for determining the single nucleotide variants present in a lung squamous cell carcinoma by determining the single nucleotide variants present in a ctDNA sample from an individual, such as an individual having or suspected of having, squamous cell carcinoma, using a ctDNA SNV amplification/sequencing workflow provided herein.

In another embodiment, provided herein is a method for detecting lung sqamous cell carcinoma in a sample of blood or a fraction thereof from an individual, such as an individual suspected of having a cancer, that includes determining the single nucleotide variants present in a sample by determining the single nucleotide variants present in a ctDNA sample using a ctDNA SNV amplification/sequencing workflow provided herein. The presence of 1, 2, 3, 4, 5, 6, 7, 8, 9, 10, 11, 12, 13, 14, or 15 SNVs on the low end of the range, and 2, 3, 4, 5, 6, 7, 8, 9, 10, 11, 12, 13, 14, 15, 16, 17, 18, 19, 20, 21, 22, 23, 24, 25, 30, 40, or 50 SNVs on the high end of the range, in the sample at the plurality of single nucleotide loci is indicative of the presence of squamous cell carcinoma.

Figure 12:
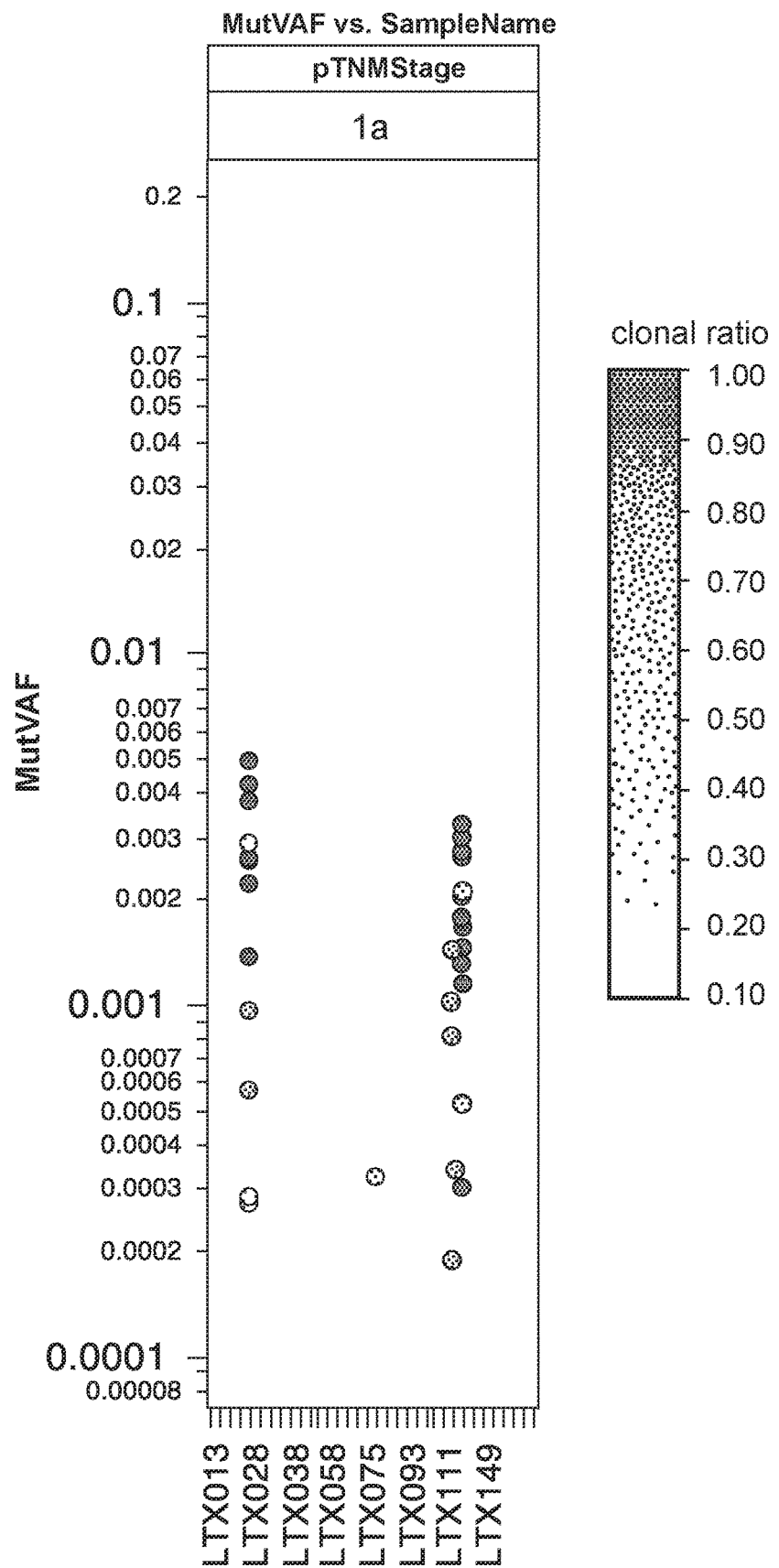
FIG. 12 shows the clonal ratios (red to blue) and mutant variant allele frequency (MutVAF) of each detected SNV. The total SNVs detected from each sample are placed in a single column and the samples are categorized by tumor stage (pTNMstage). Samples with no detected SNVs are included. The clonal ratio is defined as the ratio between the number of tumor subsections in which SNV was observed and the total number of subsections analyzed from that tumor.
Figure 12:
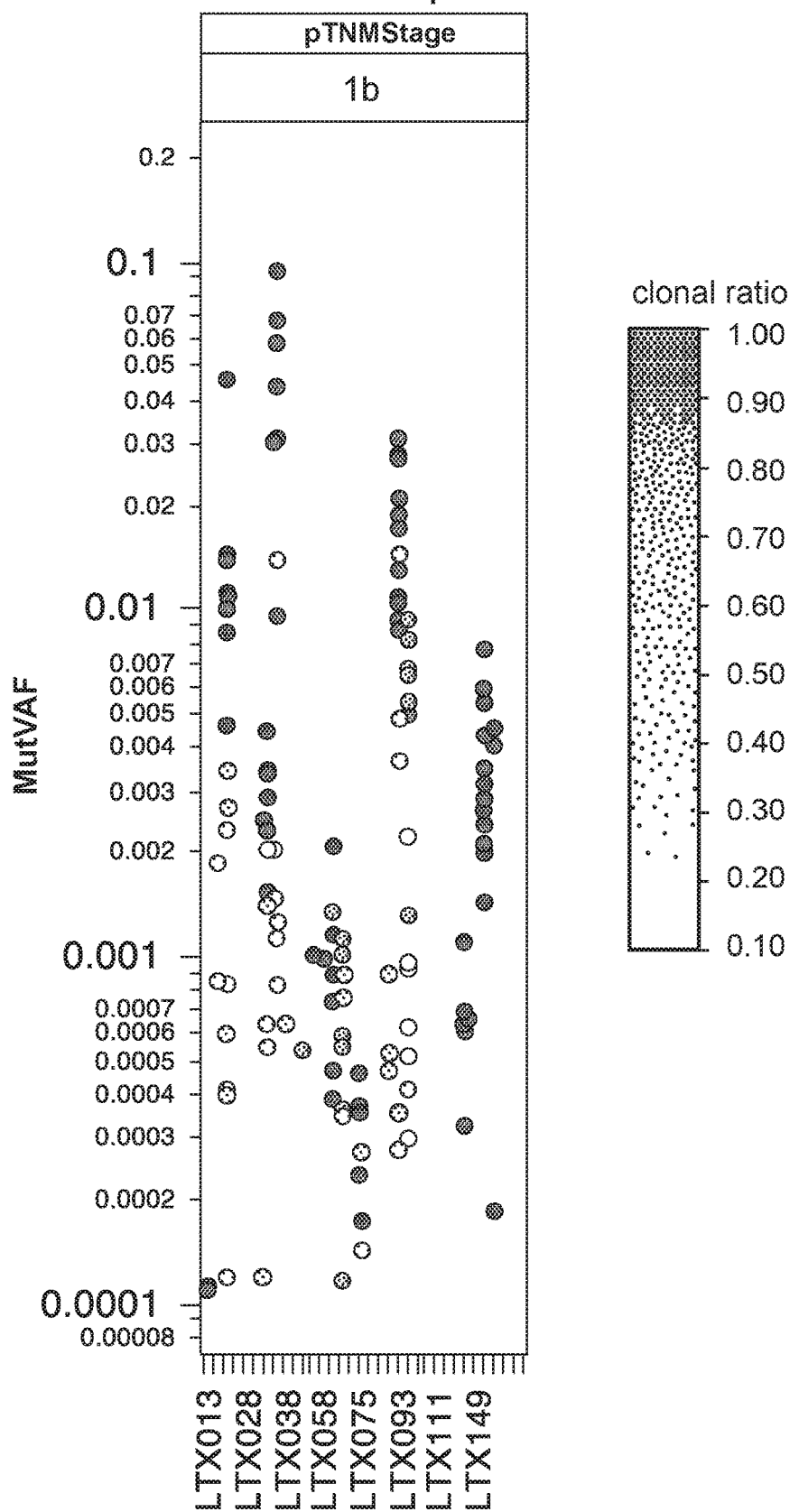
Figure 12:
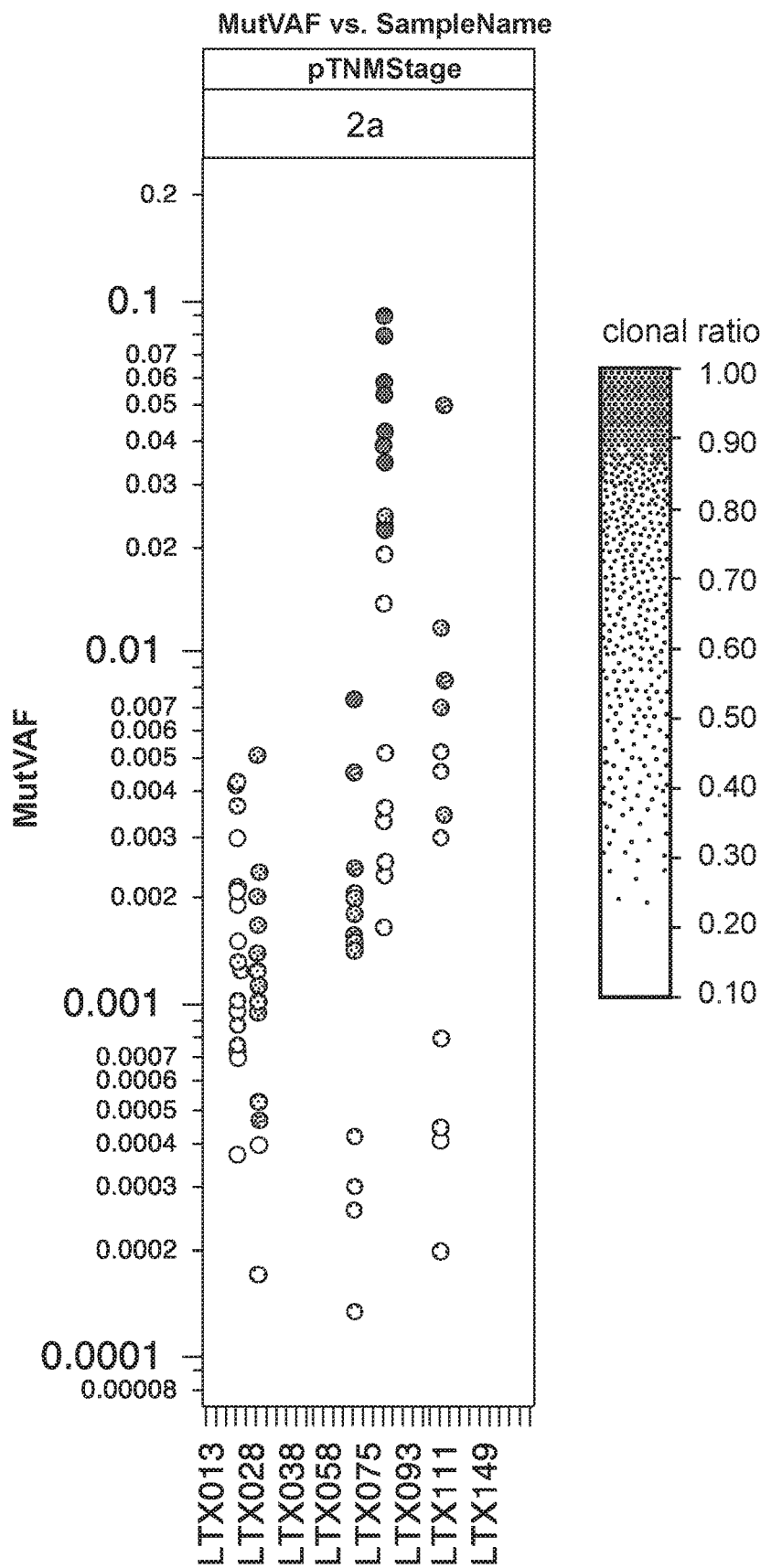
Figure 12:
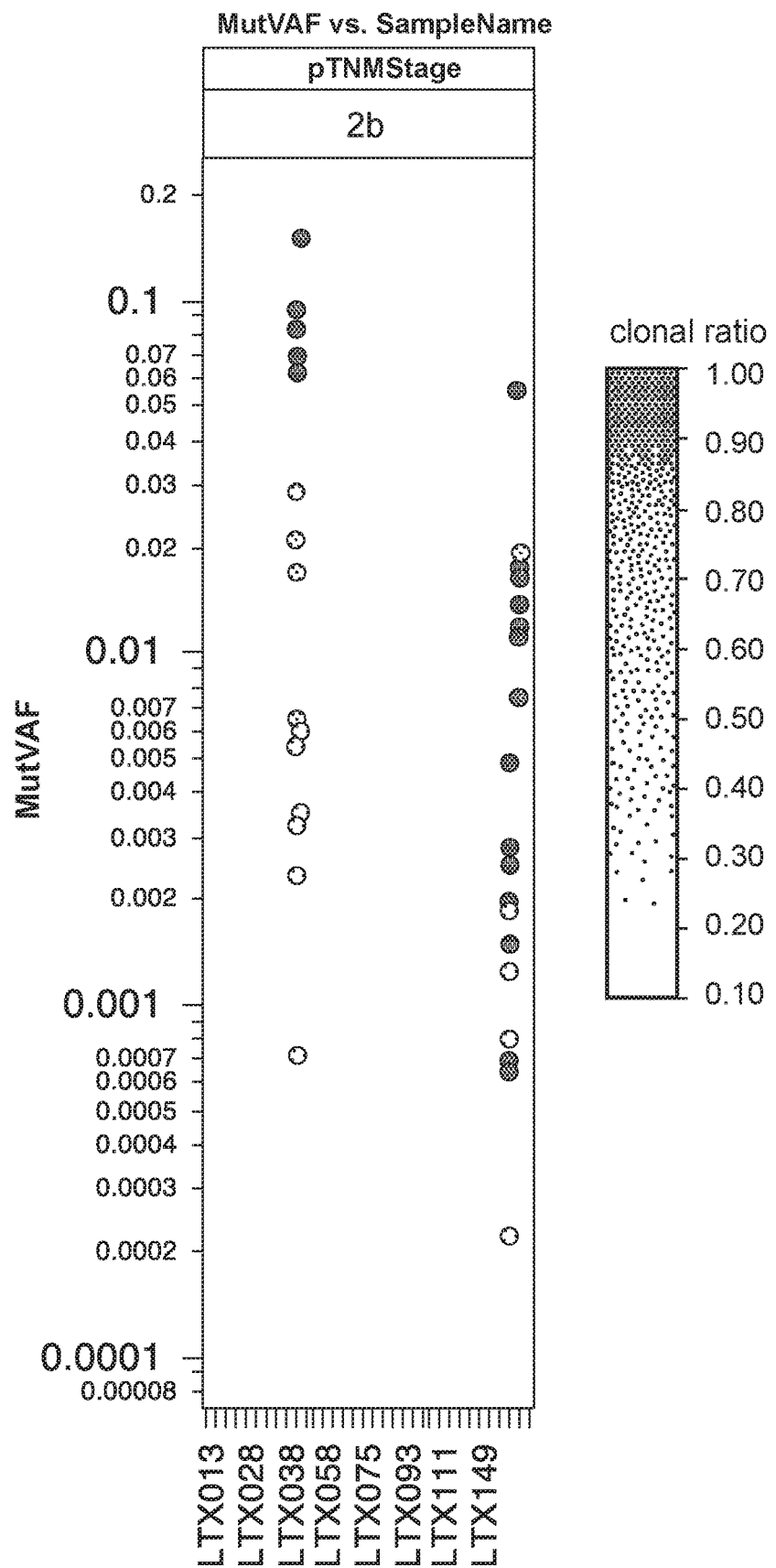
Figure 12:
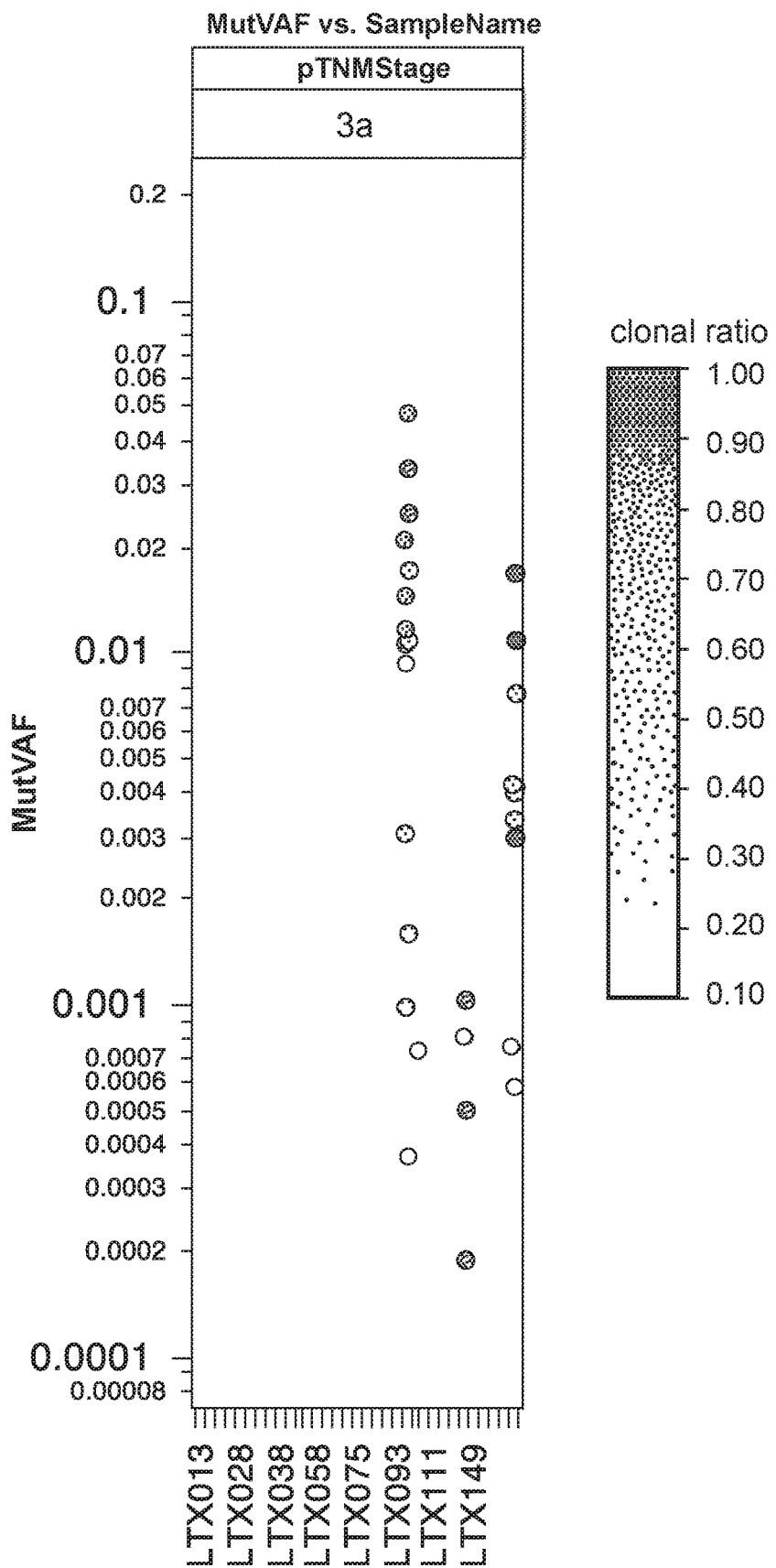

In another embodiment, provided herein is a method for detecting a clonal single nucleotide variant in a lung tumor of an individual. The method includes performing a ctDNA SNV amplification/sequencing workflow as provided herein, and determining the variant allele frequency for each of the SNV loci based on the sequence of the plurality of copies of the series of amplicons. A higher relative allele frequency compared to the other single nucleotide variants of the plurality of single nucleotide variant loci is indicative of a clonal single nucleotide variant in the tumor. Variant allele frequencies are well known in the sequencing art. Support for this embodiment, is provided, for example in FIGS. 12-14.

In certain embodiments, the method further includes determining a treatment plan, therapy and/or administering a compound to the individual that targets the one or more clonal single nucleotide variants. In certain examples, subclonal and/or other clonal SNVs are not targeted by therapy. Specific therapies and associated mutations are provided in other sections of this specification and are known in the art. Accordingly, in certain examples, the method further includes administering a compound to the individual, where the compound is known to be specifically effective in treating lung squamous cell carcinoma having one or more of the determined single nucleotide variants.

In certain aspects of this embodiment, a variant allele frequency of greater than 0.25%, 0.5%, 0.75%, 1.0%, 5% or 10% is indicative a clonal single nucleotide variant. These cutoffs are supported by the data in tabular form FIG. 20.

In certain examples of this embodiment, the squamous cell carcinoma is a stage 1a, 1b, or 2a squamous cell carcinoma. In certain examples of this embodiment, the squamous cell carcinoma is a stage 1a or 1b squamous cell carcinoma. In certain examples of the embodiment, the individual is not subjected to surgery. In certain examples of the embodiment, the individual is not subjected to a biopsy.

In some examples of this embodiment, a clonal SNV is identified or further identified if other testing such as direct tumor testing suggest an on-test SNV is a clonal SNV, for any SNV on test that has a variable allele frequency greater than at least one quarter, one third, one half, or three quarters of the other single nucleotide variants that were determined.

In some embodiments, methods herein for detecting SNVs in ctDNA can be used instead of direct analysis of DNA from a tumor. Results provided herein demonstrate that SNVs that are much more likely to be clonal SNVs have higher VAFs (See e.g. FIGS. 12-14).

In certain examples of any of the method embodiments provided herein herein, before a targeted amplification is performed on ctDNA from an individual, data is provided on SNVs that are found in a tumor from the individual. Accordingly, in these embodiments, a SNV amplification/sequencing reaction is performed on one or more tumor samples from the individual. In this methods, the ctDNA SNV amplification/sequencing reaction provided herein is still advantageous because it provides a liquid biopsy of clonal and subclonal mutations. Furthermore, as provided herein, clonal mutations can be more unambiguously identified in an individual that has lung cancer, if a high VAF percentage, for example, more than 1, 2, 3, 4, 5, 6, 7, 8, 9, 10% VAF in a ctDNA sample from the individual is determined for an SNV.

In certain embodiment, method provided herein can be used to determine whether to isolate and analyze ctDNA from circulating free nucleic acids from an individual with lung cancer. First, it is determined whether the lung cancer is an adenocarcinoma or a squamous cell carcinoma. If the lung cancer is a squamous cell carcinoma circulating free nucleic acids are isolated from individual. The method in some examples, further includes determining the stage of the lung cancer, wherein if the lung cancer is squamous cell carcinoma or stage 3a adenocarcinoma, circulating free nucleic acids are isolated from the individual. Results provided in FIG. 15 and in tabular form in FIG. 20 demonstrate that SNVs are prevalent in squamous cell carcinoma or stage 3a adenocarcinoma, However, SNVs are much less prevalent in earlier stage ADCs. Accordingly, important health care savings can be realized by saving from testing for SNVs in stage 1a, 1b, and/or 2a ADC patients.

In examples, if the lung cancer is squamous cell carcinoma or stage 3a adenocarcinoma, circulating free nucleic acids are isolated from the individual. Furthermore, in some examples, if the lung cancer is stage squamous cell carcinoma or stage 3a adenocarcinoma nucleic acids are not isolated from a lung tumor of the individual.

In some methods, provided herein are inventive compositions and/or solid supports. F1. A composition comprising circulating tumor nucleic acid fragments comprising a universal adapter, wherein the circulating tumor nucleic acids originated from a lung squamous cell carcinoma tumor.

In some embodiments, provided herein is an inventive composition that includes circulating tumor nucleic acid fragments comprising a universal adapter, wherein the circulating tumor nucleic acids originated from a sample of blood or a fraction thereof, of an individual with lung squamous cell carcinoma. Results presented in Example 1 demonstrate the surprising advantage of ctDNA SNV amplification/sequencing test methods. These methods typically include formation of ctDNA fragment that include a universal adapter. Furthermore, such methods typically include the formation of a solid support especially a solid support for high throughput sequencing, that includes a plurality of clonal populations of nucleic acids, wherein the clonal populations comprise amplicons generated from a sample of circulating free nucleic acids, wherein the ctDNA. In illustrative embodiments based on the surprising results provided herein, the ctDNA originated from a lung squamous cell carcinoma tumor.

Similarly, provided herein as an embodiment of the invention is a solid support comprising a plurality of clonal populations of nucleic acids, wherein the clonal populations comprise nucleic acid fragments generated from a sample of circulating free nucleic acids from a sample of blood or a fraction thereof, from an individual with lung squamous cell carcinoma.

In certain embodiments, the nucleic acid fragments in different clonal populations comprise the same universal adapter. Such a composition is typically formed during a high throughput sequencing reaction in methods of the present invention, as performed in Example 1.

The clonal populations of nucleic acids can be derived from nucleic acid fragments from a set of samples from two or more individuals. In these embodiments, the nucleic acid fragments comprise one of a series of molecular barcodes corresponding to a sample in the set of samples.

Detailed analytical methods are provided herein as SNV Methods 1 and SNV Method 2 in the analytical section herein. Any of the methods provided herein can further include analytical steps provided herein. Accordingly, in certain examples, the methods for determining whether a single nucleotide variant is present in the sample, includes identifying a confidence value for each allele determination at each of the set of single nucleotide variance loci, which can be based at least in part on a depth of read for the loci. The confidence limit can be set at least 75%, 80%, 85%, 90%, 95%, 96%, 96%, 98%, or 99%. The confidence limit can be set at different levels for different types of mutations.

The method can performed with a depth of read for the set of single nucleotide variance loci of at least 5, 10, 15, 20, 25, 50, 100, 150, 200, 250, 500, 1,000, 10,000, 25,000, 50,000, 100,000, 250,000, 500,000, or 1 million. FIG. 20 provides depth of read data for SNV loci successfully analyzed in Example 1.

In certain embodiments, a method of any of the embodiments herein includes determining an efficiency and/or an error rate per cycle are determined for each amplification reaction of the multiplex amplification reaction of the single nucleotide variance loci. The efficiency and the error rate can then be used to determine whether a single nucleotide variant at the set of single variant loci is present in the sample. More detailed analytical steps provided in SNV Method 2 provided in the analytical method can be included as well, in certain embodiments.

In illustrative embodiments, of any of the methods herein the set of single nucleotide variance loci includes all of the single nucleotide variance loci identified in the TCGA and COSMIC data sets for lung cancer, or for lung adenocarcinoma and/or especially lung squamous cell carcinoma.

In certain embodiments of any of the methods herein the set of single nucleotide variant loci include 2, 3, 4, 5, 6, 7, 8, 9, 10, 15, 20, 25, 30, 40, 50, 75, 100, 250, 500, 1000, 2500, 5000, or 10,000 single nucleotide variance loci known to be associated with lung cancer, lung ADC, and/or especially lung SCC on the low end of the range, and, 5, 6, 7, 8, 9, 10, 15, 20, 25, 30, 40, 50, 75, 100, 250, 500, 1000, 2500, 5000, 10,000, 20,000 and 25,000 on the high end of the range.

In any of the methods for detecting SNVs herein that include a ctDNA SNV amplification/sequencing workflow, improved amplification parameters for multiplex PCR can be employed. For example, wherein the amplification reaction is a PCR reaction and the annealing temperature is between 1, 2, 3, 4, 5, 6, 7, 8, 9, or 10° C. greater than the melting temperature on the low end of the range, and 2, 3, 4, 5, 6, 7, 8, 9, 10, 11, 12, 13, 14 or 15° on the high end the range for at least 10, 20, 25, 30, 40, 50, 06, 70, 75, 80, 90, 95 or 100% the primers of the set of primers.

In certain embodiments, wherein the amplification reaction is a PCR reaction the length of the annealing step in the PCR reaction is between 10, 15, 20, 30, 45, and 60 minutes on the low end of the range, and 15, 20, 30, 45, 60, 120, 180, or 240 minutes on the high end of the range. In certain embodiments, the primer concentration in the amplification, such as the PCR reaction is between 1 and 10 nM. Furthermore, in exemplary embodiments, the primers in the set of primers, are designed to minimize primer dimer formation.

Accordingly, in an example of any of the methods herein that include an amplification step, the amplification reaction is a PCR reaction, the annealing temperature is between 1 and 10° C. greater than the melting temperature of at least 90% of the primers of the set of primers, the length of the annealing step in the PCR reaction is between 15 and 60 minutes, the primer concentration in the amplification reaction is between 1 and 10 nM, and the primers in the set of primers, are designed to minimize primer dimer formation. In a further aspect of this example, the multiplex amplification reaction is performed under limiting primer conditions.

In another embodiment, provided herein is a method for supporting a lung cancer diagnosis for an individual, such as an individual suspected of having lung cancer, from a sample of blood or a fraction thereof from the individual, that includes performing a ctDNA SNV amplification/sequencing workflow as provided herein, to determine whether one or more single nucleotide variants are present in the plurality of single nucleotide variant loci. In this embodiment, the following elements, statements, guidelines or rules apply:

the absence of a single nucleotide variant supports a diagnosis of stage 1a, 1b, or 2a adenocarcinoma, the presence of a single nucleotide variant supports a diagnosis of squamous cell carcinoma or a stage 2b or 3a adenocarcinoma, and/or the presence of ten or more single nucleotide variants supports a diagnosis of squamous cell carcinoma or a stage 2b or 3 adenocarcinoma.

The above elements, statements, guidelines or rules are supported by the results of Example 1 (See e.g. the tabular data in FIG. 20). These results identify analysis using a ctDNA SNV amplification/sequencing workflow of lung ADC and SCC samples from an individual as a valuable method for identifying SNVs found in an ADC tumor, especially for stage 2b and 3a ADC tumors, and especially an SCC tumor at any stage (See e.g. FIG. 15 and FIG. 20).

In certain examples, this embodiment further includes determining the stage of a lung cancer lesion by a non-invasive method, For example, the size of a tumor can be determined by non-invasive methods.

In certain embodiments, methods herein for detecting SNVs can be used to direct a therapeutic regimen. Therapies are available and under development that target specific mutations associated with ADC and SCC (Nature Review Cancer. 14:535-551 (2014). For example, detection of an EGFR mutation at L858R or T790M can be informative for selecting a therapy. Erlotinib, gefitinib, afatinib, AZK9291, CO-1686, and HM61713 are current therapies approved in the U.S. or in clinical trials, that target specific EGFR mutations. In another example, a G12D, G12C, or G12V mutation in KRAS can be used to direct an individual to a therapy of a combination of Selumetinib plus docetaxel. As another example, a mutation of V600E in BRAF can be used to direct a subject to a treatment of Vemurafenib, dabrafenib, and trametinib.

A sample analyzed in methods of the present invention, in certain illustrative embodiments, is a blood sample, or a fraction thereof. Methods provided herein, in certain embodiments, are specially adapted for amplifying DNA fragments, especially tumor DNA fragments that are found in circulating tumor DNA (ctDNA). Such fragments are typically about 160 nucleotides in length.

It is known in the art that cell-free nucleic acid (cfNA), e.g cfDNA, can be released into the circulation via various forms of cell death such as apoptosis, necrosis, autophagy and necroptosis. The cfDNA, is fragmented and the size distribution of the fragments varies from 150-350 bp to >10000 bp. (see Kalnina et al. *World J Gastroenterol.* 2015 Nov. 7; 21(41): 11636-11653). For example the size distributions of plasma DNA fragments in hepatocellular carcinoma (HCC) patients spanned a range of 100-220 bp in length with a peak in count frequency at about 166 bp and the highest tumor DNA concentration in fragments of 150-180 bp in length (see: Jiang et al. *Proc Natl Acad Sci* USA 112:E1317-E1325).

In an illustrative embodiment the circulating tumor DNA (ctDNA) is isolated from blood using EDTA-2Na tube after removal of cellular debris and platelets by centrifugation. The plasma samples can be stored at −80° C. until the DNA is extracted using, for example, QIAamp DNA Mini Kit (Qiagen, Hilden, Germany), (e.g. Hamakawa et al., *Br J Cancer.* 2015; 112:352-356). Hamakava et al. reported median concentration of extracted cell free DNA of all samples 43.1 ng per ml plasma (range 9.5-1338 ng ml/) and a mutant fraction range of 0.001-77.8%, with a median of 0.90%.

In certain illustrative embodiments the sample is a tumor. Methods are known in the art for isolating nucleic acid from a tumor and for creating a nucleic acid library from such a DNA sample given the teachings here. Furthermore, given the teachings herein, a skilled artisan will recognize how to create a nucleic acid library appropriate for the methods herein from other samples such as other liquid samples where the DNA is free floating in addition to ctDNA samples.

Methods of the present invention in certain embodiments, typically include a step of generating and amplifying a nucleic acid library from the sample (i.e. library preparation). The nucleic acids from the sample during the library preparation step can have ligation adapters, often referred to as library tags or ligation adaptor tags (LTs), appended, where the ligation adapters contain a universal priming sequence, followed by a universal amplification. In an embodiment, this may be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors. In some embodiments, the adaptors may have tag designed for PCR amplification.

A number of the embodiments provided herein, include detecting the SNVs in a ctDNA sample. Such methods in illustrative embodiments, include an amplification step and a sequencing step (Sometimes referred to herein as a "ctDNA SNV amplification/sequencing workflow). In an illustrative example, a ctDNA amplification/sequencing workflow can include generating a set of amplicons by performing a multiplex amplification reaction on nucleic acids isolated from a sample of blood or a fraction thereof from an individual, such as an individual suspected of having a lung cancer, for example a squamous cell carcinoma, wherein each amplicon of the set of amplicons spans at least one single nucleotide variant loci of a set of single nucleotide variant loci, such as an SNV loci known to be associated with lung cancer; and determining the sequence of at least a segment of at each amplicon of the set of amplicons, wherein the segment comprises a single nucleotide variant loci. In this way, this exemplary method determines the single nucleotide variants present in the sample.

Exemplary ctDNA SNV amplification/sequencing workflows in more detail can include forming an amplification reaction mixture by combining a polymerase, nucleotide triphosphates, nucleic acid fragments from a nucleic acid library generated from the sample, and a set of primers that each binds an effective distance from a single nucleotide variant loci, or a set of primer pairs that each span an effective region that includes a single nucleotide variant loci. The single nucleotide variant loci, in exemplary embodiments, is one known to be associated with lung cancer, for example lung adenocarcinoma and/or in especially illustrative embodiments squamous cell carcinoma. Then, subjecting the amplification reaction mixture to amplification conditions to generate a set of amplicons comprising at least one single nucleotide variant loci of a set of single nucleotide variant loci, preferably known to be associated with lung cancer; and determining the sequence of at least a segment of each amplicon of the set of amplicons, wherein the segment comprises a single nucleotide variant loci.

The effective distance of binding of the primers can be within 1, 2, 3, 4, 5, 6, 7, 8, 9, 10, 11, 12, 13, 14, 15, 20, 25, 30, 35, 40, 45, 50, 75, 100, 125, or 150 base pairs of a SNV loci. The effective range that a pair of primers spans typically includes an SNV and is typically 160 base pairs or less, and can be 150, 140, 130, 125, 100, 75, 50 or 25 base pairs or less. In other embodiments, the effective range that a pair of primers spans is 20, 25, 30, 40, 50, 60, 70, 75, 100, 110, 120, 125, 130, 140, or 150 nucleotides from an SNV loci on the low end of the range, and 25, 30, 40, 50, 60, 70, 75, 100, 110, 120, 125, 130, 140, or 150, 160, 170, 175, or 200 on the high end of the range.

Further details regarding methods of amplification that can be used in a ctDNA SNV amplification/sequencing workflow to detect SNVs for use in methods of the invention are provided in other sections of this specification.

SNV Calling Analytics

During performance of the methods provided herein, nucleic acid sequencing data is generated for amplicons created by the tiled multiplex PCR. Algorithm design tools are available that can be used and/or adapted to analyze this data to determine within certain confidence limits, whether a mutation, such as a SNV is present in a target gene, as illustrated in Example 1 herein.

Sequencing Reads can be demultiplexed using an in-house tool and mapped using the Burrows-Wheeler alignment software, Bwa mem function (BWA, Burrows-Wheeler Alignment Software (see Li H. and Durbin R. (2010) Fast and accurate long-read alignment with Burrows-Wheeler Transform. Bioinformatics, Epub. [PMID: 20080505]) on single end mode using pear merged reads to the hg19 genome. Amplification statistics QC can be performed by analyzing total reads, number of mapped reads, number of mapped reads on target, and number of reads counted.

In certain embodiments, any analytical method for detecting an SNV from nucleic acid sequencing data detection can be used with methods of the invention methods of the invention that include a step of detecting an SNV or determining whether an SNV is present. In certain illustrative embodiments, methods of the invention that utilize SNV METHOD 1 below are used. In other, even more illustrative embodiments, methods of the invention that include a step of detecting an SNV or determining whether an SNV is present at an SNV loci, utilize SNV METHOD 2 below.

SNV Method 1:

For this embodiment, a background error model is constructed using normal plasma samples, which were sequenced on the same sequencing run to account for run-specific artifacts. In certain embodiments, 5, 10, 15, 20, 25, 30, 40, 50, 100, 150, 200, 250, or more than 250 normal plasma samples are analyzed on the same sequencing run. In certain illustrative embodiments, 20, 25, 40, or 50 normal plasma samples are analyzed on the same sequencing run. Noisy positions with normal median variant allele frequency greater than a cutoff are removed. For example this cutoff in certain embodiments is >0.1%, 0.2%, 0.25%, 0.5%, 1%, 2%, 5%, or 10%. In certain illustrative embodiments noisy positions with normal medial variant allele frequency greater than 0.5% are removed. Outlier samples were iteratively removed from the model to account for noise and contamination. In certain embodiments, samples with a Z score of greater than 5, 6, 7, 8, 9, or 10 are removed from the data analysis. For each base substitution of every genomic loci, the depth of read weighted mean and standard deviation of the error are calculated. Tumor or cell-free plasma samples' positions with at least 5 variant reads and a Z-score of 10 against the background error model for example, can be called as a candidate mutation.

SNV Method 2:

For this embodiment Single Nucleotide Variants (SNVs) are determined using plasma ctDNA data. The PCR process is modeled as a stochastic process, estimating the parameters using a training set and making the final SNV calls for a separate testing set. The propagation of the error across multiple PCR cycles is determined, and the mean and the variance of the background error are calculated, and in illustrative embodiments, background error is differentiated from real mutations.

The following parameters are estimated for each base:
p=efficiency (probability that each read is replicated in each cycle)
$p_e$=error rate per cycle for mutation type e (probability that an error of type e occurs)
$X_0$=initial number of molecules As a read is replicated over the course of PCR process, the more errors occur. Hence, the error profile of the reads is determined by the degrees of separation from the original read. We refer to a read as $k^{th}$ generation if it has gone through k replications until it has been generated.

Let us define the following variables for each base:

$X_{ij}$=number of generation i reads generated in the PCR cycle j $Y_{ij}$=total number of generation i reads at the end of cycle j $X_{ij}^e$=number of generation i reads with mutation e generated in the PCR cycle j Moreover, in addition to normal molecules $X_0$, if there are additional $f_e X_0$ molecules with the mutation e at the beginning of the PCR process (hence $f_e/(1+fe)$ will be the fraction of mutated molecules in the initial mixture).

Given the total number of generation i−1 reads at cycle j−1, the number of generation i reads generated at cycle j has a binomial distribution with a sample size of and probability parameter of p. Hence, $E(X_{ij}, |Y_{i-1,j-1}, p)=p\ Y_{i-1,j-1}$ and $Var(X_{ij}, |Y_{i-1,j-1}, p)=p(1-p)\ Y_{i-1,j-1}$.

We also have $Y_{ij}=\Sigma_{k=i}^{j} X_{ik}$. Hence, by recursion, simulation or similar methods, we can determine $E(X_{ij})$. Similarly, we can determine $Var(X_{ij})=E(Var(X_{ij}, |\ p))+Var(E(X_{ij}, |\ p))$ using the distribution of p.

finally, $E(X_{ij}^e|Y_{i-1,j-1}, p_e)=p_e\ Y_{i-1,j-1}$ and $Var(X_{ij}^e|Y_{i-1,j-1}, p)=p_e(1-p_e)\ Y_{i-1,j-1}$, and we can use these to compute $E(X_{ij}^e)$ and $Var(X_{ij}^e)$.

In certain embodiments, SNV Method 2 is performed as follows:
a) Estimate a PCR efficiency and a per cycle error rate using a training data set;
b) Estimate a number of starting molecules for the testing data set at each base using the distribution of the efficiency estimated in step (a);
c) If needed, update the estimate of the efficiency for the testing data set using the starting number of molecules estimated in step (b);
d) Estimate the mean and variance for the total number of molecules, background error molecules and real mutation molecules (for a search space consisting of an initial percentage of real mutation molecules) using testing set data and parameters estimated in steps (a), (b) and (c);
e) Fit a distribution to the number of total error molecules (background error and real mutation) in the total molecules, and calculate the likelihood for each real mutation percentage in the search space; and
f) Determine the most likely real mutation percentage and calculate the confidence using the data from in step (e).

A confidence cutoff can be used to identify an SNV at an SNV loci. For example, a 90%, 95%, 96%, 97%, 98%, or 99% confidence cutoff can be used to call an SNV.

Exemplary SNV METHOD 2 Algorithm

The algorithm starts by estimating the efficiency and error rate per cycle using the training set. Let n denote the total number of PCR cycles.

The number of reads $R_b$ at each base b can be approximated by $(1+p_b)^n X_0$, where $p_b$ is the efficiency at base b. Then $(R_b/X_0)^{1/n}$ can be used to approximate $1+p_b$. Then, we can determine the mean and the standard variation of $p_b$ across all training samples, to estimate the parameters of the probability distribution (such as normal, beta, or similar distributions) for each base.

Similarly the number of error e reads $R_b^e$ at each base b can be used to estimate $p_e$. After determining the mean and the standard deviation of the error rate across all training samples, we approximate its probability distribution (such as normal, beta, or similar distributions) whose parameters are estimated using this mean and standard deviation values.

Next, for the testing data, we estimate the initial starting copy at each base as $$\int_0^1 \frac{R_b}{(1+p_b)^n} f(p_b) dp_b$$

where f(·) is an estimated distribution from the training set.

$$\int_0^1 \frac{R_b}{(1+p_b)^n} f(p_b) dp_b$$

where f(·) is an estimated distribution from the training set.

Hence, we have estimated the parameters that will be used in the stochastic process. Then, by using these estimates, we can estimate the mean and the variance of the molecules created at each cycle (note that we do this separately for normal molecules, error molecules, and mutation molecules).

Finally, by using a probabilistic method (such as maximum likelihood or similar methods), we can determine the best $f_e$ value that fits the distribution of the error, mutation, and normal molecules the best. More specifically, we estimate the expected ratio of the error molecules to total molecules for various $f_e$ values in the final reads, and determine the likelihood of our data for each of these values, and then select the value with the highest likelihood.

Primer tails can improve the detection of fragmented DNA from universally tagged libraries. If the library tag and the primer-tails contain a homologous sequence, hybridization can be improved (for example, melting temperature (Tm) is lowered) and primers can be extended if only a portion of the primer target sequence is in the sample DNA fragment. In some embodiments, 13 or more target specific base pairs may be used. In some embodiments, 10 to 12 target specific base pairs may be used. In some embodiments, 8 to 9 target specific base pairs may be used. In some embodiments, 6 to 7 target specific base pairs may be used.

In one embodiment, Libraries are generated from the samples above by ligating adaptors to the ends of DNA fragments in the samples, or to the ends of DNA fragments generated from DNA isolated from the samples. The fragments can then be amplified using PCR, for example, according to the following exemplary protocol:

95° C., 2 min; 15×[95° C., 20 sec, 55° C., 20 sec, 68° C., 20 sec], 68° C. 2 min, 4° C. hold.

Many kits and methods are known in the art for generation of libraries of nucleic acids that include universal primer binding sites for subsequent amplification, for example clonal amplification, and for subsequence sequencing. To help facilitate ligation of adapters library preparation and amplification can include end repair and adenylation (i.e. A-tailing). Kits especially adapted for preparing libraries from small nucleic acid fragments, especially circulating free DNA, can be useful for practicing methods provided herein. For example, the NEXTflex Cell Free kits available from Bioo Scientific ( ) or the Natera Library Prep Kit (available from Natera, Inc. San Carlos, CA). However, such kits would typically be modified to include adaptors that are customized for the amplification and sequencing steps of the methods provided herein. Adaptor ligation can be performed using commercially available kits such as the ligation kit found in the AGILENT SURESELECT kit (Agilent, CA).

Target regions of the nucleic acid library generated from DNA isolated from the sample, especially a circulating free DNA sample for the methods of the present invention, are then amplified. For this amplification, a series of primers or primer pairs, which can include between 5, 10, 15, 20, 25, 50, 100, 125, 150, 250, 500, 1000, 2500, 5000, 10,000, 20,000, 25,000, or 50,000 on the low end of the range and 15, 20, 25, 50, 100, 125, 150, 250, 500, 1000, 2500, 5000, 10,000, 20,000, 25,000, 50,000, 60,000, 75,000, or 100,000 primers on the upper end of the range, that each bind to one of a series of primer binding sites.

Primer designs can be generated with Primer3 (Untergrasser A, Cutcutache I, Koressaar T, Ye J, Faircloth B C, Remm M, Rozen S G (2012) "Primer3—new capabilities and interfaces." Nucleic Acids Research 40(15):e115 and Koressaar T, Remm M (2007) "Enhancements and modifications of primer design program Primer3." Bioinformatics 23(10):1289-91) source code available at primer3.sourceforge.net). Primer specificity can be evaluated by BLAST and added to existing primer design pipeline criteria:

Primer specificities can be determined using the BLASTn program from the ncbi-blast-2.2.29+package. The task option "blastn-short" can be used to map the primers against hg19 human genome. Primer designs can be determined as "specific" if the primer has less than 100 hits to the genome and the top hit is the target complementary primer binding region of the genome and is at least two scores higher than other hits (score is defined by BLASTn program). This can be done in order to have a unique hit to the genome and to not have many other hits throughout the genome.

The final selected primers can be visualized in IGV (James T. Robinson, Helga Thorvaldsdóttir, Wendy Winckler, Mitchell Guttman, Eric S. Lander, Gad Getz, Jill P. Mesirov. Integrative Genomics Viewer. Nature Biotechnology 29, 24-26 (2011)) and UCSC browser (Kent W J, Sugnet C W, Furey T S, Roskin K M, Pringle T H, Zahler A M, Haussler D. The human genome browser at UCSC. Genome Res. 2002 June; 12(6):996-1006) using bed files and coverage maps for validation.

Methods of the present invention, in certain embodiments, include forming an amplification reaction mixture. The reaction mixture typically is formed by combining a polymerase, nucleotide triphosphates, nucleic acid fragments from a nucleic acid library generated from the sample, a set of forward and reverse primers specific for target regions that contain SNVs. The reaction mixtures provided herein, themselves forming in illustrative embodiments, a separate aspect of the invention.

An amplification reaction mixture useful for the present invention includes components known in the art for nucleic acid amplification, especially for PCR amplification. For example, the reaction mixture typically includes nucleotide triphosphates, a polymerase, and magnesium. Polymerases that are useful for the present invention can include any polymerase that can be used in an amplification reaction especially those that are useful in PCR reactions. In certain embodiments, hot start Taq polymerases are especially useful. Amplification reaction mixtures useful for practicing the methods provided herein, such as AmpliTaq Gold master mix (Life Technologies, Carlsbad, CA), are available commercially.

Amplification (e.g. temperature cycling) conditions for PCR are well known in the art. The methods provided herein can include any PCR cycling conditions that result in amplification of target nucleic acids such as target nucleic acids from a library. Non-limiting exemplary cycling conditions are provided in the Examples section herein.

There are many workflows that are possible when conducting PCR; some workflows typical to the methods disclosed herein are provided herein. The steps outlined herein are not meant to exclude other possible steps nor does it imply that any of the steps described herein are required for the method to work properly. A large number of parameter variations or other modifications are known in the literature, and may be made without affecting the essence of the invention.

In certain embodiments of the method provided herein, at least a portion and in illustrative examples the entire sequence of an amplicon, such as an outer primer target amplicon, is determined. Methods for determining the sequence of an amplicon are known in the art. Any of the sequencing methods known in the art, e.g. Sanger sequencing, can be used for such sequence determination. In illustrative embodiments high throughput next-generation sequencing techniques (also referred to herein as massively parallel sequencing techniques) such as, but not limited to, those employed in MYSEQ (ILLUMINA), HISEQ (ILLUMINA), ION TORRENT (LIFE TECHNOLOGIES), GENOME ANALYZER ILX (ILLUMINA), GS FLEX+ (ROCHE 454), can be used for sequencing the amplicons produced by the methods provided herein.

High throughput genetic sequencers are amenable to the use of barcoding (i.e., sample tagging with distinctive nucleic acid sequences) so as to identify specific samples from individuals thereby permitting the simultaneous analysis of multiple samples in a single run of the DNA sequencer. The number of times a given region of the genome in a library preparation (or other nucleic preparation of interest) is sequenced (number of reads) will be proportional to the number of copies of that sequence in the genome of interest (or expression level in the case of cDNA containing preparations). Biases in amplification efficiency can be taken into account in such quantitative determination.

Target Genes

Target genes of the present invention in exemplary embodiments, are cancer-related genes, and in many illustrative embodiments, lung cancer-related genes. A cancer-related gene (for example, a lung cancer-related gene or a lung SCC-related gene or a lung ADC-related gene) refers to a gene associated with an altered risk for a cancer (e.g. lung cancer or lung SCC or lung ADC, respectively) or an altered prognosis for a cancer. Exemplary cancer-related genes that promote cancer include oncogenes; genes that enhance cell proliferation, invasion, or metastasis; genes that inhibit apoptosis; and pro-angiogenesis genes. Cancer-related genes that inhibit cancer include, but are not limited to, tumor suppressor genes; genes that inhibit cell proliferation, invasion, or metastasis; genes that promote apoptosis; and anti-angiogenesis genes.

An embodiment of the mutation detection method begins with the selection of the region of the gene that becomes the target. The region with known mutations is used to develop primers for mPCR-NGS to amplify and detect the mutation.

Methods provided herein can be used to detect virtually any type of mutation, especially mutations known to be associated with cancer and most particularly the methods provided herein are directed to mutations, especially SNVs, associated with lung cancer, specifically adenocarcinoma and squamous cell carcinoma. Exemplary SNVs can be in one or more of the following genes: EGFR, FGFR1, FGFR2, ALK, MET, ROS1, NTRK1, RET, HER2, DDR2, PDGFRA, KRAS, NF1, BRAF, PIK3CA, MEK1, NOTCH1, MLL2, EZH2, TET2, DNMT3A, SOX2, MYC, KEAP1, CDKN2A, NRG1, TP53, LKB1, and PTEN, which have been identified in various lung cancer samples as being mutated, having increased copy numbers, or being fused to other genes and combinations thereof (Non-small-cell lung cancers: a heterogeneous set of diseases. Chen et al. Nat. Rev. Cancer. 2014 Aug. 14 (8): 535-551). In another example, the list of genes includes those listed above, where SNVs have been reported, such as in the cited Chen et al. reference. In another embodiment, the SNVs can include SNVs found in one of the genes found in FIG. 19 herein. SNVs in the genes listed in FIG. 19 were analyzed in the experiment of Example 1. SNVs in these genes were detected in tumor samples matched to the ctDNA samples of Example 1. In some embodiments. SNVs that are analyzed in methods provided berein can include any of the genes listed in this paragraph above or any of the genes in FIG. 19 that are not listed above. Provided herein, are methods that use the specific determination of a particular SNV in a particular gene to direct a targeted drug therapy.

Amplification (e.g. PCR) Reaction Mixtures:

Methods of the present invention, in certain embodiments, include forming an amplification reaction mixture. The reaction mixture typically is formed by combining a polymerase, nucleotide triphosphates, nucleic acid fragments from a nucleic acid library generated from the sample, a series of forward target-specific outer primers and a first strand reverse outer universal primer. Another illustrative embodiment is a reaction mixture that includes forward target-specific inner primers instead of the forward target-specific outer primers and amplicons from a first PCR reaction using the outer primers, instead of nucleic acid fragments from the nucleic acid library. The reaction mixtures provided herein, themselves forming in illustrative embodiments, a separate aspect of the invention. In illustrative embodiments, the reaction mixtures are PCR reaction mixtures. PCR reaction mixtures typically include magnesium.

In some embodiments, the reaction mixture includes ethylenediaminetetraacetic acid (EDTA), magnesium, tetramethyl ammonium chloride (TMAC), or any combination thereof. In some embodiments, the concentration of TMAC is between 20 and 70 mM, inclusive. While not meant to be bound to any particular theory, it is believed that TMAC binds to DNA, stabilizes duplexes, increases primer specificity, and/or equalizes the melting temperatures of different primers. In some embodiments, TMAC increases the uniformity in the amount of amplified products for the different targets. In some embodiments, the concentration of magnesium (such as magnesium from magnesium chloride) is between 1 and 8 mM.

The large number of primers used for multiplex PCR of a large number of targets may chelate a lot of the magnesium (2 phosphates in the primers chelate 1 magnesium). For example, if enough primers are used such that the concentration of phosphate from the primers is ~9 mM, then the primers may reduce the effective magnesium concentration by ~4.5 mM. In some embodiments, EDTA is used to decrease the amount of magnesium available as a cofactor for the polymerase since high concentrations of magnesium can result in PCR errors, such as amplification of non-target loci. In some embodiments, the concentration of EDTA reduces the amount of available magnesium to between 1 and 5 mM (such as between 3 and 5 mM).

In some embodiments, the pH is between 7.5 and 8.5, such as between 7.5 and 8, 8 and 8.3, or 8.3 and 8.5, inclusive. In some embodiments, Tris is used at, for example, a concentration of between 10 and 100 mM, such as between 10 and 25 mM, 25 and 50 mM, 50 and 75 mM, or 25 and 75 mM, inclusive. In some embodiments, any of these concentrations of Tris are used at a pH between 7.5 and 8.5. In some embodiments, a combination of KCl and $(NH_4)_2SO_4$ is used, such as between 50 and 150 mM KCl and between 10 and 90 mM $(NH_4)_2SO_4$, inclusive. In some embodiments, the concentration of KCl is between 0 and 30 mM, between 50 and 100 mM, or between 100 and 150 mM, inclusive. In some embodiments, the concentration of $(NH_4)_2SO_4$ is between 10 and 50 mM, 50 and 90 mM, 10 and 20 mM, 20 and 40 mM, 40 and 60 mM, or 60 and 80 mM $(NH_4)_2SO_4$, inclusive. In some embodiments, the ammonium $[NH_4^+]$ concentration is between 0 and 160 mM, such as between 0 to 50, 50 to 100, or 100 to 160 mM, inclusive. In some embodiments, the sum of the potassium and ammonium concentration ($[K^+]+[NH_4^+]$) is between 0 and 160 mM, such as between 0 to 25, 25 to 50, 50 to 150, 50 to 75, 75 to 100, 100 to 125, or 125 to 160 mM, inclusive. An exemplary buffer with $[K^+]+[NH_4^+]=120$ mM is 20 mM KCl and 50 mM $(NH_4)_2SO_4$. In some embodiments, the buffer includes 25 to 75 mM Tris, pH 7.2 to 8, 0 to 50 mM KCl, 10 to 80 mM ammonium sulfate, and 3 to 6 mM magnesium, inclusive. In some embodiments, the buffer includes 25 to 75 mM Tris pH 7 to 8.5, 3 to 6 mM $MgCl_2$, 10 to 50 mM KCl, and 20 to 80 mM $(NH_4)_2SO_4$, inclusive. In some embodiments, 100 to 200 Units/mL of polymerase are used. In some embodiments, 100 mM KCl, 50 mM $(NH_4)_2SO_4$, 3 mM $MgCl_2$, 7.5 nM of each primer in the library, 50 mM TMAC, and 7 ul DNA template in a 20 ul final volume at pH 8.1 is used.

In some embodiments, a crowding agent is used, such as polyethylene glycol (PEG, such as PEG 8,000) or glycerol. In some embodiments, the amount of PEG (such as PEG 8,000) is between 0.1 to 20%, such as between 0.5 to 15%, 1 to 10%, 2 to 8%, or 4 to 8%, inclusive. In some embodiments, the amount of glycerol is between 0.1 to 20%, such as between 0.5 to 15%, 1 to 10%, 2 to 8%, or 4 to 8%, inclusive. In some embodiments, a crowding agent allows either a low polymerase concentration and/or a shorter annealing time to be used. In some embodiments, a crowding agent improves the uniformity of the DOR and/or reduces dropouts (undetected alleles). Polymerases In some embodiments, a polymerase with proof-reading activity, a polymerase without (or with negligible) proof-reading activity, or a mixture of a polymerase with proof-reading activity and a polymerase without (or with negligible) proof-reading activity is used. In some embodiments, a hot start polymerase, a non-hot start polymerase, or a mixture of a hot start polymerase and a non-hot start polymerase is used. In some embodiments, a HotStarTaq DNA polymerase is used (see, for example, QIAGEN catalog No. 203203). In some embodiments, AmpliTaq Gold® DNA Polymerase is used. In some embodiments a PrimeSTAR GXL DNA polymerase, a high fidelity polymerase that provides efficient PCR amplification when there is excess template in the reaction mixture, and when amplifying long products, is used (Takara Clontech, Mountain View, CA). In some embodiments, KAPA Taq DNA Polymerase or KAPA Taq HotStart DNA Polymerase is used; they are based on the single-subunit, wild-type Taq DNA polymerase of the thermophilic bacterium *Thermus aquaticus*. KAPA Taq and KAPA Taq HotStart DNA Polymerase have 5'-3' polymerase and 5'-3' exonuclease activities, but no 3' to 5' exonuclease (proofreading) activity (see, for example, KAPA BIOSYSTEMS catalog No. BK1000). In some embodiments, Pfu DNA polymerase is used; it is a highly thermostable DNA polymerase from the hyperthermophilic archaeum *Pyrococcus furiosus*. The enzyme catalyzes the template-dependent polymerization of nucleotides into duplex DNA in the 5'→3' direction. Pfu DNA Polymerase also exhibits 3'→5' exonuclease (proofreading) activity that enables the polymerase to correct nucleotide incorporation errors. It has no 5'→3' exonuclease activity (see, for example, Thermo Scientific catalog No. EP0501). In some embodiments Klentaq1 is used; it is a Klenow-fragment analog of Taq DNA polymerase, it has no exonuclease or endonuclease activity (see, for example, DNA POLYMERASE TECHNOLOGY, Inc, St. Louis, Missouri, catalog No. 100). In some embodiments, the polymerase is a PHUSION DNA polymerase, such as PHUSION High Fidelity DNA polymerase (M0530S, New England BioLabs, Inc.) or PHUSION Hot Start Flex DNA polymerase (M0535S, New England BioLabs, Inc.). In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). In some embodiments, the polymerase is a T4 DNA polymerase (M0203S, New England BioLabs, Inc.).

In some embodiment, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive.

PCR Methods

In some embodiments, hot-start PCR is used to reduce or prevent polymerization prior to PCR thermocycling. Exemplary hot-start PCR methods include initial inhibition of the DNA polymerase, or physical separation of reaction components reaction until the reaction mixture reaches the higher temperatures. In some embodiments, slow release of magnesium is used. DNA polymerase requires magnesium ions for activity, so the magnesium is chemically separated from the reaction by binding to a chemical compound, and is released into the solution only at high temperature. In some embodiments, non-covalent binding of an inhibitor is used. In this method a peptide, antibody, or aptamer are non-covalently bound to the enzyme at low temperature and inhibit its activity. After incubation at elevated temperature, the inhibitor is released and the reaction starts. In some embodiments, a cold-sensitive Taq polymerase is used, such as a modified DNA polymerase with almost no activity at low temperature. In some embodiments, chemical modification is used. In this method, a molecule is covalently bound to the side chain of an amino acid in the active site of the DNA polymerase. The molecule is released from the enzyme by incubation of the reaction mixture at elevated temperature. Once the molecule is released, the enzyme is activated.

In some embodiments, the amount to template nucleic acids (such as an RNA or DNA sample) is between 20 and 5,000 ng, such as between 20 to 200, 200 to 400, 400 to 600, 600 to 1,000; 1,000 to 1,500; or 2,000 to 3,000 ng, inclusive.

In some embodiments a QIAGEN Multiplex PCR Kit is used (QIAGEN catalog No. 206143). For 100×50 µl multiplex PCR reactions, the kit includes 2×QIAGEN Multiplex PCR Master Mix (providing a final concentration of 3 mM $MgCl_2$, 3×0.85 ml), 5×Q-Solution (1×2.0 ml), and RNase-Free Water (2×1.7 ml). The QIAGEN Multiplex PCR Master Mix (MM) contains a combination of KCl and $(NH_4)_2SO_4$ as well as the PCR additive, Factor MP, which increases the local concentration of primers at the template. Factor MP stabilizes specifically bound primers, allowing efficient primer extension by HotStarTaq DNA Polymerase. HotStarTaq DNA Polymerase is a modified form of Taq DNA polymerase and has no polymerase activity at ambient temperatures. In some embodiments, HotStarTaq DNA Polymerase is activated by a 15-minute incubation at 95° C. which can be incorporated into any existing thermal-cycler program.

In some embodiments, 1×QIAGEN MM final concentration (the recommended concentration), 7.5 nM of each primer in the library, 50 mM TMAC, and 7 ul DNA template in a 20 ul final volume is used. In some embodiments, the PCR thermocycling conditions include 95° C. for 10 minutes (hot start); 20 cycles of 96° C. for 30 seconds; 65° C. for 15 minutes; and 72° C. for 30 seconds; followed by 72° C. for 2 minutes (final extension); and then a 4° C. hold.

In some embodiments, 2×QIAGEN MM final concentration (twice the recommended concentration), 2 nM of each primer in the library, 70 mM TMAC, and 7 ul DNA template in a 20 ul total volume is used. In some embodiments, up to 4 mM EDTA is also included. In some embodiments, the PCR thermocycling conditions include 95° C. for 10 minutes (hot start); 25 cycles of 96° C. for 30 seconds; 65° C. for 20, 25, 30, 45, 60, 120, or 180 minutes; and optionally 72° C. for 30 seconds); followed by 72° C. for 2 minutes (final extension); and then a 4° C. hold.

Another exemplary set of conditions includes a semi-nested PCR approach. The first PCR reaction uses 20 ul a reaction volume with 2×QIAGEN MM final concentration, 1.875 nM of each primer in the library (outer forward and reverse primers), and DNA template. Thermocycling parameters include 95° C. for 10 minutes; 25 cycles of 96° C. for 30 seconds, 65° C. for 1 minute, 58° C. for 6 minutes, 60° C. for 8 minutes, 65° C. for 4 minutes, and 72° C. for 30 seconds; and then 72° C. for 2 minutes, and then a 4° C. hold. Next, 2 ul of the resulting product, diluted 1:200, is used as input in a second PCR reaction. This reaction uses a 10 ul reaction volume with 1×QIAGEN MM final concentration, 20 nM of each inner forward primer, and 1 uM of reverse primer tag. Thermocycling parameters include 95° C. for 10 minutes; 15 cycles of 95° C. for 30 seconds, 65° C. for 1 minute, 60° C. for 5 minutes, 65° C. for 5 minutes, and 72° C. for 30 seconds; and then 72° C. for 2 minutes, and then a 4° C. hold. The annealing temperature can optionally be higher than the melting temperatures of some or all of the primers, as discussed herein (see U.S. patent application Ser. No. 14/918,544, filed Oct. 20, 2015, which is herein incorporated by reference in its entirety).

The melting temperature ($T_m$) is the temperature at which one-half (50%) of a DNA duplex of an oligonucleotide (such as a primer) and its perfect complement dissociates and becomes single strand DNA. The annealing temperature (TA) is the temperature one runs the PCR protocol at. For prior methods, it is usually 5° C. below the lowest $T_m$ of the primers used, thus close to all possible duplexes are formed (such that essentially all the primer molecules bind the template nucleic acid). While this is highly efficient, at lower temperatures there are more unspecific reactions bound to occur. One consequence of having too low a TA is that primers may anneal to sequences other than the true target, as internal single-base mismatches or partial annealing may be tolerated. In some embodiments of the present inventions, the TA is higher than $T_m$, where at a given moment only a small fraction of the targets have a primer annealed (such as only ~1-5%). If these get extended, they are removed from the equilibrium of annealing and dissociating primers and target (as extension increases $T_m$ quickly to above 70° C.), and a new ~1-5% of targets has primers. Thus, by giving the reaction a long time for annealing, one can get ~100% of the targets copied per cycle.

In various embodiments, the annealing temperature is between 1, 2, 3, 4, 5, 6, 7, 8, 9, 10, 11, 12, 13° C. and 2, 3, 4, 5, 6, 7, 8, 9, 10, 11, 12, 13, or 15° C. on the high end of the range, greater than the melting temperature (such as the empirically measured or calculated $T_m$) of at least 25, 50, 60, 70, 75, 80, 90, 95, or 100% of the non-identical primers. In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1 to 10, 1 to 5, 1 to 3, 3 to 5, 3 to 8, 5 to 10, 5 to 8, 8 to 10, 10 to 12, or 12 to 15° C., inclusive) greater than the melting temperature (such as the empirically measured or calculated $T_m$) of at least 25%, 50%, 60%, 70%, 75%, 80%, 90%, 95%, or all of the non-identical primers, and the length of the annealing step (per PCR cycle) is between 5 and 180 minutes, such as 15 and 120 minutes, 15 and 60 minutes, 15 and 45 minutes, or 20 and 60 minutes, inclusive.

Exemplary Multiplex PCR Methods

In various embodiments, long annealing times (as discussed herein and exemplified in Example 12) and/or low primer concentrations are used. In fact, in certain embodiments, limiting primer concentrations and/or conditions are used. In various embodiments, the length of the annealing step is between 15, 20, 25, 30, 35, 40, 45, or 60 minutes on the low end of the range and 20, 25, 30, 35, 40, 45, 60, 120, or 180 minutes on the high end of the range. In various embodiments, the length of the annealing step (per PCR cycle) is between 30 and 180 minutes. For example, the annealing step can be between 30 and 60 minutes and the concentration of each primer can be less than 20, 15, 10, or 5 nM. In other embodiments the primer concentration is 1, 2, 3, 4, 5, 6, 7, 8, 9, 10, 15, 20, or 25 nM on the low end of the range, and 2, 3, 4, 5, 6, 7, 8, 9, 10, 15, 20, 25, and 50 on the high end of the range.

At high level of multiplexing, the solution may become viscous due to the large amount of primers in solution. If the solution is too viscous, one can reduce the primer concentration to an amount that is still sufficient for the primers to bind the template DNA. In various embodiments, between 1,000 and 100,000 different primers are used and the concentration of each primer is less than 20 nM, such as less than 10 nM or between 1 and 10 nM, inclusive.

The following examples are put forth so as to provide those of ordinary skill in the art with a complete disclosure and description of how to use the embodiments provided herein, and are not intended to limit the scope of the disclosure nor are they intended to represent that the Examples below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

EXAMPLES

Figure 1:
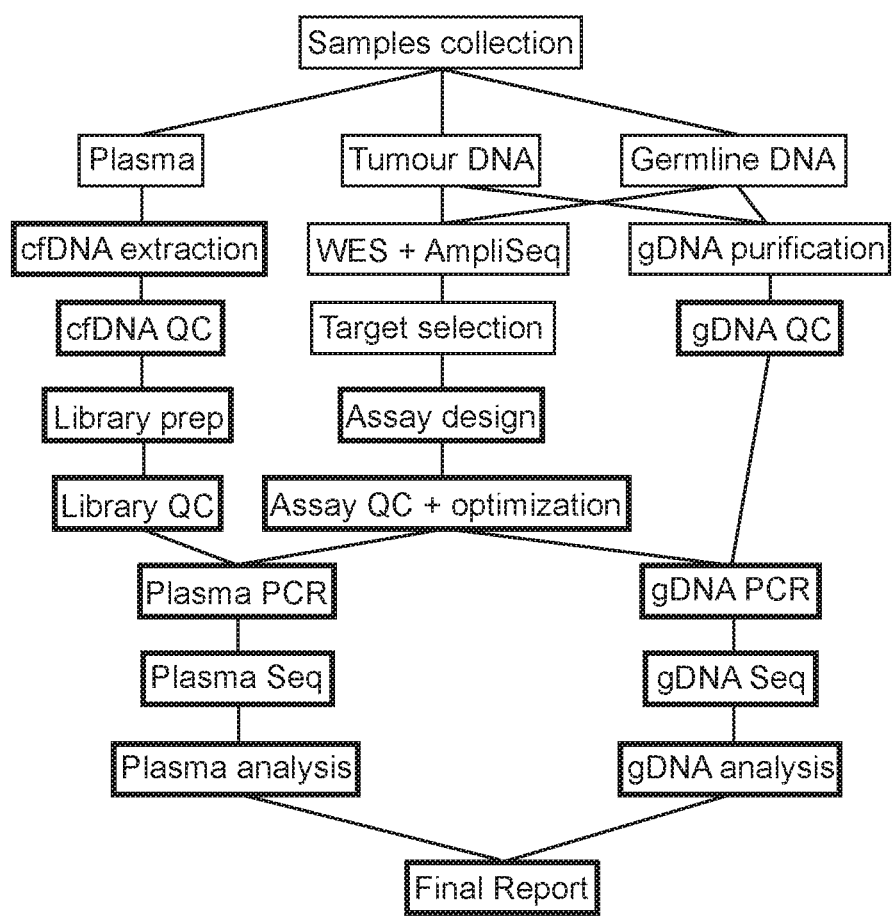
FIG. 1 is a workflow Diagram.

Example 1. Analysis of Single Nucleotide Variants (SNVs) in Circulating Tumor DNA (ctDNA) from Lung Cancer Patients A prior pilot study demonstrated the successful detection of cancer-relevant point mutations in the plasma of cancer patients. In that study, the mutation profile of 4 lung cancer tumors was determined by whole exome sequencing (WES) or Ampliseq (Life Technologies, Carlsbad, CA), and a subset of those mutations were successfully detected in the corresponding plasma samples using a multiplex PCR-Next-Generation Sequencing (mPCR-NGS) method. In this experiment, called TRACERx, the mPCR-NGS method was used to detect and track over time cancer-specific mutations in the plasma of cancer patients, and to evaluate the utility of the method in monitoring disease progression through treatment. The overall project design is shown in FIG. 1. The first phase of the project was the determination of the baseline mutation profile in the plasma of 50 treatment-naïve lung cancer patients. Purified genomic DNA samples from several tumor regions (2-7 regions per tumor), purified germline DNA samples, and intact plasma samples from 50 patients were obtained. The mutation profile of all of the tumor regions was previously determined by WES and AmpliSeq, and a subset of mutations per patient was analyzed by mPCR-NGS. Those mutations included both driver and passenger mutations and both clonal and sub-clonal mutations. Based on these data, we designed multiplex PCR assays, prepared primer pools (primers were obtained from IDT, Coralville, Iowa), QC'ed the primer pools, and optimized the mPCR protocol for each pool. Plasma cfDNA was purified, quantified, and converted into libraries. The libraries were then used as input into mPCR, and the products were sequenced and analyzed. A similar protocol was applied to the genomic DNA from tumor and matched normal samples.

Samples Description

Samples.

For each of the first 50 TRACERx patients, 4-5 ml of plasma obtained before tumor resection and prior to any therapy was isolated. Plasma samples were aliquoted in 2 ml tubes and shipped frozen on dry ice. Purified genomic DNA from up to 7 tumor subsections, from affected lymph nodes (where available), and from the white blood cell fraction (referred to as the matched normal) were purified and 500 ng purified DNA from each sample, normalized at 10 ng/µl, was analyzed. The purified DNA samples were frozen and shipped on dry ice.

SNV Information.

The mutation profile, including single nucleotide variants (SNVs) and copy number variants (CNVs), of each tumor subsection was determined by TRACERx using WES. The full mutation profile of each tumor was used to detect clonal structure and to reconstruct the phylogenetic tree of each tumor. PyClone (PyClone: statistical inference of clonal population structure in cancer. Roth et al, Nature Methods 11, 396-398 (2014)) was used to detect clonal structure. PyClone identifies a list of SNV subclones and calculates their cancer cell fraction. It also categorizes SNVs as either clonal or subclonal. The driver category of each SNV was determined and provided as the driver category (1-4, where 1 is most likely to be a driver mutation, and 4 is the least likely). For each patient, up to 108 SNVs, spanning all driver categories and including clonal and subclonal mutations, were analyzed. The detected allele fractions of each SNV in each tumor subsection, lymph node and matched normal DNA sample along with PyClone clonal/subclonal cluster information were compared.

Additional Information.

For each patient, the following information was available: tumor size (mm), tumor location (lung lobe), tumor stage, tumor pathological type, number of lymph nodes affected, vascular invasion status, as well as de-identified information on the collecting hospital.

Assay Design and Protocol Optimization.

Figure 2:
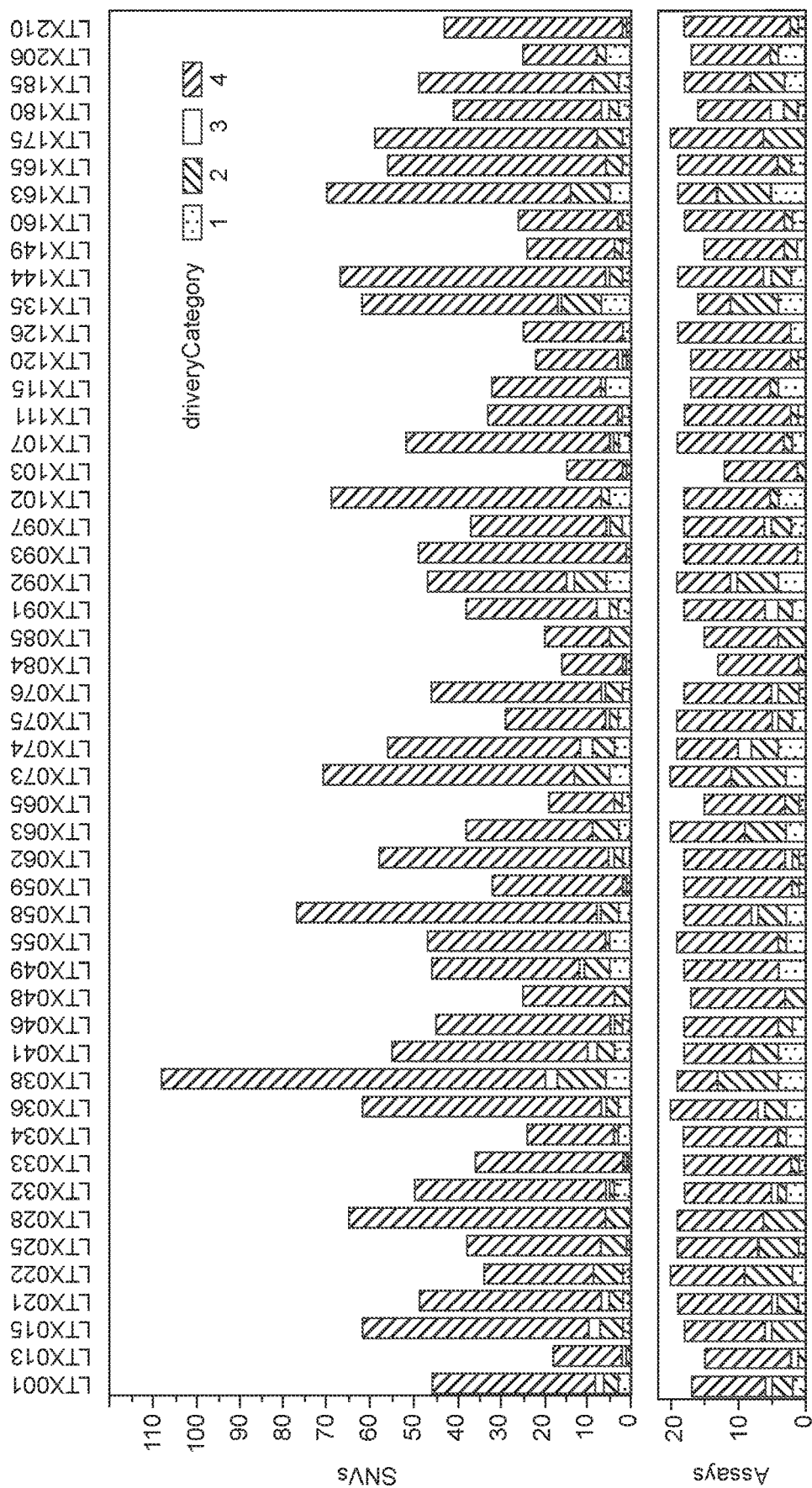
FIG. 2 Top panel: the number of SNVs per sample; bottom panel: the working assays, sorted by driver category.

Assay design. Natera's standard assay design pipeline was used to design Right and Left PCR primers for all given SNVs. A pair of Right and Left PCR primers targeting an SNV is defined as an assay for that particular SNV. Note that it is possible for one assay to cover more than 1 target SNV if they are in close proximity. For every pair of assays, the probability of forming a primer-dimer was calculated. The SNV allele fraction data in each tumor was used to reconstruct phylogenetic trees using Lichee (Fast and scalable inference of multi-sample cancer lineages. Popic et al. *Genome Biol.* 2015 May 6; 16:91). The list of assays for each sample were filtered to remove primers that are predicted to form primer dimers while giving strong priority to assays covering driver 1 and 2 SNVs. The remaining assays were used to build 5 balanced pools. All assays pooled together were compatible meaning there were no primers predicted to form primer-dimers in a pool. At each step, the assays were chosen such that assays covering driver 1 and 2 SNVs have the highest priority and for each patient the number of selected SNVs per branch was proportional to the total number of SNVs of that branch from the reconstructed phylogenetic tree. More specifically, we tried to have a uniform sampling of SNVs from branches in the reconstructed phylogeny tree, making sure selected assays provided good coverage of the reconstructed tree. The final design consisted of 972 assays, equally distributed among 5 pools, and containing 15-20 assays for each sample. The number of SNVs and the number of assays per sample by driver category are shown in FIG. 2. The genes in which the SNVs are found and the number of SNVs that were assayed per gene are found in FIG. 19.

Pool QC and Optimization.

The 972 primer pairs were obtained (IDT, Coralville, Iowa) in individual wells, desalted and normalized to 100 μM. The assays were pooled according to the pooling scheme, and each pool was used in a combined QC/optimization experiment. For the optimization experiment, several PCR parameters were varied and the effects on the sequencing performance, as well as the number of drop-out assays were evaluated from the sequence data. The PCR conditions that yielded the best percentage of on target reads, depth of read uniformity, and error rate were determined. Primers that were responsible for the majority of primer dimers were identified and removed from each pool (for each primer removed, its corresponding partner was also removed). Following this step, 908 total assays remained, equally distributed among the 5 pools.

Sample Preparation

DNA Extraction and QC.

All the plasma aliquots from each patient were pooled prior to cfDNA extraction, and the hemolysis grade of each pooled plasma sample was evaluated visually (no hemolysis, mild hemolysis or severe hemolysis). cfDNA was extracted using the Qiagen NA kit (Valencia, CA) following a protocol optimized for 5 ml of plasma. All cfDNA samples were QCed on Bioanalyzer High Sensitivity chips (Agilent, Santa Clara, CA). The same Bioanalyzer High Sensitivity runs were also used to quantify the cfDNA samples by interpolation of the mononucleosomal peak height on a calibration curve prepared from a pure cfDNA sample that was previously quantified. This was necessary because cfDNA sometimes contains an intact DNA fraction that overlaps with the high size marker on the chip, which makes quantification of the mononucleosomal peak unreliable. A representative subset of the purified genomic DNA samples (from tumor subsections, lymph nodes and white blood cells) was quantified using Nanodrops (Wilmington, DE). All of the samples quantified were in the expected range (~10 ng/μl).

cfDNA Library Preparation.

The entire cfDNA amount from each plasma sample was used as input into Library Prep using the Natera library prep kit and following the kit instructions. For two samples with extremely high cfDNA amounts, the input amount into Library Prep was restricted to ~50,000 genome equivalents (165 ng). The libraries were amplified to plateau and then purified using Ampure beads (Beckman Coulter, Brea, CA) following the manufacturer's protocol. The purified libraries were QCed on the LabChip.

cfDNA Multiplex PCR and Sequencing.

The library material from each plasma sample was used as input into multiplex PCR (mPCR) using the relevant assay pool and an optimized plasma mPCR protocol. The protocol utilized an annealing time of 15 minutes at a temperature of 60 C or 62.5 C, which was above the Tm of the primers. The Tms of the primers using theoretical calculations was 53 to 59 C. A 10 nM primer concentration was used. The mPCR products were barcoded in a separate PCR step, and the barcoded PCR products were pooled according to the assay pooling information (see section above) into 5 pools. The pools were purified using Ampure beads following the manufacturer's protocol, QCed on a Bioanalyzer DNA1000 chip (Agilent, Santa Clara, CA), and quantified using the Qubit dsDNA Broad Range kit (Thermo Fisher Scientific, Waltham, MA). Each pool contained libraries prepared as disclosed above, from 10 cancer patient plasma samples and 20 negative controls (prepared from cfDNA extracted from presumed healthy volunteers). The negative control samples were obtained following the necessary regulatory procedures. Each pool was sequenced on a separate HiSeq 2500 Rapid run (Illumina, San Diego, CA) with 50 cycle paired end single index reads.

gDNA Multiplex PCR and Sequencing.

The genomic DNA samples were used as input into a similar mPCR using the relevant assay pools and an optimized genomic mPCR protocol. The mPCR products were barcoded in a separate PCR step, and all the barcoded products were combined into one pool. The pool was purified using Ampure beads following the manufacturer's protocol, QCed on a Bioanalyzer DNA1000 chip, and quantified using the Qubit dsDNA Broad Range kit. The pool was sequenced on a single HiSeq2500 Rapid run with 50 cycle single end single index reads.

Results

FIG. 20 is a table showing detailed results of the analysis and detailed information regarding the samples that were analyzed in this study.

cfDNA Extraction and Analysis.

Figure 3:
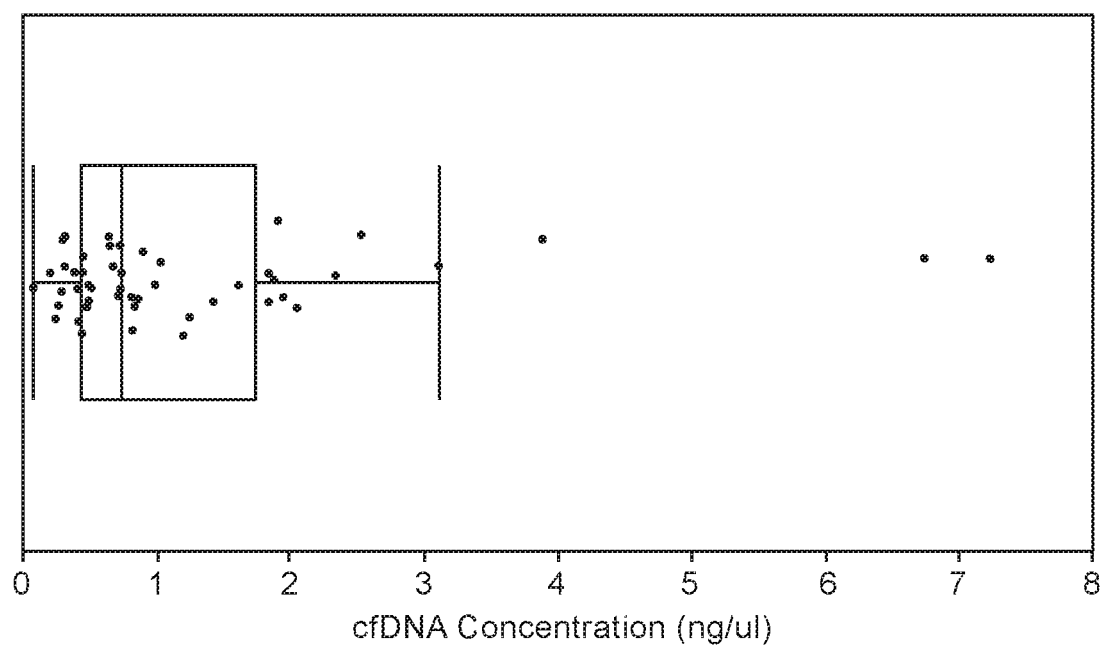
FIG. 3. Measured cfDNA concentration. Each data point refers to a plasma sample.

The distribution of cfDNA concentrations for the 50 plasma samples (FIG. 3) followed the expected distribution based on 5 ml of plasma (median of 2,200 genome copy equivalents per ml of plasma). The cfDNA concentrations, the hemolysis grade (visually estimated) and the qualitative evaluation of the cfDNA size profile (visually estimated from the Bioanalyzer traces) are shown in tabular form in FIG. 16

Cfdna Analysis.

The purified cfDNA concentration, plasma hemolysis grade and cfDNA profile are shown in FIG. 16. cfDNA concentration refers to the mononucleosomal peak only, and was determined from the mononucleosomal peak height using a calibration curve. Genome copy equivalents were calculated using a 3.3 pg/genome conversion factor; 40 µl purified cfDNA is used as input into Library Prep; green highlights: for those samples, the input into library prep was restricted to 50,000 genome equivalents. cfDNA size profile: 1: most of the cfDNA is in the mononucleosomal peak; 2: most of the cfDNA is in the mononucleosomal peak, but other sizes are seen; 3: a large peak of intact DNA (>1,000 bp) is seen along with the mononucleosomal peak and some higher molecular weight peaks. Hemolysis was estimated visually based on the plasma color. 0: no hemolysis (yellow plasma); 1: mild hemolysis (faint pink plasma); 2: severe hemolysis (bright pink or red plasma).

VAF Analysis in Tumor Subsections.

Figure 4:
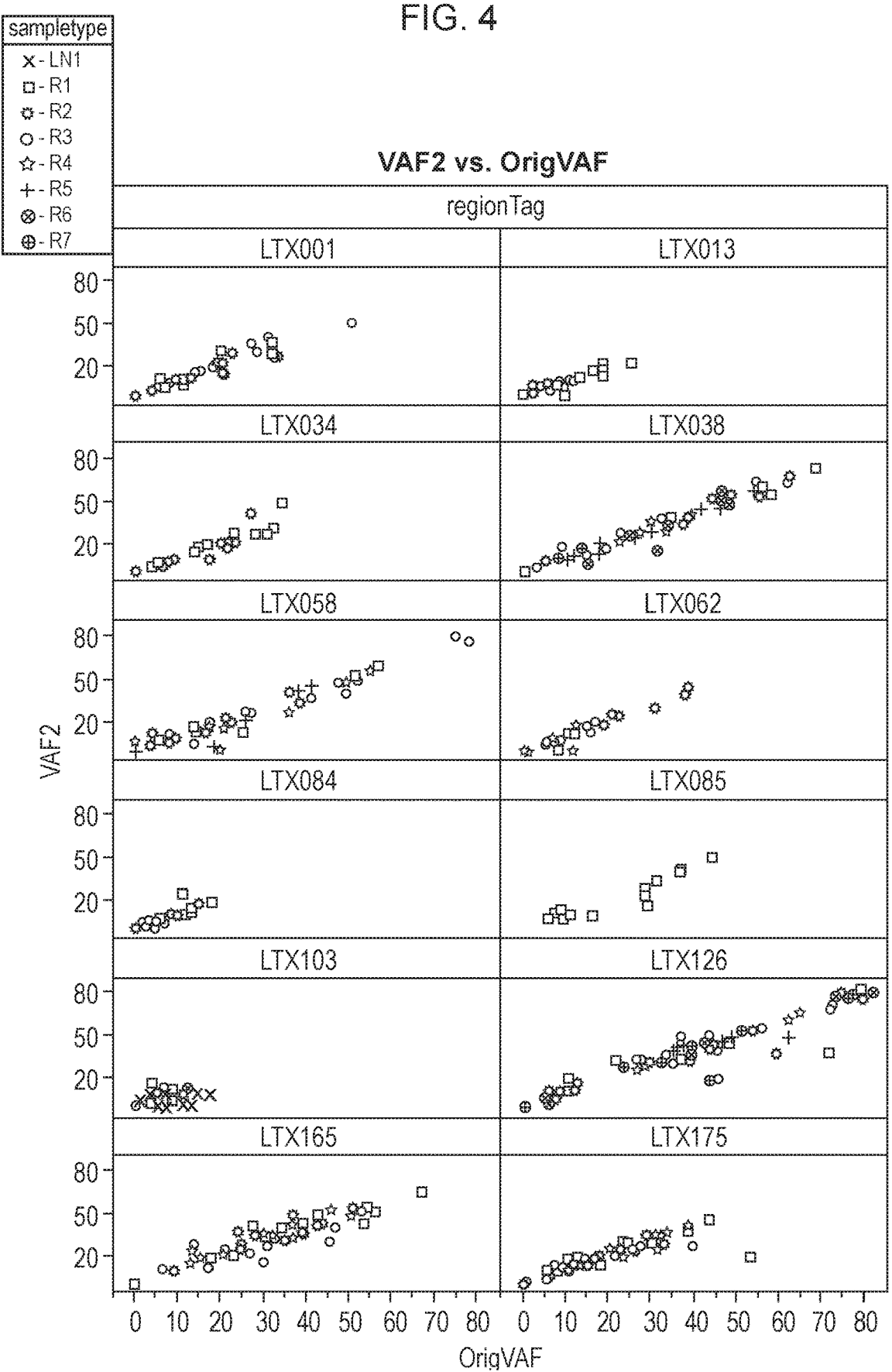
FIG. 4. Samples showing good correlation between tissue VAF measurements determined previously (x axis) and here using mPCR-NGS (y axis). Each sample is shown in a separate box, and the VAF data points are colored by tissue subsection.
Figure 4:
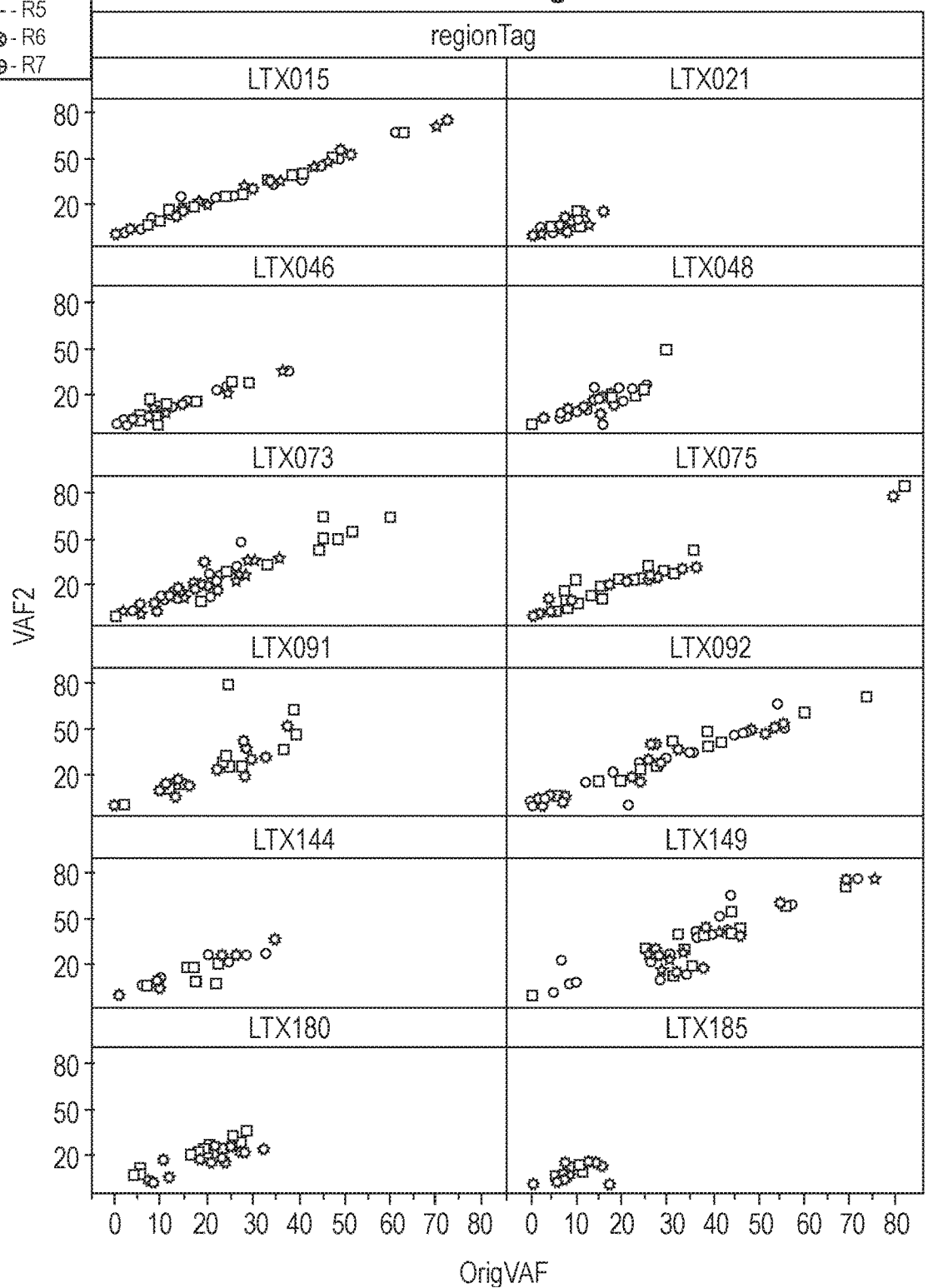
Figure 4:
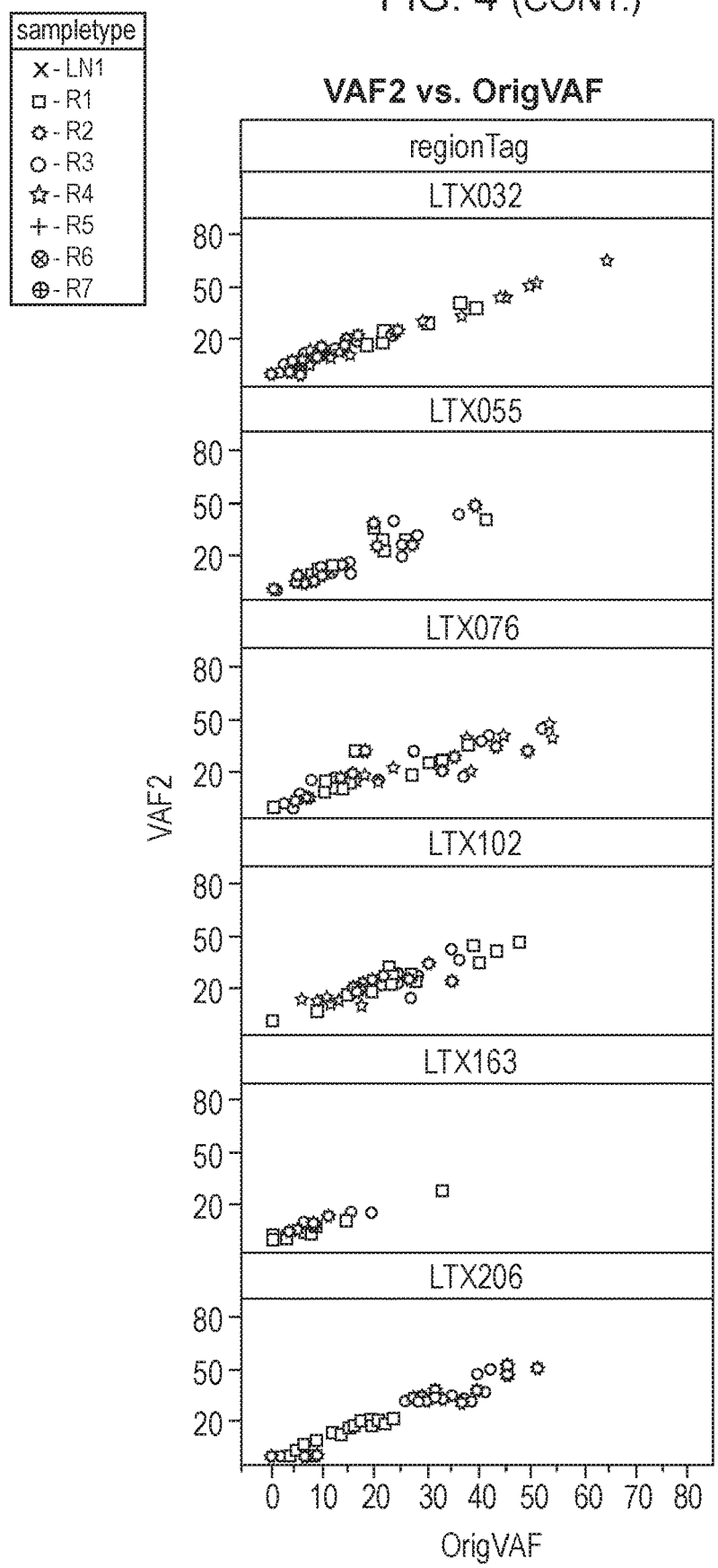
Figure 5:
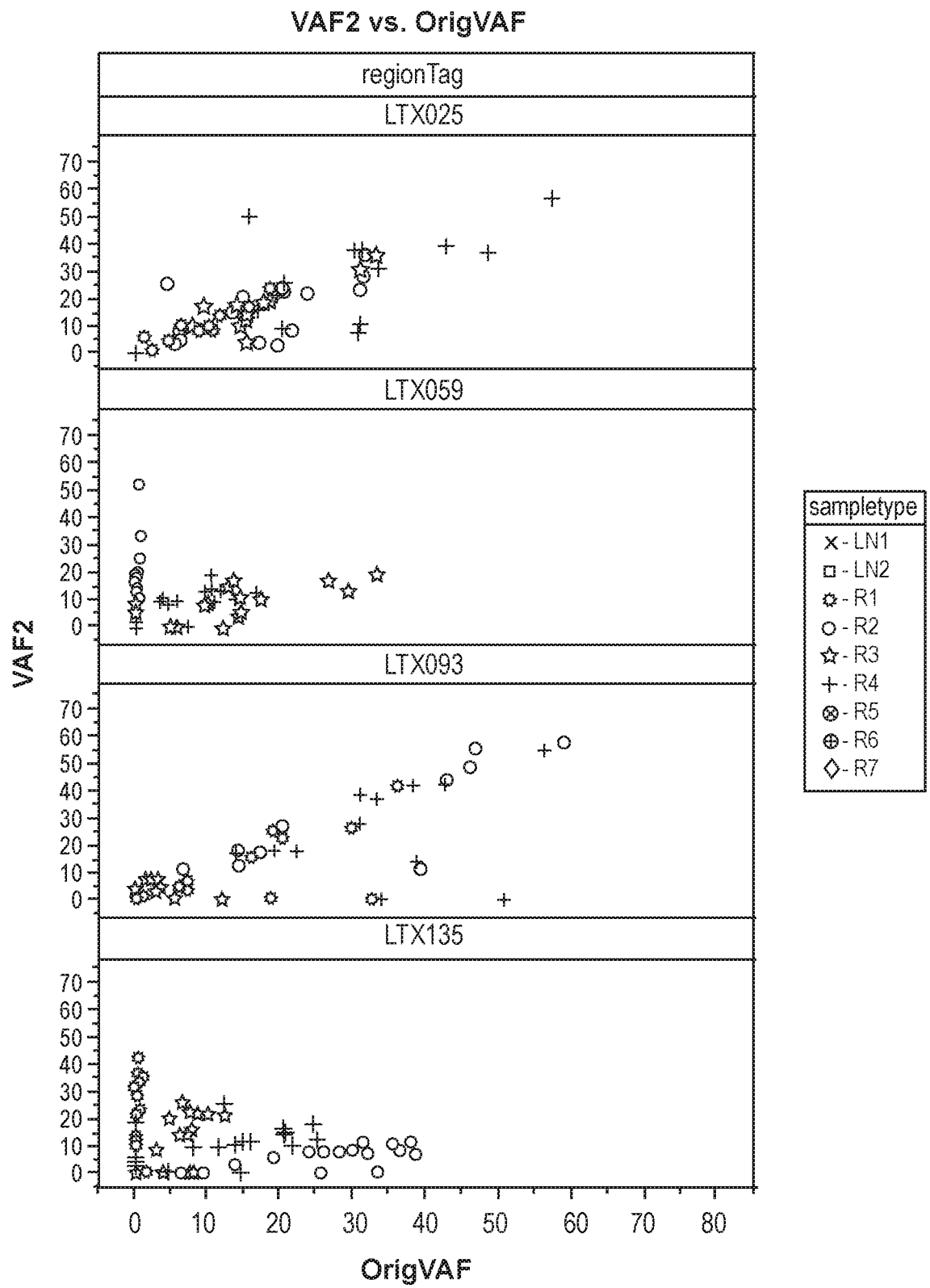
FIG. 5. Samples showing poor correlation between tissue VAF measurements determined previously (x axis) and here using mPCR-NGS (y axis). Each sample is shown in a separate box, and the VAF data points are colored by tissue subsection.
Figure 5:
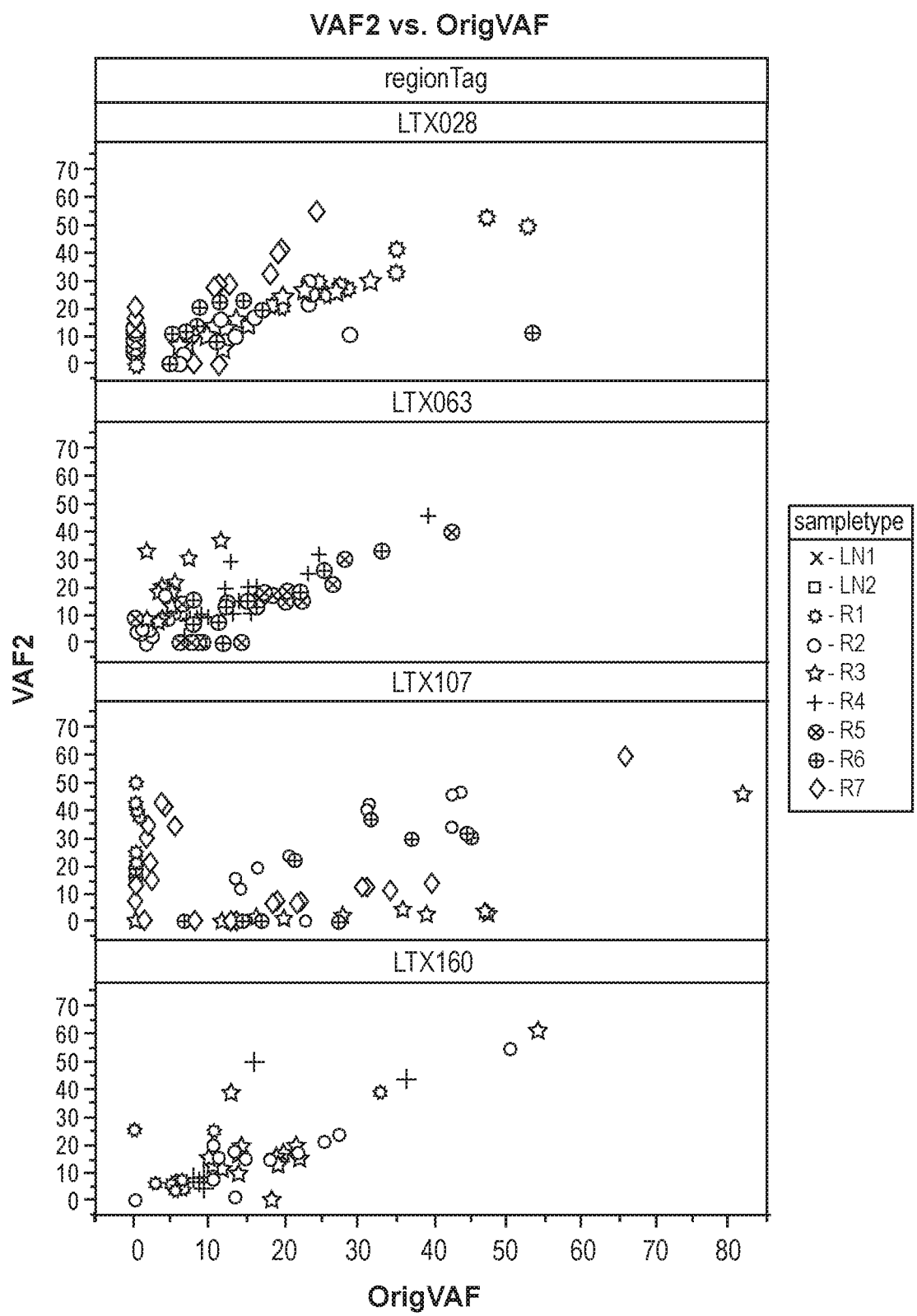
Figure 5:
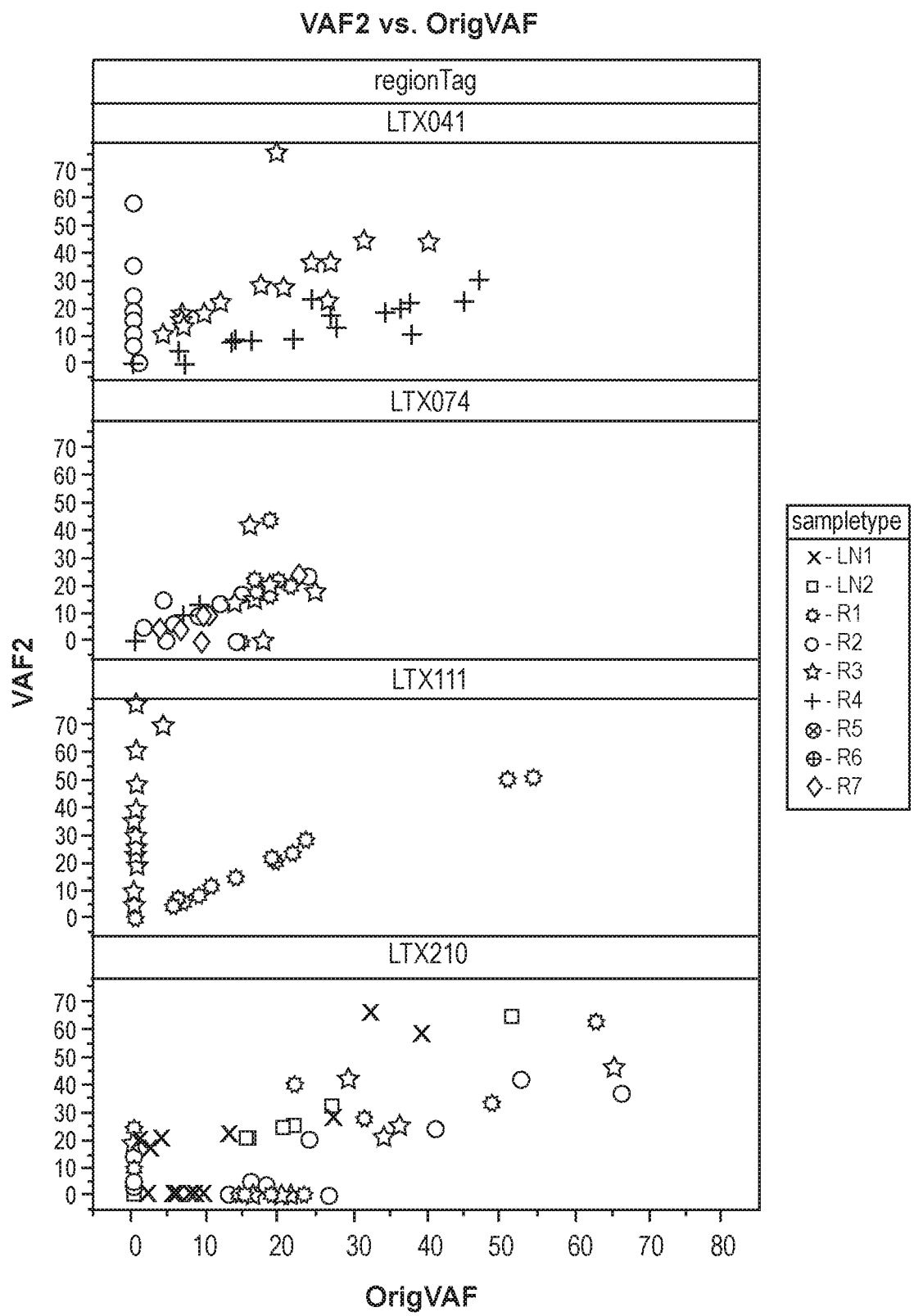

The sequence data from each of the tumor subsections was analyzed to determine the variant allele frequency (VAF) of each SNV in each tumor subsection, lymph node and matched normal sample. This data was compared with matched data provided separately from a different test site using different test methods, such as whole genome sequencing and exome sequencing. For most samples, the previously determined tissue VAF values from each tumor subsection closely matched the newly derived tissue VAF values (FIG. 4). However, there were a large number of samples in which significant discrepancies were seen (FIG. 5). Three types of discrepancies were observed: (i) for one or two subsections, all the VAFs are 0 or close to 0 in the previous analysis, but are non-zero (and span the range of VAFs seen in other subsections of the same sample) in the mPCR-NGS analysis (e.g.: LTX041, LTX111); (ii) for several assays, the VAFs are 0 in the mPCR-NGS analysis, but are non-zero (and span the range of VAFs seen in other subsections of the same sample) in the previous analysis, and no clustering by subsection was seen with this discrepancy mode (e.g.: LTX093, LTX074); (iii) for several assays or regions, none of the assays failed but concordance between VAFs obtained in the two analyses was generally poor (e.g.: LTX063, LTX059).

We also identified 16 somatic SNVs from tissue samples which were not reported in TRACERx SNV calls. Among these new somatic SNVs, 7 were called in their corresponding plasma cfDNA as well. Please see the list in FIG. 18.

One sample (U_LTX206, with 19 assays) failed sequencing and was removed from the analysis. 889 assays covering 911 SNVs were analyzed. Assays with a depth of read of less than 1,000 were considered failed, and their corresponding SNVs were marked as "no call". In total 21 "no call" SNVs were removed from the analysis; 890 total SNVs were analyzed.

Each run belonged to one assay pool and contained 10 cancer samples as well as 20 control samples. The set of SNVs covered by assays in a pool are considered as target SNVs for the associated run. To make an SNV call at a specific position of a cancer sample, first a background error model for that position was built. The error model was constructed based on the 20 negative samples and the remaining cancer samples (8 or 9) that were not expected to contain an SNV at that position, based on the information provided. Positions with VAF >20% were excluded from the background error model. A positive plasma SNV call was made if the confidence for that mutation in the corresponding plasma sample passed our confidence threshold of 95 to 98%.

The overall SNV detection rate in plasma is 35.5% (310 out of 890), similar to a prior pilot study. While the algorithm made most confident true positive calls, the number of false positive calls are at an acceptable number (<0.25%). The average mutant allele frequency for the SNVs detected with high confidence is 0.875%, ranging from 0.011% to 13.93%. A sample was considered as 'detected in plasma' if at least one SNV expected to be present in that sample was confidently detected in plasma. Using this definition, the overall sample detection rate in plasma was 69% (34 out of 49 samples), and for those, and the average number of SNVs detected in plasma was 9.1 (ranging from 1 to 19).The number of SNVs detected in plasma for each sample is shown in tabular form in FIG. 17.

Analysis of SNVs that were not Detected in Plasma.

Figure 6:
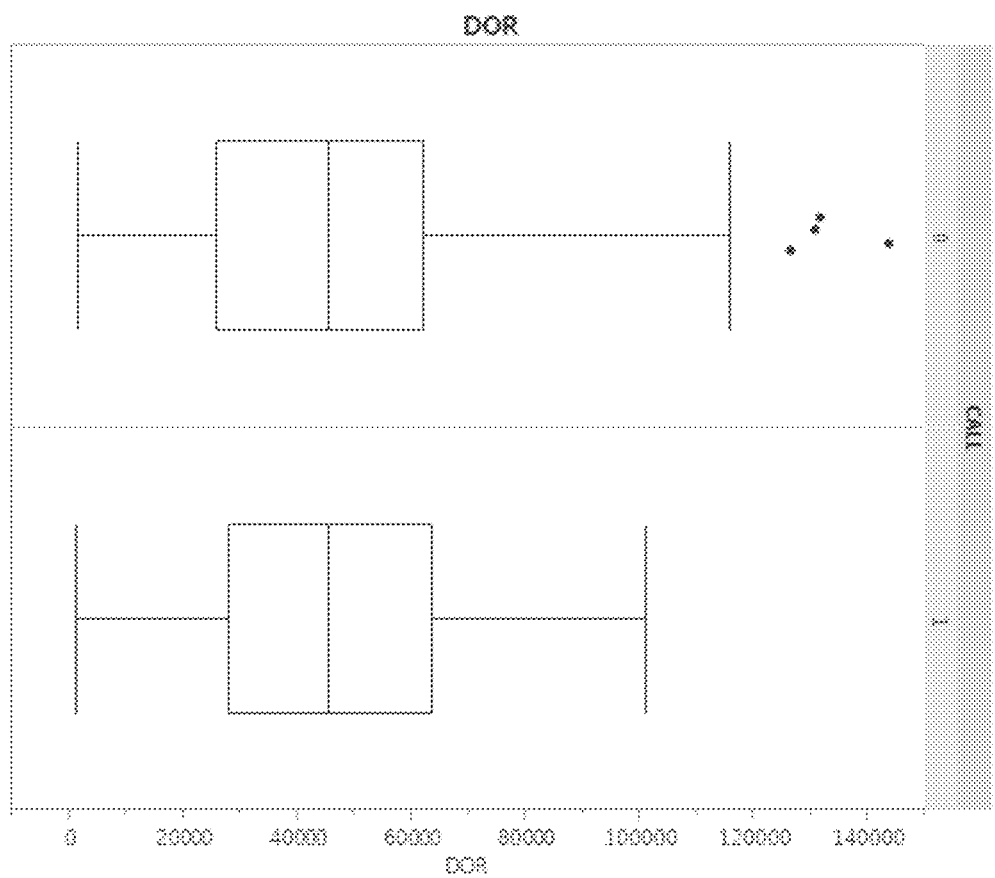
FIG. 6. Depth of read histogram as a function of the resulting call. Top: the assay did not detect the expected plasma SNV. Bottom: the assay detected the expected plasma SNV.

Several lines of evidence support the conclusion that the failure to detect >60% (580 out of 911) of the expected SNVs in the plasma is due to the fact that there is not enough evidence of presence for those mutations in the cfDNA sample, as opposed to some failure of the mPCR-NGS method: The depth of read (DOR) distribution is similar for the assays that detected the expected plasma SNV and the ones that didn't detect the expected SNV (FIG. 6a) (average DOR 45,551 for assays that detected the expected SNV vs 45,133 for the ones that didn't). This suggests assays corresponding to false negative SNV calls are as efficient as the ones for true positive calls. Furthermore, despite the high DOR at the target SNV position, the number of mutant reads is almost negligible. In fact, 36% of them have 0 mutant reads, 75% of them have more than 5 mutant reads, and the remaining 25% false negative calls have VAF <0.1%.

Factors Influencing SNV Detection in Plasma.

Several factors that influence plasma SNV detectability have been evaluated. The cfDNA amount and the tumor staging information, tumor size and the SNV frequencies in tumor subsections were determined in separate locations.

Histological Type.

Figure 7:
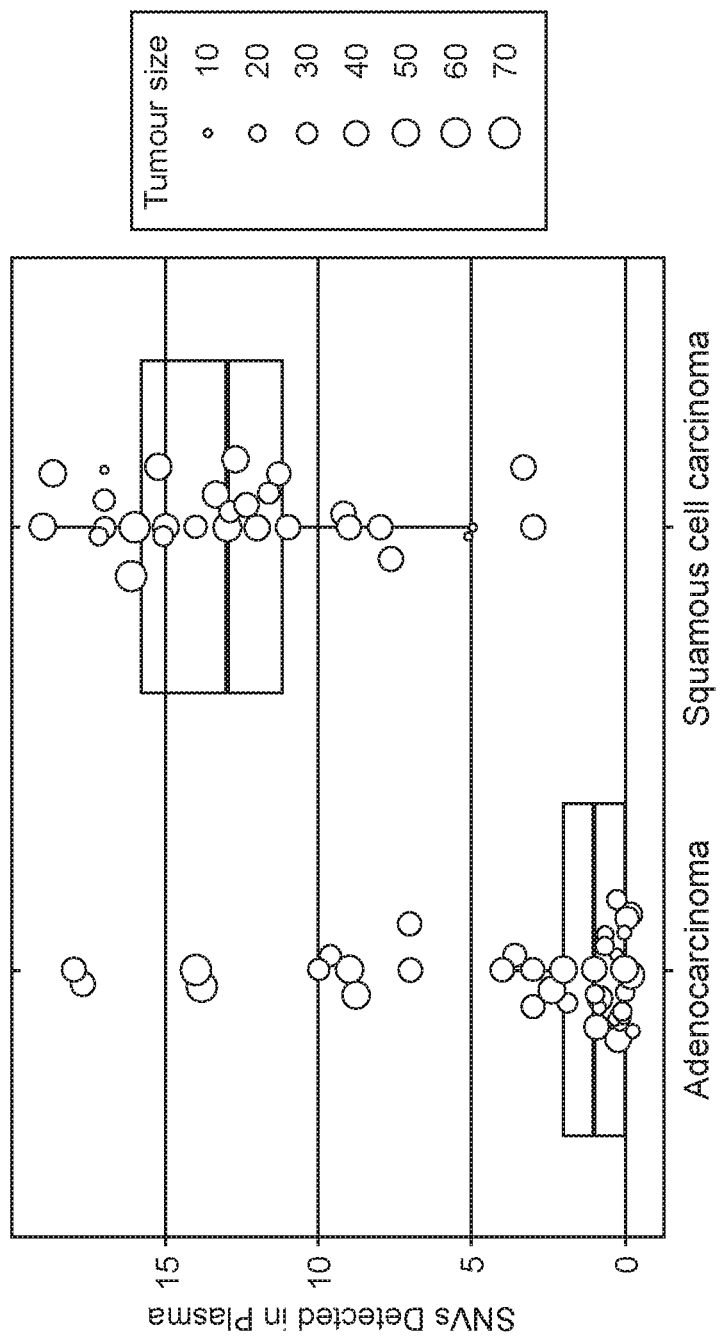
FIG. 7. Number of SNVs detected in plasma by histological type.

The most important predictor of whether a particular tumor was detected in the plasma appeared to be histological type: 100% of the squamous cell carcinoma (SQCC) tumors were detected in plasma, whereas only 50% (15/29) of the adenocarcinoma (ADC) tumors were detected in plasma in this study (FIG. 7). Moreover, the average number of SNVs detected per sample was 12.7 (median=13) for SQCC and 2.6 (median=1) for ADC. There was only one carcinosarcoma tumor and one adenosquamous tumor in this cohort, so no conclusions about their general detectability in plasma could be derived about those tumor types at this time.

Tumor Stage and Size.

Figure 8:
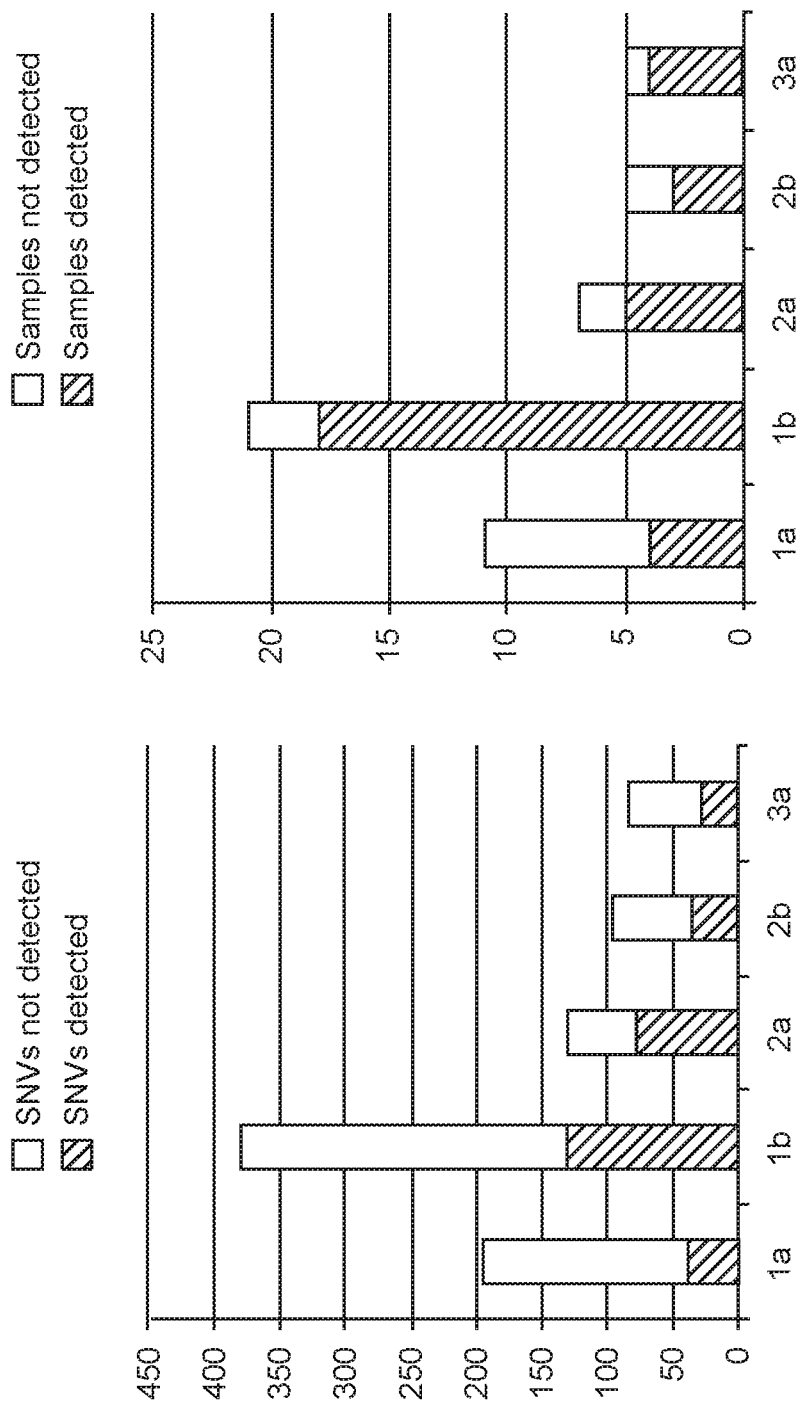
FIG. 8. SNV detection (left) and sample detection (right) in plasma by tumor stage.
Figure 9:
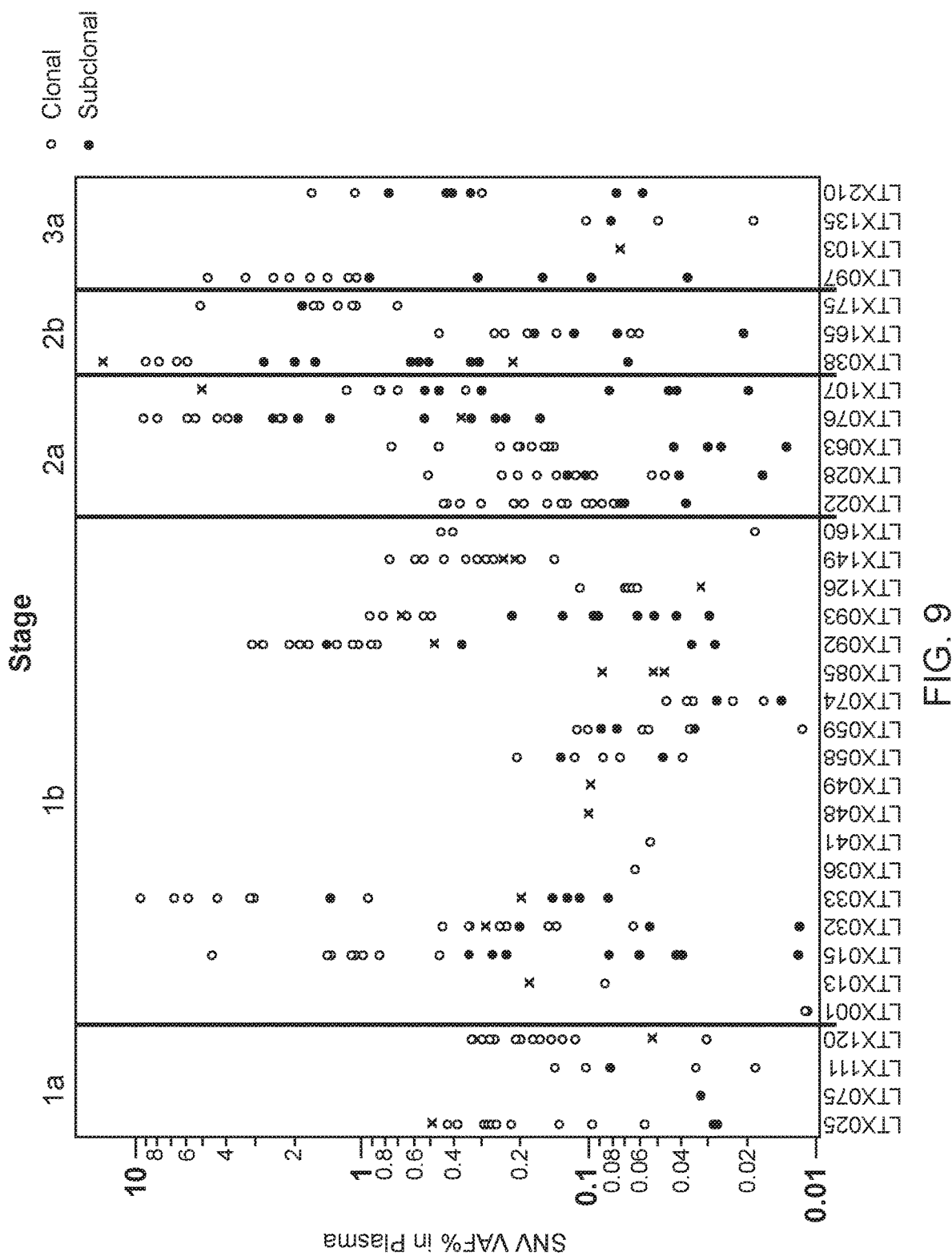
FIG. 9. Plasma VAF as a function of tumor stage and SNV clonality.
Figure 15:
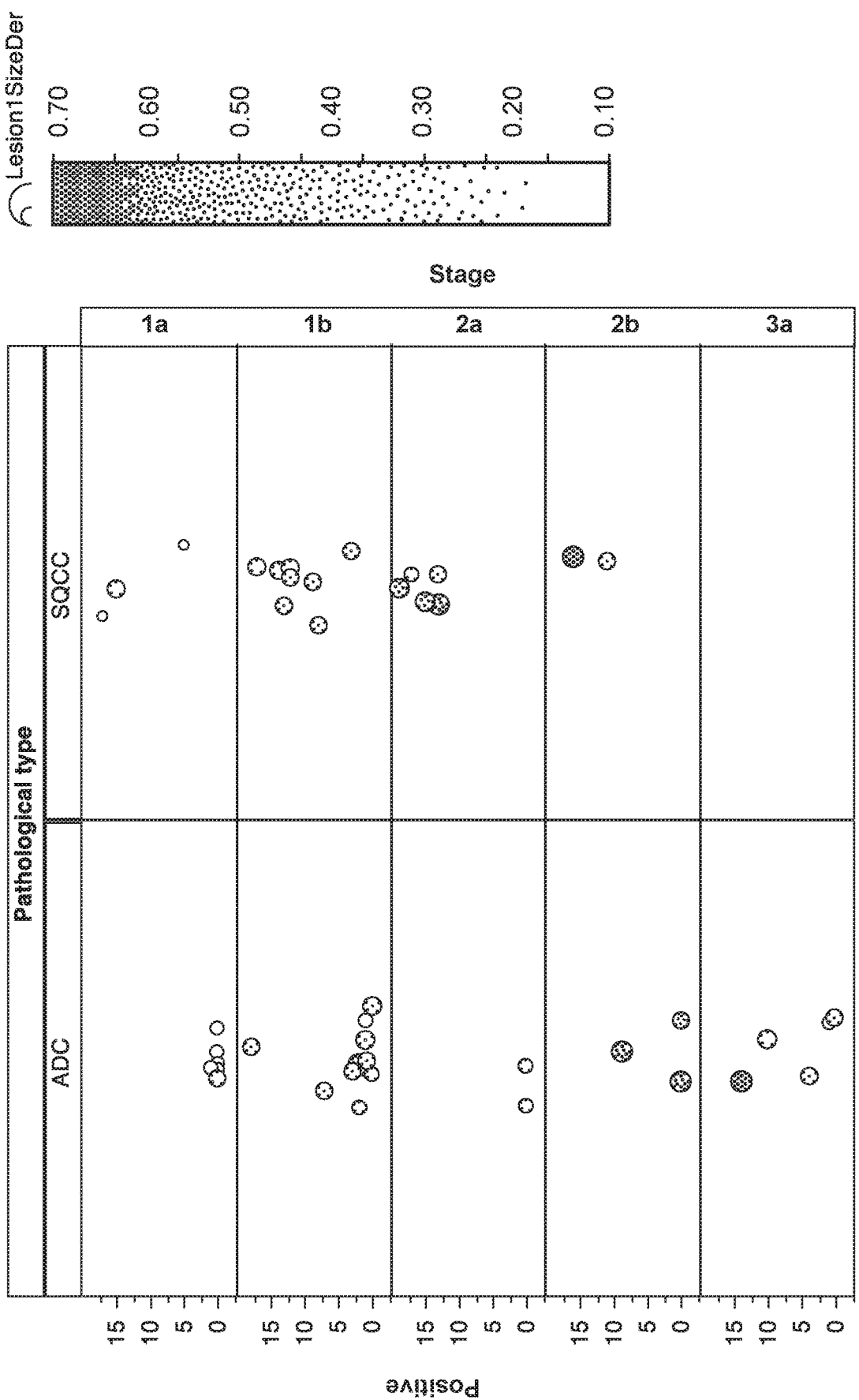
FIG. 15 shows the number of SNVs detected in plasma as a function of histological type and tumor size. The histological type and tumor stage were determined by the pathology report. Each data point is colored by size, where red denotes the largest tumor size and blue denotes the smallest tumor size.

Tumor stage and size were some of the most important factors identified that influence the number of SNVs detected in the corresponding plasma sample (FIG. 8). Stage 1a tumors had the lowest chance of having at least one SNV detected, as well as the lowest success rate of detecting SNVs in the plasma. The VAF distribution for the SNVs that were detected from stage 1a tumors was also lower than for the rest of the tumors (FIG. 9). As tumor size and stage are correlated, a similar trend was seen with tumor size. As this was not due to assay failure or sensitivity limits (see below), the most likely explanation is that such tumors tend to not have cfDNA present in the plasma in quantities that are detectable in the plasma volumes used in this study. The effect of tumor stage and size on the number of SNVs detected in ctDNA varied between ADC and SQCC samples. The ADC samples were more dependent on these factors with a general trend of far fewer SNVs detected in ctDNA than were detected in ctDNA of the SCC samples. In fact, SNVs were detected in the ctDNA of all of the SQCC samples regardless of stage: Three SNVs were detected in the ctDNA of one of the SCC samples and at least 5 SNVs detected in the ctDNA of the remainder of the SCC samples (FIG. 15). In fact, between 3 and 19 SNVs were detected in the ctDNA of SCC samples. In 6 ADC samples that were stage 1a, an SNV was only detected in one of the ctDNA samples, and in that sample only a single SNV was detected. In none of the stage 1a ADC samples were more than 1 SNV detected in the ctDNA. In stage 1b ADC samples, less than 5 SNVs were identified in all but two samples, with 7 SNVs identified in one of the stage 1b ADC samples and 18 SNVs identified in one of the stage 1b samples.

Tumor VAF and Clonality.

Figure 13:
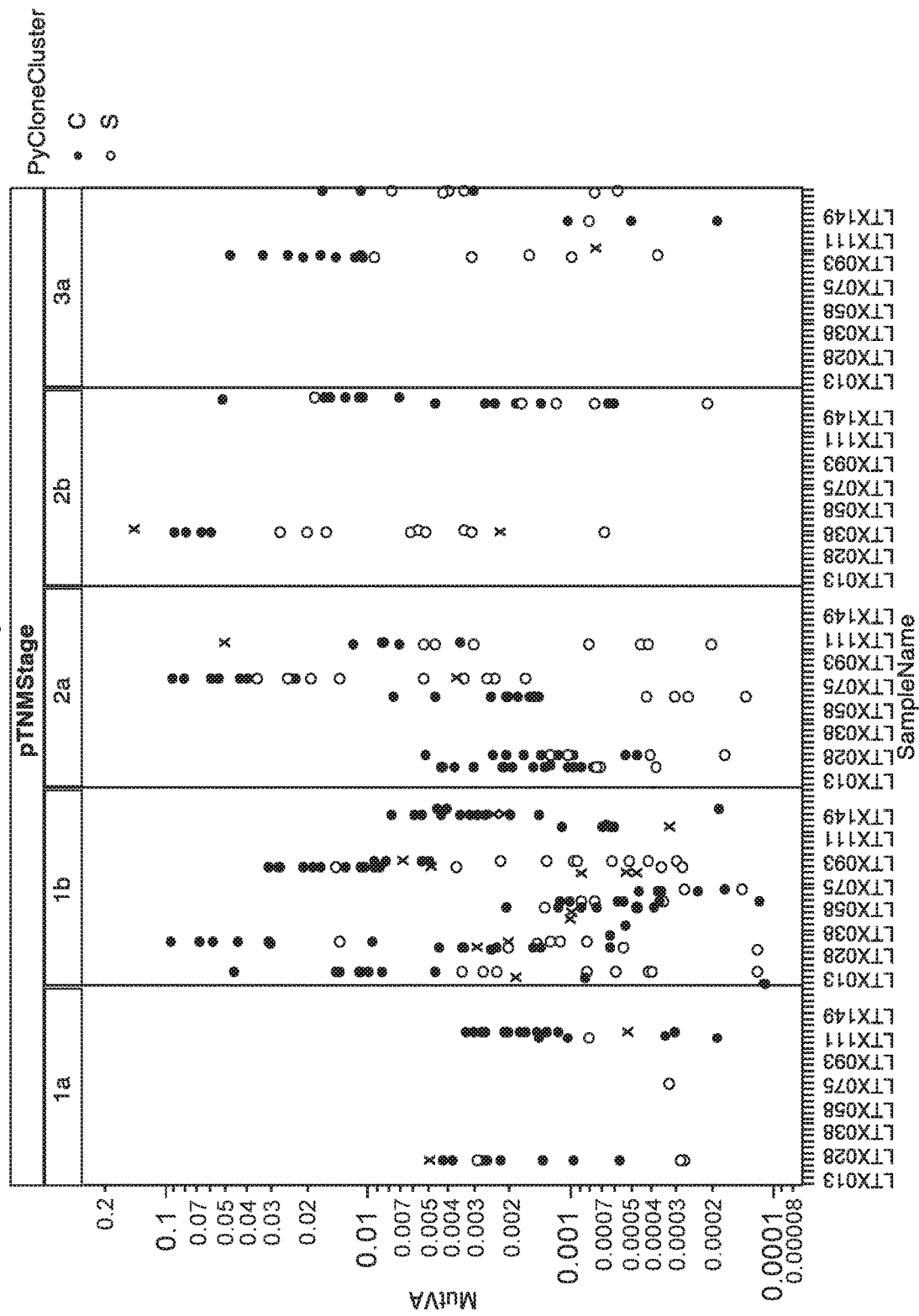
FIG. 13 shows the clonal status (blue for clonal and red for subclonal) and mutant variant allele frequency (MutVAF) of each detected SNV. The total SNVs detected from each sample are placed in a single column and the samples are categorized by tumor stage (pTNMstage). Samples with no detected SNVs are included. The clonal status was determined by PyCloneCluster using whole exome equencing data from the tumor tissue.
Figure 14:
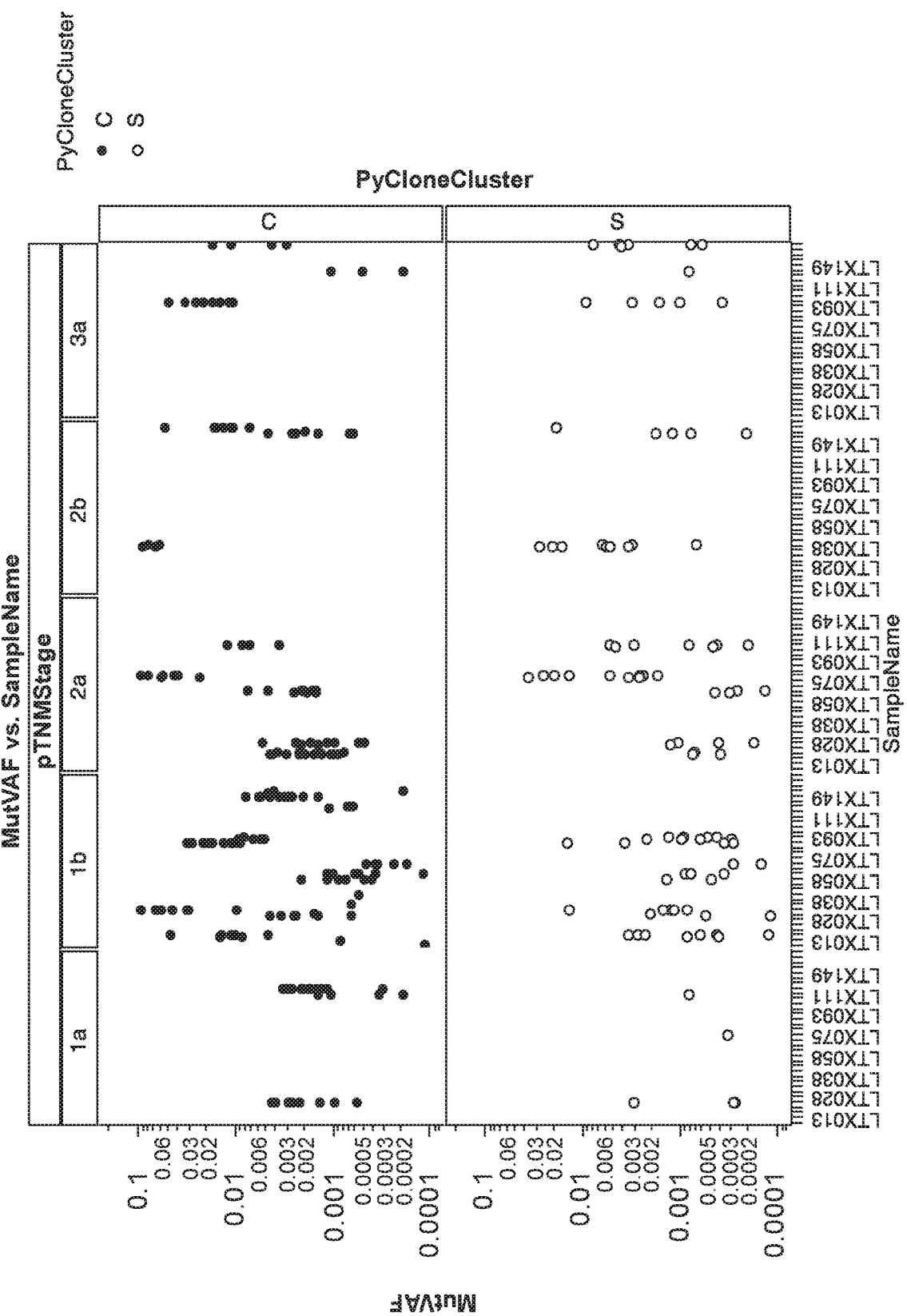
FIG. 14 shows the clonal status (blue for clonal and red for subclonal) and mutant variant allele frequency (MutVAF) of each detected SNV where the top panel shows only the clonal SNVs and the bottom panel shows only the subclonal SNVs. The total SNVs detected from each sample are placed in a single column and the samples are categorized by tumor stage (pTNMstage). Samples with no detected SNVs are included. The clonal status was determined by PyCloneCluster using whole exome equencing data from the tumor tissue.

The clonality ratio was calculated for each mutation as (number of sub-sections of a tumor where the mutation is detected)/(total number of sub-sections of that tumor analyzed). Mutations that were observed in all analyzed tumor sections are considered 'clonal', all others are considered 'sub-clonal'. The VAF of SNVs detected in plasma correlates with the 'clonality' of the mutations, with more clonal mutations being responsible for the highest plasma VAF values (FIGS. 9 and 12); similarly, SNVs present in multiple tumor sub-sections tend to be responsible for higher plasma VAFs in the corresponding plasma samples. In addition to the clonality ratio, the clonal status of each SNV was categorized by PyCloneCluster based on WES data from the tumor tissue. Clonal SNVs tended to have higher VAFs (FIGS. 13 and 14).

cfDNA Input and Tumor VAF.

Figure 10:
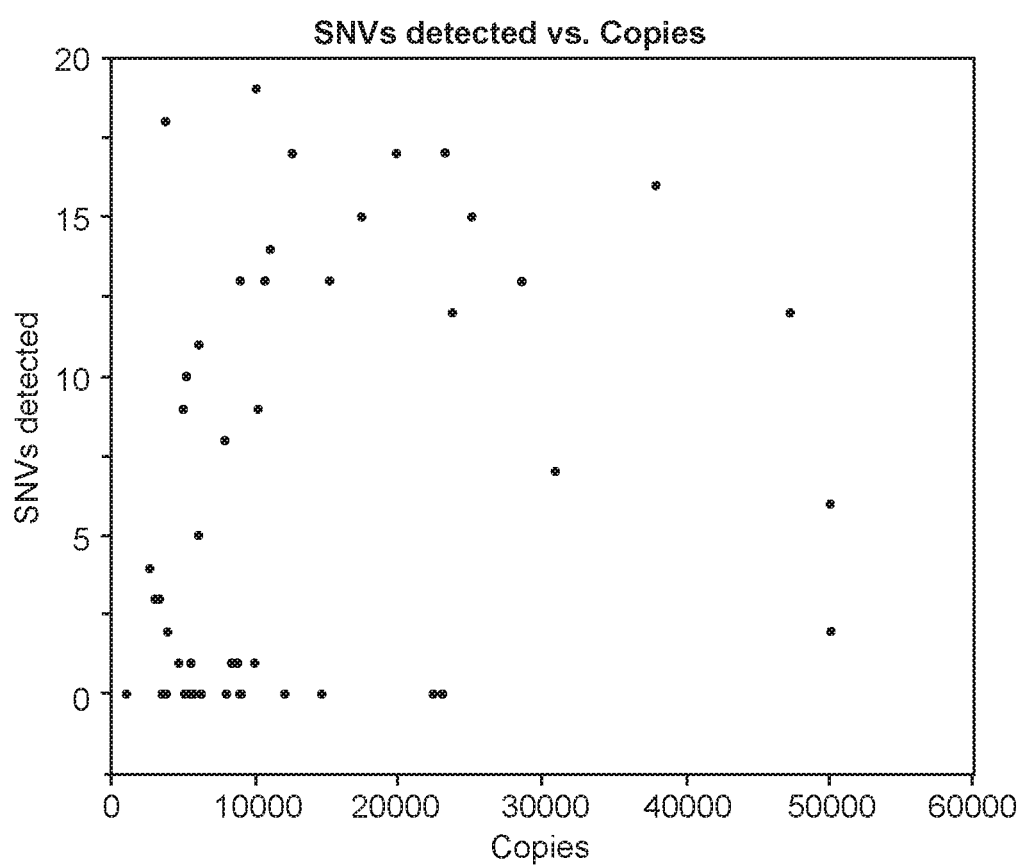
FIG. 10. Number of SNVs detected in plasma from each sample as a function of the cfDNA input amount.
Figure 11:
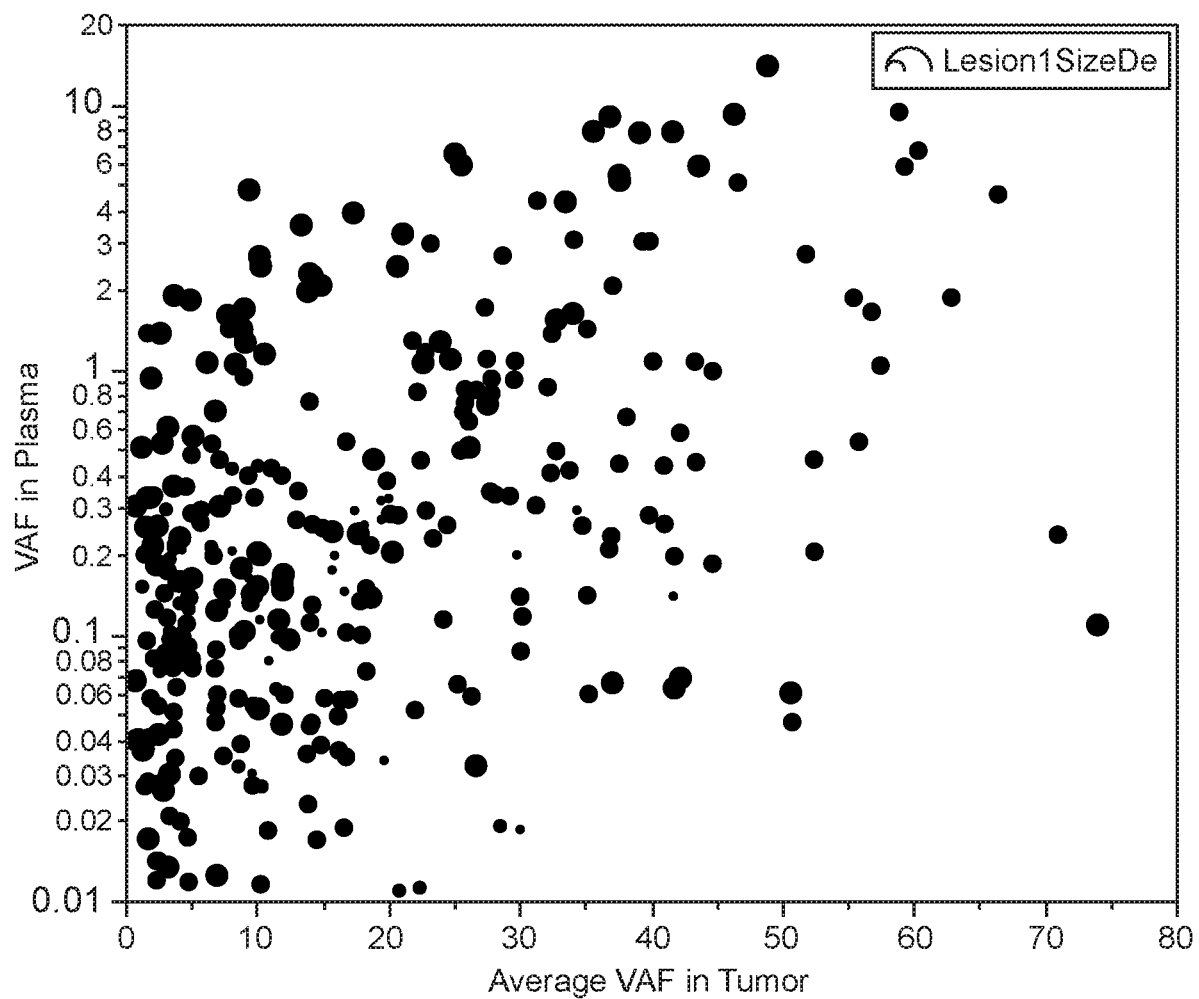
FIG. 11. Plasma VAF as a function of average tumor VAF. Average tumor VAF was calculated across all the tumor sub-sections analyzed from each tumor.

There was no correlation between the amount of cfDNA and the number and proportion of SNVs detected in the plasma samples. The number of SNVs detected in plasma is not predicted by the cfDNA input amount; however, all samples with high input (>25,000 copies) had at least one SNV detected in plasma (FIG. 10). The plasma SNV VAF also correlates with the tumor SNV VAF(FIG. 11).

Multivariate Analysis.

A regression analysis was performed to determine the variables that can be used to predict our detection of mutations. More specifically, a 0/1 response variable was used to annotate the mutations we called as present or not. The following independent variables were included in our model:

1. tumor VAF
2. PyClone cluster (categorical variable)
3. cancer stage (categorical variable)
4. size of the tumor
5. input DNA amount
6. pathological type (categorical variable)
7. number of affected lymph nodes
8. vascular invasion (categorical variable)
9. affected lobe A logistic regression showed that the following variables had statistically significant association with the detection of a mutation (with p-values <5%):

1. tumor VAF (p=4.3e-6)
2. PyClone cluster (p=1.6e-4)
3. size of the tumor (p=3.5e-4)
4. pathological type (p=8.3e-30)

Conclusions.

We demonstrate in this example the successful detection of lung cancer-related SNVs in plasma samples from patients with lung cancer. Using a custom multiplex PCR panel tailored for this sample cohort, SNVs with variant allele fraction as low as 0.01% were detected. Of the tested SNVs, 35% were detected in the plasma samples and 67% of the samples analyzed had at least one plasma SNV detected. We also identified some of the factors that contribute to the successful detection of plasma SNV. These include tumor type, tumor stage, tumor size, SNV allele frequency in tumor and, to a lesser extent, amount of cfDNA analyzed. The finding that not all SNVs were detected in plasma, and that not all samples have SNVs detectable in the plasma, does not appear to be due to assay or protocol limitations, as those assays were functional (as evidenced by their sequencing depth of read) and their limit of detection was sufficient to detect any SNVs, should they be present in the cfDNA sample. Rather, the failure to detect those SNVs was likely due to the fact that they are not present in the sample. Samples from low grade tumors and small tumors were more likely to have limited amounts of circulating tumor DNA. Similarly, SNVs that were present at low allele frequency in the tumor were less likely to be present in the plasma. However, even tumors of high grade and relatively large size can have no SNVs detected in the plasma. It is possible that other biological reasons are responsible for this (such as amount of ctDNA shedding from the tumor) and that analyzing more SNVs per sample will increase the chance of detecting some. 0.4 mM dNTPs (see FIG. 12-3C).

Those skilled in the art can devise many modifications and other embodiments within the scope and spirit of the presently disclosed inventions. Indeed, variations in the materials, methods, drawings, experiments examples and embodiments described may be made by skilled artisans without changing the fundamental aspects of the disclosed inventions. Any of the disclosed embodiments can be used in combination with any other disclosed embodiment.

The disclosed embodiments, examples and experiments are not intended to limit the scope of the disclosure nor to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Example 2. A Bespoke Multiplex PCR Protocol to Track Tumor Mutations in Plasma

Natera's bespoke multiplex PCR (mPCR) protocol is designed to estimate plasma ctDNA level by tracking a set of patient-specific mutations identified from tumor tissue sample(s). Given a patient-specific mutation profile we designed custom mPCR panels that can be applied to time-series plasma samples of the corresponding patient.

SNV targets.

The mutation profile, which included single nucleotide variants (SNVs) for each tumor subsection, was determined based on analyses of tumor sequencing. The full mutation profile of each tumor was used to reconstruct the phylogenetic tree of each tumor. PyClone (Roth, et al. (2014). PyClone: Statistical inference of clonal population structure in cancer. Nature Methods 11: 396-398) was used to identify clusters of SNVs, and calculate their cancer-cell fraction. This was used to categorize SNVs as either clonal or subclonal. The driver category of each SNV was determined (1-4, where 1 was most likely to be a driver mutation, and 4 was the least likely).

Assay Design.

Natera's standard assay design pipeline was used to design PCR primers for all given SNVs with following parameters:

Optimal melting temperature [Tm] 56° C., allowed range, 53° C.-59° C.

Amplicon length, 50-70 bp

GCcontent, 30-70%

We refer to a pair of Right and Left PCR primers targeting a SNV as an assay for that particular SNV. It is possible for one assay to cover more than 1 target SNV, if they were in close proximity. For every pair of assays, the probability of forming primer-dimer was calculated using thermodynamic approach (SantaLucia J R (1998) "A unified view of polymer, dumbbell and oligonucleotide DNA nearest-neighbor thermodynamics", Proc Natl Acad Sci 95:1460-65) to estimate the stability of the primer pair's joint hybridization structure. Assays were pooled together to minimize the number of primers with a high probability of forming primer-dimer in the same pool. For each patient, assays were prioritized such that, 1) assays covering driver SNVs had highest priority, and 2) there was uniform sampling of the phylogenetic tree.

Pool QC and Optimization.

The primers were ordered from IDT in individual wells, on desalted and normalized to 100 uM. The assays were pooled at Natera according to the pooling scheme, to create assay pools where each primer was at 250 nM in water. Each pool was used in a combined QC/optimization experiment. For the optimization experiment, PCR parameters (primer concentration and annealing temperature) were varied and the effects on the percentage of on-target reads, depth-of-read uniformity (measured as the ratio of the 80th percentile/20th percentile), and the number of drop-out assays (defined as assays with <1,000 reads) were evaluated from the sequencing data. The PCR conditions that yield the best percentage of on-target reads, depth-of-read uniformity, and the lowest number of drop-outs were determined. For all pools, the optimal conditions were 10 nM primers and 60° C. or 62.5° C. annealing temperature.

Primers that were responsible for the majority of primer dimers were identified and removed from each pool (for each primer removed, its corresponding partner was also removed).

DNA Extraction and QC.

Plasma aliquots from each patient were pooled prior to cfDNA extraction, and the hemolysis grade of each pooled plasma sample was evaluated visually and noted (no hemolysis, mild hemolysis, or severe hemolysis). cfDNA was extracted at Natera using the Qiagen NA kit following a protocol optimized for 5 ml of plasma. All cfDNA samples were QCed on Bioanalyzer High Sensitivity chips. The same Bioanalyzer High Sensitivity runs were also used to also quantify the cfDNA samples by interpolation of the mononucleosomal peak height on a calibration curve prepared from a pure cfDNA sample that was quantified previously. This is necessary because cfDNA sometimes contains an intact DNA fraction that overlaps with the high size marker on the chip, making quantification of the mononucleosomal peak unreliable.

Genomic DNA samples (from tumor subsections, lymph nodes, and white blood cells) were quantified on the Nanodrop.

cfDNA Library Preparation.

The entire cfDNA amount from each plasma sample was used as input into Library Prep using the Natera library prep kit and following the kit instructions. For two samples with extremely high cfDNA amounts, the input amount into Library Prep was restricted to ~50,000 genome equivalents (165 ng). In brief, 40 ul of DNA extracted from plasma, which is present in fragments of mononucleosomal and polynucleosomal length, were end repaired and A-tailed, and Natera custom adapters ligated. The libraries were amplified for 15 cycles to plateau and then purified using Ampure beads following the manufacturer's protocol. The purified libraries were QCed on the LabChip.

cfDNA Multiplex PCR and Sequencing.

The library material from each plasma sample was used as input into multiplex PCR using the relevant assay pool and an optimized plasma mPCR protocol. The PCR composition was: 1× in-house PCR master mix, 10 nM primers, 3 uL cfDNA library (corresponding to ~600 ng DNA), in 10 uL total reaction volume. The thermocycling conditions were: 95° C., 10 minutes; 10 cycles of (95° C., 30 seconds; 60° C. or 62.5° C., 15 minutes; 72° C., 30 seconds); 72° C., 2 minutes, 4° C. hold.

The mPCR products were barcoded in a separate PCR step, and the barcoded PCR products were pooled according to the assay pooling information.

The pools were purified using Ampure beads following the manufacturer's protocol, QCed on a Bioanalyzer DNA1000 chip, and quantified using the Qubit dsDNA Broad Range kit. Each pool contained barcoded mPCR products of 10 cancer plasma libraries and 20 negative controls (prepared from cfDNA extracted from healthy volunteers). The negative control samples were obtained following the necessary regulatory procedures. Each pool was sequenced on a separate HiSeq2500 Rapid runs with 50 cycle paired end single index reads.

Genomic DNA Multiplex PCR and Sequencing.

The genomic DNA samples (gDNA) were used as input into a similar mPCR using the relevant assay pools and an optimized genomic mPCR protocol; 50 ng gDNA was used as input. The mPCR products were barcoded in a separate PCR step, and all the barcoded products were combined into one pool. The pool was purified using Ampure beads following the manufacturer's protocol, QCed on a Bioanalyzer DNA1000 chip, and quantified using the Qubit dsDNA Broad Range kit. The pool was sequenced on a single HiSeq2500 Rapid run with 50 cycle single end single index reads.

Bioinformatics Pipeline.

Paired-end reads were mapped to the hg19 reference genome with Novoalign v2.08.02, and sorted and indexed using SAMtools (Li H.*, Handsaker B.*, Wysoker A., Fennell T., Ruan J., Homer N., Marth G., Abecasis G., Durbin R. and 1000 Genome Project Data Processing Subgroup (2009) The Sequence alignment/map (SAM) format and SAMtools. Bioinformatics, 25, 2078-9). All the paired-end reads were merged using Pear (J. Zhang, K. Kobert, T. Flouri, A. Stamatakis. PEAR: A fast and accurate Illumina Paired-End reAd mergeR. Bioinformatics 30(5): 614-620, 2014) (using default parameters). Since all amplicons are less than 70 bases long, with paired 50 bp reads generated by Illumina HiSeq 2500 all on-target reads were merged with the minimum of 30 bp overlap. Unassembled Reads are off-target and were filtered at this step. Amplicons were designed such that the target SNV positions were located in the overlapping region. Bases that did not match in forward and reverse reads or that have Phred quality score less than 20 were filtered out to minimize sequencing errors in subsequent steps. Merged reads with mapping quality higher than 30 and at most one mismatch under the sequence of primers were marked as on-target. Targets with less than 1000 reads were considered failed and were filtered from further analyses. Quality control (QC) was performed using an in-house Java program checking for a wide list of statistics per sample that included total numbers of reads, mapped reads, on-target reads, number of failed targets, and average error rate. A sample with less than 90% mapped reads and more than 3 failed targets did not pass, and needed to be resequenced.

Statistical Model.

The PCR process was modeled as a stochastic process, estimating the error parameters using a set of 29 control plasma samples and making the final SNV calls on the target cancer samples. For each target SNV, we built a target-specific background error model by estimating the following parameters from the control samples.

PCR efficiency (p): Probability that each molecule is replicated in a PCR cycle.

Error rate ($p_e$): Error rate per cycle for mutation type e (e.g wildtype allele A to mutant allele G).

Initial number of molecules ($X_0$)

Figure 21:
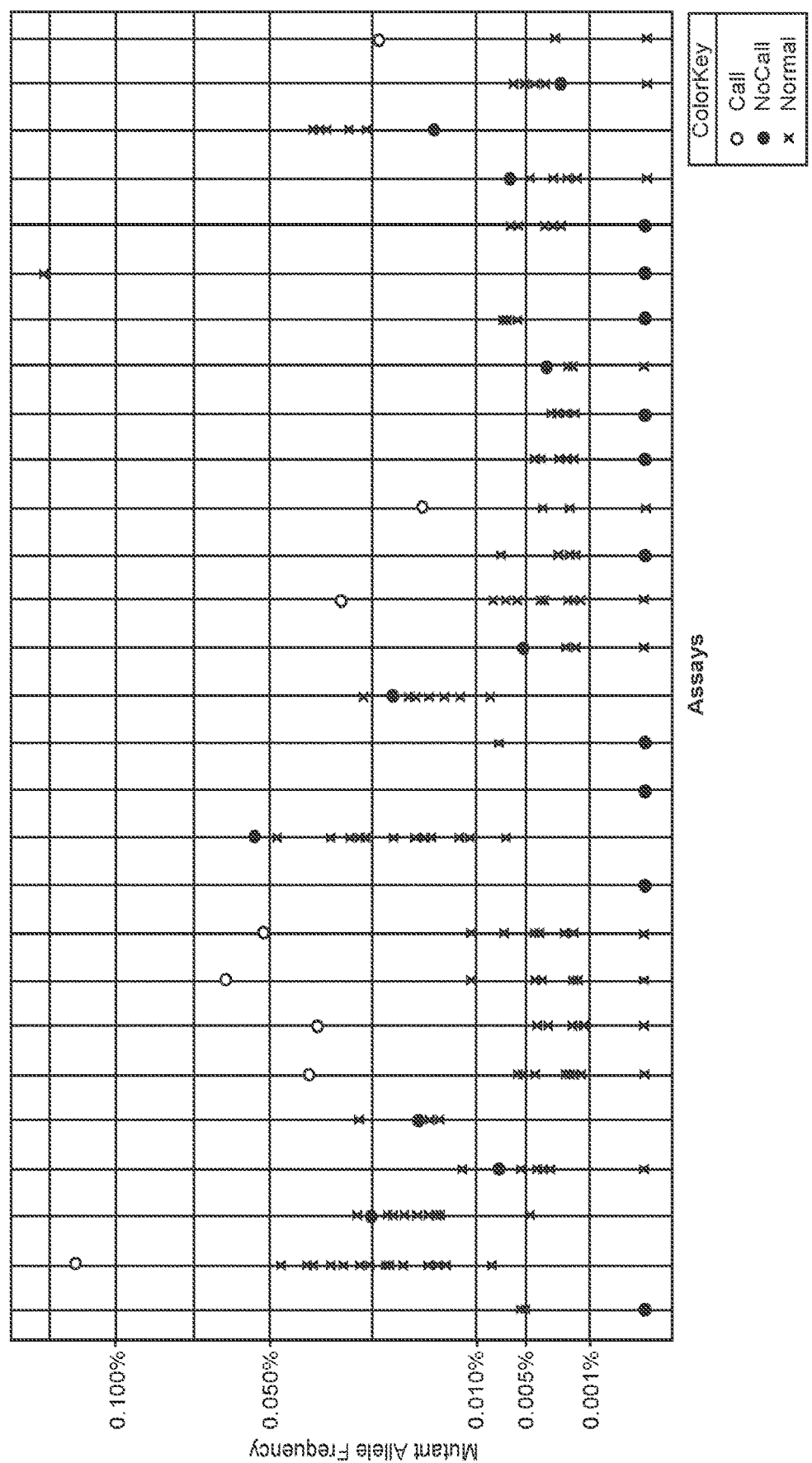
FIG. 21 is an example of detected assays and their background allele fractions for a plasma sample at relapse time (LTX103).

The target-specific error propagation model was used to characterize the distribution of error molecules. As a molecule is replicated over the course of PCR process, more errors occur. If an error occurs in cycle i and there are $X_i$ wildtype molecules in the system, that error molecule is duplicated in next cycle with probability p and new error molecules are produced from wildtype background molecules according to a binomial process $B(X_i, p_e)$. Using a recursive relation, we computed the mean and variance of number of total molecules $X_n$ and number of error molecules $E_n$ after n PCR cycles as shown in FIG. 21.

Algorithm Steps:
a. Estimating the PCR efficiency and per cycle error rate using the normal control samples.
b. Using the efficiency estimate, compute the starting number of molecules in the test set.
c. Use this starting copy number and the prior efficiency distribution from the training set to estimate the PCR efficiency in the test sample.
d. For a range of potential real mutant fraction values 0 between 0 and 1 (we used 0.15 as upper bound), we estimate the mean and variance for the total number of molecules, background error molecules and real mutation molecules using the error propagation model described in last paragraph and parameters estimated in steps a-c.
e. Use the mean and variance estimated in step d to compute the likelihood L(θ) for each potential real mutant fraction. Select the value of θ that maximizes this likelihood, (denoted by $\hat{\theta}N_{MLE}$) and compute the confidence score $$\left(as\ \frac{L(\hat{\theta}_{MLE})}{L(0) + L(\hat{\theta}_{MLE})}\right).$$

f. Call a mutation if the confidence score is ≥≥95% for transitions and ≥98% for transversions.

What is claimed is:

1. A method for treatment of an individual known to have lung squamous cell carcinoma, the method comprising:
(a) extracting cell-free DNA (cfDNA) from a plasma sample of blood obtained from the individual known to have lung squamous cell carcinoma;
(b) preparing a fraction of the DNA useful for tracking single nucleotide variants present in the individual known to have lung squamous cell carcinoma by:
generating a set of amplicons, wherein the set of amplicons are generated by performing a multiplex PCR amplification reaction on nucleic acids of the DNA extracted in (a) and the multiplex PCR amplification reaction comprises forming an amplification reaction mixture by combining a polymerase, nucleotide triphosphates, nucleic acid fragments from a nucleic acid library generated from the plasma sample, and a set of forward and reverse primers that each binds an effective distance from a single nucleotide variant loci within 25 base pairs of the single nucleotide variant loci, or a set of primer pairs that each span an effective region comprising the single nucleotide variant loci within 25 base pairs of the single nucleotide variant loci, an annealing time of 15 minutes, 20 mM etramethyl ammonium chloride (TMAC), and a primer concentration of 10 nM, wherein the single nucleotide variant loci are known to be associated with lung squamous cell carcinoma and each amplicon of the set of amplicons spans at least one single nucleotide variant loci of a set of 25 to 1000 single nucleotide variant loci known to be associated with lung squamous cell carcinoma;
(c) determining presence of at least one single nucleotide variant associated with the lung squamous cell carcinoma in the plasma sample by next generation sequencing at a depth of read of greater than 1,000,000 and determining a sequence of at least a segment of each amplicon in the set of amplicons, wherein determining the presence of the at least one single nucleotide variant further comprises:
1) estimating an efficiency of the multiplex PCR amplification reaction and per cycle error rate using normal control samples, wherein the efficiency of the multiplex PCR amplification reaction indicates a probability that each molecule in the plasma sample is replicated in the multiplex PCR amplification reaction;
2) computing a starting number of molecules in the plasma sample using the efficiency obtained in 1);
3) for a range of potential real mutant fraction values between 0 and 0.15, estimating a mean and variance for a total number of molecules, background error molecules, and real mutation molecules using parameters obtained in 1) and 2);
4) computing a likelihood L(θ) for each potential real mutant fraction;
5) selecting a value of θ that maximizes the likelihood L(θ) and denoting the maximized likelihood by $\hat{\theta}_{MLE}$;
6) computing a confidence score as:

$$\frac{L(\hat{\theta}_{MLE})}{L(0) + L(\hat{\theta}_{MLE})};$$

and
7) determining presence of a single nucleotide variant if the confidence score is ≥0.95% for transitions and ≥0.98% for transversions; wherein the segment comprises one or more single nucleotide variant loci; and
administering a compound to the individual, wherein the compound is known to be specifically effective in treating the lung squamous cell carcinoma having the one or more single nucleotide variants.

2. The method according to claim 1, wherein the lung squamous cell carcinoma is a stage 1a, 1b, or 2a squamous cell carcinoma.

3. The method according to claim 1, wherein the lung squamous cell carcinoma is a stage 1a or 1b squamous cell carcinoma.

4. The method according to claim 1, wherein the individual is not subjected to surgery.

5. The method according to claim 1, wherein the individual is not subjected to a biopsy.

6. The method according to claim 1, wherein the method further comprises determining the variant allele frequency for each of the single nucleotide variants from the sequence determination.

7. The method according to claim 6, wherein a lung squamous cell carcinoma treatment plan is identified based on the variant allele frequency determinations.

8. The method according to claim 6, where the compound is known to be specifically effective in treating the lung squamous cell carcinoma having one of the single nucleotide variants with a variable allele frequency greater than at least one half of the other single nucleotide variants that were determined.

9. The method according to claim 1, wherein the nucleic acids are isolated from a tumor of the individual and single nucleotide variants are identified in the tumor for the set of single nucleotide variant loci before determining the sequence of the at least a segment of each amplicon of the set of amplicons for the sample of blood.

10. The method of claim 1, wherein the set of single nucleotide variant loci comprises clonal single nucleotide variant loci.

11. The method according to claim 10, wherein the compound targets the clonal single nucleotide variants.

12. The method according to claim 10, wherein a variant allele frequency of greater than 1.0% is indicative a clonal single nucleotide variant.

* * * * *